(12) United States Patent
Varghese et al.

(10) Patent No.: US 6,277,615 B1
(45) Date of Patent: Aug. 21, 2001

(54) (1→3, 1→4)—β-GLUCANASE OF ENHANCED STABILITY

(75) Inventors: Joseph Noozhumurry Varghese; Thomas Peter John Garrett; Geoffrey Bruce Fincher; Peter Bordier Hoj; Lin Chen, all of Melbourne (AU)

(73) Assignees: Biomolecular Research Institute Ltd., Parkville; Luminis Pty LTD, Adelaide; La Trobe University, Bundoora, all of (AU)

( * ) Notice: Subject to any disclaimer, the term of this patent is extended or adjusted under 35 U.S.C. 154(b) by 0 days.

(21) Appl. No.: 08/584,008

(22) Filed: Jan. 11, 1996

Related U.S. Application Data

(63) Continuation-in-part of application No. PCT/AU94/00377, filed on Jul. 6, 1994.

(30) Foreign Application Priority Data

Jul. 7, 1993 (AU) .................................................... PL9821

(51) Int. Cl.[7] ...................................................... C12N 9/24

(52) U.S. Cl. .......................... 435/200; 435/69.1; 530/372

(58) Field of Search ................................. 435/69.1, 91.1, 435/172.1, 172.3, 419, 320.1, 185, 200, 468; 530/350, 370, 372; 536/23.2, 23.6; 800/205, 320

(56) References Cited

FOREIGN PATENT DOCUMENTS

51013/90  9/1990 (AU) .
95/02042 * 1/1995 (WO) .

OTHER PUBLICATIONS

Varghese et al. (1994). Three–dimensional structure of two plant B–glucan endohydrolases with distinct substrate specificities. Proc. Natl. Acad. Sci. USA 91: 2785–2789.*

Mathews et al. (1987). Enhanced protein thermostability from site–directed mutations that decreases the entropy of unfolding. Proc. Natl. Acad. Sci. USA 84: 6663–6667.*

Eijsink et al. (1992). Increasing the thermostability of a neutral protease by replacing positively charged amino acids in the N–terminal turn of α–helices. Protein Eng. 5: 165–170.*

Mrabet et al. (1992) Arginine residues as stabilizing elements in proteins. Biochem. 31: 2239–2253.*

Aurora et al. (1994). Rules for α–helix termination by glycine. Science 264: 1126–30.*

Alber. "Mutational effects on protein stability" Ann. Rev. Biochem. 58: 765–798, 1989.*

Derwent abstract No. 90–067913, DD–A–272102, Sep. 27, 1989.

Derwent abstract No. 90–210631, DD–A–275704, Jan. 31, 1990.

(List continued on next page.)

*Primary Examiner*—Robert A. Schwartzman
*Assistant Examiner*—Thomas G. Larson
(74) *Attorney, Agent, or Firm*—Jacobson, Price, Holman & Stern, PLLC

(57) ABSTRACT

This invention relates to a (1→3, 1→4)-β-glucanase (glucanase EII endohydrolase) enzyme, whose amino acid sequence has been modified in order to provide an enzyme whose three-dimensional structure confers improved thermostability and/or pH stability. Specific modifications are based upon a comparison between the three-dimensional structure (1→3, 1→4)-β-glucanase and that of (1→3)-β-glucanase. The (1→3, 1→4)-β-glucanase gene has been modified by site-directed mutagenesis, and modified enzymes have been expressed in *E. coli*. Modified sequences, DNA molecules encoding them, plasmids, expression vectors and transgenic plants are disclosed.

28 Claims, 8 Drawing Sheets

OTHER PUBLICATIONS

Figure 1:
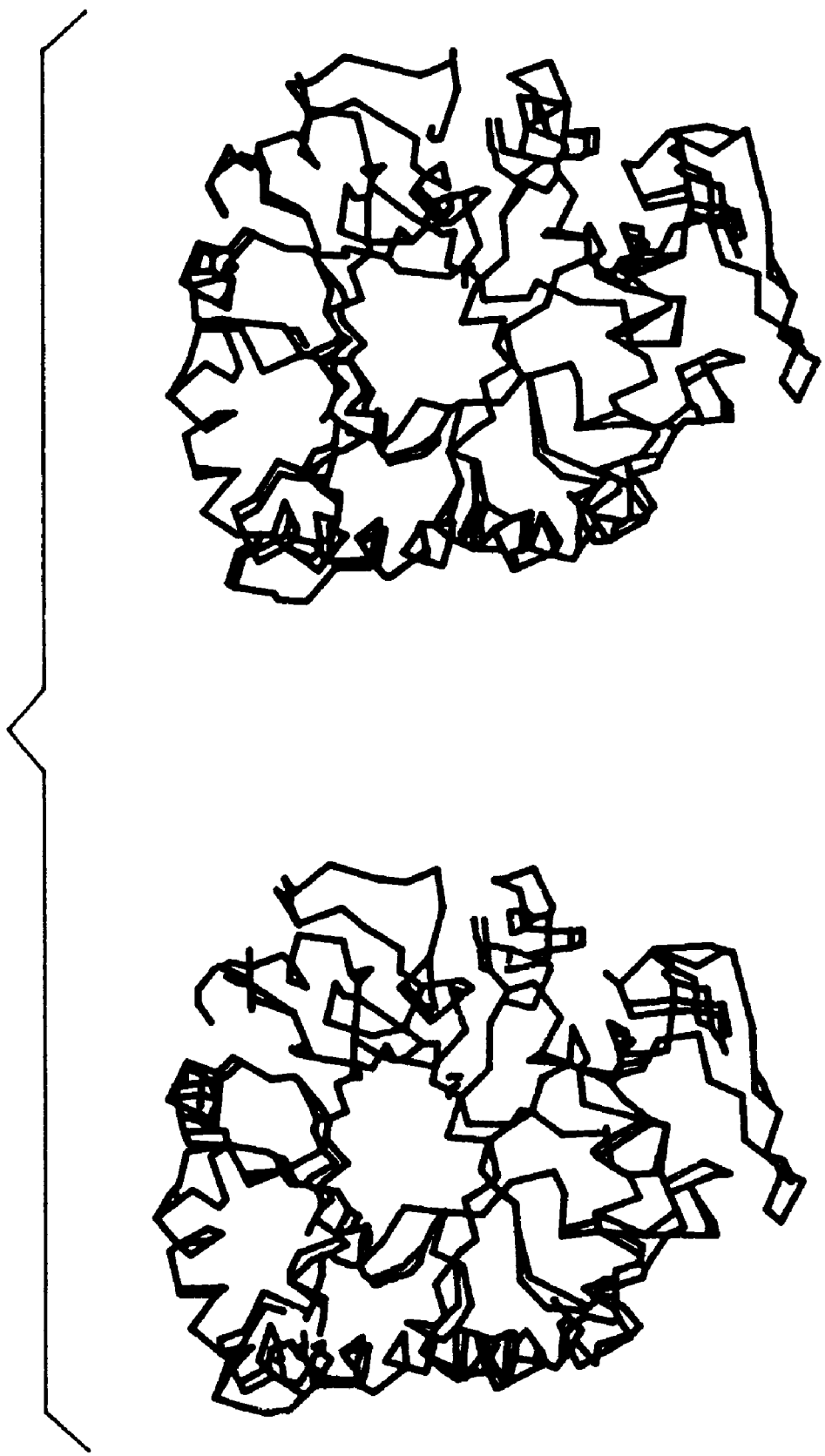

Thomsen, K.K., Eur. Bre. Conv (1990) 15 (E.B.C. Symp. Plant Biotechnol., 1989), pp. 137–145, Engineering of Heat . . . .

Phillipson, B.A., Plant Science, 91 (1993) pp. 195–206, Expression of a hybrid (1–3, 1–4) . . . .

Politz, O. et al, Eur. J. Biochem. 216 (1993) pp. 829–834, Determinants for the enhanced thermostability . . . .

Olsen, O. et al, Journal of Genetic Microbiology 137, (1991) pp. 579–585, Improvement of bacterial . . . .

Schimming, W. et al, Eur. J. Biochem., 204 (1992) pp. 13–19, Structure of the Clostridium thermocellum gene . . . .

Olsen, O. et al, Mol. Gen. Genet., 225 (1991) pp. 177–185, Hybrid Bacillus (1–3, 1–4) . . . .

* cited by examiner

FIG. 2

```
                               β6                              A6a
158 Ser Thr Gly Ala Pro Leu Leu Ala Asn Val  Tyr Pro Tyr Phe Ala Tyr Arg Asp Asn Pro
160 Arg Thr Asn Ala Pro Leu Met Ala Asn Ile  Tyr Pro Tyr Leu Ala Trp Ala Tyr Asn Pro
                               β6                              A6a

A6b                                         B6a
178 Gly Ser Ile Ser Leu Asn Tyr Ala Thr Phe Gln Pro Gly Thr Thr     Val Arg Asp Gln
180 Ser Ala Met Asp Met Gly Tyr Ala Leu Phe Asn Ala Ser Gly Thr Val Val Arg Asp
                    A6b                                         B6a

B6b                            α6
197 Asn Asn Gly     Leu Thr Tyr Thr Ser Leu Phe Asp Ala Met Val Asp Ala Val Tyr Ala
199         Gly Ala Tyr Gly Tyr Gln Asn Leu Phe Asp Thr Thr Val Asp Ala Phe Tyr Thr
              B6b                            α6

β7
216 Ala Leu Glu Lys Ala Gly Ala Pro Ala Val Lys Val Val Val Ser Glu Ser Gly Trp Pro
217 Ala Met Gly Lys His Gly Gly Ser Ser Val Lys Leu Val Val Ser Glu Ser Gly Trp Pro
                                                  β7

α7
236 Ser Ala Gly Gly Phe Ala Ala Ser Ala Gly Asn Ala Arg Thr Tyr Asn Gln Gly Leu Ile
237 Ser Gly Gly Gly Thr Ala Ala Thr Pro Ala Asn Ala Arg Phe Tyr Asn Gln His Leu Ile
                                        α7

β8
256 Asn His Val Gly Gly Gly Thr Pro Lys Lys Arg Glu Ala Leu Glu Thr Tyr Ile Phe Ala
257 Asn His Val Gly Arg Gly Thr Pro Arg His Pro Gly Ala Ile Glu Thr Tyr Ile Phe Ala
                               B7a      B7b                        β8

α8
276 Met Phe Asn Glu Asn Glu Lys Thr Gly Asp Ala Thr Glu Arg Ser Phe Gly Leu Phe Asn
277 Met Phe Asn Glu Asn Gln Lys     Asp Ser Gly Val Glu Gln Asn Trp Gly Leu Phe Tyr
                                        α8                          B8a

296 Pro Asp Lys Ser Pro Ala Tyr Asn Ile Gln Phe    GII
296 Pro Asn Met Gln His Val Tyr Pro Ile Asn Phe    EII
              B8b
```

FIG. 2A

```
         β1                                                α1
      ←------→                                       ←----------------
  1   Ile Gly Val Cys Tyr Gly Val Ile Gly Asn Asn Leu Pro Ser Arg Ser Asp Val Val Gln
  1   Ile Gly Val Cys Tyr Gly Met Ser Ala Asn Asn Leu Pro Ala Ala Ser Thr Val Val Ser
      ←------→                                       ←----------------
         β1                                                α1

----------→          β2                              α2
                        ←------→                    ←----------------
 21   Leu Tyr Arg Ser Lys Gly Ile Asn Gly Met Arg Ile Tyr Phe Ala Asp Gly Gln Ala Leu
 21   Met Phe Lys Ser Asn Gly Ile Lys Ser Met Arg Leu Tyr Ala Pro Asn Gln Ala Ala Leu
      ----------→          ←------→
                              β2                           α2

------→                   β3                              A3
                           ←----------→                   ←----------
 41   Ser Ala Leu Arg Asn Ser Gly Ile Gly Leu Ile Leu Asp Ile Gly Asn Asp Gln Leu Ala
 41   Gln Ala Val Gly Gly Thr Gly Ile Asn Val Val Val Gly Ala Pro Asn Asp Val Leu Ser
      ------→                   ←----------→
                                     β3                         A3

α3
      ---------→ ←---------------------→
 61   Asn Ile Ala Ala Ser Thr Ser Asn Ala Ala Ser Trp Val Gln Asn Asn Val Gln Pro Tyr
 61   Asn Leu Ala Ala Ser Pro Ala Ala Ala Ala Ser Trp Val Lys Ser Asn Ile Gln Ala Tyr
      ---------→                       ←---------------------→
                                              α3

β4
                        ←----------------→                  ←----------
 81   Tyr Pro Ala Val Asn Ile Lys Tyr Ile Ala Ala Gly Asn Glu Val Gln Gly Gly Ala Thr
 81       Pro Lys Val Ser Phe Arg Tyr Val Cys Val Gly Asn Glu Val Ala Gly Gly Ala Thr
                        ←----------------→                  ←---
                               β4

α4
      -----------------------------------------------
101   Gln Ser Ile Leu Pro Ala Met Arg Asn Leu Asn Ala Ala Leu Ser Ala Ala Gly Leu Gly
100   Arg Asn Leu Val Pro Ala Met Lys Asn Val His Gly Ala Leu Val Ala Ala Gly Leu Gly
      ----------------------------------------------------→
                 α4

β5                         B5a
           ←------→                   ←------→
121   Ala Ile Lys Val Ser Thr Ser Ile Arg Phe Asp Glu Val Ala Asn Ser Phe Pro Pro Ser
120   His Ile Lys Val Thr Thr Ser Val Ser Gln Ala Ile Leu Gly Val Phe Ser Pro Pro Ser
           ←------→                   ←------→
              β5                         B5a

B5b                                α5
         ←----→                           ←--------------------
141   Ala Gly Val Phe Lys     Asn     Ala Tyr Met Thr Asp Val Ala Arg Leu Leu Ala
140   Ala Gly Ser Phe Thr Gly Glu Ala Ala Phe Met Gly Pro Val Val Gln Phe Leu Ala
         ←----→        ←--------→                ←--------------------
           B5b              A5                         α5
```

Stabilities of GII & EII at pH 3.5

Stabilities of GII & EII at 50°C

Stabilities of GII & EII on heating for 15 min.

Stabilities of wildtype EII and mutant H300P on heating for 15 minutes

Stabilities of wildtype EII and mutant H300P at 48°C

Stabilities of wildtype EII and mutant H300P during mashing at 55°C

```
                          SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
         (A) LENGTH: 10 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO: 1:

Ile Arg Phe Asp Glu Val Ala Asn Ser Phe
1               5                   10

(2) INFORMATION FOR SEQ ID NO: 2:

(i) SEQUENCE CHARACTERISTICS:
         (A) LENGTH: 10 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO: 2:

Val Ser Gln Ala Ile Leu Gly Val Phe Ser
1               5                   10

(2) INFORMATION FOR SEQ ID NO: 3:

(i) SEQUENCE CHARACTERISTICS:
         (A) LENGTH: 9 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO: 3:

Phe Ala Tyr Arg Asp Asn Pro Gly Ser
1               5

(2) INFORMATION FOR SEQ ID NO: 4:

(i) SEQUENCE CHARACTERISTICS:
         (A) LENGTH: 9 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO: 4:

Leu Ala Trp Ala Tyr Asn Pro Ser Ala
1               5

(2) INFORMATION FOR SEQ ID NO: 5:

(i) SEQUENCE CHARACTERISTICS:
         (A) LENGTH: 9 amino acids
         (B) TYPE: amino acid
         (C) STRANDEDNESS:
         (D) TOPOLOGY: linear
```

(ii) MOLECULE TYPE: protein (xi) SEQUENCE DESCRIPTION: SEQ ID NO: 5:

Thr Gly Asp Ala Thr Glu Arg Ser Phe
1               5

(2) INFORMATION FOR SEQ ID NO: 6:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO: 6:

Asp Ser Gly Val Glu Gln Asn Trp
1               5

(2) INFORMATION FOR SEQ ID NO: 7:

(i) SEQUENCE CHARACTERISTICS:
            (A) LENGTH: 306 amino acids
            (B) TYPE: amino acid
            (C) STRANDEDNESS:
            (D) TOPOLOGY: linear (ii) MOLECULE TYPE: protein (xi) SEQUENCE DESCRIPTION: SEQ ID NO: 7:

Ile Gly Val Cys Tyr Gly Val Ile Gly Asn Asn Leu Pro Ser Arg Ser
1               5                   10                  15

Asp Val Val Gln Leu Tyr Arg Ser Lys Gly Ile Asn Gly Met Arg Ile
                20                  25                  30

Tyr Phe Ala Asp Gly Gln Ala Leu Ser Ala Leu Arg Asn Ser Gly Ile
                35                  40                  45

Gly Leu Ile Leu Asp Ile Gly Asn Asp Gln Leu Ala Asn Ile Ala Ala
        50                  55                  60

Ser Thr Ser Asn Ala Ala Ser Trp Val Gln Asn Asn Val Gln Pro Tyr
65                  70                  75                  80

Tyr Pro Ala Val Asn Ile Lys Tyr Ile Ala Ala Gly Asn Glu Val Gln
                85                  90                  95

Gly Gly Ala Thr Gln Ser Ile Leu Pro Ala Met Arg Asn Leu Asn Ala
                100                 105                 110

Ala Leu Ser Ala Ala Gly Leu Gly Ala Ile Lys Val Ser Thr Ser Ile
                115                 120                 125

Arg Phe Asp Glu Val Ala Asn Ser Phe Pro Pro Ser Ala Gly Val Phe
        130                 135                 140

Lys Asn Ala Tyr Met Thr Asp Val Ala Arg Leu Leu Ala Ser Thr Gly
145                 150                 155                 160

Ala Pro Leu Leu Ala Asn Val Tyr Pro Tyr Phe Ala Tyr Arg Asp Asn
                165                 170                 175

Pro Gly Ser Ile Ser Leu Asn Tyr Ala Thr Phe Gln Pro Gly Thr Thr
                180                 185                 190

Val Arg Asp Gln Asn Asn Gly Leu Thr Tyr Thr Ser Leu Phe Asp Ala
        195                 200                 205

Met Val Asp Ala Val Tyr Ala Ala Leu Glu Lys Ala Gly Ala Pro Ala
210                 215                 220

```
Val Lys Val Val Val Ser Glu Ser Gly Trp Pro Ser Ala Gly Gly Phe
225                 230                 235                 240

Ala Ala Ser Ala Gly Asn Ala Arg Thr Tyr Asn Gln Gly Leu Ile Asn
            245                 250                 255

His Val Gly Gly Gly Thr Pro Lys Lys Arg Glu Ala Leu Glu Thr Tyr
            260             265                 270

Ile Phe Ala Met Phe Asn Glu Asn Gln Lys Thr Gly Asp Ala Thr Glu
        275                 280             285

Arg Ser Phe Gly Leu Phe Asn Pro Asp Lys Ser Pro Ala Tyr Asn Ile
    290                 295             300

Gln Phe
305

(2) INFORMATION FOR SEQ ID NO: 8:

(i) SEQUENCE CHARACTERISTICS:
        (A) LENGTH: 306 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 8:

Ile Gly Val Cys Tyr Gly Met Ser Ala Asn Asn Leu Pro Ala Ala Ser
1               5                   10                  15

Thr Val Val Ser Met Phe Lys Ser Asn Gly Ile Lys Ser Met Arg Leu
            20                  25                  30

Tyr Ala Pro Asn Gln Ala Ala Leu Gln Ala Val Gly Gly Thr Gly Ile
            35                  40                  45

Asn Val Val Gly Ala Pro Asn Asp Val Leu Ser Asn Leu Ala Ala
50                  55                  60

Ser Pro Ala Ala Ala Ser Trp Val Lys Ser Asn Ile Gln Ala Tyr
65              70                  75                  80

Pro Lys Val Ser Phe Arg Tyr Val Cys Val Gly Asn Glu Val Ala Gly
                85                  90                  95

Gly Ala Thr Arg Asn Leu Val Pro Ala Met Lys Asn Val His Gly Ala
            100                 105                 110

Leu Val Ala Ala Gly Leu Gly His Ile Lys Val Thr Thr Ser Val Ser
        115                 120                 125

Gln Ala Ile Leu Gly Val Phe Ser Pro Pro Ser Ala Gly Ser Phe Thr
        130                 135                 140

Gly Glu Ala Ala Ala Phe Met Gly Pro Val Val Gln Phe Leu Ala Arg
145                 150                 155                 160

Thr Asn Ala Pro Leu Met Ala Asn Ile Tyr Pro Tyr Leu Ala Trp Ala
            165                 170                 175

Tyr Asn Pro Ser Ala Met Asp Met Gly Tyr Ala Leu Phe Asn Ala Ser
            180                 185                 190

Gly Thr Val Val Arg Asp Gly Ala Tyr Gly Tyr Gln Asn Leu Phe Asp
            195                 200                 205

Thr Thr Val Asp Ala Phe Tyr Thr Ala Met Gly Lys His Gly Gly Ser
        210                 215                 220

Ser Val Lys Leu Val Val Ser Glu Ser Gly Trp Pro Ser Gly Gly Gly
225                 230                 235                 240

Thr Ala Ala Thr Pro Ala Asn Ala Arg Phe Tyr Asn Gln His Leu Ile
            245                 250                 255
```

-continued

```
Asn His Val Gly Arg Gly Thr Pro Arg His Pro Gly Ala Ile Glu Thr
            260                 265                 270

Tyr Ile Phe Ala Met Phe Asn Glu Asn Gln Lys Asp Ser Gly Val Glu
            275                 280                 285

Gln Asn Trp Gly Leu Phe Tyr Pro Asn Met Gln His Val Tyr Pro Ile
290                 295                 300

Asn Phe
305
```

(1→3, 1→4)—β-GLUCANASE OF ENHANCED STABILITY

This application is a continuation-in-part application of PCT/AU94/00377, filed on Jul. 6, 1994, which designated the United States and is entitled to priority under 35 USC §120.

BACKGROUND OF THE INVENTION

Barley quality encompasses a range of physical and chemical attributes, depending on whether the grain is to be used in the preparation of malt for brewing purposes, in the formulation of stockfeed, or as a component of human foods. Currently, specifications or barley quality are tailored primarily for the malting and brewing industries, in which germinated barley (malt) is the principal raw material. The quality specifications include such parameters as grain size, dormancy, malt extract, grain protein content, development of enzymes for starch degradation in malt and (1→3,1→4)-β-glucan content. Malt extract is a widely-used quality indicator. It is an estimate of the percentage of malted grain that can be extracted with hot water. Barley breeders and growers strive to produce grain with high malt extract values, because greater extract percentages provide higher levels of materials for subsequent fermentative growth by yeast during brewing. Malt extract values are influenced both by the composition of the ungerminated barley and by the speed and extent of endosperm modification during malting. Given the central role of cell walls as a potential barrier against the free diffusion of starch- and protein-degrading enzymes from the scutellum or from the aleurone to their substrates in cells of the starchy endosperm, it is not surprising that wall composition and the ability of the grain to rapidly produce enzymes that hydrolyse wall constituents are important determinants of malt extract values.

The major constituents of endosperm cell walls of barley are the (1→3,1→4,-β-glucans, which account for approximately 70% by weight of the walls (Fincher, 1975). In the germinating grain (1→3,1→4)-β-glucanases function to depolymerise (1→3,1→4)-β-glucans of cell walls during endosperm mobilisation.

Total (1→3,1→4)-β-glucan in ungerminated barley grain is not highly correlated with malt extract (Henry 1986; Stuart et al, 1988). However, the residual (1→3,1→4)-β-glucan in malted barley is highly correlated, in a negative sense, with malt extract (Bourne et al, 1982; Henry 1986; Stuart et al, 1988), and this residual polysaccharide reflects a combination of the initial (1→3,1→4)-β-glucan levels in the barley and, more importantly, the capacity of the grain to rapidly produce high levels of (1→3,1→4)-β-glucanase during malting (Stuart et al, 1988). The (1→3,1→4)-β-glucanase potential of barley cultivars is also dependent on both genotype and environment, although environmental conditions during grain maturation appear to be particularly important in the development of the enzymes (Stuart et al, 1988). Monoclonal antibodies specific for barley (1→3, 1→4)-β-glucanases have been used in enzyme-linked immunoadsorbent assays (ELISA) that may be useful for the quantitation of (1→3,1→4)-β-glucanase levels in large numbers of barley lines generated in breeding programs (Høj et al, 1990). Furthermore, mutant barleys with altered (1→3,1→4)-β-glucan content (Aastrup 1983; Molina-Cona et al, 1989) or (1→3,1→4)-β-glucanase potential will be useful in future studies on the effects of these components on malting quality and may be valuable in breeding programmes.

The ability of the (1→3;1→4)-β-glucanases [E. C. 3.2.1.73] to retain enzymatic activity at elevated temperatures (thermostability) is of extreme importance during the utilization of barley in the malting and brewing industries. Malt quality, as measured by the 'malt extract' index, is highly dependent on the ability of the grain to rapidly synthesize high levels of the enzyme during germination (Stuart et al, 1988). High levels of (1→3;1→4)-β-glucanases are also desirable in the brewing process, where residual (1→3;1→4)-β-glucans in malt extracts can adversely effect wort and beer filtration due to their propensity to form aqueous solutions of high viscosity. These residuals can also contribute to the formation of certain hazes or precipitates at elevated ethanol concentrations or low temperatures in the final beer (Woodward and Fincher, 1983). The elevated temperatures used during commercial malting and brewing lead to rapid and extensive inactivation of these enzymes. The high temperatures (up to 85°) of commercial kilning processes destroy greater than 60% of the enzyme activity and much of the remaining enzyme is inactivated by the hot water used for malt extraction (Brunswick et al, 1987), Loi et al, 1987). It is therefore highly desirable to develop commercial strains of barley that express a thermostable (1→3;1→4)-β-glucanase enzyme, or to produce the (1→3;1→4)-β-glucanase enzyme exogenously as an additive to be used in the brewing process.

Barley (1→3;1→4)-β-glucans also pose problems in the stockfeed industry. In poultry formulations prepared from cereal grains, (1→3;1→4)-β-glucans significantly raise the viscosity of the gut contents of chickens. This impairs digestion and slows growth rates, and results in sticky faecal droppings that make hygienic handling of eggs and carcases difficult (Fincher and Stone, 1986). This application would require the enzyme to be stable at a range of pHs, particularly in the pH region of the foregut. It would also be an advantage for the enzyme to be sufficiently thermostable to withstand the steam pelleting processes widely used in stockfeed manufacture.

Thus it is envisaged that (1→3,1→4)-β-glucanase of amino acid sequence modified so as to provide enhanced thermostability and/or pH stability will have a variety of industrial uses, either by means of barley expressing the modified enzyme, or by addition of the modified enzyme to barley being processed.

There has been considerable interest in inserting (1→3, 1→4)-β-glucanase genes into brewing yeasts, in the expectation that low level, constitutive expression would lead to the secretion of active enzyme and the depolymerisation of residual (1→3,1→4)-β-glucan during fermentation (Hinchliffe, 1988). A barley (1→3,1→4)-β-glucanase cDNA (Fincher et al, 1986) fused with a mouse α-amylase signal peptide is expressed and secreted from yeast under the direction of the yeast alcohol dehydrogenase I gene promoter (Jackson et al, 1986). Although the gene for isoenzyme EII has not yet been isolated, the availability of almost full length cDNA for use as a probe means that such isolation can readily be carried out using conventional methods.

We have now determined the three dimensional structure of (1→3,1→4)-β-glucanase isoenzyme EII and (1→3, 1→4)-β-glucanase isoenzyme GII (E.C.3.2.1.39), and have identified regions of the structures of these enzymes which are candidates for modification in order to provide enhanced thermal and pH stability, as well as suitable point mutations for achieving such stabilisation. We have found that the 3-dimensional structures of these two enzymes, which share only 50% sequence homology, are remarkably similar in their structural framework, and that their active sites are also surprisingly similar, despite the difference in substrate specificity.

SUMMARY OF THE INVENTION

According to a first aspect, the invention provides a (1→3,1→4)-β-glucanase of enhanced thermostability and/or pH stability.

In a second aspect, the invention provides an isolated DNA sequence encoding (1→3,1→4)-β-glucanase of enhanced thermostability and/or pH stability, and plasmids, expression vectors, and transgenic plants comprising said sequence. Preferably the expression host is *E. coli* or *Saccharomyces cerevisae;* preferably the transgenic plant is barley. It will be clearly understood that barley grain from plants encoding the improved enzyme is within the scope of this invention.

In a third aspect, the invention provides a method selected from the group consisting of malting, brewing and stockfeed processing, comprising the step of
 a) using barley expressing the (1→3,1→4)-β-glucanase of this invention as a starting material, or
 b) adding (1→3,1→4)-β-glucanase of this invention to a grain to be processed.

In a fourth aspect, the invention provides a composition for use in malting, brewing, or stockfeed processing, comprising the improved (1→3,1→4)-β-glucanase of the invention, together with carriers acceptable for use in processing of beverages or of stockfeeds.

DETAILED DESCRIPTION OF THE INVENTION

The invention will now be described in detail by way of reference only to the following non-limiting examples, and to the figures, in which FIG. 1 shows a stereo view of the alpha carbon trace of the polypeptide backbone of the EII and GII glucanase enzymes. The heavy lines represent the EII enzyme and the lighter lines represent the GII enzymes. The active site groove runs north to south, and the C- and N-termini are indicated, as are the two putative active site residues glutamic acids at residues 232 and 288 (using EII sequence numbers).

FIG. 2A and FIG. 2B (a continuation of FIG. 2A) show the sequence comparison of the EII (lower line) and GII (upper line) glucanase enzymes based on the 3-dimensional structure, SEQ ID NO:7 with the sequence given using the three letter code for amino acids. Residue numbers at the start of each line are the sequence numbers of the two enzymes. The secondary structure elements of both enzymes are given above the GII sequence and below the EII sequence (see text for notation used in the description of the tertiary structure).

α represents alpha helices; β represents beta sheets; A and B represent additional alpha helices and beta sheets to those of a typical α/β barrel.

Figure 3:
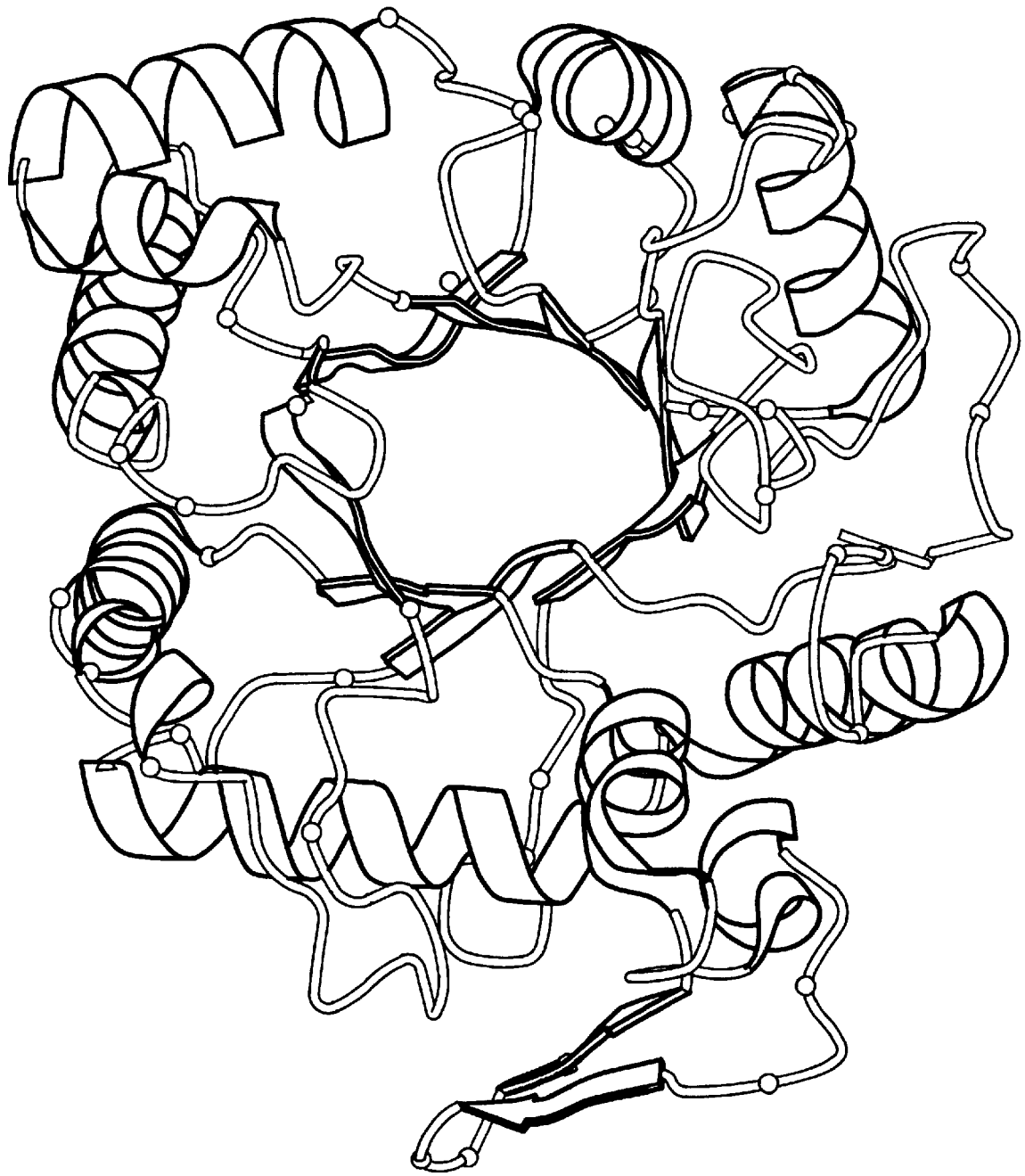

FIG. 3 is a schematic drawing of the (1→3,1→4)-β-glucanase EII enzyme. The elements with arrow heads represent beta sheet structure and the elements with a curled tape coil represent alpha helices. Some of the smaller beta sheets are not drawn. Elsewhere the chain is represented as a rope. The black dots represent amino acid locations where thermostable mutants have been proposed (see text).

Figure 4:
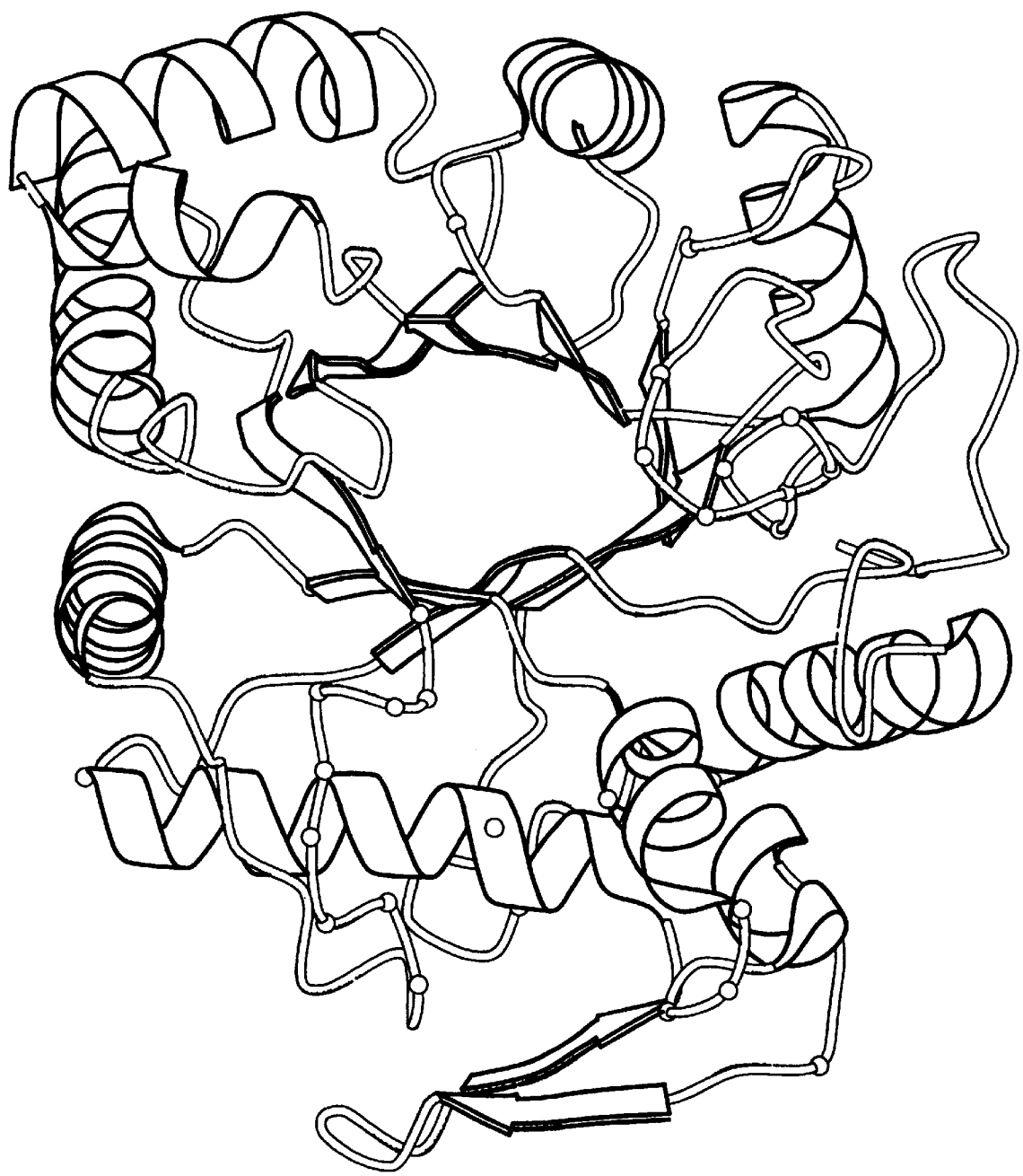

FIG. 4 is a schematic drawing of the (1→3)-β-glucanase GII enzyme. The elements with arrow head represent beta sheet structure and the elements with a curled tape coil represent alpha helices. Some of the smaller beta sheets are not drawn. Elsewhere the chain is represented as a rope. The black dots represent amino acids locations around the active site groove which confer the specific activity of the enzymes. It is proposed to modify these amino acids to change the specificity of the GII enzyme into that of the EII enzyme.

Figure 5:
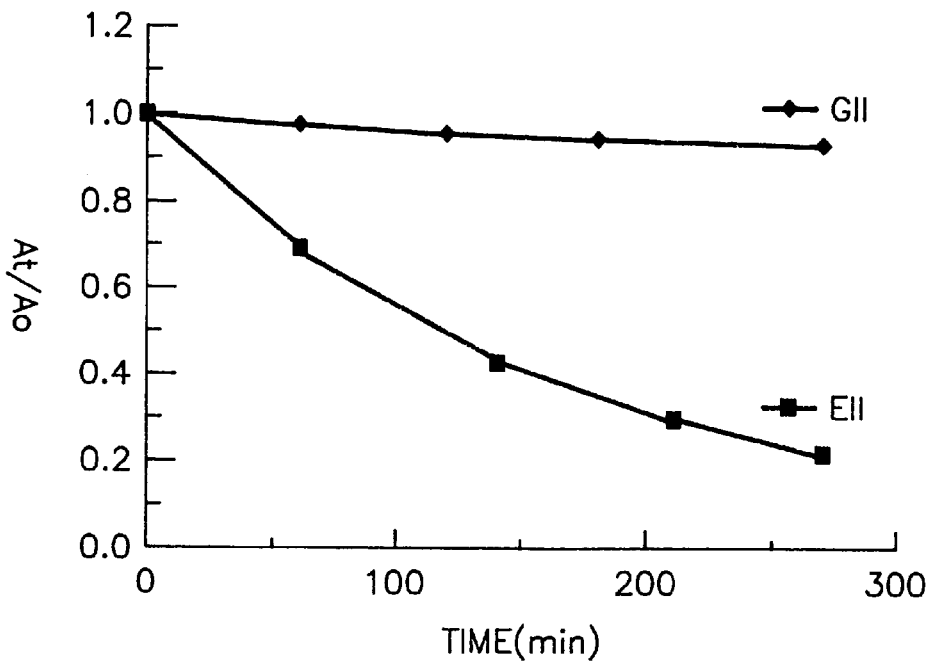

FIG. 5 shows a comparison between stability of (1→3, 1→4)-β-glucanase isoenzyme EII with that of (1→3)-β-glucanase isoenzyme GII at pH 3.5.

Figure 6:
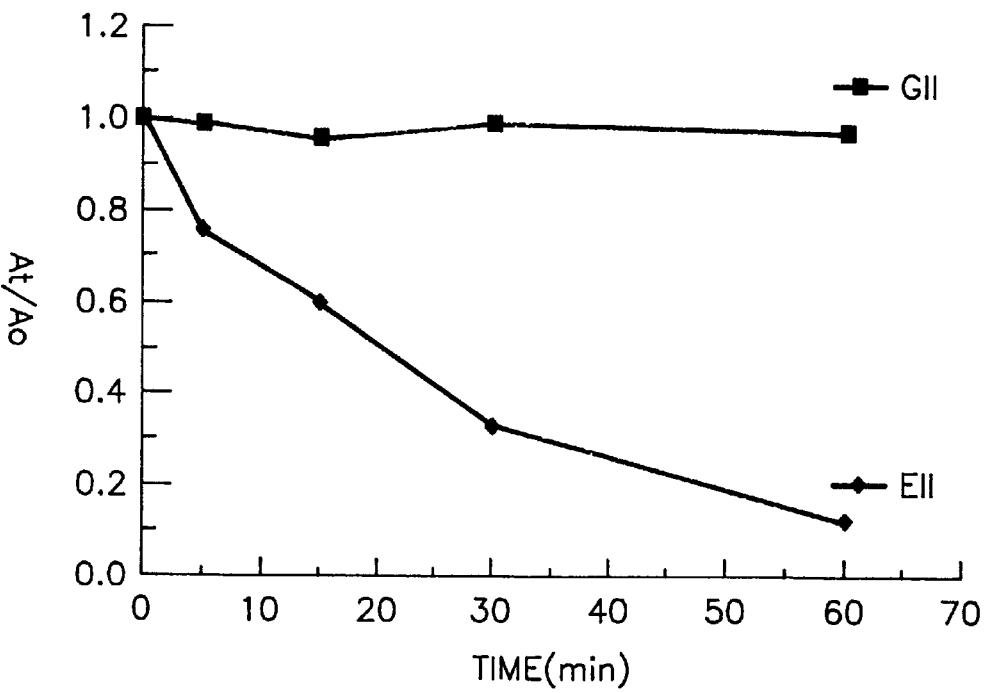

FIG. 6 compares the stabilities of (1→3,1→4)-β-glucanase isoenzymes EII with that of (1→3)-β-glucanase isoenzyme GII at 50°.

Figure 7:
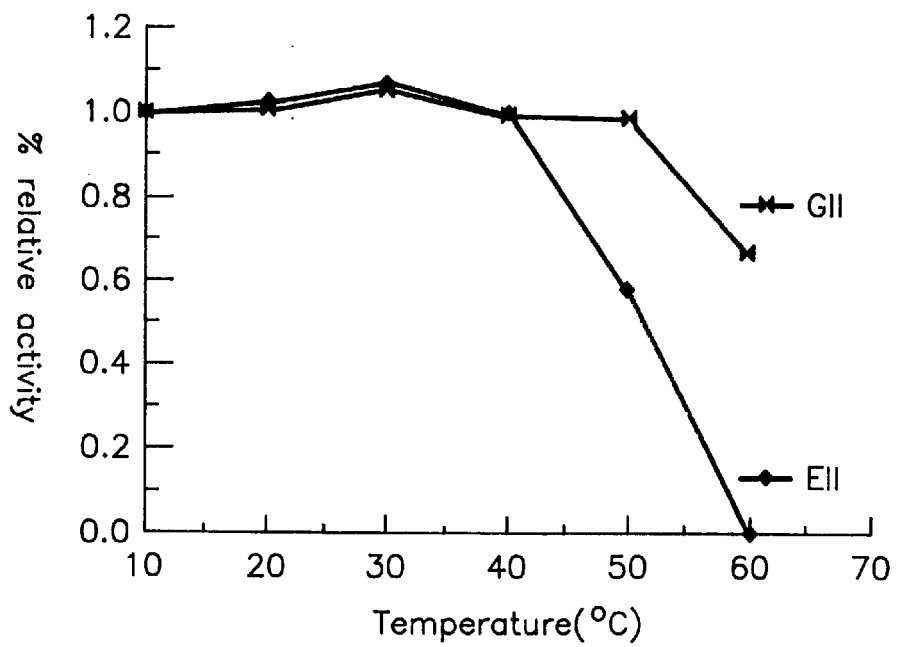

FIG. 7 compares the stabilities of (1→3,1→4)-β-glucanase isoenzyme EII with that of (1→3)-β-glucanase isoenzyme GII at increasing temperatures.

Figure 8:
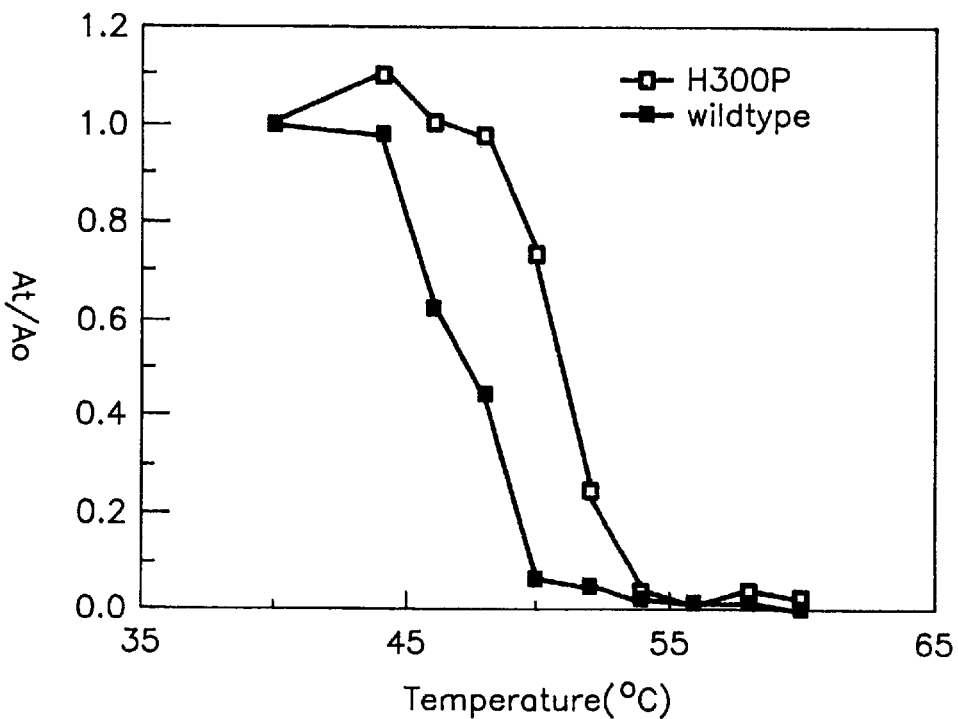

FIG. 8 compares the stabilities of wildtype (1→3,1→4)-β-glucanase isoenzyme EII and mutant H300P on heating for 15 minutes.

Figure 9:
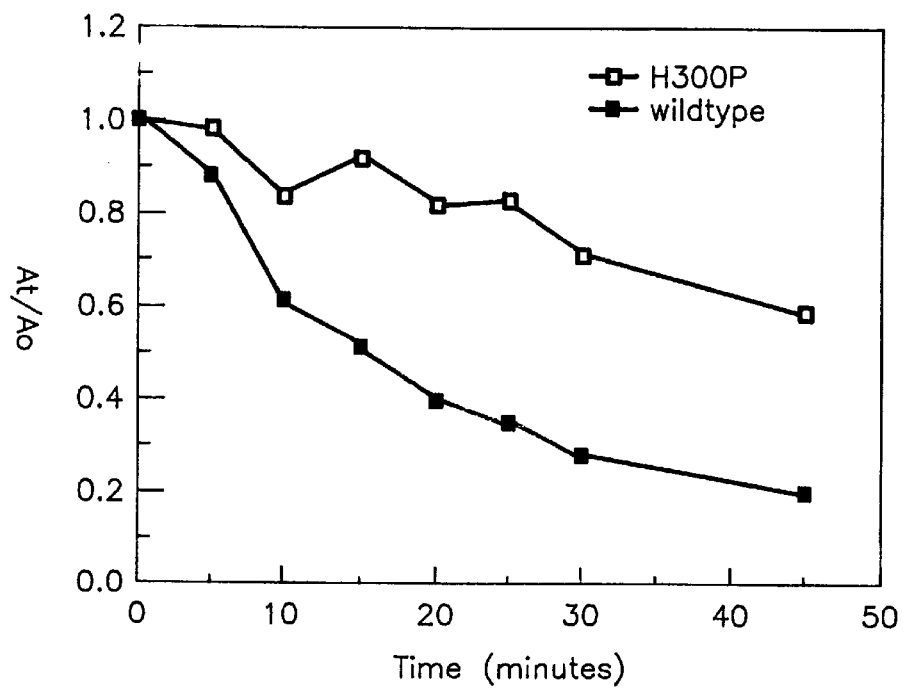

FIG. 9 compares the stabilities of wildtype (1→3,1→4)-β-glucanase isoenzyme EII and mutant H300P at 48° C.

Figure 10:
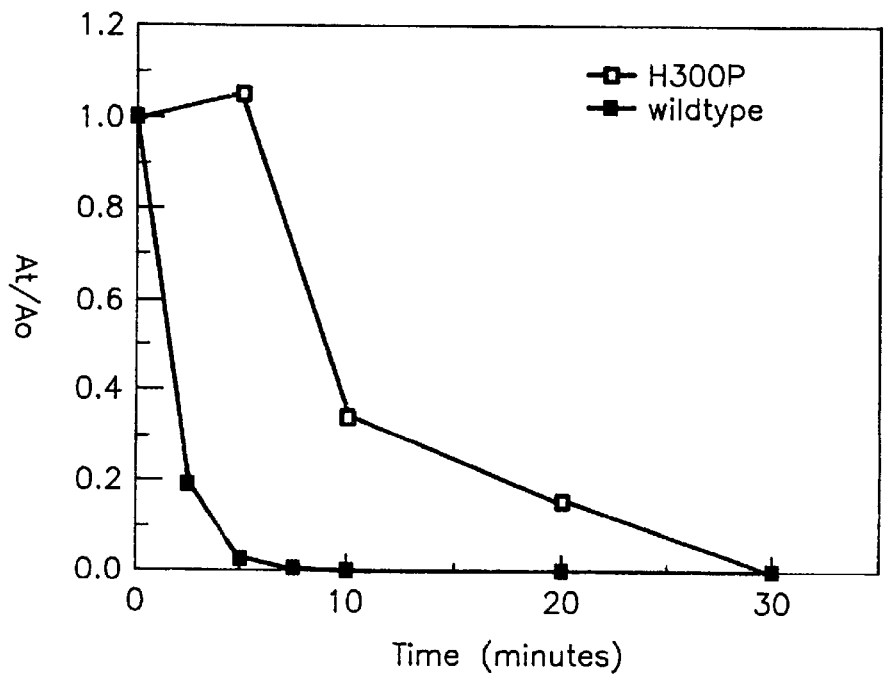

FIG. 10 compares the stabilities of wildtype (1→3,1→4)-β-glucanase isoenzyme EII and mutant H300P during mashing at 55° C.

The (1→3;1→4)-β-glucanase catalyse the hydrolysis of (1→4)-β-glucosyl linkages in (1→3;1→4)-β-glucans, only where the glucosyl residue is substituted at the C(O)3 position, as follows:

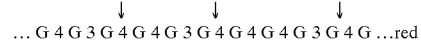

The glucosyl residues are represented by G, (1→3)- and (1→4)-β-linkages by 3 and 4, respectively, and the reducing terminus (red) of the polysaccharide chain is indicated. Thus the enzymes have an absolute requirement for adjacent (1→3)- and (1→4)-β-linked glucosyl residues in their substrates. The (1→3)-β-glucanases [EC 3.2.1.39] are unable to hydrolyse the single (1→3)-β-linkages found in (1→3;1→4)-β-glucans, but can catalyse the hydrolysis of (1→3)-β-glucosyl linkages in (1→3)-β-glucans, as follows:

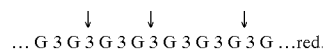

Arrows indicate the hydrolysis of (1→3)-β-linkages between glucosyl residues (G).

Furthermore, it is known that the (1→3)-62 -glucanase isoenzyme GII is more thermostable, pH stable and protease resistant than the (1→3;1→4)-β-glucanase EII enzyme. Thus using the three dimensional structures of these enzymes, we can create more stable forms of the (1→3;1→4)-β-glucanase by the following methods:
 (a) transferring the structural elements that generate the heat stability of the (1→3)-β-glucanase, on to the (1→3;1→4)-β-glucanase.
 (b) modifying the (1→3;1→4)-β-glucanase using general principles of protein structure and stability (Matthews, 1987).
 (c) engineering a thermostable or pH stable (1→3;1→4)-β-glucanase enzyme by transforming the (1→3)-β-glucanase into the (1→3;1→4)-β-glucanase. This is done by transferring elements of the catalytic site of the (1→3;1→4)-β-glucanase enzyme on to the (1→3)-β-glucanase enzyme.

(d) engineering a thermostable (1→3,1→4)-β-glucanase and (1→3)-β-glucanase by creating cysteine pairs which can form disulphide bonds across the C and N terminals.

A combination of two or more of these methods may be used.

For each of these methods knowledge of the protein structures is an important prerequisite. This knowledge enables us to separate differences between the two enzymes which govern substrate specificity from those for thermal and pH stability. It also enables us to predict which kind of changes to the sequence which will enhance the stability of the secondary structure elements. Random mutagenesis of glucanase genes will invariably reduce the stability of the protein by disrupting its structure, or may cause inactivation of the enzyme. This is due to the inability of current methods to predict protein folding and catalytic activity from amino acid sequence information alone.

EXAMPLE 1

Determination of the 3-Dimensional Structure of the Glucanase Enzymes

We have determined the 3-dimensional structure of (1→3;1→4)-β-glucanase isoenzyme EII (hereafter called EII) and (1→3)-β-glucanase isoenzyme GII (hereinafter called GII) to high resolution (2.2 Å) by X-ray crystallographic techniques described by Blundell and Johnson (1979).

In Appendix 3 we have set out the 3-dimensional coordinates and mean thermal vibration parameters (isotropic B values) of the two enzymes, as determined from the crystallographic refinement of the X-ray diffraction data obtained from single crystals of each enzyme.

The EII and GII glucanase structures have essentially identical α/β barrel folds (FIG. 1). Minor perturbations are found in the loops mainly at positions where there are sequence insertions and deletions. A sequence comparison is set out in FIG. 2. The active site groove, which runs along the full length of the upper surface of the molecule perpendicular to the barrel axis, is almost identical in the central region of the groove, and different in detail towards the ends of the groove. The carboxylate groups of the two putative active site glutamates (Chen et al, 1993) are positioned in an identical way some 7 Å apart. Also around these residues are a ring of residues which are totally conserved in all plant (1→3)-β-glucanases known (Xu et al, 1992 and sequences from the Genbank database). Details of the structure, which is a novel type of α/β barrel are given below.

In FIG. 2 elements of the secondary structure have been identified alongside the sequence alignment of the two enzymes. We shall refer to the beta barrel strands as $\beta_1$ and the major (longest) helices connecting the beta strands as $\alpha_i$, where i goes from 1 to 8. Minor β sheet and α helices are referred to as $B_i$ and $A_i$, respectively if they appear after the strand $\beta_i$ and before $\beta_{i+1}$, and a further subscript a or b, if more than one occur.

Looking at the glucanase tertiary structure from above, down the barrel axis (the long axis of the elliptical barrel running east west), the active site groove runs north to south on the upper face of the molecule, as shown in FIGS. 3 and 4.

The N-terminal starts under the molecule entering the east side of the barrel as β1 and emerges on the upper surface and the heads back towards the bottom surface as $\alpha_1$ (traversing the outside of the molecule) to meet $\beta_2$, where this motif is repeated for strands $\beta_2$ to $\beta_4$, building the upper half of a conventional α/β barrel (note that for the third α/β loop there are two helices).

The lower half of the barrel has more elaborate secondary structure elements, not previously observed in other α/β barrel structures. There is what could be called a subdomain built around the helix $\alpha_6$. This helix runs perpendicular to the groove axis and at the southern end of the groove and is supported by three two stranded antiparallel β sheet 'fingers' ($B_5$ on the upper surface, $B_7$ on the underneath surface and $B_6$ at the southern end of the groove) and three small helices ($A_5$ at the western side and $A_{6a}$ and $A_{6a}$ at the eastern side of the groove). This subdomain, which forms a platform for the residues making up the lower half of the groove, is different in detail (possibly arising from the difference in specificity) between the EII and GII enzymes; for example the helix $A_5$ is missing in GII.

The C-terminal strand, consisting of some 30 residues, starts after the strand $\beta_8$, and has an unusual turn which involves a cis peptide bond between residues Phe 275 and Ala 276 (a cis proline could not accommodate this type of turn). This turn allows the loop of residues from 276 to 286 to position the glutamate at 288, which is in a small helical turn $\alpha_8$, at the appropriate orientation to act as a catalytic acid group. The C-terminal strand then finds its way down to the underside of the molecule between the helices $\alpha_1$ and $\alpha_7$ to within 4.2 Å from the N-terminus.

EXAMPLE 2

Identification of Sites of Contact with Substrate

In order to observe which amino acids in the substrate-binding groove contacted the substrate, the structure of glucanase GII was determined after soaking crystals with 1→3 linked oligosaccharides. Three sites were found where glucose units of monomer or disaccharides bind to the protein. The coordinates of these sites are listed in Appendix 2. This establishes the orientation of the substrate within the groove, and that some of the proposed changes to GII are important for substrate binding.

EXAMPLE 3

Proposed Modification of the (1→3,1→4)-β-Glucanase of Barley to Increase the Thermostability of the Enzyme The following amino acid changes are proposed for enhancing the thermostability of (1→3,1→4)-β-glucanase EII, based on the 3-dimensional structure of the EII and GII enzymes. Some of the changes proposed involve substituting the GII amino acids that could be responsible for stabilising that protein. These substitutions are based on the principle that the proposed changes will not alter the specificity of the enzyme (leave the active site groove unaltered), and where changes would not lead to deleterious changes in the 3-dimensional structure of the protein. Where possible glycines have been replaced by prolines or alanines in helices (Matthews et al, 1987) in order to stiffen the amino acid chain and reduce the entropy of the unfolded protein. Negatively charged residues have been attached to the N-termini of helices to stabilise them (Nicholson et al, 1988, Eijsink et al, 1992). Ion pairs have been introduced to increase the binding energy of the folded protein, and lysines changed to arginines to prevent glycation and improve stability (Mrabet et al, 1992) by increasing the hydrogen-bonding with other parts of the protein. EI and EII refer to the isozymes of (1→3,1→4)-β-glucanase and GI to GVI refer to the isozymes of the (1→3)-β-glucanase (Xu et al, 1992). The locations of these substitutions are shown on FIG. 3. The mutation is described using the following notation: eg. the mutation Ala 14 Ser represents the mutation of the Alanine residue to a Serine at position 14 in the amino acid sequence (FIG. 3). The conventional 3 letter code for amino acids is used.

| Mutation | comments |
|---|---|
| Ala 14 Ser | as in GII,GV,GVI to stabilise helix $\alpha_1$ |
| Ala 15 Arg | as in GII,GIV,GV ion pair with Asp 36 at end of groove |
| Thr 17 Asp | as in GII to form ion pair with Met 298 Lys in GII |
| Lys 23 Arg | as in GI to GIV, H-bond to O46 |
| Lys 28 Arg | |
| Asn 36 Asp | as in GI,GII,GIV,GVI,EI,to stabilise helix $\alpha_2$, ibid |
| Gly 44 Arg | as in GI,GII,GV,GVI |
| Gly 45 Asn | as in GII, solvent exposed |
| Gly 53 Asp | as in GI,GII,GIII,GV, forms a stable ion pair with Arg 31 |
| Gly 53 Glu | |
| Lys 74 Arg | as in GI,GV |
| Gln 78 Arg | as in GI,GII |
| Ala 79 Pro | as in GI,GII,GVI, surface residue |
| Lys 82 Arg | |
| Ala 95 Asp | as in GIII, ion pair with Arg 128 at end of groove, Asn in GII |
| Gly 97 Pro | |
| Phe 85 Tyr | OH of Tyr H-bonds to O 76 |
| Lys 107 Arg | as in GI,GII,GIII,GIV |
| Gly 111 Ala | as in GII, helix residue |
| Gly 119 Pro | |
| Lys 122 Arg | conserved in all except GVI, H-bond to O 161 and O 120 |
| Ser 128 Arg | as in GI to GV |
| Gly 133 Ala | as in GII, on the lip of the groove, could have packing problems here with Thr 144 |
| Gly 145 Asn | different conformation in GII |
| Gly 152 Thr | as in GII, His 221 with clash with Thr so need to change His to Ala |
| Pro 153 Asp | as in GII, see below for ion pair |
| Gln 156 Arg | as in GII, need Pro 153 Asp for ion pair |
| Asn 162 Gly | |
| Gly 185 Asn | as in GII, stabilised by Asp 183 |
| Ala 191 Pro | as in GII, buried (near surface) |
| Gly 193 Ala | wrong dihedrals for a Pro |
| Gly 199 Pro | as in GI, GII has a different loop conformation solvated, so could be modified. |
| Ala 200 Gly | |
| Gly 202 Thr | as in GII, H-bond to Thr 194 and Arg 197 space for Pro here. |
| Gly 219 Glu | as in GI to GVI, ion pair with Arg 265 might need Glu 266 Lys |
| Lys 220 Arg | as in GI H-bonds to O139 |
| His 221 Ala | as in GII, ibid |
| Gly 223 Ala | as in GII (buried) |
| Ser 224 Pro | as in GI to GV |
| Lys 227 Arg | as in GI,GIV,GV, ion pair with Glu 268 |
| Gly 238 Ala | as in GI,GII,GIV,GV, could clash with Asn 290 |
| Gly 239 Gln | as in GIII wrong dihedrals form a Pro |
| Ala 242 Gly | |
| Gly 260 Glu | ion pair with Arg 261 or Pro |
| Pro 267 Arg | as in GII |

-continued

| Mutation | comments |
|---|---|
| Gly 268 Glu | as in GII, could for ion pair with Arg 227 (peptide flipped wrt GII) |
| Gly 286 Ala or Asp | as in GII to stabilise helix $\alpha 7$ |
| Gln 289 Arg | as in GII,GIV,GV |
| Met 298 Lys | as in GI,GII,GIV,GV, ibid |
| His 300 Pro | as in GI to GV |

Of the above proposed modification the following ion pairs have to be substituted at the same time.

Ala 15 Arg and Asn 36 Asp

Thr 17 Asp and Met 298 Lys

Ala 95 Asp and Ser 128 Arg

Pro 153 Asp and Gln 156 Arg

Lys 227 Arg and Gly 268 Arg

Gly 152 Thr and His 221 Ala

It will be clearly understood that, subject to this requirement for concurrent substitution of ion pairs, combinations of two or more of the proposed modifications may be used.

An additional class of mutations is proposed in which the main chain torsion angle about the N and C$\alpha$ atoms is greater than 0°. In this case a replacement by a Gly residue is energetically more favourable, particularly at the C terminal of an $\alpha$-helix (Aurora et al., 1994). These mutations are:

Asn 162 Gly as in GI, GII, GV, GVI, EI, terminus of helix $\alpha 5$

Ala 200 Gly as in GIII, GIV, GV, GIV, main chain torsion angles

Ala 242 Gly Main chain torsion angles

Met 298 Gly Main chain torsion angles

EXAMPLE 4

Proposed Modification of the (1→3)-β-Glucanase of Barley to Alter its Catalytic Activity to that of (1→3,1→4)-β-Glucanase and Increase the Thermostability and pH Stability of the Enzyme As mentioned before the most noticeable feature of both the GII and EII enzymes is a deep groove across one face of the molecule. This appears to be the substrate binding site. Using structural information from both the GII and EIII enzymes it is possible to determine which amino acid residues are likely to control substrate specificity. Furthermore, as these two enzymes are very similar in structure it is possible to graft the loops from one enzyme on to the more heat and pH stable framework of the other to change the specificity.

We propose replacing the GII loops which form the sides and bottom of the cleft by the corresponding amino acids from the EII enzyme. These changes are as follows:

| residue | 8 Ile → Ser, |
| residue | 34 Phe → Ala, |
| residue | 208 Ala → Thr, |
| residue | 209 Met → Thr, |
| residue | 213 Val → Phe |
| residue | 128–137 Ile-Arg-Phe-Asp-Glu-Val-Ala-Asn-Ser-Phe → Val-Ser-Gln-Ala-Ile-Leu-Gly-Val-Phe-Ser |

-continued

| | (SEQ. ID NO: 1), |
|---|---|
| residue | 171–179 Phe-Ala-Tyr-Arg-Asp-Asn-Pro-Gly-Ser → Leu-Ala-Trp-Ala-Tyr-Asn-Pro-Ser-Ala (SEQ. ID NO: 2) and |
| residue | 283–291 Thr-Gly-Asp-Ala-Thr-Glu-Arg-Ser-Phe → Asp-Ser-Gly-Val-Glu-Gln-Asn-Trp (SEQ. ID NO: 3) |

Some or all of these changes are necessary. The skilled person will readily be able to test the effectiveness of the substitutions.

Again combinations of two or more of these proposed modifications may be used.

Doan and Fincher (1992) showed that relative to the EI enzyme, EII is more thermostable because of the carbohydrate at residue 190. We propose to introduce a carbohydrate attachment site into the modified GII enzyme to enhance the thermostability. The mutations required are 189–191 Gln-Pro-Gly→Asn-Ala-Ser FIG. 4 is a schematic drawing of the GII enzyme structure showing locations of the proposed mutations.

EXAMPLE 5

Construction of Mutant Glucanases

Construction of the proposed mutant glucanases may be effected using the polymerase chain reaction (PCR)-based megaprimer method (Sarkar & Sommers, 1990), and single site mutants of the isozymes EI and EII have already been produced in this way by one of us (Doan and Fincher, 1992). Briefly, for each sits mutant or short series of adjacent mutations one oligonucleotide is synthesized which contains the complementary sequence required for the mutation(s) and sufficient flanking regions to anneal to the wild type cDNA. This oligonucleotide is extended against the cDNA template with a DNA polymerase. PCR is used to amplify the mutant section of cDNA, and then this is inserted back into the plasmid containing the original cDNA. For multiple mutations this process is repeated to produce the final construct. Alternatively, commercially-available site directed mutagenesis kits based on the unique site elimination method (Deng and Nickoloff, 1992) can be used.

We currently have the cDNAs for the EII and GII enzymes which from the starting points for the mutagenesis (Doan and Fincher, 1992; Høj et al., 1989). For the purposes of demonstrating improved stability or altered specificity of these enzymes and for production of the enzymes in quantity, the proteins can then be expressed in *E. coli* (Wynn et al., 1992) using the plasmid ET or other vectors or in insect cells (e.g. Sf9 cells) using a Baculovius system (Doan & Fincher, 1992). A person skilled in the art will be aware of a variety of other suitable expression systems. For example, yeast would be a suitable host, and such an engineered yeast could be used directly in the brewing process. The availability of the gene encoding (1→3, 1→4)-β-glucanase isoenzyme EI and near full-length cDNAs for isoenzymes EI and EII (Slakeski et al. 1990) presents an opportunity to accelerate or enhance (1→3, 1→4)-β-glucanase development in germinated grain through gene technology. Increased enzyme activity might be achieved by several means, for example, by splicing more efficient promoters onto the gene, by altering the existing promoter to enhance expression levels, by the use of translational enhances, or by increasing the copy number of the genes.

Two more steps are required for the mutant enzymes to be incorporated into barley and expressed in a spatially and temporally appropriate manner. These are construction of a barley glucanase gene with the appropriate control of expression, and the insertion of the gene into a viable barley plant. The sequence of the EII gene, including the promoter regions and the coding region and the signal peptide has been determined (Wolf, 1991). Thus for correct expression of the mutant glucanases we will replace a portion of this gene by the corresponding portion of a mutant cDNA using the above methods. It is expected that transformation of barley, that is to regenerate a fertile transgenic barley plant, will be possible in the near further. Foreign or manipulated DNA can be integrated into the barley genome in a stable form (Lazzeri et al, 1991) and fertile plants can be regenerated from single protoplasts, (Jahne et al, 1991a, b). Among the cereals related to barley, rice can now be routinely transformed, and transformation of both wheat and maize has been reported. Methods for effecting transformation of monocotyledonous plants such as barley using biolistic techniques are widely used, and whole plants or transgenic barley have been grown. Barley has recently been transformed using the biolistic microprojectile gun procedure (Wan and Lemaux, 1994).

EXAMPLE 6

Stability of GII and EII at pH 3.5

(1→3)-β-glucanase isoenzyme GII (9.2 μg/ml) and (1→3, 1→4)-β-glucanase isoenzyme EII (0.23 mg/ml) were incubated in 100 mM sodium acetate buffer at pH 3.5 in the presence of bovine serum albumin at 37° C. (0.5 mg/ml). Residual enzyme activities ($A_t$) were determined and compared to the initial activity at t=0 ($A_o$). The results are illustrated in FIG. 5. GII shows markedly greater stability with time at pH 3.5 than does EII. (Note: at pH 4.3 the enzymes differ only slightly in their stability and exhibit only minimal loss of activity; data not shown).

ii) Stabilities of GII and EII at 50° C.

(1→3)-β-glucanase isoenzyme GII (16 μg/ml) and (1→3, 1→4)-β-glucanase isoenzyme EII (19 μg/ml) were incubated in 50 mM sodium acetate buffer at pH 5.0 in the presence of bovine serum albumin (1 mg/ml) at 50° C. Residual enzyme activities ($A_t$) were determined and compared to the initial activity at t=0 ($A_o$). The results are illustrated in FIG. 6. GII is very much more stable at 50° C. then is EII.

iii) Stabilities of GII and EII at Increasing Temperatures (1→3)-β-glucanase isoenzyme GII (16 μg/ml) and (1→3;1→4)-β-glucanase isoenzyme EII (19 μg/ml) were incubated in 50 mM sodium acetate buffer at pH 5.0 at the indicated temperatures for 15 min. Residual enzyme activities ($A_t$) were determined and compared to the initial activity at t=0) ($A_o$). The results are illustrated in FIG. 7. EII is stable only up to 40° C., while GII is stable up to 50° C.

EXAMPLE 7

Site-directed Mutagenesis

Of the possible mutations listed in Example 3, the following alterations were considered to be the most likely to improve stability. The alterations are based on:

| | |
|---|---|
| 1. creation of ion pairs: | Gly 53 Asp |
| | Gly 53 Glu |
| | Thr 17 Asp; Met 298 Lys |
| | Ala 95 Asp; Ser 128 Arg |
| 2. removal of potential glycation sites: | Lys 122 Arg |
| | Lys 23 Arg |
| | Lys 74 Arg |
| 3. reduction in entropy of unfolded state: | Gly 44 Arg |
| | Gly 223 Ala |
| | Ala 79 Pro |
| 4. hydrophobic effects: | Phe 85 Tyr |

Site-directed mutagenesis was carried out by the unique restriction enzyme site elimination procedure using a U.S.E. Mutagenesis Kit (Pharmaceia) with double-stranded plasmid DNA as a template. Appropriate mutagenic primers were designed to generate the mutations and were synthesized on a standard DNA synthesizer. All oligonucleotide primers were phosphorylated at their 5'-end before use, and the mutagenesis procedure was performed essentially as prescribed by the manufacturer. Mutants were confirmed by dideoxynucleotide sequencing using a Sequence version 2.0 sequencing Kit (U.S. Biochemical Co.).

The following EII mutants were produced and confirmed by sequence analysis:

Lys 74 Arg
Gly 44 Arg
Phe 85 Arg
Gly 53 Glu
Lys 122 Arg
Lys 23 Arg
Ala 79 Pro

In addition, we have also made the following mutants:

Gly 223 Ala
Gly 53 Asp

EXAMPLE 8

Expression of Mutant Enzymes in *E. coli*

The mutant cDNA inserts in the expression plasmid pMAL-c2 were transformed in *E. coli* DH5" cells, and grown overnight at 37° C. in LB containing 0.2% glucose and 100 µg/ml ampicillin. Aliquots of the cell suspension were sub-cultured into the same medium and grown at 37° C. with vigorous shaking to an optical density at 600 nm of 0.5, induced for 3H with 1 mM isophenyl-β-thiogalactoside and lysed with lysozyme treatment and freeze/thawing. After removal of cell debris by centrifugation, enzyme activity was measured either in the unpurified extract or following purification.

The following EII mutants have been expressed in *E. coli* and the expressed proteins have been confirmed to be of the correct size:

Lys 122 Arg
Phe 85 Tyr
Gly 44 Arg

EXAMPLE 9

Purification of Recombinant Fusion Proteins

For the purification of the will-type enzyme, crude extract from 1 liter culture with diluted 10-fold with 15 mM Tris-Hcl buffer, pH 8.0 and applied at a flow rate of 2.5 ml/min to a DEAE-Sepharose Fast Flow (Pharmaceia) column (3×11.5 cm) equilibrated with 25 mM Tris-HCl buffer, pH 8.0. After washing the column exhaustively, bound proteins were eluted with a linear 0–250 mM NaCl gradient in 1.2 liter equilibration buffer. Fractions containing significant enzyme activity were pooled, desalted and adjusted to 25 mM NaAc, pH 5.0. After exhaustive washing, bound proteins were eluted with a linear 0–200 mM NaCl gradient in 1 liter equilibration buffer. The fractions containing pure protein were pooled to give 5.0 mg active fusion protein.

Mutant enzymes were all purified by a single ion-exchange chromatography step employing a shallow salt gradient elution. The crude extract from 4 to 5 liter culture was diluted 10 fold with 15 mM Tris-HCl (pH 8.0) and applied at a flow rate of 2.5–3.0 ml/min to a DEAE-Sepharose column (5×21 cm) equilibrated with 12.5 mM Tris-HCl (pH 8.5). After exhaustive washing, bound proteins were eluted with a 1.9 liter linear 0–80 mM NaCl gradient at a flow rate of 2.0 ml/min. Fractions containing pure fusion protein were located by SDS-PAGE, pooled, concentrated and adjusted to 2.5 mM sodium acetate (pH 5.0) by ultrafiltration before clarification by centrifugation.

EXAMPLE 10

Activity of Expressed Enzymes $(1 \rightarrow 3, 1 \rightarrow 4)$-β-Glucanase activity was measured viscometrically at 40° C., using 5 mg/ml barley $(1 \rightarrow 3, 1 \rightarrow 4)$-β-glucan in 50 mM sodium acetate pH 5.0 as substrate. A unit of activity is defined as the amount of enzyme causing an increase of 1.0 in the reciprocal specific viscosity $(\Delta 1/\eta_{sp})$ per minute. Specific activity is expressed as the activity per mg protein.

The activities of the following mutant enzymes have been measured and compared with the activity of the expressed wild type enzyme:

Lys 122 Arg activity same as well type
Phe 85 Tyr activity approx. 70% of wild type
Gly 44 Arg activity very low

EXAMPLE 11

Thermostability Assays

Aliquots of wild type of mutant fusion proteins were diluted with 50 mM sodium acetate buffer, pH 5.5 and incubated at temperatures ranging from 40° C. to 0° C. for 15 min. Samples incubated at 0° C. were used as controls. Residual enzyme activity was determined viscometrically with 550 µl $(1 \rightarrow 3, 1 \rightarrow 4)$-β-glucan substrate, as described for Example 10.

References listed herein are identified on the following pages.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

EXAMPLE 12

Increased Thermostability of Isoenzyme EII by Site-Directed Mutagenesis

Stability of $(1 \rightarrow 3, 1 \rightarrow 4)$-β-glucanase isoenzyme EII (mutant H300P)

The cDNA encoding (1→3,1→4)-β-glucanase isoenzyme EII was subjected to site-directed mutagenesis using the unique site elimination method (Deng and Nickoloff, 1992), to generate mutant H300P. The mutagenesis procedure was performed using a modified pET-3a vector containing the wild type (1→3, 1→4)-β-glucanase isoenzyme EII cDNA as a template, which enables the rapid purification of expressed foreign proteins using a nickel-based affinity resin (Hochuli et al., 1987). The expressed mutant H300P showed an increase in the $T_{50}$ value (the temperature at which only 50% of the initial activity remains) of approximately 3.8° C., after heating for 15 minutes at various temperatures. This is illustrated in FIG. 8.

An additional test for increased thermostability was provided by following the residual activity ($A_r$) of wild type isoenzyme EII and the corresponding mutant H300P over time at 48° C. The results are shown in FIG. 9. Finally, as a further indication of increased thermostability in a commercial context, activity of the wild type and mutant (1→3, 1→4)-β-glucanase isoenzyme EII was measured over time in a simulated mashing experiment at 55° C. Briefly, mashing conditions were simulated by stirring malted, dried barley grain in water at 55° C. for 40 minutes to inactivate any endogenous (1→3, 1→4)-β-glucanase activity, and then wild type or mutant H300P enzyme was added to the mash and residual activity ($A_r$) was monitored over time. The results are sown in FIG. 10.

EXAMPLE 13

Further Mutants Expected to Enhance Thermostability

| | |
|---|---|
| Met 7 Val | as GI GII GIII, allow loop 7–12 to pack tighter against C-terminus |
| Ala 9 Gly | as GII GIII GV GVI, allow loop 7–12 to pack tighter against c-terminus |
| Ala 15 Pro | as GIII GVI |
| Met 21 Leu | as GI–GVI, prevent close contact with Met 298 (or Lys) |
| Phe 22 Tyr | as GI–GVI, buried H-bond with Val 30 |
| Asn 25 Lys | as GI–GIV, cover hydrophobic patch |
| Gly 26 Asn | as GV, GVI, rigidify helix capping residue |
| Gly 240 Ala | rigidify loop |
| Asn 279 Asp | stronger H-bonds |
| Ser 285 Pro | rigidify loop |
| Val 287 Pro | rigidify loop |
| Asn 290 His | as GI GIV, His would pack tighter |
| Phe 294 Tyr | could H-bond to Asn 25 ID1 |
| Asn 297 Asp | as GI GII GVI, tighter H-bond in loop |
| Met 298 Gly | Main chain torsion angles suit Gly |
| Val 301 Ala 307 Asn | as GI–GIII, change water structure extend C terminus to make a salt bridge with Lys 28 |
| Ala 176 Arg and Gly 286 Asp | ion pair |
| Ser 237 Phe and Asn 279 Ser or Trp | close packed bridge across C-terminal tail |

As the N and C termini are close to each other it would be possible to tie down the C terminus by linking the ends together. The shortest linker with a structurally reasonable conformation is Ala-Ala-Gly (or Gly-Pro-Gly or combinations). As helix a6 and strand b7 are buried in the protein, new N and C termini at Val 226 and Gly 223 will not reduce the thermostability of the protein. Furthermore, the new termini could form an ion pair.

REFERENCES

Aastrup S. Carlsberg Res. Commun., 1983 48 307–316

Aurora, R., Strinivasan, R., and Rose, G. B. Science, 1994 264 1126–1130

Bamforth, C. W. Brewers Digest, 1983 57 22–27

Blundell, T. L. and Johnson, L. N. Protein Crystallography, 1976, Academic Press, London Bourne, D. T., Powlessland, T. and Wheeler, R. E. j. Inst. Brew., 1982 88 371–375

Brunswick, P., Manners, D. J. and Stark, J. R. J. Inst. Brew., 1987 93 181–186

Chen, L., Fincher, G. B. and Høj, P. B. J. Biol. Chem., 1993 268, in press

Deng, W. P. and Nickoloff, J. A. Analytical Biochemistry, 1992 200 81

Doan, D. N. P. and Fincher, G. B. FEBS Lett, 1992 309 265–271

Eijsink, V. G. H., Vriend, G., van den Burg, B., van der Zee, J. R. and Venema, G. Prot. Eng., 1992 5 165–170

Fincher, G. B. J. Inst. Brewing, 1975 81 116–122

Fincher, G. B., Lock, P. A., Morgan, M. M., Lingelbach, K., Wettenhall, R. E. H., Mercer, J. f. B., Brandt, A. and Thomsen, K. K. Proc. Natl. Acad. Sci. USA, 1986 83 2081–2085

Fincher, G. B. and Stone, B. A. Adv. Car. Sc. Techn., 1986 8 207–295

Henry, R. J. J. Cereal Sci., 1986 4 269–27

Høj, P. B., Hartman, D. J., Morrice, N. A., Doan, D. N. P. and Fincher, G. B. Plant Mol. Biol., 1989 13 31–42

Høj. P. B., Hoogenraad, N. J., Hartman, D. J., Yannakena, H. and Fincher, G. B. J. Cereal Science, 1990 11 261–268

Jahne, A., Lazzeri, P. A., Jager-Gussen, M. and Lorz, H. Theor. Appl. Genet., 1991 82 74–80

Lazzeri, P. A., Brettschneider, R., Luhrs, R., and Lorz, H. Theor. Appl. Genet., 1991 81 437–444

Loi, L., Barton, P. A. and Fincher, G. B. J. Cer. Sci., 1987 5 45–50

Matthews, B. W. Biochemistry, 1987 26 6885–6888

Matthews, B. W., Nicholson, H., Becktel, W. J. Proc. Natl. Acad. Sci. U.S.A., 1987 84 6663–6667

Mrabet, N. T. et al Biochem., 1992 31 2239–2253

Nicholson, H., Becktel, W. J., Matthews, B. W. Nature (London), 1988 336 651–656

Powell, W., Caligari, P. D. S., Swanston, J. S. and Jinks, J. L. Theoretical and Applied Genetics, 1989 71 461–466

Sarkar, G and Sommers, S. S. BioTequniques, 1990 4 404–407

Slakeski, N., Baulcombe, D. C., Devos, K. M. Ahluwalia, B., Mol. Gen. Genet., 1990 224 437–449

Stuart, I. M., Loi, L. and Fincher, G. B. J. Cer. Sci. 1988 7 61–71

Wan, Y and Lemaux, P. G. Plant Physiology, 1994 104 37–48

Wolf, H. Plant Physiol., 1991 96 1382–1384

Woodward, J. R. and Fincher, G. B. Brewers Digest, 1983 58 28–32

Wynn, R. M., Davie, J. R., Cox. R. P. and Chuang, D. T. J. Bio Chem. 1992 267 12400–12403

Xu, P., Wang, J. and Fincher, G. B. Gene (Amat.), 1992 120 157–165

(xi) SEQUENCE DESCRIPTION: SEQ. ID NO: 5

```
Ile Gly Val Cys Tyr Gly Met Ser Ala Asn Asn Leu Pro Ala Ala Ser Thr Val Val
 1               5                  10                 15

Ser Met Phe Lys Ser Asn Gly Ile Lys Ser Met Arg Leu Tyr Ala Pro Asn Gln Ala
 20              25                  30                 35

Ala Leu Gln Ala Val Gly Gly Thr Gly Ile Asn Val Val Gly Ala Pro Asn Asp
     40              45                  50                 55

Val Leu Ser Asn Leu Ala Ala Ser Pro Ala Ala Ala Ser Trp Val Lys Ser Asn
         60                  65                  70                 75

Ile Gln Ala Tyr Pro Lys Val Ser Phe Arg Tyr Val Cys Val Gly Asn Glu Val Ala
             80                  85                  90                 95

Gly Gly Ala Thr Arg Asn Leu Val Pro Ala Met Lys Asn Val His Gly Ala Leu Val
                100                 105                 110

Ala Ala Gly Leu Gly His Ile Lys Val Thr Thr Ser Val Ser Gln Ala Ile Leu Gly
115                 120                 125                 130

Val Phe Ser Pro Pro Ser Ala Gly Ser Phe Thr Gly Glu Ala Ala Ala Phe Met Gly
    135                 140                 145                 150

Pro Val Val Gln Phe Leu Ala Arg Thr Asn Ala Pro Leu Met Ala Asn Ile Tyr Pro
        155                 160                 165                 170

Tyr Leu Ala Trp Ala Tyr Asn Pro Ser Ala Met Asp Met Gly Tyr Ala Leu Phe Asn
            175                 180                 185                 190

Ala Ser Gly Thr Val Val Arg Asp Gly Ala Tyr Gly Tyr Gln Asn Leu Phe Asp Thr
                195                 200                 205

Thr Val Asp Ala Phe Tyr Thr Ala Met Gly Lys His Gly Gly Ser Ser Val Lys Leu
210                 215                 220                 225

Val Val Ser Glu Ser Gly Trp Pro Ser Gly Gly Gly Thr Ala Ala Thr Pro Ala Asn
    230                 235                 240                 245

Ala Arg Phe Tyr Asn Gln His Leu Ile Asn His Val Gly Arg Gly Thr Pro Arg His
        250                 255                 260                 265

Pro Gly Ala Ile Glu Thr Tyr Ile Phe Ala Met Phe Asn Glu Asn Gln Lys Asp Ser
            270                 275                 280                 285

Gly Val Glu Gln Asn Trp Gly Leu Phe Tyr Pro Asn Met Gln His Val Tyr Pro Ile
                290                 295                 300

Asn Phe
305
```

Appendix 1

Table of the atomic coordinates of the EII and GII glucanase enzymes from barley

The atomic coordinates and isotropic temperature factors of the non-hydrogen atoms of the 306 amino acids in (1-3,1-4)-β-glucanase EII enzyme of barley are listed below. 2896 atomic coordinates are in the tables, including bound water molecules found in the crystal lattice. Following this are the atomic coordinates of the two independent (1-3)-β-glucanase GII enzyme molecules found in the crystal lattice. The first molecule residues are numbered 1 to 306 and the second one 401 to 606. 4564 atomic coordinates are in the tables. Included also are the bound water molecules found in the crystal lattice.

- 31 -

Atomic coordinates of β-glucanase of barly obtained by x-ray diffraction

| | | | | | | | | | |
|---|---|---|---|---|---|---|---|---|---|
| ATOM | 1 | CB | ILE | 1 | 42.909 | -30.807 | 19.518 | 1.00 19.74 | EII |
| ATOM | 2 | CG2 | ILE | 1 | 44.297 | -31.091 | 18.767 | 1.00 23.91 | EII |
| ATOM | 3 | CG1 | ILE | 1 | 43.120 | -29.604 | 20.452 | 1.00 20.86 | EII |
| ATOM | 4 | CD1 | ILE | 1 | 43.867 | -29.879 | 21.718 | 1.00 20.90 | EII |
| ATOM | 5 | C | ILE | 1 | 43.218 | -29.739 | 17.268 | 1.00 24.60 | EII |
| ATOM | 6 | O | ILE | 1 | 42.176 | -30.269 | 16.142 | 1.00 17.61 | EII |
| ATOM | 7 | N | ILE | 1 | 41.347 | -31.875 | 17.973 | 1.00 24.03 | EII |
| ATOM | 9 | CA | ILE | 1 | 41.820 | -30.580 | 18.516 | 1.00 19.60 | EII |
| ATOM | 11 | CA | GLY | 2 | 42.568 | -28.460 | 17.449 | 1.00 19.88 | EII |
| ATOM | 12 | H | GLY | 2 | 42.926 | -27.644 | 16.308 | 1.00 16.84 | EII |
| ATOM | 14 | C | GLY | 2 | 44.411 | -27.395 | 16.335 | 1.00 18.98 | EII |
| ATOM | 15 | O | GLY | 2 | 45.051 | -27.662 | 17.350 | 1.00 22.22 | EII |
| ATOM | 16 | N | VAL | 3 | 44.966 | -26.899 | 15.233 | 1.00 16.28 | EII |
| ATOM | 17 | H | VAL | 3 | 46.385 | -26.590 | 15.159 | 1.00 14.63 | EII |
| ATOM | 19 | CA | VAL | 3 | 47.246 | -27.766 | 14.503 | 1.00 15.84 | EII |
| ATOM | 20 | CB | VAL | 3 | 48.602 | -27.262 | 14.098 | 1.00 13.49 | EII |
| ATOM | 21 | CG1 | VAL | 3 | 47.461 | -28.938 | 15.492 | 1.00 9.39 | EII |
| ATOM | 22 | CG2 | VAL | 3 | 46.501 | -25.310 | 14.335 | 1.00 16.58 | EII |
| ATOM | 23 | C | VAL | 3 | 45.773 | -25.124 | 13.340 | 1.00 16.41 | EII |
| ATOM | 24 | O | VAL | 3 | 47.383 | -24.409 | 14.776 | 1.00 17.47 | EII |
| ATOM | 25 | N | CYS | 4 | 47.611 | -23.141 | 14.080 | 1.00 13.90 | EII |
| ATOM | 27 | CA | CYS | 4 | 48.159 | -22.114 | 15.026 | 1.00 12.20 | EII |
| ATOM | 28 | CB | CYS | 4 | 47.009 | -21.706 | 16.278 | 1.00 18.93 | EII |
| ATOM | 29 | SG | CYS | 4 | 48.583 | -23.320 | 12.942 | 1.00 8.38 | EII |
| ATOM | 30 | C | CYS | 4 | 49.700 | -23.775 | 13.129 | 1.00 13.42 | EII |
| ATOM | 31 | O | CYS | 4 | 48.112 | -23.034 | 11.750 | 1.00 11.04 | EII |
| ATOM | 32 | N | TYR | 5 | 48.915 | -23.144 | 10.558 | 1.00 15.79 | EII |
| ATOM | 34 | CA | TYR | 5 | 47.963 | -23.512 | 9.428 | 1.00 17.92 | EII |
| ATOM | 35 | CB | TYR | 5 | 48.571 | -23.904 | 8.099 | 1.00 18.60 | EII |
| ATOM | 36 | CG | TYR | 5 | 47.741 | -24.243 | 7.029 | 1.00 23.27 | EII |
| ATOM | 37 | CD1 | TYR | 5 | 48.248 | -24.538 | 5.772 | 1.00 22.99 | EII |
| ATOM | 38 | CE1 | TYR | 5 | 49.938 | -23.874 | 7.881 | 1.00 18.83 | EII |
| ATOM | 39 | CD2 | TYR | 5 | 49.460 | -24.164 | 6.619 | 1.00 21.17 | EII |
| ATOM | 40 | CE2 | TYR | 5 | 50.468 | -24.502 | 5.567 | 1.00 23.75 | EII |
| ATOM | 41 | CZ | TYR | 5 | 50.066 | -24.850 | 4.320 | 1.00 23.36 | EII |
| ATOM | 42 | OH | TYR | 5 | 49.654 | -21.805 | 10.298 | 1.00 15.48 | EII |
| ATOM | 44 | C | TYR | 5 | 49.154 | -20.933 | 9.594 | 1.00 13.42 | EII |
| ATOM | 45 | O | TYR | 5 | 50.793 | -21.617 | 10.965 | 1.00 15.88 | EII |
| ATOM | 46 | N | GLY | 6 | | | | | |
| ATOM | 48 | CA | GLY | 6 | 51.588 | -20.408 | 10.795 | 1.00 14.72 | EII |
| ATOM | 49 | C | GLY | 6 | 52.478 | -20.579 | 9.582 | 1.00 17.84 | EII |
| ATOM | 50 | O | GLY | 6 | 53.053 | -21.657 | 9.375 | 1.00 14.34 | EII |
| ATOM | 51 | N | MET | 7 | 52.650 | -19.519 | 8.800 | 1.00 14.84 | EII |
| ATOM | 53 | CA | MET | 7 | 53.440 | -19.628 | 7.588 | 1.00 18.75 | EII |
| ATOM | 54 | CB | MET | 7 | 52.514 | -19.505 | 6.361 | 1.00 20.22 | EII |
| ATOM | 55 | CG | MET | 7 | 51.261 | -20.402 | 6.409 | 1.00 26.53 | EII |
| ATOM | 56 | SD | MET | 7 | 50.142 | -20.341 | 4.918 | 1.00 33.90 | EII |
| ATOM | 57 | CE | MET | 7 | 50.057 | -18.550 | 4.721 | 1.00 27.93 | EII |
| ATOM | 58 | C | MET | 7 | 54.580 | -18.631 | 7.485 | 1.00 18.41 | EII |
| ATOM | 59 | O | MET | 7 | 54.966 | -18.258 | 6.383 | 1.00 21.22 | EII |
| ATOM | 60 | N | SER | 8 | 55.193 | -18.303 | 8.613 | 1.00 13.98 | EII |
| ATOM | 62 | CA | SER | 8 | 56.284 | -17.361 | 8.642 | 1.00 12.54 | EII |
| ATOM | 63 | CB | SER | 8 | 56.233 | -16.540 | 9.910 | 1.00 19.56 | EII |
| ATOM | 64 | OG | SER | 8 | 54.876 | -16.256 | 10.246 | 1.00 31.51 | EII |
| ATOM | 66 | C | SER | 8 | 57.576 | -18.129 | 8.523 | 1.00 14.89 | EII |
| ATOM | 67 | O | SER | 8 | 58.415 | -18.135 | 9.406 | 1.00 12.02 | EII |
| ATOM | 68 | N | ALA | 9 | 57.726 | -18.779 | 7.380 | 1.00 22.87 | EII |
| ATOM | 70 | CA | ALA | 9 | 58.896 | -19.585 | 7.083 | 1.00 22.53 | EII |
| ATOM | 71 | CB | ALA | 9 | 58.691 | -21.015 | 7.634 | 1.00 24.86 | EII |
| ATOM | 72 | C | ALA | 9 | 59.062 | -19.608 | 5.571 | 1.00 25.05 | EII |
| ATOM | 73 | O | ALA | 9 | 58.105 | -19.378 | 4.825 | 1.00 26.92 | EII |
| ATOM | 74 | N | ASN | 10 | 60.284 | -19.833 | 5.117 | 1.00 25.38 | EII |
| ATOM | 76 | CA | ASN | 10 | 60.535 | -19.894 | 3.680 | 1.00 26.52 | EII |
| ATOM | 77 | CB | ASN | 10 | 61.801 | -19.126 | 3.343 | 1.00 24.44 | EII |
| ATOM | 78 | CG | ASN | 10 | 62.993 | -19.640 | 4.094 | 1.00 27.74 | EII |
| ATOM | 79 | OD1 | ASN | 10 | 63.088 | -20.823 | 4.443 | 1.00 30.55 | EII |
| ATOM | 80 | ND2 | ASN | 10 | 63.951 | -18.765 | 4.302 | 1.00 31.81 | EII |
| ATOM | 83 | C | ASN | 10 | 60.696 | -21.315 | 3.142 | 1.00 27.72 | EII |
| ATOM | 84 | O | ASN | 10 | 61.027 | -21.474 | 1.964 | 1.00 26.42 | EII |
| ATOM | 85 | N | ASN | 11 | 60.427 | -22.337 | 3.959 | 1.00 29.17 | EII |
| ATOM | 87 | CA | ASN | 11 | 60.636 | -23.727 | 3.515 | 1.00 28.66 | EII |
| ATOM | 88 | CB | ASN | 11 | 61.978 | -24.197 | 4.051 | 1.00 28.18 | EII |
| ATOM | 89 | CG | ASN | 11 | 61.986 | -24.285 | 5.568 | 1.00 28.63 | EII |
| ATOM | 90 | OD1 | ASN | 11 | 61.172 | -23.653 | 6.244 | 1.00 24.59 | EII |
| ATOM | 91 | ND2 | ASN | 11 | 62.890 | -25.086 | 6.107 | 1.00 32.83 | EII |
| ATOM | 94 | C | ASN | 11 | 59.583 | -24.763 | 3.936 | 1.00 29.88 | EII |
| ATOM | 95 | O | ASN | 11 | 59.917 | -25.915 | 4.244 | 1.00 32.04 | EII |
| ATOM | 96 | N | LEU | 12 | 58.315 | -24.387 | 3.927 | 1.00 26.30 | EII |
| ATOM | 98 | CA | LEU | 12 | 57.299 | -25.334 | 4.330 | 1.00 20.11 | EII |

- 32 -

| | | | | | | | | | | | | | | | | | | | |
|---|---|---|---|---|---|---|---|---|---|---|---|---|---|---|---|---|---|---|---|
| ATOM | 99 | CA | LEU | 12 | 56.125 | -24.610 | 4.974 | 1.00 | 20.81 | EII | ATOM | 146 | CG2 | VAL | 18 | 51.532 | -27.855 | 4.838 | 1.00 | 20.65 | EII |
| ATOM | 100 | CB | LEU | 12 | 56.555 | -23.733 | 6.158 | 1.00 | 20.59 | EII | ATOM | 147 | C | VAL | 18 | 48.600 | -30.305 | 5.201 | 1.00 | 19.24 | EII |
| ATOM | 101 | CG | LEU | 12 | 55.355 | -23.025 | 6.727 | 1.00 | 15.45 | EII | ATOM | 148 | O | VAL | 18 | 48.393 | -30.852 | 6.295 | 1.00 | 21.23 | EII |
| ATOM | 102 | CD1 | LEU | 12 | 57.267 | -24.566 | 7.238 | 1.00 | 14.37 | EII | ATOM | 149 | N | VAL | 19 | 47.666 | -30.174 | 4.264 | 1.00 | 21.49 | EII |
| ATOM | 103 | C | LEU | 12 | 56.859 | -26.108 | 3.110 | 1.00 | 20.79 | EII | ATOM | 151 | CA | VAL | 19 | 46.297 | -30.625 | 4.453 | 1.00 | 19.43 | EII |
| ATOM | 104 | O | LEU | 12 | 57.125 | -25.683 | 1.975 | 1.00 | 26.10 | EII | ATOM | 152 | CB | VAL | 19 | 45.377 | -30.080 | 3.364 | 1.00 | 20.03 | EII |
| ATOM | 105 | N | PRO | 13 | 56.217 | -27.271 | 3.324 | 1.00 | 16.58 | EII | ATOM | 153 | CG1 | VAL | 19 | 44.023 | -30.789 | 3.389 | 1.00 | 14.98 | EII |
| ATOM | 106 | CA | PRO | 13 | 56.067 | -27.892 | 4.657 | 1.00 | 18.19 | EII | ATOM | 154 | CG2 | VAL | 19 | 45.194 | -28.592 | 3.599 | 1.00 | 21.75 | EII |
| ATOM | 107 | CB | PRO | 13 | 55.519 | -28.056 | 2.314 | 1.00 | 15.01 | EII | ATOM | 155 | C | VAL | 19 | 46.197 | -32.143 | 4.616 | 1.00 | 18.15 | EII |
| ATOM | 108 | CG | PRO | 13 | 54.850 | -29.161 | 3.151 | 1.00 | 17.74 | EII | ATOM | 156 | O | VAL | 19 | 45.354 | -32.650 | 5.344 | 1.00 | 18.99 | EII |
| ATOM | 109 | CD | PRO | 13 | 55.755 | -29.311 | 4.311 | 1.00 | 18.48 | EII | ATOM | 157 | N | SER | 20 | 47.108 | -32.864 | 3.995 | 1.00 | 23.52 | EII |
| ATOM | 110 | C | PRO | 13 | 54.446 | -27.242 | 1.596 | 1.00 | 18.94 | EII | ATOM | 159 | CA | SER | 20 | 47.163 | -34.309 | 4.148 | 1.00 | 23.47 | EII |
| ATOM | 111 | O | PRO | 13 | 54.060 | -26.166 | 2.060 | 1.00 | 21.69 | EII | ATOM | 160 | CB | SER | 20 | 48.039 | -34.917 | 3.072 | 1.00 | 27.97 | EII |
| ATOM | 112 | N | ALA | 14 | 53.946 | -27.776 | 0.484 | 1.00 | 19.38 | EII | ATOM | 161 | OG | SER | 20 | 47.313 | -34.872 | 1.851 | 1.00 | 37.39 | EII |
| ATOM | 114 | CA | ALA | 14 | 52.870 | -27.132 | -1.631 | 1.00 | 20.05 | EII | ATOM | 163 | C | SER | 20 | 47.703 | -34.667 | 5.514 | 1.00 | 24.51 | EII |
| ATOM | 115 | CB | ALA | 14 | 52.651 | -27.801 | -0.267 | 1.00 | 18.90 | EII | ATOM | 164 | O | SER | 20 | 47.315 | -35.684 | 6.094 | 1.00 | 26.54 | EII |
| ATOM | 116 | C | ALA | 14 | 51.615 | -27.276 | 0.586 | 1.00 | 20.65 | EII | ATOM | 165 | N | MET | 21 | 48.633 | -33.857 | 7.335 | 1.00 | 21.82 | EII |
| ATOM | 117 | O | ALA | 14 | 51.502 | -28.214 | 1.376 | 1.00 | 20.86 | EII | ATOM | 167 | CA | MET | 21 | 49.182 | -34.063 | 7.572 | 1.00 | 19.43 | EII |
| ATOM | 118 | N | ALA | 15 | 50.682 | -26.347 | 0.413 | 1.00 | 17.26 | EII | ATOM | 168 | CB | MET | 21 | 50.337 | -33.092 | 6.832 | 1.00 | 19.21 | EII |
| ATOM | 120 | CA | ALA | 15 | 49.445 | -26.347 | 1.163 | 1.00 | 19.54 | EII | ATOM | 169 | CG | MET | 21 | 51.593 | -33.474 | 7.193 | 1.00 | 20.85 | EII |
| ATOM | 121 | CB | ALA | 15 | 48.552 | -25.247 | 0.658 | 1.00 | 21.65 | EII | ATOM | 170 | SD | MET | 21 | 52.950 | -32.392 | 8.719 | 1.00 | 22.36 | EII |
| ATOM | 122 | C | ALA | 15 | 48.724 | -27.694 | 1.136 | 1.00 | 30.21 | EII | ATOM | 171 | CE | MET | 21 | 53.366 | -32.981 | 8.403 | 1.00 | 18.87 | EII |
| ATOM | 123 | O | ALA | 15 | 48.216 | -28.182 | 2.158 | 1.00 | 22.42 | EII | ATOM | 172 | C | MET | 21 | 48.082 | -33.910 | 9.383 | 1.00 | 15.18 | EII |
| ATOM | 124 | N | SER | 16 | 48.705 | -28.307 | -0.036 | 1.00 | 22.15 | EII | ATOM | 173 | O | MET | 21 | 48.045 | -34.660 | 9.124 | 1.00 | 17.80 | EII |
| ATOM | 126 | CA | SER | 16 | 48.059 | -29.592 | -0.226 | 1.00 | 20.96 | EII | ATOM | 174 | N | PHE | 22 | 47.206 | -32.927 | 8.216 | 1.00 | 17.43 | EII |
| ATOM | 127 | CB | SER | 16 | 48.140 | -29.955 | -1.698 | 1.00 | 20.52 | EII | ATOM | 176 | CA | PHE | 22 | 45.234 | -31.506 | 9.680 | 1.00 | 11.43 | EII |
| ATOM | 128 | OG | SER | 16 | 49.402 | -29.573 | -2.217 | 1.00 | 25.54 | EII | ATOM | 177 | CB | PHE | 22 | 45.747 | -30.201 | 9.195 | 1.00 | 15.62 | EII |
| ATOM | 130 | C | SER | 16 | 48.659 | -30.702 | 0.635 | 1.00 | 18.79 | EII | ATOM | 178 | CG | PHE | 22 | 45.069 | -29.533 | 10.203 | 1.00 | 13.39 | EII |
| ATOM | 131 | O | SER | 16 | 47.947 | -31.564 | 1.156 | 1.00 | 20.24 | EII | ATOM | 179 | CD1 | PHE | 22 | 46.960 | -29.677 | 8.741 | 1.00 | 13.47 | EII |
| ATOM | 132 | N | THR | 17 | 49.978 | -30.698 | 0.740 | 1.00 | 20.24 | EII | ATOM | 181 | CD2 | PHE | 22 | 45.599 | -28.377 | 10.750 | 1.00 | 17.40 | EII |
| ATOM | 134 | CA | THR | 17 | 50.691 | -31.678 | 1.547 | 1.00 | 19.31 | EII | ATOM | 182 | CE1 | PHE | 22 | 47.495 | -28.512 | 9.291 | 1.00 | 13.35 | EII |
| ATOM | 135 | CB | THR | 17 | 52.206 | -31.515 | 1.337 | 1.00 | 15.26 | EII | ATOM | 183 | CE2 | PHE | 22 | 46.823 | -27.865 | 10.291 | 1.00 | 14.12 | EII |
| ATOM | 136 | OG1 | THR | 17 | 52.501 | -32.507 | -0.053 | 1.00 | 17.49 | EII | ATOM | 184 | CZ | PHE | 22 | 45.215 | -33.958 | 9.102 | 1.00 | 21.39 | EII |
| ATOM | 138 | CG2 | THR | 17 | 53.005 | -31.693 | 2.205 | 1.00 | 11.86 | EII | ATOM | 185 | C | PHE | 22 | 44.945 | -34.542 | 10.142 | 1.00 | 23.82 | EII |
| ATOM | 139 | C | THR | 17 | 50.353 | -31.439 | 3.043 | 1.00 | 17.74 | EII | ATOM | 186 | O | PHE | 22 | 44.829 | -34.384 | 7.899 | 1.00 | 25.04 | EII |
| ATOM | 140 | O | THR | 17 | 50.172 | -32.391 | 3.778 | 1.00 | 19.05 | EII | ATOM | 188 | N | LYS | 23 | 43.995 | -35.564 | 7.708 | 1.00 | 24.71 | EII |
| ATOM | 141 | N | VAL | 18 | 50.343 | -30.165 | 3.440 | 1.00 | 13.56 | EII | ATOM | 189 | CA | LYS | 23 | 43.758 | -35.821 | 6.226 | 1.00 | 24.89 | EII |
| ATOM | 143 | CA | VAL | 18 | 50.001 | -29.804 | 4.826 | 1.00 | 14.81 | EII | ATOM | 190 | CB | LYS | 23 | 42.763 | -34.900 | 5.576 | 1.00 | 30.03 | EII |
| ATOM | 144 | CB | VAL | 18 | 50.110 | -28.301 | 5.084 | | | | ATOM | 191 | CG | LYS | 23 | 42.599 | -35.285 | 4.128 | | | |
| ATOM | 145 | CG1 | VAL | 18 | 49.750 | -28.001 | 6.512 | | | | | | | | | | | | | | |

| | | | | | | | | | |
|---|---|---|---|---|---|---|---|---|---|
| ATOM | 192 | CE | LYS | 23 | 43.911 | -35.210 | 3.370 | 0.00 | 28.36 E1I |
| ATOM | 193 | NZ | LYS | 23 | 43.731 | -35.519 | 1.926 | 0.00 | 29.35 E1I |
| ATOM | 197 | C | LYS | 23 | 44.537 | -36.827 | 8.339 | 1.00 | 27.27 E1I |
| ATOM | 198 | O | LYS | 23 | 43.826 | -37.489 | 9.102 | 1.00 | 32.54 E1I |
| ATOM | 199 | H | SER | 24 | 45.796 | -37.150 | 8.069 | 1.00 | 24.81 E1I |
| ATOM | 201 | CA | SER | 24 | 46.357 | -38.382 | 8.592 | 1.00 | 27.81 E1I |
| ATOM | 202 | CB | SER | 24 | 47.609 | -38.788 | 7.827 | 1.00 | 28.93 E1I |
| ATOM | 203 | OG | SER | 24 | 48.664 | -37.889 | 8.058 | 1.00 | 35.51 E1I |
| ATOM | 205 | C | SER | 24 | 46.621 | -38.352 | 10.071 | 1.00 | 31.26 E1I |
| ATOM | 206 | O | SER | 24 | 46.571 | -39.386 | 10.726 | 1.00 | 36.33 E1I |
| ATOM | 207 | N | ASN | 25 | 46.928 | -37.184 | 10.609 | 1.00 | 29.18 E1I |
| ATOM | 209 | CA | ASN | 25 | 47.159 | -37.116 | 12.040 | 1.00 | 25.08 E1I |
| ATOM | 210 | CB | ASN | 25 | 48.096 | -35.975 | 12.361 | 1.00 | 27.18 E1I |
| ATOM | 211 | CG | ASN | 25 | 49.496 | -36.258 | 11.932 | 1.00 | 32.74 E1I |
| ATOM | 212 | OD1 | ASN | 25 | 50.367 | -36.526 | 12.755 | 1.00 | 31.80 E1I |
| ATOM | 213 | ND2 | ASN | 25 | 49.735 | -36.214 | 10.638 | 1.00 | 21.59 E1I |
| ATOM | 216 | C | ASN | 25 | 45.867 | -36.961 | 12.826 | 1.00 | 28.10 E1I |
| ATOM | 217 | O | ASN | 25 | 45.875 | -37.066 | 14.044 | 1.00 | 28.10 E1I |
| ATOM | 218 | N | GLY | 26 | 44.749 | -36.770 | 12.137 | 1.00 | 19.37 E1I |
| ATOM | 220 | CA | GLY | 26 | 43.486 | -36.586 | 12.827 | 1.00 | 13.76 E1I |
| ATOM | 221 | C | GLY | 26 | 43.307 | -35.198 | 13.433 | 1.00 | 22.44 E1I |
| ATOM | 222 | O | GLY | 26 | 42.668 | -35.031 | 14.487 | 1.00 | 22.71 E1I |
| ATOM | 223 | H | ILE | 27 | 43.851 | -34.179 | 12.768 | 1.00 | 25.11 E1I |
| ATOM | 225 | CA | ILE | 27 | 43.711 | -32.807 | 13.258 | 1.00 | 22.96 E1I |
| ATOM | 226 | CB | ILE | 27 | 44.895 | -31.926 | 12.907 | 1.00 | 23.98 E1I |
| ATOM | 227 | CG2 | ILE | 27 | 46.192 | -32.652 | 13.692 | 1.00 | 21.26 E1I |
| ATOM | 228 | CG1 | ILE | 27 | 45.784 | -30.620 | 13.277 | 1.00 | 21.26 E1I |
| ATOM | 229 | CD1 | ILE | 27 | 47.472 | -31.940 | 12.876 | 1.00 | 17.90 E1I |
| ATOM | 230 | C | ILE | 27 | 42.462 | -32.244 | 12.611 | 1.00 | 25.44 E1I |
| ATOM | 231 | O | ILE | 27 | 42.426 | -32.014 | 11.409 | 1.00 | 29.33 E1I |
| ATOM | 232 | N | LYS | 28 | 41.404 | -32.202 | 13.002 | 1.00 | 28.24 E1I |
| ATOM | 234 | CA | LYS | 28 | 40.085 | -31.733 | 13.089 | 1.00 | 27.81 E1I |
| ATOM | 235 | CB | LYS | 28 | 39.065 | -32.100 | 14.089 | 1.00 | 22.07 E1I |
| ATOM | 236 | CG | LYS | 28 | 38.995 | -33.588 | 14.409 | 1.00 | 24.17 E1I |
| ATOM | 237 | CD | LYS | 28 | 37.867 | -33.920 | 15.383 | 1.00 | 23.98 E1I |
| ATOM | 238 | CE | LYS | 28 | 37.982 | -35.361 | 15.854 | 0.00 | 23.98 E1I |
| ATOM | 239 | NZ | LYS | 28 | 39.320 | -35.582 | 16.453 | 0.00 | 23.98 E1I |
| ATOM | 243 | C | LYS | 28 | 39.908 | -30.260 | 12.624 | 1.00 | 27.25 E1I |
| ATOM | 244 | O | LYS | 28 | 39.016 | -29.928 | 11.828 | 1.00 | 28.38 E1I |
| ATOM | 245 | H | SER | 29 | 40.724 | -29.373 | 13.179 | 1.00 | 23.53 E1I |
| ATOM | 247 | CA | SER | 29 | 40.598 | -27.966 | 12.832 | 1.00 | 20.76 E1I |
| ATOM | 248 | CB | SER | 29 | 39.892 | -27.205 | 13.938 | 1.00 | 22.38 E1I |
| ATOM | 249 | OG | SER | 29 | 38.549 | -27.605 | 14.036 | 1.00 | 29.51 E1I |
| ATOM | 251 | C | SER | 29 | 41.909 | -27.309 | 12.505 | 1.00 | 15.69 E1I |
| ATOM | 252 | O | SER | 29 | 42.959 | -27.755 | 12.936 | 1.00 | 20.13 E1I |
| ATOM | 253 | N | MET | 30 | 41.811 | -26.203 | 11.774 | 1.00 | 21.28 E1I |
| ATOM | 255 | CA | MET | 30 | 42.940 | -25.423 | 11.279 | 1.00 | 16.44 E1I |
| ATOM | 256 | CB | MET | 30 | 43.059 | -25.681 | 9.770 | 1.00 | 18.86 E1I |
| ATOM | 257 | CG | MET | 30 | 44.118 | -24.871 | 9.059 | 1.00 | 20.66 E1I |
| ATOM | 258 | SD | MET | 30 | 44.013 | -25.077 | 7.271 | 1.00 | 23.20 E1I |
| ATOM | 259 | CE | MET | 30 | 45.087 | -26.516 | 7.153 | 1.00 | 18.03 E1I |
| ATOM | 260 | C | MET | 30 | 42.686 | -23.946 | 11.462 | 1.00 | 18.19 E1I |
| ATOM | 261 | O | MET | 30 | 41.596 | -23.461 | 11.116 | 1.00 | 13.95 E1I |
| ATOM | 262 | N | ARG | 31 | 43.729 | -23.233 | 11.897 | 1.00 | 14.61 E1I |
| ATOM | 264 | CA | ARG | 31 | 43.666 | -21.797 | 12.082 | 1.00 | 12.55 E1I |
| ATOM | 265 | CB | ARG | 31 | 43.935 | -21.357 | 13.535 | 1.00 | 11.95 E1I |
| ATOM | 266 | CG | ARG | 31 | 43.917 | -19.827 | 13.657 | 1.00 | 7.13 E1I |
| ATOM | 267 | CD | ARG | 31 | 43.949 | -19.302 | 15.059 | 1.00 | 10.77 E1I |
| ATOM | 268 | NE | ARG | 31 | 43.911 | -17.842 | 15.051 | 1.00 | 4.80 E1I |
| ATOM | 270 | CZ | ARG | 31 | 44.467 | -17.055 | 15.970 | 1.00 | 5.18 E1I |
| ATOM | 271 | NH1 | ARG | 31 | 45.106 | -17.570 | 17.006 | 1.00 | 2.25 E1I |
| ATOM | 274 | NH2 | ARG | 31 | 44.464 | -15.739 | 15.798 | 1.00 | 7.27 E1I |
| ATOM | 277 | C | ARG | 31 | 44.675 | -21.129 | 11.109 | 1.00 | 14.31 E1I |
| ATOM | 278 | O | ARG | 31 | 45.863 | -21.451 | 11.089 | 1.00 | 10.33 E1I |
| ATOM | 279 | N | LEU | 32 | 44.177 | -20.195 | 10.310 | 1.00 | 12.95 E1I |
| ATOM | 281 | CA | LEU | 32 | 44.986 | -19.495 | 9.372 | 1.00 | 17.53 E1I |
| ATOM | 282 | CB | LEU | 32 | 44.321 | -19.488 | 8.011 | 1.00 | 14.26 E1I |
| ATOM | 283 | CG | LEU | 32 | 44.218 | -20.840 | 7.315 | 1.00 | 17.93 E1I |
| ATOM | 284 | CD1 | LEU | 32 | 43.418 | -20.644 | 6.018 | 1.00 | 9.45 E1I |
| ATOM | 285 | CD2 | LEU | 32 | 45.611 | -21.376 | 7.029 | 1.00 | 11.95 E1I |
| ATOM | 286 | C | LEU | 32 | 44.983 | -18.075 | 9.885 | 1.00 | 15.41 E1I |
| ATOM | 287 | O | LEU | 32 | 43.999 | -17.648 | 10.447 | 1.00 | 11.93 E1I |
| ATOM | 288 | N | TYR | 33 | 46.008 | -17.299 | 9.595 | 1.00 | 11.20 E1I |
| ATOM | 290 | CA | TYR | 33 | 46.044 | -15.961 | 10.120 | 1.00 | 13.18 E1I |
| ATOM | 291 | CB | TYR | 33 | 47.392 | -15.702 | 10.755 | 1.00 | 17.07 E1I |
| ATOM | 292 | CG | TYR | 33 | 47.610 | -16.481 | 12.039 | 1.00 | 14.39 E1I |
| ATOM | 293 | CD1 | TYR | 33 | 47.464 | -15.853 | 13.283 | 1.00 | 11.59 E1I |
| ATOM | 294 | CE1 | TYR | 33 | 47.624 | -16.558 | 14.468 | 1.00 | 11.52 E1I |
| ATOM | 295 | CD2 | TYR | 33 | 47.937 | -17.845 | 12.018 | 1.00 | 11.52 E1I |
| ATOM | 296 | CE2 | TYR | 33 | 48.095 | -18.542 | 13.193 | 1.00 | 13.17 E1I |

- 34 -

| | | | | | | | | | |
|---|---|---|---|---|---|---|---|---|---|
| ATOM | 297 | CZ | TYR | 33 | 47.930 | -17.890 | 14.422 | 1.00 9.74 | EII |
| ATOM | 298 | OH | TYR | 33 | 47.997 | -18.587 | 15.594 | 1.00 15.65 | EII |
| ATOM | 300 | C | TYR | 33 | 45.762 | -14.947 | 9.043 | 1.00 15.31 | EII |
| ATOM | 301 | O | TYR | 33 | 45.731 | -13.742 | 9.298 | 1.00 18.87 | EII |
| ATOM | 302 | N | ALA | 34 | 45.355 | -15.441 | 7.885 | 1.00 12.05 | EII |
| ATOM | 304 | CA | ALA | 34 | 45.107 | -14.572 | 6.761 | 1.00 12.61 | EII |
| ATOM | 305 | CB | ALA | 34 | 46.387 | -13.941 | 6.283 | 1.00 10.34 | EII |
| ATOM | 306 | C | ALA | 34 | 44.546 | -15.491 | 5.707 | 1.00 13.29 | EII |
| ATOM | 307 | O | ALA | 34 | 44.781 | -16.702 | 5.743 | 1.00 15.30 | EII |
| ATOM | 308 | N | PRO | 35 | 43.696 | -14.959 | 4.818 | 1.00 15.76 | EII |
| ATOM | 309 | CD | PRO | 35 | 43.343 | -13.529 | 4.680 | 1.00 7.83 | EII |
| ATOM | 310 | CA | PRO | 35 | 43.087 | -15.770 | 3.753 | 1.00 16.30 | EII |
| ATOM | 311 | CB | PRO | 35 | 42.150 | -14.784 | 3.057 | 1.00 17.33 | EII |
| ATOM | 312 | CG | PRO | 35 | 42.077 | -13.606 | 3.958 | 1.00 13.97 | EII |
| ATOM | 313 | C | PRO | 35 | 44.147 | -16.291 | 2.760 | 1.00 18.66 | EII |
| ATOM | 314 | O | PRO | 35 | 44.405 | -15.661 | 1.748 | 1.00 26.27 | EII |
| ATOM | 315 | N | ASN | 36 | 44.799 | -17.398 | 3.049 | 1.00 17.99 | EII |
| ATOM | 317 | CA | ASN | 36 | 45.794 | -17.898 | 2.110 | 1.00 16.21 | EII |
| ATOM | 318 | CB | ASN | 36 | 46.759 | -18.818 | 2.840 | 1.00 23.52 | EII |
| ATOM | 319 | CG | ASN | 36 | 47.855 | -19.345 | 1.950 | 1.00 25.17 | EII |
| ATOM | 320 | OD1 | ASN | 36 | 47.879 | -20.529 | 1.600 | 1.00 25.07 | EII |
| ATOM | 321 | ND2 | ASN | 36 | 48.769 | -18.465 | 1.566 | 1.00 22.54 | EII |
| ATOM | 324 | C | ASN | 36 | 45.093 | -18.682 | 1.014 | 1.00 15.81 | EII |
| ATOM | 325 | O | ASN | 36 | 44.510 | -19.699 | 1.296 | 1.00 18.68 | EII |
| ATOM | 326 | N | GLN | 37 | 45.137 | -18.231 | -0.233 | 1.00 17.15 | EII |
| ATOM | 328 | CA | GLN | 37 | 44.461 | -18.959 | -1.314 | 1.00 17.78 | EII |
| ATOM | 329 | CB | GLN | 37 | 44.579 | -18.216 | -2.624 | 1.00 25.49 | EII |
| ATOM | 330 | CG | GLN | 37 | 43.734 | -18.842 | -3.714 | 1.00 37.12 | EII |
| ATOM | 331 | CD | GLN | 37 | 43.815 | -18.069 | -4.991 | 1.00 44.75 | EII |
| ATOM | 332 | OE1 | GLN | 37 | 44.686 | -17.209 | -5.145 | 1.00 54.79 | EII |
| ATOM | 333 | NE2 | GLN | 37 | 42.907 | -18.345 | -5.913 | 0.00 45.53 | EII |
| ATOM | 336 | C | GLN | 37 | 44.832 | -20.417 | -1.552 | 1.00 17.43 | EII |
| ATOM | 337 | O | GLN | 37 | 43.961 | -21.237 | -1.865 | 1.00 19.76 | EII |
| ATOM | 338 | N | ALA | 38 | 46.121 | -20.722 | -1.485 | 1.00 13.38 | EII |
| ATOM | 340 | CA | ALA | 38 | 46.615 | -22.074 | -1.642 | 1.00 12.89 | EII |
| ATOM | 341 | CB | ALA | 38 | 48.118 | -22.068 | -1.590 | 1.00 14.28 | EII |
| ATOM | 342 | C | ALA | 38 | 46.043 | -23.003 | -0.545 | 1.00 17.92 | EII |
| ATOM | 343 | O | ALA | 38 | 45.565 | -24.115 | -0.840 | 1.00 20.66 | EII |
| ATOM | 344 | N | ALA | 39 | 46.048 | -22.538 | 0.738 | 1.00 18.24 | EII |
| ATOM | 346 | CA | ALA | 39 | 45.531 | -23.327 | 1.819 | 1.00 17.99 | EII |
| ATOM | 347 | CB | ALA | 39 | 45.910 | -22.691 | 3.149 | 1.00 16.10 | EII |
| ATOM | 348 | C | ALA | 39 | 44.011 | -23.510 | 1.723 | 1.00 18.89 | EII |
| ATOM | 349 | O | ALA | 39 | 43.492 | -24.603 | 1.935 | 1.00 23.20 | EII |
| ATOM | 350 | N | LEU | 40 | 43.315 | -22.435 | 1.387 | 1.00 18.19 | EII |
| ATOM | 352 | CA | LEU | 40 | 41.869 | -22.435 | 1.259 | 1.00 20.00 | EII |
| ATOM | 353 | CB | LEU | 40 | 41.356 | -20.996 | 1.110 | 1.00 17.04 | EII |
| ATOM | 354 | CG | LEU | 40 | 40.633 | -20.357 | 2.309 | 1.00 18.44 | EII |
| ATOM | 355 | CD1 | LEU | 40 | 40.831 | -21.125 | 3.605 | 1.00 8.37 | EII |
| ATOM | 356 | CD2 | LEU | 40 | 41.094 | -18.919 | 2.469 | 1.00 18.94 | EII |
| ATOM | 357 | C | LEU | 40 | 41.418 | -23.304 | 0.099 | 1.00 20.26 | EII |
| ATOM | 358 | O | LEU | 40 | 40.398 | -23.980 | 0.189 | 1.00 23.72 | EII |
| ATOM | 359 | N | GLN | 41 | 42.196 | -23.328 | -0.977 | 1.00 24.70 | EII |
| ATOM | 361 | CA | GLN | 41 | 41.849 | -24.155 | -2.126 | 1.00 21.31 | EII |
| ATOM | 362 | CB | GLN | 41 | 42.656 | -23.754 | -3.354 | 1.00 25.06 | EII |
| ATOM | 363 | CG | GLN | 41 | 42.054 | -22.562 | -4.098 | 1.00 34.10 | EII |
| ATOM | 364 | CD | GLN | 41 | 42.973 | -21.976 | -5.191 | 1.00 42.22 | EII |
| ATOM | 365 | OE1 | GLN | 41 | 42.688 | -20.900 | -5.721 | 1.00 45.87 | EII |
| ATOM | 366 | NE2 | GLN | 41 | 44.084 | -22.657 | -5.505 | 1.00 42.47 | EII |
| ATOM | 369 | C | GLN | 41 | 42.098 | -25.611 | -1.771 | 1.00 19.87 | EII |
| ATOM | 370 | O | GLN | 41 | 41.358 | -26.492 | -2.167 | 1.00 26.84 | EII |
| ATOM | 371 | N | ALA | 42 | 43.103 | -25.846 | -0.946 | 1.00 20.98 | EII |
| ATOM | 373 | CA | ALA | 42 | 43.449 | -27.197 | -0.564 | 1.00 18.67 | EII |
| ATOM | 374 | CB | ALA | 42 | 44.882 | -27.237 | -0.064 | 1.00 10.01 | EII |
| ATOM | 375 | C | ALA | 42 | 42.519 | -27.836 | 0.444 | 1.00 16.44 | EII |
| ATOM | 376 | O | ALA | 42 | 42.048 | -28.945 | 0.231 | 1.00 17.62 | EII |
| ATOM | 377 | N | VAL | 43 | 42.158 | -27.085 | 1.474 | 1.00 20.48 | EII |
| ATOM | 379 | CA | VAL | 43 | 41.349 | -27.600 | 2.573 | 1.00 20.70 | EII |
| ATOM | 380 | CB | VAL | 43 | 41.556 | -26.686 | 3.808 | 1.00 16.25 | EII |
| ATOM | 381 | CG1 | VAL | 43 | 40.728 | -25.430 | 3.699 | 1.00 14.84 | EII |
| ATOM | 382 | CG2 | VAL | 43 | 41.338 | -27.453 | 5.099 | 1.00 10.24 | EII |
| ATOM | 383 | C | VAL | 43 | 39.860 | -27.866 | 2.239 | 1.00 22.08 | EII |
| ATOM | 384 | O | VAL | 43 | 39.189 | -28.660 | 2.907 | 1.00 20.13 | EII |
| ATOM | 385 | N | GLY | 44 | 39.388 | -27.241 | 1.163 | 1.00 21.21 | EII |
| ATOM | 387 | CA | GLY | 44 | 38.020 | -27.387 | 0.718 | 1.00 23.12 | EII |
| ATOM | 388 | C | GLY | 44 | 37.627 | -28.834 | 0.536 | 1.00 26.47 | EII |
| ATOM | 389 | O | GLY | 44 | 38.446 | -29.664 | 0.106 | 1.00 24.87 | EII |
| ATOM | 390 | N | GLY | 45 | 36.390 | -29.136 | 0.932 | 1.00 25.72 | EII |
| ATOM | 392 | CA | GLY | 45 | 35.836 | -30.482 | 0.831 | 1.00 25.85 | EII |
| ATOM | 393 | C | GLY | 45 | 36.453 | -31.563 | 1.716 | 1.00 24.73 | EII |
| ATOM | 394 | O | GLY | 45 | 36.110 | -32.727 | 1.554 | 1.00 30.99 | EII |

- 35 -

| | | | | | | | | | |
|---|---|---|---|---|---|---|---|---|---|
| ATOM | 396 | N | THR | 46 | 37.313 | -31.208 | 2.671 | 1.00 24.48 | EII |
| ATOM | 397 | CA | THR | 46 | 37.957 | -32.212 | 3.524 | 1.00 19.60 | EII |
| ATOM | 398 | CB | THR | 46 | 39.458 | -31.875 | 3.747 | 1.00 17.13 | EII |
| ATOM | 399 | CG1 | THR | 46 | 39.568 | -30.707 | 4.582 | 1.00 18.62 | EII |
| ATOM | 401 | CG2 | THR | 46 | 40.171 | -31.636 | 2.425 | 1.00 8.48 | EII |
| ATOM | 402 | C | THR | 46 | 37.320 | -32.378 | 4.911 | 1.00 19.15 | EII |
| ATOM | 403 | O | THR | 46 | 37.756 | -33.210 | 5.699 | 1.00 18.19 | EII |
| ATOM | 404 | N | GLN | 47 | 36.359 | -31.531 | 5.246 | 1.00 24.21 | EII |
| ATOM | 406 | CA | GLN | 47 | 35.735 | -31.623 | 6.557 | 1.00 22.15 | EII |
| ATOM | 407 | C | GLN | 47 | 36.566 | -30.998 | 7.671 | 1.00 24.40 | EII |
| ATOM | 408 | O | GLN | 47 | 36.162 | -31.008 | 8.818 | 1.00 31.33 | EII |
| ATOM | 409 | N | ILE | 48 | 37.754 | -30.503 | 7.364 | 1.00 23.13 | EII |
| ATOM | 411 | CA | ILE | 48 | 38.562 | -29.872 | 8.383 | 1.00 21.94 | EII |
| ATOM | 412 | CB | ILE | 48 | 40.058 | -29.721 | 7.942 | 1.00 17.90 | EII |
| ATOM | 413 | CG2 | ILE | 48 | 40.825 | -28.831 | 8.918 | 1.00 13.05 | EII |
| ATOM | 414 | CG1 | ILE | 48 | 40.732 | -31.090 | 7.852 | 1.00 19.32 | EII |
| ATOM | 415 | CD1 | ILE | 48 | 42.134 | -31.106 | 7.161 | 1.00 20.87 | EII |
| ATOM | 416 | C | ILE | 48 | 37.936 | -28.496 | 8.594 | 1.00 26.18 | EII |
| ATOM | 417 | O | ILE | 48 | 37.676 | -27.760 | 7.630 | 1.00 31.51 | EII |
| ATOM | 418 | N | ASN | 49 | 37.685 | -28.161 | 9.851 | 1.00 27.16 | EII |
| ATOM | 420 | CA | ASN | 49 | 37.108 | -26.879 | 10.195 | 1.00 25.56 | EII |
| ATOM | 421 | CB | ASN | 49 | 36.534 | -26.952 | 11.599 | 1.00 29.13 | EII |
| ATOM | 422 | CG | ASN | 49 | 35.353 | -27.888 | 11.676 | 1.00 27.51 | EII |
| ATOM | 423 | OD1 | ASN | 49 | 34.345 | -27.664 | 11.023 | 1.00 34.75 | EII |
| ATOM | 424 | ND2 | ASN | 49 | 35.493 | -28.968 | 12.420 | 1.00 31.30 | EII |
| ATOM | 427 | C | ASN | 49 | 38.182 | -25.805 | 10.094 | 1.00 23.57 | EII |
| ATOM | 428 | O | ASN | 49 | 39.329 | -26.023 | 10.481 | 1.00 22.77 | EII |
| ATOM | 429 | N | VAL | 50 | 37.782 | -24.615 | 9.672 | 1.00 20.53 | EII |
| ATOM | 431 | CA | VAL | 50 | 38.726 | -23.534 | 9.471 | 1.00 19.50 | EII |
| ATOM | 432 | CB | VAL | 50 | 38.931 | -23.262 | 7.938 | 1.00 16.95 | EII |
| ATOM | 433 | CG1 | VAL | 50 | 39.883 | -22.074 | 7.709 | 1.00 11.24 | EII |
| ATOM | 434 | CG2 | VAL | 50 | 39.454 | -24.535 | 7.244 | 1.00 13.56 | EII |
| ATOM | 435 | C | VAL | 50 | 38.312 | -22.221 | 10.121 | 1.00 19.97 | EII |
| ATOM | 436 | O | VAL | 50 | 37.157 | -21.833 | 10.072 | 1.00 13.47 | EII |
| ATOM | 437 | N | VAL | 51 | 39.290 | -21.594 | 10.768 | 1.00 18.87 | EII |
| ATOM | 439 | CA | VAL | 51 | 39.172 | -20.295 | 11.395 | 1.00 15.51 | EII |
| ATOM | 440 | CB | VAL | 51 | 39.806 | -20.280 | 12.807 | 1.00 16.19 | EII |
| ATOM | 441 | CG1 | VAL | 51 | 39.679 | -18.891 | 13.426 | 1.00 9.15 | EII |
| ATOM | 442 | CG2 | VAL | 51 | 39.119 | -21.333 | 13.669 | 1.00 12.86 | EII |
| ATOM | 443 | C | VAL | 51 | 40.044 | -19.515 | 10.435 | 1.00 11.48 | EII |
| ATOM | 444 | O | VAL | 51 | 41.182 | -19.883 | 10.214 | 1.00 17.69 | EII |
| ATOM | 445 | N | VAL | 52 | 39.466 | -18.530 | 9.766 | 1.00 15.12 | EII |
| ATOM | 447 | CA | VAL | 52 | 40.176 | -17.686 | 8.826 | 1.00 11.40 | EII |
| ATOM | 448 | CB | VAL | 52 | 39.427 | -17.600 | 7.479 | 1.00 18.87 | EII |
| ATOM | 449 | CG1 | VAL | 52 | 37.969 | -17.139 | 7.675 | 1.00 17.04 | EII |
| ATOM | 450 | CG2 | VAL | 52 | 40.173 | -16.681 | 6.507 | 1.00 14.79 | EII |
| ATOM | 451 | C | VAL | 52 | 40.259 | -16.323 | 9.483 | 1.00 15.96 | EII |
| ATOM | 452 | O | VAL | 52 | 39.275 | -15.795 | 9.986 | 1.00 18.27 | EII |
| ATOM | 453 | N | GLY | 53 | 41.445 | -15.757 | 9.501 | 1.00 13.37 | EII |
| ATOM | 455 | CA | GLY | 53 | 41.599 | -14.481 | 10.128 | 1.00 9.39 | EII |
| ATOM | 456 | C | GLY | 53 | 41.804 | -13.335 | 9.184 | 1.00 11.84 | EII |
| ATOM | 457 | O | GLY | 53 | 42.148 | -13.527 | 8.017 | 1.00 14.18 | EII |
| ATOM | 458 | N | ALA | 54 | 41.498 | -12.142 | 9.681 | 1.00 10.21 | EII |
| ATOM | 460 | CA | ALA | 54 | 41.700 | -10.939 | 8.928 | 1.00 9.20 | EII |
| ATOM | 461 | CB | ALA | 54 | 40.490 | -10.046 | 9.025 | 1.00 12.69 | EII |
| ATOM | 462 | C | ALA | 54 | 42.928 | -10.292 | 9.555 | 1.00 13.25 | EII |
| ATOM | 463 | O | ALA | 54 | 42.965 | -9.971 | 10.746 | 1.00 12.94 | EII |
| ATOM | 464 | N | PRO | 55 | 43.987 | -10.153 | 8.773 | 1.00 12.65 | EII |
| ATOM | 465 | CD | PRO | 55 | 44.107 | -10.503 | 7.346 | 1.00 9.03 | EII |
| ATOM | 466 | CA | PRO | 55 | 45.176 | -9.454 | 9.296 | 1.00 15.42 | EII |
| ATOM | 467 | CB | PRO | 55 | 46.059 | -9.312 | 8.059 | 1.00 18.62 | EII |
| ATOM | 468 | CG | PRO | 55 | 45.578 | -10.417 | 7.162 | 1.00 17.72 | EII |
| ATOM | 469 | C | PRO | 55 | 44.858 | -8.075 | 9.997 | 1.00 12.72 | EII |
| ATOM | 470 | O | PRO | 55 | 43.923 | -7.394 | 9.538 | 1.00 16.67 | EII |
| ATOM | 471 | N | ASN | 56 | 45.644 | -7.700 | 10.957 | 1.00 17.07 | EII |
| ATOM | 473 | CA | ASN | 56 | 45.481 | -6.471 | 11.701 | 1.00 18.02 | EII |
| ATOM | 474 | CB | ASN | 56 | 46.476 | -6.415 | 12.864 | 1.00 18.80 | EII |
| ATOM | 475 | CG | ASN | 56 | 46.098 | -7.357 | 14.014 | 1.00 25.14 | EII |
| ATOM | 476 | OD1 | ASN | 56 | 44.936 | -7.697 | 14.208 | 1.00 22.12 | EII |
| ATOM | 477 | ND2 | ASN | 56 | 47.085 | -7.780 | 14.774 | 1.00 21.24 | EII |
| ATOM | 480 | C | ASN | 56 | 45.630 | -5.217 | 10.857 | 1.00 21.67 | EII |
| ATOM | 481 | O | ASN | 56 | 45.012 | -4.189 | 11.168 | 1.00 20.28 | EII |
| ATOM | 482 | N | ASP | 57 | 46.413 | -5.300 | 9.778 | 1.00 19.57 | EII |
| ATOM | 484 | CA | ASP | 57 | 46.602 | -4.123 | 8.939 | 1.00 25.63 | EII |
| ATOM | 485 | CB | ASP | 57 | 47.992 | -4.123 | 8.246 | 1.00 28.53 | EII |
| ATOM | 486 | CG | ASP | 57 | 48.209 | -5.289 | 7.269 | 1.00 28.46 | EII |
| ATOM | 487 | OD1 | ASP | 57 | 49.379 | -5.531 | 6.908 | 1.00 32.32 | EII |
| ATOM | 488 | OD2 | ASP | 57 | 47.238 | -5.931 | 6.829 | 1.00 19.68 | EII |
| ATOM | 489 | C | ASP | 57 | 45.404 | -3.759 | 7.997 | 1.00 25.63 | EII |
| ATOM | 490 | O | ASP | 57 | 45.298 | -2.636 | 7.492 | 1.00 20.16 | EII |

- 36 -

```
ATOM  491  N   VAL  58      44.425  -4.654   7.895  1.00 20.84           EII
ATOM  493  CA  VAL  58      43.250  -4.401   7.060  1.00 21.83           EII
ATOM  494  CB  VAL  58      42.917  -5.658   6.179  1.00 25.12           EII
ATOM  495  CG1 VAL  58      42.275  -6.760   7.012  1.00 22.28           EII
ATOM  496  CG2 VAL  58      42.038  -5.281   4.983  1.00 25.80           EII
ATOM  497  C   VAL  58      42.029  -3.978   7.909  1.00 23.06           EII
ATOM  498  O   VAL  58      40.977  -3.585   7.371  1.00 22.70           EII
ATOM  499  H   VAL  58      42.186  -3.956   9.230  1.00 22.03           EII
ATOM  501  N   LEU  59      42.068  -3.588  10.101  1.00 22.81           EII
ATOM  502  CA  LEU  59      41.469  -3.647  11.570  1.00 26.84           EII
ATOM  503  CB  LEU  59      41.165  -4.931  12.326  1.00 29.75           EII
ATOM  504  CG  LEU  59      41.676  -6.158  11.573  1.00 27.62           EII
ATOM  505  CG2 LEU  59      41.794  -4.817  13.688  1.00 27.41           EII
ATOM  506  C   LEU  59      40.484  -2.232   9.805  1.00 23.06           EII
ATOM  507  O   LEU  59      39.274  -2.103   9.664  1.00 29.44           EII
ATOM  508  N   SER  60      41.344  -1.228   9.692  1.00 20.75           EII
ATOM  510  CB  SER  60      40.930   0.146   9.419  1.00 22.49           EII
ATOM  511  CB  SER  60      42.178   1.002   9.194  1.00 25.08           EII
ATOM  512  OG  SER  60      43.160   0.295   8.424  1.00 31.22           EII
ATOM  513  C   SER  60      40.053   0.180   8.183  1.00 23.29           EII
ATOM  515  O   SER  60      39.080   0.929   8.121  1.00 29.14           EII
ATOM  516  N   ASN  61      40.368  -0.710   7.245  1.00 27.05           EII
ATOM  518  CA  ASN  61      39.650  -0.848   5.983  1.00 26.53           EII
ATOM  519  CB  ASN  61      40.504  -1.665   5.029  1.00 28.68           EII
ATOM  520  CG  ASN  61      39.837  -1.886   3.722  1.00 31.65           EII
ATOM  521  OD1 ASN  61      39.478  -0.936   3.046  1.00 32.78           EII
ATOM  522  ND2 ASN  61      39.624  -3.147   3.365  1.00 34.74           EII
ATOM  525  C   ASN  61      38.271  -1.507   6.192  1.00 24.84           EII
ATOM  526  O   ASN  61      37.253  -1.038   5.666  1.00 24.69           EII
ATOM  527  H   ASN  61      38.246  -2.590   6.966  1.00 23.72           EII
ATOM  529  N   LEU  62      37.002  -3.291   7.212  1.00 23.73           EII
ATOM  530  CB  LEU  62      37.281  -4.663   7.923  1.00 20.58           EII
ATOM  531  CB  LEU  62      38.076  -5.722   7.136  1.00 18.20           EII
ATOM  532  CG  LEU  62      37.867  -7.057   7.867  1.00 13.38           EII
ATOM  533  CD1 LEU  62      37.461  -5.911   5.759  1.00 15.94           EII
ATOM  534  CD2 LEU  62      36.081  -2.444   8.173  1.00 21.53           EII
ATOM  535  O   LEU  62      34.862  -2.521   8.010  1.00 17.63           EII
ATOM  536  H   LEU  62      36.677  -1.610   9.016  1.00 23.90           EII
ATOM  538  CA  ALA  63      35.936  -0.756   9.929  1.00 23.13           EII
ATOM  539  CB  ALA  63      36.860  -0.185  10.952  1.00 18.39           EII
ATOM  540  C   ALA  63      35.297   0.375   9.187  1.00 25.60           EII
ATOM  541  O   ALA  63      34.124   0.636   9.357  1.00 36.57           EII
ATOM  542  N   ALA  64      36.066   1.037   8.341  1.00 29.42           EII
ATOM  544  CA  ALA  64      35.571   2.180   7.599  1.00 32.88           EII
ATOM  545  CB  ALA  64      36.695   2.797   6.809  1.00 36.85           EII
ATOM  546  C   ALA  64      34.379   1.940   6.687  1.00 34.73           EII
ATOM  547  O   ALA  64      33.428   2.709   6.701  1.00 38.86           EII
ATOM  548  N   SER  65      34.432   0.911   5.854  1.00 38.92           EII
ATOM  550  CA  SER  65      33.327   0.674   4.954  1.00 37.44           EII
ATOM  551  CB  SER  65      33.774   0.838   3.514  1.00 38.32           EII
ATOM  552  OG  SER  65      32.666  -0.637   2.669  1.00 42.58           EII
ATOM  554  C   SER  65      32.693  -0.677   5.120  1.00 34.86           EII
ATOM  555  O   SER  65      33.368  -1.697   5.070  1.00 42.13           EII
ATOM  556  N   PRO  66      31.363  -0.705   5.206  1.00 31.74           EII
ATOM  557  CD  PRO  66      30.522   0.466   5.478  1.00 28.81           EII
ATOM  558  CA  PRO  66      30.546  -1.918   5.089  1.00 29.22           EII
ATOM  559  CB  PRO  66      29.119  -1.377   5.179  1.00 30.41           EII
ATOM  560  CG  PRO  66      29.287  -0.189   6.046  1.00 29.35           EII
ATOM  561  C   PRO  66      30.776  -2.626   3.761  1.00 29.39           EII
ATOM  562  O   PRO  66      30.893  -3.862   3.707  1.00 26.11           EII
ATOM  563  N   ALA  67      30.897  -1.826   2.705  1.00 26.56           EII
ATOM  565  CA  ALA  67      31.118  -2.333   1.365  1.00 26.11           EII
ATOM  566  CB  ALA  67      31.018  -1.204   0.357  1.00 30.63           EII
ATOM  567  C   ALA  67      32.486  -2.987   1.296  1.00 24.54           EII
ATOM  568  O   ALA  67      32.665  -3.942   0.549  1.00 24.81           EII
ATOM  569  N   ALA  68      33.423  -2.474   2.190  1.00 26.24           EII
ATOM  571  CA  ALA  68      34.795  -2.990   2.103  1.00 26.04           EII
ATOM  572  CB  ALA  68      35.652  -2.095   3.078  1.00 25.11           EII
ATOM  573  C   ALA  68      34.722  -4.374   2.802  1.00 28.80           EII
ATOM  574  O   ALA  68      35.390  -5.324   2.356  1.00 32.16           EII
ATOM  575  N   ALA  69      33.948  -4.454   3.875  1.00 25.09           EII
ATOM  577  CA  ALA  69      33.728  -5.699   4.582  1.00 22.79           EII
ATOM  578  CB  ALA  69      32.768  -5.450   5.724  1.00 27.67           EII
ATOM  579  C   ALA  69      33.115  -6.697   3.607  1.00 22.29           EII
ATOM  580  O   ALA  69      33.490  -7.872   3.551  1.00 15.77           EII
ATOM  581  N   ALA  70      32.156  -6.206   2.837  1.00 21.97           EII
ATOM  583  CA  ALA  70      31.462  -7.029   1.871  1.00 22.17           EII
ATOM  584  CB  ALA  70      30.380  -6.226   1.214  1.00 21.50           EII
ATOM  585  C   ALA  70      32.407  -7.611   0.831  1.00 19.66           EII
ATOM  586  O   ALA  70      32.368  -8.808   0.541  1.00 22.05           EII
```

- 37 -

| | | | | | | | | | | | | | | | |
|---|---|---|---|---|---|---|---|---|---|---|---|---|---|---|---|
| ATOM | 587 | N | SER | 71 | 33.253 | -6.772 | 0.268 | 1.00 | 17.69 | E11 | | | | | |
| ATOM | 588 | CA | SER | 71 | 34.180 | -7.253 | -0.726 | 1.00 | 22.24 | E11 | | | | | |
| ATOM | 590 | CB | SER | 71 | 35.015 | -6.105 | -1.270 | 1.00 | 23.32 | E11 | | | | | |
| ATOM | 591 | OG | SER | 71 | 34.159 | -5.156 | -1.871 | 1.00 | 36.13 | E11 | | | | | |
| ATOM | 593 | C | SER | 71 | 35.091 | -8.331 | -0.177 | 1.00 | 24.69 | E11 | | | | | |
| ATOM | 594 | O | SER | 71 | 35.409 | -9.299 | -0.894 | 1.00 | 22.42 | E11 | | | | | |
| ATOM | 595 | N | TRP | 72 | 35.521 | -8.138 | 1.077 | 1.00 | 24.62 | E11 | | | | | |
| ATOM | 597 | CA | TRP | 72 | 36.421 | -9.064 | 1.763 | 1.00 | 22.59 | E11 | | | | | |
| ATOM | 598 | CB | TRP | 72 | 37.881 | -8.542 | 3.159 | 1.00 | 17.21 | E11 | | | | | |
| ATOM | 599 | CG | TRP | 72 | 37.881 | -9.252 | 3.789 | 1.00 | 17.72 | E11 | | | | | |
| ATOM | 600 | CD2 | TRP | 72 | 37.804 | -10.418 | 4.612 | 1.00 | 20.32 | E11 | | | | | |
| ATOM | 601 | CE2 | TRP | 72 | 39.120 | -10.751 | 4.981 | 1.00 | 18.73 | E11 | | | | | |
| ATOM | 602 | CE3 | TRP | 72 | 36.748 | -11.221 | 5.054 | 1.00 | 19.43 | E11 | | | | | |
| ATOM | 603 | CD1 | TRP | 72 | 39.191 | -8.937 | 3.699 | 1.00 | 14.07 | E11 | | | | | |
| ATOM | 604 | NE1 | TRP | 72 | 39.994 | -9.825 | 4.410 | 1.00 | 17.21 | E11 | | | | | |
| ATOM | 605 | CZ2 | TRP | 72 | 39.423 | -11.857 | 5.772 | 1.00 | 19.08 | E11 | | | | | |
| ATOM | 606 | CZ3 | TRP | 72 | 37.048 | -12.329 | 5.837 | 1.00 | 17.42 | E11 | | | | | |
| ATOM | 608 | CH2 | TRP | 72 | 38.319 | -12.636 | 6.189 | 1.00 | 19.43 | E11 | | | | | |
| ATOM | 609 | C | TRP | 72 | 35.787 | -10.428 | 1.881 | 1.00 | 22.68 | E11 | | | | | |
| ATOM | 610 | O | TRP | 72 | 36.430 | -11.459 | 1.645 | 1.00 | 17.53 | E11 | | | | | |
| ATOM | 611 | N | VAL | 73 | 34.542 | -10.425 | 2.349 | 1.00 | 26.27 | E11 | | | | | |
| ATOM | 613 | CA | VAL | 73 | 33.780 | -11.661 | 2.500 | 1.00 | 24.21 | E11 | | | | | |
| ATOM | 614 | CB | VAL | 73 | 32.474 | -11.370 | 3.244 | 1.00 | 21.77 | E11 | | | | | |
| ATOM | 615 | CG1 | VAL | 73 | 31.540 | -12.563 | 3.210 | 1.00 | 17.08 | E11 | | | | | |
| ATOM | 616 | CG2 | VAL | 73 | 32.802 | -10.998 | 4.686 | 1.00 | 19.49 | E11 | | | | | |
| ATOM | 617 | C | VAL | 73 | 33.538 | -12.346 | 1.147 | 1.00 | 25.47 | E11 | | | | | |
| ATOM | 618 | O | VAL | 73 | 33.605 | -13.575 | 1.043 | 1.00 | 28.46 | E11 | | | | | |
| ATOM | 619 | N | LYS | 74 | 33.306 | -11.557 | 0.106 | 1.00 | 24.17 | E11 | | | | | |
| ATOM | 621 | CA | LYS | 74 | 33.067 | -12.115 | -1.211 | 1.00 | 21.55 | E11 | | | | | |
| ATOM | 622 | CB | LYS | 74 | 32.642 | -11.017 | -2.172 | 1.00 | 20.51 | E11 | | | | | |
| ATOM | 623 | CG | LYS | 74 | 32.352 | -11.521 | -3.575 | 1.00 | 26.05 | E11 | | | | | |
| ATOM | 624 | CD | LYS | 74 | 31.936 | -10.392 | -4.509 | 0.00 | 24.09 | E11 | | | | | |
| ATOM | 625 | CE | LYS | 74 | 33.110 | -9.518 | -4.940 | 0.00 | 24.77 | E11 | | | | | |
| ATOM | 626 | NZ | LYS | 74 | 33.693 | -8.668 | -3.861 | 0.00 | 24.37 | E11 | | | | | |
| ATOM | 630 | C | LYS | 74 | 34.284 | -12.843 | -1.761 | 1.00 | 21.26 | E11 | | | | | |
| ATOM | 631 | O | LYS | 74 | 34.180 | -13.968 | -2.276 | 1.00 | 25.56 | E11 | | | | | |
| ATOM | 632 | N | SER | 75 | 35.448 | -12.231 | -1.588 | 1.00 | 22.43 | E11 | | | | | |
| ATOM | 634 | CA | SER | 75 | 36.695 | -12.789 | -2.097 | 1.00 | 21.41 | E11 | | | | | |
| ATOM | 635 | CB | SER | 75 | 37.671 | -11.651 | -2.375 | 1.00 | 19.06 | E11 | | | | | |
| ATOM | 636 | OG | SER | 75 | 37.469 | -10.602 | -1.461 | 1.00 | 25.30 | E11 | | | | | |
| ATOM | 638 | C | SER | 75 | 37.352 | -13.829 | -1.21 | 1.00 | 23.71 | E11 | | | | | |
| ATOM | 639 | O | SER | 75 | 37.927 | -14.800 | -1.695 | 1.00 | 29.02 | E11 | | | | | |
| ATOM | 640 | N | ASN | 76 | 37.207 | -13.657 | 0.091 | 1.00 | 25.26 | E11 | | | | | |
| ATOM | 642 | CA | ASN | 76 | 37.827 | -14.550 | 1.039 | 1.00 | 24.40 | E11 | | | | | |
| ATOM | 643 | CB | ASN | 76 | 38.513 | -13.706 | 2.090 | 1.00 | 19.18 | E11 | | | | | |
| ATOM | 644 | CG | ASN | 76 | 39.541 | -12.847 | 1.480 | 1.00 | 22.15 | E11 | | | | | |
| ATOM | 645 | OD1 | ASN | 76 | 40.502 | -13.367 | 0.938 | 1.00 | 21.71 | E11 | | | | | |
| ATOM | 646 | ND2 | ASN | 76 | 39.285 | -11.544 | 1.398 | 1.00 | 20.77 | E11 | | | | | |
| ATOM | 649 | C | ASN | 76 | 37.001 | -15.647 | 1.676 | 1.00 | 25.66 | E11 | | | | | |
| ATOM | 650 | O | ASN | 76 | 37.565 | -16.633 | 2.159 | 1.00 | 27.12 | E11 | | | | | |
| ATOM | 651 | N | ILE | 77 | 35.679 | -15.504 | 1.655 | 1.00 | 23.34 | E11 | | | | | |
| ATOM | 653 | CA | ILE | 77 | 34.818 | -16.487 | 2.279 | 1.00 | 17.93 | E11 | | | | | |
| ATOM | 654 | CB | ILE | 77 | 33.861 | -15.864 | 3.379 | 1.00 | 17.11 | E11 | | | | | |
| ATOM | 655 | CG2 | ILE | 77 | 32.896 | -16.893 | 3.912 | 1.00 | 17.69 | E11 | | | | | |
| ATOM | 656 | CG1 | ILE | 77 | 34.649 | -15.353 | 4.599 | 1.00 | 13.97 | E11 | | | | | |
| ATOM | 657 | CD1 | ILE | 77 | 35.741 | -16.252 | 5.073 | 1.00 | 16.96 | E11 | | | | | |
| ATOM | 658 | C | ILE | 77 | 34.010 | -17.116 | 1.171 | 1.00 | 17.85 | E11 | | | | | |
| ATOM | 659 | O | ILE | 77 | 34.219 | -18.298 | 0.863 | 1.00 | 15.45 | E11 | | | | | |
| ATOM | 660 | N | GLN | 78 | 33.244 | -16.283 | 0.458 | 1.00 | 17.08 | E11 | | | | | |
| ATOM | 662 | CA | GLN | 78 | 32.351 | -16.746 | -0.621 | 1.00 | 15.15 | E11 | | | | | |
| ATOM | 663 | CB | GLN | 78 | 31.462 | -15.596 | -1.114 | 1.00 | 11.72 | E11 | | | | | |
| ATOM | 664 | CG | GLN | 78 | 30.497 | -15.075 | -0.061 | 1.00 | 16.16 | E11 | | | | | |
| ATOM | 665 | CD | GLN | 78 | 29.642 | -13.953 | -0.567 | 1.00 | 20.21 | E11 | | | | | |
| ATOM | 666 | OE1 | GLN | 78 | 30.117 | -12.853 | -0.870 | 1.00 | 19.80 | E11 | | | | | |
| ATOM | 667 | NE2 | GLN | 78 | 28.357 | -14.223 | -0.687 | 1.00 | 25.36 | E11 | | | | | |
| ATOM | 670 | C | GLN | 78 | 33.034 | -17.421 | -1.816 | 1.00 | 20.24 | E11 | | | | | |
| ATOM | 671 | O | GLN | 78 | 32.443 | -18.276 | -2.497 | 1.00 | 21.44 | E11 | | | | | |
| ATOM | 672 | N | ALA | 79 | 34.287 | -17.045 | -2.046 | 1.00 | 20.00 | E11 | | | | | |
| ATOM | 674 | CA | ALA | 79 | 35.077 | -17.570 | -3.136 | 1.00 | 18.42 | E11 | | | | | |
| ATOM | 675 | CB | ALA | 79 | 36.383 | -16.790 | -3.239 | 1.00 | 17.12 | E11 | | | | | |
| ATOM | 676 | C | ALA | 79 | 35.359 | -19.032 | -2.894 | 1.00 | 21.14 | E11 | | | | | |
| ATOM | 677 | O | ALA | 79 | 35.724 | -19.759 | -3.821 | 1.00 | 25.98 | E11 | | | | | |
| ATOM | 678 | N | TYR | 80 | 35.158 | -19.480 | -1.662 | 1.00 | 23.91 | E11 | | | | | |
| ATOM | 680 | CA | TYR | 80 | 35.440 | -20.866 | -1.322 | 1.00 | 23.33 | E11 | | | | | |
| ATOM | 681 | CB | TYR | 80 | 36.588 | -20.881 | -0.344 | 1.00 | 21.40 | E11 | | | | | |
| ATOM | 682 | CG | TYR | 80 | 37.792 | -20.181 | -0.856 | 1.00 | 11.41 | E11 | | | | | |
| ATOM | 683 | CD1 | TYR | 80 | 38.119 | -18.907 | -0.419 | 1.00 | 12.32 | E11 | | | | | |
| ATOM | 684 | CE1 | TYR | 80 | 39.232 | -18.254 | -0.919 | 1.00 | 17.37 | E11 | | | | | |
| ATOM | 685 | CD2 | TYR | 80 | 38.588 | -20.798 | -1.797 | 1.00 | 8.89 | E11 | | | | | |
| ATOM | 686 | CE2 | TYR | 80 | 39.681 | -20.186 | -2.312 | 1.00 | 13.11 | E11 | | | | | |

| | | | | | | | | | | | | | | | | |
|---|---|---|---|---|---|---|---|---|---|---|---|---|---|---|---|---|
| ATOM | 687 | N | TYR | 80 | 40.022 | -18.907 | -1.882 | 1.00 | 17.54 | EII | ATOM | 736 | CE2 | PHE | 85 | 36.957 | -19.669 | 5.006 | 1.00 | 24.28 | EII |
| ATOM | 688 | CA | TYR | 80 | 41.173 | -18.341 | -2.424 | 1.00 | 22.27 | EII | ATOM | 737 | CZ | PHE | 85 | 36.392 | -19.896 | 3.748 | 1.00 | 25.28 | EII |
| ATOM | 690 | C | TYR | 80 | 34.271 | -21.642 | -0.120 | 1.00 | 25.30 | EII | ATOM | 738 | C | PHE | 85 | 33.721 | -22.075 | 9.300 | 1.00 | 18.73 | EII |
| ATOM | 691 | O | TYR | 80 | 34.211 | -21.850 | 0.492 | 1.00 | 28.16 | EII | ATOM | 739 | O | PHE | 85 | 32.511 | -22.263 | 9.330 | 1.00 | 19.32 | EII |
| ATOM | 692 | N | PRO | 81 | 33.356 | -22.139 | -1.561 | 1.00 | 25.28 | EII | ATOM | 740 | N | ARG | 86 | 34.481 | -21.927 | 10.337 | 1.00 | 20.93 | EII |
| ATOM | 693 | CD | PRO | 81 | 33.422 | -22.129 | -3.026 | 1.00 | 25.19 | EII | ATOM | 742 | CA | ARG | 86 | 33.989 | -21.980 | 11.745 | 1.00 | 22.92 | EII |
| ATOM | 694 | CA | PRO | 81 | 32.066 | -22.666 | -1.111 | 1.00 | 25.19 | EII | ATOM | 743 | CB | ARG | 86 | 34.982 | -22.699 | 12.671 | 1.00 | 29.45 | EII |
| ATOM | 695 | CB | PRO | 81 | 31.290 | -22.804 | -2.408 | 1.00 | 27.52 | EII | ATOM | 744 | CG | ARG | 86 | 34.469 | -24.013 | 13.263 | 1.00 | 33.01 | EII |
| ATOM | 696 | CG | PRO | 81 | 32.003 | -21.880 | -3.356 | 1.00 | 27.81 | EII | ATOM | 745 | CD | ARG | 86 | 34.098 | -23.946 | 14.744 | 1.00 | 31.02 | EII |
| ATOM | 697 | C | PRO | 81 | 32.209 | -24.034 | -0.455 | 1.00 | 27.22 | EII | ATOM | 746 | NE | ARG | 86 | 33.776 | -25.286 | 15.212 | 1.00 | 38.52 | EII |
| ATOM | 698 | O | PRO | 81 | 31.297 | -24.496 | 0.232 | 1.00 | 30.43 | EII | ATOM | 748 | CZ | ARG | 86 | 34.674 | -26.270 | 15.363 | 1.00 | 46.41 | EII |
| ATOM | 699 | N | LYS | 82 | 33.318 | -24.713 | -0.727 | 1.00 | 26.41 | EII | ATOM | 749 | NH1 | ARG | 86 | 35.968 | -26.070 | 15.110 | 1.00 | 47.38 | EII |
| ATOM | 701 | CA | LYS | 82 | 33.532 | -26.027 | -0.151 | 1.00 | 23.98 | EII | ATOM | 752 | NH2 | ARG | 86 | 34.286 | -27.483 | 15.738 | 1.00 | 50.37 | EII |
| ATOM | 702 | CB | LYS | 82 | 34.060 | -26.995 | -1.197 | 1.00 | 32.16 | EII | ATOM | 755 | C | ARG | 86 | 33.824 | -20.539 | 12.219 | 1.00 | 22.05 | EII |
| ATOM | 703 | CG | LYS | 82 | 33.144 | -27.129 | -2.391 | 1.00 | 39.38 | EII | ATOM | 756 | O | ARG | 86 | 32.736 | -20.140 | 12.646 | 1.00 | 20.17 | EII |
| ATOM | 704 | CD | LYS | 82 | 33.404 | -28.427 | -3.126 | 1.00 | 50.19 | EII | ATOM | 757 | N | TYR | 87 | 34.926 | -19.793 | 12.209 | 1.00 | 17.64 | EII |
| ATOM | 705 | CE | LYS | 82 | 34.865 | -28.547 | -3.529 | 1.00 | 55.41 | EII | ATOM | 759 | CA | TYR | 87 | 34.910 | -18.396 | 12.607 | 1.00 | 20.00 | EII |
| ATOM | 706 | NZ | LYS | 82 | 35.169 | -29.885 | -4.135 | 1.00 | 61.54 | EII | ATOM | 760 | CB | TYR | 87 | 35.476 | -18.175 | 14.018 | 1.00 | 19.18 | EII |
| ATOM | 710 | C | LYS | 82 | 34.369 | -26.119 | 1.113 | 1.00 | 20.64 | EII | ATOM | 761 | CG | TYR | 87 | 35.050 | -19.161 | 15.077 | 1.00 | 16.85 | EII |
| ATOM | 711 | O | LYS | 82 | 34.577 | -27.219 | 1.608 | 1.00 | 23.09 | EII | ATOM | 762 | CD1 | TYR | 87 | 35.941 | -20.129 | 15.541 | 1.00 | 16.37 | EII |
| ATOM | 712 | N | VAL | 83 | 34.839 | -24.983 | 1.641 | 1.00 | 22.87 | EII | ATOM | 763 | CE1 | TYR | 87 | 35.580 | -21.036 | 16.530 | 1.00 | 19.08 | EII |
| ATOM | 714 | CA | VAL | 83 | 35.622 | -24.956 | 2.890 | 1.00 | 24.29 | EII | ATOM | 764 | CD2 | TYR | 87 | 33.776 | -19.116 | 15.624 | 1.00 | 18.07 | EII |
| ATOM | 715 | CB | VAL | 83 | 36.520 | -23.692 | 2.999 | 1.00 | 21.90 | EII | ATOM | 765 | CE2 | TYR | 87 | 33.387 | -20.020 | 16.622 | 1.00 | 19.85 | EII |
| ATOM | 716 | CG1 | VAL | 83 | 37.244 | -23.671 | 4.345 | 1.00 | 19.37 | EII | ATOM | 766 | CZ | TYR | 87 | 34.297 | -20.976 | 17.076 | 1.00 | 22.06 | EII |
| ATOM | 717 | CG2 | VAL | 83 | 37.510 | -23.630 | 1.859 | 1.00 | 23.80 | EII | ATOM | 767 | OH | TYR | 87 | 33.945 | -21.843 | 18.089 | 1.00 | 14.80 | EII |
| ATOM | 718 | C | VAL | 83 | 34.659 | -24.900 | 4.068 | 1.00 | 16.87 | EII | ATOM | 769 | C | TYR | 87 | 35.792 | -17.588 | 11.690 | 1.00 | 19.71 | EII |
| ATOM | 719 | O | VAL | 83 | 33.613 | -24.246 | 3.968 | 1.00 | 17.54 | EII | ATOM | 770 | O | TYR | 87 | 36.629 | -18.127 | 10.982 | 1.00 | 16.27 | EII |
| ATOM | 720 | N | SER | 84 | 35.056 | -25.470 | 5.211 | 1.00 | 19.48 | EII | ATOM | 771 | N | VAL | 88 | 35.543 | -16.286 | 11.704 | 1.00 | 22.25 | EII |
| ATOM | 722 | CA | SER | 84 | 34.204 | -25.450 | 6.403 | 1.00 | 17.86 | EII | ATOM | 773 | CA | VAL | 88 | 36.324 | -15.277 | 10.999 | 1.00 | 21.13 | EII |
| ATOM | 723 | CB | SER | 84 | 34.205 | -26.818 | 7.073 | 1.00 | 17.53 | EII | ATOM | 774 | CB | VAL | 88 | 35.447 | -14.283 | 10.170 | 1.00 | 20.08 | EII |
| ATOM | 724 | OG | SER | 84 | 33.451 | -27.719 | 6.293 | 1.00 | 23.80 | EII | ATOM | 775 | CG1 | VAL | 88 | 36.321 | -13.150 | 9.663 | 1.00 | 14.55 | EII |
| ATOM | 726 | C | SER | 84 | 34.582 | -24.364 | 7.417 | 1.00 | 16.87 | EII | ATOM | 776 | CG2 | VAL | 88 | 34.750 | -14.991 | 9.033 | 1.00 | 19.84 | EII |
| ATOM | 727 | O | SER | 84 | 35.207 | -24.648 | 8.446 | 1.00 | 17.54 | EII | ATOM | 777 | C | VAL | 88 | 36.891 | -14.483 | 12.197 | 1.00 | 24.05 | EII |
| ATOM | 728 | N | PHE | 85 | 34.169 | -23.132 | 7.123 | 1.00 | 19.48 | EII | ATOM | 778 | O | VAL | 88 | 36.116 | -13.848 | 12.916 | 1.00 | 27.17 | EII |
| ATOM | 730 | CA | PHE | 85 | 34.457 | -21.980 | 7.983 | 1.00 | 19.80 | EII | ATOM | 779 | N | CYS | 89 | 38.194 | -14.620 | 12.461 | 1.00 | 18.87 | EII |
| ATOM | 731 | CB | PHE | 85 | 34.098 | -20.669 | 7.295 | 1.00 | 19.01 | EII | ATOM | 781 | CA | CYS | 89 | 38.880 | -13.941 | 13.546 | 1.00 | 19.45 | EII |
| ATOM | 732 | CG | PHE | 85 | 34.902 | -20.393 | 6.059 | 1.00 | 21.80 | EII | ATOM | 782 | CB | CYS | 89 | 40.037 | -14.809 | 14.015 | 1.00 | 19.13 | EII |
| ATOM | 733 | CD1 | PHE | 85 | 34.205 | -20.612 | 4.798 | 1.00 | 23.35 | EII | ATOM | 783 | SG | CYS | 89 | 40.718 | -14.233 | 15.541 | 1.00 | 20.04 | EII |
| ATOM | 734 | CD2 | PHE | 85 | 36.204 | -19.921 | 6.153 | 1.00 | 24.88 | EII | ATOM | 784 | C | CYS | 89 | 39.412 | -12.599 | 13.073 | 1.00 | 20.04 | EII |
| ATOM | 735 | CE1 | PHE | 85 | 35.104 | -20.366 | 3.647 | 1.00 | 20.54 | EII | ATOM | 785 | O | CYS | 89 | 40.479 | -12.536 | 12.446 | 1.00 | 23.67 | EII |

- 38 -

- 39 -

| ATOM | 786 | N | VAL | 90 | 38.684 | -11.525 | 13.375 | 1.00 | 19.71 | E11 |
|------|-----|------|-----|-----|--------|---------|--------|------|-------|-----|
| ATOM | 788 | CA | VAL | 90 | 39.060 | -10.175 | 12.939 | 1.00 | 18.94 | E11 |
| ATOM | 789 | CB | VAL | 90 | 37.780 | -9.270 | 12.852 | 1.00 | 18.80 | E11 |
| ATOM | 790 | CG1 | VAL | 90 | 38.090 | -7.857 | 12.353 | 1.00 | 9.54 | E11 |
| ATOM | 791 | CG2 | VAL | 90 | 36.750 | -9.928 | 11.917 | 1.00 | 14.80 | E11 |
| ATOM | 792 | C | VAL | 90 | 40.068 | -9.633 | 13.938 | 1.00 | 21.76 | E11 |
| ATOM | 793 | O | VAL | 90 | 39.713 | -9.255 | 15.051 | 1.00 | 26.22 | E11 |
| ATOM | 794 | N | GLY | 91 | 41.332 | -9.607 | 13.548 | 1.00 | 20.81 | E11 |
| ATOM | 796 | CA | GLY | 91 | 42.365 | -9.127 | 14.441 | 1.00 | 17.50 | E11 |
| ATOM | 797 | C | GLY | 91 | 42.946 | -10.227 | 15.316 | 1.00 | 21.60 | E11 |
| ATOM | 798 | O | GLY | 91 | 42.278 | -11.206 | 15.644 | 1.00 | 19.80 | E11 |
| ATOM | 799 | N | ASN | 92 | 44.251 | -10.137 | 15.557 | 1.00 | 21.01 | E11 |
| ATOM | 801 | CA | ASN | 92 | 44.944 | -11.066 | 16.437 | 1.00 | 19.52 | E11 |
| ATOM | 802 | CB | ASN | 92 | 45.831 | -12.039 | 15.686 | 1.00 | 15.96 | E11 |
| ATOM | 803 | CG | ASN | 92 | 46.607 | -12.959 | 16.621 | 1.00 | 16.52 | E11 |
| ATOM | 804 | OD1 | ASN | 92 | 47.829 | -12.958 | 16.611 | 1.00 | 17.74 | E11 |
| ATOM | 805 | ND2 | ASN | 92 | 45.908 | -13.713 | 17.454 | 1.00 | 11.94 | E11 |
| ATOM | 806 | C | ASN | 92 | 45.807 | -10.229 | 17.350 | 1.00 | 19.99 | E11 |
| ATOM | 808 | O | ASN | 92 | 46.820 | -9.689 | 16.931 | 1.00 | 19.30 | E11 |
| ATOM | 809 | N | GLU | 93 | 45.409 | -10.147 | 18.609 | 1.00 | 19.66 | E11 |
| ATOM | 810 | CA | GLU | 93 | 46.140 | -9.361 | 19.593 | 1.00 | 19.36 | E11 |
| ATOM | 812 | CB | GLU | 93 | 47.494 | -10.012 | 19.892 | 1.00 | 21.17 | E11 |
| ATOM | 813 | CG | GLU | 93 | 47.362 | -11.423 | 20.451 | 1.00 | 21.08 | E11 |
| ATOM | 814 | CD | GLU | 93 | 48.672 | -12.011 | 20.901 | 1.00 | 24.02 | E11 |
| ATOM | 815 | OE1 | GLU | 93 | 49.660 | -11.250 | 21.025 | 1.00 | 28.58 | E11 |
| ATOM | 816 | OE2 | GLU | 93 | 48.708 | -13.237 | 21.168 | 1.00 | 28.58 | E11 |
| ATOM | 817 | C | GLU | 93 | 46.319 | -7.890 | 19.198 | 1.00 | 20.01 | E11 |
| ATOM | 818 | O | GLU | 93 | 47.397 | -7.323 | 19.358 | 1.00 | 18.58 | E11 |
| ATOM | 819 | N | VAL | 94 | 45.240 | -7.277 | 18.717 | 1.00 | 20.15 | E11 |
| ATOM | 820 | CA | VAL | 94 | 45.267 | -5.870 | 18.339 | 1.00 | 22.55 | E11 |
| ATOM | 822 | CB | VAL | 94 | 43.904 | -5.450 | 17.723 | 1.00 | 18.79 | E11 |
| ATOM | 823 | CG1 | VAL | 94 | 43.875 | -3.985 | 17.426 | 1.00 | 14.04 | E11 |
| ATOM | 824 | CG2 | VAL | 94 | 43.653 | -6.231 | 16.447 | 1.00 | 18.59 | E11 |
| ATOM | 825 | C | VAL | 94 | 43.615 | -5.005 | 19.569 | 1.00 | 26.22 | E11 |
| ATOM | 826 | O | VAL | 94 | 44.926 | -5.058 | 20.606 | 1.00 | 28.29 | E11 |
| ATOM | 827 | N | ALA | 95 | 46.706 | -4.249 | 19.465 | 1.00 | 27.52 | E11 |
| ATOM | 828 | CA | ALA | 95 | 47.153 | -3.373 | 20.547 | 1.00 | 29.76 | E11 |
| ATOM | 830 | CB | ALA | 95 | 48.643 | -3.491 | 20.754 | 1.00 | 33.96 | E11 |
| ATOM | 831 | C | ALA | 95 | 46.772 | -1.923 | 20.267 | 1.00 | 32.39 | E11 |
| ATOM | 832 | O | ALA | 95 | 46.428 | -1.582 | 19.143 | 1.00 | 31.98 | E11 |
| ATOM | 834 | N | GLY | 96 | 46.883 | -1.095 | 21.309 | 1.00 | 33.58 | E11 |
| ATOM | 836 | CA | GLY | 96 | 46.534 | 0.313 | 21.302 | 1.00 | 31.73 | E11 |
| ATOM | 837 | C | GLY | 96 | 46.101 | 1.023 | 20.049 | 1.00 | 33.19 | E11 |
| ATOM | 838 | O | GLY | 96 | 46.553 | 0.686 | 18.969 | 1.00 | 42.91 | E11 |
| ATOM | 839 | N | GLY | 97 | 45.249 | 2.035 | 20.199 | 1.00 | 31.36 | E11 |
| ATOM | 841 | CA | GLY | 97 | 44.820 | 2.832 | 19.061 | 1.00 | 26.65 | E11 |
| ATOM | 842 | C | GLY | 97 | 44.058 | 2.097 | 17.992 | 1.00 | 29.45 | E11 |
| ATOM | 843 | O | GLY | 97 | 42.935 | 2.472 | 17.670 | 1.00 | 33.34 | E11 |
| ATOM | 844 | N | ALA | 98 | 44.699 | 1.101 | 17.391 | 1.00 | 29.33 | E11 |
| ATOM | 846 | CA | ALA | 98 | 44.103 | 0.267 | 16.373 | 1.00 | 25.57 | E11 |
| ATOM | 847 | CB | ALA | 98 | 45.112 | -0.732 | 15.872 | 1.00 | 29.17 | E11 |
| ATOM | 848 | C | ALA | 98 | 42.892 | -0.442 | 16.943 | 1.00 | 25.33 | E11 |
| ATOM | 849 | O | ALA | 98 | 41.981 | -0.800 | 16.208 | 1.00 | 32.32 | E11 |
| ATOM | 850 | N | THR | 99 | 42.857 | -0.611 | 18.259 | 1.00 | 23.17 | E11 |
| ATOM | 852 | CA | THR | 99 | 41.724 | -1.256 | 18.918 | 1.00 | 22.94 | E11 |
| ATOM | 853 | CB | THR | 99 | 41.971 | -1.400 | 20.419 | 1.00 | 21.96 | E11 |
| ATOM | 854 | OG1 | THR | 99 | 42.281 | -0.115 | 20.955 | 1.00 | 27.95 | E11 |
| ATOM | 856 | CG2 | THR | 99 | 43.146 | -2.335 | 20.685 | 1.00 | 19.71 | E11 |
| ATOM | 857 | C | THR | 99 | 40.424 | -0.464 | 18.712 | 1.00 | 25.12 | E11 |
| ATOM | 858 | O | THR | 99 | 39.334 | -0.962 | 19.001 | 1.00 | 26.30 | E11 |
| ATOM | 859 | N | ARG | 100 | 40.549 | 0.772 | 18.227 | 1.00 | 27.60 | E11 |
| ATOM | 861 | CA | ARG | 100 | 39.407 | 1.638 | 17.970 | 1.00 | 25.72 | E11 |
| ATOM | 862 | CB | ARG | 100 | 39.894 | 3.036 | 17.587 | 1.00 | 29.73 | E11 |
| ATOM | 863 | CG | ARG | 100 | 38.781 | 4.067 | 17.419 | 0.00 | 28.42 | E11 |
| ATOM | 864 | CD | ARG | 100 | 37.996 | 4.272 | 18.711 | 0.00 | 28.92 | E11 |
| ATOM | 865 | NE | ARG | 100 | 38.836 | 4.773 | 19.797 | 0.00 | 29.00 | E11 |
| ATOM | 867 | CZ | ARG | 100 | 38.441 | 4.885 | 21.062 | 0.00 | 29.15 | E11 |
| ATOM | 868 | NH1 | ARG | 100 | 37.212 | 4.530 | 21.417 | 0.00 | 29.18 | E11 |
| ATOM | 871 | NH2 | ARG | 100 | 39.276 | 5.359 | 21.977 | 0.00 | 29.17 | E11 |
| ATOM | 874 | C | ARG | 100 | 38.595 | 1.075 | 16.817 | 1.00 | 26.99 | E11 |
| ATOM | 875 | O | ARG | 100 | 37.401 | 1.325 | 16.711 | 1.00 | 25.79 | E11 |
| ATOM | 876 | N | ASN | 101 | 39.260 | 0.322 | 15.947 | 1.00 | 23.98 | E11 |
| ATOM | 878 | CA | ASN | 101 | 38.615 | -0.245 | 14.775 | 1.00 | 25.37 | E11 |
| ATOM | 879 | CB | ASN | 101 | 39.568 | -0.196 | 13.578 | 1.00 | 23.53 | E11 |
| ATOM | 880 | CG | ASN | 101 | 39.901 | 1.224 | 13.163 | 1.00 | 24.69 | E11 |
| ATOM | 881 | OD1 | ASN | 101 | 41.033 | 1.514 | 12.754 | 1.00 | 24.16 | E11 |
| ATOM | 882 | ND2 | ASN | 101 | 38.919 | 2.124 | 13.265 | 1.00 | 19.72 | E11 |
| ATOM | 885 | C | ASN | 101 | 38.117 | -1.652 | 14.968 | 1.00 | 23.11 | E11 |
| ATOM | 886 | O | ASN | 101 | 37.494 | -2.221 | 14.084 | 1.00 | 22.33 | E11 |
| ATOM | 887 | N | LEU | 102 | 38.378 | -2.204 | 16.141 | 1.00 | 25.04 | E11 |

- 40 -

| ATOM | 889 | N | LEU | 102 | 37.961 | -3.570 | 16.464 | 1.00 | 20.19 | E11 | ATOM | 933 | NZ | LYS | 107 | 29.058 | -2.995 | 17.632 | 0.00 | 35.98 | E11 |
|---|---|---|---|---|---|---|---|---|---|---|---|---|---|---|---|---|---|---|---|---|---|
| ATOM | 890 | H | LEU | 102 | 38.360 | -3.899 | 17.898 | 1.00 | 18.00 | E11 | ATOM | 937 | C | LYS | 107 | 30.022 | -5.483 | 11.462 | 1.00 | 23.82 | E11 |
| ATOM | 891 | CG | LEU | 102 | 38.770 | -5.345 | 18.096 | 1.00 | 19.27 | E11 | ATOM | 938 | O | LYS | 107 | 29.070 | -6.125 | 10.975 | 1.00 | 26.60 | E11 |
| ATOM | 892 | CD1 | LEU | 102 | 39.656 | -5.792 | 16.930 | 1.00 | 11.88 | E11 | ATOM | 939 | N | ASN | 108 | 30.932 | -4.879 | 10.715 | 1.00 | 20.53 | E11 |
| ATOM | 893 | CD2 | LEU | 102 | 39.500 | -5.476 | 19.428 | 1.00 | 16.59 | E11 | ATOM | 941 | CA | ASN | 108 | 30.848 | -4.929 | 9.279 | 1.00 | 20.34 | E11 |
| ATOM | 894 | C | LEU | 102 | 36.134 | -4.586 | 16.232 | 1.00 | 18.66 | E11 | ATOM | 942 | CB | ASN | 108 | 31.797 | -3.906 | 8.656 | 1.00 | 22.18 | E11 |
| ATOM | 895 | O | LEU | 102 | 36.488 | -3.310 | 15.307 | 1.00 | 20.44 | E11 | ATOM | 943 | CG | ASN | 108 | 31.387 | -2.463 | 8.951 | 1.00 | 21.63 | E11 |
| ATOM | 896 | N | VAL | 103 | 35.619 | -3.550 | 17.066 | 1.00 | 21.11 | E11 | ATOM | 944 | OD1 | ASN | 108 | 30.250 | -2.181 | 9.378 | 1.00 | 18.08 | E11 |
| ATOM | 898 | CA | VAL | 103 | 34.170 | -2.897 | 16.955 | 1.00 | 21.06 | E11 | ATOM | 945 | ND2 | ASN | 108 | 32.314 | -1.545 | 8.732 | 1.00 | 17.80 | E11 |
| ATOM | 899 | CB | VAL | 103 | 33.382 | -3.406 | 18.120 | 1.00 | 16.38 | E11 | ATOM | 948 | C | ASN | 108 | 31.032 | -6.305 | 8.657 | 1.00 | 20.14 | E11 |
| ATOM | 900 | CG1 | VAL | 103 | 31.958 | -3.406 | 18.098 | 1.00 | 9.59 | E11 | ATOM | 949 | O | ASN | 108 | 30.308 | -6.630 | 7.735 | 1.00 | 27.18 | E11 |
| ATOM | 901 | CG2 | VAL | 103 | 34.006 | -3.259 | 19.410 | 1.00 | 15.15 | E11 | ATOM | 950 | N | VAL | 109 | 31.941 | -7.133 | 9.169 | 1.00 | 14.59 | E11 |
| ATOM | 902 | C | VAL | 103 | 33.492 | -3.201 | 15.614 | 1.00 | 17.66 | E11 | ATOM | 952 | CA | VAL | 109 | 32.178 | -8.462 | 8.602 | 1.00 | 16.93 | E11 |
| ATOM | 903 | O | VAL | 103 | 32.684 | -3.984 | 15.111 | 1.00 | 21.01 | E11 | ATOM | 953 | CB | VAL | 109 | 33.462 | -9.102 | 9.227 | 1.00 | 12.18 | E11 |
| ATOM | 904 | N | PRO | 104 | 33.827 | -2.042 | 15.015 | 1.00 | 18.81 | E11 | ATOM | 954 | CG1 | VAL | 109 | 33.544 | -10.605 | 8.966 | 1.00 | 19.89 | E11 |
| ATOM | 905 | CG | PRO | 104 | 34.703 | -0.992 | 15.566 | 1.00 | 18.76 | E11 | ATOM | 955 | CG2 | VAL | 109 | 34.716 | -8.408 | 8.657 | 1.00 | 19.76 | E11 |
| ATOM | 906 | CB | PRO | 104 | 33.323 | 1.624 | 13.697 | 1.00 | 17.71 | E11 | ATOM | 956 | C | VAL | 109 | 30.925 | -9.276 | 8.897 | 1.00 | 18.45 | E11 |
| ATOM | 907 | CB | PRO | 104 | 34.019 | -0.280 | 13.483 | 1.00 | 15.77 | E11 | ATOM | 957 | O | VAL | 109 | 30.342 | -9.923 | 8.008 | 1.00 | 19.40 | E11 |
| ATOM | 908 | CG | PRO | 104 | 34.191 | 0.224 | 14.867 | 1.00 | 12.44 | E11 | ATOM | 958 | N | HIS | 110 | 30.449 | -9.129 | 10.131 | 1.00 | 17.21 | E11 |
| ATOM | 909 | C | PRO | 104 | 33.700 | -2.603 | 12.593 | 1.00 | 17.96 | E11 | ATOM | 960 | CA | HIS | 110 | 29.261 | -9.805 | 10.581 | 1.00 | 17.25 | E11 |
| ATOM | 910 | O | PRO | 104 | 32.902 | -2.857 | 11.688 | 1.00 | 21.40 | E11 | ATOM | 961 | CB | HIS | 110 | 28.998 | -9.457 | 12.040 | 1.00 | 14.81 | E11 |
| ATOM | 911 | N | ALA | 105 | 34.940 | -3.094 | 12.614 | 1.00 | 14.40 | E11 | ATOM | 962 | CG | HIS | 110 | 27.724 | -10.071 | 12.568 | 1.00 | 13.50 | E11 |
| ATOM | 913 | CA | ALA | 105 | 35.347 | -4.068 | 11.616 | 1.00 | 14.37 | E11 | ATOM | 963 | CD2 | HIS | 110 | 27.267 | -11.341 | 12.533 | 1.00 | 15.45 | E11 |
| ATOM | 914 | CB | ALA | 105 | 36.845 | -4.386 | 11.725 | 1.00 | 13.55 | E11 | ATOM | 964 | ND1 | HIS | 110 | 26.701 | -9.307 | 13.076 | 1.00 | 14.73 | E11 |
| ATOM | 915 | C | ALA | 105 | 34.521 | -5.327 | 11.886 | 1.00 | 17.26 | E11 | ATOM | 966 | CE1 | HIS | 110 | 25.656 | -10.080 | 13.313 | 1.00 | 14.73 | E11 |
| ATOM | 916 | O | ALA | 105 | 34.007 | -5.940 | 10.945 | 1.00 | 19.91 | E11 | ATOM | 967 | NE2 | HIS | 110 | 25.974 | -11.320 | 12.998 | 1.00 | 12.16 | E11 |
| ATOM | 917 | N | MET | 106 | 34.429 | -5.733 | 13.157 | 1.00 | 16.38 | E11 | ATOM | 969 | C | HIS | 110 | 28.043 | -9.515 | 9.693 | 1.00 | 19.56 | E11 |
| ATOM | 919 | CA | MET | 106 | 33.663 | -6.911 | 13.525 | 1.00 | 20.32 | E11 | ATOM | 970 | O | HIS | 110 | 27.394 | -10.459 | 9.201 | 1.00 | 18.91 | E11 |
| ATOM | 920 | CB | MET | 106 | 33.795 | -7.220 | 15.025 | 1.00 | 17.57 | E11 | ATOM | 971 | N | GLY | 111 | 27.767 | -8.232 | 9.448 | 1.00 | 16.88 | E11 |
| ATOM | 921 | CG | MET | 106 | 35.163 | -7.719 | 15.476 | 1.00 | 23.04 | E11 | ATOM | 973 | CA | GLY | 111 | 26.636 | -7.858 | 8.613 | 1.00 | 17.54 | E11 |
| ATOM | 922 | SD | MET | 106 | 35.205 | -8.444 | 17.191 | 1.00 | 23.36 | E11 | ATOM | 974 | C | GLY | 111 | 26.754 | -8.422 | 7.200 | 1.00 | 19.51 | E11 |
| ATOM | 923 | CE | MET | 106 | 35.238 | -6.985 | 18.221 | 1.00 | 21.92 | E11 | ATOM | 975 | O | GLY | 111 | 25.771 | -8.889 | 6.615 | 1.00 | 21.08 | E11 |
| ATOM | 924 | C | MET | 106 | 32.186 | -6.752 | 13.133 | 1.00 | 23.48 | E11 | ATOM | 976 | N | ALA | 112 | 27.964 | -8.355 | 6.648 | 1.00 | 19.68 | E11 |
| ATOM | 925 | O | MET | 106 | 31.566 | -7.694 | 12.637 | 1.00 | 21.62 | E11 | ATOM | 978 | CA | ALA | 112 | 28.264 | -8.890 | 5.325 | 1.00 | 19.14 | E11 |
| ATOM | 926 | N | LYS | 107 | 31.623 | -5.569 | 13.338 | 1.00 | 23.06 | E11 | ATOM | 979 | CB | ALA | 112 | 29.724 | -8.680 | 5.010 | 1.00 | 14.31 | E11 |
| ATOM | 928 | CA | LYS | 107 | 30.225 | -5.346 | 12.975 | 1.00 | 23.25 | E11 | ATOM | 980 | C | ALA | 112 | 27.959 | -10.379 | 5.257 | 1.00 | 19.95 | E11 |
| ATOM | 929 | CB | LYS | 107 | 29.771 | -3.964 | 13.423 | 1.00 | 27.08 | E11 | ATOM | 981 | O | ALA | 112 | 27.394 | -10.871 | 4.271 | 1.00 | 27.32 | E11 |
| ATOM | 930 | CG | LYS | 107 | 29.476 | -3.862 | 14.881 | 1.00 | 33.96 | E11 | ATOM | 982 | N | LEU | 113 | 28.278 | -11.085 | 6.334 | 1.00 | 21.29 | E11 |
| ATOM | 931 | CD | LYS | 107 | 28.911 | -2.503 | 15.191 | 1.00 | 33.96 | E11 | ATOM | 984 | CA | LEU | 113 | 28.084 | -12.531 | 6.415 | 1.00 | 20.25 | E11 |
| ATOM | 932 | CE | LYS | 107 | 28.187 | -2.498 | 16.538 | 1.00 | 37.38 | E11 | ATOM | 985 | CB | LEU | 113 | 28.876 | -13.152 | 7.587 | 1.00 | 18.63 | E11 |

- 41 -

| ATOM | 986 | CG | LEU | 113 | 30.411 | -13.345 | 7.526 | 1.00 | 20.64 | E11 | ATOM | 1033 | CB | HIS | 120 | 26.380 | -21.013 | 10.123 | 1.00 | 22.51 | E11 |
|------|-----|------|-----|-----|--------|---------|-------|------|-------|-----|------|------|------|-----|-----|--------|---------|--------|------|-------|-----|
| ATOM | 987 | CD1 | LEU | 113 | 30.902 | -13.843 | 8.881 | 1.00 | 22.14 | E11 | ATOM | 1034 | CG | HIS | 120 | 27.088 | -21.126 | 8.807 | 1.00 | 26.06 | E11 |
| ATOM | 988 | CD2 | LEU | 113 | 30.817 | -14.358 | 6.429 | 1.00 | 16.54 | E11 | ATOM | 1035 | CD2 | HIS | 120 | 26.800 | -20.589 | 7.594 | 1.00 | 26.54 | E11 |
| ATOM | 989 | C | LEU | 113 | 30.601 | -12.850 | 6.539 | 1.00 | 21.94 | E11 | ATOM | 1036 | ND1 | HIS | 120 | 28.207 | -21.909 | 8.625 | 1.00 | 23.50 | E11 |
| ATOM | 990 | O | LEU | 113 | 26.109 | -13.770 | 5.874 | 1.00 | 20.15 | E11 | ATOM | 1038 | CE1 | HIS | 120 | 28.579 | -21.856 | 7.355 | 1.00 | 24.07 | E11 |
| ATOM | 991 | N | VAL | 114 | 25.887 | 12.082 | 7.364 | 1.00 | 17.61 | E11 | ATOM | 1039 | NE2 | HIS | 120 | 27.740 | -21.060 | 6.711 | 1.00 | 23.79 | E11 |
| ATOM | 993 | H | VAL | 114 | 24.460 | 12.280 | 7.547 | 1.00 | 13.34 | E11 | ATOM | 1041 | C | HIS | 120 | 28.026 | -19.525 | 11.145 | 1.00 | 20.88 | E11 |
| ATOM | 994 | CA | VAL | 114 | 23.939 | -11.403 | 8.704 | 1.00 | 11.74 | E11 | ATOM | 1042 | O | HIS | 120 | 28.566 | -20.304 | 11.913 | 1.00 | 28.45 | E11 |
| ATOM | 995 | CG1 | VAL | 114 | 22.450 | -11.247 | 8.631 | 1.00 | 9.52 | E11 | ATOM | 1043 | N | ILE | 121 | 28.687 | -18.661 | 10.394 | 1.00 | 20.65 | E11 |
| ATOM | 996 | CG2 | VAL | 114 | 24.328 | -12.016 | 10.007 | 1.00 | 7.08 | E11 | ATOM | 1045 | CA | ILE | 121 | 30.102 | -18.416 | 10.579 | 1.00 | 21.10 | E11 |
| ATOM | 997 | C | VAL | 114 | 23.748 | -11.961 | 6.220 | 1.00 | 16.80 | E11 | ATOM | 1046 | CB | ILE | 121 | 30.780 | -18.063 | 9.265 | 1.00 | 20.09 | E11 |
| ATOM | 998 | O | VAL | 114 | 22.848 | -12.674 | 5.810 | 1.00 | 21.94 | E11 | ATOM | 1047 | CG2 | ILE | 121 | 32.256 | -17.800 | 9.504 | 1.00 | 18.09 | E11 |
| ATOM | 999 | N | ALA | 115 | 24.212 | -10.944 | 5.503 | 1.00 | 20.11 | E11 | ATOM | 1048 | CG1 | ILE | 121 | 30.528 | -19.162 | 8.229 | 1.00 | 21.22 | E11 |
| ATOM | 1001 | CA | ALA | 115 | 23.610 | -10.589 | 4.222 | 1.00 | 18.66 | E11 | ATOM | 1049 | CD1 | ILE | 121 | 30.822 | -18.733 | 6.795 | 1.00 | 17.07 | E11 |
| ATOM | 1002 | CB | ALA | 115 | 24.243 | -9.334 | 3.659 | 1.00 | 15.05 | E11 | ATOM | 1050 | C | ILE | 121 | 30.268 | -17.232 | 11.499 | 1.00 | 23.82 | E11 |
| ATOM | 1003 | C | ALA | 115 | 23.764 | -11.716 | 3.205 | 1.00 | 17.87 | E11 | ATOM | 1051 | O | ILE | 121 | 30.037 | -16.093 | 11.083 | 1.00 | 24.64 | E11 |
| ATOM | 1004 | O | ALA | 115 | 22.858 | -11.929 | 2.402 | 1.00 | 15.44 | E11 | ATOM | 1052 | N | LYS | 122 | 30.675 | -17.513 | 12.736 | 1.00 | 24.45 | E11 |
| ATOM | 1005 | N | ALA | 116 | 24.875 | -12.460 | 3.267 | 1.00 | 18.01 | E11 | ATOM | 1054 | CA | LYS | 122 | 30.873 | -16.501 | 13.762 | 1.00 | 20.95 | E11 |
| ATOM | 1007 | CA | ALA | 116 | 25.152 | -13.533 | 2.311 | 1.00 | 14.70 | E11 | ATOM | 1055 | CB | LYS | 122 | 30.859 | -17.142 | 15.149 | 1.00 | 24.44 | E11 |
| ATOM | 1008 | CB | ALA | 116 | 26.668 | -13.805 | 2.254 | 1.00 | 15.50 | E11 | ATOM | 1056 | CG | LYS | 122 | 29.604 | -17.955 | 15.435 | 1.00 | 25.87 | E11 |
| ATOM | 1009 | C | ALA | 116 | 24.458 | -14.790 | 2.713 | 1.00 | 14.17 | E11 | ATOM | 1057 | CD | LYS | 122 | 28.367 | -17.078 | 15.465 | 1.00 | 33.72 | E11 |
| ATOM | 1010 | O | ALA | 116 | 24.486 | -15.772 | 1.976 | 1.00 | 19.57 | E11 | ATOM | 1058 | CE | LYS | 122 | 27.144 | -17.838 | 15.981 | 1.00 | 37.35 | E11 |
| ATOM | 1011 | N | GLY | 117 | 23.878 | -14.779 | 3.902 | 1.00 | 14.63 | E11 | ATOM | 1059 | NZ | LYS | 122 | 26.792 | -19.036 | 15.161 | 0.00 | 35.72 | E11 |
| ATOM | 1013 | CA | GLY | 117 | 24.228 | -15.967 | 4.386 | 1.00 | 13.94 | E11 | ATOM | 1063 | C | LYS | 122 | 32.121 | -15.659 | 13.603 | 1.00 | 19.09 | E11 |
| ATOM | 1014 | C | GLY | 117 | 24.268 | -16.946 | 4.900 | 1.00 | 15.26 | E11 | ATOM | 1064 | O | LYS | 122 | 31.953 | -14.369 | 13.886 | 1.00 | 16.10 | E11 |
| ATOM | 1015 | O | GLY | 117 | 24.083 | -18.159 | 4.772 | 1.00 | 20.26 | E11 | ATOM | 1067 | CA | VAL | 123 | 32.995 | -13.363 | 13.810 | 1.00 | 15.39 | E11 |
| ATOM | 1016 | N | LEU | 118 | 25.379 | -16.442 | 5.431 | 1.00 | 20.98 | E11 | ATOM | 1068 | CB | VAL | 123 | 32.424 | -12.055 | 13.239 | 1.00 | 11.67 | E11 |
| ATOM | 1018 | CA | LEU | 118 | 26.423 | -17.305 | 5.997 | 1.00 | 22.07 | E11 | ATOM | 1069 | CG1 | VAL | 123 | 33.423 | -10.904 | 13.376 | 1.00 | 6.31 | E11 |
| ATOM | 1019 | CB | LEU | 118 | 27.743 | -17.115 | 5.260 | 1.00 | 20.47 | E11 | ATOM | 1070 | CG2 | VAL | 123 | 32.051 | -12.274 | 11.813 | 1.00 | 9.19 | E11 |
| ATOM | 1020 | CG | LEU | 118 | 27.833 | -17.450 | 3.766 | 1.00 | 17.96 | E11 | ATOM | 1071 | C | VAL | 123 | 33.490 | -13.113 | 15.231 | 1.00 | 19.43 | E11 |
| ATOM | 1021 | CD1 | LEU | 118 | 29.156 | -16.883 | 3.230 | 1.00 | 13.96 | E11 | ATOM | 1072 | O | VAL | 123 | 32.696 | -12.914 | 16.156 | 1.00 | 22.00 | E11 |
| ATOM | 1022 | CD2 | LEU | 118 | 27.752 | -18.937 | 3.505 | 1.00 | 21.10 | E11 | ATOM | 1073 | N | THR | 124 | 34.790 | -13.089 | 15.418 | 1.00 | 16.25 | E11 |
| ATOM | 1023 | C | LEU | 118 | 26.601 | -16.969 | 7.485 | 1.00 | 19.85 | E11 | ATOM | 1075 | CA | THR | 124 | 35.281 | -12.879 | 16.755 | 1.00 | 17.42 | E11 |
| ATOM | 1024 | O | LEU | 118 | 27.680 | -17.098 | 8.050 | 1.00 | 25.77 | E11 | ATOM | 1076 | CB | THR | 124 | 35.345 | -14.272 | 17.511 | 1.00 | 16.30 | E11 |
| ATOM | 1025 | N | GLY | 119 | 25.503 | -16.589 | 8.128 | 1.00 | 23.41 | E11 | ATOM | 1077 | OG1 | THR | 124 | 35.800 | -14.084 | 18.859 | 1.00 | 15.42 | E11 |
| ATOM | 1027 | CA | GLY | 119 | 25.538 | -16.239 | 9.537 | 1.00 | 22.55 | E11 | ATOM | 1079 | CG2 | THR | 124 | 36.211 | -15.317 | 16.751 | 1.00 | 8.83 | E11 |
| ATOM | 1028 | C | GLY | 119 | 25.937 | -17.362 | 10.476 | 1.00 | 24.22 | E11 | ATOM | 1080 | C | THR | 124 | 36.631 | -12.172 | 16.654 | 1.00 | 18.46 | E11 |
| ATOM | 1029 | O | GLY | 119 | 25.971 | -17.159 | 11.687 | 1.00 | 19.73 | E11 | ATOM | 1081 | O | THR | 124 | 36.933 | -11.572 | 15.619 | 1.00 | 16.30 | E11 |
| ATOM | 1030 | N | HIS | 120 | 26.150 | -18.566 | 9.957 | 1.00 | 20.48 | E11 | ATOM | 1082 | N | THR | 125 | 37.390 | -12.154 | 17.742 | 1.00 | 20.41 | E11 |
| ATOM | 1032 | CA | HIS | 120 | 26.568 | -19.671 | 10.816 | 1.00 | 20.48 | E11 | | | | | | | | | | | |

| | | | | | | | | | | | | | | |
|---|---|---|---|---|---|---|---|---|---|---|---|---|---|---|
| ATOM | 1084 | CA | THR | 125 | 38.721 | -11.549 | 17.736 | 1.00 | 16.04 | EII | ATOM | 1135 | CA | ILE | 131 | 45.436 | -8.398 | 28.780 | 1.00 | 13.27 | EII |
| ATOM | 1085 | CB | THR | 125 | 38.689 | -10.051 | 18.117 | 1.00 | 19.18 | EII | ATOM | 1136 | CB | ILE | 131 | 44.256 | -8.253 | 27.757 | 1.00 | 12.64 | EII |
| ATOM | 1086 | OG1 | THR | 125 | 39.949 | -9.441 | 17.778 | 1.00 | 21.22 | EII | ATOM | 1137 | CG2 | ILE | 131 | 44.754 | -7.835 | 26.417 | 1.00 | 12.50 | EII |
| ATOM | 1088 | CG2 | THR | 125 | 38.377 | -9.848 | 19.627 | 1.00 | 20.31 | EII | ATOM | 1138 | CG1 | ILE | 131 | 43.407 | -9.509 | 27.668 | 1.00 | 14.45 | EII |
| ATOM | 1089 | C | THR | 125 | 39.568 | -12.414 | 18.674 | 1.00 | 13.58 | EII | ATOM | 1139 | CD1 | ILE | 131 | 41.981 | -9.166 | 27.284 | 1.00 | 14.53 | EII |
| ATOM | 1090 | O | THR | 125 | 39.016 | -13.208 | 19.428 | 1.00 | 16.04 | EII | ATOM | 1140 | C | ILE | 131 | 44.907 | -8.580 | 30.192 | 1.00 | 8.50 | EII |
| ATOM | 1091 | N | SER | 126 | 40.885 | -12.284 | 18.647 | 1.00 | 14.03 | EII | ATOM | 1141 | O | ILE | 131 | 44.191 | -7.741 | 30.694 | 1.00 | 12.91 | EII |
| ATOM | 1093 | CA | SER | 126 | 41.741 | -13.129 | 19.464 | 1.00 | 9.15 | EII | ATOM | 1142 | N | LEU | 132 | 45.240 | -9.696 | 30.822 | 1.00 | 14.32 | EII |
| ATOM | 1094 | CB | SER | 126 | 42.670 | -13.769 | 18.562 | 1.00 | 7.45 | EII | ATOM | 1144 | CA | LEU | 132 | 44.822 | -9.954 | 32.206 | 1.00 | 18.09 | EII |
| ATOM | 1095 | OG | SER | 126 | 43.668 | -14.577 | 19.291 | 1.00 | 21.18 | EII | ATOM | 1145 | CB | LEU | 132 | 44.816 | -11.462 | 32.532 | 1.00 | 10.55 | EII |
| ATOM | 1097 | C | SER | 126 | 42.534 | -12.231 | 20.342 | 1.00 | 11.06 | EII | ATOM | 1146 | CG | LEU | 132 | 43.742 | -12.368 | 31.910 | 1.00 | 16.79 | EII |
| ATOM | 1098 | O | SER | 126 | 43.198 | -11.322 | 19.853 | 1.00 | 11.92 | EII | ATOM | 1147 | CD1 | LEU | 132 | 43.983 | -13.787 | 32.357 | 1.00 | 8.56 | EII |
| ATOM | 1099 | N | VAL | 127 | 42.519 | -12.497 | 21.643 | 1.00 | 9.13 | EII | ATOM | 1148 | CD2 | LEU | 132 | 42.334 | -11.949 | 32.318 | 1.00 | 8.10 | EII |
| ATOM | 1101 | CA | VAL | 127 | 43.250 | -11.627 | 22.552 | 1.00 | 8.28 | EII | ATOM | 1149 | C | LEU | 132 | 45.719 | -9.232 | 33.219 | 1.00 | 17.12 | EII |
| ATOM | 1102 | CB | VAL | 127 | 42.328 | -11.026 | 23.642 | 1.00 | 9.27 | EII | ATOM | 1150 | O | LEU | 132 | 46.913 | -9.472 | 33.278 | 1.00 | 22.27 | EII |
| ATOM | 1103 | CG1 | VAL | 127 | 41.272 | -10.135 | 22.999 | 1.00 | 8.14 | EII | ATOM | 1151 | N | GLY | 133 | 45.165 | -8.278 | 33.946 | 1.00 | 17.71 | EII |
| ATOM | 1104 | CG2 | VAL | 127 | 41.665 | -12.140 | 24.449 | 1.00 | 8.57 | EII | ATOM | 1153 | CA | GLY | 133 | 45.946 | -7.606 | 34.954 | 1.00 | 21.46 | EII |
| ATOM | 1105 | C | VAL | 127 | 44.395 | -12.377 | 23.200 | 1.00 | 12.85 | EII | ATOM | 1154 | C | GLY | 133 | 46.163 | -8.581 | 36.108 | 1.00 | 22.05 | EII |
| ATOM | 1106 | O | VAL | 127 | 44.447 | -13.606 | 23.797 | 1.00 | 17.82 | EII | ATOM | 1155 | O | GLY | 133 | 45.102 | -8.733 | 36.614 | 1.00 | 22.29 | EII |
| ATOM | 1107 | N | SER | 128 | 45.288 | -11.613 | 23.455 | 1.00 | 16.23 | EII | ATOM | 1156 | N | VAL | 134 | 47.281 | -9.281 | 36.497 | 1.00 | 21.78 | EII |
| ATOM | 1109 | CA | SER | 128 | 46.459 | -12.140 | 24.172 | 1.00 | 13.33 | EII | ATOM | 1158 | CA | VAL | 134 | 45.195 | -10.254 | 37.584 | 1.00 | 20.18 | EII |
| ATOM | 1110 | CB | SER | 128 | 46.628 | -13.439 | 25.136 | 1.00 | 17.17 | EII | ATOM | 1159 | CB | VAL | 134 | 44.363 | -9.789 | 38.839 | 1.00 | 20.27 | EII |
| ATOM | 1111 | OG | SER | 128 | 47.298 | -14.747 | 25.957 | 1.00 | 19.99 | EII | ATOM | 1160 | CG1 | VAL | 134 | 44.645 | -10.697 | 40.044 | 1.00 | 16.68 | EII |
| ATOM | 1113 | C | SER | 128 | 48.796 | -14.668 | 25.136 | 1.00 | 15.99 | EII | ATOM | 1161 | CG2 | VAL | 134 | 44.676 | -8.339 | 39.182 | 1.00 | 16.37 | EII |
| ATOM | 1114 | O | SER | 128 | 46.244 | -12.197 | 26.551 | 1.00 | 13.96 | EII | ATOM | 1162 | C | VAL | 134 | 45.102 | -11.549 | 37.032 | 1.00 | 19.47 | EII |
| ATOM | 1115 | N | GLN | 129 | 45.683 | -11.277 | 26.574 | 1.00 | 20.08 | EII | ATOM | 1163 | O | VAL | 134 | 43.555 | -11.525 | 36.405 | 1.00 | 24.54 | EII |
| ATOM | 1117 | CA | GLN | 129 | 46.714 | -17.084 | 28.715 | 1.00 | 9.26 | EII | ATOM | 1164 | N | PHE | 135 | 45.295 | -12.672 | 37.251 | 1.00 | 21.45 | EII |
| ATOM | 1118 | CB | GLN | 129 | 46.628 | -13.277 | 28.016 | 1.00 | 16.21 | EII | ATOM | 1166 | CA | PHE | 135 | 44.791 | -13.946 | 36.724 | 1.00 | 27.04 | EII |
| ATOM | 1119 | CG | GLN | 129 | 47.298 | -14.747 | 28.443 | 1.00 | 16.59 | EII | ATOM | 1167 | CB | PHE | 135 | 45.655 | -14.438 | 35.556 | 1.00 | 28.22 | EII |
| ATOM | 1120 | CD | GLN | 129 | 48.796 | -14.668 | 28.547 | 1.00 | 13.90 | EII | ATOM | 1168 | CG | PHE | 135 | 47.061 | -14.818 | 35.945 | 1.00 | 32.70 | EII |
| ATOM | 1121 | OE1 | GLN | 129 | 49.471 | -16.018 | 28.795 | 1.00 | 18.08 | EII | ATOM | 1169 | CD1 | PHE | 135 | 47.333 | -16.068 | 36.523 | 1.00 | 35.80 | EII |
| ATOM | 1122 | NE2 | GLN | 129 | 50.706 | -16.094 | 28.918 | 1.00 | 19.61 | EII | ATOM | 1170 | CD2 | PHE | 135 | 48.121 | -13.948 | 35.706 | 1.00 | 33.97 | EII |
| ATOM | 1125 | C | GLN | 129 | 48.682 | -17.084 | 28.839 | 1.00 | 17.05 | EII | ATOM | 1171 | CE1 | PHE | 135 | 48.649 | -16.453 | 36.860 | 1.00 | 37.66 | EII |
| ATOM | 1126 | O | GLN | 129 | 47.299 | -12.257 | 28.715 | 1.00 | 20.96 | EII | ATOM | 1172 | CE2 | PHE | 135 | 49.437 | -14.316 | 36.034 | 1.00 | 33.85 | EII |
| ATOM | 1127 | N | ALA | 130 | 47.072 | -12.006 | 29.894 | 1.00 | 14.25 | EII | ATOM | 1173 | CZ | PHE | 135 | 49.705 | -15.576 | 36.615 | 1.00 | 36.89 | EII |
| ATOM | 1129 | CA | ALA | 130 | 48.057 | -11.467 | 27.965 | 1.00 | 17.29 | EII | ATOM | 1174 | C | PHE | 135 | 47.790 | -15.020 | 37.790 | 1.00 | 28.22 | EII |
| ATOM | 1130 | CB | ALA | 130 | 48.717 | -10.319 | 27.602 | 1.00 | 17.62 | EII | ATOM | 1175 | O | PHE | 135 | 44.724 | -15.020 | 37.514 | 1.00 | 29.78 | EII |
| ATOM | 1131 | C | ALA | 130 | 49.742 | -9.754 | 28.546 | 1.00 | 17.50 | EII | ATOM | 1176 | N | SER | 136 | 44.369 | -16.171 | 38.990 | 1.00 | 29.67 | EII |
| ATOM | 1132 | O | ALA | 130 | 47.686 | -9.255 | 28.881 | 1.00 | 20.49 | EII | ATOM | 1178 | CA | SER | 136 | 45.159 | -14.660 | 40.106 | 1.00 | 29.62 | EII |
| ATOM | 1133 | N | ILE | 131 | 48.050 | -8.257 | 29.490 | 1.00 | 15.13 | EII | ATOM | 1179 | CB | SER | 136 | 45.139 | -15.577 | 40.259 | 1.00 | 31.49 | EII |
| ATOM | | | | | 46.435 | -9.409 | 28.430 | | | | ATOM | | | | | 46.465 | -16.316 | | | | |

| ATOM | 1181 | OG | SER | 136 | 46.395 | -17.239 | 41.337 | 1.00 | 30.26 | EII |
|------|------|-----|-----|-----|--------|---------|--------|------|-------|-----|
| ATOM | 1182 | C | SER | 136 | 44.835 | -14.757 | 41.340 | 1.00 | 29.17 | EII |
| ATOM | 1183 | O | SER | 136 | 45.382 | -13.664 | 41.514 | 1.00 | 32.51 | EII |
| ATOM | 1184 | N | PRO | 137 | 43.902 | -15.245 | 42.176 | 1.00 | 24.82 | EII |
| ATOM | 1185 | CD | PRO | 137 | 43.442 | -14.637 | 43.434 | 1.00 | 21.92 | EII |
| ATOM | 1186 | CA | PRO | 137 | 43.144 | -16.463 | 41.885 | 1.00 | 21.08 | EII |
| ATOM | 1187 | CB | PRO | 137 | 42.569 | -16.818 | 43.254 | 1.00 | 24.77 | EII |
| ATOM | 1188 | CG | PRO | 137 | 43.793 | -15.480 | 43.793 | 1.00 | 23.68 | EII |
| ATOM | 1189 | C | PRO | 137 | 42.224 | -16.135 | 40.879 | 1.00 | 18.17 | EII |
| ATOM | 1190 | O | PRO | 137 | 42.037 | -14.987 | 40.769 | 1.00 | 16.79 | EII |
| ATOM | 1191 | N | PRO | 138 | 41.611 | -17.152 | 40.160 | 1.00 | 18.08 | EII |
| ATOM | 1192 | CD | PRO | 138 | 41.542 | -18.572 | 40.327 | 1.00 | 19.32 | EII |
| ATOM | 1193 | CA | PRO | 138 | 41.920 | -17.011 | 39.118 | 1.00 | 18.81 | EII |
| ATOM | 1194 | CB | PRO | 138 | 40.516 | -17.011 | 39.120 | 1.00 | 17.59 | EII |
| ATOM | 1195 | CG | PRO | 138 | 41.278 | -19.215 | 39.460 | 1.00 | 10.24 | EII |
| ATOM | 1196 | C | PRO | 138 | 39.357 | -16.050 | 39.120 | 1.00 | 22.18 | EII |
| ATOM | 1197 | O | PRO | 138 | 38.905 | -15.287 | 38.606 | 1.00 | 20.31 | EII |
| ATOM | 1198 | N | SER | 139 | 38.918 | -16.053 | 30.717 | 1.00 | 23.40 | EII |
| ATOM | 1199 | CA | SER | 139 | 37.825 | -15.196 | 41.149 | 1.00 | 25.51 | EII |
| ATOM | 1200 | CB | SER | 139 | 37.306 | -15.623 | 42.522 | 1.00 | 28.22 | EII |
| ATOM | 1201 | OG | SER | 139 | 38.351 | -15.708 | 43.482 | 1.00 | 26.99 | EII |
| ATOM | 1202 | C | SER | 139 | 38.225 | -13.734 | 41.171 | 1.00 | 26.36 | EII |
| ATOM | 1203 | O | SER | 139 | 37.367 | -12.852 | 41.219 | 1.00 | 30.98 | EII |
| ATOM | 1204 | N | ALA | 140 | 39.527 | -13.483 | 41.169 | 1.00 | 24.45 | EII |
| ATOM | 1205 | CA | ALA | 140 | 40.060 | -12.125 | 41.162 | 1.00 | 26.86 | EII |
| ATOM | 1206 | CB | ALA | 140 | 41.216 | -12.016 | 42.144 | 1.00 | 25.41 | EII |
| ATOM | 1207 | C | ALA | 140 | 40.547 | -11.752 | 39.745 | 1.00 | 27.95 | EII |
| ATOM | 1208 | O | ALA | 140 | 41.391 | -10.871 | 39.597 | 1.00 | 29.14 | EII |
| ATOM | 1209 | N | GLY | 141 | 39.992 | -12.402 | 38.722 | 1.00 | 21.64 | EII |
| ATOM | 1210 | CA | GLY | 141 | 40.408 | -12.154 | 37.360 | 1.00 | 19.01 | EII |
| ATOM | 1211 | C | GLY | 141 | 40.027 | -10.776 | 36.906 | 1.00 | 22.49 | EII |
| ATOM | 1212 | O | GLY | 141 | 38.912 | -10.310 | 37.202 | 1.00 | 22.85 | EII |
| ATOM | 1213 | N | SER | 142 | 40.943 | -10.111 | 36.203 | 1.00 | 18.60 | EII |
| ATOM | 1214 | CA | SER | 142 | 40.666 | -8.774 | 35.703 | 1.00 | 22.53 | EII |
| ATOM | 1215 | CB | SER | 142 | 40.559 | -7.774 | 36.859 | 1.00 | 18.70 | EII |
| ATOM | 1216 | OG | SER | 142 | 41.670 | -8.292 | 37.568 | 1.00 | 29.13 | EII |
| ATOM | 1217 | C | SER | 142 | 41.670 | -7.694 | 34.653 | 1.00 | 19.11 | EII |
| ATOM | 1218 | O | SER | 142 | 42.841 | -8.645 | 34.708 | 1.00 | 20.60 | EII |
| ATOM | 1225 | N | PHE | 143 | 41.163 | -7.524 | 33.691 | 1.00 | 16.68 | EII |
| ATOM | 1227 | CA | PHE | 143 | 41.934 | -6.961 | 32.599 | 1.00 | 17.02 | EII |
| ATOM | 1228 | CB | PHE | 143 | 41.017 | -6.353 | 31.506 | 1.00 | 9.66 | EII |
| ATOM | 1229 | CG | PHE | 143 | 40.097 | -7.347 | 30.814 | 1.00 | 15.11 | EII |
| ATOM | 1230 | CD1 | PHE | 143 | 38.752 | -7.032 | 30.597 | 1.00 | 17.84 | EII |
| ATOM | 1231 | CD2 | PHE | 143 | 40.571 | -8.579 | 30.343 | 1.00 | 18.29 | EII |
| ATOM | 1232 | CE1 | PHE | 143 | 37.890 | -7.924 | 29.913 | 1.00 | 18.60 | EII |
| ATOM | 1233 | CE2 | PHE | 143 | 39.722 | -9.473 | 29.665 | 1.00 | 18.95 | EII |
| ATOM | 1234 | CZ | PHE | 143 | 38.371 | -9.143 | 29.448 | 1.00 | 10.32 | EII |
| ATOM | 1235 | C | PHE | 143 | 42.770 | -5.821 | 33.131 | 1.00 | 15.65 | EII |
| ATOM | 1236 | O | PHE | 143 | 42.538 | -5.285 | 34.203 | 1.00 | 21.02 | EII |
| ATOM | 1237 | N | THR | 144 | 43.738 | -5.424 | 32.341 | 1.00 | 17.78 | EII |
| ATOM | 1239 | CA | THR | 144 | 44.538 | -4.287 | 32.701 | 1.00 | 14.92 | EII |
| ATOM | 1240 | CB | THR | 144 | 45.743 | -4.175 | 31.753 | 1.00 | 12.89 | EII |
| ATOM | 1241 | OG1 | THR | 144 | 45.251 | -4.029 | 30.425 | 1.00 | 18.01 | EII |
| ATOM | 1243 | CG2 | THR | 144 | 46.613 | -5.431 | 31.780 | 1.00 | 12.19 | EII |
| ATOM | 1244 | C | THR | 144 | 43.557 | -3.093 | 32.473 | 1.00 | 16.29 | EII |
| ATOM | 1245 | O | THR | 144 | 42.455 | -3.271 | 31.964 | 1.00 | 17.25 | EII |
| ATOM | 1246 | N | GLY | 145 | 43.975 | -1.881 | 32.809 | 1.00 | 19.98 | EII |
| ATOM | 1248 | CA | GLY | 145 | 43.123 | -0.717 | 32.623 | 1.00 | 23.74 | EII |
| ATOM | 1249 | C | GLY | 145 | 43.090 | -0.281 | 31.168 | 1.00 | 25.56 | EII |
| ATOM | 1250 | O | GLY | 145 | 42.120 | 0.328 | 30.696 | 1.00 | 26.45 | EII |
| ATOM | 1251 | N | GLU | 146 | 44.184 | -0.571 | 30.471 | 1.00 | 28.46 | EII |
| ATOM | 1253 | CA | GLU | 146 | 44.335 | -0.254 | 29.058 | 1.00 | 29.55 | EII |
| ATOM | 1254 | CB | GLU | 146 | 45.770 | -0.534 | 28.641 | 1.00 | 35.72 | EII |
| ATOM | 1255 | CG | GLU | 146 | 46.136 | -0.024 | 27.251 | 1.00 | 48.28 | EII |
| ATOM | 1256 | CD | GLU | 146 | 47.608 | -0.256 | 26.896 | 1.00 | 52.95 | EII |
| ATOM | 1257 | OE1 | GLU | 146 | 48.325 | -0.945 | 27.669 | 1.00 | 57.40 | EII |
| ATOM | 1258 | OE2 | GLU | 146 | 48.040 | 0.245 | 25.829 | 1.00 | 56.88 | EII |
| ATOM | 1259 | C | GLU | 146 | 43.402 | -1.149 | 28.264 | 1.00 | 27.83 | EII |
| ATOM | 1260 | O | GLU | 146 | 42.676 | -0.694 | 27.373 | 1.00 | 27.74 | EII |
| ATOM | 1261 | N | ALA | 147 | 43.411 | -2.429 | 28.623 | 1.00 | 25.33 | EII |
| ATOM | 1263 | CA | ALA | 147 | 42.577 | -3.420 | 27.974 | 1.00 | 23.99 | EII |
| ATOM | 1264 | CB | ALA | 147 | 43.039 | -4.817 | 28.351 | 1.00 | 25.45 | EII |
| ATOM | 1265 | C | ALA | 147 | 41.135 | -3.217 | 28.398 | 1.00 | 25.33 | EII |
| ATOM | 1266 | O | ALA | 147 | 40.217 | -3.379 | 27.591 | 1.00 | 29.48 | EII |
| ATOM | 1267 | N | ALA | 148 | 40.940 | -2.876 | 29.671 | 1.00 | 21.39 | EII |
| ATOM | 1269 | CA | ALA | 148 | 39.610 | -2.664 | 30.221 | 1.00 | 20.14 | EII |
| ATOM | 1270 | CB | ALA | 148 | 39.694 | -2.252 | 31.677 | 1.00 | 22.28 | EII |
| ATOM | 1271 | C | ALA | 148 | 38.852 | -1.624 | 29.427 | 1.00 | 21.80 | EII |
| ATOM | 1272 | O | ALA | 148 | 37.633 | -1.748 | 29.242 | 1.00 | 25.99 | EII |
| ATOM | 1273 | N | ALA | 149 | 39.585 | -0.610 | 28.965 | 1.00 | 20.83 | EII |

- 44 -

| ATOM | 1275 | CA | ALA | 149 | 39.056 | 0.496 | 28.171 | 1.00 | 22.56 | EII |
|------|------|-----|-----|-----|--------|--------|--------|------|-------|-----|
| ATOM | 1276 | CB | ALA | 149 | 40.156 | 1.553 | 27.931 | 1.00 | 20.10 | EII |
| ATOM | 1277 | C | ALA | 149 | 38.438 | 0.063 | 26.826 | 1.00 | 23.78 | EII |
| ATOM | 1278 | O | ALA | 149 | 37.479 | 0.671 | 26.387 | 1.00 | 22.84 | EII |
| ATOM | 1279 | N | PHE | 150 | 39.006 | -0.933 | 26.141 | 1.00 | 25.83 | EII |
| ATOM | 1280 | CA | PHE | 150 | 38.417 | -1.372 | 24.871 | 1.00 | 26.63 | EII |
| ATOM | 1281 | CB | PHE | 150 | 39.456 | -1.431 | 23.743 | 1.00 | 22.07 | EII |
| ATOM | 1282 | CG | PHE | 150 | 40.469 | -2.539 | 23.896 | 1.00 | 26.47 | EII |
| ATOM | 1283 | CD1 | PHE | 150 | 40.186 | -3.020 | 23.443 | 1.00 | 23.68 | EII |
| ATOM | 1284 | CD2 | PHE | 150 | 41.708 | -2.302 | 24.487 | 1.00 | 22.55 | EII |
| ATOM | 1285 | CE1 | PHE | 150 | 41.115 | -4.853 | 23.578 | 1.00 | 23.20 | EII |
| ATOM | 1286 | CE2 | PHE | 150 | 42.637 | -3.328 | 24.620 | 1.00 | 22.09 | EII |
| ATOM | 1287 | CZ | PHE | 150 | 42.335 | -4.608 | 24.165 | 1.00 | 16.63 | EII |
| ATOM | 1288 | C | PHE | 150 | 37.664 | -2.699 | 24.961 | 1.00 | 24.39 | EII |
| ATOM | 1289 | O | PHE | 150 | 36.758 | -2.944 | 24.177 | 1.00 | 30.55 | EII |
| ATOM | 1290 | N | MET | 151 | 37.982 | -3.518 | 25.953 | 1.00 | 21.82 | EII |
| ATOM | 1291 | CA | MET | 151 | 37.330 | -4.819 | 26.090 | 1.00 | 21.52 | EII |
| ATOM | 1292 | CB | MET | 151 | 38.068 | -5.704 | 27.085 | 1.00 | 20.06 | EII |
| ATOM | 1293 | CG | MET | 151 | 39.333 | -6.300 | 26.463 | 1.00 | 13.78 | EII |
| ATOM | 1294 | SD | MET | 151 | 39.048 | -7.292 | 24.914 | 1.00 | 11.52 | EII |
| ATOM | 1295 | CE | MET | 151 | 38.328 | -8.725 | 25.667 | 1.00 | 19.93 | EII |
| ATOM | 1296 | C | MET | 151 | 35.846 | -4.818 | 26.383 | 1.00 | 20.57 | EII |
| ATOM | 1297 | O | MET | 151 | 35.132 | -5.759 | 26.014 | 1.00 | 23.29 | EII |
| ATOM | 1298 | N | GLY | 152 | 35.362 | -3.739 | 26.982 | 1.00 | 19.16 | EII |
| ATOM | 1299 | CA | GLY | 152 | 33.942 | -3.657 | 27.293 | 1.00 | 16.01 | EII |
| ATOM | 1300 | C | GLY | 152 | 33.026 | -3.842 | 26.097 | 1.00 | 16.88 | EII |
| ATOM | 1301 | O | GLY | 152 | 32.267 | -4.805 | 26.044 | 1.00 | 18.74 | EII |
| ATOM | 1302 | N | PRO | 153 | 33.076 | -2.938 | 25.108 | 1.00 | 18.28 | EII |
| ATOM | 1303 | CA | PRO | 153 | 32.278 | -2.978 | 23.876 | 1.00 | 19.77 | EII |
| ATOM | 1304 | CB | PRO | 153 | 32.778 | -1.761 | 23.113 | 1.00 | 19.96 | EII |
| ATOM | 1305 | CG | PRO | 153 | 33.239 | -0.848 | 24.209 | 1.00 | 19.98 | EII |
| ATOM | 1306 | CD | PRO | 153 | 32.481 | -4.265 | 23.066 | 1.00 | 21.42 | EII |
| ATOM | 1307 | C | PRO | 153 | 31.534 | -4.729 | 22.410 | 1.00 | 18.40 | EII |
| ATOM | 1308 | O | PRO | 153 | 33.718 | -4.784 | 23.051 | 1.00 | 18.19 | EII |
| ATOM | 1309 | N | VAL | 154 | 34.018 | -2.938 | 22.356 | 1.00 | 17.58 | EII |
| ATOM | 1310 | CA | VAL | 154 | 35.515 | -6.363 | 22.432 | 1.00 | 13.15 | EII |
| ATOM | 1311 | CB | VAL | 154 | 35.787 | -7.736 | 21.931 | 1.00 | 14.81 | EII |
| ATOM | 1312 | CG1 | VAL | 154 | 36.307 | -5.391 | 21.610 | 1.00 | 17.13 | EII |
| ATOM | 1313 | CG2 | VAL | 154 | 33.224 | -7.179 | 22.998 | 1.00 | 19.09 | EII |
| ATOM | 1319 | O | VAL | 154 | 32.490 | -7.880 | 22.319 | 1.00 | 21.85 | EII |
| ATOM | 1320 | N | VAL | 155 | 33.326 | -7.328 | 24.319 | 1.00 | 21.59 | EII |
| ATOM | 1322 | CA | VAL | 155 | 32.634 | -8.406 | 25.036 | 1.00 | 21.07 | EII |
| ATOM | 1323 | CB | VAL | 155 | 33.014 | -8.400 | 26.531 | 1.00 | 19.33 | EII |
| ATOM | 1324 | CG1 | VAL | 155 | 31.924 | -8.946 | 27.354 | 1.00 | 21.54 | EII |
| ATOM | 1325 | CG2 | VAL | 155 | 34.232 | -9.243 | 26.746 | 1.00 | 22.38 | EII |
| ATOM | 1326 | C | VAL | 155 | 31.116 | -8.390 | 24.834 | 1.00 | 24.83 | EII |
| ATOM | 1327 | O | VAL | 155 | 30.487 | -9.421 | 24.521 | 1.00 | 24.56 | EII |
| ATOM | 1328 | N | GLN | 156 | 30.543 | -7.198 | 24.952 | 1.00 | 25.40 | EII |
| ATOM | 1330 | CA | GLN | 156 | 29.119 | -7.015 | 24.781 | 1.00 | 23.68 | EII |
| ATOM | 1331 | CB | GLN | 156 | 28.734 | -5.577 | 25.138 | 1.00 | 20.95 | EII |
| ATOM | 1332 | CG | GLN | 156 | 29.134 | -5.174 | 26.578 | 1.00 | 23.89 | EII |
| ATOM | 1333 | CD | GLN | 156 | 28.605 | -3.798 | 26.990 | 1.00 | 24.62 | EII |
| ATOM | 1334 | OE1 | GLN | 156 | 27.519 | -3.400 | 26.576 | 1.00 | 27.99 | EII |
| ATOM | 1335 | NE2 | GLN | 156 | 29.362 | -3.078 | 27.822 | 1.00 | 23.16 | EII |
| ATOM | 1338 | C | GLN | 156 | 28.696 | -7.391 | 23.367 | 1.00 | 22.90 | EII |
| ATOM | 1339 | O | GLN | 156 | 27.692 | -8.068 | 23.197 | 1.00 | 30.63 | EII |
| ATOM | 1340 | N | PHE | 157 | 29.487 | -7.016 | 22.355 | 1.00 | 21.81 | EII |
| ATOM | 1342 | CA | PHE | 157 | 29.185 | -7.330 | 20.961 | 1.00 | 17.32 | EII |
| ATOM | 1343 | CB | PHE | 157 | 30.319 | -6.851 | 20.045 | 1.00 | 21.95 | EII |
| ATOM | 1344 | CG | PHE | 157 | 30.155 | -7.253 | 18.595 | 1.00 | 22.85 | EII |
| ATOM | 1345 | CD1 | PHE | 157 | 29.265 | -6.582 | 17.757 | 1.00 | 19.94 | EII |
| ATOM | 1346 | CD2 | PHE | 157 | 30.866 | -8.328 | 18.080 | 1.00 | 20.42 | EII |
| ATOM | 1347 | CE1 | PHE | 157 | 29.084 | -6.966 | 16.449 | 1.00 | 23.80 | EII |
| ATOM | 1348 | CE2 | PHE | 157 | 30.686 | -8.729 | 16.755 | 1.00 | 25.63 | EII |
| ATOM | 1349 | CZ | PHE | 157 | 29.791 | -8.044 | 15.940 | 1.00 | 17.08 | EII |
| ATOM | 1350 | C | PHE | 157 | 29.051 | -8.821 | 20.789 | 1.00 | 14.45 | EII |
| ATOM | 1351 | O | PHE | 157 | 28.076 | -9.320 | 20.210 | 1.00 | 16.50 | EII |
| ATOM | 1352 | N | LEU | 158 | 30.049 | -9.516 | 21.322 | 1.00 | 18.52 | EII |
| ATOM | 1354 | CA | LEU | 158 | 30.115 | -10.971 | 21.251 | 1.00 | 14.63 | EII |
| ATOM | 1355 | CB | LEU | 158 | 31.374 | -11.472 | 21.943 | 1.00 | 14.63 | EII |
| ATOM | 1356 | CG | LEU | 158 | 32.711 | -11.770 | 21.225 | 1.00 | 13.22 | EII |
| ATOM | 1357 | CD1 | LEU | 158 | 32.704 | -11.411 | 19.775 | 1.00 | 7.52 | EII |
| ATOM | 1358 | CD2 | LEU | 158 | 33.861 | -11.099 | 21.987 | 1.00 | 11.20 | EII |
| ATOM | 1359 | C | LEU | 158 | 28.863 | -11.561 | 21.903 | 1.00 | 20.14 | EII |
| ATOM | 1360 | O | LEU | 158 | 28.173 | -12.405 | 21.326 | 1.00 | 17.52 | EII |
| ATOM | 1361 | N | ALA | 159 | 28.520 | -11.044 | 23.075 | 1.00 | 21.40 | EII |
| ATOM | 1363 | CA | ALA | 159 | 27.331 | -11.478 | 23.766 | 1.00 | 18.39 | EII |
| ATOM | 1364 | CB | ALA | 159 | 27.184 | -10.709 | 25.052 | 1.00 | 16.14 | EII |
| ATOM | 1365 | C | ALA | 159 | 26.112 | -11.262 | 22.879 | 1.00 | 22.51 | EII |

- 45 -

| | | | | | | | | | | | | | |
|---|---|---|---|---|---|---|---|---|---|---|---|---|---|
| ATOM | 1366 | C | ALA | 159 | 25.262 | -12.137 | 22.749 | 1.00 | 27.16 | E11 | | | |
| ATOM | 1367 | O | ALA | 159 | 26.020 | -10.110 | 22.236 | 1.00 | 24.18 | E11 | | | |
| ATOM | 1369 | N | ARG | 160 | 24.862 | -9.834 | 21.400 | 1.00 | 27.01 | E11 | | | |
| ATOM | 1370 | CA | ARG | 160 | 24.849 | -8.359 | 21.038 | 1.00 | 31.21 | E11 | | | |
| ATOM | 1371 | CB | ARG | 160 | 24.874 | -7.437 | 22.283 | 1.00 | 36.86 | E11 | | | |
| ATOM | 1372 | CG | ARG | 160 | 24.831 | -5.949 | 21.927 | 0.00 | 34.47 | E11 | | | |
| ATOM | 1373 | CD | ARG | 160 | 23.585 | -5.555 | 21.272 | 0.00 | 34.88 | E11 | | | |
| ATOM | 1374 | NE | ARG | 160 | 23.050 | -4.338 | 21.336 | 0.00 | 34.58 | E11 | | | |
| ATOM | 1375 | CZ | ARG | 160 | 23.643 | -3.373 | 22.029 | 0.00 | 34.67 | E11 | | | |
| ATOM | 1376 | NH1 | ARG | 160 | 21.914 | -4.084 | 20.150 | 0.00 | 34.67 | E11 | | | |
| ATOM | 1379 | NH2 | ARG | 160 | 24.768 | -10.693 | 20.702 | 1.00 | 29.59 | E11 | | | |
| ATOM | 1382 | C | ARG | 160 | 23.675 | -11.091 | 19.633 | 1.00 | 31.49 | E11 | | | |
| ATOM | 1383 | O | ARG | 160 | 25.897 | -11.170 | 19.657 | 1.00 | 29.30 | E11 | | | |
| ATOM | 1384 | N | THR | 161 | 25.892 | -11.961 | 18.448 | 1.00 | 23.87 | E11 | | | |
| ATOM | 1386 | CA | THR | 161 | 26.964 | -11.442 | 17.519 | 1.00 | 25.64 | E11 | | | |
| ATOM | 1387 | CB | THR | 161 | 28.202 | -11.417 | 18.237 | 1.00 | 35.45 | E11 | | | |
| ATOM | 1388 | OG1 | THR | 161 | 26.650 | -10.019 | 17.099 | 1.00 | 25.20 | E11 | | | |
| ATOM | 1390 | CG2 | THR | 161 | 26.117 | -13.436 | 18.700 | 1.00 | 20.87 | E11 | | | |
| ATOM | 1391 | C | THR | 161 | 26.268 | -14.212 | 17.765 | 1.00 | 28.69 | E11 | | | |
| ATOM | 1392 | O | THR | 161 | 26.144 | -13.838 | 19.955 | 1.00 | 20.69 | E11 | | | |
| ATOM | 1393 | N | ASN | 162 | 26.335 | -15.252 | 20.297 | 1.00 | 21.37 | E11 | | | |
| ATOM | 1395 | CA | ASN | 162 | 25.101 | -16.065 | 19.850 | 1.00 | 21.45 | E11 | | | |
| ATOM | 1396 | CB | ASN | 162 | 24.896 | -17.322 | 20.667 | 1.00 | 24.95 | E11 | | | |
| ATOM | 1397 | CG | ASN | 162 | 24.061 | -17.350 | 21.569 | 0.00 | 23.59 | E11 | | | |
| ATOM | 1398 | ND2 | ASN | 162 | 25.658 | -18.369 | 20.365 | 0.00 | 23.59 | E11 | | | |
| ATOM | 1399 | C | ASN | 162 | 27.650 | -15.836 | 19.721 | 1.00 | 18.45 | E11 | | | |
| ATOM | 1402 | O | ASN | 162 | 27.692 | -16.947 | 19.198 | 1.00 | 21.27 | E11 | | | |
| ATOM | 1403 | N | ALA | 163 | 28.731 | -15.071 | 19.832 | 1.00 | 21.25 | E11 | | | |
| ATOM | 1404 | CA | ALA | 163 | 30.581 | -14.406 | 19.338 | 1.00 | 15.07 | E11 | | | |
| ATOM | 1406 | CB | ALA | 163 | 30.042 | -15.474 | 18.428 | 1.00 | 14.66 | E11 | | | |
| ATOM | 1407 | C | ALA | 163 | 30.950 | -15.644 | 20.537 | 1.00 | 18.39 | E11 | | | |
| ATOM | 1408 | O | ALA | 163 | 30.711 | -15.027 | 21.576 | 1.00 | 19.02 | E11 | | | |
| ATOM | 1409 | N | PRO | 164 | 31.994 | -16.501 | 20.441 | 1.00 | 18.89 | E11 | | | |
| ATOM | 1410 | CD | PRO | 164 | 32.430 | -17.356 | 19.320 | 1.00 | 18.20 | E11 | | | |
| ATOM | 1411 | CA | PRO | 164 | 32.902 | -16.680 | 21.569 | 1.00 | 15.20 | E11 | | | |
| ATOM | 1413 | CB | PRO | 164 | 33.476 | -18.049 | 21.288 | 1.00 | 12.76 | E11 | | | |
| ATOM | 1414 | CG | PRO | 164 | 33.733 | -17.953 | 19.832 | 1.00 | 15.39 | E11 | | | |
| ATOM | 1415 | C | PRO | 164 | 34.008 | -15.652 | 21.503 | 1.00 | 15.48 | E11 | | | |
| ATOM | 1416 | O | PRO | 164 | 34.060 | -14.853 | 20.575 | 1.00 | 16.54 | E11 | | | |
| ATOM | 1417 | N | LEU | 165 | 34.909 | -15.724 | 22.479 | 1.00 | 16.07 | E11 | | | |
| ATOM | 1419 | CA | LEU | 165 | 36.094 | -14.871 | 22.566 | 1.00 | 14.18 | E11 | | | |
| ATOM | 1420 | CB | LEU | 165 | 36.252 | -14.192 | 23.926 | 1.00 | 12.99 | E11 | | | |
| ATOM | 1421 | CG | LEU | 165 | 37.556 | -13.378 | 24.107 | 1.00 | 12.73 | E11 | | | |
| ATOM | 1422 | CD1 | LEU | 165 | 37.687 | -12.239 | 23.083 | 1.00 | 7.60 | E11 | | | |
| ATOM | 1423 | CD2 | LEU | 165 | 37.659 | -12.827 | 25.503 | 1.00 | 15.41 | E11 | | | |
| ATOM | 1424 | C | LEU | 165 | 37.229 | -15.877 | 22.382 | 1.00 | 17.35 | E11 | | | |
| ATOM | 1425 | O | LEU | 165 | 37.135 | -17.012 | 22.851 | 1.00 | 17.24 | E11 | | | |
| ATOM | 1426 | N | MET | 166 | 38.327 | -15.455 | 21.769 | 1.00 | 18.39 | E11 | | | |
| ATOM | 1428 | CA | MET | 166 | 39.420 | -16.384 | 21.525 | 1.00 | 15.20 | E11 | | | |
| ATOM | 1429 | CB | MET | 166 | 39.778 | -16.422 | 20.053 | 1.00 | 12.45 | E11 | | | |
| ATOM | 1430 | CG | MET | 166 | 38.842 | -17.251 | 19.224 | 1.00 | 14.21 | E11 | | | |
| ATOM | 1431 | SD | MET | 166 | 39.443 | -17.354 | 17.543 | 1.00 | 17.89 | E11 | | | |
| ATOM | 1432 | CE | MET | 166 | 38.508 | -18.684 | 17.086 | 1.00 | 19.34 | E11 | | | |
| ATOM | 1433 | C | MET | 166 | 40.568 | -15.836 | 22.309 | 1.00 | 9.37 | E11 | | | |
| ATOM | 1434 | O | MET | 166 | 40.742 | -14.623 | 22.348 | 1.00 | 8.75 | E11 | | | |
| ATOM | 1435 | N | ALA | 167 | 41.246 | -16.689 | 23.061 | 1.00 | 10.41 | E11 | | | |
| ATOM | 1437 | CA | ALA | 167 | 42.356 | -16.228 | 23.883 | 1.00 | 8.72 | E11 | | | |
| ATOM | 1438 | CB | ALA | 167 | 42.024 | -16.359 | 25.364 | 1.00 | 10.72 | E11 | | | |
| ATOM | 1439 | C | ALA | 167 | 43.560 | -17.082 | 23.562 | 1.00 | 9.26 | E11 | | | |
| ATOM | 1440 | O | ALA | 167 | 43.405 | -18.282 | 23.301 | 1.00 | 7.80 | E11 | | | |
| ATOM | 1441 | N | ASN | 168 | 44.706 | -16.418 | 23.417 | 1.00 | 10.70 | E11 | | | |
| ATOM | 1443 | CA | ASN | 168 | 45.969 | -17.080 | 23.139 | 1.00 | 10.70 | E11 | | | |
| ATOM | 1444 | CB | ASN | 168 | 46.873 | -16.188 | 22.253 | 1.00 | 11.37 | E11 | | | |
| ATOM | 1445 | CG | ASN | 168 | 46.232 | -15.836 | 20.887 | 1.00 | 15.39 | E11 | | | |
| ATOM | 1446 | OD1 | ASN | 168 | 45.580 | -16.657 | 20.286 | 1.00 | 11.28 | E11 | | | |
| ATOM | 1447 | ND2 | ASN | 168 | 46.373 | -14.585 | 20.446 | 1.00 | 16.69 | E11 | | | |
| ATOM | 1450 | C | ASN | 168 | 46.552 | -17.285 | 24.554 | 1.00 | 11.56 | E11 | | | |
| ATOM | 1451 | O | ASN | 168 | 46.955 | -16.335 | 25.210 | 1.00 | 12.66 | E11 | | | |
| ATOM | 1452 | N | ILE | 169 | 46.527 | -18.534 | 25.015 | 1.00 | 12.33 | E11 | | | |
| ATOM | 1454 | CA | ILE | 169 | 46.955 | -18.916 | 26.359 | 1.00 | 12.64 | E11 | | | |
| ATOM | 1455 | CB | ILE | 169 | 45.754 | -19.572 | 27.121 | 1.00 | 10.51 | E11 | | | |
| ATOM | 1456 | CG2 | ILE | 169 | 46.194 | -20.132 | 28.457 | 1.00 | 14.10 | E11 | | | |
| ATOM | 1457 | CG1 | ILE | 169 | 44.649 | -18.511 | 27.341 | 1.00 | 8.64 | E11 | | | |
| ATOM | 1458 | CD1 | ILE | 169 | 43.285 | -19.047 | 27.696 | 1.00 | 8.65 | E11 | | | |
| ATOM | 1459 | C | ILE | 169 | 48.229 | -19.737 | 26.464 | 1.00 | 12.08 | E11 | | | |
| ATOM | 1460 | O | ILE | 169 | 48.307 | -20.862 | 25.946 | 1.00 | 15.16 | E11 | | | |
| ATOM | 1461 | N | TYR | 170 | 49.253 | -19.142 | 27.077 | 1.00 | 11.67 | E11 | | | |
| ATOM | 1463 | CA | TYR | 170 | 50.536 | -19.806 | 27.233 | 1.00 | 14.66 | E11 | | | |
| ATOM | 1464 | CB | TYR | 170 | 51.578 | -19.112 | 26.388 | 1.00 | 10.69 | E11 | | | |
| ATOM | 1465 | CG | TYR | 170 | 51.337 | -19.165 | 24.882 | 1.00 | 12.85 | E11 | | | |

- 46 -

| | | | | | | | | | | | |
|---|---|---|---|---|---|---|---|---|---|---|---|
| ATOM | 1466 | C | TYR | 170 | 50.608 | -18.169 | 24.240 | 1.00 | 10.45 | | E11 |
| ATOM | 1467 | CE1 | TYR | 170 | 50.397 | -18.191 | 22.901 | 1.00 | 7.11 | | E11 |
| ATOM | 1468 | CD2 | TYR | 170 | 51.871 | -20.214 | 24.098 | 1.00 | 13.16 | | E11 |
| ATOM | 1469 | CE2 | TYR | 170 | 51.671 | -20.245 | 22.732 | 1.00 | 5.20 | | E11 |
| ATOM | 1470 | CZ | TYR | 170 | 50.913 | -19.218 | 22.143 | 1.00 | 8.47 | | E11 |
| ATOM | 1471 | OH | TYR | 170 | 50.769 | -19.205 | 20.780 | 1.00 | 9.17 | | E11 |
| ATOM | 1472 | C | TYR | 170 | 50.995 | -19.773 | 28.686 | 1.00 | 13.03 | | E11 |
| ATOM | 1473 | O | TYR | 170 | 51.663 | -18.829 | 29.073 | 1.00 | 17.64 | | E11 |
| ATOM | 1474 | N | PRO | 171 | 50.731 | -20.831 | 29.472 | 1.00 | 19.44 | | E11 |
| ATOM | 1475 | CD | PRO | 171 | 49.702 | -21.865 | 29.235 | 1.00 | 21.27 | | E11 |
| ATOM | 1476 | CA | PRO | 171 | 51.390 | -21.034 | 30.772 | 1.00 | 20.72 | | E11 |
| ATOM | 1477 | CB | PRO | 171 | 50.962 | -22.452 | 31.141 | 1.00 | 18.31 | | E11 |
| ATOM | 1478 | CG | PRO | 171 | 49.577 | -22.496 | 30.604 | 1.00 | 18.71 | | E11 |
| ATOM | 1479 | C | PRO | 171 | 52.916 | -20.898 | 30.709 | 1.00 | 21.14 | | E11 |
| ATOM | 1480 | O | PRO | 171 | 53.536 | -20.305 | 31.592 | 1.00 | 18.28 | | E11 |
| ATOM | 1481 | N | TYR | 172 | 53.522 | -21.465 | 29.672 | 1.00 | 21.66 | | E11 |
| ATOM | 1482 | CA | TYR | 172 | 54.976 | -21.384 | 29.540 | 1.00 | 22.68 | | E11 |
| ATOM | 1483 | CB | TYR | 172 | 55.482 | -22.004 | 28.217 | 1.00 | 22.35 | | E11 |
| ATOM | 1484 | CG | TYR | 172 | 55.967 | -21.769 | 27.986 | 1.00 | 20.99 | | E11 |
| ATOM | 1485 | CD1 | TYR | 172 | 57.421 | -20.592 | 27.380 | 1.00 | 22.29 | | E11 |
| ATOM | 1486 | CE1 | TYR | 172 | 58.776 | -20.327 | 27.234 | 1.00 | 23.09 | | E11 |
| ATOM | 1487 | CD2 | TYR | 172 | 57.917 | -22.678 | 28.430 | 1.00 | 18.32 | | E11 |
| ATOM | 1488 | CE2 | TYR | 172 | 59.289 | -22.423 | 28.288 | 1.00 | 19.78 | | E11 |
| ATOM | 1489 | CZ | TYR | 172 | 59.711 | -21.244 | 27.693 | 1.00 | 21.61 | | E11 |
| ATOM | 1490 | OH | TYR | 172 | 61.050 | -20.927 | 27.568 | 1.00 | 26.44 | | E11 |
| ATOM | 1491 | C | TYR | 172 | 55.437 | -19.943 | 29.647 | 1.00 | 19.27 | | E11 |
| ATOM | 1492 | O | TYR | 172 | 56.352 | -19.630 | 30.384 | 1.00 | 24.02 | | E11 |
| ATOM | 1493 | N | LEU | 173 | 54.730 | -19.060 | 28.975 | 1.00 | 20.92 | | E11 |
| ATOM | 1494 | CA | LEU | 173 | 55.088 | -17.666 | 28.996 | 1.00 | 21.14 | | E11 |
| ATOM | 1495 | CB | LEU | 173 | 54.356 | -16.916 | 27.900 | 1.00 | 18.72 | | E11 |
| ATOM | 1496 | CG | LEU | 173 | 55.038 | -16.902 | 26.527 | 1.00 | 17.85 | | E11 |
| ATOM | 1497 | CD1 | LEU | 173 | 55.646 | -18.222 | 26.158 | 1.00 | 24.14 | | E11 |
| ATOM | 1498 | CD2 | LEU | 173 | 54.012 | -16.508 | 25.494 | 1.00 | 13.38 | | E11 |
| ATOM | 1499 | C | LEU | 173 | 54.832 | -17.037 | 30.360 | 1.00 | 22.76 | | E11 |
| ATOM | 1500 | O | LEU | 173 | 55.656 | -16.268 | 30.827 | 1.00 | 21.69 | | E11 |
| ATOM | 1501 | N | ALA | 174 | 53.750 | -17.422 | 31.041 | 1.00 | 24.39 | | E11 |
| ATOM | 1502 | CA | ALA | 174 | 53.460 | -16.857 | 32.362 | 1.00 | 20.26 | | E11 |
| ATOM | 1503 | CB | ALA | 174 | 52.132 | -17.379 | 32.887 | 1.00 | 16.06 | | E11 |
| ATOM | 1504 | C | ALA | 174 | 54.581 | -17.256 | 33.308 | 1.00 | 23.24 | | E11 |
| ATOM | 1505 | O | ALA | 174 | 55.042 | -16.450 | 34.127 | 1.00 | 22.69 | | E11 |
| ATOM | 1511 | N | TRP | 175 | 54.985 | -18.521 | 33.210 | 1.00 | 24.72 | | E11 |
| ATOM | 1513 | CA | TRP | 175 | 56.036 | -19.077 | 34.042 | 1.00 | 26.41 | | E11 |
| ATOM | 1514 | CB | TRP | 175 | 56.043 | -20.600 | 33.943 | 1.00 | 29.50 | | E11 |
| ATOM | 1515 | CG | TRP | 175 | 57.304 | -21.241 | 34.496 | 1.00 | 36.22 | | E11 |
| ATOM | 1516 | CD2 | TRP | 175 | 58.476 | -21.603 | 33.753 | 1.00 | 37.66 | | E11 |
| ATOM | 1517 | CE2 | TRP | 175 | 59.420 | -22.100 | 34.680 | 1.00 | 38.30 | | E11 |
| ATOM | 1518 | CE3 | TRP | 175 | 58.827 | -21.549 | 32.397 | 1.00 | 36.59 | | E11 |
| ATOM | 1519 | CD1 | TRP | 175 | 57.576 | -21.535 | 35.806 | 1.00 | 38.11 | | E11 |
| ATOM | 1520 | NE1 | TRP | 175 | 58.844 | -22.047 | 35.922 | 1.00 | 40.07 | | E11 |
| ATOM | 1522 | CZ2 | TRP | 175 | 60.693 | -22.528 | 34.294 | 1.00 | 39.77 | | E11 |
| ATOM | 1523 | CZ3 | TRP | 175 | 60.090 | -21.970 | 32.017 | 1.00 | 35.49 | | E11 |
| ATOM | 1524 | CH2 | TRP | 175 | 61.008 | -22.459 | 32.963 | 1.00 | 37.93 | | E11 |
| ATOM | 1525 | C | TRP | 175 | 57.427 | -18.554 | 33.754 | 1.00 | 27.83 | | E11 |
| ATOM | 1526 | O | TRP | 175 | 58.178 | -18.252 | 34.667 | 1.00 | 27.51 | | E11 |
| ATOM | 1527 | N | ALA | 176 | 57.773 | -18.467 | 32.480 | 1.00 | 33.89 | | E11 |
| ATOM | 1529 | CA | ALA | 176 | 59.096 | -18.040 | 32.073 | 1.00 | 33.49 | | E11 |
| ATOM | 1530 | CB | ALA | 176 | 59.243 | -18.202 | 30.598 | 1.00 | 31.75 | | E11 |
| ATOM | 1531 | C | ALA | 176 | 59.412 | -16.627 | 32.501 | 1.00 | 37.53 | | E11 |
| ATOM | 1532 | O | ALA | 176 | 60.573 | -16.302 | 32.766 | 1.00 | 40.41 | | E11 |
| ATOM | 1533 | N | TYR | 177 | 58.376 | -15.790 | 32.553 | 1.00 | 42.63 | | E11 |
| ATOM | 1535 | CA | TYR | 177 | 58.498 | -14.387 | 32.958 | 1.00 | 44.57 | | E11 |
| ATOM | 1536 | CB | TYR | 177 | 57.102 | -13.774 | 33.093 | 1.00 | 45.07 | | E11 |
| ATOM | 1537 | CG | TYR | 177 | 57.105 | -12.321 | 33.521 | 1.00 | 47.58 | | E11 |
| ATOM | 1538 | CD1 | TYR | 177 | 57.472 | -11.311 | 32.623 | 1.00 | 46.01 | | E11 |
| ATOM | 1539 | CE1 | TYR | 177 | 57.494 | -9.971 | 33.012 | 1.00 | 47.65 | | E11 |
| ATOM | 1540 | CD2 | TYR | 177 | 56.756 | -11.954 | 34.829 | 1.00 | 50.18 | | E11 |
| ATOM | 1541 | CE2 | TYR | 177 | 56.776 | -10.614 | 35.234 | 1.00 | 47.08 | | E11 |
| ATOM | 1542 | CZ | TYR | 177 | 57.145 | -9.628 | 34.320 | 1.00 | 47.96 | | E11 |
| ATOM | 1543 | OH | TYR | 177 | 57.165 | -8.304 | 34.708 | 1.00 | 47.44 | | E11 |
| ATOM | 1545 | C | TYR | 177 | 59.258 | -14.244 | 34.284 | 0.00 | 47.31 | | E11 |
| ATOM | 1546 | O | TYR | 177 | 60.054 | -13.317 | 34.465 | 0.00 | 46.70 | | E11 |
| ATOM | 1547 | N | ASN | 178 | 58.956 | -15.138 | 35.222 | 1.00 | 43.45 | | E11 |
| ATOM | 1549 | CA | ASN | 178 | 59.603 | -15.159 | 36.530 | 1.00 | 50.99 | | E11 |
| ATOM | 1550 | CB | ASN | 178 | 58.922 | -14.166 | 37.481 | 1.00 | 56.87 | | E11 |
| ATOM | 1551 | CG | ASN | 178 | 59.538 | -14.164 | 38.874 | 1.00 | 60.68 | | E11 |
| ATOM | 1552 | OD1 | ASN | 178 | 60.639 | -14.689 | 39.097 | 1.00 | 60.91 | | E11 |
| ATOM | 1553 | ND2 | ASN | 178 | 58.817 | -13.578 | 39.827 | 1.00 | 64.33 | | E11 |
| ATOM | 1556 | C | ASN | 178 | 59.545 | -16.575 | 37.101 | 1.00 | 47.19 | | E11 |
| ATOM | 1557 | O | ASN | 178 | 58.657 | -16.900 | 37.895 | 1.00 | 47.07 | | E11 |
| ATOM | 1558 | N | PRO | 179 | 60.480 | -17.447 | 36.680 | 1.00 | 45.82 | | E11 |

- 47 -

| ATOM | 1559 | CD | PRO | 179 | 61.580 | -17.148 | 35.747 | 1.00 | 45.15 | EII | ATOM | 1605 | O | MET | 184 | 55.503 | -26.452 | 35.183 | 1.00 | 34.11 | EII |
| --- | --- | --- | --- | --- | --- | --- | --- | --- | --- | --- | --- | --- | --- | --- | --- | --- | --- | --- | --- | --- | --- |
| ATOM | 1560 | CA | PRO | 179 | 60.470 | -18.874 | 37.018 | 1.00 | 46.49 | EII | ATOM | 1606 | N | GLY | 185 | 56.011 | -27.188 | 37.242 | 1.00 | 30.10 | EII |
| ATOM | 1561 | CB | PRO | 179 | 61.733 | -19.390 | 36.330 | 1.00 | 42.49 | EII | ATOM | 1608 | CA | GLY | 185 | 55.078 | -28.298 | 37.134 | 1.00 | 25.01 | EII |
| ATOM | 1562 | CG | PRO | 179 | 61.859 | -18.493 | 35.146 | 1.00 | 45.39 | EII | ATOM | 1609 | C | GLY | 185 | 53.656 | -27.778 | 37.023 | 1.00 | 21.60 | EII |
| ATOM | 1563 | C | PRO | 179 | 61.859 | -19.088 | 38.526 | 1.00 | 49.98 | EII | ATOM | 1610 | O | GLY | 185 | 52.824 | -28.355 | 36.347 | 1.00 | 23.07 | EII |
| ATOM | 1564 | O | PRO | 179 | 60.309 | -20.193 | 39.026 | 1.00 | 51.01 | EII | ATOM | 1611 | N | TYR | 186 | 53.378 | -26.709 | 37.759 | 1.00 | 20.69 | EII |
| ATOM | 1565 | N | SER | 180 | 60.894 | -18.621 | 39.234 | 1.00 | 52.56 | EII | ATOM | 1613 | CA | TYR | 186 | 52.082 | -26.041 | 37.779 | 1.00 | 21.71 | EII |
| ATOM | 1567 | CA | SER | 180 | 61.024 | -18.032 | 40.683 | 1.00 | 53.52 | EII | ATOM | 1614 | CB | TYR | 186 | 52.158 | -24.841 | 38.730 | 1.00 | 19.59 | EII |
| ATOM | 1568 | CB | SER | 180 | 61.993 | -16.927 | 41.093 | 1.00 | 53.47 | EII | ATOM | 1615 | CG | TYR | 186 | 50.928 | -23.966 | 38.803 | 1.00 | 18.00 | EII |
| ATOM | 1569 | OG | SER | 180 | 62.865 | -16.609 | 40.012 | 1.00 | 58.82 | EII | ATOM | 1616 | CD1 | TYR | 186 | 51.040 | -22.579 | 38.751 | 1.00 | 14.43 | EII |
| ATOM | 1571 | C | SER | 180 | 59.681 | -17.810 | 41.371 | 1.00 | 54.30 | EII | ATOM | 1617 | CD2 | TYR | 186 | 49.917 | -21.770 | 38.839 | 1.00 | 15.55 | EII |
| ATOM | 1572 | O | SER | 180 | 59.542 | -18.051 | 42.555 | 1.00 | 57.62 | EII | ATOM | 1618 | CE1 | TYR | 186 | 49.660 | -24.518 | 38.945 | 1.00 | 15.79 | EII |
| ATOM | 1573 | N | ALA | 181 | 58.705 | -17.276 | 40.643 | 1.00 | 53.10 | EII | ATOM | 1619 | CE2 | TYR | 186 | 48.530 | -23.712 | 39.038 | 1.00 | 19.09 | EII |
| ATOM | 1575 | CA | ALA | 181 | 57.390 | -17.021 | 41.220 | 1.00 | 52.66 | EII | ATOM | 1620 | CZ | TYR | 186 | 48.671 | -22.349 | 38.988 | 1.00 | 14.05 | EII |
| ATOM | 1576 | CB | ALA | 181 | 56.693 | -15.914 | 40.459 | 1.00 | 53.48 | EII | ATOM | 1621 | OH | TYR | 186 | 47.537 | -21.586 | 39.106 | 1.00 | 15.85 | EII |
| ATOM | 1577 | C | ALA | 181 | 56.484 | -18.255 | 41.317 | 1.00 | 51.01 | EII | ATOM | 1623 | C | TYR | 186 | 51.690 | -25.621 | 36.350 | 1.00 | 22.71 | EII |
| ATOM | 1578 | O | ALA | 181 | 55.662 | -18.345 | 42.232 | 1.00 | 51.93 | EII | ATOM | 1624 | O | TYR | 186 | 50.546 | -25.813 | 35.937 | 1.00 | 24.33 | EII |
| ATOM | 1579 | N | MET | 182 | 56.571 | -19.163 | 40.347 | 1.00 | 46.22 | EII | ATOM | 1625 | N | ALA | 187 | 52.667 | -25.151 | 35.577 | 1.00 | 23.47 | EII |
| ATOM | 1581 | CA | MET | 182 | 55.749 | -20.371 | 40.383 | 1.00 | 41.48 | EII | ATOM | 1627 | CA | ALA | 187 | 52.474 | -24.735 | 34.194 | 1.00 | 22.91 | EII |
| ATOM | 1582 | CB | MET | 182 | 54.495 | -21.428 | 39.506 | 1.00 | 41.86 | EII | ATOM | 1628 | CB | ALA | 187 | 53.528 | -23.721 | 33.233 | 1.00 | 21.79 | EII |
| ATOM | 1583 | CG | MET | 182 | 54.704 | -19.742 | 39.350 | 1.00 | 40.55 | EII | ATOM | 1629 | C | ALA | 187 | 52.506 | -25.908 | 33.560 | 1.00 | 22.64 | EII |
| ATOM | 1584 | SD | MET | 182 | 53.094 | -19.474 | 40.337 | 1.00 | 35.40 | EII | ATOM | 1630 | O | ALA | 187 | 51.788 | -26.938 | 32.685 | 1.00 | 22.78 | EII |
| ATOM | 1585 | CE | MET | 182 | 52.746 | -17.747 | 37.517 | 1.00 | 39.20 | EII | ATOM | 1631 | N | LEU | 188 | 53.284 | -26.114 | 32.872 | 1.00 | 21.06 | EII |
| ATOM | 1586 | C | MET | 182 | 56.547 | -21.569 | 39.974 | 1.00 | 43.48 | EII | ATOM | 1633 | CA | LEU | 188 | 53.418 | -28.651 | 31.831 | 1.00 | 20.53 | EII |
| ATOM | 1587 | O | MET | 182 | 57.589 | -21.428 | 40.337 | 1.00 | 37.62 | EII | ATOM | 1634 | CB | LEU | 188 | 54.791 | -28.775 | 32.316 | 1.00 | 19.98 | EII |
| ATOM | 1588 | N | ASP | 183 | 56.072 | -22.751 | 40.337 | 1.00 | 38.76 | EII | ATOM | 1635 | CG | LEU | 188 | 55.907 | -28.651 | 30.503 | 1.00 | 24.31 | EII |
| ATOM | 1590 | CA | ASP | 183 | 56.787 | -23.952 | 39.978 | 1.00 | 45.11 | EII | ATOM | 1636 | CD1 | LEU | 188 | 57.138 | -29.366 | 32.821 | 1.00 | 24.59 | EII |
| ATOM | 1591 | CB | ASP | 183 | 56.758 | -25.004 | 41.119 | 1.00 | 50.97 | EII | ATOM | 1637 | CD2 | LEU | 188 | 55.488 | -29.244 | 32.223 | 1.00 | 23.78 | EII |
| ATOM | 1592 | CG | ASP | 183 | 55.661 | -26.055 | 40.969 | 1.00 | 49.44 | EII | ATOM | 1638 | C | LEU | 188 | 52.369 | -29.218 | 33.548 | 1.00 | 21.82 | EII |
| ATOM | 1593 | OD1 | ASP | 183 | 55.959 | -27.126 | 40.386 | 1.00 | 52.87 | EII | ATOM | 1639 | O | LEU | 188 | 52.538 | -30.259 | 33.746 | 1.00 | 26.37 | EII |
| ATOM | 1594 | OD2 | ASP | 183 | 54.532 | -25.837 | 41.488 | 1.00 | 37.60 | EII | ATOM | 1640 | N | PHE | 189 | 51.279 | -29.113 | 32.403 | 1.00 | 21.98 | EII |
| ATOM | 1595 | C | ASP | 183 | 56.348 | -24.473 | 38.607 | 1.00 | 33.52 | EII | ATOM | 1642 | CA | PHE | 189 | 50.299 | -30.060 | 31.759 | 1.00 | 13.03 | EII |
| ATOM | 1596 | O | ASP | 183 | 55.160 | -24.575 | 38.302 | 1.00 | 35.05 | EII | ATOM | 1643 | CB | PHE | 189 | 49.767 | -30.592 | 30.542 | 1.00 | 14.20 | EII |
| ATOM | 1597 | N | MET | 184 | 57.343 | -24.716 | 37.763 | 1.00 | 33.93 | EII | ATOM | 1644 | CG | PHE | 189 | 48.757 | -29.709 | 32.353 | 1.00 | 15.29 | EII |
| ATOM | 1599 | CA | MET | 184 | 57.142 | -25.192 | 36.411 | 1.00 | 35.68 | EII | ATOM | 1645 | CD1 | PHE | 189 | 49.018 | -29.113 | 30.903 | 1.00 | 15.30 | EII |
| ATOM | 1600 | CB | MET | 184 | 58.483 | -25.573 | 35.803 | 1.00 | 35.55 | EII | ATOM | 1646 | CD2 | PHE | 189 | 47.519 | -29.508 | 29.903 | 1.00 | 16.23 | EII |
| ATOM | 1601 | CG | MET | 184 | 58.483 | -25.555 | 34.287 | 1.00 | 36.92 | EII | ATOM | 1647 | CE1 | PHE | 189 | 48.048 | -28.312 | 31.738 | 1.00 | 17.34 | EII |
| ATOM | 1602 | SD | MET | 184 | 59.998 | -26.286 | 33.702 | 1.00 | 33.09 | EII | ATOM | 1648 | CE2 | PHE | 189 | 46.552 | -28.723 | 30.520 | 1.00 | 26.60 | EII |
| ATOM | 1603 | CE | MET | 184 | 59.601 | -27.971 | 33.745 | 1.00 | 32.23 | EII | ATOM | 1649 | CZ | PHE | 189 | 46.807 | -28.126 | 34.541 | 1.00 | 26.60 | EII |
| ATOM | 1604 | C | MET | 184 | 56.145 | -26.339 | 36.232 | | | | ATOM | 1650 | C | PHE | 189 | 50.971 | -31.202 | | | | |

– 48 –

| ATOM | 1651 | D | PHE | 189 | 50.629 | -32.387 | 34.398 | 1.00 | 30.56 | EII |
|------|------|---|-----|-----|--------|---------|--------|------|-------|-----|
| ATOM | 1652 | H | ASN | 190 | 51.863 | -30.836 | 35.447 | 1.00 | 29.60 | EII |
| ATOM | 1653 | CA | ASN | 190 | 52.572 | -31.828 | 36.224 | 1.00 | 33.18 | EII |
| ATOM | 1654 | CB | ASN | 190 | 53.940 | -32.086 | 35.614 | 1.00 | 34.41 | EII |
| ATOM | 1655 | CG | ASN | 190 | 54.516 | -33.386 | 36.060 | 1.00 | 36.83 | EII |
| ATOM | 1656 | OD1 | ASN | 190 | 55.121 | -33.505 | 36.261 | 1.00 | 44.49 | EII |
| ATOM | 1657 | ND2 | ASN | 190 | 53.658 | -34.384 | 36.235 | 1.00 | 41.34 | EII |
| ATOM | 1658 | C | ASN | 190 | 52.722 | -31.474 | 37.697 | 1.00 | 36.39 | EII |
| ATOM | 1659 | O | ASN | 190 | 53.816 | -31.597 | 38.267 | 1.00 | 36.86 | EII |
| ATOM | 1660 | H | ALA | 191 | 51.632 | -31.002 | 38.301 | 1.00 | 35.68 | EII |
| ATOM | 1661 | CA | ALA | 191 | 51.624 | -30.664 | 39.720 | 1.00 | 34.99 | EII |
| ATOM | 1662 | CB | ALA | 191 | 50.826 | -29.380 | 39.987 | 1.00 | 33.74 | EII |
| ATOM | 1663 | C | ALA | 191 | 50.977 | -31.867 | 40.400 | 1.00 | 36.67 | EII |
| ATOM | 1664 | O | ALA | 191 | 50.214 | -32.622 | 39.779 | 1.00 | 33.44 | EII |
| ATOM | 1665 | H | SER | 192 | 51.354 | -32.102 | 41.647 | 1.00 | 41.61 | EII |
| ATOM | 1666 | CA | SER | 192 | 50.834 | -33.248 | 42.385 | 1.00 | 48.37 | EII |
| ATOM | 1667 | CB | SER | 192 | 51.684 | -33.501 | 43.622 | 1.00 | 49.68 | EII |
| ATOM | 1668 | OG | SER | 192 | 53.056 | -33.569 | 43.249 | 1.00 | 57.40 | EII |
| ATOM | 1669 | C | SER | 192 | 49.389 | -33.034 | 42.762 | 1.00 | 49.46 | EII |
| ATOM | 1670 | O | SER | 192 | 48.547 | -33.914 | 42.565 | 1.00 | 52.46 | EII |
| ATOM | 1671 | H | GLY | 193 | 49.086 | -31.834 | 43.240 | 1.00 | 49.30 | EII |
| ATOM | 1672 | CA | GLY | 193 | 47.718 | -31.551 | 43.615 | 1.00 | 46.14 | EII |
| ATOM | 1673 | C | GLY | 193 | 47.444 | -30.075 | 43.606 | 1.00 | 44.65 | EII |
| ATOM | 1674 | O | GLY | 193 | 48.303 | -29.287 | 43.210 | 1.00 | 46.96 | EII |
| ATOM | 1675 | H | THR | 194 | 46.255 | -29.710 | 44.071 | 1.00 | 41.44 | EII |
| ATOM | 1676 | CA | THR | 194 | 45.829 | -28.325 | 44.125 | 1.00 | 38.33 | EII |
| ATOM | 1677 | CB | THR | 194 | 44.702 | -28.150 | 45.123 | 1.00 | 38.10 | EII |
| ATOM | 1678 | OG1 | THR | 194 | 43.654 | -29.056 | 44.770 | 1.00 | 41.63 | EII |
| ATOM | 1679 | CG2 | THR | 194 | 44.157 | -26.713 | 45.094 | 1.00 | 37.66 | EII |
| ATOM | 1680 | C | THR | 194 | 46.961 | -27.403 | 44.474 | 1.00 | 36.48 | EII |
| ATOM | 1681 | O | THR | 194 | 47.725 | -27.663 | 45.400 | 1.00 | 38.14 | EII |
| ATOM | 1682 | H | VAL | 195 | 47.112 | -26.365 | 43.666 | 1.00 | 35.24 | EII |
| ATOM | 1683 | CA | VAL | 195 | 48.159 | -25.382 | 43.856 | 1.00 | 32.99 | EII |
| ATOM | 1684 | CB | VAL | 195 | 48.892 | -25.142 | 42.543 | 1.00 | 30.84 | EII |
| ATOM | 1685 | CG1 | VAL | 195 | 49.871 | -23.983 | 42.669 | 1.00 | 31.85 | EII |
| ATOM | 1686 | CG2 | VAL | 195 | 49.620 | -26.401 | 42.153 | 1.00 | 30.91 | EII |
| ATOM | 1687 | C | VAL | 195 | 47.531 | -24.094 | 44.321 | 1.00 | 32.03 | EII |
| ATOM | 1688 | O | VAL | 195 | 48.144 | -23.311 | 45.041 | 1.00 | 33.10 | EII |
| ATOM | 1689 | H | VAL | 196 | 46.289 | -23.897 | 43.897 | 1.00 | 31.68 | EII |
| ATOM | 1690 | CA | VAL | 196 | 45.503 | -22.726 | 44.222 | 1.00 | 28.08 | EII |
| ATOM | 1702 | CB | VAL | 196 | 45.387 | -21.799 | 42.986 | 1.00 | 27.85 | EII |
| ATOM | 1703 | CG1 | VAL | 196 | 44.313 | -20.755 | 43.208 | 1.00 | 24.00 | EII |
| ATOM | 1704 | CG2 | VAL | 196 | 46.741 | -21.146 | 42.686 | 1.00 | 24.97 | EII |
| ATOM | 1705 | C | VAL | 196 | 44.099 | -23.163 | 44.666 | 1.00 | 28.69 | EII |
| ATOM | 1706 | O | VAL | 196 | 43.430 | -23.929 | 43.985 | 1.00 | 28.07 | EII |
| ATOM | 1707 | N | ARG | 197 | 43.703 | -22.764 | 45.862 | 1.00 | 28.14 | EII |
| ATOM | 1709 | CA | ARG | 197 | 42.374 | -23.083 | 46.337 | 1.00 | 26.43 | EII |
| ATOM | 1710 | CB | ARG | 197 | 42.447 | -23.638 | 47.758 | 1.00 | 24.57 | EII |
| ATOM | 1711 | CG | ARG | 197 | 41.094 | -23.972 | 48.371 | 1.00 | 26.51 | EII |
| ATOM | 1712 | CD | ARG | 197 | 40.353 | -25.029 | 47.562 | 0.00 | 27.03 | EII |
| ATOM | 1713 | NE | ARG | 197 | 41.072 | -26.302 | 47.508 | 0.00 | 27.90 | EII |
| ATOM | 1715 | CZ | ARG | 197 | 40.600 | -27.404 | 46.931 | 0.00 | 28.17 | EII |
| ATOM | 1716 | NH1 | ARG | 197 | 39.405 | -27.394 | 46.355 | 0.00 | 28.57 | EII |
| ATOM | 1719 | NH2 | ARG | 197 | 41.320 | -28.517 | 46.932 | 0.00 | 28.58 | EII |
| ATOM | 1722 | C | ARG | 197 | 41.604 | -21.759 | 46.277 | 1.00 | 30.55 | EII |
| ATOM | 1723 | O | ARG | 197 | 41.964 | -20.779 | 46.944 | 1.00 | 29.05 | EII |
| ATOM | 1724 | N | ASP | 198 | 40.685 | -21.670 | 45.327 | 1.00 | 30.67 | EII |
| ATOM | 1726 | CA | ASP | 198 | 39.880 | -20.472 | 45.175 | 1.00 | 34.34 | EII |
| ATOM | 1727 | CB | ASP | 198 | 39.893 | -19.982 | 43.736 | 1.00 | 36.17 | EII |
| ATOM | 1728 | CG | ASP | 198 | 39.235 | -18.630 | 43.579 | 1.00 | 37.77 | EII |
| ATOM | 1729 | OD1 | ASP | 198 | 38.958 | -18.234 | 42.429 | 1.00 | 36.00 | EII |
| ATOM | 1730 | OD2 | ASP | 198 | 38.995 | -17.956 | 44.600 | 1.00 | 38.48 | EII |
| ATOM | 1731 | C | ASP | 198 | 38.455 | -20.742 | 45.600 | 1.00 | 36.23 | EII |
| ATOM | 1732 | O | ASP | 198 | 37.654 | -21.268 | 44.825 | 1.00 | 38.68 | EII |
| ATOM | 1733 | N | GLY | 199 | 38.126 | -20.330 | 46.819 | 1.00 | 37.32 | EII |
| ATOM | 1735 | CA | GLY | 199 | 36.793 | -20.543 | 47.332 | 1.00 | 33.27 | EII |
| ATOM | 1736 | C | GLY | 199 | 36.611 | -22.029 | 47.486 | 1.00 | 30.86 | EII |
| ATOM | 1737 | O | GLY | 199 | 37.357 | -22.662 | 48.227 | 1.00 | 31.43 | EII |
| ATOM | 1738 | N | ALA | 200 | 35.679 | -22.592 | 46.727 | 1.00 | 27.98 | EII |
| ATOM | 1740 | CA | ALA | 200 | 35.420 | -24.014 | 46.797 | 1.00 | 28.24 | EII |
| ATOM | 1741 | CB | ALA | 200 | 33.943 | -24.272 | 46.879 | 1.00 | 26.43 | EII |
| ATOM | 1742 | C | ALA | 200 | 35.992 | -24.706 | 45.582 | 1.00 | 30.53 | EII |
| ATOM | 1743 | O | ALA | 200 | 35.584 | -25.827 | 45.268 | 1.00 | 35.34 | EII |
| ATOM | 1744 | N | TYR | 201 | 36.878 | -24.020 | 44.854 | 1.00 | 30.27 | EII |
| ATOM | 1746 | CA | TYR | 201 | 37.490 | -24.598 | 43.656 | 1.00 | 25.69 | EII |
| ATOM | 1747 | CB | TYR | 201 | 37.121 | -23.788 | 42.417 | 1.00 | 24.19 | EII |
| ATOM | 1748 | CG | TYR | 201 | 35.624 | -23.552 | 42.285 | 1.00 | 22.80 | EII |
| ATOM | 1749 | CD1 | TYR | 201 | 35.010 | -22.489 | 42.949 | 1.00 | 26.28 | EII |
| ATOM | 1750 | CE1 | TYR | 201 | 33.658 | -22.285 | 42.865 | 1.00 | 24.57 | EII |
| ATOM | 1751 | CD2 | TYR | 201 | 34.825 | -24.405 | 41.528 | 1.00 | 20.01 | EII |

- 49 -

| ATOM | 1752 | CE2 | TYR | 201 | 33.469 | -24.208 | 41.431 | 1.00 | 18.44 | EII |
|------|------|-----|-----|-----|--------|---------|--------|------|-------|-----|
| ATOM | 1753 | CZ | TYR | 201 | 32.889 | -23.141 | 42.101 | 1.00 | 25.01 | EII |
| ATOM | 1754 | OH | TYR | 201 | 31.531 | -22.884 | 41.992 | 1.00 | 33.80 | EII |
| ATOM | 1755 | C | TYR | 201 | 38.988 | -24.656 | 43.835 | 1.00 | 24.09 | EII |
| ATOM | 1756 | O | TYR | 201 | 39.581 | -23.744 | 44.394 | 1.00 | 26.74 | EII |
| ATOM | 1757 | N | GLY | 202 | 39.589 | -25.767 | 43.430 | 1.00 | 21.98 | EII |
| ATOM | 1758 | CA | GLY | 202 | 39.021 | -25.906 | 43.564 | 1.00 | 24.68 | EII |
| ATOM | 1759 | C | GLY | 202 | 41.615 | -26.156 | 42.198 | 1.00 | 25.92 | EII |
| ATOM | 1760 | O | GLY | 202 | 41.120 | -27.008 | 41.451 | 1.00 | 29.56 | EII |
| ATOM | 1761 | N | TYR | 203 | 42.619 | -25.354 | 41.858 | 1.00 | 22.41 | EII |
| ATOM | 1762 | CA | TYR | 203 | 43.324 | -25.433 | 40.597 | 1.00 | 23.29 | EII |
| ATOM | 1763 | CB | TYR | 203 | 43.545 | -24.008 | 40.068 | 1.00 | 21.60 | EII |
| ATOM | 1764 | CG | TYR | 203 | 42.230 | -23.352 | 39.690 | 1.00 | 18.34 | EII |
| ATOM | 1765 | CD1 | TYR | 203 | 41.380 | -22.839 | 40.671 | 1.00 | 22.19 | EII |
| ATOM | 1766 | CD2 | TYR | 203 | 40.101 | -22.341 | 40.356 | 1.00 | 19.27 | EII |
| ATOM | 1767 | CE1 | TYR | 203 | 41.776 | -23.331 | 38.357 | 1.00 | 22.67 | EII |
| ATOM | 1768 | CE2 | TYR | 203 | 40.499 | -22.838 | 38.026 | 1.00 | 19.55 | EII |
| ATOM | 1769 | CZ | TYR | 203 | 39.680 | -22.346 | 39.052 | 1.00 | 20.95 | EII |
| ATOM | 1770 | OH | TYR | 203 | 38.440 | -21.849 | 38.807 | 1.00 | 20.04 | EII |
| ATOM | 1771 | C | TYR | 203 | 44.633 | -26.217 | 40.719 | 1.00 | 25.87 | EII |
| ATOM | 1772 | O | TYR | 203 | 45.421 | -25.992 | 41.635 | 1.00 | 20.80 | EII |
| ATOM | 1773 | N | GLN | 204 | 44.856 | -27.114 | 39.759 | 1.00 | 28.26 | EII |
| ATOM | 1774 | CA | GLN | 204 | 46.029 | -27.960 | 39.727 | 1.00 | 28.93 | EII |
| ATOM | 1775 | CB | GLN | 204 | 45.569 | -29.455 | 39.734 | 1.00 | 27.24 | EII |
| ATOM | 1776 | CG | GLN | 204 | 46.698 | -30.495 | 39.794 | 0.00 | 26.58 | EII |
| ATOM | 1777 | CD | GLN | 204 | 46.357 | -31.786 | 39.061 | 0.00 | 25.94 | EII |
| ATOM | 1778 | OE1 | GLN | 204 | 45.495 | -31.805 | 38.184 | 0.00 | 25.70 | EII |
| ATOM | 1779 | NE2 | GLN | 204 | 47.038 | -32.868 | 39.410 | 1.00 | 25.69 | EII |
| ATOM | 1780 | C | GLN | 204 | 46.935 | -27.697 | 38.508 | 1.00 | 31.33 | EII |
| ATOM | 1781 | O | GLN | 204 | 47.890 | -28.451 | 38.248 | 1.00 | 36.03 | EII |
| ATOM | 1782 | N | ASN | 205 | 46.598 | -26.663 | 37.725 | 1.00 | 30.66 | EII |
| ATOM | 1783 | CA | ASN | 205 | 47.387 | -26.266 | 36.553 | 1.00 | 24.28 | EII |
| ATOM | 1784 | CB | ASN | 205 | 47.227 | -27.330 | 35.378 | 1.00 | 19.69 | EII |
| ATOM | 1785 | CG | ASN | 205 | 45.803 | -27.330 | 34.869 | 1.00 | 16.35 | EII |
| ATOM | 1786 | OD1 | ASN | 205 | 45.326 | -26.469 | 34.117 | 1.00 | 18.65 | EII |
| ATOM | 1787 | ND2 | ASN | 205 | 45.122 | -28.394 | 35.252 | 1.00 | 16.73 | EII |
| ATOM | 1788 | C | ASN | 205 | 47.055 | -24.862 | 36.098 | 1.00 | 25.35 | EII |
| ATOM | 1789 | O | ASN | 205 | 45.901 | -24.426 | 36.180 | 1.00 | 30.34 | EII |
| ATOM | 1790 | N | LEU | 206 | 48.096 | -24.160 | 35.649 | 1.00 | 24.16 | EII |
| ATOM | 1791 | CA | LEU | 206 | 48.020 | -22.785 | 35.167 | 1.00 | 19.10 | EII |
| ATOM | 1792 | CB | LEU | 206 | 49.407 | -22.288 | 34.786 | 1.00 | 16.15 | EII |
| ATOM | 1793 | CG | LEU | 206 | 49.804 | -20.898 | 35.286 | 1.00 | 13.64 | EII |
| ATOM | 1794 | CD1 | LEU | 206 | 51.072 | -20.530 | 34.528 | 1.00 | 13.13 | EII |
| ATOM | 1795 | CD2 | LEU | 206 | 48.707 | -19.827 | 35.139 | 1.00 | 6.22 | EII |
| ATOM | 1796 | C | LEU | 206 | 47.083 | -22.548 | 33.975 | 1.00 | 20.68 | EII |
| ATOM | 1797 | O | LEU | 206 | 46.702 | -21.394 | 33.732 | 1.00 | 24.00 | EII |
| ATOM | 1798 | N | PHE | 207 | 46.777 | -23.582 | 33.191 | 1.00 | 18.36 | EII |
| ATOM | 1799 | CA | PHE | 207 | 45.887 | -23.410 | 32.045 | 1.00 | 18.46 | EII |
| ATOM | 1800 | CB | PHE | 207 | 45.869 | -24.699 | 31.200 | 1.00 | 20.87 | EII |
| ATOM | 1801 | CG | PHE | 207 | 44.979 | -24.637 | 29.970 | 1.00 | 20.92 | EII |
| ATOM | 1802 | CD1 | PHE | 207 | 45.482 | -24.166 | 28.757 | 1.00 | 22.23 | EII |
| ATOM | 1803 | CD2 | PHE | 207 | 43.650 | -25.068 | 30.020 | 1.00 | 21.54 | EII |
| ATOM | 1804 | CE1 | PHE | 207 | 44.676 | -24.126 | 27.605 | 1.00 | 23.97 | EII |
| ATOM | 1805 | CE2 | PHE | 207 | 42.835 | -25.028 | 28.874 | 1.00 | 21.55 | EII |
| ATOM | 1806 | CZ | PHE | 207 | 43.352 | -24.557 | 27.667 | 1.00 | 20.48 | EII |
| ATOM | 1807 | C | PHE | 207 | 44.497 | -23.100 | 32.590 | 1.00 | 18.20 | EII |
| ATOM | 1808 | O | PHE | 207 | 43.914 | -22.066 | 32.249 | 1.00 | 17.26 | EII |
| ATOM | 1809 | N | ASP | 208 | 44.001 | -23.950 | 33.496 | 1.00 | 20.36 | EII |
| ATOM | 1810 | CA | ASP | 208 | 42.676 | -23.736 | 34.075 | 1.00 | 24.96 | EII |
| ATOM | 1811 | CB | ASP | 208 | 42.336 | -24.834 | 35.069 | 1.00 | 25.19 | EII |
| ATOM | 1812 | CG | ASP | 208 | 42.295 | -26.205 | 34.434 | 1.00 | 24.40 | EII |
| ATOM | 1813 | OD1 | ASP | 208 | 42.140 | -26.292 | 33.195 | 1.00 | 21.27 | EII |
| ATOM | 1814 | OD2 | ASP | 208 | 42.399 | -27.195 | 35.187 | 1.00 | 24.24 | EII |
| ATOM | 1815 | C | ASP | 208 | 42.578 | -22.393 | 34.773 | 1.00 | 22.22 | EII |
| ATOM | 1816 | O | ASP | 208 | 41.621 | -21.641 | 34.589 | 1.00 | 20.23 | EII |
| ATOM | 1817 | N | THR | 209 | 43.536 | -22.122 | 35.644 | 1.00 | 20.01 | EII |
| ATOM | 1818 | CA | THR | 209 | 43.560 | -20.855 | 36.356 | 1.00 | 22.17 | EII |
| ATOM | 1819 | CB | THR | 209 | 44.904 | -20.649 | 37.049 | 1.00 | 25.31 | EII |
| ATOM | 1820 | OG1 | THR | 209 | 45.181 | -21.758 | 37.904 | 1.00 | 20.23 | EII |
| ATOM | 1821 | CG2 | THR | 209 | 44.886 | -19.397 | 37.861 | 1.00 | 22.28 | EII |
| ATOM | 1822 | C | THR | 209 | 43.310 | -19.663 | 35.427 | 1.00 | 18.63 | EII |
| ATOM | 1823 | O | THR | 209 | 42.500 | -18.794 | 35.765 | 1.00 | 18.41 | EII |
| ATOM | 1824 | N | THR | 210 | 44.033 | -19.622 | 34.294 | 1.00 | 19.61 | EII |
| ATOM | 1825 | CA | THR | 210 | 43.933 | -18.549 | 33.297 | 1.00 | 12.93 | EII |
| ATOM | 1826 | CB | THR | 210 | 45.027 | -18.680 | 32.194 | 1.00 | 16.19 | EII |
| ATOM | 1827 | OG1 | THR | 210 | 46.285 | -18.925 | 32.822 | 1.00 | 16.29 | EII |
| ATOM | 1828 | CG2 | THR | 210 | 45.121 | -17.380 | 31.303 | 1.00 | 20.38 | EII |
| ATOM | 1829 | C | THR | 210 | 42.573 | -18.483 | 32.619 | 1.00 | 12.67 | EII |
| ATOM | 1830 | O | THR | 210 | 42.007 | -17.407 | 32.489 | | | EII |
| ATOM | 1831 | N | VAL | 211 | 42.123 | -19.615 | 32.094 | | | EII |

- 50 -

| ATOM | 1850 | CA  | VAL | 211 | 40.831 | -19.723 | 31.437 | 1.00 | 14.30 | EII |
|------|------|-----|-----|-----|--------|---------|--------|------|-------|-----|
| ATOM | 1851 | CB  | VAL | 211 | 40.538 | -21.216 | 31.080 | 1.00 | 12.30 | EII |
| ATOM | 1852 | CG1 | VAL | 211 | 39.125 | -21.396 | 30.612 | 1.00 | 15.63 | EII |
| ATOM | 1853 | CG2 | VAL | 211 | 41.490 | -21.729 | 30.010 | 1.00 | 14.81 | EII |
| ATOM | 1854 | C   | VAL | 211 | 39.719 | -19.186 | 32.375 | 1.00 | 20.59 | EII |
| ATOM | 1855 | O   | VAL | 211 | 38.816 | -18.348 | 31.981 | 1.00 | 22.49 | EII |
| ATOM | 1856 | H   | ASP | 212 | 39.731 | -19.634 | 33.630 | 1.00 | 20.71 | EII |
| ATOM | 1857 | CA  | ASP | 212 | 38.718 | -19.212 | 34.577 | 1.00 | 16.15 | EII |
| ATOM | 1858 | CB  | ASP | 212 | 38.703 | -20.119 | 35.792 | 1.00 | 17.31 | EII |
| ATOM | 1859 | CG  | ASP | 212 | 37.934 | -21.412 | 35.526 | 1.00 | 15.32 | EII |
| ATOM | 1860 | OD1 | ASP | 212 | 37.334 | -21.524 | 34.444 | 1.00 | 17.29 | EII |
| ATOM | 1861 | OD2 | ASP | 212 | 37.890 | -22.299 | 36.396 | 1.00 | 14.65 | EII |
| ATOM | 1862 | C   | ASP | 212 | 38.838 | -17.756 | 34.940 | 1.00 | 18.30 | EII |
| ATOM | 1863 | O   | ASP | 212 | 37.821 | -17.073 | 35.122 | 1.00 | 21.15 | EII |
| ATOM | 1864 | H   | ALA | 213 | 40.080 | -17.269 | 34.968 | 1.00 | 17.51 | EII |
| ATOM | 1865 | CA  | ALA | 213 | 40.356 | -15.866 | 35.236 | 1.00 | 13.54 | EII |
| ATOM | 1866 | CB  | ALA | 213 | 41.841 | -15.627 | 35.327 | 1.00 | 11.55 | EII |
| ATOM | 1867 | C   | ALA | 213 | 39.767 | -15.058 | 34.083 | 1.00 | 16.31 | EII |
| ATOM | 1868 | O   | ALA | 213 | 39.218 | -13.976 | 34.309 | 1.00 | 20.34 | EII |
| ATOM | 1869 | H   | PHE | 214 | 39.848 | -15.594 | 32.859 | 1.00 | 16.60 | EII |
| ATOM | 1870 | CA  | PHE | 214 | 39.309 | -14.908 | 31.686 | 1.00 | 15.32 | EII |
| ATOM | 1871 | CB  | PHE | 214 | 39.652 | -15.654 | 30.389 | 1.00 | 16.10 | EII |
| ATOM | 1872 | CG  | PHE | 214 | 40.996 | -15.606 | 29.586 | 1.00 | 12.37 | EII |
| ATOM | 1873 | CD1 | PHE | 214 | 41.996 | -13.776 | 29.450 | 1.00 | 8.31  | EII |
| ATOM | 1874 | CD2 | PHE | 214 | 40.547 | -13.776 | 28.999 | 1.00 | 10.51 | EII |
| ATOM | 1875 | CE1 | PHE | 214 | 43.041 | -14.969 | 28.729 | 1.00 | 14.21 | EII |
| ATOM | 1876 | CE2 | PHE | 214 | 41.592 | -13.128 | 28.274 | 1.00 | 17.26 | EII |
| ATOM | 1877 | CZ  | PHE | 214 | 42.843 | -13.737 | 28.147 | 1.00 | 10.20 | EII |
| ATOM | 1878 | C   | PHE | 214 | 37.814 | -14.776 | 31.811 | 1.00 | 15.91 | EII |
| ATOM | 1879 | O   | PHE | 214 | 37.273 | -13.691 | 31.608 | 1.00 | 21.35 | EII |
| ATOM | 1880 | H   | TYR | 215 | 37.159 | -15.857 | 32.220 | 1.00 | 18.15 | EII |
| ATOM | 1881 | CA  | TYR | 215 | 35.709 | -15.856 | 32.373 | 1.00 | 14.70 | EII |
| ATOM | 1882 | CB  | TYR | 215 | 35.254 | -17.244 | 32.167 | 1.00 | 13.16 | EII |
| ATOM | 1883 | CG  | TYR | 215 | 34.976 | -18.130 | 31.512 | 1.00 | 14.48 | EII |
| ATOM | 1884 | CD1 | TYR | 215 | 35.728 | -19.283 | 31.323 | 1.00 | 11.38 | EII |
| ATOM | 1885 | CE1 | TYR | 215 | 35.424 | -20.102 | 30.238 | 1.00 | 14.22 | EII |
| ATOM | 1886 | CD2 | TYR | 215 | 33.930 | -17.828 | 30.710 | 1.00 | 11.85 | EII |
| ATOM | 1887 | CE2 | TYR | 215 | 33.623 | -18.653 | 29.631 | 1.00 | 16.58 | EII |
| ATOM | 1888 | CZ  | TYR | 215 | 34.360 | -19.776 | 29.404 | 1.00 | 10.52 | EII |
| ATOM | 1889 | OH  | TYR | 215 | 33.961 | -20.589 | 28.376 | 1.00 | 19.94 | EII |
| ATOM | 1895 | C   | TYR | 215 | 35.219 | -14.820 | 33.380 | 1.00 | 16.61 | EII |
| ATOM | 1896 | O   | TYR | 215 | 34.205 | -14.147 | 33.160 | 1.00 | 22.54 | EII |
| ATOM | 1897 | N   | THR | 216 | 35.974 | -14.673 | 34.460 | 1.00 | 18.02 | EII |
| ATOM | 1899 | CA  | THR | 216 | 35.673 | -13.737 | 35.529 | 1.00 | 15.58 | EII |
| ATOM | 1900 | CB  | THR | 216 | 36.661 | -13.902 | 36.684 | 1.00 | 14.28 | EII |
| ATOM | 1901 | OG1 | THR | 216 | 36.558 | -15.219 | 37.226 | 1.00 | 13.22 | EII |
| ATOM | 1903 | CG2 | THR | 216 | 36.385 | -12.897 | 37.736 | 1.00 | 10.50 | EII |
| ATOM | 1904 | C   | THR | 216 | 35.806 | -12.294 | 35.059 | 1.00 | 19.62 | EII |
| ATOM | 1905 | O   | THR | 216 | 35.000 | -11.438 | 35.445 | 1.00 | 21.98 | EII |
| ATOM | 1906 | N   | ALA | 217 | 36.855 | -12.033 | 34.269 | 1.00 | 19.65 | EII |
| ATOM | 1908 | CA  | ALA | 217 | 37.130 | -10.699 | 33.764 | 1.00 | 18.27 | EII |
| ATOM | 1909 | CB  | ALA | 217 | 38.531 | -10.623 | 33.158 | 1.00 | 18.47 | EII |
| ATOM | 1910 | C   | ALA | 217 | 36.073 | -10.375 | 32.728 | 1.00 | 19.12 | EII |
| ATOM | 1911 | O   | ALA | 217 | 35.517 | -9.288  | 32.715 | 1.00 | 25.70 | EII |
| ATOM | 1912 | N   | MET | 218 | 35.745 | -11.353 | 31.903 | 1.00 | 18.77 | EII |
| ATOM | 1914 | CA  | MET | 218 | 34.740 | -11.160 | 30.883 | 1.00 | 19.39 | EII |
| ATOM | 1915 | CB  | MET | 218 | 34.606 | -12.429 | 30.058 | 1.00 | 18.56 | EII |
| ATOM | 1916 | CG  | MET | 218 | 35.600 | -12.603 | 28.963 | 1.00 | 23.88 | EII |
| ATOM | 1917 | SD  | MET | 218 | 35.312 | -14.215 | 28.271 | 1.00 | 34.15 | EII |
| ATOM | 1918 | CE  | MET | 218 | 33.975 | -13.874 | 27.373 | 1.00 | 29.64 | EII |
| ATOM | 1919 | C   | MET | 218 | 33.386 | -10.833 | 31.515 | 1.00 | 21.83 | EII |
| ATOM | 1920 | O   | MET | 218 | 32.615 | -10.011 | 30.998 | 1.00 | 19.19 | EII |
| ATOM | 1921 | N   | GLY | 219 | 33.119 | -11.461 | 32.655 | 1.00 | 22.10 | EII |
| ATOM | 1923 | CA  | GLY | 219 | 31.862 | -11.265 | 33.342 | 1.00 | 24.57 | EII |
| ATOM | 1924 | C   | GLY | 219 | 31.637 | -9.848  | 33.809 | 1.00 | 24.18 | EII |
| ATOM | 1925 | O   | GLY | 219 | 30.516 | -9.337  | 33.725 | 1.00 | 31.58 | EII |
| ATOM | 1926 | N   | LYS | 220 | 32.718 | -9.193  | 34.221 | 1.00 | 24.93 | EII |
| ATOM | 1928 | CA  | LYS | 220 | 32.683 | -7.822  | 34.730 | 1.00 | 22.70 | EII |
| ATOM | 1929 | CB  | LYS | 220 | 34.033 | -7.466  | 35.358 | 1.00 | 26.94 | EII |
| ATOM | 1930 | CG  | LYS | 220 | 34.372 | -8.324  | 36.588 | 1.00 | 30.80 | EII |
| ATOM | 1931 | CD  | LYS | 220 | 35.831 | -8.118  | 37.055 | 1.00 | 39.08 | EII |
| ATOM | 1932 | CE  | LYS | 220 | 36.166 | -6.619  | 37.140 | 1.00 | 44.47 | EII |
| ATOM | 1933 | NZ  | LYS | 220 | 37.448 | -6.314  | 37.829 | 1.00 | 45.90 | EII |
| ATOM | 1937 | C   | LYS | 220 | 32.313 | -6.791  | 33.676 | 1.00 | 24.18 | EII |
| ATOM | 1938 | O   | LYS | 220 | 32.220 | -5.597  | 33.965 | 1.00 | 23.34 | EII |
| ATOM | 1939 | N   | HIS | 221 | 32.161 | -7.230  | 32.434 | 1.00 | 20.47 | EII |
| ATOM | 1941 | CA  | HIS | 221 | 31.801 | -6.300  | 31.386 | 1.00 | 15.79 | EII |
| ATOM | 1942 | CB  | HIS | 221 | 33.013 | -6.018  | 30.534 | 1.00 | 17.34 | EII |
| ATOM | 1943 | CG  | HIS | 221 | 34.135 | -5.390  | 31.290 | 1.00 | 16.38 | EII |
| ATOM | 1944 | CD2 | HIS | 221 | 35.049 | -5.923  | 32.129 | 1.00 | 17.64 | EII |

- 51 -

| ATOM | 1946 | NH1 | HIS | 221 | 34.453 | -4.054 | 31.169 | 1.00 | 15.90 | E11 |
| --- | --- | --- | --- | --- | --- | --- | --- | --- | --- | --- |
| ATOM | 1947 | CE1 | HIS | 221 | 35.525 | -3.795 | 31.898 | 1.00 | 17.36 | E11 |
| ATOM | 1948 | NE2 | HIS | 221 | 35.907 | -4.915 | 32.484 | 1.00 | 18.50 | E11 |
| ATOM | 1950 | C | HIS | 221 | 30.633 | -6.764 | 30.551 | 1.00 | 18.15 | E11 |
| ATOM | 1951 | O | HIS | 221 | 30.445 | -6.347 | 29.392 | 1.00 | 18.29 | E11 |
| ATOM | 1952 | N | GLY | 222 | 29.847 | -7.639 | 31.159 | 1.00 | 22.17 | E11 |
| ATOM | 1953 | CA | GLY | 222 | 28.662 | -8.163 | 30.517 | 1.00 | 27.66 | E11 |
| ATOM | 1954 | C | GLY | 222 | 28.942 | -9.280 | 29.537 | 1.00 | 26.64 | E11 |
| ATOM | 1955 | O | GLY | 222 | 28.315 | -9.336 | 28.475 | 1.00 | 32.44 | E11 |
| ATOM | 1956 | N | GLY | 223 | 29.919 | -10.126 | 29.869 | 1.00 | 28.08 | E11 |
| ATOM | 1957 | CA | GLY | 223 | 30.266 | -11.251 | 29.020 | 1.00 | 23.54 | E11 |
| ATOM | 1958 | C | GLY | 223 | 29.665 | -12.600 | 29.168 | 1.00 | 27.82 | E11 |
| ATOM | 1959 | O | GLY | 223 | 30.454 | -13.619 | 30.755 | 1.00 | 30.96 | E11 |
| ATOM | 1960 | N | SER | 224 | 29.191 | -12.626 | 31.452 | 1.00 | 26.04 | E11 |
| ATOM | 1961 | CA | SER | 224 | 28.850 | -13.874 | 32.675 | 1.00 | 25.88 | E11 |
| ATOM | 1962 | CB | SER | 224 | 27.957 | -13.345 | 33.821 | 1.00 | 24.31 | E11 |
| ATOM | 1964 | OG | SER | 224 | 28.739 | -13.624 | 30.585 | 1.00 | 28.61 | E11 |
| ATOM | 1965 | C | SER | 224 | 28.174 | -14.923 | 30.996 | 1.00 | 25.69 | E11 |
| ATOM | 1966 | O | SER | 224 | 28.046 | -16.077 | 29.385 | 1.00 | 27.24 | E11 |
| ATOM | 1968 | N | SER | 225 | 27.762 | -14.533 | 28.463 | 1.00 | 24.82 | E11 |
| ATOM | 1969 | CA | SER | 225 | 27.097 | -15.433 | 27.899 | 1.00 | 24.29 | E11 |
| ATOM | 1970 | CB | SER | 225 | 25.879 | -14.715 | 27.549 | 1.00 | 25.01 | E11 |
| ATOM | 1972 | OG | SER | 225 | 28.039 | -15.828 | 27.315 | 1.00 | 27.52 | E11 |
| ATOM | 1973 | C | SER | 225 | 27.675 | -16.646 | 26.491 | 1.00 | 23.57 | E11 |
| ATOM | 1974 | O | SER | 225 | 29.215 | -15.202 | 27.235 | 1.00 | 27.12 | E11 |
| ATOM | 1976 | N | VAL | 226 | 30.205 | -15.462 | 26.168 | 1.00 | 24.26 | E11 |
| ATOM | 1977 | CA | VAL | 226 | 31.054 | -14.213 | 25.958 | 1.00 | 13.79 | E11 |
| ATOM | 1978 | CB | VAL | 226 | 31.989 | -14.372 | 24.758 | 1.00 | 16.18 | E11 |
| ATOM | 1980 | CG1 | VAL | 226 | 30.161 | -12.984 | 25.872 | 1.00 | 15.00 | E11 |
| ATOM | 1981 | CG2 | VAL | 226 | 31.144 | -16.633 | 26.513 | 1.00 | 15.92 | E11 |
| ATOM | 1982 | C | VAL | 226 | 31.597 | -16.752 | 27.654 | 1.00 | 16.42 | E11 |
| ATOM | 1983 | O | VAL | 226 | 31.460 | -17.476 | 25.533 | 1.00 | 15.07 | E11 |
| ATOM | 1985 | N | LYS | 227 | 32.340 | -18.620 | 25.764 | 1.00 | 15.12 | E11 |
| ATOM | 1986 | CA | LYS | 227 | 31.935 | -19.840 | 24.927 | 1.00 | 13.62 | E11 |
| ATOM | 1988 | CB | LYS | 227 | 30.808 | -20.614 | 25.500 | 1.00 | 17.74 | E11 |
| ATOM | 1989 | CG | LYS | 227 | 30.376 | -21.765 | 24.527 | 1.00 | 16.84 | E11 |
| ATOM | 1990 | CD | LYS | 227 | 29.163 | -22.522 | 25.047 | 1.00 | 17.48 | E11 |
| ATOM | 1992 | CE | LYS | 227 | 28.034 | -21.579 | 25.263 | 1.00 | 17.61 | E11 |
| ATOM | 1993 | NZ | LYS | 227 | 33.734 | -18.255 | 25.353 | 1.00 | 12.79 | E11 |
| ATOM | 1998 | O | LYS | 227 | 33.931 | -17.404 | 24.539 | 1.00 | 17.29 | E11 |
| ATOM | 1999 | N | LEU | 228 | 34.706 | -18.945 | 25.899 | 1.00 | 11.45 | E11 |
| ATOM | 2001 | CA | LEU | 228 | 36.082 | -18.699 | 25.542 | 1.00 | 10.84 | E11 |
| ATOM | 2002 | CB | LEU | 228 | 36.916 | -18.600 | 26.802 | 1.00 | 11.08 | E11 |
| ATOM | 2003 | CG | LEU | 228 | 38.310 | -18.025 | 26.611 | 1.00 | 14.54 | E11 |
| ATOM | 2004 | CD1 | LEU | 228 | 38.214 | -16.525 | 26.567 | 1.00 | 4.74 | E11 |
| ATOM | 2005 | CD2 | LEU | 228 | 39.222 | -18.477 | 27.732 | 1.00 | 11.45 | E11 |
| ATOM | 2006 | C | LEU | 228 | 36.609 | -19.848 | 24.665 | 1.00 | 14.59 | E11 |
| ATOM | 2007 | O | LEU | 228 | 36.284 | -21.010 | 24.877 | 1.00 | 13.19 | E11 |
| ATOM | 2008 | N | VAL | 229 | 37.339 | -19.516 | 23.612 | 1.00 | 16.22 | E11 |
| ATOM | 2010 | CA | VAL | 229 | 37.958 | -20.523 | 22.735 | 1.00 | 16.08 | E11 |
| ATOM | 2011 | CB | VAL | 229 | 37.530 | -20.328 | 21.220 | 1.00 | 17.31 | E11 |
| ATOM | 2012 | CG1 | VAL | 229 | 38.450 | -21.103 | 20.278 | 1.00 | 16.81 | E11 |
| ATOM | 2013 | CG2 | VAL | 229 | 36.100 | -20.805 | 21.016 | 1.00 | 17.76 | E11 |
| ATOM | 2014 | C | VAL | 229 | 39.445 | -20.254 | 22.908 | 1.00 | 13.02 | E11 |
| ATOM | 2015 | O | VAL | 229 | 39.842 | -19.094 | 22.954 | 1.00 | 7.64 | E11 |
| ATOM | 2016 | N | VAL | 230 | 40.248 | -21.299 | 23.107 | 1.00 | 14.32 | E11 |
| ATOM | 2018 | CA | VAL | 230 | 41.709 | -21.142 | 23.280 | 1.00 | 9.00 | E11 |
| ATOM | 2019 | CB | VAL | 230 | 42.310 | -22.309 | 24.126 | 1.00 | 10.47 | E11 |
| ATOM | 2020 | CG1 | VAL | 230 | 43.841 | -22.167 | 24.215 | 1.00 | 9.76 | E11 |
| ATOM | 2021 | CG2 | VAL | 230 | 41.671 | -22.334 | 25.548 | 1.00 | 8.63 | E11 |
| ATOM | 2022 | C | VAL | 230 | 42.283 | -21.195 | 21.883 | 1.00 | 7.76 | E11 |
| ATOM | 2023 | O | VAL | 230 | 42.603 | -22.281 | 21.413 | 1.00 | 16.66 | E11 |
| ATOM | 2024 | N | SER | 231 | 42.547 | -20.033 | 21.283 | 1.00 | 11.94 | E11 |
| ATOM | 2026 | CA | SER | 231 | 42.989 | -19.965 | 19.883 | 1.00 | 11.06 | E11 |
| ATOM | 2027 | CB | SER | 231 | 42.628 | -18.607 | 19.262 | 1.00 | 14.45 | E11 |
| ATOM | 2028 | OG | SER | 231 | 43.053 | -17.504 | 20.072 | 1.00 | 12.29 | E11 |
| ATOM | 2030 | C | SER | 231 | 44.440 | -20.268 | 19.648 | 1.00 | 18.88 | E11 |
| ATOM | 2031 | O | SER | 231 | 44.858 | -20.380 | 18.516 | 1.00 | 10.67 | E11 |
| ATOM | 2032 | N | GLU | 232 | 45.194 | -20.416 | 20.723 | 1.00 | 8.96 | E11 |
| ATOM | 2034 | CA | GLU | 232 | 46.610 | -20.717 | 20.674 | 1.00 | 9.65 | E11 |
| ATOM | 2035 | CB | GLU | 232 | 47.445 | -19.466 | 20.423 | 1.00 | 12.70 | E11 |
| ATOM | 2036 | CG | GLU | 232 | 47.699 | -19.127 | 19.006 | 1.00 | 10.84 | E11 |
| ATOM | 2037 | CD | GLU | 232 | 48.460 | -17.843 | 18.877 | 1.00 | 17.00 | E11 |
| ATOM | 2038 | OE1 | GLU | 232 | 48.343 | -17.172 | 17.841 | 1.00 | 18.71 | E11 |
| ATOM | 2039 | OE2 | GLU | 232 | 49.189 | -17.492 | 19.810 | 1.00 | 13.04 | E11 |
| ATOM | 2040 | C | GLU | 232 | 47.028 | -21.203 | 22.044 | 1.00 | 13.88 | E11 |
| ATOM | 2041 | O | GLU | 232 | 46.648 | -20.628 | 23.083 | 1.00 | 15.66 | E11 |
| ATOM | 2042 | N | SER | 233 | 47.873 | -22.221 | 22.048 | 1.00 | 15.10 | E11 |
| ATOM | 2044 | CA | SER | 233 | 48.447 | -22.719 | 23.281 | | | E11 |

| | | | | | | | | | | | | | | | | | | |
|---|---|---|---|---|---|---|---|---|---|---|---|---|---|---|---|---|---|---|
| ATOM | 2045 | N | SER | 233 | 47.428 | -23.447 | 24.147 | 1.00 | 17.52 | EII | ATOM | 2093 | CA | GLY | 239 | 65.574 | -21.769 | 22.466 | 1.00 | 20.08 | EII |
| ATOM | 2046 | CA | SER | 233 | 47.998 | -23.682 | 25.424 | 1.00 | 15.32 | EII | ATOM | 2094 | C | GLY | 239 | 65.466 | -21.012 | 23.742 | 1.00 | 23.18 | EII |
| ATOM | 2048 | C | SER | 233 | 49.564 | -23.626 | 22.809 | 1.00 | 14.53 | EII | ATOM | 2095 | O | GLY | 239 | 65.618 | -19.793 | 23.744 | 1.00 | 27.89 | EII |
| ATOM | 2049 | O | SER | 233 | 49.459 | -24.224 | 21.731 | 1.00 | 13.76 | EII | ATOM | 2096 | N | GLY | 240 | 65.163 | -21.701 | 24.829 | 1.00 | 23.66 | EII |
| ATOM | 2050 | N | GLY | 234 | 50.684 | -23.622 | 23.527 | 1.00 | 13.82 | EII | ATOM | 2098 | CA | GLY | 240 | 65.021 | -20.991 | 26.082 | 1.00 | 27.94 | EII |
| ATOM | 2052 | CA | GLY | 234 | 51.807 | -24.459 | 23.149 | 1.00 | 7.33 | EII | ATOM | 2099 | C | GLY | 240 | 64.824 | -21.948 | 27.224 | 1.00 | 30.25 | EII |
| ATOM | 2053 | C | GLY | 234 | 52.945 | -24.290 | 24.122 | 1.00 | 13.92 | EII | ATOM | 2100 | O | GLY | 240 | 64.701 | -23.155 | 26.998 | 1.00 | 33.00 | EII |
| ATOM | 2054 | O | GLY | 234 | 52.823 | -23.537 | 25.101 | 1.00 | 14.99 | EII | ATOM | 2101 | N | THR | 241 | 64.799 | -21.400 | 28.437 | 1.00 | 30.01 | EII |
| ATOM | 2055 | N | TRP | 235 | 54.064 | -24.946 | 23.820 | 1.00 | 15.91 | EII | ATOM | 2103 | CA | THR | 241 | 64.614 | -22.148 | 29.671 | 1.00 | 28.71 | EII |
| ATOM | 2057 | CA | TRP | 235 | 55.280 | -24.924 | 24.641 | 1.00 | 19.33 | EII | ATOM | 2104 | CB | THR | 241 | 64.350 | -21.190 | 30.835 | 1.00 | 31.58 | EII |
| ATOM | 2058 | CB | TRP | 235 | 55.202 | -26.058 | 25.717 | 1.00 | 16.35 | EII | ATOM | 2105 | OG1 | THR | 241 | 65.194 | -20.039 | 30.677 | 1.00 | 34.07 | EII |
| ATOM | 2059 | CG | TRP | 235 | 56.292 | -26.058 | 26.781 | 1.00 | 13.75 | EII | ATOM | 2107 | CG2 | THR | 241 | 64.676 | -21.869 | 32.161 | 1.00 | 32.31 | EII |
| ATOM | 2060 | CD2 | TRP | 235 | 56.155 | -25.765 | 28.181 | 1.00 | 17.23 | EII | ATOM | 2108 | C | THR | 241 | 63.432 | -23.071 | 29.551 | 1.00 | 25.71 | EII |
| ATOM | 2061 | CE2 | TRP | 235 | 57.430 | -25.383 | 28.776 | 1.00 | 17.10 | EII | ATOM | 2109 | O | THR | 241 | 62.376 | -22.687 | 29.073 | 1.00 | 25.34 | EII |
| ATOM | 2062 | CE3 | TRP | 235 | 55.060 | -25.913 | 28.989 | 1.00 | 11.51 | EII | ATOM | 2110 | N | ALA | 242 | 63.657 | -24.319 | 29.923 | 1.00 | 23.07 | EII |
| ATOM | 2063 | CD1 | TRP | 235 | 57.613 | -26.365 | 26.591 | 1.00 | 11.11 | EII | ATOM | 2112 | CA | ALA | 242 | 62.637 | -25.351 | 29.867 | 1.00 | 22.69 | EII |
| ATOM | 2064 | NE1 | TRP | 235 | 58.307 | -26.288 | 27.785 | 1.00 | 12.66 | EII | ATOM | 2113 | CB | ALA | 242 | 61.449 | -24.992 | 30.775 | 1.00 | 21.84 | EII |
| ATOM | 2066 | CZ2 | TRP | 235 | 57.653 | -25.701 | 30.149 | 1.00 | 16.57 | EII | ATOM | 2114 | C | ALA | 242 | 62.181 | -25.686 | 28.442 | 1.00 | 18.91 | EII |
| ATOM | 2067 | CZ3 | TRP | 235 | 55.281 | -25.175 | 30.362 | 1.00 | 7.97 | EII | ATOM | 2115 | O | ALA | 242 | 61.318 | -26.534 | 28.245 | 1.00 | 27.03 | EII |
| ATOM | 2068 | CH2 | TRP | 235 | 56.564 | -25.331 | 30.924 | 1.00 | 16.17 | EII | ATOM | 2116 | N | ALA | 243 | 62.814 | -25.088 | 27.448 | 1.00 | 18.25 | EII |
| ATOM | 2069 | C | TRP | 235 | 56.443 | -25.175 | 23.652 | 1.00 | 16.87 | EII | ATOM | 2118 | CA | ALA | 243 | 62.455 | -25.366 | 26.070 | 1.00 | 16.60 | EII |
| ATOM | 2070 | O | TRP | 235 | 56.324 | -26.053 | 22.804 | 1.00 | 19.48 | EII | ATOM | 2119 | CB | ALA | 243 | 62.757 | -24.177 | 25.220 | 1.00 | 13.11 | EII |
| ATOM | 2071 | N | PRO | 236 | 57.539 | -24.388 | 23.721 | 1.00 | 18.84 | EII | ATOM | 2120 | C | ALA | 243 | 63.175 | -26.597 | 25.531 | 1.00 | 18.50 | EII |
| ATOM | 2072 | CD | PRO | 236 | 57.894 | -23.350 | 24.700 | 1.00 | 20.49 | EII | ATOM | 2121 | O | ALA | 243 | 64.321 | -26.506 | 25.103 | 1.00 | 23.27 | EII |
| ATOM | 2073 | CA | PRO | 236 | 58.602 | -24.492 | 22.721 | 1.00 | 17.72 | EII | ATOM | 2124 | CA | THR | 244 | 62.505 | -27.746 | 25.559 | 1.00 | 20.43 | EII |
| ATOM | 2074 | CB | PRO | 236 | 59.355 | -23.157 | 22.860 | 1.00 | 16.10 | EII | ATOM | 2125 | CB | THR | 244 | 63.070 | -28.996 | 25.059 | 1.00 | 19.04 | EII |
| ATOM | 2075 | CG | PRO | 236 | 58.552 | -22.348 | 23.828 | 1.00 | 16.21 | EII | ATOM | 2126 | OG1 | THR | 244 | 63.754 | -29.803 | 26.208 | 1.00 | 21.24 | EII |
| ATOM | 2076 | C | PRO | 236 | 59.550 | -25.665 | 23.015 | 1.00 | 19.89 | EII | ATOM | 2128 | CG2 | THR | 244 | 62.769 | -30.326 | 27.098 | 1.00 | 23.92 | EII |
| ATOM | 2077 | O | PRO | 236 | 59.799 | -25.995 | 24.185 | 1.00 | 18.73 | EII | ATOM | 2129 | C | THR | 244 | 64.647 | -28.899 | 27.032 | 1.00 | 19.86 | EII |
| ATOM | 2078 | N | SER | 237 | 60.115 | -26.231 | 21.945 | 1.00 | 16.20 | EII | ATOM | 2130 | O | THR | 244 | 61.906 | -29.801 | 24.456 | 1.00 | 20.96 | EII |
| ATOM | 2080 | CA | SER | 237 | 61.035 | -27.361 | 22.015 | 1.00 | 13.46 | EII | ATOM | 2131 | N | PRO | 245 | 60.731 | -29.514 | 24.745 | 1.00 | 22.40 | EII |
| ATOM | 2081 | CB | SER | 237 | 60.765 | -28.339 | 20.903 | 1.00 | 7.29 | EII | ATOM | 2132 | CD | PRO | 245 | 62.198 | -30.811 | 23.619 | 1.00 | 21.19 | EII |
| ATOM | 2082 | C | SER | 237 | 60.666 | -27.952 | 19.664 | 1.00 | 23.55 | EII | ATOM | 2133 | CA | PRO | 245 | 63.498 | -31.192 | 23.044 | 1.00 | 16.05 | EII |
| ATOM | 2084 | C | SER | 237 | 62.512 | -26.952 | 21.969 | 1.00 | 13.63 | EII | ATOM | 2134 | CB | PRO | 245 | 61.134 | -31.704 | 23.131 | 1.00 | 19.50 | EII |
| ATOM | 2085 | O | SER | 237 | 63.399 | -27.788 | 21.612 | 1.00 | 17.13 | EII | ATOM | 2135 | CG | PRO | 245 | 61.889 | -32.626 | 22.157 | 1.00 | 17.61 | EII |
| ATOM | 2086 | N | GLY | 238 | 62.775 | -25.659 | 22.076 | 1.00 | 16.21 | EII | ATOM | 2136 | C | PRO | 245 | 63.082 | -31.816 | 21.756 | 1.00 | 15.09 | EII |
| ATOM | 2088 | CA | GLY | 238 | 64.140 | -25.210 | 22.103 | 1.00 | 16.01 | EII | ATOM | 2137 | O | PRO | 245 | 60.390 | -32.518 | 24.220 | 1.00 | 19.32 | EII |
| ATOM | 2089 | C | GLY | 238 | 64.212 | -23.717 | 22.063 | 1.00 | 17.97 | EII | ATOM | 2138 | N | ALA | 246 | 59.193 | -32.808 | 24.091 | 1.00 | 16.96 | EII |
| ATOM | 2090 | O | GLY | 238 | 63.216 | -23.059 | 21.761 | 1.00 | 18.27 | EII | ATOM | 2139 | CA | ALA | 246 | 61.084 | -32.848 | 25.308 | 1.00 | 20.00 | EII |
| ATOM | 2091 | N | GLY | 239 | 65.337 | -23.195 | 22.537 | 1.00 | 20.09 | EII | ATOM | 2140 | CA | ALA | 246 | 60.496 | -33.625 | 26.396 | 1.00 | 19.40 | EII |

- 53 -

| | | | | | | | | | | |
|---|---|---|---|---|---|---|---|---|---|---|
| ATOM | 2141 | CB | ALA | 246 | 61.556 | -34.019 | 27.370 | 1.00 | 12.06 | E11 |
| ATOM | 2142 | C | ALA | 246 | 59.405 | -32.825 | 27.089 | 1.00 | 22.07 | E11 |
| ATOM | 2143 | O | ALA | 246 | 58.301 | -33.335 | 27.329 | 1.00 | 23.38 | E11 |
| ATOM | 2144 | N | ASN | 247 | 59.730 | -31.560 | 27.362 | 1.00 | 21.43 | E11 |
| ATOM | 2146 | CA | ASN | 247 | 58.833 | -30.618 | 28.001 | 1.00 | 17.93 | E11 |
| ATOM | 2147 | CB | ASN | 247 | 59.573 | -29.348 | 28.444 | 1.00 | 20.95 | E11 |
| ATOM | 2148 | CG | ASN | 247 | 60.456 | -29.590 | 29.651 | 1.00 | 18.22 | E11 |
| ATOM | 2149 | OD1 | ASN | 247 | 60.573 | -30.719 | 30.101 | 1.00 | 19.55 | E11 |
| ATOM | 2150 | ND2 | ASN | 247 | 61.096 | -28.547 | 30.159 | 1.00 | 18.31 | E11 |
| ATOM | 2153 | C | ASN | 247 | 57.711 | -30.239 | 27.069 | 1.00 | 17.68 | E11 |
| ATOM | 2154 | O | ASN | 247 | 56.562 | -30.298 | 27.475 | 1.00 | 26.48 | E11 |
| ATOM | 2155 | N | ALA | 248 | 58.022 | -29.983 | 25.794 | 1.00 | 19.95 | E11 |
| ATOM | 2157 | CA | ALA | 248 | 57.007 | -29.566 | 24.823 | 1.00 | 14.26 | E11 |
| ATOM | 2158 | CB | ALA | 248 | 57.647 | -29.124 | 23.537 | 1.00 | 9.42 | E11 |
| ATOM | 2159 | C | ALA | 248 | 54.813 | -30.697 | 24.574 | 1.00 | 19.58 | E11 |
| ATOM | 2160 | O | ALA | 248 | 54.813 | -30.460 | 24.585 | 1.00 | 23.61 | E11 |
| ATOM | 2161 | N | ARG | 249 | 56.504 | -31.931 | 24.387 | 1.00 | 19.93 | E11 |
| ATOM | 2163 | CA | ARG | 249 | 55.653 | -33.073 | 24.169 | 1.00 | 17.16 | E11 |
| ATOM | 2164 | CB | ARG | 249 | 56.493 | -34.335 | 23.837 | 1.00 | 19.14 | E11 |
| ATOM | 2165 | CG | ARG | 249 | 55.672 | -35.594 | 24.616 | 1.00 | 23.39 | E11 |
| ATOM | 2166 | CD | ARG | 249 | 56.146 | -36.853 | 24.616 | 1.00 | 32.83 | E11 |
| ATOM | 2167 | NE | ARG | 249 | 56.227 | -36.676 | 26.085 | 1.00 | 43.30 | E11 |
| ATOM | 2168 | CZ | ARG | 249 | 57.378 | -36.515 | 26.766 | 1.00 | 51.48 | E11 |
| ATOM | 2169 | NH1 | ARG | 249 | 58.544 | -36.514 | 26.118 | 1.00 | 57.23 | E11 |
| ATOM | 2170 | NH2 | ARG | 249 | 57.380 | -36.281 | 28.082 | 1.00 | 49.58 | E11 |
| ATOM | 2173 | C | ARG | 249 | 54.782 | -33.257 | 25.620 | 1.00 | 20.35 | E11 |
| ATOM | 2176 | O | ARG | 249 | 53.577 | -33.509 | 25.502 | 1.00 | 20.76 | E11 |
| ATOM | 2177 | N | PHE | 250 | 55.378 | -33.115 | 26.809 | 1.00 | 21.84 | E11 |
| ATOM | 2178 | CA | PHE | 250 | 54.643 | -33.306 | 28.066 | 1.00 | 20.86 | E11 |
| ATOM | 2180 | CB | PHE | 250 | 55.542 | -33.105 | 29.279 | 1.00 | 23.27 | E11 |
| ATOM | 2181 | CG | PHE | 250 | 54.884 | -33.486 | 30.581 | 1.00 | 27.40 | E11 |
| ATOM | 2182 | CD1 | PHE | 250 | 54.939 | -34.794 | 31.057 | 1.00 | 23.71 | E11 |
| ATOM | 2183 | CD2 | PHE | 250 | 54.203 | -32.544 | 31.337 | 1.00 | 29.81 | E11 |
| ATOM | 2184 | CE1 | PHE | 250 | 54.325 | -35.148 | 32.262 | 1.00 | 28.55 | E11 |
| ATOM | 2185 | CE2 | PHE | 250 | 53.594 | -32.895 | 32.538 | 1.00 | 29.15 | E11 |
| ATOM | 2186 | CZ | PHE | 250 | 53.658 | -34.191 | 32.995 | 1.00 | 31.18 | E11 |
| ATOM | 2187 | C | PHE | 250 | 53.495 | -32.320 | 28.120 | 1.00 | 26.31 | E11 |
| ATOM | 2188 | O | PHE | 250 | 52.348 | -32.709 | 28.381 | 1.00 | 26.08 | E11 |
| ATOM | 2189 | N | TYR | 251 | 53.795 | -31.067 | 27.777 | 1.00 | 19.72 | E11 |
| ATOM | 2192 | CA | TYR | 251 | 52.808 | -30.018 | 27.767 | 1.00 | 20.90 | E11 |
| ATOM | 2193 | CB | TYR | 251 | 53.448 | -28.624 | 27.555 | 1.00 | 19.37 | E11 |
| ATOM | 2194 | CG | TYR | 251 | 52.403 | -27.549 | 27.507 | 1.00 | 17.93 | E11 |
| ATOM | 2195 | CD1 | TYR | 251 | 51.867 | -27.013 | 28.685 | 1.00 | 24.01 | E11 |
| ATOM | 2196 | CE1 | TYR | 251 | 50.713 | -26.185 | 28.650 | 1.00 | 19.94 | E11 |
| ATOM | 2197 | CD2 | TYR | 251 | 51.790 | -27.220 | 26.300 | 1.00 | 15.85 | E11 |
| ATOM | 2198 | CE2 | TYR | 251 | 50.662 | -26.426 | 26.254 | 1.00 | 18.74 | E11 |
| ATOM | 2199 | CZ | TYR | 251 | 50.127 | -25.920 | 27.423 | 1.00 | 15.89 | E11 |
| ATOM | 2200 | OH | TYR | 251 | 48.994 | -25.174 | 27.349 | 1.00 | 20.18 | E11 |
| ATOM | 2202 | C | TYR | 251 | 51.712 | -30.259 | 26.719 | 1.00 | 25.14 | E11 |
| ATOM | 2203 | O | TYR | 251 | 50.515 | -30.308 | 27.041 | 1.00 | 21.35 | E11 |
| ATOM | 2204 | N | ASN | 252 | 52.108 | -30.390 | 25.461 | 1.00 | 17.76 | E11 |
| ATOM | 2206 | CA | ASN | 252 | 51.112 | -30.549 | 24.409 | 1.00 | 14.23 | E11 |
| ATOM | 2207 | CB | ASN | 252 | 51.720 | -30.394 | 23.013 | 1.00 | 19.54 | E11 |
| ATOM | 2208 | CG | ASN | 252 | 51.905 | -28.923 | 22.647 | 1.00 | 16.38 | E11 |
| ATOM | 2209 | OD1 | ASN | 252 | 51.203 | -28.062 | 23.181 | 1.00 | 15.03 | E11 |
| ATOM | 2210 | ND2 | ASN | 252 | 52.875 | -28.618 | 21.805 | 1.00 | 14.95 | E11 |
| ATOM | 2213 | C | ASN | 252 | 50.240 | -31.757 | 24.524 | 1.00 | 16.97 | E11 |
| ATOM | 2214 | O | ASN | 252 | 49.051 | -31.663 | 24.286 | 1.00 | 19.56 | E11 |
| ATOM | 2215 | N | GLN | 253 | 50.815 | -32.898 | 24.880 | 1.00 | 20.10 | E11 |
| ATOM | 2217 | CA | GLN | 253 | 50.010 | -34.086 | 25.035 | 1.00 | 18.91 | E11 |
| ATOM | 2218 | CB | GLN | 253 | 50.885 | -35.298 | 25.269 | 1.00 | 18.29 | E11 |
| ATOM | 2219 | CG | GLN | 253 | 50.125 | -36.577 | 25.149 | 1.00 | 19.54 | E11 |
| ATOM | 2220 | CD | GLN | 253 | 49.736 | -36.577 | 23.719 | 1.00 | 21.60 | E11 |
| ATOM | 2221 | OE1 | GLN | 253 | 48.553 | -36.868 | 23.381 | 1.00 | 20.99 | E11 |
| ATOM | 2222 | NE2 | GLN | 253 | 50.739 | -36.914 | 22.862 | 1.00 | 20.70 | E11 |
| ATOM | 2225 | C | GLN | 253 | 49.022 | -37.067 | 26.185 | 1.00 | 17.90 | E11 |
| ATOM | 2226 | O | GLN | 253 | 47.886 | -34.348 | 26.072 | 1.00 | 19.95 | E11 |
| ATOM | 2227 | N | HIS | 254 | 49.454 | -33.372 | 27.311 | 1.00 | 23.20 | E11 |
| ATOM | 2229 | CA | HIS | 254 | 48.523 | -33.166 | 28.430 | 1.00 | 25.23 | E11 |
| ATOM | 2230 | CB | HIS | 254 | 49.254 | -32.721 | 29.682 | 1.00 | 27.73 | E11 |
| ATOM | 2231 | CG | HIS | 254 | 50.008 | -33.806 | 30.342 | 1.00 | 31.02 | E11 |
| ATOM | 2232 | CD2 | HIS | 254 | 51.068 | -33.806 | 31.181 | 1.00 | 33.34 | E11 |
| ATOM | 2233 | ND1 | HIS | 254 | 49.725 | -35.151 | 30.120 | 1.00 | 29.85 | E11 |
| ATOM | 2235 | CE1 | HIS | 254 | 50.577 | -35.905 | 30.786 | 1.00 | 28.62 | E11 |
| ATOM | 2236 | NE2 | HIS | 254 | 51.403 | -35.112 | 31.437 | 1.00 | 32.09 | E11 |
| ATOM | 2238 | C | HIS | 254 | 47.420 | -32.172 | 28.088 | 1.00 | 25.91 | E11 |
| ATOM | 2239 | O | HIS | 254 | 46.298 | -32.301 | 28.576 | 1.00 | 26.41 | E11 |
| ATOM | 2240 | N | LEU | 255 | 47.748 | -31.175 | 27.270 | 1.00 | 23.73 | E11 |
| ATOM | 2242 | CA | LEU | 255 | 46.783 | -30.181 | 26.821 | 1.00 | 23.06 | E11 |
| ATOM | 2243 | CB | LEU | 255 | 47.461 | -29.188 | 25.865 | 1.00 | 15.01 | E11 |

- 54 -

| ATOM | 2244 | CG | LEU | 255 | 46.592 | -28.017 | 25.389 | 1.00 | 14.07 | EII |
|------|------|----|-----|-----|--------|---------|--------|------|-------|-----|
| ATOM | 2245 | CD1 | LEU | 255 | 45.980 | -27.326 | 26.576 | 1.00 | 14.77 | EII |
| ATOM | 2246 | CD2 | LEU | 255 | 47.403 | -27.045 | 24.573 | 1.00 | 13.38 | EII |
| ATOM | 2247 | C | LEU | 255 | 45.677 | -30.953 | 26.090 | 1.00 | 23.45 | EII |
| ATOM | 2248 | O | LEU | 255 | 44.480 | -30.878 | 26.424 | 1.00 | 24.52 | EII |
| ATOM | 2249 | N | ILE | 256 | 46.113 | -31.729 | 25.112 | 1.00 | 23.83 | EII |
| ATOM | 2251 | CA | ILE | 256 | 45.220 | -32.528 | 24.292 | 1.00 | 23.43 | EII |
| ATOM | 2252 | CB | ILE | 256 | 46.013 | -33.364 | 23.293 | 1.00 | 20.67 | EII |
| ATOM | 2253 | CG2 | ILE | 256 | 45.090 | -34.257 | 22.527 | 1.00 | 19.55 | EII |
| ATOM | 2254 | CG1 | ILE | 256 | 46.763 | -32.429 | 22.334 | 1.00 | 20.24 | EII |
| ATOM | 2255 | CD1 | ILE | 256 | 47.608 | -33.163 | 21.323 | 1.00 | 22.83 | EII |
| ATOM | 2256 | C | ILE | 256 | 44.314 | -33.425 | 25.107 | 1.00 | 20.76 | EII |
| ATOM | 2257 | O | ILE | 256 | 43.113 | -33.517 | 24.844 | 1.00 | 21.78 | EII |
| ATOM | 2258 | N | ASN | 257 | 44.891 | -34.089 | 26.093 | 1.00 | 22.42 | EII |
| ATOM | 2260 | CA | ASN | 257 | 44.121 | -34.981 | 26.927 | 1.00 | 17.31 | EII |
| ATOM | 2261 | CB | ASN | 257 | 45.040 | -35.912 | 27.672 | 1.00 | 20.56 | EII |
| ATOM | 2262 | CG | ASN | 257 | 45.829 | -36.827 | 26.739 | 1.00 | 24.27 | EII |
| ATOM | 2263 | OD1 | ASN | 257 | 46.936 | -37.241 | 27.057 | 1.00 | 23.05 | EII |
| ATOM | 2264 | ND2 | ASN | 257 | 45.262 | -37.137 | 25.589 | 1.00 | 21.49 | EII |
| ATOM | 2267 | C | ASN | 257 | 43.240 | -34.203 | 27.880 | 1.00 | 28.92 | EII |
| ATOM | 2268 | O | ASN | 257 | 42.085 | -34.578 | 28.096 | 1.00 | 23.33 | EII |
| ATOM | 2269 | N | HIS | 258 | 43.713 | -33.032 | 28.301 | 1.00 | 19.76 | EII |
| ATOM | 2271 | CA | HIS | 258 | 42.978 | -32.194 | 29.240 | 1.00 | 18.43 | EII |
| ATOM | 2272 | CB | HIS | 258 | 43.919 | -31.171 | 29.872 | 1.00 | 19.22 | EII |
| ATOM | 2273 | CG | HIS | 258 | 43.290 | -30.373 | 30.964 | 1.00 | 24.01 | EII |
| ATOM | 2274 | CD2 | HIS | 258 | 42.525 | -29.256 | 30.931 | 1.00 | 22.29 | EII |
| ATOM | 2275 | ND1 | HIS | 258 | 43.334 | -30.766 | 32.280 | 1.00 | 26.63 | EII |
| ATOM | 2277 | CE1 | HIS | 258 | 42.610 | -29.933 | 33.011 | 1.00 | 23.25 | EII |
| ATOM | 2278 | NE2 | HIS | 258 | 42.108 | -29.012 | 32.216 | 1.00 | 19.47 | EII |
| ATOM | 2280 | C | HIS | 258 | 41.741 | -31.448 | 28.763 | 1.00 | 17.98 | EII |
| ATOM | 2281 | O | HIS | 258 | 40.696 | -31.550 | 29.362 | 1.00 | 24.79 | EII |
| ATOM | 2282 | N | VAL | 259 | 41.849 | -30.700 | 27.678 | 1.00 | 21.84 | EII |
| ATOM | 2284 | CA | VAL | 259 | 40.740 | -29.844 | 27.236 | 1.00 | 17.27 | EII |
| ATOM | 2285 | CB | VAL | 259 | 41.114 | -29.058 | 25.973 | 1.00 | 16.23 | EII |
| ATOM | 2286 | CG1 | VAL | 259 | 42.280 | -28.132 | 26.298 | 1.00 | 17.32 | EII |
| ATOM | 2287 | CG2 | VAL | 259 | 41.506 | -29.994 | 24.866 | 1.00 | 17.32 | EII |
| ATOM | 2288 | C | VAL | 259 | 39.296 | -30.343 | 27.182 | 1.00 | 23.73 | EII |
| ATOM | 2289 | O | VAL | 259 | 38.368 | -29.562 | 27.409 | 1.00 | 25.69 | EII |
| ATOM | 2290 | N | GLY | 260 | 39.092 | -31.635 | 26.944 | 1.00 | 26.69 | EII |
| ATOM | 2292 | CA | GLY | 260 | 37.733 | -32.155 | 26.903 | 1.00 | 27.11 | EII |
| ATOM | 2293 | C | GLY | 260 | 36.984 | -32.073 | 28.232 | 1.00 | 27.66 | EII |
| ATOM | 2294 | O | GLY | 260 | 35.761 | -32.031 | 28.263 | 1.00 | 28.93 | EII |
| ATOM | 2295 | N | ARG | 261 | 37.722 | -32.020 | 29.333 | 1.00 | 31.58 | EII |
| ATOM | 2297 | CA | ARG | 261 | 37.141 | -31.962 | 30.669 | 1.00 | 33.51 | EII |
| ATOM | 2298 | CB | ARG | 261 | 38.130 | -32.499 | 31.715 | 1.00 | 32.73 | EII |
| ATOM | 2299 | CG | ARG | 261 | 38.563 | -33.937 | 31.484 | 1.00 | 33.14 | EII |
| ATOM | 2300 | CD | ARG | 261 | 39.549 | -34.398 | 32.547 | 0.00 | 33.24 | EII |
| ATOM | 2301 | NE | ARG | 261 | 39.957 | -35.785 | 32.338 | 0.00 | 33.26 | EII |
| ATOM | 2303 | CZ | ARG | 261 | 40.736 | -36.477 | 33.165 | 0.00 | 33.29 | EII |
| ATOM | 2304 | NH1 | ARG | 261 | 41.207 | -35.924 | 34.276 | 0.00 | 33.30 | EII |
| ATOM | 2307 | NH2 | ARG | 261 | 41.054 | -37.730 | 32.872 | 0.00 | 33.30 | EII |
| ATOM | 2310 | C | ARG | 261 | 36.715 | -30.549 | 31.030 | 1.00 | 31.16 | EII |
| ATOM | 2311 | O | ARG | 261 | 35.637 | -30.333 | 31.580 | 1.00 | 36.07 | EII |
| ATOM | 2312 | N | GLY | 262 | 37.545 | -29.574 | 30.713 | 1.00 | 29.97 | EII |
| ATOM | 2314 | CA | GLY | 262 | 37.162 | -28.219 | 31.035 | 1.00 | 26.12 | EII |
| ATOM | 2315 | C | GLY | 262 | 37.922 | -27.747 | 32.239 | 1.00 | 23.66 | EII |
| ATOM | 2316 | O | GLY | 262 | 39.014 | -28.241 | 32.501 | 1.00 | 24.55 | EII |
| ATOM | 2317 | N | THR | 263 | 37.389 | -26.735 | 32.915 | 1.00 | 20.28 | EII |
| ATOM | 2319 | CA | THR | 263 | 38.027 | -26.164 | 34.091 | 1.00 | 19.15 | EII |
| ATOM | 2320 | CB | THR | 263 | 38.210 | -24.672 | 33.772 | 1.00 | 19.52 | EII |
| ATOM | 2321 | OG1 | THR | 263 | 36.908 | -24.077 | 33.916 | 1.00 | 21.27 | EII |
| ATOM | 2323 | CG2 | THR | 263 | 39.069 | -24.358 | 32.688 | 1.00 | 14.96 | EII |
| ATOM | 2324 | C | THR | 263 | 37.130 | -26.374 | 35.305 | 1.00 | 20.99 | EII |
| ATOM | 2325 | O | THR | 263 | 35.955 | -26.733 | 35.170 | 1.00 | 23.56 | EII |
| ATOM | 2326 | N | PRO | 264 | 37.674 | -26.162 | 36.518 | 1.00 | 19.68 | EII |
| ATOM | 2327 | CD | PRO | 264 | 39.114 | -25.947 | 36.772 | 1.00 | 15.99 | EII |
| ATOM | 2328 | CA | PRO | 264 | 36.920 | -26.169 | 37.783 | 1.00 | 19.02 | EII |
| ATOM | 2329 | CB | PRO | 264 | 37.888 | -25.499 | 38.744 | 1.00 | 19.57 | EII |
| ATOM | 2330 | CG | PRO | 264 | 39.210 | -26.060 | 38.287 | 1.00 | 21.74 | EII |
| ATOM | 2331 | C | PRO | 264 | 35.561 | -25.450 | 37.759 | 1.00 | 17.65 | EII |
| ATOM | 2332 | O | PRO | 264 | 34.536 | -26.027 | 38.104 | 1.00 | 21.17 | EII |
| ATOM | 2333 | N | ARG | 265 | 35.544 | -24.196 | 37.343 | 1.00 | 16.83 | EII |
| ATOM | 2335 | CA | ARG | 265 | 34.291 | -23.462 | 37.321 | 1.00 | 19.86 | EII |
| ATOM | 2336 | CB | ARG | 265 | 34.542 | -22.008 | 37.691 | 1.00 | 18.70 | EII |
| ATOM | 2337 | CG | ARG | 265 | 34.979 | -21.754 | 39.105 | 1.00 | 18.29 | EII |
| ATOM | 2338 | CD | ARG | 265 | 35.187 | -20.258 | 39.245 | 1.00 | 21.36 | EII |
| ATOM | 2339 | NE | ARG | 265 | 35.116 | -19.780 | 40.609 | 1.00 | 27.88 | EII |
| ATOM | 2341 | CZ | ARG | 265 | 36.152 | -19.712 | 41.432 | 1.00 | 27.02 | EII |
| ATOM | 2342 | NH1 | ARG | 265 | 37.357 | -20.086 | 41.030 | 1.00 | 28.18 | EII |
| ATOM | 2345 | NH2 | ARG | 265 | 35.961 | -19.347 | 42.688 | 1.00 | 31.22 | EII |

| ATOM | 2349 | C | ARG | 265 | 33.561 | -23.511 | 35.964 | 1.00 | 21.25 | E11 |
|---|---|---|---|---|---|---|---|---|---|---|
| ATOM | 2349 | O | ARG | 265 | 32.419 | -23.066 | 35.838 | 1.00 | 23.07 | E11 |
| ATOM | 2350 | N | HIS | 266 | 34.173 | -24.086 | 34.996 | 1.00 | 25.48 | E11 |
| ATOM | 2351 | CA | HIS | 266 | 33.600 | -24.173 | 33.645 | 1.00 | 20.92 | E11 |
| ATOM | 2352 | CB | HIS | 266 | 34.242 | -23.106 | 32.752 | 1.00 | 15.11 | E11 |
| ATOM | 2353 | CG | HIS | 266 | 33.762 | -21.753 | 33.287 | 1.00 | 15.11 | E11 |
| ATOM | 2354 | ND1 | HIS | 266 | 34.505 | -21.022 | 34.209 | 1.00 | 15.21 | E11 |
| ATOM | 2355 | CE1 | HIS | 266 | 33.843 | -19.913 | 34.486 | 1.00 | 15.21 | E11 |
| ATOM | 2356 | NE2 | HIS | 266 | 32.730 | -19.896 | 33.797 | 1.00 | 15.24 | E11 |
| ATOM | 2357 | CD2 | HIS | 266 | 32.642 | -21.021 | 33.039 | 1.00 | 15.27 | E11 |
| ATOM | 2358 | C | HIS | 266 | 33.868 | -25.557 | 33.052 | 1.00 | 27.16 | E11 |
| ATOM | 2359 | O | HIS | 266 | 34.759 | -25.724 | 32.206 | 1.00 | 32.85 | E11 |
| ATOM | 2360 | N | PRO | 267 | 33.108 | -26.571 | 33.408 | 1.00 | 28.66 | E11 |
| ATOM | 2361 | CD | PRO | 267 | 32.036 | -26.534 | 34.418 | 1.00 | 24.81 | E11 |
| ATOM | 2362 | CA | PRO | 267 | 33.332 | -27.945 | 32.919 | 1.00 | 28.00 | E11 |
| ATOM | 2363 | CB | PRO | 267 | 32.582 | -28.781 | 33.938 | 1.00 | 24.20 | E11 |
| ATOM | 2364 | CG | PRO | 267 | 31.395 | -27.897 | 34.261 | 1.00 | 26.53 | E11 |
| ATOM | 2365 | C | PRO | 267 | 32.751 | -28.109 | 31.519 | 1.00 | 25.88 | E11 |
| ATOM | 2366 | O | PRO | 267 | 31.661 | -27.637 | 31.232 | 1.00 | 31.93 | E11 |
| ATOM | 2367 | N | GLY | 268 | 33.478 | -28.774 | 30.643 | 1.00 | 26.16 | E11 |
| ATOM | 2368 | CA | GLY | 268 | 33.001 | -28.926 | 29.280 | 1.00 | 25.80 | E11 |
| ATOM | 2369 | C | GLY | 268 | 34.136 | -28.626 | 28.322 | 1.00 | 26.52 | E11 |
| ATOM | 2370 | O | GLY | 268 | 34.889 | -27.684 | 28.534 | 1.00 | 28.52 | E11 |
| ATOM | 2371 | N | ALA | 269 | 34.249 | -29.419 | 27.266 | 1.00 | 24.59 | E11 |
| ATOM | 2372 | CA | ALA | 269 | 35.335 | -29.272 | 26.316 | 1.00 | 21.90 | E11 |
| ATOM | 2373 | CB | ALA | 269 | 35.093 | -30.136 | 25.142 | 1.00 | 20.93 | E11 |
| ATOM | 2374 | C | ALA | 269 | 35.517 | -27.852 | 25.864 | 1.00 | 20.52 | E11 |
| ATOM | 2375 | O | ALA | 269 | 34.644 | -27.144 | 25.913 | 1.00 | 24.01 | E11 |
| ATOM | 2376 | N | ILE | 270 | 36.837 | -27.434 | 25.496 | 1.00 | 21.68 | E11 |
| ATOM | 2377 | CA | ILE | 270 | 37.250 | -26.092 | 26.365 | 1.00 | 26.43 | E11 |
| ATOM | 2378 | CB | ILE | 270 | 38.411 | -25.543 | 26.051 | 1.00 | 22.93 | E11 |
| ATOM | 2379 | CG2 | ILE | 270 | 38.658 | -24.061 | 27.859 | 1.00 | 26.81 | E11 |
| ATOM | 2380 | CG1 | ILE | 270 | 38.132 | -25.749 | 28.730 | 1.00 | 27.31 | E11 |
| ATOM | 2381 | CD1 | ILE | 270 | 39.339 | -25.500 | 24.105 | 1.00 | 22.28 | E11 |
| ATOM | 2382 | C | ILE | 270 | 37.806 | -26.245 | 23.903 | 1.00 | 24.90 | E11 |
| ATOM | 2383 | O | ILE | 270 | 38.718 | -27.053 | 23.146 | 1.00 | 17.94 | E11 |
| ATOM | 2384 | N | GLU | 271 | 37.280 | -25.487 | 21.783 | 1.00 | 13.91 | E11 |
| ATOM | 2385 | CA | GLU | 271 | 37.794 | -25.571 | 20.839 | 1.00 | 10.91 | E11 |
| ATOM | 2386 | CB | GLU | 271 | 36.929 | -24.741 | 19.410 | 1.00 | 17.95 | E11 |
| ATOM | 2387 | CG | GLU | 271 | 37.426 | -24.688 | | | | |
| ATOM | 2392 | CD | GLU | 271 | 36.379 | -24.169 | 18.440 | 1.00 | 23.49 | E11 |
| ATOM | 2393 | OE1 | GLU | 271 | 36.645 | -24.162 | 17.221 | 1.00 | 22.55 | E11 |
| ATOM | 2394 | OE2 | GLU | 271 | 35.278 | -23.805 | 18.896 | 1.00 | 26.55 | E11 |
| ATOM | 2395 | C | GLU | 271 | 39.237 | -25.044 | 21.908 | 1.00 | 13.93 | E11 |
| ATOM | 2396 | O | GLU | 271 | 39.435 | -23.961 | 22.481 | 1.00 | 15.44 | E11 |
| ATOM | 2397 | N | THR | 272 | 40.209 | -25.770 | 21.335 | 1.00 | 11.96 | E11 |
| ATOM | 2398 | CA | THR | 272 | 41.627 | -25.424 | 21.469 | 1.00 | 12.30 | E11 |
| ATOM | 2399 | CB | THR | 272 | 42.297 | -26.270 | 22.597 | 1.00 | 13.43 | E11 |
| ATOM | 2400 | OG1 | THR | 272 | 41.596 | -26.045 | 23.827 | 1.00 | 14.63 | E11 |
| ATOM | 2401 | CG2 | THR | 272 | 43.725 | -25.856 | 22.817 | 1.00 | 16.79 | E11 |
| ATOM | 2402 | C | THR | 272 | 42.418 | -25.598 | 20.170 | 1.00 | 10.95 | E11 |
| ATOM | 2403 | O | THR | 272 | 42.222 | -26.575 | 19.441 | 1.00 | 12.39 | E11 |
| ATOM | 2404 | N | TYR | 273 | 43.353 | -24.677 | 19.936 | 1.00 | 7.16 | E11 |
| ATOM | 2405 | CA | TYR | 273 | 44.171 | -24.697 | 18.739 | 1.00 | 9.31 | E11 |
| ATOM | 2406 | CB | TYR | 273 | 43.897 | -23.474 | 17.846 | 1.00 | 5.23 | E11 |
| ATOM | 2407 | CG | TYR | 273 | 42.536 | -23.562 | 17.137 | 1.00 | 13.26 | E11 |
| ATOM | 2408 | CD1 | TYR | 273 | 41.329 | -23.296 | 17.826 | 1.00 | 12.16 | E11 |
| ATOM | 2409 | CE1 | TYR | 273 | 40.073 | -23.457 | 17.188 | 1.00 | 12.16 | E11 |
| ATOM | 2410 | CD2 | TYR | 273 | 42.457 | -23.948 | 15.794 | 1.00 | 7.38 | E11 |
| ATOM | 2411 | CE2 | TYR | 273 | 41.208 | -24.104 | 15.169 | 1.00 | 15.63 | E11 |
| ATOM | 2412 | CZ | TYR | 273 | 40.029 | -23.854 | 15.862 | 1.00 | 18.76 | E11 |
| ATOM | 2413 | OH | TYR | 273 | 38.829 | -24.141 | 15.237 | 1.00 | 21.67 | E11 |
| ATOM | 2414 | C | TYR | 273 | 45.581 | -24.616 | 19.255 | 1.00 | 12.26 | E11 |
| ATOM | 2415 | O | TYR | 273 | 45.914 | -23.813 | 20.072 | 1.00 | 12.15 | E11 |
| ATOM | 2416 | N | ILE | 274 | 46.395 | -25.659 | 18.856 | 1.00 | 10.71 | E11 |
| ATOM | 2417 | CA | ILE | 274 | 47.785 | -25.715 | 19.302 | 1.00 | 14.34 | E11 |
| ATOM | 2418 | CB | ILE | 274 | 48.300 | -27.147 | 19.372 | 1.00 | 16.34 | E11 |
| ATOM | 2419 | CG2 | ILE | 274 | 49.833 | -27.175 | 19.539 | 1.00 | 10.47 | E11 |
| ATOM | 2420 | CG1 | ILE | 274 | 47.596 | -27.896 | 20.502 | 1.00 | 14.42 | E11 |
| ATOM | 2421 | CD1 | ILE | 274 | 47.918 | -29.364 | 20.493 | 1.00 | 20.21 | E11 |
| ATOM | 2422 | C | ILE | 274 | 48.692 | -24.926 | 18.374 | 1.00 | 16.07 | E11 |
| ATOM | 2423 | O | ILE | 274 | 48.534 | -24.975 | 17.139 | 1.00 | 15.86 | E11 |
| ATOM | 2424 | N | PHE | 275 | 49.526 | -24.073 | 18.961 | 1.00 | 19.22 | E11 |
| ATOM | 2425 | CA | PHE | 275 | 50.486 | -23.308 | 18.173 | 1.00 | 19.15 | E11 |
| ATOM | 2426 | CB | PHE | 275 | 50.585 | -21.874 | 18.708 | 1.00 | 17.86 | E11 |
| ATOM | 2427 | CG | PHE | 275 | 51.273 | -20.935 | 17.759 | 1.00 | 20.77 | E11 |
| ATOM | 2428 | CD1 | PHE | 275 | 50.577 | -20.381 | 16.680 | 1.00 | 15.97 | E11 |
| ATOM | 2429 | CD2 | PHE | 275 | 52.634 | -20.654 | 17.892 | 1.00 | 19.50 | E11 |
| ATOM | 2430 | CE1 | PHE | 275 | 51.216 | -19.592 | 15.768 | 1.00 | 17.43 | E11 |
| ATOM | 2431 | CE2 | PHE | 275 | 53.303 | -19.837 | 16.961 | 1.00 | 17.19 | E11 |

– 56 –

| ATOM | 2438 | CZ | PHE | 275 | 52.586 | -19.311 | 15.900 | 1.00 | 14.96 | E11 |
|---|---|---|---|---|---|---|---|---|---|---|
| ATOM | 2439 | C | PHE | 275 | 51.876 | -23.992 | 18.235 | 1.00 | 19.39 | E11 |
| ATOM | 2440 | O | PHE | 275 | 52.478 | -24.049 | 19.327 | 1.00 | 20.17 | E11 |
| ATOM | 2441 | N | ALA | 276 | 52.367 | -24.570 | 17.121 | 1.00 | 17.11 | E11 |
| ATOM | 2442 | CA | ALA | 276 | 51.830 | -24.420 | 15.751 | 1.00 | 16.85 | E11 |
| ATOM | 2443 | CB | ALA | 276 | 52.344 | -23.132 | 15.064 | 1.00 | 8.59 | E11 |
| ATOM | 2444 | C | ALA | 276 | 52.267 | -25.625 | 14.947 | 1.00 | 14.89 | E11 |
| ATOM | 2445 | O | ALA | 276 | 53.049 | -26.429 | 15.428 | 1.00 | 20.94 | E11 |
| ATOM | 2446 | N | MET | 277 | 51.749 | -25.769 | 13.731 | 1.00 | 17.36 | E11 |
| ATOM | 2447 | CA | MET | 277 | 52.118 | -26.921 | 12.908 | 1.00 | 18.79 | E11 |
| ATOM | 2448 | CB | MET | 277 | 51.360 | -26.930 | 11.567 | 1.00 | 18.48 | E11 |
| ATOM | 2449 | CG | MET | 277 | 51.486 | -28.252 | 10.762 | 1.00 | 13.46 | E11 |
| ATOM | 2450 | SD | MET | 277 | 50.413 | -29.590 | 11.459 | 1.00 | 12.51 | E11 |
| ATOM | 2451 | CE | MET | 277 | 50.415 | -30.850 | 10.212 | 1.00 | 17.84 | E11 |
| ATOM | 2452 | C | MET | 277 | 53.637 | -27.146 | 12.706 | 1.00 | 20.71 | E11 |
| ATOM | 2453 | O | MET | 277 | 54.104 | -28.260 | 12.910 | 1.00 | 18.35 | E11 |
| ATOM | 2454 | N | PHE | 278 | 54.388 | -26.131 | 12.260 | 1.00 | 18.02 | E11 |
| ATOM | 2455 | CA | PHE | 278 | 55.842 | -26.258 | 12.029 | 1.00 | 19.17 | E11 |
| ATOM | 2456 | CB | PHE | 278 | 56.164 | -26.050 | 10.544 | 1.00 | 16.58 | E11 |
| ATOM | 2457 | CG | PHE | 278 | 55.344 | -26.881 | 9.633 | 1.00 | 13.88 | E11 |
| ATOM | 2458 | CD1 | PHE | 278 | 54.225 | -26.342 | 9.002 | 1.00 | 10.84 | E11 |
| ATOM | 2459 | CD2 | PHE | 278 | 55.671 | -28.203 | 9.401 | 1.00 | 16.99 | E11 |
| ATOM | 2460 | CE1 | PHE | 278 | 53.464 | -27.123 | 8.121 | 1.00 | 10.46 | E11 |
| ATOM | 2461 | CE2 | PHE | 278 | 54.919 | -28.982 | 8.524 | 1.00 | 14.38 | E11 |
| ATOM | 2462 | CZ | PHE | 278 | 53.811 | -28.443 | 7.893 | 1.00 | 18.98 | E11 |
| ATOM | 2463 | C | PHE | 278 | 56.676 | -25.226 | 12.751 | 1.00 | 20.98 | E11 |
| ATOM | 2464 | O | PHE | 278 | 56.139 | -24.232 | 13.239 | 1.00 | 17.92 | E11 |
| ATOM | 2465 | N | ASN | 279 | 57.987 | -25.455 | 12.809 | 1.00 | 18.94 | E11 |
| ATOM | 2466 | CA | ASN | 279 | 58.868 | -24.463 | 13.411 | 1.00 | 21.05 | E11 |
| ATOM | 2467 | CB | ASN | 279 | 60.268 | -25.037 | 13.602 | 1.00 | 23.04 | E11 |
| ATOM | 2468 | CG | ASN | 279 | 60.323 | -26.072 | 14.688 | 1.00 | 29.07 | E11 |
| ATOM | 2469 | OD1 | ASN | 279 | 59.339 | -26.277 | 15.392 | 1.00 | 20.28 | E11 |
| ATOM | 2470 | ND2 | ASN | 279 | 61.467 | -26.737 | 14.838 | 1.00 | 18.54 | E11 |
| ATOM | 2471 | C | ASN | 279 | 58.884 | -23.381 | 12.322 | 1.00 | 13.56 | E11 |
| ATOM | 2472 | O | ASN | 279 | 58.807 | -23.728 | 11.138 | 1.00 | 17.18 | E11 |
| ATOM | 2473 | N | GLU | 280 | 58.939 | -21.030 | 12.693 | 1.00 | 19.40 | E11 |
| ATOM | 2474 | CA | GLU | 280 | 58.936 | -21.030 | 11.690 | 1.00 | 19.40 | E11 |
| ATOM | 2475 | CB | GLU | 280 | 57.765 | -20.076 | 11.883 | 1.00 | 23.55 | E11 |
| ATOM | 2476 | CG | GLU | 280 | 56.439 | -20.685 | 11.427 | 1.00 | 31.12 | E11 |
| ATOM | 2477 | CD | GLU | 280 | 55.243 | -19.943 | 11.955 | 1.00 | 34.28 | E11 |
| ATOM | 2485 | OE1 | GLU | 280 | 54.854 | -20.190 | 13.110 | 1.00 | 45.59 | E11 |
| ATOM | 2486 | OE2 | GLU | 280 | 54.662 | -19.139 | 11.218 | 1.00 | 36.53 | E11 |
| ATOM | 2487 | C | GLU | 280 | 60.266 | -20.305 | 11.694 | 1.00 | 21.83 | E11 |
| ATOM | 2488 | O | GLU | 280 | 60.559 | -19.484 | 12.573 | 1.00 | 28.08 | E11 |
| ATOM | 2489 | N | ASN | 281 | 60.968 | -20.474 | 10.585 | 1.00 | 20.82 | E11 |
| ATOM | 2491 | CA | ASN | 281 | 62.312 | -19.974 | 10.412 | 1.00 | 20.82 | E11 |
| ATOM | 2492 | CB | ASN | 281 | 63.055 | -20.869 | 9.434 | 1.00 | 18.95 | E11 |
| ATOM | 2493 | CG | ASN | 281 | 62.918 | -20.433 | 7.990 | 1.00 | 20.06 | E11 |
| ATOM | 2494 | OD1 | ASN | 281 | 61.878 | -19.962 | 7.542 | 1.00 | 23.88 | E11 |
| ATOM | 2495 | ND2 | ASN | 281 | 63.997 | -20.603 | 7.250 | 1.00 | 22.88 | E11 |
| ATOM | 2498 | C | ASN | 281 | 62.465 | -18.519 | 10.050 | 1.00 | 22.22 | E11 |
| ATOM | 2499 | O | ASN | 281 | 63.586 | -18.031 | 9.948 | 1.00 | 26.05 | E11 |
| ATOM | 2500 | N | GLN | 282 | 61.353 | -17.830 | 9.843 | 1.00 | 22.43 | E11 |
| ATOM | 2502 | CA | GLN | 282 | 61.407 | -16.419 | 9.538 | 1.00 | 23.74 | E11 |
| ATOM | 2503 | CB | GLN | 282 | 60.451 | -16.049 | 8.415 | 1.00 | 23.81 | E11 |
| ATOM | 2504 | CG | GLN | 282 | 60.857 | -16.572 | 7.036 | 1.00 | 26.46 | E11 |
| ATOM | 2505 | CD | GLN | 282 | 62.308 | -16.302 | 6.730 | 1.00 | 22.42 | E11 |
| ATOM | 2506 | OE1 | GLN | 282 | 63.142 | -16.740 | 6.904 | 1.00 | 23.31 | E11 |
| ATOM | 2507 | NE2 | GLN | 282 | 62.628 | -15.075 | 6.333 | 1.00 | 23.29 | E11 |
| ATOM | 2510 | C | GLN | 282 | 61.118 | -15.597 | 10.783 | 1.00 | 22.88 | E11 |
| ATOM | 2511 | O | GLN | 282 | 61.000 | -14.338 | 10.693 | 1.00 | 27.86 | E11 |
| ATOM | 2512 | N | LYS | 283 | 60.942 | -16.263 | 11.927 | 1.00 | 23.57 | E11 |
| ATOM | 2514 | CA | LYS | 283 | 60.707 | -15.590 | 13.216 | 1.00 | 24.27 | E11 |
| ATOM | 2515 | CB | LYS | 283 | 59.893 | -16.483 | 14.168 | 1.00 | 22.23 | E11 |
| ATOM | 2516 | CG | LYS | 283 | 58.476 | -16.740 | 13.736 | 1.00 | 25.06 | E11 |
| ATOM | 2517 | CD | LYS | 283 | 57.694 | -17.369 | 14.862 | 1.00 | 32.66 | E11 |
| ATOM | 2518 | CE | LYS | 283 | 56.192 | -17.403 | 14.569 | 1.00 | 35.09 | E11 |
| ATOM | 2519 | NZ | LYS | 283 | 55.592 | -16.065 | 14.252 | 1.00 | 39.27 | E11 |
| ATOM | 2523 | C | LYS | 283 | 62.080 | -15.297 | 13.845 | 1.00 | 28.66 | E11 |
| ATOM | 2524 | O | LYS | 283 | 63.095 | -15.886 | 13.456 | 1.00 | 30.07 | E11 |
| ATOM | 2525 | N | ASP | 284 | 62.114 | -14.454 | 14.868 | 1.00 | 30.69 | E11 |
| ATOM | 2527 | CA | ASP | 284 | 63.387 | -14.109 | 15.486 | 1.00 | 29.50 | E11 |
| ATOM | 2528 | CB | ASP | 284 | 63.227 | -12.933 | 16.452 | 1.00 | 31.11 | E11 |
| ATOM | 2529 | CG | ASP | 284 | 62.990 | -11.591 | 15.740 | 1.00 | 30.32 | E11 |
| ATOM | 2530 | OD1 | ASP | 284 | 62.987 | -11.522 | 14.487 | 1.00 | 33.95 | E11 |
| ATOM | 2531 | OD2 | ASP | 284 | 62.833 | -10.580 | 16.460 | 1.00 | 34.78 | E11 |
| ATOM | 2532 | C | ASP | 284 | 63.948 | -15.311 | 16.192 | 1.00 | 27.91 | E11 |
| ATOM | 2533 | O | ASP | 284 | 63.203 | -16.126 | 16.696 | 1.00 | 29.88 | E11 |
| ATOM | 2534 | N | SER | 285 | 65.267 | -15.419 | 16.220 | 1.00 | 32.57 | E11 |
| ATOM | 2536 | CA | SER | 285 | 65.933 | -16.548 | 16.861 | 1.00 | 32.63 | E11 |

- 57 -

| | | | | | | | | | | | | |
|---|---|---|---|---|---|---|---|---|---|---|---|---|
| ATOM | 2537 | CB | SER | 285 | 67.443 | -16.337 | 16.846 | 1.00 | 35.75 | E11 | ATOM | 2587 | O | ASH | 290 | 59.022 | -24.751 | 19.412 | 1.00 | 19.46 | E11 |
| ATOM | 2538 | OG | SER | 285 | 67.993 | -16.334 | 15.517 | 1.00 | 46.94 | E11 | ATOM | 2588 | N | TRP | 291 | 58.026 | -23.428 | 17.909 | 1.00 | 13.42 | E11 |
| ATOM | 2540 | C | SER | 285 | 65.465 | -16.684 | 18.296 | 1.00 | 30.86 | E11 | ATOM | 2590 | CA | TRP | 291 | 56.728 | -23.788 | 18.474 | 1.00 | 17.70 | E11 |
| ATOM | 2541 | O | SER | 285 | 65.202 | -15.667 | 18.956 | 1.00 | 28.94 | E11 | ATOM | 2591 | CB | TRP | 291 | 55.728 | -22.641 | 18.367 | 1.00 | 11.88 | E11 |
| ATOM | 2542 | N | GLY | 286 | 65.418 | -17.921 | 18.793 | 1.00 | 27.04 | E11 | ATOM | 2592 | CG | TRP | 291 | 56.088 | -21.470 | 19.169 | 1.00 | 15.27 | E11 |
| ATOM | 2544 | CA | GLY | 286 | 64.964 | -18.154 | 20.155 | 1.00 | 24.62 | E11 | ATOM | 2593 | CD2 | TRP | 291 | 55.875 | -21.297 | 20.584 | 1.00 | 16.00 | E11 |
| ATOM | 2545 | C | GLY | 286 | 63.863 | -19.186 | 20.152 | 1.00 | 23.23 | E11 | ATOM | 2594 | CE2 | TRP | 291 | 56.444 | -20.059 | 20.945 | 1.00 | 16.54 | E11 |
| ATOM | 2546 | O | GLY | 286 | 63.832 | -20.024 | 19.257 | 1.00 | 24.80 | E11 | ATOM | 2595 | CE3 | TRP | 291 | 55.246 | -22.068 | 21.574 | 1.00 | 11.36 | E11 |
| ATOM | 2547 | N | VAL | 287 | 62.910 | -19.076 | 21.077 | 1.00 | 26.98 | E11 | ATOM | 2596 | CD1 | TRP | 291 | 56.746 | -20.346 | 18.741 | 1.00 | 15.08 | E11 |
| ATOM | 2549 | CA | VAL | 287 | 61.796 | -20.030 | 21.168 | 1.00 | 26.29 | E11 | ATOM | 2597 | NE1 | TRP | 291 | 56.970 | -19.498 | 19.806 | 1.00 | 20.11 | E11 |
| ATOM | 2550 | CB | VAL | 287 | 61.037 | -19.978 | 22.548 | 1.00 | 27.54 | E11 | ATOM | 2599 | CZ2 | TRP | 291 | 56.406 | -19.574 | 22.264 | 1.00 | 19.59 | E11 |
| ATOM | 2551 | CG1 | VAL | 287 | 61.996 | -20.181 | 23.662 | 1.00 | 29.45 | E11 | ATOM | 2600 | CZ3 | TRP | 291 | 55.203 | -21.587 | 22.867 | 1.00 | 12.96 | E11 |
| ATOM | 2552 | CG2 | VAL | 287 | 60.301 | -18.647 | 22.757 | 1.00 | 27.63 | E11 | ATOM | 2601 | CH2 | TRP | 291 | 55.779 | -20.353 | 23.206 | 1.00 | 16.99 | E11 |
| ATOM | 2553 | C | VAL | 287 | 60.807 | -19.807 | 20.041 | 1.00 | 24.73 | E11 | ATOM | 2602 | C | TRP | 291 | 56.144 | -25.025 | 17.784 | 1.00 | 16.14 | E11 |
| ATOM | 2554 | O | VAL | 287 | 60.141 | -20.738 | 19.621 | 1.00 | 30.01 | E11 | ATOM | 2603 | O | TRP | 291 | 55.287 | -25.704 | 18.345 | 1.00 | 24.25 | E11 |
| ATOM | 2555 | N | GLU | 288 | 60.778 | -18.599 | 19.482 | 1.00 | 24.80 | E11 | ATOM | 2604 | N | GLY | 292 | 56.642 | -25.309 | 16.583 | 1.00 | 18.29 | E11 |
| ATOM | 2557 | CA | GLU | 288 | 59.853 | -18.286 | 18.395 | 1.00 | 22.78 | E11 | ATOM | 2606 | CA | GLY | 292 | 56.149 | -26.393 | 15.764 | 1.00 | 15.77 | E11 |
| ATOM | 2558 | CB | GLU | 288 | 59.972 | -16.828 | 17.970 | 1.00 | 21.38 | E11 | ATOM | 2607 | C | GLY | 292 | 56.082 | -27.800 | 16.268 | 1.00 | 18.12 | E11 |
| ATOM | 2559 | CG | GLU | 288 | 59.518 | -15.813 | 19.020 | 1.00 | 29.28 | E11 | ATOM | 2608 | O | GLY | 292 | 56.972 | -28.285 | 16.964 | 1.00 | 23.80 | E11 |
| ATOM | 2560 | CD | GLU | 288 | 58.041 | -15.936 | 19.376 | 1.00 | 34.59 | E11 | ATOM | 2609 | N | LEU | 293 | 55.027 | -28.482 | 15.854 | 1.00 | 17.04 | E11 |
| ATOM | 2561 | OE1 | GLU | 288 | 57.701 | -16.451 | 20.470 | 1.00 | 39.23 | E11 | ATOM | 2611 | CA | LEU | 293 | 54.854 | -29.870 | 16.209 | 1.00 | 19.23 | E11 |
| ATOM | 2562 | OE2 | GLU | 288 | 57.206 | -15.503 | 18.565 | 1.00 | 39.72 | E11 | ATOM | 2612 | CB | LEU | 293 | 53.376 | -30.247 | 16.095 | 1.00 | 21.98 | E11 |
| ATOM | 2563 | C | GLU | 288 | 59.994 | -19.175 | 17.177 | 1.00 | 21.48 | E11 | ATOM | 2613 | CG | LEU | 293 | 52.440 | -29.724 | 17.194 | 1.00 | 23.52 | E11 |
| ATOM | 2564 | O | GLU | 288 | 59.016 | -19.435 | 16.478 | 1.00 | 23.71 | E11 | ATOM | 2614 | CD1 | LEU | 293 | 51.032 | -29.490 | 16.660 | 1.00 | 22.68 | E11 |
| ATOM | 2565 | N | GLN | 289 | 61.180 | -19.713 | 16.951 | 1.00 | 23.47 | E11 | ATOM | 2615 | CD2 | LEU | 293 | 52.432 | -30.695 | 18.355 | 1.00 | 21.08 | E11 |
| ATOM | 2567 | CA | GLN | 289 | 61.373 | -20.549 | 15.787 | 1.00 | 24.53 | E11 | ATOM | 2616 | C | LEU | 293 | 55.684 | -30.665 | 15.208 | 1.00 | 19.55 | E11 |
| ATOM | 2568 | CB | GLN | 289 | 62.767 | -20.325 | 15.184 | 1.00 | 25.15 | E11 | ATOM | 2617 | O | LEU | 293 | 56.135 | -31.776 | 15.514 | 1.00 | 19.22 | E11 |
| ATOM | 2569 | CG | GLN | 289 | 63.147 | -18.898 | 14.782 | 1.00 | 25.07 | E11 | ATOM | 2618 | N | PHE | 294 | 55.958 | -30.050 | 14.060 | 1.00 | 17.77 | E11 |
| ATOM | 2570 | CD | GLN | 289 | 64.588 | -18.841 | 14.260 | 1.00 | 26.63 | E11 | ATOM | 2620 | CA | PHE | 294 | 56.702 | -30.685 | 12.953 | 1.00 | 22.47 | E11 |
| ATOM | 2571 | OE1 | GLN | 289 | 65.243 | -19.863 | 14.165 | 1.00 | 32.62 | E11 | ATOM | 2621 | CB | PHE | 294 | 55.759 | -30.911 | 11.765 | 1.00 | 18.48 | E11 |
| ATOM | 2572 | NE2 | GLN | 289 | 65.071 | -17.668 | 13.915 | 1.00 | 28.67 | E11 | ATOM | 2622 | CG | PHE | 294 | 54.713 | -31.982 | 11.989 | 1.00 | 18.46 | E11 |
| ATOM | 2575 | C | GLN | 289 | 61.224 | -22.014 | 16.180 | 1.00 | 23.23 | E11 | ATOM | 2623 | CD1 | PHE | 294 | 53.422 | -31.646 | 12.351 | 1.00 | 19.05 | E11 |
| ATOM | 2576 | O | GLN | 289 | 61.538 | -22.897 | 15.368 | 1.00 | 21.52 | E11 | ATOM | 2624 | CD2 | PHE | 294 | 55.032 | -33.341 | 11.847 | 1.00 | 15.00 | E11 |
| ATOM | 2577 | N | ASN | 290 | 60.623 | -22.266 | 17.350 | 1.00 | 20.60 | E11 | ATOM | 2625 | CE1 | PHE | 294 | 52.428 | -32.654 | 12.566 | 1.00 | 16.39 | E11 |
| ATOM | 2579 | CA | ASN | 290 | 60.476 | -23.626 | 17.862 | 1.00 | 16.82 | E11 | ATOM | 2626 | CE2 | PHE | 294 | 54.062 | -34.316 | 12.055 | 1.00 | 17.14 | E11 |
| ATOM | 2580 | CB | ASN | 290 | 61.529 | -23.886 | 18.938 | 1.00 | 17.54 | E11 | ATOM | 2627 | CZ | PHE | 294 | 52.757 | -33.987 | 12.428 | 1.00 | 13.90 | E11 |
| ATOM | 2581 | CG | ASN | 290 | 62.933 | -23.811 | 18.418 | 1.00 | 18.87 | E11 | ATOM | 2628 | C | PHE | 294 | 57.880 | -29.826 | 12.479 | 1.00 | 23.58 | E11 |
| ATOM | 2582 | OD1 | ASN | 290 | 63.389 | -24.697 | 17.705 | 1.00 | 21.61 | E11 | ATOM | 2629 | O | PHE | 294 | 57.920 | -28.605 | 12.662 | 1.00 | 26.52 | E11 |
| ATOM | 2583 | ND2 | ASN | 290 | 63.650 | -22.783 | 18.813 | 1.00 | 16.02 | E11 | ATOM | 2630 | N | TYR | 295 | 58.808 | -30.486 | 11.794 | 1.00 | 21.48 | E11 |
| ATOM | 2586 | C | ASN | 290 | 59.106 | -23.977 | 18.448 | 1.00 | 19.02 | E11 | ATOM | 2632 | CA | TYR | 295 | 59.919 | -29.792 | 11.183 | 1.00 | 16.43 | E11 |

| ATOM | 2633 | CB | TYR | 295 | 61.122 | -30.710 | 11.160 | 1.00 | 8.79 | EII | | ATOM | 2681 | C | GLN | 299 | 58.575 | -34.468 | 11.950 | 1.00 | 26.54 | EII |
|------|------|----|-----|-----|--------|---------|--------|------|-------|-----|---|------|------|----|-----|-----|--------|---------|--------|------|-------|-----|
| ATOM | 2634 | CG | TYR | 295 | 61.874 | -30.790 | 12.473 | 1.00 | 11.30 | EII | | ATOM | 2682 | O | GLN | 299 | 58.591 | -33.237 | 12.071 | 1.00 | 28.35 | EII |
| ATOM | 2635 | CD1 | TYR | 295 | 61.979 | -31.993 | 13.176 | 1.00 | 13.07 | EII | | ATOM | 2683 | N | HIS | 300 | 57.974 | -35.256 | 12.842 | 1.00 | 25.14 | EII |
| ATOM | 2636 | CE1 | TYR | 295 | 62.657 | -32.059 | 14.383 | 1.00 | 11.61 | EII | | ATOM | 2685 | CA | HIS | 300 | 57.460 | -34.738 | 14.116 | 1.00 | 24.87 | EII |
| ATOM | 2637 | CD2 | TYR | 295 | 62.474 | -29.657 | 13.005 | 1.00 | 12.19 | EII | | ATOM | 2686 | CB | HIS | 300 | 56.781 | -35.834 | 14.942 | 1.00 | 25.81 | EII |
| ATOM | 2638 | CE2 | TYR | 295 | 63.149 | -29.703 | 14.210 | 1.00 | 16.16 | EII | | ATOM | 2687 | CG | HIS | 300 | 55.518 | -36.374 | 14.336 | 1.00 | 29.78 | EII |
| ATOM | 2639 | CZ | TYR | 295 | 63.235 | -30.907 | 14.905 | 1.00 | 15.71 | EII | | ATOM | 2688 | CD2 | HIS | 300 | 55.301 | -37.126 | 13.239 | 1.00 | 30.17 | EII |
| ATOM | 2640 | OH | TYR | 295 | 63.868 | -30.915 | 16.148 | 1.00 | 22.72 | EII | | ATOM | 2689 | ND1 | HIS | 300 | 54.283 | -36.191 | 14.929 | 1.00 | 31.83 | EII |
| ATOM | 2642 | C | TYR | 295 | 59.396 | -29.554 | 9.756 | 1.00 | 21.35 | EII | | ATOM | 2691 | CE1 | HIS | 300 | 53.359 | -36.808 | 14.212 | 1.00 | 29.54 | EII |
| ATOM | 2643 | O | TYR | 295 | 58.497 | -30.277 | 9.271 | 1.00 | 24.38 | EII | | ATOM | 2692 | NE2 | HIS | 300 | 53.952 | -37.379 | 13.179 | 1.00 | 27.07 | EII |
| ATOM | 2644 | N | PRO | 296 | 59.951 | -28.573 | 9.042 | 1.00 | 21.59 | EII | | ATOM | 2694 | C | HIS | 300 | 58.675 | -34.304 | 14.923 | 1.00 | 24.50 | EII |
| ATOM | 2645 | CD | PRO | 296 | 60.878 | -27.503 | 9.444 | 1.00 | 22.13 | EII | | ATOM | 2695 | O | HIS | 300 | 59.747 | -34.871 | 14.776 | 1.00 | 27.16 | EII |
| ATOM | 2646 | CA | PRO | 296 | 59.554 | -28.427 | 7.639 | 1.00 | 21.35 | EII | | ATOM | 2696 | N | VAL | 301 | 58.530 | -33.265 | 15.733 | 1.00 | 22.87 | EII |
| ATOM | 2647 | CB | PRO | 296 | 60.505 | -27.361 | 7.135 | 1.00 | 19.29 | EII | | ATOM | 2698 | CA | VAL | 301 | 59.638 | -32.831 | 16.580 | 1.00 | 20.60 | EII |
| ATOM | 2648 | CG | PRO | 296 | 60.659 | -26.484 | 8.360 | 1.00 | 20.28 | EII | | ATOM | 2699 | CB | VAL | 301 | 59.457 | -31.370 | 17.044 | 1.00 | 20.09 | EII |
| ATOM | 2649 | C | PRO | 296 | 59.710 | -29.745 | 6.877 | 1.00 | 23.89 | EII | | ATOM | 2700 | CG1 | VAL | 301 | 60.656 | -30.933 | 17.892 | 1.00 | 19.51 | EII |
| ATOM | 2650 | O | PRO | 296 | 58.860 | -30.106 | 6.050 | 1.00 | 23.22 | EII | | ATOM | 2701 | CD1 | VAL | 301 | 59.255 | -30.453 | 15.852 | 1.00 | 16.16 | EII |
| ATOM | 2651 | N | ASN | 297 | 60.746 | -30.510 | 7.225 | 1.00 | 25.10 | EII | | ATOM | 2702 | C | VAL | 301 | 59.597 | -33.755 | 17.805 | 1.00 | 20.40 | EII |
| ATOM | 2653 | CA | ASN | 297 | 60.999 | -31.781 | 6.555 | 1.00 | 26.66 | EII | | ATOM | 2703 | O | VAL | 301 | 60.598 | -34.235 | 18.478 | 1.00 | 23.74 | EII |
| ATOM | 2654 | CB | ASN | 297 | 62.352 | -32.367 | 6.975 | 1.00 | 27.53 | EII | | ATOM | 2704 | N | TYR | 302 | 58.398 | -34.406 | 18.115 | 1.00 | 20.65 | EII |
| ATOM | 2655 | CG | ASN | 297 | 62.370 | -32.836 | 8.405 | 1.00 | 27.50 | EII | | ATOM | 2706 | CA | TYR | 302 | 58.101 | -35.149 | 19.217 | 1.00 | 18.27 | EII |
| ATOM | 2656 | OD1 | ASN | 297 | 61.335 | -33.079 | 9.012 | 1.00 | 30.54 | EII | | ATOM | 2707 | CB | TYR | 302 | 57.307 | -34.406 | 20.557 | 1.00 | 15.84 | EII |
| ATOM | 2657 | ND2 | ASN | 297 | 63.555 | -32.972 | 8.955 | 1.00 | 33.80 | EII | | ATOM | 2708 | CG | TYR | 302 | 55.918 | -33.137 | 20.538 | 1.00 | 11.58 | EII |
| ATOM | 2660 | C | ASN | 297 | 59.876 | -32.782 | 6.798 | 1.00 | 25.34 | EII | | ATOM | 2709 | CD1 | TYR | 302 | 55.181 | -33.157 | 20.626 | 1.00 | 11.98 | EII |
| ATOM | 2661 | O | ASN | 297 | 59.967 | -33.936 | 6.372 | 1.00 | 26.26 | EII | | ATOM | 2710 | CE1 | TYR | 302 | 55.181 | -31.997 | 20.536 | 1.00 | 11.91 | EII |
| ATOM | 2662 | N | MET | 298 | 58.831 | -32.329 | 7.491 | 1.00 | 22.48 | EII | | ATOM | 2711 | CD2 | TYR | 302 | 57.940 | -31.915 | 20.368 | 1.00 | 10.72 | EII |
| ATOM | 2664 | CA | MET | 298 | 57.664 | -33.126 | 7.789 | 1.00 | 19.03 | EII | | ATOM | 2712 | CE2 | TYR | 302 | 57.213 | -30.750 | 20.280 | 1.00 | 15.77 | EII |
| ATOM | 2665 | CB | MET | 298 | 57.178 | -33.790 | 6.517 | 1.00 | 22.91 | EII | | ATOM | 2713 | CZ | TYR | 302 | 55.833 | -30.797 | 20.362 | 1.00 | 12.88 | EII |
| ATOM | 2666 | CG | MET | 298 | 55.596 | -33.566 | 5.477 | 1.00 | 23.01 | EII | | ATOM | 2716 | OH | TYR | 302 | 55.104 | -29.637 | 20.242 | 1.00 | 14.19 | EII |
| ATOM | 2667 | SD | MET | 298 | 56.662 | -34.944 | 4.304 | 1.00 | 27.29 | EII | | ATOM | 2717 | C | TYR | 302 | 56.797 | -35.791 | 18.909 | 1.00 | 21.79 | EII |
| ATOM | 2668 | CE | MET | 298 | 57.761 | -34.124 | 3.837 | 1.00 | 27.69 | EII | | ATOM | 2718 | O | TYR | 302 | 55.975 | -35.219 | 18.175 | 1.00 | 24.98 | EII |
| ATOM | 2669 | C | MET | 298 | 56.759 | -34.740 | 8.948 | 1.00 | 21.99 | EII | | ATOM | 2719 | N | PRO | 303 | 56.558 | -37.002 | 19.428 | 1.00 | 20.23 | EII |
| ATOM | 2670 | O | MET | 298 | 56.955 | -34.272 | 9.329 | 1.00 | 17.86 | EII | | ATOM | 2720 | CD | PRO | 303 | 57.528 | -37.769 | 20.221 | 1.00 | 12.90 | EII |
| ATOM | 2671 | N | GLN | 299 | 59.152 | -35.140 | 9.516 | 1.00 | 20.99 | EII | | ATOM | 2721 | CA | PRO | 303 | 55.344 | -37.789 | 19.144 | 1.00 | 18.35 | EII |
| ATOM | 2673 | CA | GLN | 299 | 60.644 | -35.369 | 10.674 | 1.00 | 27.28 | EII | | ATOM | 2722 | CB | PRO | 303 | 55.693 | -39.163 | 19.703 | 1.00 | 16.34 | EII |
| ATOM | 2674 | CB | GLN | 299 | 60.908 | -34.989 | 9.989 | 1.00 | 32.90 | EII | | ATOM | 2723 | CG | PRO | 303 | 57.209 | -39.159 | 19.806 | 1.00 | 20.09 | EII |
| ATOM | 2675 | CG | GLN | 299 | 10.376 | -36.357 | 10.908 | 1.00 | 44.84 | EII | | ATOM | 2724 | C | PRO | 303 | 54.125 | -37.229 | 19.864 | 1.00 | 16.20 | EII |
| ATOM | 2676 | CD | GLN | 299 | 61.325 | -36.586 | 11.565 | 1.00 | 54.13 | EII | | ATOM | 2725 | O | PRO | 303 | 54.164 | -36.989 | 21.062 | 1.00 | 21.64 | EII |
| ATOM | 2677 | OE1 | GLN | 299 | 62.784 | -36.552 | 11.565 | 1.00 | 58.53 | EII | | ATOM | 2726 | N | ILE | 304 | 52.999 | -37.144 | 19.173 | 1.00 | 20.01 | EII |
| ATOM | 2678 | NE2 | GLN | 299 | 63.147 | -36.824 | 9.372 | 1.00 | 56.78 | EII | | ATOM | 2727 | CA | ILE | 304 | 51.780 | -36.588 | 19.770 | 1.00 | 22.24 | EII |

- 58 -

- 59 -

| ATOM | 2728 | CB  | ILE | 304 | 51.580 | -35.087 | 19.377 | 1.00 | 20.79 | EII  | ATOM | 2800 | OH2 | H2O | 417 | 36.687 | -1.124  | 18.709 | 1.00 | 23.14 | SOLV |
| ---- | ---- | --- | --- | --- | ------ | ------- | ------ | ---- | ----- | ---- | ---- | ---- | --- | --- | --- | ------ | ------- | ------ | ---- | ----- | ---- |
| ATOM | 2729 | CG2 | ILE | 304 | 50.234 | 34.589  | 19.857 | 1.00 | 17.14 | EII  | ATOM | 2803 | OH2 | H2O | 418 | 37.024 | -27.451 | 4.776  | 1.00 | 26.52 | SOLV |
| ATOM | 2730 | CG1 | ILE | 304 | 52.685 | -33.919 | 19.998 | 1.00 | 23.16 | EII  | ATOM | 2806 | OH2 | H2O | 419 | 51.321 | -16.872 | 9.284  | 1.00 | 15.66 | SOLV |
| ATOM | 2731 | CD1 | ILE | 304 | 52.488 | -33.222 | 21.496 | 1.00 | 20.18 | EII  | ATOM | 2809 | OH2 | H2O | 420 | 28.572 | -5.002  | 6.276  | 1.00 | 38.23 | SOLV |
| ATOM | 2732 | C   | ILE | 304 | 50.576 | -37.380 | 19.304 | 1.00 | 22.63 | EII  | ATOM | 2812 | OH2 | H2O | 421 | 62.726 | -27.506 | 17.428 | 1.00 | 28.36 | SOLV |
| ATOM | 2733 | O   | ILE | 304 | 50.575 | -37.884 | 18.197 | 1.00 | 28.17 | EII  | ATOM | 2815 | OH2 | H2O | 422 | 45.305 | -9.050  | 23.051 | 1.00 | 16.57 | SOLV |
| ATOM | 2734 | N   | ASN | 305 | 49.551 | -37.488 | 20.136 | 1.00 | 25.63 | EII  | ATOM | 2818 | OH2 | H2O | 423 | 44.058 | -13.542 | 13.041 | 1.00 | 51.05 | SOLV |
| ATOM | 2735 | CA  | ASN | 305 | 48.365 | -38.229 | 19.756 | 1.00 | 26.31 | EII  | ATOM | 2821 | OH2 | H2O | 424 | 43.121 | -33.812 | 33.358 | 1.00 | 35.56 | SOLV |
| ATOM | 2736 | CB  | ASN | 305 | 48.133 | -39.348 | 20.759 | 1.00 | 31.68 | EII  | ATOM | 2824 | OH2 | H2O | 425 | 48.073 | -18.604 | -2.179 | 1.00 | 19.03 | SOLV |
| ATOM | 2737 | CG  | ASN | 305 | 49.246 | -40.406 | 20.731 | 1.00 | 37.77 | EII  | ATOM | 2827 | OH2 | H2O | 426 | 53.437 | -23.318 | 11.551 | 1.00 | 25.64 | SOLV |
| ATOM | 2738 | OD1 | ASN | 305 | 49.471 | -41.079 | 19.718 | 1.00 | 40.26 | EII  | ATOM | 2830 | OH2 | H2O | 429 | 35.193 | -29.369 | 4.177  | 1.00 | 30.72 | SOLV |
| ATOM | 2739 | ND2 | ASN | 305 | 49.952 | -40.543 | 21.842 | 1.00 | 40.67 | EII  | ATOM | 2833 | OH2 | H2O | 430 | 42.746 | -27.358 | 37.942 | 1.00 | 31.07 | SOLV |
| ATOM | 2740 | C   | ASN | 305 | 47.255 | -37.211 | 19.790 | 1.00 | 28.02 | EII  | ATOM | 2836 | OH2 | H2O | 431 | 63.143 | -26.515 | 12.529 | 1.00 | 27.73 | SOLV |
| ATOM | 2741 | O   | ASN | 305 | 46.913 | -36.720 | 20.861 | 1.00 | 27.96 | EII  | ATOM | 2839 | OH2 | H2O | 432 | 29.882 | -10.584 | 0.430  | 1.00 | 28.14 | SOLV |
| ATOM | 2742 | N   | PHE | 306 | 46.739 | -36.839 | 18.621 | 1.00 | 27.61 | EII  | ATOM | 2842 | OH2 | H2O | 439 | 52.751 | -34.739 | 39.272 | 1.00 | 39.39 | SOLV |
| ATOM | 2743 | CA  | PHE | 306 | 45.687 | -35.827 | 18.547 | 1.00 | 28.89 | EII  | ATOM | 2845 | OH2 | H2O | 441 | 48.255 | -18.972 | 39.703 | 1.00 | 39.53 | SOLV |
| ATOM | 2744 | CB  | PHE | 306 | 45.694 | -35.115 | 17.192 | 1.00 | 27.57 | EII  | ATOM | 2848 | OH2 | H2O | 442 | 48.309 | -16.144 | 3.115  | 1.00 | 30.24 | SOLV |
| ATOM | 2745 | CG  | PHE | 306 | 47.004 | -34.493 | 16.856 | 1.00 | 25.08 | EII  | ATOM | 2851 | OH2 | H2O | 443 | 35.695 | -24.236 | -2.117 | 1.00 | 34.21 | SOLV |
| ATOM | 2746 | CD1 | PHE | 306 | 47.998 | -35.234 | 17.207 | 1.00 | 25.71 | EII  | ATOM | 2854 | OH2 | H2O | 444 | 63.172 | -33.514 | 17.460 | 1.00 | 42.14 | SOLV |
| ATOM | 2747 | CD2 | PHE | 306 | 47.273 | -33.185 | 15.935 | 1.00 | 24.37 | EII  | ATOM | 2857 | OH2 | H2O | 445 | 50.807 | -22.688 | 0.238  | 1.00 | 45.99 | SOLV |
| ATOM | 2748 | CE1 | PHE | 306 | 49.250 | -34.664 | 16.921 | 1.00 | 26.60 | EII  | ATOM | 2860 | OH2 | H2O | 450 | 53.117 | -17.116 | 12.268 | 1.00 | 38.39 | SOLV |
| ATOM | 2749 | CE2 | PHE | 306 | 48.517 | -32.620 | 16.289 | 1.00 | 22.64 | EII  | ATOM | 2863 | OH2 | H2O | 451 | 65.518 | -28.728 | 20.550 | 1.00 | 44.39 | SOLV |
| ATOM | 2750 | CZ  | PHE | 306 | 49.501 | -33.362 | 16.829 | 1.00 | 32.96 | EII  | ATOM | 2866 | OH2 | H2O | 452 | 46.316 | -2.083  | 24.516 | 1.00 | 24.17 | SOLV |
| ATOM | 2751 | C   | PHE | 306 | 44.315 | -36.384 | 18.997 | 1.00 | 37.80 | EII  | ATOM | 2869 | OH2 | H2O | 455 | 31.589 | -15.107 | 33.011 | 1.00 | 78.98 | SOLV |
| ATOM | 2752 | O   | PHE | 306 | 44.212 | -37.627 | 18.931 | 1.00 | 33.47 | EII  | ATOM | 2872 | OH2 | H2O | 460 | 60.874 | -23.258 | 9.170  | 1.00 | 52.60 | SOLV |
| ATOM | 2753 | OT  | PHE | 306 | 43.378 | -35.553 | 18.931 | 1.00 | 9.40  | SOLV | ATOM | 2875 | OH2 | H2O | 461 | 20.592 | -10.358 | 1.788  | 1.00 | 43.28 | SOLV |
| ATOM | 2754 | OH  | H2O | W1  | 35.213 | -23.276 | 23.978 | 1.00 | 11.85 | SOLV | ATOM | 2878 | OH2 | H2O | 462 | 34.113 | 0.226   | 31.484 | 1.00 | 38.34 | SOLV |
| ATOM | 2755 | OH  | H2O | W2  | 52.348 | -23.134 | 27.668 | 1.00 | 11.51 | SOLV | ATOM | 2881 | OH2 | H2O | 465 | 37.244 | -31.752 | 11.259 | 1.00 | 40.52 | SOLV |
| ATOM | 2756 | OH  | H2O | W3  | 31.999 | -2.015  | 30.198 | 1.00 | 18.36 | SOLV | ATOM | 2884 | OH2 | H2O | 466 | 45.548 | -32.881 | 32.807 | 1.00 | 35.29 | SOLV |
| ATOM | 2757 | OH  | H2O | W4  | 53.979 | -26.111 | 20.763 | 1.00 | 21.88 | SOLV | ATOM | 2887 | OH2 | H2O | 467 | 67.202 | -24.793 | 26.105 | 1.00 | 35.32 | SOLV |
| ATOM | 2758 | OH  | H2O | W5  | 54.297 | -33.977 | 16.661 | 1.00 | 16.75 | SOLV | ATOM | 2890 | OH2 | H2O | 468 | 63.707 | -31.842 | 29.284 | 1.00 | 44.68 | SOLV |
| ATOM | 2761 | OH  | H2O | W6  | 42.427 | -8.747  | 19.160 | 1.00 | 15.03 | SOLV | ATOM | 2893 | OH2 | H2O | 470 | 48.845 | -26.325 | -2.284 | 1.00 | 39.74 | SOLV |
| ATOM | 2764 | OH  | H2O | W7  | 52.721 | -24.499 | 3.525  | 1.00 | 16.17 | SOLV | ATOM | 2896 | OH2 | H2O | 475 | 51.153 | -24.567 | -2.863 | 1.00 | 36.71 | SOLV |
| ATOM | 2767 | OH  | H2O | W9  | 48.199 | -18.524 | 8.785  | 1.00 | 20.46 | SOLV | END  |      |     |     |     |        |         |        |      |       |      |
| ATOM | 2770 | OH  | H2O | W10 | 43.131 | -16.283 | 13.064 | 1.00 | 18.97 | SOLV |      |      |     |     |     |        |         |        |      |       |      |
| ATOM | 2773 | OH  | H2O | W11 | 56.750 | -27.463 | 20.505 | 1.00 | 28.20 | SOLV |      |      |     |     |     |        |         |        |      |       |      |
| ATOM | 2776 | OH  | H2O | W13 | 48.688 | -18.900 | 31.371 | 1.00 | 32.08 | SOLV |      |      |     |     |     |        |         |        |      |       |      |
| ATOM | 2779 | OH  | H2O | W14 | 57.818 | -21.830 | 15.286 | 1.00 | 29.05 | SOLV |      |      |     |     |     |        |         |        |      |       |      |
| ATOM | 2782 | OH  | H2O | W15 | 29.587 | -16.986 | 23.413 | 1.00 | 24.90 | SOLV |      |      |     |     |     |        |         |        |      |       |      |
| ATOM | 2785 | OH  | H2O | W16 | 48.883 | -25.876 | 32.267 | 1.00 | 24.90 | SOLV |      |      |     |     |     |        |         |        |      |       |      |

- 60 -

Atomic coordinates of G2 glucanase of barley obtained by x-ray diffractio

| | | | | | | | | | |
|---|---|---|---|---|---|---|---|---|---|
| ATOM | 1 | CB | ILE | 1 | 51.578 | 8.909 | 77.695 | 1.00 16.56 | A |
| ATOM | 2 | CG2 | ILE | 1 | 50.410 | 8.910 | 78.730 | 1.00 16.49 | A |
| ATOM | 3 | CG1 | ILE | 1 | 52.905 | 8.620 | 78.393 | 1.00 15.49 | A |
| ATOM | 4 | CD1 | ILE | 1 | 53.278 | 9.654 | 79.407 | 1.00 13.05 | A |
| ATOM | 5 | C | ILE | 1 | 50.649 | 6.582 | 77.033 | 1.00 17.29 | A |
| ATOM | 6 | O | ILE | 1 | 49.462 | 6.340 | 76.721 | 1.00 18.27 | A |
| ATOM | 9 | N | ILE | 1 | 50.469 | 8.473 | 75.492 | 1.00 16.51 | A |
| ATOM | 11 | CA | ILE | 1 | 45.215 | 7.873 | 76.528 | 1.00 16.50 | A |
| ATOM | 12 | N | GLY | 2 | 51.331 | 5.737 | 77.754 | 1.00 16.14 | A |
| ATOM | 14 | CA | GLY | 2 | 51.410 | 4.516 | 78.294 | 1.00 13.73 | A |
| ATOM | 15 | C | GLY | 2 | 50.856 | 4.554 | 79.807 | 1.00 12.54 | A |
| ATOM | 16 | O | GLY | 2 | 50.635 | 5.435 | 80.495 | 1.00 11.85 | A |
| ATOM | 17 | N | VAL | 3 | 51.163 | 3.708 | 80.301 | 1.00 9.94 | A |
| ATOM | 19 | CA | VAL | 3 | 49.737 | 3.626 | 81.712 | 1.00 9.46 | A |
| ATOM | 20 | CB | VAL | 3 | 49.537 | 4.306 | 82.205 | 1.00 9.04 | A |
| ATOM | 21 | CG1 | VAL | 3 | 48.255 | 4.138 | 83.734 | 1.00 8.77 | A |
| ATOM | 22 | CG2 | VAL | 3 | 48.249 | 5.804 | 81.855 | 1.00 9.82 | A |
| ATOM | 23 | C | VAL | 3 | 49.552 | 2.155 | 82.121 | 1.00 10.25 | A |
| ATOM | 24 | O | VAL | 3 | 48.923 | 1.318 | 81.473 | 1.00 9.94 | A |
| ATOM | 25 | N | CYS | 4 | 50.371 | 1.846 | 83.135 | 1.00 10.92 | A |
| ATOM | 27 | CA | CYS | 4 | 50.497 | 0.498 | 83.707 | 1.00 11.09 | A |
| ATOM | 28 | CB | CYS | 4 | 51.614 | 0.456 | 84.734 | 1.00 11.48 | A |
| ATOM | 29 | SG | CYS | 4 | 53.247 | 0.787 | 84.048 | 1.00 11.26 | A |
| ATOM | 30 | C | CYS | 4 | 49.200 | 0.153 | 84.403 | 1.00 11.56 | A |
| ATOM | 31 | O | CYS | 4 | 48.630 | 0.984 | 85.149 | 1.00 12.68 | A |
| ATOM | 32 | N | TYR | 5 | 48.750 | -1.075 | 84.198 | 1.00 11.62 | A |
| ATOM | 34 | CA | TYR | 5 | 47.498 | -1.540 | 84.775 | 1.00 12.71 | A |
| ATOM | 35 | CB | TYR | 5 | 46.548 | -1.911 | 83.627 | 1.00 15.01 | A |
| ATOM | 36 | CG | TYR | 5 | 45.272 | -2.642 | 84.011 | 1.00 16.07 | A |
| ATOM | 37 | CD1 | TYR | 5 | 44.737 | -3.624 | 83.114 | 1.00 15.82 | A |
| ATOM | 38 | CE1 | TYR | 5 | 43.552 | -4.309 | 83.440 | 1.00 14.41 | A |
| ATOM | 39 | CD2 | TYR | 5 | 44.581 | -2.359 | 85.201 | 1.00 15.07 | A |
| ATOM | 40 | CE2 | TYR | 5 | 43.365 | -3.053 | 85.599 | 1.00 14.94 | A |
| ATOM | 41 | CZ | TYR | 5 | 42.878 | -4.022 | 84.604 | 1.00 15.95 | A |
| ATOM | 42 | OH | TYR | 5 | 41.719 | -4.703 | 84.814 | 1.00 10.98 | A |
| ATOM | 44 | C | TYR | 5 | 47.686 | -2.705 | 85.391 | 1.00 10.71 | A |
| ATOM | 45 | N | TYR | 5 | 47.864 | -3.848 | 85.777 | 1.00 11.29 | A |
| ATOM | 46 | N | GLY | 6 | 47.674 | -2.362 | 87.061 | 1.00 11.29 | A |
| ATOM | 48 | CA | GLY | 6 | 47.809 | -3.326 | 88.134 | 1.00 10.57 | A |
| ATOM | 49 | C | GLY | 6 | 46.457 | -3.626 | 88.771 | 1.00 12.01 | A |
| ATOM | 50 | O | GLY | 6 | 45.613 | -2.715 | 88.989 | 1.00 10.86 | A |
| ATOM | 51 | N | VAL | 7 | 46.309 | -4.883 | 89.177 | 1.00 11.90 | A |
| ATOM | 53 | CA | VAL | 7 | 45.069 | -5.370 | 89.755 | 1.00 12.97 | A |
| ATOM | 54 | CB | VAL | 7 | 44.466 | -6.472 | 88.842 | 1.00 12.49 | A |
| ATOM | 55 | CG1 | VAL | 7 | 44.203 | -5.906 | 87.463 | 1.00 12.11 | A |
| ATOM | 56 | CG2 | VAL | 7 | 45.444 | -7.617 | 88.679 | 1.00 12.26 | A |
| ATOM | 57 | C | VAL | 7 | 45.215 | -5.894 | 91.177 | 1.00 14.30 | A |
| ATOM | 58 | O | VAL | 7 | 44.478 | -6.782 | 91.590 | 1.00 15.68 | A |
| ATOM | 59 | N | ILE | 8 | 46.153 | -5.342 | 91.939 | 1.00 15.50 | A |
| ATOM | 61 | CA | ILE | 8 | 46.314 | -5.773 | 93.332 | 1.00 16.50 | A |
| ATOM | 62 | CB | ILE | 8 | 47.790 | -5.689 | 93.764 | 1.00 15.61 | A |
| ATOM | 63 | CG2 | ILE | 8 | 47.954 | -6.353 | 95.113 | 1.00 15.89 | A |
| ATOM | 64 | CG1 | ILE | 8 | 48.635 | -6.437 | 92.778 | 1.00 15.96 | A |
| ATOM | 65 | CD1 | ILE | 8 | 48.147 | -7.869 | 92.613 | 1.00 16.45 | A |
| ATOM | 66 | C | ILE | 8 | 45.507 | -4.973 | 94.331 | 1.00 17.23 | A |
| ATOM | 67 | O | ILE | 8 | 46.032 | -4.214 | 95.135 | 1.00 15.90 | A |
| ATOM | 68 | N | GLY | 9 | 44.200 | -5.146 | 94.238 | 1.00 18.04 | A |
| ATOM | 70 | CA | GLY | 9 | 43.278 | -4.467 | 95.118 | 1.00 20.11 | A |
| ATOM | 71 | C | GLY | 9 | 41.954 | -5.217 | 95.086 | 1.00 21.24 | A |
| ATOM | 72 | O | GLY | 9 | 41.740 | -6.024 | 94.197 | 1.00 20.73 | A |
| ATOM | 73 | N | ASN | 10 | 41.050 | -4.954 | 96.025 | 1.00 22.70 | A |
| ATOM | 75 | CA | ASN | 10 | 39.766 | -5.663 | 96.019 | 1.00 23.03 | A |
| ATOM | 76 | CB | ASN | 10 | 39.449 | -6.149 | 97.412 | 1.00 22.61 | A |
| ATOM | 77 | CG | ASN | 10 | 39.541 | -5.049 | 98.410 | 1.00 22.14 | A |
| ATOM | 78 | OD1 | ASN | 10 | 39.067 | -3.935 | 98.186 | 1.00 21.35 | A |
| ATOM | 79 | ND2 | ASN | 10 | 40.198 | -5.327 | 99.505 | 1.00 22.67 | A |
| ATOM | 82 | C | ASN | 10 | 38.565 | -4.844 | 95.541 | 1.00 23.43 | A |
| ATOM | 83 | O | ASN | 10 | 37.420 | -5.303 | 95.684 | 1.00 25.15 | A |
| ATOM | 84 | N | ASN | 11 | 38.795 | -3.709 | 94.892 | 1.00 22.65 | A |
| ATOM | 86 | CA | ASN | 11 | 37.687 | -2.862 | 94.493 | 1.00 22.07 | A |
| ATOM | 87 | CB | ASN | 11 | 37.520 | -1.833 | 95.605 | 1.00 23.54 | A |
| ATOM | 88 | CG | ASN | 11 | 38.862 | -1.284 | 96.099 | 1.00 24.72 | A |
| ATOM | 89 | OD1 | ASN | 11 | 39.840 | -1.220 | 95.358 | 1.00 23.97 | A |
| ATOM | 90 | ND2 | ASN | 11 | 38.918 | -0.928 | 97.369 | 1.00 25.96 | A |
| ATOM | 93 | C | ASN | 11 | 37.841 | -2.150 | 93.142 | 1.00 22.10 | A |
| ATOM | 94 | O | ASN | 11 | 37.249 | -1.076 | 92.920 | 1.00 21.25 | A |
| ATOM | 95 | N | LEU | 12 | 38.651 | -2.747 | 92.261 | 1.00 21.24 | A |
| ATOM | 97 | CA | LEU | 12 | 38.947 | -2.210 | 90.926 | 1.00 19.85 | A |

- 61 -

| | | | | | | | | | |
|---|---|---|---|---|---|---|---|---|---|
| ATOM | 98 | CB | LEU | 12 | 40.297 | -2.774 | 90.464 | 1.00 20.16 | A |
| ATOM | 99 | CG | LEU | 12 | 41.536 | -2.521 | 91.317 | 1.00 19.85 | A |
| ATOM | 100 | CD1 | LEU | 12 | 42.809 | -2.873 | 90.585 | 1.00 20.05 | A |
| ATOM | 101 | CD2 | LEU | 12 | 41.565 | -1.073 | 91.630 | 1.00 22.30 | A |
| ATOM | 102 | C | LEU | 12 | 37.836 | -2.527 | 89.885 | 1.00 18.22 | A |
| ATOM | 103 | O | LEU | 12 | 37.032 | -3.443 | 90.090 | 1.00 17.41 | A |
| ATOM | 104 | N | PRO | 13 | 37.774 | -1.777 | 88.761 | 1.00 17.48 | A |
| ATOM | 105 | CA | PRO | 13 | 38.471 | -0.539 | 88.386 | 1.00 16.44 | A |
| ATOM | 106 | CB | PRO | 13 | 36.722 | -2.070 | 87.776 | 1.00 17.64 | A |
| ATOM | 107 | CB | PRO | 13 | 36.790 | -0.854 | 86.829 | 1.00 16.12 | A |
| ATOM | 108 | CG | PRO | 13 | 37.387 | 0.189 | 87.628 | 1.00 15.33 | A |
| ATOM | 109 | C | PRO | 13 | 36.910 | -3.382 | 86.984 | 1.00 17.42 | A |
| ATOM | 110 | O | PRO | 13 | 37.932 | -4.059 | 87.102 | 1.00 18.14 | A |
| ATOM | 111 | N | SER | 14 | 35.894 | -3.760 | 86.220 | 1.00 17.79 | A |
| ATOM | 112 | CA | SER | 14 | 35.981 | -4.941 | 85.351 | 1.00 18.05 | A |
| ATOM | 113 | CB | SER | 14 | 34.622 | -5.220 | 84.685 | 1.00 18.49 | A |
| ATOM | 114 | OG | SER | 14 | 34.341 | -4.267 | 83.651 | 1.00 18.23 | A |
| ATOM | 115 | C | SER | 14 | 36.993 | -4.614 | 84.225 | 1.00 17.66 | A |
| ATOM | 116 | O | SER | 14 | 37.093 | -3.463 | 83.784 | 1.00 17.62 | A |
| ATOM | 117 | N | ARG | 15 | 37.682 | -5.621 | 83.713 | 1.00 17.19 | A |
| ATOM | 118 | CA | ARG | 15 | 38.044 | -5.384 | 82.634 | 1.00 17.37 | A |
| ATOM | 119 | CB | ARG | 15 | 39.191 | -6.692 | 82.038 | 1.00 16.22 | A |
| ATOM | 120 | CG | ARG | 15 | 40.357 | -7.321 | 82.781 | 1.00 14.23 | A |
| ATOM | 121 | CD | ARG | 15 | 39.992 | -7.675 | 84.195 | 1.00 13.11 | A |
| ATOM | 122 | NE | ARG | 15 | 41.100 | -8.345 | 84.851 | 1.00 12.63 | A |
| ATOM | 123 | CZ | ARG | 15 | 41.094 | -8.674 | 86.124 | 1.00 11.48 | A |
| ATOM | 124 | NH1 | ARG | 15 | 40.043 | -8.390 | 86.855 | 1.00 12.49 | A |
| ATOM | 125 | NH2 | ARG | 15 | 42.120 | -9.298 | 86.667 | 1.00 13.12 | A |
| ATOM | 126 | C | ARG | 15 | 38.044 | -4.585 | 81.508 | 1.00 17.82 | A |
| ATOM | 127 | O | ARG | 15 | 38.643 | -3.620 | 81.057 | 1.00 17.97 | A |
| ATOM | 128 | N | SER | 16 | 36.863 | -4.960 | 81.055 | 1.00 19.69 | A |
| ATOM | 129 | CA | SER | 16 | 36.273 | -4.227 | 79.947 | 1.00 19.69 | A |
| ATOM | 130 | CB | SER | 16 | 35.120 | -5.013 | 79.267 | 1.00 20.87 | A |
| ATOM | 131 | OG | SER | 16 | 34.157 | -5.465 | 80.191 | 1.00 24.18 | A |
| ATOM | 132 | C | SER | 16 | 35.924 | -2.782 | 80.327 | 1.00 19.03 | A |
| ATOM | 133 | O | SER | 16 | 36.019 | -1.872 | 79.480 | 1.00 19.21 | A |
| ATOM | 134 | N | ASP | 17 | 35.614 | -2.559 | 81.607 | 1.00 18.59 | A |
| ATOM | 135 | CA | ASP | 17 | 35.361 | -1.201 | 82.099 | 1.00 18.70 | A |
| ATOM | 136 | CB | ASP | 17 | 35.027 | -1.193 | 83.604 | 1.00 21.06 | A |
| ATOM | 137 | CG | ASP | 17 | 33.545 | -1.278 | 83.888 | 1.00 22.89 | A |
| ATOM | 149 | OD1 | ASP | 17 | 32.773 | -1.321 | 82.904 | 1.00 24.69 | A |
| ATOM | 150 | OD2 | ASP | 17 | 33.164 | -1.323 | 85.093 | 1.00 24.31 | A |
| ATOM | 151 | C | ASP | 17 | 36.679 | -0.458 | 81.970 | 1.00 17.14 | A |
| ATOM | 152 | O | ASP | 17 | 36.734 | 0.719 | 81.617 | 1.00 16.95 | A |
| ATOM | 153 | N | VAL | 18 | 37.743 | -1.178 | 82.280 | 1.00 15.64 | A |
| ATOM | 155 | CA | VAL | 18 | 39.066 | -0.604 | 82.267 | 1.00 14.12 | A |
| ATOM | 156 | CB | VAL | 18 | 40.128 | -1.579 | 82.907 | 1.00 12.15 | A |
| ATOM | 157 | CG1 | VAL | 18 | 41.525 | -0.932 | 82.914 | 1.00 10.23 | A |
| ATOM | 158 | CG2 | VAL | 18 | 39.740 | -1.940 | 84.312 | 1.00 10.95 | A |
| ATOM | 159 | C | VAL | 18 | 39.482 | -0.153 | 80.883 | 1.00 13.92 | A |
| ATOM | 160 | O | VAL | 18 | 39.987 | 0.962 | 80.712 | 1.00 14.22 | A |
| ATOM | 161 | N | VAL | 19 | 39.309 | -1.029 | 79.902 | 1.00 13.98 | A |
| ATOM | 163 | CA | VAL | 19 | 39.687 | -0.718 | 78.519 | 1.00 13.53 | A |
| ATOM | 164 | CB | VAL | 19 | 39.411 | -1.929 | 77.599 | 1.00 12.04 | A |
| ATOM | 165 | CG1 | VAL | 19 | 39.684 | -1.558 | 76.162 | 1.00 10.81 | A |
| ATOM | 166 | CG2 | VAL | 19 | 40.274 | -3.108 | 78.024 | 1.00 10.15 | A |
| ATOM | 167 | C | VAL | 19 | 38.947 | 0.515 | 77.994 | 1.00 14.24 | A |
| ATOM | 168 | O | VAL | 19 | 39.519 | 1.349 | 77.274 | 1.00 12.95 | A |
| ATOM | 169 | N | GLN | 20 | 37.678 | 0.621 | 78.393 | 1.00 16.41 | A |
| ATOM | 171 | CA | GLN | 20 | 36.800 | 1.725 | 77.992 | 1.00 18.53 | A |
| ATOM | 172 | CB | GLN | 20 | 35.338 | 1.455 | 78.416 | 1.00 21.50 | A |
| ATOM | 173 | CG | GLN | 20 | 34.377 | 2.624 | 78.120 | 1.00 26.46 | A |
| ATOM | 174 | CD | GLN | 20 | 33.021 | 2.174 | 78.305 | 1.00 29.99 | A |
| ATOM | 175 | OE1 | GLN | 20 | 32.165 | 1.659 | 78.305 | 1.00 31.63 | A |
| ATOM | 176 | NE2 | GLN | 20 | 32.808 | 2.384 | 76.247 | 1.00 31.45 | A |
| ATOM | 179 | C | GLN | 20 | 37.277 | 3.059 | 78.548 | 1.00 17.64 | A |
| ATOM | 180 | O | GLN | 20 | 37.286 | 4.067 | 77.822 | 1.00 18.69 | A |
| ATOM | 181 | N | LEU | 21 | 37.694 | 3.047 | 79.809 | 1.00 16.17 | A |
| ATOM | 183 | CA | LEU | 21 | 38.195 | 4.222 | 80.467 | 1.00 15.58 | A |
| ATOM | 184 | CB | LEU | 21 | 38.633 | 3.902 | 81.880 | 1.00 16.49 | A |
| ATOM | 185 | CG | LEU | 21 | 38.232 | 4.891 | 82.988 | 1.00 17.74 | A |
| ATOM | 186 | CD1 | LEU | 21 | 39.249 | 4.773 | 84.121 | 1.00 16.51 | A |
| ATOM | 187 | CD2 | LEU | 21 | 38.171 | 6.355 | 82.451 | 1.00 17.00 | A |
| ATOM | 188 | C | LEU | 21 | 39.409 | 4.688 | 79.716 | 1.00 16.21 | A |
| ATOM | 189 | O | LEU | 21 | 39.581 | 5.886 | 79.514 | 1.00 17.53 | A |
| ATOM | 190 | N | TYR | 22 | 40.274 | 3.745 | 79.358 | 1.00 16.08 | A |
| ATOM | 192 | CA | TYR | 22 | 41.505 | 4.011 | 78.611 | 1.00 16.42 | A |
| ATOM | 193 | CB | TYR | 22 | 42.239 | 2.689 | 78.290 | 1.00 15.56 | A |
| ATOM | 194 | CG | TYR | 22 | 43.317 | 2.301 | 79.268 | 1.00 14.05 | A |
| ATOM | 195 | CD1 | TYR | 22 | 42.998 | 1.662 | 80.481 | 1.00 13.71 | A |

- 62 -

| ATOM | 196 | CE1 | TYR | 22 | 43.991 | 1.321 | 81.403 | 1.00 | 12.32 | A | ATOM | 251 | CG2 | ILE | 27 | 46.708 | 5.025 | 78.269 | 1.00 | 17.20 | A |
|---|---|---|---|---|---|---|---|---|---|---|---|---|---|---|---|---|---|---|---|---|---|
| ATOM | 197 | CD2 | TYR | 22 | 44.657 | 2.585 | 79.003 | 1.00 | 13.29 | A | ATOM | 252 | CG1 | ILE | 27 | 45.273 | 6.972 | 79.051 | 1.00 | 18.35 | A |
| ATOM | 198 | CE2 | TYR | 22 | 45.666 | 2.243 | 79.937 | 1.00 | 13.81 | A | ATOM | 253 | CD1 | ILE | 27 | 44.470 | 6.601 | 80.314 | 1.00 | 20.24 | A |
| ATOM | 199 | CZ | TYR | 22 | 45.312 | 1.616 | 81.126 | 1.00 | 12.31 | A | ATOM | 254 | C | ILE | 27 | 45.818 | 5.417 | 75.556 | 1.00 | 18.32 | A |
| ATOM | 200 | OH | TYR | 22 | 46.272 | 1.306 | 82.038 | 1.00 | 12.46 | A | ATOM | 255 | O | ILE | 27 | 44.970 | 4.558 | 75.332 | 1.00 | 18.04 | A |
| ATOM | 202 | C | TYR | 22 | 46.223 | 4.723 | 77.301 | 1.00 | 17.15 | A | ATOM | 256 | N | ASN | 28 | 47.016 | 5.416 | 74.976 | 1.00 | 17.72 | A |
| ATOM | 203 | O | TYR | 22 | 41.824 | 5.754 | 76.981 | 1.00 | 17.02 | A | ATOM | 258 | CA | ASN | 28 | 47.329 | 4.453 | 73.933 | 1.00 | 18.20 | A |
| ATOM | 204 | N | ARG | 23 | 40.333 | 4.130 | 76.518 | 1.00 | 18.83 | A | ATOM | 259 | CB | ASN | 28 | 47.815 | 5.191 | 72.706 | 1.00 | 21.29 | A |
| ATOM | 206 | CA | ARG | 23 | 39.977 | 4.700 | 75.237 | 1.00 | 20.20 | A | ATOM | 260 | CG | ASN | 28 | 49.026 | 6.005 | 73.002 | 1.00 | 24.56 | A |
| ATOM | 207 | CB | ARG | 23 | 39.117 | 3.727 | 74.472 | 1.00 | 21.94 | A | ATOM | 261 | OD1 | ASN | 28 | 49.139 | 6.598 | 74.080 | 1.00 | 27.22 | A |
| ATOM | 208 | CG | ARG | 23 | 39.631 | 2.315 | 74.566 | 1.00 | 26.13 | A | ATOM | 262 | ND2 | ASN | 28 | 49.980 | 5.985 | 72.102 | 1.00 | 26.59 | A |
| ATOM | 209 | CD | ARG | 23 | 39.057 | 1.426 | 73.512 | 1.00 | 28.85 | A | ATOM | 265 | C | ASN | 28 | 48.328 | 3.366 | 74.278 | 1.00 | 17.33 | A |
| ATOM | 210 | NE | ARG | 23 | 39.432 | 1.916 | 72.186 | 1.00 | 32.06 | A | ATOM | 266 | O | ASN | 28 | 48.867 | 2.720 | 73.381 | 1.00 | 16.67 | A |
| ATOM | 212 | CZ | ARG | 23 | 38.570 | 2.155 | 71.197 | 1.00 | 33.01 | A | ATOM | 267 | N | GLY | 29 | 48.560 | 3.128 | 75.560 | 1.00 | 15.40 | A |
| ATOM | 213 | NH1 | ARG | 23 | 37.267 | 1.944 | 71.367 | 1.00 | 32.53 | A | ATOM | 269 | CA | GLY | 29 | 49.503 | 2.104 | 75.900 | 1.00 | 13.65 | A |
| ATOM | 216 | NH2 | ARG | 23 | 39.021 | 2.631 | 70.041 | 1.00 | 34.18 | A | ATOM | 270 | C | GLY | 29 | 49.140 | 1.506 | 77.221 | 1.00 | 13.40 | A |
| ATOM | 219 | C | ARG | 23 | 39.275 | 6.042 | 75.433 | 1.00 | 20.89 | A | ATOM | 271 | O | GLY | 29 | 48.693 | 2.218 | 78.115 | 1.00 | 14.65 | A |
| ATOM | 220 | O | ARG | 23 | 39.454 | 6.991 | 74.642 | 1.00 | 20.76 | A | ATOM | 272 | N | MET | 30 | 49.350 | 0.211 | 77.375 | 1.00 | 11.87 | A |
| ATOM | 221 | N | SER | 24 | 38.524 | 6.207 | 76.514 | 1.00 | 21.98 | A | ATOM | 274 | CA | MET | 30 | 49.028 | -0.453 | 78.634 | 1.00 | 10.20 | A |
| ATOM | 223 | CA | SER | 24 | 37.872 | 7.497 | 76.763 | 1.00 | 23.68 | A | ATOM | 275 | CB | MET | 30 | 47.722 | -1.236 | 78.500 | 1.00 | 8.31 | A |
| ATOM | 224 | CB | SER | 24 | 36.960 | 7.403 | 77.970 | 1.00 | 24.17 | A | ATOM | 276 | CG | MET | 30 | 47.260 | -1.914 | 79.788 | 1.00 | 8.50 | A |
| ATOM | 225 | OG | SER | 24 | 35.955 | 6.445 | 77.687 | 1.00 | 28.90 | A | ATOM | 277 | SD | MET | 30 | 45.730 | -2.867 | 79.651 | 1.00 | 9.05 | A |
| ATOM | 227 | C | SER | 24 | 38.906 | 8.596 | 76.989 | 1.00 | 23.18 | A | ATOM | 278 | CE | MET | 30 | 44.356 | -1.661 | 79.839 | 1.00 | 3.07 | A |
| ATOM | 228 | O | SER | 24 | 38.848 | 9.647 | 76.370 | 1.00 | 24.77 | A | ATOM | 279 | C | MET | 30 | 50.134 | -1.437 | 78.948 | 1.00 | 10.16 | A |
| ATOM | 229 | N | LYS | 25 | 39.886 | 8.307 | 77.839 | 1.00 | 23.16 | A | ATOM | 280 | O | MET | 30 | 50.777 | -1.943 | 78.030 | 1.00 | 12.41 | A |
| ATOM | 231 | CA | LYS | 25 | 40.965 | 9.228 | 78.182 | 1.00 | 21.38 | A | ATOM | 281 | N | ARG | 31 | 50.484 | -1.571 | 80.215 | 1.00 | 8.80 | A |
| ATOM | 232 | CB | LYS | 25 | 41.689 | 8.714 | 79.399 | 1.00 | 21.09 | A | ATOM | 283 | CA | ARG | 31 | 51.427 | -2.603 | 80.597 | 1.00 | 8.74 | A |
| ATOM | 233 | CG | LYS | 25 | 40.795 | 8.713 | 80.571 | 1.00 | 22.04 | A | ATOM | 284 | CB | ARG | 31 | 52.630 | -2.069 | 81.364 | 1.00 | 6.81 | A |
| ATOM | 234 | CD | LYS | 25 | 40.218 | 10.086 | 80.778 | 1.00 | 21.12 | A | ATOM | 285 | CG | ARG | 31 | 53.432 | -3.192 | 81.976 | 1.00 | 5.46 | A |
| ATOM | 235 | CE | LYS | 25 | 38.962 | 9.974 | 81.605 | 1.00 | 24.09 | A | ATOM | 286 | CD | ARG | 31 | 54.805 | -2.744 | 82.379 | 1.00 | 6.76 | A |
| ATOM | 236 | NZ | LYS | 25 | 38.497 | 11.313 | 82.027 | 1.00 | 24.54 | A | ATOM | 287 | NE | ARG | 31 | 55.607 | -3.852 | 82.889 | 1.00 | 6.47 | A |
| ATOM | 240 | C | LYS | 25 | 41.966 | 9.431 | 77.076 | 1.00 | 21.26 | A | ATOM | 289 | CZ | ARG | 31 | 56.702 | -3.688 | 83.620 | 1.00 | 7.52 | A |
| ATOM | 241 | O | LYS | 25 | 42.791 | 10.360 | 77.140 | 1.00 | 20.53 | A | ATOM | 290 | NH1 | ARG | 31 | 57.104 | -2.469 | 83.929 | 1.00 | 7.80 | A |
| ATOM | 242 | N | GLY | 26 | 41.953 | 8.527 | 76.102 | 1.00 | 19.57 | A | ATOM | 293 | NH2 | ARG | 31 | 57.431 | -4.730 | 83.985 | 1.00 | 7.53 | A |
| ATOM | 244 | CA | GLY | 26 | 42.889 | 8.672 | 75.007 | 1.00 | 20.09 | A | ATOM | 296 | C | ARG | 31 | 50.598 | -3.498 | 81.522 | 1.00 | 10.14 | A |
| ATOM | 245 | C | GLY | 26 | 44.265 | 8.125 | 75.330 | 1.00 | 19.26 | A | ATOM | 297 | O | ARG | 31 | 49.689 | -3.006 | 82.193 | 1.00 | 11.37 | A |
| ATOM | 246 | O | GLY | 26 | 45.279 | 8.594 | 74.813 | 1.00 | 18.37 | A | ATOM | 298 | N | ILE | 32 | 50.788 | -4.818 | 81.454 | 1.00 | 11.45 | A |
| ATOM | 247 | N | ILE | 27 | 44.292 | 7.135 | 76.216 | 1.00 | 19.55 | A | ATOM | 300 | CA | ILE | 32 | 50.082 | -5.713 | 82.380 | 1.00 | 10.67 | A |
| ATOM | 249 | CA | ILE | 27 | 45.546 | 6.492 | 76.602 | 1.00 | 18.74 | A | ATOM | 301 | CB | ILE | 32 | 48.838 | -6.394 | 81.782 | 1.00 | 10.17 | A |
| ATOM | 250 | CB | ILE | 27 | 45.445 | 5.858 | 78.007 | 1.00 | 18.08 | A | ATOM | 302 | CG2 | ILE | 32 | 47.885 | -5.317 | 81.382 | 1.00 | 10.14 | A |

- 63 -

| | | | | | | | | | | | | | | | | |
|---|---|---|---|---|---|---|---|---|---|---|---|---|---|---|---|---|
| ATOM | 303 | CG1 | ILE | 32 | 49.155 | -7.338 | 80.612 | 1.00 | 9.86 | A | ATOM | 348 | N | GLY | 37 | 44.194 | -13.102 | 80.990 | 1.00 | 18.25 | A |
| ATOM | 304 | CD1 | ILE | 32 | 47.941 | -8.178 | 80.180 | 1.00 | 6.70 | A | ATOM | 350 | CA | GLY | 37 | 43.241 | -13.401 | 79.918 | 1.00 | 18.79 | A |
| ATOM | 305 | C | ILE | 32 | 51.146 | -6.655 | 82.891 | 1.00 | 11.29 | A | ATOM | 351 | C | GLY | 37 | 42.038 | -12.472 | 79.739 | 1.00 | 19.91 | A |
| ATOM | 306 | O | ILE | 32 | 52.101 | -6.917 | 82.162 | 1.00 | 12.06 | A | ATOM | 352 | O | GLY | 37 | 41.618 | -12.179 | 78.616 | 1.00 | 18.61 | A |
| ATOM | 307 | N | TYR | 33 | 51.017 | -7.063 | 84.164 | 1.00 | 10.72 | A | ATOM | 353 | N | GLN | 38 | 41.450 | -12.019 | 80.836 | 1.00 | 20.09 | A |
| ATOM | 309 | CA | TYR | 33 | 52.000 | -7.877 | 84.881 | 1.00 | 9.67 | A | ATOM | 355 | CA | GLN | 38 | 40.329 | -11.113 | 80.703 | 1.00 | 20.80 | A |
| ATOM | 310 | CB | TYR | 33 | 52.141 | -7.357 | 86.325 | 1.00 | 8.91 | A | ATOM | 356 | CB | GLN | 38 | 39.674 | -10.899 | 82.026 | 1.00 | 22.45 | A |
| ATOM | 311 | CG | TYR | 33 | 52.570 | -5.902 | 86.349 | 1.00 | 8.80 | A | ATOM | 357 | CG | GLN | 38 | 39.264 | -12.114 | 82.714 | 1.00 | 26.07 | A |
| ATOM | 312 | CD1 | TYR | 33 | 51.630 | -4.846 | 86.244 | 1.00 | 9.84 | A | ATOM | 358 | CD | GLN | 38 | 39.130 | -11.830 | 84.184 | 1.00 | 28.97 | A |
| ATOM | 313 | CE1 | TYR | 33 | 52.049 | -3.497 | 86.146 | 1.00 | 8.28 | A | ATOM | 359 | OE1 | GLN | 38 | 38.021 | -11.645 | 84.683 | 1.00 | 31.77 | A |
| ATOM | 314 | CD2 | TYR | 33 | 53.910 | -5.569 | 86.362 | 1.00 | 8.88 | A | ATOM | 360 | NE2 | GLN | 38 | 40.265 | -11.712 | 84.881 | 1.00 | 29.85 | A |
| ATOM | 315 | CE2 | TYR | 33 | 54.330 | -4.235 | 86.247 | 1.00 | 8.80 | A | ATOM | 363 | C | GLN | 38 | 40.765 | -9.739 | 80.184 | 1.00 | 20.28 | A |
| ATOM | 316 | CZ | TYR | 33 | 53.412 | -3.224 | 86.154 | 1.00 | 8.01 | A | ATOM | 364 | O | GLN | 38 | 39.956 | -9.031 | 79.607 | 1.00 | 21.54 | A |
| ATOM | 317 | OH | TYR | 33 | 53.887 | -1.950 | 86.115 | 1.00 | 6.25 | A | ATOM | 365 | N | ALA | 39 | 41.986 | -9.306 | 80.514 | 1.00 | 19.78 | A |
| ATOM | 319 | C | TYR | 33 | 51.976 | -9.391 | 84.787 | 1.00 | 8.82 | A | ATOM | 367 | CA | ALA | 39 | 42.498 | -8.005 | 80.071 | 1.00 | 19.16 | A |
| ATOM | 320 | O | TYR | 33 | 52.847 | -10.053 | 85.263 | 1.00 | 9.53 | A | ATOM | 368 | CB | ALA | 39 | 43.817 | -7.644 | 80.790 | 1.00 | 18.30 | A |
| ATOM | 321 | N | PHE | 34 | 50.994 | -9.935 | 84.123 | 1.00 | 10.90 | A | ATOM | 369 | C | ALA | 39 | 42.721 | -8.127 | 78.567 | 1.00 | 18.75 | A |
| ATOM | 323 | CA | PHE | 34 | 50.957 | -11.362 | 83.879 | 1.00 | 10.77 | A | ATOM | 370 | O | ALA | 39 | 42.207 | -7.331 | 77.793 | 1.00 | 20.23 | A |
| ATOM | 324 | CB | PHE | 34 | 50.450 | -12.150 | 85.090 | 1.00 | 10.32 | A | ATOM | 371 | N | LEU | 40 | 43.401 | -9.196 | 78.173 | 1.00 | 17.57 | A |
| ATOM | 325 | CG | PHE | 34 | 49.096 | -11.733 | 85.582 | 1.00 | 9.54 | A | ATOM | 373 | CA | LEU | 40 | 43.699 | -9.497 | 76.778 | 1.00 | 17.38 | A |
| ATOM | 326 | CD1 | PHE | 34 | 47.980 | -12.506 | 85.304 | 1.00 | 9.33 | A | ATOM | 374 | CB | LEU | 40 | 44.525 | -10.788 | 76.694 | 1.00 | 16.67 | A |
| ATOM | 327 | CD2 | PHE | 34 | 48.947 | -10.608 | 86.371 | 1.00 | 9.73 | A | ATOM | 375 | CG | LEU | 40 | 45.896 | -10.693 | 77.369 | 1.00 | 14.61 | A |
| ATOM | 328 | CE1 | PHE | 34 | 46.732 | -12.165 | 85.806 | 1.00 | 10.62 | A | ATOM | 376 | CD1 | LEU | 40 | 46.293 | -12.041 | 77.924 | 1.00 | 12.08 | A |
| ATOM | 329 | CE2 | PHE | 34 | 47.701 | -10.253 | 86.884 | 1.00 | 11.78 | A | ATOM | 377 | CD2 | LEU | 40 | 46.905 | -10.121 | 76.402 | 1.00 | 12.98 | A |
| ATOM | 330 | CZ | PHE | 34 | 46.584 | -11.040 | 86.597 | 1.00 | 10.71 | A | ATOM | 378 | C | LEU | 40 | 42.494 | -9.026 | 75.873 | 1.00 | 17.60 | A |
| ATOM | 331 | C | PHE | 34 | 50.050 | -11.540 | 82.680 | 1.00 | 11.55 | A | ATOM | 379 | O | LEU | 40 | 41.408 | -10.299 | 76.296 | 1.00 | 17.81 | A |
| ATOM | 332 | O | PHE | 34 | 49.410 | -10.577 | 82.220 | 1.00 | 11.52 | A | ATOM | 380 | N | SER | 41 | 40.197 | -10.404 | 75.483 | 1.00 | 17.53 | A |
| ATOM | 333 | N | ALA | 35 | 50.021 | -12.740 | 82.136 | 1.00 | 13.14 | A | ATOM | 382 | CA | SER | 41 | 39.164 | -11.319 | 76.113 | 1.00 | 17.04 | A |
| ATOM | 335 | CA | ALA | 35 | 49.135 | -13.010 | 81.018 | 1.00 | 15.02 | A | ATOM | 383 | CB | SER | 41 | 39.828 | -12.314 | 76.844 | 1.00 | 17.77 | A |
| ATOM | 336 | CB | ALA | 35 | 49.469 | -14.370 | 80.407 | 1.00 | 14.62 | A | ATOM | 384 | OG | SER | 41 | 39.580 | -9.039 | 75.352 | 1.00 | 21.43 | A |
| ATOM | 337 | C | ALA | 35 | 47.702 | -12.993 | 81.570 | 1.00 | 15.04 | A | ATOM | 386 | C | SER | 41 | 39.165 | -8.634 | 74.266 | 1.00 | 16.35 | A |
| ATOM | 338 | O | ALA | 35 | 47.144 | -14.021 | 81.868 | 1.00 | 16.49 | A | ATOM | 387 | O | SER | 41 | 39.526 | -8.322 | 76.463 | 1.00 | 17.33 | A |
| ATOM | 339 | N | ASP | 36 | 47.126 | -11.819 | 81.755 | 1.00 | 15.05 | A | ATOM | 388 | N | ALA | 42 | 38.967 | -6.996 | 76.442 | 1.00 | 14.79 | A |
| ATOM | 341 | CA | ASP | 36 | 45.766 | -11.730 | 82.267 | 1.00 | 15.72 | A | ATOM | 390 | CA | ALA | 42 | 38.929 | -6.439 | 77.865 | 1.00 | 13.66 | A |
| ATOM | 342 | CB | ASP | 36 | 45.611 | -10.360 | 82.950 | 1.00 | 14.76 | A | ATOM | 391 | CB | ALA | 42 | 39.784 | -6.110 | 77.844 | 1.00 | 11.91 | A |
| ATOM | 343 | CG | ASP | 36 | 44.236 | -10.105 | 83.519 | 1.00 | 12.67 | A | ATOM | 392 | C | ALA | 42 | 39.233 | -5.260 | 75.484 | 1.00 | 11.91 | A |
| ATOM | 344 | OD1 | ASP | 36 | 43.271 | -10.828 | 83.227 | 1.00 | 13.69 | A | ATOM | 393 | O | ALA | 42 | 41.071 | -6.396 | 75.308 | 1.00 | 13.40 | A |
| ATOM | 345 | OD2 | ASP | 36 | 44.113 | -9.117 | 84.259 | 1.00 | 12.92 | A | ATOM | 394 | N | LEU | 43 | 41.948 | -5.584 | 74.818 | 1.00 | 15.80 | A |
| ATOM | 346 | C | ASP | 36 | 44.784 | -11.911 | 81.092 | 1.00 | 17.11 | A | ATOM | 396 | CA | LEU | 43 | 41.948 | -5.584 | 74.460 | 1.00 | 13.08 | A |
| ATOM | 347 | O | ASP | 36 | 44.557 | -10.984 | 80.296 | 1.00 | 17.79 | A | ATOM | 397 | CB | LEU | 43 | 43.400 | -5.778 | 74.933 | 1.00 | 10.77 | A |

- 64 -

| | | | | | | | | | | | | | | | | |
|---|---|---|---|---|---|---|---|---|---|---|---|---|---|---|---|---|
| ATOM | 398 | CG | LEU | 43 | 43.750 | -5.132 | 76.265 | 1.00 | 7.95 | A | ATOM | 451 | C | ILE | 48 | 47.364 | -0.800 | 72.567 | 1.00 | 10.55 | A |
| ATOM | 399 | CD1 | LEU | 43 | 44.931 | -5.813 | 76.889 | 1.00 | 6.70 | A | ATOM | 452 | O | ILE | 48 | 47.217 | -2.024 | 72.542 | 1.00 | 11.79 | A |
| ATOM | 400 | CD2 | LEU | 43 | 44.010 | -3.653 | 76.036 | 1.00 | 6.59 | A | ATOM | 453 | N | GLY | 49 | 48.555 | -0.207 | 72.484 | 1.00 | 9.22 | A |
| ATOM | 401 | C | LEU | 43 | 41.871 | -5.750 | 72.925 | 1.00 | 13.05 | A | ATOM | 455 | CA | GLY | 49 | 49.780 | -0.985 | 72.411 | 1.00 | 8.27 | A |
| ATOM | 402 | O | LEU | 43 | 42.492 | -4.982 | 72.150 | 1.00 | 11.69 | A | ATOM | 456 | C | GLY | 49 | 49.968 | -1.587 | 73.787 | 1.00 | 8.76 | A |
| ATOM | 403 | N | ARG | 44 | 41.134 | -6.755 | 72.485 | 1.00 | 14.56 | A | ATOM | 457 | O | GLY | 49 | 49.677 | -0.943 | 74.808 | 1.00 | 7.91 | A |
| ATOM | 405 | CA | ARG | 44 | 40.995 | -7.055 | 71.067 | 1.00 | 15.68 | A | ATOM | 458 | N | LEU | 50 | 50.547 | -2.773 | 73.846 | 1.00 | 9.36 | A |
| ATOM | 406 | CB | ARG | 44 | 40.058 | -8.256 | 70.923 | 1.00 | 17.33 | A | ATOM | 460 | CA | LEU | 50 | 50.695 | -3.430 | 75.124 | 1.00 | 9.53 | A |
| ATOM | 407 | CG | ARG | 44 | 40.644 | -9.610 | 71.363 | 1.00 | 19.70 | A | ATOM | 461 | CB | LEU | 50 | 49.663 | -4.576 | 75.190 | 1.00 | 8.94 | A |
| ATOM | 408 | CD | ARG | 44 | 39.679 | -10.770 | 71.068 | 1.00 | 21.78 | A | ATOM | 462 | CG | LEU | 50 | 49.624 | -5.499 | 76.420 | 1.00 | 9.83 | A |
| ATOM | 409 | NE | ARG | 44 | 38.648 | -10.842 | 72.106 | 1.00 | 27.78 | A | ATOM | 463 | CD1 | LEU | 50 | 49.052 | -4.717 | 77.592 | 1.00 | 10.67 | A |
| ATOM | 411 | CZ | ARG | 44 | 37.506 | -11.542 | 72.054 | 1.00 | 29.42 | A | ATOM | 464 | CD2 | LEU | 50 | 48.790 | -6.759 | 76.170 | 1.00 | 8.44 | A |
| ATOM | 412 | NH1 | ARG | 44 | 37.180 | -12.279 | 70.997 | 1.00 | 32.21 | A | ATOM | 465 | C | LEU | 50 | 52.057 | -3.999 | 75.431 | 1.00 | 10.06 | A |
| ATOM | 415 | NH2 | ARG | 44 | 36.660 | -11.497 | 73.076 | 1.00 | 30.80 | A | ATOM | 466 | O | LEU | 50 | 52.738 | -4.476 | 74.519 | 1.00 | 9.99 | A |
| ATOM | 418 | C | ARG | 44 | 40.531 | -5.833 | 70.205 | 1.00 | 15.54 | A | ATOM | 467 | N | ILE | 50 | 52.490 | -3.843 | 76.690 | 1.00 | 9.74 | A |
| ATOM | 419 | O | ARG | 44 | 39.499 | -5.260 | 70.432 | 1.00 | 13.58 | A | ATOM | 469 | CA | ILE | 51 | 53.701 | -4.516 | 77.186 | 1.00 | 9.43 | A |
| ATOM | 420 | N | ASN | 45 | 41.311 | -5.473 | 69.193 | 1.00 | 16.44 | A | ATOM | 470 | CB | ILE | 51 | 54.561 | -3.688 | 78.174 | 1.00 | 10.77 | A |
| ATOM | 422 | CA | ASN | 45 | 41.003 | -4.329 | 68.331 | 1.00 | 18.05 | A | ATOM | 471 | CG1 | ILE | 51 | 55.586 | -4.574 | 78.851 | 1.00 | 9.59 | A |
| ATOM | 423 | CB | ASN | 45 | 39.871 | -4.682 | 67.392 | 1.00 | 18.53 | A | ATOM | 472 | CD1 | ILE | 51 | 55.377 | -2.601 | 77.477 | 1.00 | 8.85 | A |
| ATOM | 424 | CG | ASN | 45 | 40.261 | -5.788 | 66.454 | 1.00 | 20.08 | A | ATOM | 473 | CD1 | ILE | 51 | 55.962 | -1.633 | 78.499 | 1.00 | 11.06 | A |
| ATOM | 425 | OD1 | ASN | 45 | 41.264 | -5.693 | 65.710 | 1.00 | 18.40 | A | ATOM | 474 | C | ILE | 51 | 53.085 | -5.680 | 78.013 | 1.00 | 9.64 | A |
| ATOM | 426 | ND2 | ASN | 45 | 39.490 | -6.871 | 66.494 | 1.00 | 20.47 | A | ATOM | 475 | O | ILE | 51 | 52.280 | -5.425 | 78.952 | 1.00 | 9.51 | A |
| ATOM | 429 | C | ASN | 45 | 40.728 | -2.973 | 69.002 | 1.00 | 17.59 | A | ATOM | 476 | N | LEU | 52 | 53.394 | -6.926 | 77.619 | 1.00 | 8.21 | A |
| ATOM | 430 | O | ASN | 45 | 40.080 | -2.122 | 68.401 | 1.00 | 17.92 | A | ATOM | 478 | CA | LEU | 52 | 52.909 | -8.128 | 78.304 | 1.00 | 6.99 | A |
| ATOM | 431 | N | SER | 46 | 41.344 | -2.739 | 70.169 | 1.00 | 17.60 | A | ATOM | 479 | CB | LEU | 52 | 52.396 | -9.148 | 77.294 | 1.00 | 7.76 | A |
| ATOM | 433 | CA | SER | 46 | 41.169 | -1.522 | 70.977 | 1.00 | 16.24 | A | ATOM | 480 | CG | LEU | 52 | 51.933 | -10.525 | 77.825 | 1.00 | 6.94 | A |
| ATOM | 434 | CB | SER | 46 | 41.397 | -1.849 | 72.442 | 1.00 | 15.31 | A | ATOM | 481 | CD1 | LEU | 52 | 50.694 | -10.398 | 78.668 | 1.00 | 7.39 | A |
| ATOM | 435 | OG | SER | 46 | 42.721 | -2.313 | 72.623 | 1.00 | 15.09 | A | ATOM | 482 | CD2 | LEU | 52 | 51.643 | -11.410 | 76.676 | 1.00 | 5.84 | A |
| ATOM | 437 | C | SER | 46 | 42.147 | -0.432 | 70.594 | 1.00 | 16.19 | A | ATOM | 483 | C | LEU | 52 | 53.997 | -8.788 | 79.131 | 1.00 | 7.20 | A |
| ATOM | 438 | O | SER | 46 | 41.995 | 0.717 | 70.996 | 1.00 | 16.72 | A | ATOM | 484 | O | LEU | 52 | 54.935 | -9.372 | 78.578 | 1.00 | 7.45 | A |
| ATOM | 439 | N | GLY | 47 | 43.162 | -0.819 | 69.837 | 1.00 | 15.87 | A | ATOM | 485 | N | ASP | 53 | 53.940 | -8.656 | 80.454 | 1.00 | 7.28 | A |
| ATOM | 441 | CA | GLY | 47 | 44.189 | 0.102 | 69.412 | 1.00 | 15.39 | A | ATOM | 487 | CA | ASP | 53 | 54.954 | -9.318 | 81.288 | 1.00 | 7.20 | A |
| ATOM | 442 | C | GLY | 47 | 45.202 | 0.454 | 70.490 | 1.00 | 15.72 | A | ATOM | 488 | CB | ASP | 53 | 54.912 | -8.770 | 82.702 | 1.00 | 8.55 | A |
| ATOM | 443 | O | GLY | 47 | 46.015 | 1.369 | 70.282 | 1.00 | 18.63 | A | ATOM | 489 | CG | ASP | 53 | 55.486 | -7.371 | 82.825 | 1.00 | 10.65 | A |
| ATOM | 444 | N | ILE | 48 | 45.199 | -0.240 | 71.626 | 1.00 | 13.11 | A | ATOM | 490 | OD1 | ASP | 53 | 55.908 | -7.005 | 83.947 | 1.00 | 10.32 | A |
| ATOM | 446 | CA | ILE | 48 | 46.152 | 0.095 | 72.671 | 1.00 | 10.33 | A | ATOM | 491 | OD2 | ASP | 53 | 55.541 | -6.642 | 81.824 | 1.00 | 11.82 | A |
| ATOM | 447 | CB | ILE | 48 | 45.507 | -0.042 | 74.077 | 1.00 | 10.42 | A | ATOM | 492 | C | ASP | 53 | 54.595 | -10.814 | 81.365 | 1.00 | 7.17 | A |
| ATOM | 448 | CG2 | ILE | 48 | 46.543 | 0.252 | 75.205 | 1.00 | 8.33 | A | ATOM | 493 | O | ASP | 53 | 53.421 | -11.162 | 81.353 | 1.00 | 4.77 | A |
| ATOM | 449 | CG1 | ILE | 48 | 44.285 | 0.891 | 74.174 | 1.00 | 10.32 | A | ATOM | 494 | N | ILE | 54 | 55.591 | -11.702 | 81.404 | 1.00 | 7.83 | A |
| ATOM | 450 | CD1 | ILE | 48 | 43.303 | 0.579 | 75.363 | 1.00 | 12.37 | A | ATOM | 496 | CA | ILE | 54 | 55.289 | -13.147 | 81.497 | 1.00 | 7.07 | A |

| ATOM | 497 | CB | ILE | 54 | 56.509 | -14.018 | 81.108 | 1.00 | 6.32 | A |
|---|---|---|---|---|---|---|---|---|---|---|
| ATOM | 498 | CG2 | ILE | 54 | 56.780 | -13.956 | 79.597 | 1.00 | 3.97 | A |
| ATOM | 499 | CG1 | ILE | 54 | 57.736 | -13.593 | 81.935 | 1.00 | 5.32 | A |
| ATOM | 500 | CD1 | ILE | 54 | 58.865 | -14.628 | 81.970 | 1.00 | 4.36 | A |
| ATOM | 501 | C | ILE | 54 | 54.822 | -13.554 | 82.921 | 1.00 | 7.61 | A |
| ATOM | 502 | O | ILE | 54 | 53.941 | -14.407 | 83.067 | 1.00 | 7.64 | A |
| ATOM | 503 | N | GLY | 55 | 55.396 | -12.901 | 83.941 | 1.00 | 7.53 | A |
| ATOM | 504 | CA | GLY | 55 | 55.123 | -13.190 | 85.342 | 1.00 | 7.96 | A |
| ATOM | 505 | C | GLY | 55 | 56.383 | -13.863 | 85.905 | 1.00 | 10.01 | A |
| ATOM | 506 | O | GLY | 55 | 56.833 | -14.846 | 85.344 | 1.00 | 10.00 | A |
| ATOM | 507 | N | ASN | 56 | 56.991 | -13.324 | 86.967 | 1.00 | 12.01 | A |
| ATOM | 508 | CA | ASN | 56 | 58.229 | -13.891 | 87.521 | 1.00 | 12.56 | A |
| ATOM | 509 | CB | ASN | 56 | 58.701 | -13.080 | 88.723 | 1.00 | 10.66 | A |
| ATOM | 510 | CG | ASN | 56 | 59.245 | -11.728 | 88.329 | 1.00 | 11.65 | A |
| ATOM | 511 | OD1 | ASN | 56 | 59.605 | -11.521 | 87.184 | 1.00 | 12.56 | A |
| ATOM | 512 | ND2 | ASN | 56 | 59.302 | -10.799 | 89.270 | 1.00 | 9.23 | A |
| ATOM | 513 | C | ASN | 56 | 58.182 | -15.377 | 87.853 | 1.00 | 13.34 | A |
| ATOM | 514 | O | ASN | 56 | 59.197 | -16.095 | 87.743 | 1.00 | 12.17 | A |
| ATOM | 515 | N | ASP | 57 | 56.985 | -15.848 | 88.188 | 1.00 | 14.52 | A |
| ATOM | 516 | CA | ASP | 57 | 56.784 | -17.251 | 88.571 | 1.00 | 16.32 | A |
| ATOM | 517 | CB | ASP | 57 | 55.394 | -17.398 | 89.199 | 1.00 | 19.63 | A |
| ATOM | 518 | CG | ASP | 57 | 54.282 | -16.949 | 88.237 | 1.00 | 24.26 | A |
| ATOM | 519 | OD1 | ASP | 57 | 54.077 | -17.570 | 87.159 | 1.00 | 26.71 | A |
| ATOM | 520 | OD2 | ASP | 57 | 53.651 | -15.911 | 88.504 | 1.00 | 28.53 | A |
| ATOM | 521 | C | ASP | 57 | 56.863 | -18.163 | 87.351 | 1.00 | 15.73 | A |
| ATOM | 522 | O | ASP | 57 | 56.705 | -19.384 | 87.468 | 1.00 | 15.68 | A |
| ATOM | 523 | N | GLN | 58 | 56.936 | -17.547 | 86.169 | 1.00 | 14.76 | A |
| ATOM | 524 | CA | GLN | 58 | 56.998 | -18.271 | 84.883 | 1.00 | 13.65 | A |
| ATOM | 525 | CB | GLN | 58 | 56.176 | -17.533 | 83.827 | 1.00 | 15.15 | A |
| ATOM | 526 | CG | GLN | 58 | 54.705 | -17.372 | 84.155 | 1.00 | 17.49 | A |
| ATOM | 527 | CD | GLN | 58 | 54.038 | -18.703 | 84.279 | 1.00 | 20.17 | A |
| ATOM | 528 | OE1 | GLN | 58 | 54.476 | -19.689 | 83.673 | 1.00 | 23.80 | A |
| ATOM | 529 | NE2 | GLN | 58 | 52.980 | -18.766 | 85.076 | 1.00 | 22.23 | A |
| ATOM | 530 | C | GLN | 58 | 58.418 | -18.339 | 84.370 | 1.00 | 12.78 | A |
| ATOM | 531 | O | GLN | 58 | 58.749 | -19.149 | 83.515 | 1.00 | 12.74 | A |
| ATOM | 532 | N | LEU | 59 | 59.265 | -17.480 | 84.906 | 1.00 | 12.25 | A |
| ATOM | 533 | CA | LEU | 59 | 60.611 | -17.410 | 84.436 | 1.00 | 12.23 | A |
| ATOM | 534 | CB | LEU | 59 | 61.367 | -16.368 | 85.251 | 1.00 | 13.35 | A |
| ATOM | 535 | CG | LEU | 59 | 62.728 | -15.867 | 84.771 | 1.00 | 14.82 | A |
| ATOM | 536 | CD1 | LEU | 59 | 62.607 | -14.860 | 83.619 | 1.00 | 14.81 | A |
| ATOM | 546 | CD2 | LEU | 59 | 63.433 | -15.229 | 85.994 | 1.00 | 16.03 | A |
| ATOM | 547 | C | LEU | 59 | 61.326 | -18.765 | 84.328 | 1.00 | 10.90 | A |
| ATOM | 548 | O | LEU | 59 | 61.764 | -19.133 | 83.246 | 1.00 | 11.83 | A |
| ATOM | 549 | N | ALA | 60 | 61.335 | -19.552 | 85.397 | 1.00 | 9.22 | A |
| ATOM | 551 | CA | ALA | 60 | 61.992 | -20.841 | 85.387 | 1.00 | 8.57 | A |
| ATOM | 552 | CB | ALA | 60 | 62.002 | -21.444 | 86.777 | 1.00 | 7.07 | A |
| ATOM | 553 | C | ALA | 60 | 61.413 | -21.822 | 84.390 | 1.00 | 9.23 | A |
| ATOM | 554 | O | ALA | 60 | 62.148 | -22.580 | 83.754 | 1.00 | 11.12 | A |
| ATOM | 555 | N | ASN | 61 | 60.105 | -21.810 | 84.228 | 1.00 | 10.28 | A |
| ATOM | 557 | CA | ASN | 61 | 59.412 | -22.751 | 83.333 | 1.00 | 11.22 | A |
| ATOM | 558 | CB | ASN | 61 | 57.922 | -22.613 | 83.561 | 1.00 | 12.27 | A |
| ATOM | 559 | CG | ASN | 61 | 57.140 | -23.725 | 82.935 | 1.00 | 14.36 | A |
| ATOM | 560 | OD1 | ASN | 61 | 56.802 | -24.685 | 83.611 | 1.00 | 17.06 | A |
| ATOM | 561 | ND2 | ASN | 61 | 56.804 | -23.592 | 81.647 | 1.00 | 15.50 | A |
| ATOM | 564 | C | ASN | 61 | 59.752 | -22.439 | 81.895 | 1.00 | 11.18 | A |
| ATOM | 565 | O | ASN | 61 | 60.055 | -23.316 | 81.084 | 1.00 | 12.85 | A |
| ATOM | 566 | N | ILE | 62 | 59.778 | -21.152 | 81.603 | 1.00 | 10.53 | A |
| ATOM | 568 | CA | ILE | 62 | 60.106 | -20.699 | 80.269 | 1.00 | 10.17 | A |
| ATOM | 569 | CB | ILE | 62 | 59.566 | -19.261 | 80.028 | 1.00 | 8.22 | A |
| ATOM | 570 | CG2 | ILE | 62 | 60.225 | -18.643 | 78.799 | 1.00 | 10.30 | A |
| ATOM | 571 | CG1 | ILE | 62 | 58.045 | -19.333 | 79.840 | 1.00 | 5.61 | A |
| ATOM | 572 | CD1 | ILE | 62 | 57.380 | -18.053 | 79.857 | 1.00 | 3.67 | A |
| ATOM | 573 | C | ILE | 62 | 61.604 | -20.827 | 79.964 | 1.00 | 10.21 | A |
| ATOM | 574 | O | ILE | 62 | 61.985 | -21.109 | 78.829 | 1.00 | 10.35 | A |
| ATOM | 575 | N | ALA | 63 | 62.454 | -20.648 | 80.968 | 1.00 | 9.39 | A |
| ATOM | 577 | CA | ALA | 63 | 63.882 | -20.788 | 80.734 | 1.00 | 8.74 | A |
| ATOM | 578 | CB | ALA | 63 | 64.642 | -20.236 | 81.903 | 1.00 | 7.21 | A |
| ATOM | 579 | C | ALA | 63 | 64.288 | -22.245 | 80.412 | 1.00 | 8.97 | A |
| ATOM | 580 | O | ALA | 63 | 65.302 | -22.506 | 79.826 | 1.00 | 9.18 | A |
| ATOM | 581 | N | ALA | 64 | 63.464 | -23.197 | 80.908 | 1.00 | 9.15 | A |
| ATOM | 583 | CA | ALA | 64 | 63.810 | -24.611 | 80.786 | 1.00 | 8.36 | A |
| ATOM | 584 | CB | ALA | 64 | 62.850 | -25.440 | 81.594 | 1.00 | 9.78 | A |
| ATOM | 585 | C | ALA | 64 | 63.895 | -25.164 | 79.385 | 1.00 | 9.54 | A |
| ATOM | 586 | O | ALA | 64 | 64.867 | -25.861 | 79.033 | 1.00 | 8.28 | A |
| ATOM | 587 | N | SER | 65 | 62.863 | -24.877 | 78.596 | 1.00 | 8.68 | A |
| ATOM | 589 | CA | SER | 65 | 62.806 | -25.376 | 77.255 | 1.00 | 10.56 | A |
| ATOM | 590 | CB | SER | 65 | 62.097 | -26.713 | 77.276 | 1.00 | 12.59 | A |
| ATOM | 591 | OG | SER | 65 | 60.792 | -26.519 | 77.817 | 1.00 | 18.23 | A |
| ATOM | 593 | C | SER | 65 | 62.060 | -24.471 | 76.291 | 1.00 | 9.81 | A |
| ATOM | 594 | O | SER | 65 | 61.273 | -23.641 | 76.704 | 1.00 | 10.42 | A |

- 65 -

| | | | | | | | | | | |
|---|---|---|---|---|---|---|---|---|---|---|
| ATOM | 595 | N | THR | 66 | 62.291 | -24.687 | 74.998 | 1.00 | 9.36 | A |
| ATOM | 597 | CA | THR | 66 | 61.612 | -23.951 | 73.963 | 1.00 | 9.43 | A |
| ATOM | 598 | CB | THR | 66 | 62.345 | -24.064 | 72.653 | 1.00 | 11.27 | A |
| ATOM | 599 | OG1 | THR | 66 | 62.385 | -25.431 | 72.264 | 1.00 | 14.11 | A |
| ATOM | 601 | CG2 | THR | 66 | 63.770 | -23.570 | 72.785 | 1.00 | 10.70 | A |
| ATOM | 602 | C | THR | 66 | 60.193 | -24.556 | 73.873 | 1.00 | 8.99 | A |
| ATOM | 603 | O | THR | 66 | 59.239 | -23.840 | 73.558 | 1.00 | 9.95 | A |
| ATOM | 604 | N | SER | 67 | 60.030 | -25.855 | 74.120 | 1.00 | 6.94 | A |
| ATOM | 606 | CA | SER | 67 | 58.672 | -26.377 | 74.132 | 1.00 | 8.25 | A |
| ATOM | 607 | CB | SER | 67 | 58.628 | -27.890 | 74.209 | 1.00 | 8.13 | A |
| ATOM | 608 | OG | SER | 67 | 59.441 | -28.349 | 75.254 | 1.00 | 12.10 | A |
| ATOM | 610 | C | SER | 67 | 57.847 | -25.725 | 75.266 | 1.00 | 8.26 | A |
| ATOM | 611 | O | SER | 67 | 56.655 | -25.482 | 75.084 | 1.00 | 8.13 | A |
| ATOM | 612 | N | ASN | 68 | 58.485 | -25.382 | 76.399 | 1.00 | 8.05 | A |
| ATOM | 614 | CA | ASN | 68 | 57.794 | -24.693 | 77.486 | 1.00 | 6.50 | A |
| ATOM | 615 | CB | ASN | 68 | 58.711 | -24.547 | 78.727 | 1.00 | 7.81 | A |
| ATOM | 616 | CG | ASN | 68 | 58.689 | -25.782 | 79.632 | 1.00 | 7.40 | A |
| ATOM | 617 | OD1 | ASN | 68 | 57.833 | -26.633 | 79.503 | 1.00 | 5.06 | A |
| ATOM | 618 | ND2 | ASN | 68 | 59.650 | -25.886 | 80.518 | 1.00 | 7.82 | A |
| ATOM | 621 | C | ASN | 68 | 57.383 | -23.292 | 76.969 | 1.00 | 5.96 | A |
| ATOM | 622 | O | ASN | 68 | 56.251 | -22.844 | 77.176 | 1.00 | 4.47 | A |
| ATOM | 623 | N | ALA | 69 | 58.326 | -22.575 | 76.358 | 1.00 | 6.45 | A |
| ATOM | 625 | CA | ALA | 69 | 58.047 | -21.231 | 75.773 | 1.00 | 6.87 | A |
| ATOM | 626 | CB | ALA | 69 | 59.311 | -20.632 | 75.225 | 1.00 | 6.36 | A |
| ATOM | 627 | C | ALA | 69 | 56.985 | -21.265 | 74.664 | 1.00 | 7.72 | A |
| ATOM | 628 | O | ALA | 69 | 56.147 | -20.375 | 74.561 | 1.00 | 7.80 | A |
| ATOM | 629 | N | ALA | 70 | 56.990 | -22.312 | 73.855 | 1.00 | 8.41 | A |
| ATOM | 631 | CA | ALA | 70 | 56.011 | -22.415 | 72.763 | 1.00 | 11.33 | A |
| ATOM | 632 | CB | ALA | 70 | 56.386 | -23.577 | 71.760 | 1.00 | 9.54 | A |
| ATOM | 633 | C | ALA | 70 | 54.591 | -22.590 | 73.297 | 1.00 | 10.89 | A |
| ATOM | 634 | O | ALA | 70 | 53.645 | -22.037 | 72.739 | 1.00 | 11.29 | A |
| ATOM | 635 | N | SER | 71 | 54.451 | -23.429 | 74.313 | 1.00 | 10.93 | A |
| ATOM | 637 | CA | SER | 71 | 53.177 | -23.686 | 74.967 | 1.00 | 11.42 | A |
| ATOM | 638 | CB | SER | 71 | 53.419 | -24.771 | 76.020 | 1.00 | 13.76 | A |
| ATOM | 639 | OG | SER | 71 | 52.233 | -25.227 | 76.623 | 1.00 | 15.94 | A |
| ATOM | 641 | C | SER | 71 | 52.659 | -22.368 | 75.591 | 1.00 | 11.15 | A |
| ATOM | 642 | O | SER | 71 | 51.507 | -22.027 | 75.450 | 1.00 | 13.46 | A |
| ATOM | 643 | N | TRP | 72 | 53.518 | -21.588 | 76.233 | 1.00 | 10.29 | A |
| ATOM | 645 | CA | TRP | 72 | 53.087 | -20.321 | 76.784 | 1.00 | 8.94 | A |
| ATOM | 646 | CB | TRP | 72 | 54.235 | -19.591 | 77.518 | 1.00 | 8.41 | A |
| ATOM | 647 | CG | TRP | 72 | 53.795 | -18.381 | 78.373 | 1.00 | 7.78 | A |
| ATOM | 648 | CD2 | TRP | 72 | 53.757 | -16.990 | 77.978 | 1.00 | 7.63 | A |
| ATOM | 649 | CE2 | TRP | 72 | 53.280 | -16.252 | 79.090 | 1.00 | 8.08 | A |
| ATOM | 650 | CE3 | TRP | 72 | 54.059 | -16.298 | 76.799 | 1.00 | 6.17 | A |
| ATOM | 651 | CD1 | TRP | 72 | 53.355 | -18.409 | 79.685 | 1.00 | 6.83 | A |
| ATOM | 652 | NE1 | TRP | 72 | 53.044 | -17.144 | 80.110 | 1.00 | 7.37 | A |
| ATOM | 654 | CZ2 | TRP | 72 | 53.100 | -14.838 | 79.040 | 1.00 | 6.83 | A |
| ATOM | 655 | CZ3 | TRP | 72 | 53.866 | -14.908 | 76.755 | 1.00 | 5.80 | A |
| ATOM | 656 | CH2 | TRP | 72 | 53.392 | -14.201 | 77.870 | 1.00 | 4.61 | A |
| ATOM | 657 | C | TRP | 72 | 52.599 | -19.447 | 75.641 | 1.00 | 9.78 | A |
| ATOM | 658 | O | TRP | 72 | 51.583 | -18.788 | 75.783 | 1.00 | 12.42 | A |
| ATOM | 659 | N | VAL | 73 | 53.375 | -19.335 | 74.565 | 1.00 | 8.67 | A |
| ATOM | 661 | CA | VAL | 73 | 53.000 | -18.504 | 73.408 | 1.00 | 8.08 | A |
| ATOM | 662 | CB | VAL | 73 | 54.167 | -18.463 | 72.333 | 1.00 | 7.73 | A |
| ATOM | 663 | CG1 | VAL | 73 | 55.753 | -17.723 | 71.047 | 1.00 | 5.34 | A |
| ATOM | 664 | CG2 | VAL | 73 | 55.403 | -17.751 | 72.944 | 1.00 | 5.25 | A |
| ATOM | 665 | C | VAL | 73 | 51.660 | -18.968 | 72.806 | 1.00 | 8.15 | A |
| ATOM | 666 | O | VAL | 73 | 50.726 | -18.184 | 72.651 | 1.00 | 8.73 | A |
| ATOM | 667 | N | GLN | 74 | 51.529 | -20.269 | 72.092 | 1.00 | 10.41 | A |
| ATOM | 669 | CA | GLN | 74 | 50.332 | -20.838 | 72.347 | 1.00 | 9.20 | A |
| ATOM | 670 | CB | GLN | 74 | 50.508 | -22.347 | 71.937 | 1.00 | 8.89 | A |
| ATOM | 671 | CG | GLN | 74 | 49.283 | -23.030 | 71.433 | 1.00 | 8.90 | A |
| ATOM | 672 | CD | GLN | 74 | 49.587 | -24.408 | 70.904 | 1.00 | 9.27 | A |
| ATOM | 673 | OE1 | GLN | 74 | 50.673 | -24.651 | 70.403 | 1.00 | 9.77 | A |
| ATOM | 674 | NE2 | GLN | 74 | 48.607 | -25.296 | 70.957 | 1.00 | 12.06 | A |
| ATOM | 677 | C | GLN | 74 | 49.094 | -20.527 | 72.913 | 1.00 | 12.54 | A |
| ATOM | 678 | O | GLN | 74 | 48.003 | -20.318 | 72.377 | 1.00 | 12.64 | A |
| ATOM | 679 | N | ASN | 75 | 49.267 | -20.473 | 74.219 | 1.00 | 13.76 | A |
| ATOM | 681 | CA | ASN | 75 | 48.134 | -20.239 | 75.083 | 1.00 | 15.19 | A |
| ATOM | 682 | CB | ASN | 75 | 48.373 | -20.917 | 76.433 | 1.00 | 16.69 | A |
| ATOM | 683 | CG | ASN | 75 | 48.227 | -22.364 | 76.365 | 1.00 | 20.09 | A |
| ATOM | 684 | OD1 | ASN | 75 | 47.429 | -22.851 | 75.597 | 1.00 | 19.33 | A |
| ATOM | 685 | ND2 | ASN | 75 | 48.962 | -23.090 | 77.196 | 1.00 | 12.95 | A |
| ATOM | 688 | C | ASN | 75 | 47.844 | -18.810 | 75.396 | 1.00 | 13.83 | A |
| ATOM | 689 | O | ASN | 75 | 46.717 | -18.443 | 75.527 | 1.00 | 12.60 | A |
| ATOM | 690 | N | ASN | 76 | 48.891 | -18.019 | 75.554 | 1.00 | 11.61 | A |
| ATOM | 692 | CA | ASN | 76 | 48.778 | -16.665 | 76.013 | 1.00 | 9.32 | A |
| ATOM | 693 | CB | ASN | 76 | 49.692 | -16.523 | 77.252 | 1.00 | 10.74 | A |
| ATOM | 694 | CG | ASN | 76 | 49.296 | -17.510 | 78.361 | 1.00 | 8.85 | A |
| ATOM | 695 | OD1 | ASN | 76 | 48.206 | -17.399 | 78.959 | | | |

| | | | | | | | | | |
|---|---|---|---|---|---|---|---|---|---|
| ATOM | 696 | ND2 | ASN | 76 | 50.129 | -18.529 | 78.585 | 1.00 10.57 | A |
| ATOM | 699 | C | ASN | 76 | 48.990 | -15.544 | 75.037 | 1.00 11.70 | A |
| ATOM | 700 | O | ASN | 76 | 48.682 | -15.413 | 75.356 | 1.00 12.85 | A |
| ATOM | 701 | N | VAL | 77 | 49.539 | -15.839 | 73.869 | 1.00 11.84 | A |
| ATOM | 703 | CA | VAL | 77 | 49.790 | -14.802 | 72.864 | 1.00 12.15 | A |
| ATOM | 704 | CB | VAL | 77 | 51.281 | -14.723 | 72.552 | 1.00 11.52 | A |
| ATOM | 705 | CG1 | VAL | 77 | 51.575 | -13.701 | 71.443 | 1.00 11.55 | A |
| ATOM | 706 | CG2 | VAL | 77 | 52.031 | -14.389 | 73.818 | 1.00 9.61 | A |
| ATOM | 707 | C | VAL | 77 | 49.005 | -15.105 | 71.595 | 1.00 13.64 | A |
| ATOM | 708 | O | VAL | 77 | 48.195 | -14.283 | 71.131 | 1.00 14.89 | A |
| ATOM | 709 | N | ARG | 78 | 49.196 | -16.322 | 71.097 | 1.00 14.51 | A |
| ATOM | 711 | CA | ARG | 78 | 48.551 | -16.849 | 69.900 | 1.00 15.06 | A |
| ATOM | 712 | CB | ARG | 78 | 48.738 | -18.374 | 69.843 | 1.00 16.75 | A |
| ATOM | 713 | CG | ARG | 78 | 49.954 | -18.861 | 69.103 | 1.00 19.00 | A |
| ATOM | 714 | CD | ARG | 78 | 49.560 | -19.275 | 67.707 | 0.00 21.09 | A |
| ATOM | 715 | NE | ARG | 78 | 49.231 | -18.125 | 66.875 | 0.00 23.28 | A |
| ATOM | 717 | CZ | ARG | 78 | 49.903 | -17.814 | 65.758 | 1.00 25.26 | A |
| ATOM | 718 | NH1 | ARG | 78 | 50.940 | -18.577 | 65.344 | 1.00 23.67 | A |
| ATOM | 721 | NH2 | ARG | 78 | 49.559 | -16.724 | 65.064 | 1.00 26.18 | A |
| ATOM | 724 | C | ARG | 78 | 47.056 | -16.511 | 69.710 | 1.00 14.11 | A |
| ATOM | 725 | O | ARG | 78 | 46.640 | -16.178 | 68.594 | 1.00 13.32 | A |
| ATOM | 726 | N | PRO | 79 | 46.244 | -16.583 | 70.783 | 1.00 12.20 | A |
| ATOM | 727 | CD | PRO | 79 | 46.467 | -17.118 | 72.136 | 1.00 12.56 | A |
| ATOM | 728 | CA | PRO | 79 | 44.837 | -16.272 | 70.591 | 1.00 11.66 | A |
| ATOM | 729 | CB | PRO | 79 | 44.159 | -16.928 | 71.810 | 1.00 11.44 | A |
| ATOM | 730 | CG | PRO | 79 | 45.193 | -17.862 | 72.398 | 1.00 10.99 | A |
| ATOM | 731 | C | PRO | 79 | 44.489 | -14.806 | 70.560 | 1.00 12.00 | A |
| ATOM | 732 | O | PRO | 79 | 43.355 | -14.472 | 70.290 | 1.00 12.62 | A |
| ATOM | 733 | N | TYR | 80 | 45.409 | -13.916 | 70.885 | 1.00 12.21 | A |
| ATOM | 735 | CA | TYR | 80 | 45.032 | -12.513 | 70.930 | 1.00 11.94 | A |
| ATOM | 736 | CB | TYR | 80 | 45.349 | -11.960 | 72.316 | 1.00 11.11 | A |
| ATOM | 737 | CG | TYR | 80 | 44.754 | -12.814 | 73.398 | 1.00 10.91 | A |
| ATOM | 738 | CD1 | TYR | 80 | 45.549 | -13.712 | 74.146 | 1.00 12.13 | A |
| ATOM | 739 | CE1 | TYR | 80 | 44.976 | -14.556 | 75.089 | 1.00 10.35 | A |
| ATOM | 740 | CD2 | TYR | 80 | 43.382 | -12.791 | 73.634 | 1.00 10.66 | A |
| ATOM | 741 | CE2 | TYR | 80 | 42.811 | -13.624 | 74.562 | 1.00 10.20 | A |
| ATOM | 742 | CZ | TYR | 80 | 43.600 | -14.498 | 75.282 | 1.00 10.49 | A |
| ATOM | 743 | OH | TYR | 80 | 42.973 | -15.312 | 76.191 | 1.00 12.08 | A |
| ATOM | 745 | C | TYR | 80 | 45.630 | -11.620 | 69.880 | 1.00 12.12 | A |
| ATOM | 746 | O | TYR | 80 | 45.072 | -10.585 | 69.527 | 1.00 12.72 | A |
| ATOM | 747 | N | TYR | 81 | 46.745 | -12.058 | 69.342 | 1.00 11.99 | A |
| ATOM | 749 | CA | TYR | 81 | 47.477 | -11.281 | 68.373 | 1.00 11.92 | A |
| ATOM | 750 | CB | TYR | 81 | 48.943 | -11.527 | 68.653 | 1.00 11.65 | A |
| ATOM | 751 | CG | TYR | 81 | 49.883 | -10.739 | 67.819 | 1.00 12.62 | A |
| ATOM | 752 | CD1 | TYR | 81 | 50.358 | -9.513 | 68.261 | 1.00 12.11 | A |
| ATOM | 753 | CE1 | TYR | 81 | 51.310 | -8.840 | 67.545 | 1.00 12.41 | A |
| ATOM | 754 | CD2 | TYR | 81 | 50.385 | -11.262 | 66.627 | 1.00 12.23 | A |
| ATOM | 755 | CE2 | TYR | 81 | 51.330 | -10.602 | 65.922 | 1.00 11.86 | A |
| ATOM | 756 | CZ | TYR | 81 | 51.798 | -9.399 | 66.386 | 1.00 11.54 | A |
| ATOM | 757 | OH | TYR | 81 | 52.826 | -8.787 | 65.733 | 1.00 11.92 | A |
| ATOM | 759 | C | TYR | 81 | 47.102 | -11.806 | 66.993 | 1.00 12.22 | A |
| ATOM | 760 | O | TYR | 81 | 46.996 | -13.026 | 66.828 | 1.00 11.22 | A |
| ATOM | 761 | N | PRO | 82 | 47.001 | -10.907 | 65.972 | 1.00 11.73 | A |
| ATOM | 762 | CD | PRO | 82 | 47.096 | -11.259 | 64.546 | 1.00 10.43 | A |
| ATOM | 763 | CA | PRO | 82 | 47.234 | -9.470 | 66.123 | 1.00 10.89 | A |
| ATOM | 764 | CB | PRO | 82 | 47.823 | -9.093 | 64.769 | 1.00 10.57 | A |
| ATOM | 765 | CG | PRO | 82 | 47.076 | -9.907 | 63.878 | 1.00 11.94 | A |
| ATOM | 766 | C | PRO | 82 | 46.115 | -8.512 | 66.538 | 1.00 9.64 | A |
| ATOM | 767 | O | PRO | 82 | 46.348 | -7.326 | 66.555 | 1.00 9.30 | A |
| ATOM | 768 | N | ALA | 83 | 44.943 | -9.006 | 66.916 | 1.00 9.55 | A |
| ATOM | 770 | CA | ALA | 83 | 43.848 | -8.145 | 67.325 | 1.00 9.28 | A |
| ATOM | 771 | CB | ALA | 83 | 42.743 | -8.953 | 67.765 | 1.00 9.38 | A |
| ATOM | 772 | C | ALA | 83 | 44.278 | -7.218 | 68.447 | 1.00 10.76 | A |
| ATOM | 773 | O | ALA | 83 | 43.810 | -6.095 | 68.550 | 1.00 10.80 | A |
| ATOM | 774 | N | VAL | 84 | 45.086 | -7.752 | 69.356 | 1.00 12.03 | A |
| ATOM | 776 | CA | VAL | 84 | 45.641 | -6.993 | 70.463 | 1.00 12.66 | A |
| ATOM | 777 | CB | VAL | 84 | 45.736 | -7.825 | 71.774 | 1.00 12.99 | A |
| ATOM | 778 | CG1 | VAL | 84 | 46.355 | -6.977 | 72.900 | 1.00 11.67 | A |
| ATOM | 779 | CG2 | VAL | 84 | 44.367 | -8.326 | 72.175 | 1.00 13.88 | A |
| ATOM | 780 | C | VAL | 84 | 47.048 | -6.644 | 69.997 | 1.00 11.84 | A |
| ATOM | 781 | O | VAL | 84 | 47.795 | -7.513 | 69.546 | 1.00 12.45 | A |
| ATOM | 782 | N | ASN | 85 | 47.420 | -5.384 | 70.114 | 1.00 11.73 | A |
| ATOM | 784 | CA | ASN | 85 | 48.691 | -4.918 | 69.632 | 1.00 11.98 | A |
| ATOM | 785 | CB | ASN | 85 | 48.574 | -3.448 | 69.219 | 1.00 10.87 | A |
| ATOM | 786 | CG | ASN | 85 | 49.808 | -2.934 | 68.493 | 1.00 13.17 | A |
| ATOM | 787 | OD1 | ASN | 85 | 50.044 | -1.741 | 68.456 | 1.00 15.64 | A |
| ATOM | 788 | ND2 | ASN | 85 | 50.567 | -3.817 | 67.865 | 1.00 14.70 | A |
| ATOM | 791 | C | ASN | 85 | 49.795 | -5.141 | 70.650 | 1.00 12.79 | A |
| ATOM | 792 | O | ASN | 85 | 50.274 | -4.192 | 71.297 | 1.00 12.74 | A |
| ATOM | 793 | N | ILE | 86 | 50.214 | -6.393 | 70.813 | 1.00 12.26 | A |

- 68 -

| | | | | | | | | | |
|---|---|---|---|---|---|---|---|---|---|
| ATOM | 795 | CA | ILE | 86 | 51.290 | -6.629 | 71.778 | 1.00 12.74 | A |
| ATOM | 796 | CB | ILE | 86 | 51.472 | -8.104 | 72.156 | 1.00 13.17 | A |
| ATOM | 797 | CG2 | ILE | 86 | 52.597 | -8.241 | 73.203 | 1.00 11.73 | A |
| ATOM | 798 | CG1 | ILE | 86 | 50.146 | -8.721 | 72.635 | 1.00 12.88 | A |
| ATOM | 799 | CD1 | ILE | 86 | 50.238 | -10.228 | 72.757 | 1.00 12.69 | A |
| ATOM | 800 | C | ILE | 86 | 52.575 | -6.156 | 71.130 | 1.00 12.24 | A |
| ATOM | 801 | O | ILE | 86 | 52.992 | -6.660 | 70.122 | 1.00 13.88 | A |
| ATOM | 802 | N | LYS | 87 | 53.261 | -5.265 | 71.781 | 1.00 12.21 | A |
| ATOM | 803 | CA | LYS | 87 | 54.474 | -4.738 | 71.250 | 1.00 12.55 | A |
| ATOM | 804 | CB | LYS | 87 | 54.470 | -3.244 | 71.539 | 1.00 15.11 | A |
| ATOM | 805 | CG | LYS | 87 | 53.207 | -2.547 | 71.019 | 1.00 15.46 | A |
| ATOM | 806 | CD | LYS | 87 | 53.321 | -1.071 | 71.244 | 1.00 18.33 | A |
| ATOM | 807 | CE | LYS | 87 | 54.526 | -0.496 | 70.544 | 1.00 20.24 | A |
| ATOM | 808 | NZ | LYS | 87 | 54.688 | 0.981 | 70.811 | 1.00 24.38 | A |
| ATOM | 809 | C | LYS | 87 | 55.719 | -5.406 | 71.817 | 1.00 12.83 | A |
| ATOM | 813 | O | LYS | 87 | 56.614 | -5.727 | 71.071 | 1.00 13.21 | A |
| ATOM | 814 | N | TYR | 88 | 55.751 | -5.584 | 73.141 | 1.00 12.66 | A |
| ATOM | 815 | CA | TYR | 88 | 56.871 | -6.203 | 73.835 | 1.00 12.27 | A |
| ATOM | 817 | CB | TYR | 88 | 57.625 | -5.155 | 74.643 | 1.00 12.51 | A |
| ATOM | 818 | CG | TYR | 88 | 57.867 | -3.865 | 73.907 | 1.00 13.39 | A |
| ATOM | 819 | CD1 | TYR | 88 | 57.317 | -2.675 | 74.350 | 1.00 12.20 | A |
| ATOM | 820 | CE1 | TYR | 88 | 57.529 | -1.500 | 73.671 | 1.00 12.81 | A |
| ATOM | 821 | CD2 | TYR | 88 | 58.643 | -3.844 | 72.753 | 1.00 14.16 | A |
| ATOM | 822 | CE2 | TYR | 88 | 58.864 | -2.677 | 72.067 | 1.00 14.50 | A |
| ATOM | 823 | CZ | TYR | 88 | 58.303 | -1.511 | 72.533 | 1.00 14.09 | A |
| ATOM | 824 | OH | TYR | 88 | 58.551 | -0.366 | 71.841 | 1.00 14.10 | A |
| ATOM | 825 | C | TYR | 88 | 56.389 | -7.249 | 74.818 | 1.00 12.42 | A |
| ATOM | 827 | O | TYR | 88 | 55.227 | -7.248 | 75.217 | 1.00 12.52 | A |
| ATOM | 828 | N | ILE | 89 | 57.279 | -8.173 | 75.155 | 1.00 11.81 | A |
| ATOM | 829 | CA | ILE | 89 | 57.015 | -9.204 | 76.150 | 1.00 11.14 | A |
| ATOM | 831 | CB | ILE | 89 | 56.983 | -10.650 | 75.536 | 1.00 11.00 | A |
| ATOM | 832 | CG2 | ILE | 89 | 57.088 | -11.709 | 76.643 | 1.00 11.27 | A |
| ATOM | 833 | CG1 | ILE | 89 | 55.711 | -10.836 | 74.712 | 1.00 9.15 | A |
| ATOM | 834 | CD1 | ILE | 89 | 55.534 | -12.175 | 74.081 | 1.00 8.08 | A |
| ATOM | 835 | C | ILE | 89 | 58.190 | -9.043 | 77.137 | 1.00 11.33 | A |
| ATOM | 836 | O | ILE | 89 | 59.348 | -8.938 | 76.728 | 1.00 10.91 | A |
| ATOM | 837 | N | ALA | 90 | 57.866 | -8.841 | 78.409 | 1.00 10.97 | A |
| ATOM | 840 | CA | ALA | 90 | 58.869 | -8.686 | 79.451 | 1.00 11.14 | A |
| ATOM | 841 | CB | ALA | 90 | 58.410 | -7.644 | 80.478 | 1.00 10.86 | A |
| ATOM | 842 | C | ALA | 90 | 59.059 | -10.041 | 80.139 | 1.00 11.61 | A |
| ATOM | 843 | O | ALA | 90 | 58.136 | -10.547 | 80.831 | 1.00 9.12 | A |
| ATOM | 844 | N | ALA | 91 | 60.220 | -10.654 | 79.895 | 1.00 11.85 | A |
| ATOM | 846 | CA | ALA | 91 | 60.551 | -11.996 | 80.502 | 1.00 12.99 | A |
| ATOM | 847 | CB | ALA | 91 | 61.590 | -12.759 | 79.609 | 1.00 12.89 | A |
| ATOM | 848 | C | ALA | 91 | 61.135 | -11.647 | 81.882 | 1.00 12.88 | A |
| ATOM | 849 | O | ALA | 91 | 62.333 | -11.698 | 82.085 | 1.00 12.46 | A |
| ATOM | 850 | N | GLY | 92 | 60.276 | -11.262 | 82.812 | 1.00 14.39 | A |
| ATOM | 852 | CA | GLY | 92 | 60.735 | -10.944 | 84.164 | 1.00 14.85 | A |
| ATOM | 853 | C | GLY | 92 | 60.645 | -9.460 | 84.499 | 1.00 14.54 | A |
| ATOM | 854 | O | GLY | 92 | 60.751 | -8.600 | 83.598 | 1.00 13.85 | A |
| ATOM | 855 | N | ASN | 93 | 60.396 | -9.164 | 85.776 | 1.00 12.88 | A |
| ATOM | 857 | CA | ASN | 93 | 60.289 | -7.791 | 86.245 | 1.00 11.91 | A |
| ATOM | 858 | CB | ASN | 93 | 58.828 | -7.376 | 86.463 | 1.00 10.51 | A |
| ATOM | 859 | CG | ASN | 93 | 58.667 | -5.887 | 86.872 | 1.00 9.77 | A |
| ATOM | 860 | OD1 | ASN | 93 | 59.410 | -5.009 | 86.425 | 1.00 10.75 | A |
| ATOM | 861 | ND2 | ASN | 93 | 57.695 | -5.616 | 87.738 | 1.00 8.12 | A |
| ATOM | 864 | C | ASN | 93 | 61.059 | -7.631 | 87.519 | 1.00 12.88 | A |
| ATOM | 865 | O | ASN | 93 | 60.719 | -8.229 | 88.545 | 1.00 12.80 | A |
| ATOM | 866 | N | GLU | 94 | 62.154 | -6.880 | 87.416 | 1.00 14.69 | A |
| ATOM | 868 | CA | GLU | 94 | 63.029 | -6.573 | 88.544 | 1.00 15.45 | A |
| ATOM | 869 | CB | GLU | 94 | 62.322 | -5.610 | 89.505 | 1.00 14.88 | A |
| ATOM | 870 | CG | GLU | 94 | 61.904 | -4.298 | 88.851 | 1.00 16.74 | A |
| ATOM | 871 | CD | GLU | 94 | 61.474 | -3.213 | 89.858 | 1.00 17.31 | A |
| ATOM | 872 | OE1 | GLU | 94 | 61.282 | -3.509 | 91.071 | 1.00 17.85 | A |
| ATOM | 873 | OE2 | GLU | 94 | 61.358 | -2.042 | 89.436 | 1.00 16.84 | A |
| ATOM | 874 | C | GLU | 94 | 63.458 | -7.862 | 89.259 | 1.00 17.04 | A |
| ATOM | 875 | O | GLU | 94 | 63.404 | -7.959 | 90.490 | 1.00 17.38 | A |
| ATOM | 876 | N | VAL | 95 | 63.880 | -8.850 | 88.474 | 1.00 17.65 | A |
| ATOM | 878 | CA | VAL | 95 | 64.310 | -10.109 | 89.017 | 1.00 19.33 | A |
| ATOM | 879 | CB | VAL | 95 | 64.388 | -11.185 | 87.912 | 1.00 18.29 | A |
| ATOM | 880 | CG1 | VAL | 95 | 65.079 | -12.457 | 88.436 | 1.00 17.26 | A |
| ATOM | 881 | CG2 | VAL | 95 | 62.992 | -11.534 | 87.465 | 1.00 17.06 | A |
| ATOM | 882 | C | VAL | 95 | 65.622 | -10.002 | 89.829 | 1.00 21.47 | A |
| ATOM | 883 | O | VAL | 95 | 66.534 | -9.232 | 89.493 | 1.00 21.42 | A |
| ATOM | 884 | N | GLN | 96 | 65.690 | -10.782 | 90.910 | 1.00 23.73 | A |
| ATOM | 886 | CA | GLN | 96 | 66.838 | -10.795 | 91.801 | 1.00 24.87 | A |
| ATOM | 887 | CB | GLN | 96 | 66.488 | -9.970 | 93.032 | 1.00 27.38 | A |
| ATOM | 888 | CG | GLN | 96 | 67.376 | -8.767 | 93.197 | 1.00 30.41 | A |
| ATOM | 889 | CD | GLN | 96 | 66.587 | -7.543 | 93.501 | 1.00 32.38 | A |
| ATOM | 890 | OE1 | GLN | 96 | 66.341 | -7.236 | 94.668 | 1.00 33.89 | A |

- 69 -

| ATOM | 891 | NE2 | GLN | 96 | 66.147 | -6.838 | 92.451 | 1.00 | 32.90 | A |
| --- | --- | --- | --- | --- | --- | --- | --- | --- | --- | --- |
| ATOM | 894 | C | GLN | 96 | 67.268 | -12.178 | 92.262 | 1.00 | 24.32 | A |
| ATOM | 895 | O | GLN | 96 | 66.455 | -13.074 | 92.426 | 1.00 | 24.70 | A |
| ATOM | 896 | N | GLY | 97 | 68.561 | -12.341 | 92.490 | 1.00 | 24.59 | A |
| ATOM | 898 | CA | GLY | 97 | 69.067 | -13.600 | 92.996 | 1.00 | 23.27 | A |
| ATOM | 899 | C | GLY | 97 | 69.587 | -14.484 | 91.905 | 1.00 | 23.35 | A |
| ATOM | 900 | O | GLY | 97 | 70.089 | -14.015 | 90.897 | 1.00 | 23.55 | A |
| ATOM | 901 | N | GLY | 98 | 69.521 | -15.783 | 92.131 | 1.00 | 23.95 | A |
| ATOM | 903 | CA | GLY | 98 | 69.967 | -16.705 | 91.105 | 1.00 | 23.65 | A |
| ATOM | 904 | C | GLY | 98 | 68.917 | -16.732 | 90.006 | 1.00 | 22.95 | A |
| ATOM | 905 | O | GLY | 98 | 69.133 | -17.323 | 88.942 | 1.00 | 23.35 | A |
| ATOM | 906 | N | ALA | 99 | 67.763 | -16.109 | 90.280 | 1.00 | 20.63 | A |
| ATOM | 908 | CA | ALA | 99 | 66.706 | -16.063 | 89.301 | 1.00 | 19.14 | A |
| ATOM | 909 | CB | ALA | 99 | 65.487 | -15.431 | 89.880 | 1.00 | 19.02 | A |
| ATOM | 910 | C | ALA | 99 | 67.220 | -15.266 | 88.118 | 1.00 | 18.08 | A |
| ATOM | 911 | O | ALA | 99 | 66.860 | -15.540 | 86.989 | 1.00 | 18.56 | A |
| ATOM | 912 | N | THR | 100 | 68.059 | -14.268 | 88.368 | 1.00 | 16.77 | A |
| ATOM | 914 | CA | THR | 100 | 68.592 | -13.502 | 87.260 | 1.00 | 17.11 | A |
| ATOM | 915 | CB | THR | 100 | 69.682 | -12.469 | 87.663 | 1.00 | 15.41 | A |
| ATOM | 916 | OG1 | THR | 100 | 70.716 | -13.128 | 88.376 | 1.00 | 15.23 | A |
| ATOM | 918 | CG2 | THR | 100 | 69.116 | -11.370 | 88.499 | 1.00 | 15.09 | A |
| ATOM | 919 | C | THR | 100 | 69.205 | -14.470 | 86.248 | 1.00 | 17.44 | A |
| ATOM | 920 | O | THR | 100 | 69.188 | -14.201 | 85.065 | 1.00 | 17.93 | A |
| ATOM | 921 | N | GLN | 101 | 69.730 | -15.593 | 86.724 | 1.00 | 18.24 | A |
| ATOM | 923 | CA | GLN | 101 | 70.337 | -16.609 | 85.850 | 1.00 | 18.30 | A |
| ATOM | 924 | CB | GLN | 101 | 70.847 | -17.794 | 86.694 | 1.00 | 17.98 | A |
| ATOM | 925 | CG | GLN | 101 | 72.091 | -17.506 | 87.540 | 1.00 | 19.16 | A |
| ATOM | 926 | CD | GLN | 101 | 72.349 | -18.566 | 88.594 | 0.00 | 18.79 | A |
| ATOM | 927 | OE1 | GLN | 101 | 72.378 | -18.272 | 89.787 | 0.00 | 18.89 | A |
| ATOM | 928 | NE2 | GLN | 101 | 72.545 | -19.804 | 88.160 | 0.00 | 18.89 | A |
| ATOM | 931 | C | GLN | 101 | 69.367 | -17.160 | 84.805 | 1.00 | 17.74 | A |
| ATOM | 932 | O | GLN | 101 | 69.779 | -17.790 | 83.852 | 1.00 | 20.04 | A |
| ATOM | 933 | N | SER | 102 | 68.076 | -16.975 | 85.012 | 1.00 | 17.50 | A |
| ATOM | 935 | CA | SER | 102 | 67.065 | -17.502 | 84.110 | 1.00 | 16.74 | A |
| ATOM | 936 | CB | SER | 102 | 65.831 | -17.936 | 84.914 | 1.00 | 17.70 | A |
| ATOM | 937 | OG | SER | 102 | 66.129 | -18.957 | 85.842 | 1.00 | 18.93 | A |
| ATOM | 939 | C | SER | 102 | 66.585 | -16.557 | 83.023 | 1.00 | 15.99 | A |
| ATOM | 940 | O | SER | 102 | 65.952 | -16.996 | 82.072 | 1.00 | 17.44 | A |
| ATOM | 941 | N | ILE | 103 | 66.884 | -15.282 | 83.151 | 1.00 | 13.29 | A |
| ATOM | 943 | CA | ILE | 103 | 66.399 | -14.285 | 82.203 | 1.00 | 12.59 | A |
| ATOM | 944 | CB | ILE | 103 | 66.701 | -12.843 | 82.681 | 1.00 | 9.46 | A |
| ATOM | 945 | CG2 | ILE | 103 | 66.318 | -11.838 | 81.596 | 1.00 | 10.20 | A |
| ATOM | 946 | CG1 | ILE | 103 | 66.037 | -12.563 | 84.022 | 1.00 | 7.09 | A |
| ATOM | 947 | CD1 | ILE | 103 | 66.678 | -11.441 | 84.755 | 1.00 | 4.09 | A |
| ATOM | 948 | C | ILE | 103 | 66.900 | -14.420 | 80.778 | 1.00 | 12.94 | A |
| ATOM | 949 | O | ILE | 103 | 66.131 | -14.200 | 79.848 | 1.00 | 15.50 | A |
| ATOM | 950 | N | LEU | 104 | 68.173 | -14.719 | 80.574 | 1.00 | 13.04 | A |
| ATOM | 952 | CA | LEU | 104 | 68.670 | -14.856 | 79.202 | 1.00 | 14.07 | A |
| ATOM | 953 | CB | LEU | 104 | 70.196 | -14.763 | 79.161 | 1.00 | 17.22 | A |
| ATOM | 954 | CG | LEU | 104 | 70.715 | -14.557 | 77.736 | 1.00 | 18.10 | A |
| ATOM | 955 | CD1 | LEU | 104 | 70.430 | -13.120 | 77.363 | 1.00 | 18.66 | A |
| ATOM | 956 | CD2 | LEU | 104 | 72.201 | -14.835 | 77.693 | 1.00 | 19.43 | A |
| ATOM | 957 | C | LEU | 104 | 68.151 | -16.134 | 78.480 | 1.00 | 12.60 | A |
| ATOM | 958 | O | LEU | 104 | 67.741 | -16.070 | 77.337 | 1.00 | 13.21 | A |
| ATOM | 959 | N | PRO | 105 | 68.230 | -17.307 | 79.121 | 1.00 | 12.08 | A |
| ATOM | 960 | CD | PRO | 105 | 69.007 | -17.656 | 80.339 | 1.00 | 12.55 | A |
| ATOM | 961 | CA | PRO | 105 | 67.714 | -18.505 | 78.444 | 1.00 | 10.69 | A |
| ATOM | 962 | CB | PRO | 105 | 68.089 | -19.644 | 79.421 | 1.00 | 11.56 | A |
| ATOM | 963 | CG | PRO | 105 | 68.366 | -18.937 | 80.802 | 1.00 | 10.56 | A |
| ATOM | 964 | C | PRO | 105 | 66.178 | -18.405 | 78.170 | 1.00 | 9.75 | A |
| ATOM | 965 | O | PRO | 105 | 65.671 | -18.943 | 77.176 | 1.00 | 10.41 | A |
| ATOM | 966 | N | ALA | 106 | 65.443 | -17.674 | 79.008 | 1.00 | 8.20 | A |
| ATOM | 968 | CA | ALA | 106 | 63.994 | -17.494 | 78.809 | 1.00 | 5.71 | A |
| ATOM | 969 | CB | ALA | 106 | 63.337 | -16.933 | 80.058 | 1.00 | 4.63 | A |
| ATOM | 970 | C | ALA | 106 | 63.769 | -16.554 | 77.623 | 1.00 | 6.04 | A |
| ATOM | 971 | O | ALA | 106 | 62.874 | -16.786 | 76.787 | 1.00 | 3.26 | A |
| ATOM | 972 | N | MET | 107 | 64.602 | -15.511 | 77.554 | 1.00 | 6.14 | A |
| ATOM | 974 | CA | MET | 107 | 64.575 | -14.540 | 76.468 | 1.00 | 7.36 | A |
| ATOM | 975 | CB | MET | 107 | 65.596 | -13.419 | 76.706 | 1.00 | 8.85 | A |
| ATOM | 976 | CG | MET | 107 | 65.088 | -12.282 | 77.565 | 1.00 | 7.34 | A |
| ATOM | 977 | SD | MET | 107 | 66.370 | -11.064 | 77.880 | 1.00 | 12.15 | A |
| ATOM | 978 | CE | MET | 107 | 66.468 | -10.194 | 76.328 | 1.00 | 8.30 | A |
| ATOM | 979 | C | MET | 107 | 64.845 | -15.189 | 75.115 | 1.00 | 8.47 | A |
| ATOM | 980 | O | MET | 107 | 64.245 | -14.808 | 74.105 | 1.00 | 10.13 | A |
| ATOM | 981 | N | ARG | 108 | 65.797 | -16.109 | 75.091 | 1.00 | 8.52 | A |
| ATOM | 983 | CA | ARG | 108 | 66.159 | -16.833 | 73.889 | 1.00 | 9.64 | A |
| ATOM | 984 | CB | ARG | 108 | 67.369 | -17.741 | 74.169 | 1.00 | 11.91 | A |
| ATOM | 985 | CG | ARG | 108 | 68.615 | -17.110 | 74.785 | 1.00 | 15.45 | A |
| ATOM | 986 | CD | ARG | 108 | 69.830 | -18.012 | 74.429 | 1.00 | 21.24 | A |
| ATOM | 987 | NE | ARG | 108 | 70.953 | -17.974 | 75.384 | 1.00 | 24.84 | A |

| | | | | | | | | |
|---|---|---|---|---|---|---|---|---|
| ATOM | 989 | CZ | ARG | 108 | 72.112 | -17.352 | 75.158 | 1.00 25.44 | A |
| ATOM | 990 | NH1 | ARG | 108 | 72.319 | -16.707 | 74.017 | 0.00 25.39 | A |
| ATOM | 993 | NH2 | ARG | 108 | 73.073 | -17.400 | 76.067 | 0.00 25.39 | A |
| ATOM | 996 | C | ARG | 108 | 65.002 | -17.716 | 73.481 | 1.00 10.28 | A |
| ATOM | 997 | O | ARG | 108 | 64.551 | -17.780 | 72.325 | 1.00 10.21 | A |
| ATOM | 998 | N | ASN | 109 | 64.597 | -18.568 | 74.440 | 1.00 11.06 | A |
| ATOM | 1000 | CA | ASN | 109 | 63.523 | -19.505 | 74.273 | 1.00 10.67 | A |
| ATOM | 1001 | CB | ASN | 109 | 63.233 | -20.197 | 75.610 | 1.00 10.72 | A |
| ATOM | 1002 | CG | ASN | 109 | 64.196 | -21.313 | 75.896 | 1.00 11.67 | A |
| ATOM | 1003 | OD1 | ASN | 109 | 65.080 | -21.577 | 75.103 | 1.00 11.83 | A |
| ATOM | 1004 | ND2 | ASN | 109 | 64.014 | -22.000 | 77.006 | 1.00 12.62 | A |
| ATOM | 1007 | C | ASN | 109 | 62.276 | -18.865 | 73.713 | 1.00 10.37 | A |
| ATOM | 1008 | O | ASN | 109 | 61.636 | -19.439 | 72.850 | 1.00 12.51 | A |
| ATOM | 1009 | N | LEU | 110 | 61.921 | -17.684 | 74.190 | 1.00 11.07 | A |
| ATOM | 1011 | CA | LEU | 110 | 60.725 | -17.001 | 73.730 | 1.00 9.80 | A |
| ATOM | 1012 | CB | LEU | 110 | 60.388 | -15.847 | 74.676 | 1.00 10.99 | A |
| ATOM | 1013 | CG | LEU | 110 | 59.189 | -15.732 | 75.658 | 1.00 9.59 | A |
| ATOM | 1014 | CD1 | LEU | 110 | 58.400 | -17.016 | 75.925 | 1.00 9.40 | A |
| ATOM | 1015 | CD2 | LEU | 110 | 59.704 | -15.125 | 76.942 | 1.00 8.74 | A |
| ATOM | 1016 | C | LEU | 110 | 60.982 | -16.519 | 72.311 | 1.00 10.46 | A |
| ATOM | 1017 | O | LEU | 110 | 60.121 | -16.696 | 71.436 | 1.00 10.83 | A |
| ATOM | 1018 | N | ASN | 111 | 62.191 | -16.016 | 72.047 | 1.00 9.61 | A |
| ATOM | 1020 | CA | ASN | 111 | 62.567 | -15.573 | 70.676 | 1.00 9.50 | A |
| ATOM | 1021 | CB | ASN | 111 | 64.008 | -15.048 | 70.589 | 1.00 10.84 | A |
| ATOM | 1022 | CG | ASN | 111 | 64.148 | -13.599 | 70.060 | 1.00 9.53 | A |
| ATOM | 1023 | OD1 | ASN | 111 | 63.270 | -12.794 | 70.833 | 1.00 10.75 | A |
| ATOM | 1024 | ND2 | ASN | 111 | 65.251 | -13.281 | 71.681 | 1.00 8.82 | A |
| ATOM | 1027 | C | ASN | 111 | 62.457 | -16.671 | 69.654 | 1.00 8.61 | A |
| ATOM | 1028 | O | ASN | 111 | 62.106 | -16.434 | 68.509 | 1.00 7.56 | A |
| ATOM | 1029 | N | ALA | 112 | 62.784 | -17.881 | 70.060 | 1.00 9.27 | A |
| ATOM | 1031 | CA | ALA | 112 | 62.729 | -19.004 | 69.133 | 1.00 9.73 | A |
| ATOM | 1032 | CB | ALA | 112 | 63.502 | -20.178 | 69.700 | 1.00 8.79 | A |
| ATOM | 1033 | C | ALA | 112 | 61.298 | -19.407 | 68.857 | 1.00 10.54 | A |
| ATOM | 1034 | O | ALA | 112 | 60.898 | -19.638 | 67.715 | 1.00 9.64 | A |
| ATOM | 1035 | N | ALA | 113 | 60.516 | -19.413 | 69.929 | 1.00 11.42 | A |
| ATOM | 1037 | CA | ALA | 113 | 59.115 | -19.802 | 69.881 | 1.00 12.92 | A |
| ATOM | 1038 | CB | ALA | 113 | 58.575 | -19.985 | 71.369 | 1.00 12.48 | A |
| ATOM | 1039 | C | ALA | 113 | 58.252 | -18.808 | 69.083 | 1.00 12.95 | A |
| ATOM | 1040 | O | ALA | 113 | 57.344 | -19.192 | 68.337 | 1.00 13.21 | A |
| ATOM | 1041 | N | LEU | 114 | 58.498 | -17.530 | 69.312 | 1.00 12.62 | A |
| ATOM | 1043 | CA | LEU | 114 | 57.793 | -16.473 | 68.619 | 1.00 12.91 | A |
| ATOM | 1044 | CB | LEU | 114 | 58.236 | -15.121 | 69.204 | 1.00 12.25 | A |
| ATOM | 1045 | CG | LEU | 114 | 57.598 | -14.807 | 70.571 | 1.00 12.03 | A |
| ATOM | 1046 | CD1 | LEU | 114 | 58.266 | -13.604 | 71.215 | 1.00 10.36 | A |
| ATOM | 1047 | CD2 | LEU | 114 | 56.043 | -14.583 | 70.410 | 1.00 9.08 | A |
| ATOM | 1048 | C | LEU | 114 | 58.140 | -16.592 | 67.114 | 1.00 13.42 | A |
| ATOM | 1049 | O | LEU | 114 | 57.270 | -16.612 | 66.207 | 1.00 13.67 | A |
| ATOM | 1050 | N | SER | 115 | 59.415 | -16.763 | 66.866 | 1.00 12.71 | A |
| ATOM | 1052 | CA | SER | 115 | 59.886 | -16.915 | 65.527 | 1.00 13.74 | A |
| ATOM | 1053 | CB | SER | 115 | 61.384 | -17.158 | 65.602 | 1.00 14.96 | A |
| ATOM | 1054 | OG | SER | 115 | 61.978 | -17.239 | 64.320 | 1.00 18.12 | A |
| ATOM | 1056 | C | SER | 115 | 59.164 | -18.080 | 64.829 | 1.00 12.89 | A |
| ATOM | 1057 | O | SER | 115 | 58.504 | -17.902 | 63.844 | 1.00 14.53 | A |
| ATOM | 1058 | N | ALA | 116 | 59.191 | -19.267 | 65.389 | 1.00 13.04 | A |
| ATOM | 1060 | CA | ALA | 116 | 58.522 | -20.380 | 64.737 | 1.00 12.01 | A |
| ATOM | 1061 | CB | ALA | 116 | 58.846 | -21.652 | 65.420 | 1.00 10.26 | A |
| ATOM | 1062 | C | ALA | 116 | 57.024 | -20.215 | 64.614 | 1.00 12.86 | A |
| ATOM | 1063 | O | ALA | 116 | 56.404 | -20.895 | 63.811 | 1.00 14.85 | A |
| ATOM | 1064 | N | ALA | 117 | 56.413 | -19.347 | 65.412 | 1.00 13.86 | A |
| ATOM | 1066 | CA | ALA | 117 | 54.958 | -19.150 | 65.341 | 1.00 13.39 | A |
| ATOM | 1067 | CB | ALA | 117 | 54.411 | -18.728 | 66.678 | 1.00 13.42 | A |
| ATOM | 1068 | C | ALA | 117 | 54.677 | -18.086 | 64.324 | 1.00 13.64 | A |
| ATOM | 1069 | O | ALA | 117 | 53.533 | -17.742 | 64.069 | 1.00 15.02 | A |
| ATOM | 1070 | N | GLY | 118 | 55.736 | -17.595 | 63.709 | 1.00 13.91 | A |
| ATOM | 1072 | CA | GLY | 118 | 55.585 | -16.538 | 62.760 | 1.00 14.63 | A |
| ATOM | 1073 | C | GLY | 118 | 55.147 | -15.257 | 63.451 | 1.00 16.58 | A |
| ATOM | 1074 | O | GLY | 118 | 54.541 | -14.415 | 62.798 | 1.00 18.30 | A |
| ATOM | 1075 | N | LEU | 119 | 55.415 | -15.091 | 64.753 | 1.00 17.41 | A |
| ATOM | 1077 | CA | LEU | 119 | 55.043 | -13.851 | 65.465 | 1.00 17.06 | A |
| ATOM | 1078 | CB | LEU | 119 | 54.347 | -14.197 | 66.755 | 1.00 17.36 | A |
| ATOM | 1079 | CG | LEU | 119 | 53.229 | -15.176 | 66.584 | 1.00 16.87 | A |
| ATOM | 1080 | CD1 | LEU | 119 | 52.666 | -15.510 | 67.947 | 1.00 19.39 | A |
| ATOM | 1081 | CD2 | LEU | 119 | 52.176 | -14.524 | 65.742 | 1.00 19.79 | A |
| ATOM | 1082 | C | LEU | 119 | 56.277 | -12.990 | 65.780 | 1.00 17.12 | A |
| ATOM | 1083 | O | LEU | 119 | 56.390 | -12.416 | 66.875 | 1.00 18.38 | A |
| ATOM | 1084 | N | GLY | 120 | 57.179 | -12.895 | 64.805 | 1.00 15.83 | A |
| ATOM | 1086 | CA | GLY | 120 | 58.429 | -12.160 | 64.942 | 1.00 14.06 | A |
| ATOM | 1087 | C | GLY | 120 | 58.413 | -10.654 | 65.080 | 1.00 13.82 | A |
| ATOM | 1088 | O | GLY | 120 | 59.459 | -10.017 | 65.303 | 1.00 14.11 | A |
| ATOM | 1089 | N | ALA | 121 | 57.254 | -10.045 | 64.894 | 1.00 13.70 | A |

- 71 -

| ATOM | 1091 | CA | ALA | 121 | 57.187 | -8.610 | 65.079 | 1.00 | 12.80 | A |
|---|---|---|---|---|---|---|---|---|---|---|
| ATOM | 1092 | CB | ALA | 121 | 55.920 | -8.062 | 64.466 | 1.00 | 10.46 | A |
| ATOM | 1093 | C | ALA | 121 | 57.234 | -8.350 | 66.621 | 1.00 | 14.19 | A |
| ATOM | 1094 | O | ALA | 121 | 57.845 | -7.362 | 67.092 | 1.00 | 15.20 | A |
| ATOM | 1095 | N | ILE | 122 | 56.628 | -9.246 | 67.406 | 1.00 | 13.68 | A |
| ATOM | 1097 | CA | ILE | 122 | 56.637 | -9.074 | 68.846 | 1.00 | 12.79 | A |
| ATOM | 1098 | CB | ILE | 122 | 55.787 | -10.128 | 69.538 | 1.00 | 11.04 | A |
| ATOM | 1099 | CG2 | ILE | 122 | 55.650 | -9.769 | 70.967 | 1.00 | 10.47 | A |
| ATOM | 1100 | CG1 | ILE | 122 | 54.375 | -10.148 | 68.930 | 1.00 | 10.24 | A |
| ATOM | 1101 | CD1 | ILE | 122 | 53.432 | -11.096 | 69.585 | 1.00 | 6.71 | A |
| ATOM | 1102 | C | ILE | 122 | 58.065 | -9.177 | 69.356 | 1.00 | 13.87 | A |
| ATOM | 1103 | O | ILE | 122 | 58.743 | -10.166 | 69.074 | 1.00 | 15.29 | A |
| ATOM | 1104 | N | LYS | 123 | 58.503 | -8.179 | 70.124 | 1.00 | 13.48 | A |
| ATOM | 1106 | CA | LYS | 123 | 59.857 | -8.120 | 70.696 | 1.00 | 13.29 | A |
| ATOM | 1107 | CB | LYS | 123 | 60.385 | -6.687 | 70.568 | 1.00 | 14.22 | A |
| ATOM | 1108 | CG | LYS | 123 | 60.544 | -6.240 | 69.144 | 1.00 | 16.22 | A |
| ATOM | 1109 | CD | LYS | 123 | 61.682 | -7.012 | 68.541 | 1.00 | 19.45 | A |
| ATOM | 1110 | CE | LYS | 123 | 61.821 | -6.806 | 67.022 | 1.00 | 22.94 | A |
| ATOM | 1111 | NZ | LYS | 123 | 63.112 | -7.377 | 66.447 | 1.00 | 23.11 | A |
| ATOM | 1115 | C | LYS | 123 | 59.973 | -8.581 | 72.162 | 1.00 | 11.90 | A |
| ATOM | 1116 | O | LYS | 123 | 59.160 | -8.212 | 73.004 | 1.00 | 11.56 | A |
| ATOM | 1117 | N | VAL | 124 | 61.046 | -9.300 | 72.477 | 1.00 | 11.78 | A |
| ATOM | 1119 | CA | VAL | 124 | 61.303 | -9.843 | 73.830 | 1.00 | 10.81 | A |
| ATOM | 1120 | CB | VAL | 124 | 61.601 | -11.338 | 73.740 | 1.00 | 10.92 | A |
| ATOM | 1121 | CG1 | VAL | 124 | 62.136 | -11.856 | 75.023 | 1.00 | 10.87 | A |
| ATOM | 1122 | CG2 | VAL | 124 | 60.374 | -12.062 | 73.279 | 1.00 | 12.44 | A |
| ATOM | 1123 | C | VAL | 124 | 62.413 | -9.102 | 74.622 | 1.00 | 15.04 | A |
| ATOM | 1124 | O | VAL | 124 | 63.550 | -8.958 | 74.170 | 1.00 | 11.07 | A |
| ATOM | 1125 | N | SER | 125 | 62.087 | -7.887 | 75.826 | 1.00 | 10.68 | A |
| ATOM | 1127 | CA | SER | 125 | 63.029 | -7.485 | 76.630 | 1.00 | 9.67 | A |
| ATOM | 1128 | CB | SER | 125 | 62.702 | -6.386 | 77.034 | 1.00 | 10.92 | A |
| ATOM | 1129 | OG | SER | 125 | 63.630 | -5.512 | 78.119 | 1.00 | 11.37 | A |
| ATOM | 1132 | C | SER | 125 | 62.877 | -8.296 | 78.441 | 1.00 | 9.76 | A |
| ATOM | 1133 | O | SER | 125 | 62.376 | -9.388 | 79.017 | 1.00 | 9.61 | A |
| ATOM | 1135 | N | THR | 126 | 63.399 | -7.485 | 80.436 | 1.00 | 10.17 | A |
| ATOM | 1136 | CA | THR | 126 | 63.264 | -8.577 | 80.962 | 1.00 | 8.21 | A |
| ATOM | 1137 | CB | THR | 126 | 64.431 | -9.275 | 82.154 | 1.00 | 8.10 | A |
| ATOM | 1139 | OG1 | THR | 126 | 64.026 | -7.662 | 81.224 | 1.00 | 11.25 | A |
| ATOM | 1140 | CG2 | THR | 126 | 65.657 | -6.377 | 81.125 | 1.00 | 11.25 | A |
| ATOM | 1141 | C | THR | 126 | 63.754 | -5.371 | 80.629 | 1.00 | 9.68 | A |
| ATOM | 1142 | O | SER | 127 | 62.347 | -6.306 | 82.165 | 1.00 | 10.89 | A |
| ATOM | 1144 | N | SER | 127 | 62.150 | -5.062 | 82.887 | 1.00 | 12.16 | A |
| ATOM | 1145 | CA | SER | 127 | 60.683 | -4.936 | 83.263 | 1.00 | 12.56 | A |
| ATOM | 1146 | CB | SER | 127 | 60.340 | -3.593 | 83.542 | 1.00 | 13.86 | A |
| ATOM | 1148 | OG | SER | 127 | 63.047 | -4.949 | 84.135 | 1.00 | 13.57 | A |
| ATOM | 1149 | C | SER | 127 | 63.060 | -5.827 | 84.998 | 1.00 | 13.26 | A |
| ATOM | 1150 | O | ILE | 128 | 63.802 | -3.859 | 84.223 | 1.00 | 14.43 | A |
| ATOM | 1152 | CA | ILE | 128 | 64.702 | -3.641 | 85.341 | 1.00 | 15.30 | A |
| ATOM | 1153 | CB | ILE | 128 | 66.214 | -3.627 | 84.878 | 1.00 | 15.76 | A |
| ATOM | 1154 | CG2 | ILE | 128 | 66.560 | -4.904 | 84.074 | 1.00 | 14.98 | A |
| ATOM | 1155 | CG1 | ILE | 128 | 66.515 | -2.355 | 84.056 | 1.00 | 15.86 | A |
| ATOM | 1156 | CD1 | ILE | 128 | 67.983 | -1.902 | 84.071 | 1.00 | 14.20 | A |
| ATOM | 1157 | C | ILE | 128 | 64.464 | -2.337 | 86.117 | 1.00 | 15.44 | A |
| ATOM | 1158 | O | ILE | 128 | 63.884 | -1.363 | 85.630 | 1.00 | 14.40 | A |
| ATOM | 1159 | N | ARG | 129 | 64.971 | -2.336 | 87.334 | 1.00 | 16.63 | A |
| ATOM | 1161 | CA | ARG | 129 | 64.913 | -1.174 | 88.180 | 1.00 | 18.37 | A |
| ATOM | 1162 | CB | ARG | 129 | 64.654 | -1.539 | 89.621 | 1.00 | 20.31 | A |
| ATOM | 1163 | CG | ARG | 129 | 65.274 | -2.830 | 90.036 | 1.00 | 23.81 | A |
| ATOM | 1164 | CD | ARG | 129 | 64.646 | -3.270 | 91.301 | 1.00 | 27.04 | A |
| ATOM | 1165 | NE | ARG | 129 | 65.510 | -2.975 | 92.416 | 1.00 | 29.70 | A |
| ATOM | 1167 | CZ | ARG | 129 | 65.528 | -3.697 | 93.522 | 1.00 | 31.18 | A |
| ATOM | 1168 | NH1 | ARG | 129 | 64.695 | -4.739 | 93.645 | 1.00 | 31.07 | A |
| ATOM | 1171 | NH2 | ARG | 129 | 66.459 | -3.444 | 94.442 | 1.00 | 31.97 | A |
| ATOM | 1174 | C | ARG | 129 | 66.243 | -0.457 | 88.055 | 1.00 | 18.18 | A |
| ATOM | 1175 | O | ARG | 129 | 67.275 | -1.036 | 87.735 | 1.00 | 16.92 | A |
| ATOM | 1176 | N | PHE | 130 | 66.190 | 0.825 | 88.346 | 1.00 | 19.07 | A |
| ATOM | 1178 | CA | PHE | 130 | 57.329 | 1.693 | 88.253 | 1.00 | 19.35 | A |
| ATOM | 1179 | CB | PHE | 130 | 66.889 | 3.102 | 88.629 | 1.00 | 17.28 | A |
| ATOM | 1180 | CG | PHE | 130 | 67.843 | 4.141 | 88.187 | 1.00 | 17.26 | A |
| ATOM | 1181 | CD1 | PHE | 130 | 67.890 | 4.521 | 86.858 | 1.00 | 17.23 | A |
| ATOM | 1182 | CD2 | PHE | 130 | 68.761 | 4.675 | 89.067 | 1.00 | 15.31 | A |
| ATOM | 1183 | CE1 | PHE | 130 | 68.848 | 5.410 | 86.421 | 1.00 | 17.58 | A |
| ATOM | 1184 | CE2 | PHE | 130 | 69.719 | 5.564 | 88.640 | 1.00 | 16.06 | A |
| ATOM | 1185 | CZ | PHE | 130 | 69.773 | 5.935 | 87.321 | 1.00 | 17.26 | A |
| ATOM | 1186 | C | PHE | 130 | 68.537 | 1.267 | 89.082 | 1.00 | 20.06 | A |
| ATOM | 1187 | O | PHE | 130 | 69.676 | 1.480 | 88.660 | 1.00 | 21.09 | A |
| ATOM | 1188 | N | ASP | 131 | 68.292 | 0.628 | 90.229 | 1.00 | 21.10 | A |
| ATOM | 1190 | CA | ASP | 131 | 69.358 | 0.198 | 91.156 | 1.00 | 22.06 | A |
| ATOM | 1191 | CB | ASP | 131 | 68.781 | -0.207 | 92.552 | 1.00 | 21.74 | A |

| | | | | | | | | |
|---|---|---|---|---|---|---|---|---|
| ATOM | 1192 | CG | ASP | 131 | 68.730 | -1.735 | 92.783 | 1.00 25.27 A |
| ATOM | 1193 | OD1 | ASP | 131 | 68.196 | -2.504 | 91.929 | 1.00 25.25 A |
| ATOM | 1194 | OD2 | ASP | 131 | 69.212 | -2.178 | 93.863 | 1.00 26.91 A |
| ATOM | 1195 | C | ASP | 131 | 70.325 | -0.832 | 90.530 | 1.00 22.02 A |
| ATOM | 1196 | O | ASP | 131 | 71.277 | -1.289 | 91.169 | 1.00 22.52 A |
| ATOM | 1197 | N | GLU | 132 | 70.071 | -1.151 | 89.263 | 1.00 21.03 A |
| ATOM | 1198 | CA | GLU | 132 | 70.902 | -2.039 | 88.460 | 1.00 21.06 A |
| ATOM | 1199 | CB | GLU | 132 | 70.098 | -2.546 | 87.271 | 1.00 21.92 A |
| ATOM | 1200 | CG | GLU | 132 | 69.474 | -3.894 | 87.517 | 1.00 24.36 A |
| ATOM | 1201 | CD | GLU | 132 | 70.488 | -4.930 | 87.948 | 1.00 24.60 A |
| ATOM | 1202 | OE1 | GLU | 132 | 71.648 | -4.936 | 87.439 | 1.00 26.46 A |
| ATOM | 1203 | OE2 | GLU | 132 | 70.108 | -5.738 | 88.814 | 1.00 26.42 A |
| ATOM | 1204 | C | GLU | 132 | 72.089 | -1.883 | 87.884 | 1.00 19.83 A |
| ATOM | 1205 | O | GLU | 132 | 73.059 | 0.046 | 87.808 | 1.00 18.97 A |
| ATOM | 1206 | N | VAL | 133 | 71.923 | 0.970 | 87.258 | 1.00 19.78 A |
| ATOM | 1207 | CA | VAL | 133 | 72.898 | 2.029 | 86.404 | 1.00 19.92 A |
| ATOM | 1208 | CB | VAL | 133 | 72.187 | 2.134 | 85.812 | 1.00 19.98 A |
| ATOM | 1209 | CG1 | VAL | 133 | 73.193 | 3.026 | 85.287 | 1.00 20.69 A |
| ATOM | 1210 | CG2 | VAL | 133 | 71.383 | 1.344 | 88.325 | 1.00 19.89 A |
| ATOM | 1211 | C | VAL | 133 | 73.699 | 1.689 | 89.125 | 1.00 20.20 A |
| ATOM | 1212 | O | VAL | 133 | 73.122 | 2.392 | 88.336 | 1.00 21.63 A |
| ATOM | 1213 | N | ALA | 134 | 75.017 | 1.486 | 89.273 | 1.00 20.59 A |
| ATOM | 1214 | CA | ALA | 134 | 75.942 | 1.177 | 89.706 | 1.00 21.26 A |
| ATOM | 1215 | CB | ALA | 134 | 77.041 | 3.370 | 88.625 | 1.00 19.88 A |
| ATOM | 1216 | C | ALA | 134 | 76.561 | 3.582 | 87.431 | 1.00 21.76 A |
| ATOM | 1217 | O | ALA | 134 | 76.440 | 4.174 | 89.450 | 1.00 21.39 A |
| ATOM | 1218 | N | ASN | 135 | 77.215 | 5.430 | 89.073 | 1.00 23.40 A |
| ATOM | 1219 | CA | ASN | 135 | 77.865 | 5.180 | 88.416 | 1.00 25.37 A |
| ATOM | 1220 | CB | ASN | 135 | 79.209 | 4.457 | 89.314 | 1.00 28.00 A |
| ATOM | 1221 | CG | ASN | 135 | 80.152 | 4.580 | 90.562 | 1.00 30.30 A |
| ATOM | 1222 | OD1 | ASN | 135 | 80.087 | 3.654 | 88.706 | 1.00 31.22 A |
| ATOM | 1223 | ND2 | ASN | 135 | 81.023 | 6.331 | 88.198 | 1.00 31.27 A |
| ATOM | 1224 | C | ASN | 135 | 77.039 | 6.991 | 87.318 | 1.00 25.56 A |
| ATOM | 1225 | O | ASN | 135 | 77.564 | 6.444 | 88.525 | 1.00 25.43 A |
| ATOM | 1226 | N | SER | 136 | 75.763 | 7.253 | 87.753 | 1.00 26.11 A |
| ATOM | 1227 | CA | SER | 136 | 74.850 | 6.907 | 88.118 | 1.00 27.19 A |
| ATOM | 1228 | CB | SER | 136 | 73.400 | 6.835 | 89.518 | 1.00 27.37 A |
| ATOM | 1229 | OG | SER | 136 | 73.227 | 8.745 | 87.825 | 1.00 29.74 A |
| ATOM | 1230 | C | SER | 136 | 75.115 | 9.550 | 87.242 | 1.00 27.41 A |
| ATOM | 1231 | O | SER | 136 | 74.366 | | | 1.00 28.25 A |
| ATOM | 1240 | N | PHE | 137 | 76.129 | 9.135 | 88.585 | 1.00 27.74 A |
| ATOM | 1242 | CA | PHE | 137 | 76.475 | 10.545 | 88.645 | 1.00 28.26 A |
| ATOM | 1243 | CB | PHE | 137 | 76.004 | 11.257 | 89.905 | 1.00 29.07 A |
| ATOM | 1244 | CG | PHE | 137 | 76.166 | 12.746 | 89.791 | 1.00 31.77 A |
| ATOM | 1245 | CD1 | PHE | 137 | 75.305 | 13.479 | 88.969 | 1.00 32.45 A |
| ATOM | 1246 | CD2 | PHE | 137 | 77.266 | 13.401 | 90.368 | 1.00 32.71 A |
| ATOM | 1247 | CE1 | PHE | 137 | 75.544 | 14.837 | 88.713 | 1.00 33.75 A |
| ATOM | 1248 | CE2 | PHE | 137 | 77.516 | 14.766 | 90.121 | 1.00 33.22 A |
| ATOM | 1249 | CZ | PHE | 137 | 76.655 | 15.480 | 89.290 | 1.00 33.43 A |
| ATOM | 1250 | C | PHE | 137 | 77.956 | 10.837 | 88.445 | 1.00 27.41 A |
| ATOM | 1251 | O | PHE | 137 | 78.803 | 10.289 | 89.159 | 1.00 28.54 A |
| ATOM | 1252 | N | PRO | 138 | 78.291 | 11.632 | 87.416 | 1.00 25.93 A |
| ATOM | 1253 | CD | PRO | 138 | 79.678 | 11.840 | 86.968 | 1.00 25.55 A |
| ATOM | 1254 | CA | PRO | 138 | 77.370 | 12.239 | 86.462 | 1.00 24.52 A |
| ATOM | 1255 | CB | PRO | 138 | 78.309 | 13.038 | 85.585 | 1.00 24.62 A |
| ATOM | 1256 | CG | PRO | 138 | 79.494 | 12.173 | 85.500 | 1.00 24.67 A |
| ATOM | 1257 | C | PRO | 138 | 76.726 | 11.098 | 85.676 | 1.00 24.21 A |
| ATOM | 1258 | O | PRO | 138 | 77.219 | 9.964 | 85.725 | 1.00 23.57 A |
| ATOM | 1259 | N | PRO | 139 | 75.646 | 11.382 | 84.915 | 1.00 24.21 A |
| ATOM | 1260 | CD | PRO | 139 | 74.980 | 12.680 | 84.672 | 1.00 23.08 A |
| ATOM | 1261 | CA | PRO | 139 | 74.980 | 10.325 | 84.150 | 1.00 23.01 A |
| ATOM | 1262 | CB | PRO | 139 | 73.935 | 11.101 | 83.363 | 1.00 22.85 A |
| ATOM | 1263 | CG | PRO | 139 | 73.621 | 12.237 | 84.251 | 1.00 24.31 A |
| ATOM | 1264 | C | PRO | 139 | 75.929 | 9.549 | 83.228 | 1.00 24.12 A |
| ATOM | 1265 | O | PRO | 139 | 75.748 | 8.346 | 82.992 | 1.00 24.24 A |
| ATOM | 1266 | N | SER | 140 | 76.960 | 10.237 | 82.740 | 1.00 23.99 A |
| ATOM | 1268 | CA | SER | 140 | 77.941 | 9.635 | 81.849 | 1.00 25.50 A |
| ATOM | 1269 | CB | SER | 140 | 78.857 | 10.740 | 81.295 | 1.00 25.53 A |
| ATOM | 1270 | OG | SER | 140 | 79.432 | 11.521 | 82.359 | 1.00 23.60 A |
| ATOM | 1272 | C | SER | 140 | 78.766 | 8.541 | 82.561 | 1.00 23.75 A |
| ATOM | 1273 | O | SER | 140 | 79.512 | 7.793 | 81.942 | 1.00 23.67 A |
| ATOM | 1274 | N | ALA | 141 | 78.668 | 8.477 | 83.875 | 1.00 22.84 A |
| ATOM | 1276 | CA | ALA | 141 | 79.400 | 7.469 | 84.616 | 1.00 21.82 A |
| ATOM | 1277 | CB | ALA | 141 | 78.510 | 8.060 | 85.888 | 1.00 22.87 A |
| ATOM | 1278 | C | ALA | 141 | 78.882 | 6.229 | 84.872 | 1.00 22.88 A |
| ATOM | 1279 | O | ALA | 141 | 77.337 | 5.309 | 85.607 | 1.00 22.06 A |
| ATOM | 1280 | N | GLY | 142 | 76.485 | 5.042 | 84.251 | 1.00 21.72 A |
| ATOM | 1282 | CA | GLY | 142 | 77.107 | 3.758 | 83.934 | 1.00 21.11 A |
| ATOM | 1283 | C | GLY | 142 | 77.562 | 3.124 | 82.778 | 1.00 21.47 A |
| ATOM | 1284 | O | GLY | 142 | | | | |

- 72 -

| | | | | | | | | |
|---|---|---|---|---|---|---|---|---|
| ATOM | 1285 | N | VAL | 143 | 77.077 | 2.700 | 84.745 | 1.00 20.21 A |
| ATOM | 1287 | CA | VAL | 143 | 77.618 | 1.391 | 84.376 | 1.00 20.23 A |
| ATOM | 1288 | CB | VAL | 143 | 79.117 | 1.300 | 84.815 | 1.00 21.19 A |
| ATOM | 1289 | CG1 | VAL | 143 | 79.245 | 0.907 | 86.294 | 1.00 20.95 A |
| ATOM | 1290 | CG2 | VAL | 143 | 79.872 | 0.376 | 83.928 | 1.00 20.58 A |
| ATOM | 1291 | C | VAL | 143 | 76.790 | 0.259 | 85.030 | 1.00 19.57 A |
| ATOM | 1292 | O | VAL | 143 | 76.381 | 0.368 | 86.182 | 1.00 19.01 A |
| ATOM | 1293 | N | PHE | 144 | 76.467 | 0.784 | 84.278 | 1.00 19.49 A |
| ATOM | 1295 | CA | PHE | 144 | 75.698 | -1.889 | 84.845 | 1.00 20.31 A |
| ATOM | 1296 | CB | PHE | 144 | 75.297 | -2.946 | 83.787 | 1.00 18.00 A |
| ATOM | 1297 | CG | PHE | 144 | 74.207 | -2.488 | 82.833 | 1.00 17.76 A |
| ATOM | 1298 | CD1 | PHE | 144 | 74.305 | -2.748 | 81.467 | 1.00 15.02 A |
| ATOM | 1299 | CD2 | PHE | 144 | 73.084 | -1.785 | 83.297 | 1.00 15.87 A |
| ATOM | 1300 | CE1 | PHE | 144 | 73.334 | -2.331 | 80.604 | 1.00 14.15 A |
| ATOM | 1301 | CE2 | PHE | 144 | 72.107 | -1.370 | 82.405 | 1.00 14.33 A |
| ATOM | 1302 | CZ | PHE | 144 | 72.242 | -1.648 | 81.062 | 1.00 13.41 A |
| ATOM | 1303 | C | PHE | 144 | 76.557 | -2.554 | 85.894 | 1.00 21.56 A |
| ATOM | 1304 | O | PHE | 144 | 77.676 | -2.995 | 85.588 | 1.00 21.03 A |
| ATOM | 1305 | N | LYS | 145 | 76.029 | -2.659 | 87.114 | 1.00 22.88 A |
| ATOM | 1307 | CA | LYS | 145 | 76.786 | -3.283 | 88.194 | 1.00 24.21 A |
| ATOM | 1308 | CB | LYS | 145 | 76.362 | -2.736 | 89.571 | 1.00 25.42 A |
| ATOM | 1309 | CG | LYS | 145 | 74.942 | -3.087 | 90.024 | 1.00 26.38 A |
| ATOM | 1310 | CD | LYS | 145 | 74.687 | -2.680 | 91.476 | 1.00 28.20 A |
| ATOM | 1311 | CE | LYS | 145 | 73.802 | -3.729 | 92.197 | 1.00 29.64 A |
| ATOM | 1312 | NZ | LYS | 145 | 72.402 | -3.897 | 91.666 | 1.00 28.88 A |
| ATOM | 1316 | C | LYS | 145 | 76.786 | -4.830 | 88.179 | 1.00 24.66 A |
| ATOM | 1317 | O | LYS | 145 | 77.719 | -5.460 | 88.684 | 1.00 25.61 A |
| ATOM | 1318 | N | ASN | 146 | 75.796 | -5.444 | 87.540 | 1.00 25.05 A |
| ATOM | 1320 | CA | ASN | 146 | 75.723 | -6.913 | 87.496 | 1.00 24.78 A |
| ATOM | 1321 | CB | ASN | 146 | 74.303 | -7.370 | 87.807 | 1.00 24.82 A |
| ATOM | 1322 | CG | ASN | 146 | 73.896 | -7.026 | 89.225 | 1.00 25.15 A |
| ATOM | 1323 | OD1 | ASN | 146 | 74.681 | -7.193 | 90.151 | 1.00 25.04 A |
| ATOM | 1324 | ND2 | ASN | 146 | 72.677 | -6.540 | 89.403 | 1.00 23.63 A |
| ATOM | 1327 | C | ASN | 146 | 76.216 | -7.484 | 86.179 | 1.00 24.41 A |
| ATOM | 1328 | O | ASN | 146 | 75.968 | -6.908 | 85.107 | 1.00 25.26 A |
| ATOM | 1329 | N | ALA | 147 | 76.931 | -8.604 | 86.233 | 1.00 23.35 A |
| ATOM | 1331 | CA | ALA | 147 | 77.473 | -9.183 | 84.993 | 1.00 22.31 A |
| ATOM | 1332 | CB | ALA | 147 | 78.447 | -10.310 | 85.311 | 1.00 22.61 A |
| ATOM | 1333 | C | ALA | 147 | 76.429 | -9.646 | 83.967 | 1.00 21.63 A |
| ATOM | 1334 | O | ALA | 147 | 76.582 | -9.421 | 82.760 | 1.00 21.51 A |
| ATOM | 1335 | N | TYR | 148 | 75.352 | -10.247 | 84.467 | 1.00 20.88 A |
| ATOM | 1337 | CA | TYR | 148 | 74.283 | -10.755 | 83.621 | 1.00 21.34 A |
| ATOM | 1338 | CB | TYR | 148 | 73.223 | -11.449 | 84.479 | 1.00 20.15 A |
| ATOM | 1339 | CG | TYR | 148 | 72.208 | -10.509 | 85.056 | 1.00 20.77 A |
| ATOM | 1340 | CD1 | TYR | 148 | 70.986 | -10.268 | 84.403 | 1.00 20.83 A |
| ATOM | 1341 | CD2 | TYR | 148 | 72.068 | -9.397 | 84.931 | 1.00 21.25 A |
| ATOM | 1342 | CE1 | TYR | 148 | 72.462 | -9.850 | 86.243 | 1.00 20.74 A |
| ATOM | 1343 | CE2 | TYR | 148 | 71.557 | -8.990 | 86.778 | 1.00 21.46 A |
| ATOM | 1344 | CZ | TYR | 148 | 70.368 | -8.761 | 86.132 | 1.00 21.94 A |
| ATOM | 1345 | OH | TYR | 148 | 69.493 | -7.897 | 86.729 | 1.00 22.43 A |
| ATOM | 1347 | C | TYR | 148 | 73.658 | -9.701 | 82.701 | 1.00 20.88 A |
| ATOM | 1348 | O | TYR | 148 | 73.172 | -10.011 | 81.622 | 1.00 20.84 A |
| ATOM | 1349 | N | MET | 149 | 73.701 | -8.453 | 83.114 | 1.00 22.25 A |
| ATOM | 1351 | CA | MET | 149 | 73.137 | -7.380 | 82.318 | 1.00 23.80 A |
| ATOM | 1352 | CB | MET | 149 | 72.968 | -6.106 | 83.161 | 1.00 24.28 A |
| ATOM | 1353 | CG | MET | 149 | 71.632 | -6.023 | 83.877 | 1.00 24.75 A |
| ATOM | 1354 | SD | MET | 149 | 70.212 | -6.441 | 82.787 | 1.00 25.47 A |
| ATOM | 1355 | CE | MET | 149 | 70.095 | -4.951 | 81.760 | 1.00 24.65 A |
| ATOM | 1356 | C | MET | 149 | 73.917 | -7.080 | 81.051 | 1.00 23.81 A |
| ATOM | 1357 | O | MET | 149 | 73.390 | -6.465 | 80.136 | 1.00 25.01 A |
| ATOM | 1358 | N | THR | 150 | 75.173 | -7.483 | 80.969 | 1.00 24.49 A |
| ATOM | 1360 | CA | THR | 150 | 75.887 | -7.208 | 79.730 | 1.00 24.76 A |
| ATOM | 1361 | CB | THR | 150 | 77.412 | -7.263 | 79.879 | 1.00 25.63 A |
| ATOM | 1362 | OG1 | THR | 150 | 77.809 | -6.523 | 81.042 | 1.00 27.35 A |
| ATOM | 1364 | CG2 | THR | 150 | 78.070 | -6.663 | 78.709 | 1.00 25.27 A |
| ATOM | 1365 | C | THR | 150 | 75.433 | -8.230 | 77.533 | 1.00 24.76 A |
| ATOM | 1366 | O | THR | 150 | 75.282 | -7.900 | 79.165 | 1.00 24.98 A |
| ATOM | 1367 | N | ASP | 151 | 75.235 | -9.472 | 78.314 | 1.00 24.84 A |
| ATOM | 1369 | CA | ASP | 151 | 74.754 | -10.558 | 78.314 | 1.00 25.22 A |
| ATOM | 1370 | CB | ASP | 151 | 74.565 | -11.828 | 79.139 | 1.00 27.10 A |
| ATOM | 1371 | CG | ASP | 151 | 75.869 | -12.450 | 79.597 | 1.00 28.78 A |
| ATOM | 1372 | OD1 | ASP | 151 | 75.906 | -12.963 | 80.753 | 1.00 29.64 A |
| ATOM | 1373 | OD2 | ASP | 151 | 76.825 | -12.482 | 78.788 | 1.00 29.01 A |
| ATOM | 1374 | C | ASP | 151 | 73.376 | -10.172 | 77.129 | 1.00 25.10 A |
| ATOM | 1375 | O | ASP | 151 | 73.071 | -10.454 | 76.566 | 1.00 27.10 A |
| ATOM | 1376 | N | VAL | 152 | 72.540 | -9.562 | 78.565 | 1.00 24.11 A |
| ATOM | 1378 | CA | VAL | 152 | 71.216 | -9.153 | 78.166 | 1.00 23.89 A |
| ATOM | 1379 | CB | VAL | 152 | 70.357 | -8.728 | 79.376 | 1.00 23.14 A |
| ATOM | 1380 | CG1 | VAL | 152 | 69.020 | -8.256 | 78.930 | 1.00 21.84 A |
| ATOM | 1381 | CG2 | VAL | 152 | 70.174 | -9.887 | 80.306 | 1.00 22.64 A |

- 73 -

| ATOM | 1382 | C | VAL | 152 | 71.301 | -8.021 | 77.161 | 1.00 | 24.67 | A |
|---|---|---|---|---|---|---|---|---|---|---|
| ATOM | 1383 | O | VAL | 152 | 70.691 | -8.100 | 76.083 | 1.00 | 24.99 | A |
| ATOM | 1384 | N | ALA | 153 | 72.091 | -6.998 | 77.459 | 1.00 | 24.23 | A |
| ATOM | 1385 | CA | ALA | 153 | 72.180 | -5.874 | 76.519 | 1.00 | 24.58 | A |
| ATOM | 1386 | CB | ALA | 153 | 73.107 | -4.765 | 77.060 | 1.00 | 25.09 | A |
| ATOM | 1387 | C | ALA | 153 | 72.633 | -6.313 | 75.133 | 1.00 | 24.18 | A |
| ATOM | 1388 | O | ALA | 153 | 72.160 | -5.788 | 74.113 | 1.00 | 24.39 | A |
| ATOM | 1389 | N | ARG | 154 | 73.567 | -7.258 | 75.111 | 1.00 | 24.17 | A |
| ATOM | 1390 | CA | ARG | 154 | 74.115 | -7.803 | 73.869 | 1.00 | 23.53 | A |
| ATOM | 1391 | CB | ARG | 154 | 75.313 | -8.704 | 74.160 | 1.00 | 23.52 | A |
| ATOM | 1392 | CG | ARG | 154 | 76.525 | -7.900 | 74.627 | 1.00 | 24.31 | A |
| ATOM | 1393 | CD | ARG | 154 | 77.800 | -8.746 | 74.706 | 1.00 | 25.07 | A |
| ATOM | 1394 | NE | ARG | 154 | 77.646 | -9.920 | 75.560 | 0.00 | 25.44 | A |
| ATOM | 1395 | CZ | ARG | 154 | 78.537 | -10.903 | 75.648 | 0.00 | 25.69 | A |
| ATOM | 1396 | NH1 | ARG | 154 | 79.655 | -10.862 | 74.935 | 0.00 | 25.86 | A |
| ATOM | 1397 | NH2 | ARG | 154 | 78.304 | -11.940 | 76.439 | 0.00 | 25.86 | A |
| ATOM | 1398 | C | ARG | 154 | 73.046 | -8.532 | 73.081 | 1.00 | 21.85 | A |
| ATOM | 1399 | O | ARG | 154 | 72.925 | -8.338 | 71.876 | 1.00 | 22.89 | A |
| ATOM | 1400 | N | LEU | 155 | 72.214 | -9.298 | 73.773 | 1.00 | 20.76 | A |
| ATOM | 1401 | CA | LEU | 155 | 71.129 | -10.019 | 73.119 | 1.00 | 18.53 | A |
| ATOM | 1402 | CB | LEU | 155 | 70.431 | -10.982 | 74.094 | 1.00 | 16.53 | A |
| ATOM | 1403 | CG | LEU | 155 | 69.147 | -11.608 | 73.514 | 1.00 | 17.43 | A |
| ATOM | 1404 | CD1 | LEU | 155 | 69.406 | -12.212 | 72.141 | 1.00 | 16.13 | A |
| ATOM | 1405 | CD2 | LEU | 155 | 68.560 | -12.661 | 74.405 | 1.00 | 16.49 | A |
| ATOM | 1406 | C | LEU | 155 | 70.152 | -8.992 | 72.579 | 1.00 | 17.41 | A |
| ATOM | 1407 | O | LEU | 155 | 69.709 | -9.091 | 71.442 | 1.00 | 18.55 | A |
| ATOM | 1408 | N | LEU | 156 | 69.832 | -7.980 | 73.370 | 1.00 | 17.48 | A |
| ATOM | 1409 | CA | LEU | 156 | 68.904 | -6.933 | 72.914 | 1.00 | 17.87 | A |
| ATOM | 1410 | CB | LEU | 156 | 68.685 | -5.899 | 74.012 | 1.00 | 17.57 | A |
| ATOM | 1411 | CG | LEU | 156 | 67.921 | -6.383 | 75.234 | 1.00 | 15.82 | A |
| ATOM | 1412 | CD1 | LEU | 156 | 67.889 | -5.295 | 76.200 | 1.00 | 15.48 | A |
| ATOM | 1413 | CD2 | LEU | 156 | 66.527 | -6.805 | 74.860 | 1.00 | 16.22 | A |
| ATOM | 1414 | C | LEU | 156 | 69.418 | -6.229 | 71.655 | 1.00 | 17.95 | A |
| ATOM | 1415 | O | LEU | 156 | 68.654 | -5.925 | 70.740 | 1.00 | 18.46 | A |
| ATOM | 1416 | N | ALA | 157 | 70.724 | -5.995 | 71.614 | 1.00 | 18.96 | A |
| ATOM | 1417 | CA | ALA | 157 | 71.381 | -5.349 | 70.485 | 1.00 | 19.45 | A |
| ATOM | 1418 | CB | ALA | 157 | 72.872 | -5.183 | 70.763 | 1.00 | 19.00 | A |
| ATOM | 1419 | C | ALA | 157 | 71.178 | -6.140 | 69.195 | 1.00 | 20.43 | A |
| ATOM | 1420 | O | ALA | 157 | 70.735 | -5.582 | 68.182 | 1.00 | 21.29 | A |
| ATOM | 1421 | N | SER | 158 | 71.491 | -7.437 | 69.232 | 1.00 | 20.44 | A |
| ATOM | 1433 | CA | SER | 158 | 71.363 | -8.272 | 68.055 | 1.00 | 18.81 | A |
| ATOM | 1434 | CB | SER | 158 | 72.153 | -9.582 | 68.202 | 1.00 | 19.09 | A |
| ATOM | 1435 | OG | SER | 158 | 71.774 | -10.324 | 69.343 | 1.00 | 19.91 | A |
| ATOM | 1437 | C | SER | 158 | 69.937 | -8.538 | 67.631 | 1.00 | 19.08 | A |
| ATOM | 1438 | O | SER | 158 | 69.682 | -8.764 | 66.433 | 1.00 | 20.98 | A |
| ATOM | 1439 | N | THR | 159 | 69.000 | -8.498 | 68.574 | 1.00 | 17.92 | A |
| ATOM | 1441 | CA | THR | 159 | 67.601 | -8.750 | 68.245 | 1.00 | 16.31 | A |
| ATOM | 1442 | CB | THR | 159 | 66.911 | -9.624 | 69.320 | 1.00 | 16.21 | A |
| ATOM | 1443 | OG1 | THR | 159 | 66.790 | -8.909 | 70.552 | 1.00 | 16.89 | A |
| ATOM | 1445 | CG2 | THR | 159 | 67.756 | -10.827 | 69.592 | 1.00 | 16.73 | A |
| ATOM | 1446 | C | THR | 159 | 66.795 | -7.479 | 67.946 | 1.00 | 15.74 | A |
| ATOM | 1447 | O | THR | 159 | 65.670 | -7.523 | 67.438 | 1.00 | 15.92 | A |
| ATOM | 1448 | N | GLY | 160 | 67.377 | -6.322 | 68.193 | 1.00 | 14.63 | A |
| ATOM | 1450 | CA | GLY | 160 | 66.610 | -5.137 | 67.913 | 1.00 | 13.17 | A |
| ATOM | 1451 | C | GLY | 160 | 65.458 | -4.949 | 68.883 | 1.00 | 13.00 | A |
| ATOM | 1452 | O | GLY | 160 | 64.426 | -4.379 | 68.517 | 1.00 | 15.49 | A |
| ATOM | 1453 | N | ALA | 161 | 65.607 | -5.435 | 70.114 | 1.00 | 11.24 | A |
| ATOM | 1455 | CA | ALA | 161 | 64.582 | -5.249 | 71.117 | 1.00 | 9.17 | A |
| ATOM | 1456 | CB | ALA | 161 | 64.340 | -6.492 | 71.857 | 1.00 | 8.62 | A |
| ATOM | 1457 | C | ALA | 161 | 65.147 | -4.181 | 72.045 | 1.00 | 9.79 | A |
| ATOM | 1458 | O | ALA | 161 | 66.371 | -4.065 | 72.208 | 1.00 | 9.88 | A |
| ATOM | 1459 | N | PRO | 162 | 64.283 | -3.322 | 72.607 | 1.00 | 9.62 | A |
| ATOM | 1460 | CD | PRO | 162 | 62.834 | -3.217 | 72.365 | 1.00 | 9.55 | A |
| ATOM | 1461 | CA | PRO | 162 | 64.740 | -2.266 | 73.510 | 1.00 | 10.02 | A |
| ATOM | 1462 | CB | PRO | 162 | 63.609 | -1.263 | 73.425 | 1.00 | 11.44 | A |
| ATOM | 1463 | CG | PRO | 162 | 62.410 | -2.186 | 73.376 | 1.00 | 10.03 | A |
| ATOM | 1464 | C | PRO | 162 | 64.795 | -2.799 | 74.894 | 1.00 | 10.55 | A |
| ATOM | 1465 | O | PRO | 162 | 64.372 | -3.930 | 75.124 | 1.00 | 11.67 | A |
| ATOM | 1466 | N | LEU | 163 | 65.203 | -1.942 | 75.833 | 1.00 | 10.63 | A |
| ATOM | 1468 | CA | LEU | 163 | 65.651 | -2.302 | 77.247 | 1.00 | 9.50 | A |
| ATOM | 1469 | CB | LEU | 163 | 66.894 | -1.909 | 77.818 | 1.00 | 9.74 | A |
| ATOM | 1470 | CG | LEU | 163 | 66.664 | -2.105 | 79.310 | 1.00 | 10.58 | A |
| ATOM | 1471 | CD1 | LEU | 163 | 68.348 | -3.597 | 79.603 | 1.00 | 9.85 | A |
| ATOM | 1472 | CD2 | LEU | 163 | 64.170 | -1.669 | 79.740 | 1.00 | 10.33 | A |
| ATOM | 1473 | C | LEU | 163 | 63.938 | -1.570 | 77.997 | 1.00 | 8.34 | A |
| ATOM | 1474 | O | LEU | 163 | 62.399 | -0.395 | 79.614 | 1.00 | 6.95 | A |
| ATOM | 1475 | N | LEU | 164 | 61.181 | -2.269 | 77.755 | 1.00 | 7.84 | A |
| ATOM | 1477 | CA | LEU | 164 | 63.458 | -1.623 | 78.876 | 1.00 | 9.11 | A |
| ATOM | 1478 | CB | LEU | 164 | 62.399 | -2.525 | 79.689 | 1.00 | 9.98 | A |
| ATOM | 1479 | CG | LEU | 164 | 60.770 | -3.330 | 78.451 | 1.00 | 11.36 | A |

- 75 -

| | | | | | | | | | |
|---|---|---|---|---|---|---|---|---|---|
| ATOM | 1480 | CD1 | LEU | 164 | 59.639 | -4.216 | 78.900 | 1.00 11.67 | A |
| ATOM | 1481 | CD2 | LEU | 164 | 60.354 | -2.461 | 77.225 | 1.00 10.23 | A |
| ATOM | 1482 | C | LEU | 164 | 62.954 | -1.274 | 81.006 | 1.00 9.07 | A |
| ATOM | 1483 | O | LEU | 164 | 63.477 | -2.140 | 81.702 | 1.00 6.43 | A |
| ATOM | 1484 | N | ALA | 165 | 62.874 | 0.011 | 81.359 | 1.00 9.75 | A |
| ATOM | 1485 | CA | ALA | 165 | 63.376 | 0.524 | 82.635 | 1.00 10.75 | A |
| ATOM | 1486 | CB | ALA | 165 | 64.531 | 1.481 | 82.351 | 1.00 10.33 | A |
| ATOM | 1487 | C | ALA | 165 | 62.327 | 1.212 | 83.532 | 1.00 10.97 | A |
| ATOM | 1488 | O | ALA | 165 | 61.590 | 2.091 | 83.073 | 1.00 12.55 | A |
| ATOM | 1489 | N | ASN | 166 | 62.244 | 0.787 | 84.796 | 1.00 11.61 | A |
| ATOM | 1490 | CA | ASN | 166 | 61.335 | 1.363 | 85.824 | 1.00 10.94 | A |
| ATOM | 1491 | CB | ASN | 166 | 60.996 | 0.307 | 86.858 | 1.00 10.21 | A |
| ATOM | 1492 | CG | ASN | 166 | 60.289 | -0.847 | 86.245 | 1.00 10.62 | A |
| ATOM | 1493 | ND1 | ASN | 166 | 59.615 | -0.667 | 85.250 | 1.00 12.05 | A |
| ATOM | 1494 | ND2 | ASN | 166 | 60.463 | -2.049 | 86.782 | 1.00 10.09 | A |
| ATOM | 1495 | C | ASN | 166 | 62.104 | 2.513 | 86.476 | 1.00 11.04 | A |
| ATOM | 1496 | O | ASN | 166 | 63.020 | 2.276 | 87.261 | 1.00 10.77 | A |
| ATOM | 1497 | N | VAL | 167 | 61.793 | 3.752 | 86.062 | 1.00 11.23 | A |
| ATOM | 1498 | CA | VAL | 167 | 62.486 | 4.947 | 86.527 | 1.00 11.45 | A |
| ATOM | 1499 | CB | VAL | 167 | 63.085 | 7.054 | 85.329 | 1.00 11.14 | A |
| ATOM | 1500 | CG1 | VAL | 167 | 63.737 | 4.885 | 84.582 | 1.00 12.23 | A |
| ATOM | 1501 | CG2 | VAL | 167 | 64.128 | 5.809 | 87.347 | 1.00 11.10 | A |
| ATOM | 1502 | C | VAL | 167 | 61.545 | 6.246 | 86.871 | 1.00 10.81 | A |
| ATOM | 1503 | O | VAL | 167 | 61.946 | 6.046 | 88.590 | 1.00 10.34 | A |
| ATOM | 1504 | N | TYR | 168 | 61.171 | 6.822 | 89.544 | 1.00 10.92 | A |
| ATOM | 1505 | CA | TYR | 168 | 60.686 | 5.909 | 90.674 | 1.00 8.77 | A |
| ATOM | 1506 | CB | TYR | 168 | 59.610 | 4.951 | 90.273 | 1.00 7.98 | A |
| ATOM | 1507 | CG | TYR | 168 | 59.897 | 3.686 | 89.744 | 1.00 7.32 | A |
| ATOM | 1508 | CD1 | TYR | 168 | 58.876 | 2.802 | 89.439 | 1.00 6.96 | A |
| ATOM | 1509 | CE1 | TYR | 168 | 58.299 | 5.299 | 90.471 | 1.00 7.95 | A |
| ATOM | 1510 | CD2 | TYR | 168 | 57.277 | 4.454 | 90.186 | 1.00 9.15 | A |
| ATOM | 1511 | CE2 | TYR | 168 | 57.535 | 3.209 | 89.678 | 1.00 9.84 | A |
| ATOM | 1512 | CZ | TYR | 168 | 56.401 | 2.423 | 89.478 | 1.00 8.00 | A |
| ATOM | 1513 | OH | TYR | 168 | 61.975 | 7.923 | 90.202 | 1.00 11.49 | A |
| ATOM | 1514 | C | TYR | 168 | 62.684 | 7.646 | 91.167 | 1.00 13.27 | A |
| ATOM | 1515 | N | PRO | 169 | 61.889 | 9.180 | 89.716 | 1.00 11.72 | A |
| ATOM | 1516 | CA | PRO | 169 | 61.423 | 9.677 | 88.403 | 1.00 10.90 | A |
| ATOM | 1517 | CB | PRO | 169 | 62.676 | 10.212 | 90.402 | 1.00 11.73 | A |
| ATOM | 1518 | CG | PRO | 169 | 62.350 | 11.461 | 89.577 | 1.00 10.69 | A |
| ATOM | 1527 | CG | PRO | 169 | 62.259 | 10.931 | 88.219 | 1.00 11.11 | A |
| ATOM | 1528 | C | PRO | 169 | 62.251 | 10.358 | 91.899 | 1.00 13.19 | A |
| ATOM | 1529 | O | PRO | 169 | 63.039 | 10.816 | 92.740 | 1.00 13.35 | A |
| ATOM | 1530 | N | TYR | 170 | 61.006 | 9.967 | 92.214 | 1.00 14.80 | A |
| ATOM | 1532 | CA | TYR | 170 | 60.474 | 10.070 | 93.575 | 1.00 16.05 | A |
| ATOM | 1533 | CB | TYR | 170 | 59.015 | 9.590 | 93.673 | 1.00 15.61 | A |
| ATOM | 1534 | CG | TYR | 170 | 58.490 | 9.461 | 95.111 | 1.00 16.70 | A |
| ATOM | 1535 | CD1 | TYR | 170 | 58.253 | 10.600 | 95.912 | 1.00 18.02 | A |
| ATOM | 1536 | CE1 | TYR | 170 | 57.856 | 10.474 | 97.275 | 1.00 17.13 | A |
| ATOM | 1537 | CD2 | TYR | 170 | 58.307 | 8.207 | 95.705 | 1.00 17.30 | A |
| ATOM | 1538 | CE2 | TYR | 170 | 57.915 | 8.075 | 97.071 | 1.00 16.60 | A |
| ATOM | 1539 | CZ | TYR | 170 | 57.285 | 9.207 | 97.849 | 1.00 17.37 | A |
| ATOM | 1540 | OH | TYR | 170 | 57.690 | 9.079 | 99.186 | 1.00 15.96 | A |
| ATOM | 1542 | C | TYR | 170 | 61.322 | 9.289 | 95.677 | 1.00 16.98 | A |
| ATOM | 1543 | O | TYR | 170 | 61.561 | 9.775 | 94.176 | 1.00 18.38 | A |
| ATOM | 1544 | N | PHE | 171 | 61.776 | 8.092 | 95.100 | 1.00 17.16 | A |
| ATOM | 1546 | CA | PHE | 171 | 62.568 | 7.285 | 94.590 | 1.00 17.94 | A |
| ATOM | 1547 | CB | PHE | 171 | 62.704 | 5.852 | 94.553 | 1.00 18.94 | A |
| ATOM | 1548 | CG | PHE | 171 | 61.414 | 5.083 | 94.562 | 1.00 18.77 | A |
| ATOM | 1549 | CD1 | PHE | 171 | 61.226 | 4.089 | 93.624 | 1.00 19.41 | A |
| ATOM | 1550 | CD2 | PHE | 171 | 60.392 | 5.361 | 95.429 | 1.00 20.53 | A |
| ATOM | 1551 | CE1 | PHE | 171 | 60.032 | 3.373 | 93.560 | 1.00 19.50 | A |
| ATOM | 1552 | CE2 | PHE | 171 | 59.173 | 4.638 | 95.373 | 1.00 21.35 | A |
| ATOM | 1553 | CZ | PHE | 171 | 59.009 | 3.645 | 94.430 | 1.00 19.92 | A |
| ATOM | 1554 | C | PHE | 171 | 63.953 | 7.923 | 95.332 | 1.00 18.54 | A |
| ATOM | 1555 | O | PHE | 171 | 64.495 | 7.923 | 96.460 | 1.00 16.76 | A |
| ATOM | 1556 | N | ALA | 172 | 64.518 | 8.484 | 94.263 | 1.00 18.94 | A |
| ATOM | 1558 | CA | ALA | 172 | 65.814 | 9.142 | 94.375 | 1.00 19.65 | A |
| ATOM | 1559 | CB | ALA | 172 | 66.295 | 9.585 | 92.986 | 1.00 18.23 | A |
| ATOM | 1560 | C | ALA | 172 | 65.613 | 10.355 | 95.314 | 1.00 20.48 | A |
| ATOM | 1561 | O | ALA | 172 | 66.273 | 10.499 | 96.342 | 1.00 20.12 | A |
| ATOM | 1562 | N | TYR | 173 | 64.624 | 11.166 | 94.990 | 1.00 22.46 | A |
| ATOM | 1564 | CA | TYR | 173 | 64.316 | 12.327 | 95.791 | 1.00 25.15 | A |
| ATOM | 1565 | CB | TYR | 173 | 63.095 | 13.037 | 95.240 | 1.00 26.78 | A |
| ATOM | 1566 | CG | TYR | 173 | 62.699 | 14.216 | 96.092 | 1.00 29.52 | A |
| ATOM | 1567 | CD1 | TYR | 173 | 63.599 | 15.258 | 96.325 | 1.00 30.81 | A |
| ATOM | 1568 | CE1 | TYR | 173 | 63.282 | 16.316 | 97.135 | 1.00 31.16 | A |
| ATOM | 1569 | CD2 | TYR | 173 | 61.456 | 14.273 | 96.697 | 1.00 29.99 | A |
| ATOM | 1570 | CE2 | TYR | 173 | 61.126 | 15.333 | 97.520 | 1.00 32.77 | A |
| ATOM | 1571 | CZ | TYR | 173 | 62.056 | 16.349 | 97.736 | 1.00 32.45 | A |

| ATOM | 1572 | OH  | TYR | 173 | 61.773 | 17.361 | 98.618 | 1.00 | 34.60 | A | | ATOM | 1624 | O   | GLY | 178 | 69.741 | 18.623 | 99.215 | 1.00 | 35.39 | A |
|------|------|-----|-----|-----|--------|--------|--------|------|-------|---|-|------|------|-----|-----|-----|--------|--------|--------|------|-------|---|
| ATOM | 1574 | C   | TYR | 173 | 64.038 | 11.985 | 97.248 | 1.00 | 26.23 | A | | ATOM | 1625 | N   | SER | 179 | 70.448 | 16.499 | 99.073 | 1.00 | 33.76 | A |
| ATOM | 1575 | O   | TYR | 173 | 64.599 | 12.615 | 98.144 | 1.00 | 26.68 | A | | ATOM | 1627 | CA  | SER | 179 | 71.133 | 16.757 | 97.818 | 1.00 | 32.86 | A |
| ATOM | 1576 | N   | ARG | 174 | 63.166 | 11.005 | 97.482 | 1.00 | 28.34 | A | | ATOM | 1628 | CB  | SER | 179 | 72.051 | 15.589 | 97.416 | 1.00 | 33.15 | A |
| ATOM | 1578 | CA  | ARG | 174 | 62.780 | 10.624 | 98.841 | 1.00 | 29.01 | A | | ATOM | 1629 | OG  | SER | 179 | 71.321 | 14.412 | 97.087 | 1.00 | 35.36 | A |
| ATOM | 1579 | CB  | ARG | 174 | 61.741 | 9.492  | 98.799 | 1.00 | 28.93 | A | | ATOM | 1531 | C   | SER | 179 | 70.210 | 17.108 | 96.675 | 1.00 | 32.25 | A |
| ATOM | 1580 | CG  | ARG | 174 | 61.158 | 9.094  | 100.141| 1.00 | 29.32 | A | | ATOM | 1632 | O   | SER | 179 | 70.573 | 17.931 | 95.843 | 1.00 | 32.51 | A |
| ATOM | 1581 | CD  | ARG | 174 | 60.345 | 7.778  | 100.064| 1.00 | 31.00 | A | | ATOM | 1633 | N   | ILE | 180 | 69.009 | 16.531 | 96.662 | 1.00 | 31.14 | A |
| ATOM | 1582 | NE  | ARG | 174 | 59.813 | 7.412  | 101.391| 1.00 | 30.03 | A | | ATOM | 1635 | CA  | ILE | 180 | 68.040 | 16.751 | 95.578 | 1.00 | 29.81 | A |
| ATOM | 1584 | CZ  | ARG | 174 | 58.694 | 6.719  | 101.641| 1.00 | 28.61 | A | | ATOM | 1636 | CB  | ILE | 180 | 67.513 | 15.375 | 95.094 | 1.00 | 29.56 | A |
| ATOM | 1585 | NH1 | ARG | 174 | 57.932 | 6.607  | 100.655| 1.00 | 30.21 | A | | ATOM | 1637 | CG2 | ILE | 180 | 66.607 | 15.531 | 93.871 | 1.00 | 29.41 | A |
| ATOM | 1588 | NH2 | ARG | 174 | 58.285 | 6.584  | 102.900| 1.00 | 29.14 | A | | ATOM | 1638 | CG1 | ILE | 180 | 68.691 | 14.453 | 94.786 | 1.00 | 29.65 | A |
| ATOM | 1591 | C   | ARG | 174 | 63.983 | 10.257 | 99.716 | 1.00 | 29.41 | A | | ATOM | 1639 | CD1 | ILE | 180 | 68.282 | 13.041 | 94.540 | 1.00 | 28.67 | A |
| ATOM | 1592 | O   | ARG | 174 | 64.117 | 10.759 | 100.807| 1.00 | 30.46 | A | | ATOM | 1640 | C   | ILE | 180 | 66.830 | 17.693 | 95.884 | 1.00 | 29.10 | A |
| ATOM | 1593 | N   | ASP | 175 | 64.886 | 9.438  | 99.195 | 1.00 | 31.62 | A | | ATOM | 1641 | O   | ILE | 180 | 66.106 | 17.496 | 96.874 | 1.00 | 28.15 | A |
| ATOM | 1595 | CA  | ASP | 175 | 66.078 | 9.011  | 99.923 | 1.00 | 32.24 | A | | ATOM | 1642 | N   | ILE | 181 | 66.572 | 18.646 | 94.978 | 1.00 | 27.52 | A |
| ATOM | 1596 | CB  | ASP | 175 | 66.849 | 7.946  | 99.122 | 1.00 | 32.58 | A | | ATOM | 1644 | CA  | ILE | 181 | 65.457 | 19.595 | 95.122 | 1.00 | 26.54 | A |
| ATOM | 1597 | CG  | ASP | 175 | 66.102 | 6.628  | 98.973 | 1.00 | 33.00 | A | | ATOM | 1645 | CB  | ILE | 181 | 65.830 | 20.934 | 94.493 | 1.00 | 27.04 | A |
| ATOM | 1598 | OD1 | ASP | 175 | 64.911 | 6.517  | 99.369 | 1.00 | 33.00 | A | | ATOM | 1646 | C   | ILE | 181 | 66.508 | 20.750 | 93.267 | 1.00 | 29.84 | A |
| ATOM | 1599 | OD2 | ASP | 175 | 66.740 | 5.690  | 98.428 | 1.00 | 33.44 | A | | ATOM | 1648 | O   | SER | 181 | 64.150 | 19.109 | 94.508 | 1.00 | 25.47 | A |
| ATOM | 1600 | C   | ASP | 175 | 67.060 | 10.152 | 100.134| 1.00 | 32.00 | A | | ATOM | 1649 | N   | SER | 181 | 64.165 | 18.482 | 93.439 | 1.00 | 24.84 | A |
| ATOM | 1601 | O   | ASP | 175 | 67.871 | 10.117 | 101.057| 1.00 | 32.52 | A | | ATOM | 1650 | CA  | LEU | 182 | 63.017 | 19.485 | 95.114 | 1.00 | 23.94 | A |
| ATOM | 1602 | N   | ASN | 176 | 67.094 | 11.084 | 99.189 | 1.00 | 32.65 | A | | ATOM | 1652 | CB  | LEU | 182 | 61.717 | 19.043 | 94.612 | 1.00 | 22.59 | A |
| ATOM | 1604 | CA  | ASN | 176 | 68.044 | 12.199 | 99.268 | 1.00 | 33.12 | A | | ATOM | 1653 | CG  | LEU | 182 | 60.578 | 19.476 | 95.533 | 1.00 | 21.74 | A |
| ATOM | 1605 | CB  | ASN | 176 | 69.164 | 11.972 | 98.254 | 1.00 | 35.04 | A | | ATOM | 1654 | CD1 | LEU | 182 | 59.200 | 18.880 | 95.168 | 1.00 | 21.61 | A |
| ATOM | 1606 | CG  | ASN | 176 | 70.464 | 11.736 | 98.923 | 1.00 | 36.52 | A | | ATOM | 1655 | CD2 | LEU | 182 | 59.234 | 17.381 | 95.057 | 1.00 | 20.54 | A |
| ATOM | 1607 | OD1 | ASN | 176 | 71.097 | 12.687 | 99.403 | 1.00 | 37.94 | A | | ATOM | 1656 | C   | LEU | 182 | 58.153 | 19.286 | 96.207 | 1.00 | 22.90 | A |
| ATOM | 1608 | ND2 | ASN | 176 | 70.824 | 10.469 | 99.940 | 1.00 | 37.56 | A | | ATOM | 1657 | O   | LEU | 182 | 61.460 | 19.496 | 93.173 | 1.00 | 22.20 | A |
| ATOM | 1611 | C   | ASN | 176 | 67.523 | 13.632 | 99.138 | 1.00 | 31.85 | A | | ATOM | 1658 | O   | LEU | 182 | 60.867 | 18.773 | 92.365 | 1.00 | 21.25 | A |
| ATOM | 1612 | O   | ASN | 176 | 68.021 | 14.392 | 98.313 | 1.00 | 31.05 | A | | ATOM | 1659 | N   | ASN | 183 | 61.948 | 20.674 | 92.843 | 1.00 | 21.59 | A |
| ATOM | 1613 | N   | PRO | 177 | 66.603 | 14.040 | 100.048| 1.00 | 31.57 | A | | ATOM | 1661 | CA  | ASN | 183 | 61.790 | 21.184 | 91.496 | 1.00 | 21.80 | A |
| ATOM | 1614 | CD  | PRO | 177 | 66.076 | 13.234 | 101.151| 1.00 | 31.25 | A | | ATOM | 1662 | CB  | ASN | 183 | 62.442 | 22.554 | 91.378 | 1.00 | 22.75 | A |
| ATOM | 1615 | CA  | PRO | 177 | 65.994 | 15.370 | 100.048| 1.00 | 31.69 | A | | ATOM | 1663 | CG  | ASN | 183 | 61.541 | 23.659 | 91.826 | 1.00 | 24.42 | A |
| ATOM | 1616 | CB  | PRO | 177 | 64.998 | 15.285 | 101.212| 1.00 | 31.57 | A | | ATOM | 1664 | OD1 | ASN | 183 | 60.332 | 23.464 | 92.053 | 1.00 | 25.75 | A |
| ATOM | 1617 | CG  | PRO | 177 | 64.698 | 13.837 | 101.335| 1.00 | 31.86 | A | | ATOM | 1665 | ND2 | ASN | 183 | 62.108 | 24.842 | 91.953 | 1.00 | 25.28 | A |
| ATOM | 1618 | C   | PRO | 177 | 67.003 | 16.490 | 100.260| 1.00 | 31.88 | A | | ATOM | 1668 | C   | ASN | 183 | 62.450 | 20.237 | 90.503 | 1.00 | 21.24 | A |
| ATOM | 1619 | O   | PRO | 177 | 66.728 | 17.634 | 99.940 | 1.00 | 31.93 | A | | ATOM | 1669 | O   | ASN | 183 | 61.783 | 19.681 | 89.624 | 1.00 | 21.34 | A |
| ATOM | 1620 | N   | GLY | 178 | 68.161 | 16.164 | 100.821| 1.00 | 32.80 | A | | ATOM | 1670 | N   | TYR | 184 | 63.739 | 19.987 | 90.727 | 1.00 | 20.37 | A |
| ATOM | 1622 | CA  | GLY | 178 | 69.178 | 17.175 | 101.039| 1.00 | 33.52 | A | | ATOM | 1672 | CA  | TYR | 184 | 64.547 | 19.120 | 89.873 | 1.00 | 19.82 | A |
| ATOM | 1623 | C   | GLY | 178 | 69.848 | 17.501 | 99.714 | 1.00 | 34.34 | A | | ATOM | 1673 | CB  | TYR | 184 | 65.902 | 18.889 | 90.544 | 1.00 | 19.06 | A |

- 77 -

| ATOM | 1674 | CG | TYR | 184 | 66.934 | 18.232 | 89.687 | 1.00 | 18.02 | A |
|---|---|---|---|---|---|---|---|---|---|---|
| ATOM | 1675 | CD1 | TYR | 184 | 67.193 | 18.707 | 88.416 | 1.00 | 18.28 | A |
| ATOM | 1676 | CE1 | TYR | 184 | 68.165 | 18.132 | 87.627 | 1.00 | 20.18 | A |
| ATOM | 1677 | CD2 | TYR | 184 | 67.678 | 17.155 | 90.159 | 1.00 | 18.92 | A |
| ATOM | 1678 | CE2 | TYR | 184 | 68.665 | 16.569 | 89.369 | 1.00 | 18.74 | A |
| ATOM | 1679 | CZ | TYR | 184 | 68.892 | 17.067 | 88.103 | 1.00 | 19.08 | A |
| ATOM | 1680 | OH | TYR | 184 | 69.821 | 16.515 | 87.268 | 1.00 | 21.42 | A |
| ATOM | 1682 | C | TYR | 184 | 63.833 | 17.791 | 89.698 | 1.00 | 19.81 | A |
| ATOM | 1683 | O | TYR | 184 | 63.838 | 17.190 | 88.627 | 1.00 | 20.83 | A |
| ATOM | 1684 | N | ALA | 185 | 63.212 | 17.340 | 90.773 | 1.00 | 20.07 | A |
| ATOM | 1686 | CA | ALA | 185 | 62.495 | 16.102 | 90.774 | 1.00 | 20.48 | A |
| ATOM | 1687 | CB | ALA | 185 | 62.212 | 15.677 | 92.213 | 1.00 | 18.81 | A |
| ATOM | 1688 | C | ALA | 185 | 61.186 | 16.176 | 89.978 | 1.00 | 21.55 | A |
| ATOM | 1689 | O | ALA | 185 | 60.889 | 15.304 | 89.162 | 1.00 | 22.22 | A |
| ATOM | 1690 | N | THR | 186 | 60.452 | 17.264 | 90.131 | 1.00 | 22.45 | A |
| ATOM | 1692 | CA | THR | 186 | 59.139 | 17.352 | 89.515 | 1.00 | 21.64 | A |
| ATOM | 1693 | CB | THR | 186 | 58.107 | 17.926 | 90.524 | 1.00 | 21.81 | A |
| ATOM | 1694 | OG1 | THR | 186 | 58.587 | 19.180 | 91.051 | 1.00 | 20.74 | A |
| ATOM | 1696 | CG2 | THR | 186 | 57.864 | 16.934 | 91.674 | 1.00 | 19.80 | A |
| ATOM | 1697 | C | THR | 186 | 59.033 | 18.082 | 88.202 | 1.00 | 22.07 | A |
| ATOM | 1698 | O | THR | 186 | 57.934 | 18.443 | 87.775 | 1.00 | 20.84 | A |
| ATOM | 1699 | N | PHE | 187 | 60.168 | 18.222 | 87.533 | 1.00 | 22.86 | A |
| ATOM | 1701 | CA | PHE | 187 | 60.223 | 18.907 | 86.233 | 1.00 | 24.06 | A |
| ATOM | 1702 | CB | PHE | 187 | 59.203 | 18.344 | 85.229 | 1.00 | 22.17 | A |
| ATOM | 1703 | CG | PHE | 187 | 59.469 | 16.948 | 84.801 | 1.00 | 19.65 | A |
| ATOM | 1704 | CD1 | PHE | 187 | 58.667 | 15.916 | 85.264 | 1.00 | 18.89 | A |
| ATOM | 1705 | CD2 | PHE | 187 | 60.505 | 16.669 | 83.933 | 1.00 | 18.75 | A |
| ATOM | 1706 | CE1 | PHE | 187 | 58.890 | 14.634 | 84.874 | 1.00 | 18.58 | A |
| ATOM | 1707 | CE2 | PHE | 187 | 60.744 | 15.376 | 83.531 | 1.00 | 19.62 | A |
| ATOM | 1708 | CZ | PHE | 187 | 59.934 | 14.352 | 84.003 | 1.00 | 18.58 | A |
| ATOM | 1709 | C | PHE | 187 | 59.938 | 20.377 | 86.373 | 1.00 | 25.33 | A |
| ATOM | 1710 | O | PHE | 187 | 59.233 | 20.955 | 85.535 | 1.00 | 25.86 | A |
| ATOM | 1711 | N | GLN | 188 | 60.498 | 20.996 | 87.404 | 1.00 | 27.12 | A |
| ATOM | 1713 | CA | GLN | 188 | 60.273 | 22.416 | 87.626 | 1.00 | 28.18 | A |
| ATOM | 1714 | CB | GLN | 188 | 59.538 | 22.627 | 88.939 | 1.00 | 27.32 | A |
| ATOM | 1715 | CG | GLN | 188 | 58.087 | 23.234 | 88.862 | 1.00 | 26.22 | A |
| ATOM | 1716 | CD | GLN | 188 | 57.235 | 23.295 | 88.191 | 1.00 | 26.43 | A |
| ATOM | 1717 | OE1 | GLN | 188 | 57.208 | 23.410 | 86.967 | 0.00 | 26.31 | A |
| ATOM | 1718 | NE2 | GLN | 188 | 56.545 | 24.091 | 88.996 | 0.00 | 26.31 | A |
| ATOM | 1721 | C | GLN | 188 | 61.548 | 23.234 | 87.550 | 1.00 | 29.35 | A |
| ATOM | 1722 | O | GLN | 188 | 62.633 | 22.731 | 87.867 | 1.00 | 29.73 | A |
| ATOM | 1723 | N | PRO | 189 | 61.445 | 24.473 | 87.017 | 1.00 | 30.71 | A |
| ATOM | 1724 | CD | PRO | 189 | 60.212 | 25.042 | 86.437 | 1.00 | 31.10 | A |
| ATOM | 1725 | CA | PRO | 189 | 62.553 | 25.422 | 86.851 | 1.00 | 31.01 | A |
| ATOM | 1726 | CB | PRO | 189 | 61.850 | 26.687 | 86.308 | 1.00 | 31.06 | A |
| ATOM | 1727 | CG | PRO | 189 | 60.397 | 26.501 | 86.678 | 1.00 | 30.66 | A |
| ATOM | 1728 | C | PRO | 189 | 63.350 | 25.681 | 88.124 | 1.00 | 30.64 | A |
| ATOM | 1729 | O | PRO | 189 | 62.798 | 25.748 | 89.215 | 1.00 | 30.17 | A |
| ATOM | 1730 | N | GLY | 190 | 64.663 | 25.741 | 87.981 | 1.00 | 31.07 | A |
| ATOM | 1732 | CA | GLY | 190 | 65.489 | 25.976 | 89.143 | 1.00 | 32.36 | A |
| ATOM | 1733 | C | GLY | 190 | 66.888 | 25.374 | 89.165 | 1.00 | 32.90 | A |
| ATOM | 1734 | O | GLY | 190 | 67.659 | 26.102 | 89.351 | 1.00 | 34.30 | A |
| ATOM | 1735 | N | THR | 191 | 67.012 | 24.064 | 88.974 | 1.00 | 32.57 | A |
| ATOM | 1737 | CA | THR | 191 | 68.317 | 23.396 | 89.019 | 1.00 | 30.69 | A |
| ATOM | 1738 | CB | THR | 191 | 68.180 | 22.137 | 89.877 | 1.00 | 31.29 | A |
| ATOM | 1739 | OG1 | THR | 191 | 67.748 | 22.531 | 91.189 | 1.00 | 32.09 | A |
| ATOM | 1741 | CG2 | THR | 191 | 69.491 | 21.315 | 89.930 | 1.00 | 30.50 | A |
| ATOM | 1742 | C | THR | 191 | 68.907 | 23.050 | 87.640 | 1.00 | 29.75 | A |
| ATOM | 1743 | O | THR | 191 | 68.167 | 22.715 | 86.714 | 1.00 | 27.78 | A |
| ATOM | 1744 | N | THR | 192 | 70.241 | 23.135 | 87.538 | 1.00 | 29.50 | A |
| ATOM | 1746 | CA | THR | 192 | 71.016 | 22.838 | 86.314 | 1.00 | 29.00 | A |
| ATOM | 1747 | CB | THR | 192 | 71.465 | 24.105 | 85.607 | 1.00 | 27.79 | A |
| ATOM | 1748 | OG1 | THR | 192 | 70.356 | 24.688 | 84.925 | 1.00 | 28.38 | A |
| ATOM | 1750 | CG2 | THR | 192 | 72.601 | 23.811 | 84.639 | 1.00 | 26.33 | A |
| ATOM | 1751 | C | THR | 192 | 72.290 | 22.092 | 86.706 | 1.00 | 29.23 | A |
| ATOM | 1752 | O | THR | 192 | 73.092 | 22.592 | 87.482 | 1.00 | 30.06 | A |
| ATOM | 1753 | N | VAL | 193 | 72.498 | 20.924 | 86.129 | 1.00 | 29.07 | A |
| ATOM | 1755 | CA | VAL | 193 | 73.649 | 20.105 | 86.447 | 1.00 | 29.40 | A |
| ATOM | 1756 | CB | VAL | 193 | 73.169 | 18.776 | 87.032 | 1.00 | 29.86 | A |
| ATOM | 1757 | CG1 | VAL | 193 | 74.353 | 17.835 | 87.339 | 1.00 | 29.62 | A |
| ATOM | 1758 | CG2 | VAL | 193 | 72.308 | 19.051 | 88.260 | 1.00 | 29.84 | A |
| ATOM | 1759 | C | VAL | 193 | 74.383 | 19.844 | 85.152 | 1.00 | 29.76 | A |
| ATOM | 1760 | O | VAL | 193 | 73.759 | 19.511 | 84.156 | 1.00 | 29.93 | A |
| ATOM | 1761 | N | ARG | 194 | 75.697 | 19.996 | 85.131 | 1.00 | 30.41 | A |
| ATOM | 1763 | CA | ARG | 194 | 76.403 | 19.757 | 83.876 | 1.00 | 31.29 | A |
| ATOM | 1764 | CB | ARG | 194 | 77.234 | 20.987 | 83.485 | 1.00 | 30.78 | A |
| ATOM | 1765 | CG | ARG | 194 | 77.738 | 21.009 | 82.031 | 1.00 | 31.35 | A |
| ATOM | 1766 | CD | ARG | 194 | 78.632 | 22.211 | 81.779 | 0.00 | 30.68 | A |
| ATOM | 1767 | NE | ARG | 194 | 79.193 | 22.208 | 80.430 | 0.00 | 30.43 | A |
| ATOM | 1769 | CZ | ARG | 194 | 78.571 | 22.681 | 79.354 | 0.00 | 30.23 | A |

- 78 -

| ATOM | 1770 | NH1 | ARG | 194 | 77.356 | 23.203 | 79.456 | 0.00 | 30.13 | A |
|------|------|-----|-----|-----|--------|--------|--------|------|-------|---|
| ATOM | 1773 | NH2 | ARG | 194 | 79.167 | 22.630 | 78.171 | 0.00 | 30.13 | A |
| ATOM | 1776 | C | ARG | 194 | 77.261 | 18.486 | 83.913 | 1.00 | 31.75 | A |
| ATOM | 1777 | O | ARG | 194 | 78.007 | 18.253 | 84.859 | 1.00 | 31.87 | A |
| ATOM | 1778 | N | ASP | 195 | 77.098 | 17.623 | 82.917 | 1.00 | 32.70 | A |
| ATOM | 1780 | CA | ASP | 195 | 77.894 | 16.418 | 82.863 | 1.00 | 33.27 | A |
| ATOM | 1781 | CB | ASP | 195 | 77.277 | 15.405 | 81.924 | 1.00 | 33.40 | A |
| ATOM | 1782 | CG | ASP | 195 | 77.939 | 14.065 | 82.030 | 1.00 | 33.29 | A |
| ATOM | 1783 | OD1 | ASP | 195 | 79.086 | 13.920 | 81.554 | 1.00 | 32.88 | A |
| ATOM | 1784 | OD2 | ASP | 195 | 77.307 | 13.164 | 82.614 | 1.00 | 33.24 | A |
| ATOM | 1785 | C | ASP | 195 | 79.230 | 16.867 | 82.309 | 1.00 | 34.30 | A |
| ATOM | 1786 | O | ASP | 195 | 79.319 | 17.252 | 81.144 | 1.00 | 34.12 | A |
| ATOM | 1787 | N | GLN | 196 | 80.275 | 16.814 | 83.128 | 1.00 | 34.92 | A |
| ATOM | 1789 | CA | GLN | 196 | 81.573 | 17.273 | 82.669 | 1.00 | 35.73 | A |
| ATOM | 1790 | CB | GLN | 196 | 82.583 | 17.236 | 83.812 | 1.00 | 36.40 | A |
| ATOM | 1791 | CG | GLN | 196 | 83.634 | 18.349 | 83.736 | 1.00 | 36.99 | A |
| ATOM | 1792 | CD | GLN | 196 | 84.599 | 18.180 | 82.579 | 1.00 | 36.96 | A |
| ATOM | 1793 | OE1 | GLN | 196 | 85.306 | 17.178 | 82.488 | 0.00 | 37.06 | A |
| ATOM | 1794 | NE2 | GLN | 196 | 84.637 | 19.163 | 81.692 | 0.00 | 37.06 | A |
| ATOM | 1797 | C | GLN | 196 | 82.084 | 16.519 | 81.438 | 1.00 | 36.06 | A |
| ATOM | 1798 | O | GLN | 196 | 82.494 | 17.145 | 80.453 | 1.00 | 35.89 | A |
| ATOM | 1799 | N | ASN | 197 | 81.934 | 15.196 | 81.460 | 1.00 | 36.28 | A |
| ATOM | 1801 | CA | ASN | 197 | 82.378 | 14.318 | 80.389 | 1.00 | 36.41 | A |
| ATOM | 1802 | CB | ASN | 197 | 82.002 | 12.872 | 80.688 | 1.00 | 38.10 | A |
| ATOM | 1803 | CG | ASN | 197 | 82.524 | 12.412 | 82.041 | 1.00 | 41.01 | A |
| ATOM | 1804 | OD1 | ASN | 197 | 83.336 | 13.110 | 82.666 | 1.00 | 42.99 | A |
| ATOM | 1805 | ND2 | ASN | 197 | 82.033 | 11.265 | 82.529 | 1.00 | 41.95 | A |
| ATOM | 1808 | C | ASN | 197 | 81.898 | 14.689 | 79.011 | 1.00 | 36.35 | A |
| ATOM | 1809 | O | ASN | 197 | 82.717 | 14.919 | 78.111 | 1.00 | 37.57 | A |
| ATOM | 1810 | N | ASN | 198 | 80.588 | 14.752 | 78.818 | 1.00 | 34.62 | A |
| ATOM | 1812 | CA | ASN | 198 | 80.067 | 15.074 | 77.490 | 1.00 | 32.85 | A |
| ATOM | 1813 | CB | ASN | 198 | 78.928 | 14.115 | 77.109 | 1.00 | 32.87 | A |
| ATOM | 1814 | CG | ASN | 198 | 77.792 | 14.079 | 78.133 | 1.00 | 32.87 | A |
| ATOM | 1815 | OD1 | ASN | 198 | 77.631 | 14.983 | 78.972 | 1.00 | 33.44 | A |
| ATOM | 1816 | ND2 | ASN | 198 | 76.995 | 13.032 | 78.060 | 1.00 | 31.77 | A |
| ATOM | 1819 | C | ASN | 198 | 79.613 | 16.517 | 77.366 | 1.00 | 31.88 | A |
| ATOM | 1820 | O | ASN | 198 | 79.260 | 16.989 | 76.271 | 1.00 | 31.09 | A |
| ATOM | 1821 | N | GLY | 199 | 79.588 | 17.189 | 78.511 | 1.00 | 30.70 | A |
| ATOM | 1823 | CA | GLY | 199 | 79.171 | 18.578 | 78.568 | 1.00 | 29.72 | A |
| ATOM | 1824 | C | GLY | 199 | 77.672 | 18.848 | 78.466 | 1.00 | 28.33 | A |
| ATOM | 1825 | O | GLY | 199 | 77.263 | 20.002 | 78.287 | 1.00 | 28.35 | A |
| ATOM | 1826 | N | LEU | 200 | 76.833 | 17.821 | 78.570 | 1.00 | 26.42 | A |
| ATOM | 1828 | CA | LEU | 200 | 75.397 | 18.073 | 78.472 | 1.00 | 24.01 | A |
| ATOM | 1829 | CB | LEU | 200 | 74.620 | 16.789 | 78.093 | 1.00 | 23.79 | A |
| ATOM | 1830 | CG | LEU | 200 | 75.023 | 15.994 | 76.854 | 1.00 | 23.60 | A |
| ATOM | 1831 | CD1 | LEU | 200 | 74.031 | 14.819 | 76.646 | 1.00 | 23.40 | A |
| ATOM | 1832 | CD2 | LEU | 200 | 75.134 | 16.739 | 75.591 | 1.00 | 21.81 | A |
| ATOM | 1833 | C | LEU | 200 | 74.876 | 18.697 | 79.777 | 1.00 | 22.76 | A |
| ATOM | 1834 | O | LEU | 200 | 75.465 | 18.550 | 80.846 | 1.00 | 21.27 | A |
| ATOM | 1835 | N | THR | 201 | 73.796 | 19.449 | 79.667 | 1.00 | 22.85 | A |
| ATOM | 1837 | CA | THR | 201 | 73.212 | 20.076 | 80.824 | 1.00 | 23.31 | A |
| ATOM | 1838 | CB | THR | 201 | 73.011 | 21.589 | 80.613 | 1.00 | 25.19 | A |
| ATOM | 1839 | OG1 | THR | 201 | 74.280 | 22.253 | 80.725 | 1.00 | 25.95 | A |
| ATOM | 1841 | CG2 | THR | 201 | 72.016 | 22.175 | 81.660 | 1.00 | 25.13 | A |
| ATOM | 1842 | C | THR | 201 | 71.914 | 19.418 | 81.217 | 1.00 | 23.07 | A |
| ATOM | 1843 | O | THR | 201 | 71.071 | 19.100 | 80.377 | 1.00 | 22.60 | A |
| ATOM | 1844 | N | TYR | 202 | 71.739 | 19.250 | 82.522 | 1.00 | 23.63 | A |
| ATOM | 1846 | CA | TYR | 202 | 70.551 | 18.612 | 83.058 | 1.00 | 22.80 | A |
| ATOM | 1847 | CB | TYR | 202 | 70.945 | 17.329 | 83.781 | 1.00 | 20.88 | A |
| ATOM | 1848 | CG | TYR | 202 | 71.435 | 16.294 | 82.798 | 1.00 | 21.45 | A |
| ATOM | 1849 | CD1 | TYR | 202 | 72.791 | 16.228 | 82.426 | 1.00 | 20.63 | A |
| ATOM | 1850 | CE1 | TYR | 202 | 73.223 | 15.280 | 81.472 | 1.00 | 19.96 | A |
| ATOM | 1851 | CD2 | TYR | 202 | 70.536 | 15.390 | 82.194 | 1.00 | 20.38 | A |
| ATOM | 1852 | CE2 | TYR | 202 | 70.960 | 14.458 | 81.256 | 1.00 | 18.50 | A |
| ATOM | 1853 | CZ | TYR | 202 | 72.294 | 14.398 | 80.895 | 1.00 | 19.98 | A |
| ATOM | 1854 | OH | TYR | 202 | 72.708 | 13.440 | 79.973 | 1.00 | 19.37 | A |
| ATOM | 1856 | C | TYR | 202 | 69.728 | 19.543 | 83.922 | 1.00 | 22.16 | A |
| ATOM | 1857 | O | TYR | 202 | 70.258 | 20.363 | 84.670 | 1.00 | 24.37 | A |
| ATOM | 1858 | N | THR | 203 | 68.429 | 19.507 | 83.720 | 1.00 | 21.66 | A |
| ATOM | 1860 | CA | THR | 203 | 67.527 | 20.332 | 84.492 | 1.00 | 20.82 | A |
| ATOM | 1861 | CB | THR | 203 | 66.861 | 21.442 | 83.631 | 1.00 | 21.96 | A |
| ATOM | 1862 | OG1 | THR | 203 | 66.251 | 20.874 | 82.453 | 1.00 | 22.52 | A |
| ATOM | 1864 | CG2 | THR | 203 | 67.909 | 22.526 | 83.216 | 1.00 | 22.52 | A |
| ATOM | 1865 | C | THR | 203 | 66.452 | 19.497 | 85.159 | 1.00 | 20.36 | A |
| ATOM | 1866 | O | THR | 203 | 65.610 | 20.056 | 85.853 | 1.00 | 22.39 | A |
| ATOM | 1867 | N | SER | 204 | 66.408 | 18.186 | 84.882 | 1.00 | 24.31 | A |
| ATOM | 1869 | CA | SER | 204 | 65.426 | 17.308 | 85.523 | 1.00 | 18.76 | A |
| ATOM | 1870 | CB | SER | 204 | 64.171 | 17.114 | 84.685 | 1.00 | 17.23 | A |
| ATOM | 1871 | OG | SER | 204 | 64.405 | 16.336 | 83.528 | 1.00 | 17.50 | A |
| ATOM | 1873 | C | SER | 204 | 66.010 | 15.966 | 85.905 | 1.00 | 16.95 | A |

| | | | | | | | | | | | | | | | | |
|---|---|---|---|---|---|---|---|---|---|---|---|---|---|---|---|---|
| ATOM | 1874 | O | SER | 204 | 66.837 | 15.402 | 85.197 | 1.00 | 16.36 | A | ATOM | 1919 | O | MET | 209 | 68.946 | 7.190 | 83.874 | 1.00 | 16.17 | A |
| ATOM | 1875 | N | LEU | 205 | 65.601 | 15.484 | 87.065 | 1.00 | 16.90 | A | ATOM | 1920 | N | VAL | 210 | 67.335 | 8.539 | 83.076 | 1.00 | 17.10 | A |
| ATOM | 1877 | CA | LEU | 205 | 66.061 | 14.202 | 87.605 | 1.00 | 17.30 | A | ATOM | 1922 | CA | VAL | 210 | 67.246 | 7.829 | 81.809 | 1.00 | 17.64 | A |
| ATOM | 1878 | CB | LEU | 205 | 65.381 | 13.962 | 88.963 | 1.00 | 17.74 | A | ATOM | 1923 | CB | VAL | 210 | 66.186 | 8.484 | 80.906 | 1.00 | 17.39 | A |
| ATOM | 1879 | CG | LEU | 205 | 65.941 | 12.839 | 89.811 | 1.00 | 16.76 | A | ATOM | 1924 | CG1 | VAL | 210 | 66.220 | 7.863 | 79.492 | 1.00 | 17.20 | A |
| ATOM | 1880 | CD1 | LEU | 205 | 67.415 | 13.040 | 89.928 | 1.00 | 15.35 | A | ATOM | 1925 | CG2 | VAL | 210 | 64.806 | 8.291 | 81.539 | 1.00 | 16.40 | A |
| ATOM | 1881 | CD2 | LEU | 205 | 65.288 | 12.871 | 91.178 | 1.00 | 17.18 | A | ATOM | 1926 | C | VAL | 210 | 68.625 | 7.805 | 81.110 | 1.00 | 18.41 | A |
| ATOM | 1882 | C | LEU | 205 | 65.720 | 13.055 | 86.640 | 1.00 | 17.44 | A | ATOM | 1927 | O | VAL | 210 | 69.092 | 6.766 | 80.562 | 1.00 | 18.26 | A |
| ATOM | 1883 | O | LEU | 205 | 66.495 | 12.100 | 86.491 | 1.00 | 17.54 | A | ATOM | 1928 | N | ASP | 211 | 69.292 | 8.955 | 81.048 | 1.00 | 19.56 | A |
| ATOM | 1884 | N | PHE | 206 | 64.525 | 13.114 | 86.043 | 1.00 | 17.07 | A | ATOM | 1930 | CA | ASP | 211 | 70.601 | 9.048 | 80.428 | 1.00 | 18.03 | A |
| ATOM | 1886 | CA | PHE | 206 | 64.115 | 12.102 | 85.092 | 1.00 | 15.51 | A | ATOM | 1931 | CB | ASP | 211 | 70.988 | 10.493 | 80.250 | 1.00 | 18.08 | A |
| ATOM | 1887 | CB | PHE | 206 | 62.789 | 12.480 | 84.483 | 1.00 | 12.12 | A | ATOM | 1932 | CG | ASP | 211 | 70.318 | 11.105 | 79.042 | 1.00 | 17.11 | A |
| ATOM | 1888 | CG | PHE | 206 | 62.234 | 11.428 | 83.579 | 1.00 | 9.19 | A | ATOM | 1933 | OD1 | ASP | 211 | 69.516 | 10.386 | 78.388 | 1.00 | 15.44 | A |
| ATOM | 1889 | CD1 | PHE | 206 | 61.680 | 10.272 | 84.110 | 1.00 | 7.63 | A | ATOM | 1934 | OD2 | ASP | 211 | 70.596 | 12.284 | 78.744 | 1.00 | 15.09 | A |
| ATOM | 1890 | CD2 | PHE | 206 | 62.228 | 11.604 | 82.193 | 1.00 | 8.12 | A | ATOM | 1935 | C | ASP | 211 | 71.706 | 8.235 | 81.047 | 1.00 | 18.54 | A |
| ATOM | 1891 | CE1 | PHE | 206 | 61.117 | 9.302 | 83.285 | 1.00 | 6.89 | A | ATOM | 1936 | O | ASP | 211 | 72.685 | 7.881 | 80.355 | 1.00 | 18.97 | A |
| ATOM | 1892 | CE2 | PHE | 206 | 61.660 | 10.634 | 81.353 | 1.00 | 6.51 | A | ATOM | 1937 | N | ALA | 212 | 71.550 | 7.012 | 82.320 | 1.00 | 18.53 | A |
| ATOM | 1893 | CZ | PHE | 206 | 61.105 | 9.492 | 81.904 | 1.00 | 5.42 | A | ATOM | 1939 | CA | ALA | 212 | 72.520 | 7.056 | 82.993 | 1.00 | 18.73 | A |
| ATOM | 1894 | C | PHE | 206 | 65.194 | 11.987 | 83.985 | 1.00 | 15.92 | A | ATOM | 1940 | CB | ALA | 212 | 72.343 | 5.564 | 84.510 | 1.00 | 18.04 | A |
| ATOM | 1895 | O | PHE | 206 | 65.771 | 10.904 | 83.736 | 1.00 | 16.60 | A | ATOM | 1941 | C | ALA | 212 | 72.298 | 4.782 | 82.455 | 1.00 | 18.43 | A |
| ATOM | 1896 | N | ASP | 207 | 65.509 | 13.111 | 83.356 | 1.00 | 16.57 | A | ATOM | 1942 | O | ALA | 212 | 73.240 | 5.228 | 82.304 | 1.00 | 18.77 | A |
| ATOM | 1898 | CA | ASP | 207 | 66.522 | 13.070 | 82.303 | 1.00 | 18.57 | A | ATOM | 1943 | N | VAL | 213 | 71.059 | 3.923 | 82.133 | 1.00 | 17.74 | A |
| ATOM | 1899 | CB | ASP | 207 | 66.797 | 14.456 | 81.724 | 1.00 | 18.68 | A | ATOM | 1945 | CA | VAL | 213 | 70.756 | 3.753 | 81.567 | 1.00 | 18.12 | A |
| ATOM | 1900 | CG | ASP | 207 | 65.637 | 14.993 | 80.927 | 1.00 | 18.86 | A | ATOM | 1946 | CB | VAL | 213 | 69.255 | 2.419 | 81.424 | 1.00 | 18.89 | A |
| ATOM | 1901 | OD1 | ASP | 207 | 64.696 | 14.224 | 80.624 | 1.00 | 19.25 | A | ATOM | 1947 | CG1 | VAL | 213 | 68.916 | 3.885 | 80.746 | 1.00 | 18.00 | A |
| ATOM | 1902 | OD2 | ASP | 207 | 65.694 | 16.185 | 80.586 | 1.00 | 19.33 | A | ATOM | 1948 | CG2 | VAL | 213 | 68.633 | 3.809 | 82.826 | 1.00 | 19.47 | A |
| ATOM | 1903 | C | ASP | 207 | 67.837 | 12.458 | 82.745 | 1.00 | 18.14 | A | ATOM | 1949 | C | VAL | 213 | 71.407 | 2.752 | 80.200 | 1.00 | 19.59 | A |
| ATOM | 1904 | O | ASP | 207 | 68.371 | 11.581 | 82.070 | 1.00 | 18.50 | A | ATOM | 1950 | O | VAL | 213 | 71.900 | 4.880 | 79.832 | 1.00 | 20.75 | A |
| ATOM | 1905 | N | ALA | 208 | 68.411 | 13.007 | 83.806 | 1.00 | 17.62 | A | ATOM | 1951 | N | TYR | 214 | 71.328 | 4.928 | 79.413 | 1.00 | 20.47 | A |
| ATOM | 1907 | CA | ALA | 208 | 69.670 | 12.500 | 84.321 | 1.00 | 16.92 | A | ATOM | 1953 | CA | TYR | 214 | 71.967 | 6.219 | 78.101 | 1.00 | 20.46 | A |
| ATOM | 1908 | CB | ALA | 208 | 70.024 | 13.231 | 85.614 | 1.00 | 15.98 | A | ATOM | 1954 | CB | TYR | 214 | 71.558 | 6.072 | 77.375 | 1.00 | 19.52 | A |
| ATOM | 1909 | C | ALA | 208 | 69.584 | 10.978 | 84.542 | 1.00 | 16.23 | A | ATOM | 1955 | CG | TYR | 214 | 70.259 | 7.038 | 76.613 | 1.00 | 20.65 | A |
| ATOM | 1910 | O | ALA | 208 | 70.522 | 10.263 | 84.228 | 1.00 | 17.52 | A | ATOM | 1956 | CD1 | TYR | 214 | 69.243 | 6.856 | 76.677 | 1.00 | 20.86 | A |
| ATOM | 1911 | N | MET | 209 | 68.456 | 10.483 | 85.034 | 1.00 | 15.50 | A | ATOM | 1957 | CE1 | TYR | 214 | 68.013 | 4.937 | 75.969 | 1.00 | 21.85 | A |
| ATOM | 1913 | CA | MET | 209 | 68.266 | 9.031 | 85.274 | 1.00 | 16.01 | A | ATOM | 1958 | CD2 | TYR | 214 | 70.030 | 5.837 | 75.837 | 1.00 | 21.10 | A |
| ATOM | 1914 | CB | MET | 209 | 67.035 | 8.757 | 86.168 | 1.00 | 14.46 | A | ATOM | 1959 | CE2 | TYR | 214 | 68.834 | 4.747 | 75.143 | 1.00 | 22.01 | A |
| ATOM | 1915 | CG | MET | 209 | 67.273 | 9.116 | 87.627 | 1.00 | 14.70 | A | ATOM | 1960 | CZ | TYR | 214 | 67.834 | 5.693 | 75.205 | 1.00 | 22.51 | A |
| ATOM | 1916 | SD | MET | 209 | 65.863 | 8.883 | 88.664 | 1.00 | 17.08 | A | ATOM | 1961 | OH | TYR | 214 | 66.684 | 5.428 | 74.482 | 1.00 | 22.11 | A |
| ATOM | 1917 | CE | MET | 209 | 66.232 | 7.369 | 89.503 | 1.00 | 18.07 | A | ATOM | 1963 | C | TYR | 214 | 67.834 | 4.829 | 78.288 | 1.00 | 20.96 | A |
| ATOM | 1918 | C | MET | 209 | 68.211 | 8.171 | 84.005 | 1.00 | 16.51 | A | ATOM | 1964 | O | TYR | 214 | 74.213 | 4.148 | 77.534 | 1.00 | 20.68 | A |

- 80 -

| ATOM | 1965 | N | ALA | 215 | 74.032 | 5.477 | 79.320 | 1.00 | 21.67 | A |
|---|---|---|---|---|---|---|---|---|---|---|
| ATOM | 1967 | CA | ALA | 215 | 75.474 | 5.405 | 79.561 | 1.00 | 21.26 | A |
| ATOM | 1968 | CB | ALA | 215 | 75.870 | 6.214 | 80.794 | 1.00 | 21.43 | A |
| ATOM | 1969 | C | ALA | 215 | 75.862 | 3.949 | 79.729 | 1.00 | 21.56 | A |
| ATOM | 1970 | O | ALA | 215 | 76.734 | 3.456 | 78.999 | 1.00 | 21.85 | A |
| ATOM | 1971 | N | ALA | 216 | 75.380 | 3.243 | 80.594 | 1.00 | 21.24 | A |
| ATOM | 1973 | CA | ALA | 216 | 75.124 | 1.832 | 80.887 | 1.00 | 21.61 | A |
| ATOM | 1974 | CB | ALA | 216 | 74.461 | 1.355 | 82.021 | 1.00 | 19.97 | A |
| ATOM | 1975 | C | ALA | 216 | 75.242 | 0.917 | 79.661 | 1.00 | 22.42 | A |
| ATOM | 1976 | O | ALA | 216 | 75.998 | -0.050 | 79.499 | 1.00 | 23.06 | A |
| ATOM | 1977 | N | LEU | 217 | 74.269 | 1.202 | 78.798 | 1.00 | 23.42 | A |
| ATOM | 1979 | CA | LEU | 217 | 74.057 | 0.392 | 77.596 | 1.00 | 22.87 | A |
| ATOM | 1980 | CB | LEU | 217 | 72.849 | 0.897 | 76.823 | 1.00 | 22.11 | A |
| ATOM | 1981 | CG | LEU | 217 | 71.412 | 0.526 | 77.365 | 1.00 | 21.11 | A |
| ATOM | 1982 | CD1 | LEU | 217 | 70.386 | 1.259 | 76.555 | 1.00 | 20.97 | A |
| ATOM | 1983 | CD2 | LEU | 217 | 71.307 | -0.997 | 77.316 | 1.00 | 20.74 | A |
| ATOM | 1984 | C | LEU | 217 | 75.287 | 0.433 | 76.712 | 1.00 | 23.81 | A |
| ATOM | 1985 | O | LEU | 217 | 75.798 | -0.624 | 76.310 | 1.00 | 24.16 | A |
| ATOM | 1986 | N | LEU | 218 | 75.789 | 1.645 | 76.459 | 1.00 | 24.36 | A |
| ATOM | 1988 | CA | GLU | 218 | 76.968 | 1.853 | 75.626 | 1.00 | 24.94 | A |
| ATOM | 1989 | CB | GLU | 218 | 77.307 | 3.323 | 75.530 | 1.00 | 26.88 | A |
| ATOM | 1990 | CG | GLU | 218 | 76.227 | 4.203 | 74.916 | 1.00 | 30.21 | A |
| ATOM | 1991 | CD | GLU | 218 | 76.802 | 5.520 | 74.397 | 1.00 | 31.61 | A |
| ATOM | 1992 | OE1 | GLU | 218 | 76.528 | 6.587 | 75.004 | 1.00 | 31.91 | A |
| ATOM | 1993 | OE2 | GLU | 218 | 77.555 | 5.470 | 73.389 | 1.00 | 33.26 | A |
| ATOM | 1994 | C | GLU | 218 | 78.174 | 1.109 | 76.145 | 1.00 | 24.50 | A |
| ATOM | 1995 | O | GLU | 218 | 78.870 | 0.466 | 75.380 | 1.00 | 24.72 | A |
| ATOM | 1996 | N | LYS | 219 | 78.423 | 1.177 | 77.444 | 1.00 | 24.80 | A |
| ATOM | 1998 | CA | LYS | 219 | 79.562 | 0.456 | 78.021 | 1.00 | 25.70 | A |
| ATOM | 1999 | CB | LYS | 219 | 79.748 | 0.758 | 79.506 | 1.00 | 24.07 | A |
| ATOM | 2000 | CG | LYS | 219 | 80.289 | 2.126 | 79.792 | 1.00 | 24.83 | A |
| ATOM | 2001 | CD | LYS | 219 | 80.292 | 2.415 | 81.286 | 1.00 | 24.45 | A |
| ATOM | 2002 | CE | LYS | 219 | 80.735 | 3.854 | 81.554 | 1.00 | 24.96 | A |
| ATOM | 2003 | NZ | LYS | 219 | 79.666 | 4.868 | 81.313 | 1.00 | 24.55 | A |
| ATOM | 2007 | C | LYS | 219 | 79.416 | -1.050 | 77.852 | 1.00 | 25.84 | A |
| ATOM | 2008 | O | LYS | 219 | 80.407 | -1.744 | 77.702 | 1.00 | 26.77 | A |
| ATOM | 2009 | N | ALA | 220 | 78.182 | -1.545 | 77.900 | 1.00 | 25.76 | A |
| ATOM | 2011 | CA | ALA | 220 | 77.896 | -2.964 | 77.762 | 1.00 | 25.29 | A |
| ATOM | 2012 | CB | ALA | 220 | 76.460 | -3.250 | 78.147 | 1.00 | 25.16 | A |
| ATOM | 2013 | C | ALA | 220 | 78.125 | -3.400 | 76.344 | 1.00 | 25.83 | A |
| ATOM | 2014 | O | ALA | 220 | 78.153 | -4.593 | 76.066 | 1.00 | 26.37 | A |
| ATOM | 2015 | N | GLY | 221 | 78.264 | -2.428 | 75.449 | 1.00 | 25.95 | A |
| ATOM | 2017 | CA | GLY | 221 | 78.464 | -2.720 | 74.045 | 1.00 | 25.87 | A |
| ATOM | 2018 | C | GLY | 221 | 77.167 | -2.650 | 73.266 | 1.00 | 26.26 | A |
| ATOM | 2019 | O | GLY | 221 | 77.102 | -3.156 | 72.167 | 1.00 | 27.17 | A |
| ATOM | 2020 | N | ALA | 222 | 76.136 | -2.014 | 73.819 | 1.00 | 27.76 | A |
| ATOM | 2022 | CA | ALA | 222 | 74.820 | -1.881 | 73.150 | 1.00 | 27.89 | A |
| ATOM | 2023 | CB | ALA | 222 | 73.757 | -2.620 | 73.943 | 1.00 | 27.14 | A |
| ATOM | 2024 | C | ALA | 222 | 74.408 | -0.406 | 72.916 | 1.00 | 28.55 | A |
| ATOM | 2025 | O | ALA | 222 | 73.359 | -0.072 | 73.382 | 1.00 | 28.72 | A |
| ATOM | 2026 | N | PRO | 223 | 75.220 | 0.325 | 72.143 | 1.00 | 28.52 | A |
| ATOM | 2027 | CD | PRO | 223 | 76.446 | -0.150 | 71.487 | 1.00 | 28.35 | A |
| ATOM | 2028 | CA | PRO | 223 | 74.995 | 1.736 | 71.819 | 1.00 | 28.09 | A |
| ATOM | 2029 | CB | PRO | 223 | 76.189 | 2.060 | 70.919 | 1.00 | 28.60 | A |
| ATOM | 2030 | CG | PRO | 223 | 77.228 | 1.115 | 71.397 | 1.00 | 28.26 | A |
| ATOM | 2031 | C | PRO | 223 | 73.676 | 2.080 | 71.126 | 1.00 | 27.31 | A |
| ATOM | 2032 | O | PRO | 223 | 73.036 | 3.043 | 71.494 | 1.00 | 27.77 | A |
| ATOM | 2033 | N | ALA | 224 | 73.265 | 1.300 | 70.133 | 1.00 | 27.01 | A |
| ATOM | 2035 | CA | ALA | 224 | 72.024 | 1.590 | 69.412 | 1.00 | 26.46 | A |
| ATOM | 2036 | CB | ALA | 224 | 72.116 | 1.063 | 67.995 | 1.00 | 26.01 | A |
| ATOM | 2037 | C | ALA | 224 | 70.711 | 1.115 | 70.089 | 1.00 | 26.30 | A |
| ATOM | 2038 | O | ALA | 224 | 69.609 | 1.354 | 69.558 | 1.00 | 26.81 | A |
| ATOM | 2039 | N | VAL | 225 | 70.827 | 0.461 | 71.249 | 1.00 | 25.14 | A |
| ATOM | 2041 | CA | VAL | 225 | 69.656 | -0.029 | 71.991 | 1.00 | 23.46 | A |
| ATOM | 2042 | CB | VAL | 225 | 70.063 | -1.033 | 73.122 | 1.00 | 22.23 | A |
| ATOM | 2043 | CG1 | VAL | 225 | 68.869 | -1.446 | 73.946 | 1.00 | 23.00 | A |
| ATOM | 2044 | CG2 | VAL | 225 | 70.619 | -2.275 | 72.509 | 1.00 | 21.82 | A |
| ATOM | 2045 | C | VAL | 225 | 68.816 | 1.132 | 72.552 | 1.00 | 22.53 | A |
| ATOM | 2046 | O | VAL | 225 | 69.349 | 2.118 | 73.068 | 1.00 | 22.03 | A |
| ATOM | 2047 | N | LYS | 226 | 67.503 | 1.036 | 72.356 | 1.00 | 21.34 | A |
| ATOM | 2049 | CA | LYS | 226 | 66.568 | 2.031 | 72.831 | 1.00 | 19.72 | A |
| ATOM | 2050 | CB | LYS | 226 | 65.405 | 2.169 | 71.854 | 1.00 | 20.36 | A |
| ATOM | 2051 | CG | LYS | 226 | 65.680 | 3.124 | 70.691 | 1.00 | 23.30 | A |
| ATOM | 2052 | CD | LYS | 226 | 64.632 | 2.985 | 69.552 | 1.00 | 24.08 | A |
| ATOM | 2053 | CE | LYS | 226 | 64.906 | 3.964 | 68.417 | 0.00 | 23.66 | A |
| ATOM | 2054 | NZ | LYS | 226 | 66.237 | 3.737 | 67.789 | 0.00 | 23.78 | A |
| ATOM | 2058 | C | LYS | 226 | 66.062 | 1.629 | 74.227 | 1.00 | 21.82 | A |
| ATOM | 2059 | O | LYS | 226 | 66.108 | 0.456 | 74.611 | 1.00 | 18.60 | A |
| ATOM | 2060 | N | VAL | 227 | 65.612 | 2.630 | 74.979 | 1.00 | 18.67 | A |
| ATOM | 2062 | CA | VAL | 227 | 65.094 | 2.462 | 76.324 | 1.00 | 16.88 | A |

- 81 -

| ATOM | 2063 | CB | VAL | 227 | 65.840 | 3.429 | 77.326 | 1.00 | 13.78 | A |
| --- | --- | --- | --- | --- | --- | --- | --- | --- | --- | --- |
| ATOM | 2064 | CG1 | VAL | 227 | 65.056 | 3.671 | 78.600 | 1.00 | 12.63 | A |
| ATOM | 2065 | CG2 | VAL | 227 | 67.164 | 2.875 | 77.674 | 1.00 | 14.84 | A |
| ATOM | 2066 | C | VAL | 227 | 63.614 | 2.822 | 76.278 | 1.00 | 12.09 | A |
| ATOM | 2067 | O | VAL | 227 | 63.240 | 3.791 | 75.604 | 1.00 | 11.41 | A |
| ATOM | 2068 | N | VAL | 228 | 62.794 | 1.962 | 76.878 | 1.00 | 9.74 | A |
| ATOM | 2070 | CA | VAL | 228 | 61.354 | 2.157 | 77.053 | 1.00 | 9.40 | A |
| ATOM | 2071 | CB | VAL | 228 | 60.565 | 0.957 | 76.453 | 1.00 | 9.77 | A |
| ATOM | 2072 | CG1 | VAL | 228 | 59.080 | 1.009 | 76.792 | 1.00 | 6.83 | A |
| ATOM | 2073 | CG2 | VAL | 228 | 60.722 | 0.994 | 74.942 | 1.00 | 10.07 | A |
| ATOM | 2074 | C | VAL | 228 | 61.191 | 2.317 | 78.615 | 1.00 | 9.91 | A |
| ATOM | 2075 | O | VAL | 228 | 61.748 | 1.519 | 79.391 | 1.00 | 10.07 | A |
| ATOM | 2076 | N | VAL | 229 | 60.618 | 3.429 | 79.077 | 1.00 | 9.10 | A |
| ATOM | 2078 | CA | VAL | 229 | 60.467 | 3.662 | 80.517 | 1.00 | 8.19 | A |
| ATOM | 2079 | CB | VAL | 229 | 60.336 | 5.206 | 80.849 | 1.00 | 9.18 | A |
| ATOM | 2080 | CG1 | VAL | 229 | 60.147 | 5.436 | 82.349 | 1.00 | 8.17 | A |
| ATOM | 2081 | CG2 | VAL | 229 | 61.584 | 5.958 | 80.400 | 1.00 | 7.88 | A |
| ATOM | 2082 | C | VAL | 229 | 59.233 | 2.868 | 80.566 | 1.00 | 8.51 | A |
| ATOM | 2083 | O | VAL | 229 | 58.088 | 3.292 | 80.863 | 1.00 | 7.81 | A |
| ATOM | 2084 | N | SER | 230 | 59.472 | 1.651 | 81.363 | 1.00 | 8.29 | A |
| ATOM | 2086 | CA | SER | 230 | 58.379 | 0.759 | 81.671 | 1.00 | 7.34 | A |
| ATOM | 2087 | CB | SER | 230 | 58.812 | -0.720 | 81.635 | 1.00 | 7.28 | A |
| ATOM | 2088 | OG | SER | 230 | 59.945 | -1.005 | 82.440 | 1.00 | 5.35 | A |
| ATOM | 2089 | C | SER | 230 | 57.554 | 1.103 | 82.896 | 1.00 | 8.15 | A |
| ATOM | 2090 | O | SER | 230 | 56.485 | 0.507 | 83.105 | 1.00 | 7.17 | A |
| ATOM | 2091 | N | GLU | 231 | 58.038 | 2.060 | 83.702 | 1.00 | 8.85 | A |
| ATOM | 2092 | CA | GLU | 231 | 57.311 | 2.550 | 84.883 | 1.00 | 8.05 | A |
| ATOM | 2094 | CB | GLU | 231 | 57.400 | 1.614 | 86.074 | 1.00 | 7.44 | A |
| ATOM | 2095 | CG | GLU | 231 | 56.489 | 0.389 | 86.062 | 1.00 | 8.56 | A |
| ATOM | 2096 | CD | GLU | 231 | 56.719 | -0.501 | 87.279 | 1.00 | 9.35 | A |
| ATOM | 2097 | OE1 | GLU | 231 | 57.424 | -0.099 | 88.228 | 1.00 | 10.10 | A |
| ATOM | 2098 | OE2 | GLU | 231 | 56.178 | -1.601 | 87.311 | 1.00 | 10.72 | A |
| ATOM | 2099 | C | GLU | 231 | 57.915 | 3.830 | 85.362 | 1.00 | 10.46 | A |
| ATOM | 2100 | O | GLU | 231 | 59.145 | 3.947 | 85.424 | 1.00 | 11.60 | A |
| ATOM | 2101 | N | SER | 232 | 57.046 | 4.775 | 85.715 | 1.00 | 11.58 | A |
| ATOM | 2103 | CA | SER | 232 | 57.416 | 6.053 | 86.334 | 1.00 | 11.69 | A |
| ATOM | 2104 | CB | SER | 232 | 57.995 | 7.037 | 85.339 | 1.00 | 11.65 | A |
| ATOM | 2105 | OG | SER | 232 | 58.738 | 7.997 | 86.052 | 1.00 | 12.10 | A |
| ATOM | 2106 | C | SER | 232 | 56.106 | 6.580 | 86.982 | 1.00 | 12.11 | A |
| ATOM | 2108 | O | SER | 232 | 55.012 | 6.344 | 86.440 | 1.00 | 12.15 | A |
| ATOM | 2110 | N | GLY | 233 | 56.193 | 7.177 | 88.172 | 1.00 | 11.56 | A |
| ATOM | 2112 | CA | GLY | 233 | 54.983 | 7.665 | 88.843 | 1.00 | 11.71 | A |
| ATOM | 2113 | C | GLY | 233 | 55.289 | 8.356 | 90.168 | 1.00 | 12.14 | A |
| ATOM | 2114 | O | GLY | 233 | 56.430 | 8.350 | 90.623 | 1.00 | 10.94 | A |
| ATOM | 2115 | N | TRP | 234 | 54.280 | 8.932 | 90.817 | 1.00 | 12.27 | A |
| ATOM | 2117 | CA | TRP | 234 | 54.510 | 9.643 | 92.078 | 1.00 | 12.53 | A |
| ATOM | 2118 | CB | TRP | 234 | 54.694 | 11.137 | 91.813 | 1.00 | 13.09 | A |
| ATOM | 2119 | CG | TRP | 234 | 55.284 | 11.897 | 92.972 | 1.00 | 13.18 | A |
| ATOM | 2120 | CD2 | TRP | 234 | 56.580 | 12.522 | 93.011 | 1.00 | 12.79 | A |
| ATOM | 2121 | CE2 | TRP | 234 | 56.669 | 13.220 | 94.250 | 1.00 | 12.30 | A |
| ATOM | 2122 | CE3 | TRP | 234 | 57.666 | 12.573 | 92.116 | 1.00 | 12.99 | A |
| ATOM | 2123 | CD1 | TRP | 234 | 54.670 | 12.207 | 94.176 | 1.00 | 12.48 | A |
| ATOM | 2124 | NE1 | TRP | 234 | 55.497 | 13.001 | 94.933 | 1.00 | 12.79 | A |
| ATOM | 2126 | CZ2 | TRP | 234 | 57.791 | 13.960 | 94.608 | 1.00 | 11.75 | A |
| ATOM | 2127 | CZ3 | TRP | 234 | 58.808 | 13.321 | 92.481 | 1.00 | 12.59 | A |
| ATOM | 2128 | CH2 | TRP | 234 | 58.852 | 14.004 | 93.717 | 1.00 | 12.10 | A |
| ATOM | 2129 | C | TRP | 234 | 53.258 | 9.412 | 92.911 | 1.00 | 12.95 | A |
| ATOM | 2130 | O | TRP | 234 | 52.152 | 9.752 | 92.467 | 1.00 | 13.65 | A |
| ATOM | 2131 | N | PRO | 235 | 53.409 | 8.895 | 94.150 | 1.00 | 12.42 | A |
| ATOM | 2132 | CD | PRO | 235 | 54.691 | 8.702 | 94.861 | 1.00 | 12.83 | A |
| ATOM | 2133 | CA | PRO | 235 | 52.284 | 8.599 | 95.047 | 1.00 | 12.01 | A |
| ATOM | 2134 | CB | PRO | 235 | 52.944 | 7.713 | 96.106 | 1.00 | 11.48 | A |
| ATOM | 2135 | CG | PRO | 235 | 54.252 | 8.348 | 96.274 | 1.00 | 11.18 | A |
| ATOM | 2136 | C | PRO | 235 | 51.597 | 9.823 | 95.625 | 1.00 | 12.22 | A |
| ATOM | 2137 | O | PRO | 235 | 52.221 | 10.849 | 95.852 | 1.00 | 12.45 | A |
| ATOM | 2138 | N | SER | 236 | 50.291 | 9.711 | 95.825 | 1.00 | 14.05 | A |
| ATOM | 2140 | CA | SER | 236 | 49.457 | 10.794 | 96.344 | 1.00 | 14.41 | A |
| ATOM | 2141 | CB | SER | 236 | 48.120 | 10.790 | 95.602 | 1.00 | 13.30 | A |
| ATOM | 2142 | OG | SER | 236 | 47.451 | 9.565 | 95.835 | 1.00 | 10.82 | A |
| ATOM | 2144 | C | SER | 236 | 49.193 | 10.757 | 97.861 | 1.00 | 15.28 | A |
| ATOM | 2145 | O | SER | 236 | 48.554 | 11.673 | 98.386 | 1.00 | 16.59 | A |
| ATOM | 2146 | N | ALA | 237 | 49.718 | 9.744 | 98.560 | 1.00 | 16.42 | A |
| ATOM | 2148 | CA | ALA | 237 | 49.549 | 9.569 | 100.016 | 1.00 | 15.68 | A |
| ATOM | 2149 | CB | ALA | 237 | 48.075 | 9.262 | 100.332 | 1.00 | 14.71 | A |
| ATOM | 2150 | C | ALA | 237 | 50.405 | 8.396 | 100.497 | 1.00 | 15.98 | A |
| ATOM | 2151 | O | ALA | 237 | 50.896 | 7.609 | 99.689 | 1.00 | 17.96 | A |
| ATOM | 2152 | N | GLY | 238 | 50.614 | 8.311 | 101.812 | 1.00 | 16.13 | A |
| ATOM | 2154 | CA | GLY | 238 | 51.353 | 7.215 | 102.429 | 1.00 | 15.08 | A |
| ATOM | 2155 | C | GLY | 238 | 52.799 | 7.397 | 102.849 | 1.00 | 14.82 | A |
| ATOM | 2156 | O | GLY | 238 | 53.454 | 6.426 | 103.276 | 1.00 | 14.22 | A |

- 82 -

| ATOM | 2157 | N | GLY | 239 | 53.293 | 8.626 | 102.758 | 1.00 | 14.15 | A | | ATOM | 2205 | N | ASN | 246 | 51.822 | 17.153 | 94.377 | 1.00 | 17.48 | A |
|------|------|---|-----|-----|--------|-------|---------|------|-------|---|---|------|------|---|-----|-----|--------|--------|--------|------|-------|---|
| ATOM | 2159 | CA | GLY | 239 | 54.665 | 8.809 | 103.118 | 1.00 | 14.07 | A | | ATOM | 2207 | CA | ASN | 246 | 53.128 | 16.615 | 93.950 | 1.00 | 18.75 | A |
| ATOM | 2160 | C | GLY | 239 | 55.150 | 10.256 | 102.706 | 1.00 | 15.76 | A | | ATOM | 2208 | CB | ASN | 246 | 53.936 | 16.083 | 95.144 | 1.00 | 18.85 | A |
| ATOM | 2161 | O | GLY | 239 | 54.338 | 11.109 | 102.279 | 1.00 | 14.93 | A | | ATOM | 2209 | CG | ASN | 246 | 54.705 | 17.181 | 95.871 | 1.00 | 19.88 | A |
| ATOM | 2162 | N | PHE | 240 | 56.481 | 10.424 | 102.771 | 1.00 | 15.87 | A | | ATOM | 2210 | OD1 | ASN | 246 | 54.755 | 18.340 | 95.426 | 1.00 | 18.81 | A |
| ATOM | 2164 | CA | PHE | 240 | 57.173 | 11.664 | 102.481 | 1.00 | 16.31 | A | | ATOM | 2211 | ND2 | ASN | 246 | 55.347 | 16.809 | 96.979 | 1.00 | 20.86 | A |
| ATOM | 2165 | CB | PHE | 240 | 58.652 | 11.522 | 102.831 | 1.00 | 16.80 | A | | ATOM | 2214 | C | ASN | 246 | 52.987 | 15.535 | 92.846 | 1.00 | 18.46 | A |
| ATOM | 2166 | CG | PHE | 240 | 59.497 | 12.646 | 102.337 | 1.00 | 16.87 | A | | ATOM | 2215 | O | ASN | 246 | 53.740 | 15.540 | 91.865 | 1.00 | 18.02 | A |
| ATOM | 2167 | CD1 | PHE | 240 | 59.490 | 13.883 | 102.988 | 1.00 | 17.38 | A | | ATOM | 2216 | N | ALA | 247 | 52.013 | 14.638 | 93.016 | 1.00 | 18.28 | A |
| ATOM | 2168 | CD2 | PHE | 240 | 60.305 | 12.483 | 101.212 | 1.00 | 16.14 | A | | ATOM | 2218 | CA | ALA | 247 | 51.733 | 13.593 | 92.054 | 1.00 | 17.85 | A |
| ATOM | 2169 | CE1 | PHE | 240 | 60.291 | 14.954 | 102.503 | 1.00 | 17.44 | A | | ATOM | 2219 | CB | ALA | 247 | 50.816 | 12.592 | 92.658 | 1.00 | 16.03 | A |
| ATOM | 2170 | CE2 | PHE | 240 | 61.107 | 13.536 | 100.723 | 1.00 | 15.27 | A | | ATOM | 2220 | C | ALA | 247 | 51.120 | 14.175 | 90.742 | 1.00 | 19.40 | A |
| ATOM | 2171 | CZ | PHE | 240 | 61.102 | 14.761 | 101.357 | 1.00 | 16.98 | A | | ATOM | 2221 | O | ALA | 247 | 51.466 | 13.708 | 89.635 | 1.00 | 20.05 | A |
| ATOM | 2172 | C | PHE | 240 | 57.018 | 12.164 | 101.066 | 1.00 | 17.12 | A | | ATOM | 2222 | N | ARG | 248 | 50.221 | 15.173 | 90.852 | 1.00 | 18.87 | A |
| ATOM | 2173 | O | PHE | 240 | 57.345 | 11.464 | 100.119 | 1.00 | 18.95 | A | | ATOM | 2224 | CA | ARG | 248 | 49.616 | 15.814 | 89.664 | 1.00 | 18.23 | A |
| ATOM | 2174 | N | ALA | 241 | 56.562 | 13.410 | 100.955 | 1.00 | 17.16 | A | | ATOM | 2225 | CB | ARG | 248 | 48.583 | 16.891 | 90.031 | 1.00 | 18.11 | A |
| ATOM | 2176 | CA | ALA | 241 | 56.338 | 14.127 | 99.702 | 1.00 | 16.68 | A | | ATOM | 2226 | CG | ARG | 248 | 47.714 | 17.371 | 88.844 | 1.00 | 20.02 | A |
| ATOM | 2177 | CB | ALA | 241 | 57.624 | 14.212 | 98.848 | 1.00 | 16.77 | A | | ATOM | 2227 | CD | ARG | 248 | 47.699 | 18.900 | 88.586 | 1.00 | 21.03 | A |
| ATOM | 2178 | C | ALA | 241 | 55.189 | 13.592 | 98.864 | 1.00 | 17.06 | A | | ATOM | 2228 | NE | ARG | 248 | 47.478 | 19.648 | 89.817 | 1.00 | 22.49 | A |
| ATOM | 2179 | O | ALA | 241 | 55.020 | 14.048 | 97.730 | 1.00 | 16.03 | A | | ATOM | 2230 | CZ | ARG | 248 | 48.290 | 20.596 | 90.283 | 1.00 | 23.58 | A |
| ATOM | 2180 | N | ALA | 242 | 54.412 | 12.651 | 99.405 | 1.00 | 16.05 | A | | ATOM | 2231 | NH1 | ARG | 248 | 49.377 | 20.954 | 89.612 | 1.00 | 25.03 | A |
| ATOM | 2182 | CA | ALA | 242 | 53.286 | 12.080 | 98.685 | 1.00 | 16.75 | A | | ATOM | 2234 | NH2 | ARG | 248 | 48.095 | 21.099 | 91.495 | 1.00 | 24.58 | A |
| ATOM | 2183 | CB | ALA | 242 | 52.993 | 10.673 | 99.187 | 1.00 | 16.54 | A | | ATOM | 2237 | C | ARG | 248 | 50.769 | 16.481 | 88.946 | 1.00 | 17.19 | A |
| ATOM | 2184 | C | ALA | 242 | 52.045 | 12.946 | 98.841 | 1.00 | 17.72 | A | | ATOM | 2238 | O | ARG | 248 | 51.066 | 16.190 | 87.779 | 1.00 | 18.34 | A |
| ATOM | 2185 | O | ALA | 242 | 51.555 | 13.134 | 99.947 | 1.00 | 18.85 | A | | ATOM | 2239 | N | THR | 249 | 51.462 | 17.335 | 89.672 | 1.00 | 15.98 | A |
| ATOM | 2186 | N | SER | 243 | 51.517 | 13.467 | 97.745 | 1.00 | 17.34 | A | | ATOM | 2241 | CA | THR | 249 | 52.600 | 18.035 | 89.110 | 1.00 | 14.97 | A |
| ATOM | 2188 | CA | SER | 243 | 50.336 | 14.294 | 97.822 | 1.00 | 17.51 | A | | ATOM | 2242 | CB | THR | 249 | 53.292 | 18.896 | 90.189 | 1.00 | 14.22 | A |
| ATOM | 2189 | CB | SER | 243 | 50.685 | 15.689 | 98.386 | 1.00 | 17.27 | A | | ATOM | 2243 | OG1 | THR | 249 | 52.338 | 19.807 | 90.739 | 1.00 | 16.44 | A |
| ATOM | 2190 | OG | SER | 243 | 51.690 | 16.373 | 97.650 | 1.00 | 17.81 | A | | ATOM | 2245 | CG2 | THR | 249 | 54.425 | 19.686 | 89.612 | 1.00 | 12.66 | A |
| ATOM | 2192 | C | SER | 243 | 49.776 | 14.396 | 96.419 | 1.00 | 18.35 | A | | ATOM | 2246 | C | THR | 249 | 53.610 | 17.098 | 88.415 | 1.00 | 14.74 | A |
| ATOM | 2193 | O | SER | 243 | 50.436 | 14.007 | 95.452 | 1.00 | 19.78 | A | | ATOM | 2247 | O | THR | 249 | 54.020 | 17.391 | 87.287 | 1.00 | 15.10 | A |
| ATOM | 2194 | N | ALA | 244 | 48.556 | 14.897 | 96.286 | 1.00 | 17.72 | A | | ATOM | 2248 | N | TYR | 250 | 53.986 | 15.975 | 89.042 | 1.00 | 14.08 | A |
| ATOM | 2196 | CA | ALA | 244 | 47.968 | 15.027 | 94.963 | 1.00 | 18.92 | A | | ATOM | 2250 | CA | TYR | 250 | 54.960 | 15.052 | 88.424 | 1.00 | 14.05 | A |
| ATOM | 2197 | CB | ALA | 244 | 46.446 | 15.299 | 95.057 | 1.00 | 17.27 | A | | ATOM | 2251 | CB | TYR | 250 | 55.052 | 13.987 | 89.434 | 1.00 | 13.18 | A |
| ATOM | 2198 | C | ALA | 244 | 48.652 | 16.118 | 94.149 | 1.00 | 17.40 | A | | ATOM | 2252 | CG | TYR | 250 | 56.468 | 13.028 | 88.839 | 1.00 | 16.56 | A |
| ATOM | 2199 | O | ALA | 244 | 48.858 | 15.969 | 92.955 | 1.00 | 17.11 | A | | ATOM | 2253 | CD1 | TYR | 250 | 57.841 | 13.362 | 88.755 | 1.00 | 17.73 | A |
| ATOM | 2200 | N | GLY | 245 | 49.035 | 17.214 | 94.798 | 1.00 | 15.90 | A | | ATOM | 2254 | CE1 | TYR | 250 | 58.752 | 12.550 | 88.001 | 1.00 | 17.62 | A |
| ATOM | 2202 | CA | GLY | 245 | 49.693 | 18.285 | 94.089 | 1.00 | 17.21 | A | | ATOM | 2255 | CD2 | TYR | 250 | 56.047 | 11.858 | 88.193 | 1.00 | 16.49 | A |
| ATOM | 2203 | C | GLY | 245 | 51.021 | 17.820 | 93.531 | 1.00 | 16.87 | A | | ATOM | 2256 | CE2 | TYR | 250 | 56.935 | 11.057 | 87.461 | 1.00 | 17.45 | A |
| ATOM | 2204 | O | GLY | 245 | 51.342 | 18.126 | 92.367 | 1.00 | | A | | ATOM | 2257 | CZ | TYR | 250 | 58.268 | 11.408 | 87.354 | 1.00 | 17.26 | A |

- 83 -

| | | | | | | | | | |
|---|---|---|---|---|---|---|---|---|---|
| ATOM | 2258 | OH | TYR | 250 | 59.055 | 10.657 | 86.514 | 1.00 17.42 | A |
| ATOM | 2260 | C | TYR | 250 | 54.443 | 14.391 | 87.115 | 1.00 14.08 | A |
| ATOM | 2261 | O | TYR | 250 | 55.053 | 14.505 | 87.193 | 1.00 14.37 | A |
| ATOM | 2262 | N | ASN | 251 | 53.279 | 13.772 | 87.193 | 1.00 14.00 | A |
| ATOM | 2264 | CA | ASN | 251 | 52.680 | 13.081 | 86.075 | 1.00 14.00 | A |
| ATOM | 2265 | CB | ASN | 251 | 51.495 | 12.244 | 86.574 | 1.00 13.83 | A |
| ATOM | 2266 | CG | ASN | 251 | 51.954 | 11.051 | 87.095 | 1.00 14.47 | A |
| ATOM | 2267 | OD1 | ASN | 251 | 52.996 | 10.467 | 88.452 | 1.00 15.99 | A |
| ATOM | 2268 | ND2 | ASN | 251 | 51.211 | 10.692 | 84.893 | 1.00 12.89 | A |
| ATOM | 2271 | C | ASN | 251 | 52.328 | 13.974 | 84.893 | 1.00 14.62 | A |
| ATOM | 2272 | O | ASN | 251 | 51.706 | 15.133 | 85.130 | 1.00 13.92 | A |
| ATOM | 2273 | N | GLN | 252 | 51.387 | 16.033 | 84.029 | 1.00 14.95 | A |
| ATOM | 2275 | CA | GLN | 252 | 50.604 | 17.255 | 84.498 | 1.00 15.64 | A |
| ATOM | 2276 | CB | GLN | 252 | 50.002 | 18.034 | 83.341 | 1.00 15.86 | A |
| ATOM | 2277 | CG | GLN | 252 | 49.020 | 17.199 | 82.489 | 1.00 16.34 | A |
| ATOM | 2278 | CD | GLN | 252 | 47.897 | 16.876 | 82.906 | 1.00 16.51 | A |
| ATOM | 2279 | OE1 | GLN | 252 | 49.436 | 16.891 | 81.275 | 1.00 14.06 | A |
| ATOM | 2280 | NE2 | GLN | 252 | 52.703 | 16.498 | 83.463 | 1.00 17.87 | A |
| ATOM | 2283 | C | GLN | 252 | 52.909 | 16.572 | 82.237 | 1.00 16.29 | A |
| ATOM | 2284 | O | GLN | 252 | 53.616 | 16.800 | 84.364 | 1.00 18.37 | A |
| ATOM | 2285 | N | GLY | 253 | 54.931 | 17.250 | 83.944 | 1.00 16.69 | A |
| ATOM | 2287 | CA | GLY | 253 | 55.582 | 16.279 | 82.984 | 1.00 17.35 | A |
| ATOM | 2288 | C | GLY | 253 | 56.116 | 16.701 | 81.975 | 1.00 17.32 | A |
| ATOM | 2289 | O | GLY | 253 | 55.508 | 14.992 | 83.355 | 1.00 16.91 | A |
| ATOM | 2290 | N | LEU | 254 | 56.078 | 13.862 | 82.616 | 1.00 17.63 | A |
| ATOM | 2292 | CA | LEU | 254 | 55.908 | 12.567 | 83.435 | 1.00 16.93 | A |
| ATOM | 2293 | CB | LEU | 254 | 56.397 | 11.238 | 82.840 | 1.00 15.26 | A |
| ATOM | 2294 | CG | LEU | 254 | 57.903 | 11.311 | 82.566 | 1.00 15.10 | A |
| ATOM | 2295 | CD1 | LEU | 254 | 56.054 | 10.067 | 83.768 | 1.00 14.84 | A |
| ATOM | 2296 | CD2 | LEU | 254 | 55.397 | 13.744 | 81.267 | 1.00 13.88 | A |
| ATOM | 2297 | C | LEU | 254 | 56.062 | 13.681 | 80.236 | 1.00 16.98 | A |
| ATOM | 2298 | O | LEU | 254 | 54.076 | 13.788 | 81.277 | 1.00 17.83 | A |
| ATOM | 2299 | N | ILE | 255 | 53.321 | 13.700 | 80.057 | 1.00 16.27 | A |
| ATOM | 2301 | CA | ILE | 255 | 51.803 | 13.788 | 80.298 | 1.00 17.17 | A |
| ATOM | 2302 | CB | ILE | 255 | 51.057 | 14.071 | 78.956 | 1.00 18.07 | A |
| ATOM | 2303 | CG2 | ILE | 255 | 51.291 | 12.476 | 80.902 | 1.00 17.91 | A |
| ATOM | 2304 | CG1 | ILE | 255 | 49.900 | 12.575 | 81.488 | 1.00 18.53 | A |
| ATOM | 2305 | CD1 | ILE | 255 | 53.701 | 14.825 | 79.112 | 1.00 19.67 | A |
| ATOM | 2306 | C | ILE | 255 | 53.807 | 14.599 | 77.889 | 1.00 17.71 | A |
| ATOM | 2307 | O | ILE | 255 | | | | 1.00 18.73 | A |
| ATOM | 2308 | N | ASN | 256 | 53.945 | 16.019 | 79.645 | 1.00 16.28 | A |
| ATOM | 2310 | CA | ASN | 256 | 54.270 | 17.122 | 78.760 | 1.00 15.34 | A |
| ATOM | 2311 | CB | ASN | 256 | 53.951 | 18.457 | 79.406 | 1.00 15.69 | A |
| ATOM | 2312 | CG | ASN | 256 | 52.494 | 18.626 | 79.679 | 1.00 17.19 | A |
| ATOM | 2313 | OD1 | ASN | 256 | 51.664 | 18.029 | 79.003 | 1.00 20.52 | A |
| ATOM | 2314 | ND2 | ASN | 256 | 52.154 | 19.445 | 80.663 | 1.00 18.03 | A |
| ATOM | 2317 | C | ASN | 256 | 55.712 | 17.148 | 78.428 | 1.00 15.51 | A |
| ATOM | 2318 | O | ASN | 256 | 18.035 | | 77.717 | 1.00 16.47 | A |
| ATOM | 2319 | N | HIS | 257 | 56.132 | 18.035 | 77.717 | 1.00 16.47 | A |
| ATOM | 2321 | CA | HIS | 257 | 56.489 | 16.200 | 78.927 | 1.00 15.26 | A |
| ATOM | 2322 | CB | HIS | 257 | 57.935 | 16.219 | 78.708 | 1.00 15.75 | A |
| ATOM | 2323 | CG | HIS | 257 | 58.599 | 16.079 | 80.087 | 1.00 16.31 | A |
| ATOM | 2324 | CD2 | HIS | 257 | 60.076 | 15.855 | 80.052 | 1.00 17.27 | A |
| ATOM | 2325 | ND1 | HIS | 257 | 60.800 | 14.721 | 79.919 | 1.00 16.80 | A |
| ATOM | 2327 | CE1 | HIS | 257 | 60.991 | 16.869 | 80.277 | 1.00 19.25 | A |
| ATOM | 2328 | NE2 | HIS | 257 | 62.212 | 16.365 | 80.290 | 1.00 18.51 | A |
| ATOM | 2330 | C | HIS | 257 | 62.121 | 15.063 | 80.073 | 1.00 18.56 | A |
| ATOM | 2331 | O | HIS | 257 | 58.608 | 15.257 | 77.742 | 1.00 16.48 | A |
| ATOM | 2332 | N | VAL | 258 | 59.507 | 15.669 | 76.992 | 1.00 15.74 | A |
| ATOM | 2334 | CA | VAL | 258 | 58.240 | 13.970 | 77.852 | 1.00 18.08 | A |
| ATOM | 2335 | CB | VAL | 258 | 58.835 | 12.848 | 77.093 | 1.00 19.09 | A |
| ATOM | 2336 | CG1 | VAL | 258 | 58.220 | 11.431 | 77.527 | 1.00 18.57 | A |
| ATOM | 2337 | CG2 | VAL | 258 | 58.430 | 11.168 | 78.999 | 1.00 18.46 | A |
| ATOM | 2338 | C | VAL | 258 | 56.719 | 11.327 | 77.218 | 1.00 17.85 | A |
| ATOM | 2339 | O | VAL | 258 | 58.882 | 12.954 | 75.556 | 1.00 20.11 | A |
| ATOM | 2340 | N | GLY | 259 | 59.704 | 12.300 | 74.898 | 1.00 19.41 | A |
| ATOM | 2342 | CA | GLY | 259 | 58.022 | 13.799 | 73.559 | 1.00 21.72 | A |
| ATOM | 2343 | C | GLY | 259 | 57.987 | 13.979 | 72.975 | 1.00 23.84 | A |
| ATOM | 2344 | O | GLY | 259 | 59.236 | 14.614 | 14.702 | 1.00 25.38 | A |
| ATOM | 2345 | N | GLY | 260 | 59.380 | 14.702 | 71.764 | 1.00 26.91 | A |
| ATOM | 2347 | CA | GLY | 260 | 60.132 | 15.089 | 73.826 | 1.00 26.78 | A |
| ATOM | 2348 | C | GLY | 260 | 61.349 | 15.710 | 73.344 | 1.00 26.73 | A |
| ATOM | 2349 | O | GLY | 260 | 62.595 | 14.964 | 73.778 | 1.00 27.40 | A |
| ATOM | 2350 | N | GLY | 261 | 63.706 | 15.477 | 73.662 | 1.00 27.51 | A |
| ATOM | 2352 | CA | GLY | 261 | 62.428 | 13.751 | 74.274 | 1.00 26.77 | A |
| ATOM | 2353 | C | GLY | 261 | 63.600 | 13.021 | 74.688 | 1.00 27.35 | A |
| ATOM | 2354 | O | GLY | 261 | 64.418 | 13.623 | 75.831 | 1.00 27.81 | A |
| ATOM | 2355 | N | THR | 262 | 63.881 | 14.280 | 76.739 | 1.00 28.25 | A |
| ATOM | 2357 | CA | THR | 262 | 65.734 | 13.405 | 75.752 | 1.00 27.11 | A |
| ATOM | 2358 | CB | THR | 262 | 66.704 | 13.824 | 76.747 | 1.00 25.99 | A |
| ATOM | | | THR | 262 | 67.218 | 12.568 | 77.544 | 1.00 26.78 | A |

- 84 -

| | | | | | | | | | |
|---|---|---|---|---|---|---|---|---|---|
| ATOM | 2359 | OG1 | THR | 262 | 68.002 | 11.721 | 76.680 | 1.00 26.18 | A |
| ATOM | 2361 | CG2 | THR | 262 | 66.054 | 11.759 | 78.113 | 1.00 25.36 | A |
| ATOM | 2362 | C | THR | 262 | 67.908 | 14.420 | 76.027 | 1.00 25.47 | A |
| ATOM | 2363 | O | THR | 262 | 68.010 | 14.336 | 74.799 | 1.00 24.18 | A |
| ATOM | 2364 | N | PRO | 263 | 68.849 | 15.016 | 76.782 | 1.00 25.74 | A |
| ATOM | 2365 | CD | PRO | 263 | 68.791 | 15.351 | 78.211 | 1.00 25.66 | A |
| ATOM | 2366 | CA | PRO | 263 | 70.049 | 15.609 | 76.183 | 1.00 26.05 | A |
| ATOM | 2367 | CB | PRO | 263 | 70.822 | 16.101 | 77.400 | 1.00 25.61 | A |
| ATOM | 2368 | CG | PRO | 263 | 69.744 | 16.525 | 78.288 | 1.00 25.13 | A |
| ATOM | 2369 | C | PRO | 263 | 70.863 | 14.619 | 75.337 | 1.00 26.54 | A |
| ATOM | 2370 | O | PRO | 263 | 71.474 | 15.009 | 74.370 | 1.00 28.32 | A |
| ATOM | 2371 | N | LYS | 264 | 70.929 | 13.353 | 75.722 | 1.00 27.12 | A |
| ATOM | 2373 | CA | LYS | 264 | 71.647 | 12.357 | 74.922 | 1.00 27.39 | A |
| ATOM | 2374 | CB | LYS | 264 | 71.854 | 11.090 | 75.733 | 1.00 27.47 | A |
| ATOM | 2375 | CG | LYS | 264 | 73.087 | 11.128 | 76.504 | 1.00 28.09 | A |
| ATOM | 2376 | CD | LYS | 264 | 74.233 | 10.829 | 75.609 | 1.00 29.69 | A |
| ATOM | 2377 | CE | LYS | 264 | 74.189 | 9.370 | 75.165 | 1.00 30.48 | A |
| ATOM | 2378 | NZ | LYS | 264 | 75.515 | 8.997 | 74.558 | 1.00 32.24 | A |
| ATOM | 2382 | C | LYS | 264 | 70.887 | 11.974 | 73.644 | 1.00 27.77 | A |
| ATOM | 2383 | O | LYS | 264 | 71.493 | 11.745 | 72.594 | 1.00 28.18 | A |
| ATOM | 2384 | N | LYS | 265 | 69.560 | 11.890 | 73.752 | 1.00 27.97 | A |
| ATOM | 2386 | CA | LYS | 265 | 68.691 | 11.509 | 72.645 | 1.00 27.48 | A |
| ATOM | 2387 | CB | LYS | 265 | 68.392 | 10.014 | 72.740 | 1.00 28.08 | A |
| ATOM | 2388 | CG | LYS | 265 | 69.563 | 9.110 | 72.386 | 1.00 27.71 | A |
| ATOM | 2389 | CD | LYS | 265 | 69.147 | 7.650 | 72.368 | 1.00 27.75 | A |
| ATOM | 2390 | CE | LYS | 265 | 70.309 | 6.752 | 71.976 | 1.00 27.73 | A |
| ATOM | 2391 | NZ | LYS | 265 | 69.909 | 5.319 | 71.928 | 1.00 27.72 | A |
| ATOM | 2395 | C | LYS | 265 | 67.380 | 12.311 | 72.604 | 1.00 27.42 | A |
| ATOM | 2396 | O | LYS | 265 | 66.458 | 12.073 | 73.379 | 1.00 26.57 | A |
| ATOM | 2397 | N | ARG | 266 | 67.284 | 13.215 | 71.641 | 1.00 27.71 | A |
| ATOM | 2399 | CA | ARG | 266 | 66.118 | 14.057 | 71.494 | 1.00 27.46 | A |
| ATOM | 2400 | CB | ARG | 266 | 66.526 | 15.380 | 70.863 | 1.00 28.34 | A |
| ATOM | 2401 | CG | ARG | 266 | 67.426 | 16.177 | 71.782 | 1.00 30.05 | A |
| ATOM | 2402 | CD | ARG | 266 | 66.718 | 16.288 | 73.105 | 1.00 32.39 | A |
| ATOM | 2403 | NE | ARG | 266 | 67.406 | 17.070 | 74.123 | 1.00 34.98 | A |
| ATOM | 2405 | CZ | ARG | 266 | 66.958 | 17.188 | 75.372 | 1.00 36.36 | A |
| ATOM | 2406 | NH1 | ARG | 266 | 65.843 | 16.577 | 75.744 | 1.00 37.42 | A |
| ATOM | 2409 | NH2 | ARG | 266 | 67.639 | 17.876 | 76.266 | 1.00 37.05 | A |
| ATOM | 2411 | C | ARG | 266 | 64.900 | 13.488 | 70.796 | 1.00 27.14 | A |
| ATOM | 2413 | O | ARG | 266 | 64.033 | 14.257 | 70.379 | 1.00 28.74 | A |
| ATOM | 2414 | N | GLU | 267 | 64.809 | 12.157 | 70.687 | 1.00 26.23 | A |
| ATOM | 2416 | CA | GLU | 267 | 63.659 | 11.485 | 70.045 | 1.00 23.78 | A |
| ATOM | 2417 | CB | GLU | 267 | 64.007 | 10.055 | 69.567 | 1.00 25.09 | A |
| ATOM | 2418 | CG | GLU | 267 | 65.306 | 9.854 | 68.763 | 1.00 26.34 | A |
| ATOM | 2419 | CD | GLU | 267 | 65.553 | 8.401 | 68.408 | 0.00 26.05 | A |
| ATOM | 2420 | OE1 | GLU | 267 | 65.163 | 7.986 | 67.297 | 0.00 26.20 | A |
| ATOM | 2421 | OE2 | GLU | 267 | 66.139 | 7.674 | 69.239 | 0.00 26.20 | A |
| ATOM | 2422 | C | GLU | 267 | 62.583 | 11.352 | 71.114 | 1.00 22.53 | A |
| ATOM | 2423 | O | GLU | 267 | 62.876 | 11.436 | 72.307 | 1.00 21.49 | A |
| ATOM | 2424 | N | ALA | 268 | 61.340 | 11.128 | 70.703 | 1.00 20.95 | A |
| ATOM | 2426 | CA | ALA | 268 | 60.294 | 10.956 | 71.686 | 1.00 20.63 | A |
| ATOM | 2427 | CB | ALA | 268 | 58.974 | 10.821 | 71.019 | 1.00 20.48 | A |
| ATOM | 2428 | C | ALA | 268 | 60.637 | 9.677 | 72.455 | 1.00 20.74 | A |
| ATOM | 2429 | O | ALA | 268 | 61.082 | 8.677 | 71.815 | 1.00 21.32 | A |
| ATOM | 2430 | N | LEU | 269 | 60.426 | 9.700 | 73.775 | 1.00 19.33 | A |
| ATOM | 2432 | CA | LEU | 269 | 60.727 | 8.550 | 74.656 | 1.00 18.46 | A |
| ATOM | 2433 | CB | LEU | 269 | 61.412 | 9.064 | 75.931 | 1.00 17.90 | A |
| ATOM | 2434 | CG | LEU | 269 | 61.749 | 8.175 | 77.122 | 1.00 17.89 | A |
| ATOM | 2435 | CD1 | LEU | 269 | 62.648 | 7.039 | 76.714 | 1.00 17.80 | A |
| ATOM | 2436 | CD2 | LEU | 269 | 62.426 | 9.029 | 78.191 | 1.00 17.81 | A |
| ATOM | 2437 | C | LEU | 269 | 59.462 | 7.771 | 75.028 | 1.00 16.95 | A |
| ATOM | 2438 | O | LEU | 269 | 58.557 | 8.362 | 75.592 | 1.00 17.52 | A |
| ATOM | 2439 | N | GLU | 270 | 59.378 | 6.474 | 74.703 | 1.00 16.22 | A |
| ATOM | 2441 | CA | GLU | 270 | 58.178 | 5.679 | 75.059 | 1.00 14.75 | A |
| ATOM | 2442 | CB | GLU | 270 | 58.141 | 4.364 | 74.316 | 1.00 16.27 | A |
| ATOM | 2443 | CG | GLU | 270 | 56.874 | 3.535 | 74.610 | 1.00 17.76 | A |
| ATOM | 2444 | CD | GLU | 270 | 56.698 | 2.389 | 73.625 | 1.00 18.60 | A |
| ATOM | 2445 | OE1 | GLU | 270 | 57.638 | 2.132 | 72.821 | 1.00 18.80 | A |
| ATOM | 2446 | OE2 | GLU | 270 | 55.621 | 1.770 | 73.651 | 1.00 17.43 | A |
| ATOM | 2447 | C | GLU | 270 | 58.157 | 5.446 | 76.559 | 1.00 13.25 | A |
| ATOM | 2448 | O | GLU | 270 | 59.078 | 4.840 | 77.113 | 1.00 12.80 | A |
| ATOM | 2449 | N | THR | 271 | 57.050 | 5.838 | 77.173 | 1.00 11.76 | A |
| ATOM | 2451 | CA | THR | 271 | 56.896 | 5.857 | 78.634 | 1.00 10.94 | A |
| ATOM | 2452 | CB | THR | 271 | 57.426 | 7.349 | 79.100 | 1.00 10.44 | A |
| ATOM | 2453 | OG1 | THR | 271 | 58.425 | 7.785 | 78.716 | 1.00 11.83 | A |
| ATOM | 2455 | CG2 | THR | 271 | 56.904 | 7.544 | 80.588 | 1.00 10.50 | A |
| ATOM | 2456 | C | THR | 271 | 55.546 | 5.370 | 79.169 | 1.00 10.00 | A |
| ATOM | 2457 | O | THR | 271 | 55.843 | 5.627 | 78.567 | 1.00 10.46 | A |
| ATOM | 2458 | N | TYR | 272 | 54.521 | 4.620 | 80.271 | 1.00 10.31 | A |
| ATOM | 2460 | CA | TYR | 272 | 54.345 | 4.105 | 80.894 | 1.00 10.34 | A |

| ATOM | 2461 | CB  | TYR | 272 | 54.328 | 2.567  | 80.949 | 1.00 | 9.11  | A |
|------|------|-----|-----|-----|--------|--------|--------|------|-------|---|
| ATOM | 2462 | CG  | TYR | 272 | 54.281 | 1.971  | 79.583 | 1.00 | 9.43  | A |
| ATOM | 2463 | CD1 | TYR | 272 | 55.374 | 2.078  | 78.720 | 1.00 | 8.37  | A |
| ATOM | 2464 | CE1 | TYR | 272 | 55.292 | 1.657  | 77.364 | 1.00 | 9.61  | A |
| ATOM | 2465 | CD2 | TYR | 272 | 53.108 | 1.420  | 79.096 | 1.00 | 7.17  | A |
| ATOM | 2466 | CE2 | TYR | 272 | 53.012 | 1.000  | 77.764 | 1.00 | 9.16  | A |
| ATOM | 2467 | CZ  | TYR | 272 | 54.106 | 1.122  | 76.897 | 1.00 | 8.74  | A |
| ATOM | 2468 | OH  | TYR | 272 | 53.984 | 0.710  | 75.581 | 1.00 | 7.21  | A |
| ATOM | 2470 | C   | TYR | 272 | 54.232 | 4.651  | 82.293 | 1.00 | 9.78  | A |
| ATOM | 2471 | O   | TYR | 272 | 55.130 | 4.468  | 83.071 | 1.00 | 8.92  | A |
| ATOM | 2472 | N   | ILE | 273 | 53.128 | 5.313  | 82.601 | 1.00 | 10.73 | A |
| ATOM | 2474 | CA  | ILE | 273 | 52.907 | 5.878  | 83.934 | 1.00 | 11.93 | A |
| ATOM | 2475 | CB  | ILE | 273 | 51.874 | 7.035  | 83.901 | 1.00 | 12.73 | A |
| ATOM | 2476 | CG2 | ILE | 273 | 51.511 | 7.466  | 85.340 | 1.00 | 12.18 | A |
| ATOM | 2477 | CG1 | ILE | 273 | 52.389 | 8.228  | 83.085 | 1.00 | 12.89 | A |
| ATOM | 2478 | CD1 | ILE | 273 | 51.243 | 9.229  | 82.767 | 1.00 | 14.03 | A |
| ATOM | 2479 | C   | ILE | 273 | 52.350 | 4.774  | 84.852 | 1.00 | 12.74 | A |
| ATOM | 2480 | O   | ILE | 273 | 51.449 | 4.013  | 84.452 | 1.00 | 13.17 | A |
| ATOM | 2481 | N   | PHE | 274 | 52.940 | 4.660  | 86.039 | 1.00 | 11.35 | A |
| ATOM | 2483 | CA  | PHE | 274 | 52.560 | 3.690  | 87.052 | 1.00 | 10.45 | A |
| ATOM | 2484 | CB  | PHE | 274 | 53.809 | 3.138  | 87.756 | 1.00 | 8.76  | A |
| ATOM | 2485 | CG  | PHE | 274 | 53.492 | 2.062  | 88.734 | 1.00 | 10.47 | A |
| ATOM | 2486 | CD1 | PHE | 274 | 53.265 | 0.753  | 88.293 | 1.00 | 10.83 | A |
| ATOM | 2487 | CD2 | PHE | 274 | 53.285 | 2.357  | 90.079 | 1.00 | 9.86  | A |
| ATOM | 2488 | CE1 | PHE | 274 | 52.820 | -0.254 | 89.182 | 1.00 | 11.26 | A |
| ATOM | 2489 | CE2 | PHE | 274 | 52.839 | 1.363  | 90.984 | 1.00 | 10.43 | A |
| ATOM | 2490 | CZ  | PHE | 274 | 52.604 | 0.051  | 90.524 | 1.00 | 10.98 | A |
| ATOM | 2491 | C   | PHE | 274 | 52.377 | 5.236  | 88.807 | 1.00 | 10.35 | A |
| ATOM | 2492 | O   | PHE | 274 | 51.749 | 4.451  | 88.097 | 1.00 | 10.38 | A |
| ATOM | 2494 | CA  | ALA | 275 | 49.608 | 3.235  | 87.554 | 1.00 | 11.36 | A |
| ATOM | 2495 | CB  | ALA | 275 | 49.612 | 1.859  | 88.269 | 1.00 | 10.08 | A |
| ATOM | 2496 | C   | ALA | 275 | 48.182 | 3.762  | 87.425 | 1.00 | 11.58 | A |
| ATOM | 2497 | O   | ALA | 275 | 47.893 | 4.825  | 87.919 | 1.00 | 11.18 | A |
| ATOM | 2498 | N   | ALA | 275 | 50.445 | 4.208  | 88.267 | 1.00 | 10.23 | A |
| ATOM | 2499 | N   | MET | 276 | 47.304 | 3.010  | 86.754 | 1.00 | 12.82 | A |
| ATOM | 2501 | CA  | MET | 276 | 45.899 | 3.405  | 86.545 | 1.00 | 13.10 | A |
| ATOM | 2502 | CB  | MET | 276 | 45.185 | 2.425  | 85.587 | 1.00 | 12.34 | A |
| ATOM | 2503 | CG  | MET | 276 | 43.903 | 3.000  | 84.935 | 1.00 | 12.46 | A |
| ATOM | 2504 | SD  | MET | 276 | 44.171 | 4.484  | 83.945 | 1.00 | 16.68 | A |
| ATOM | 2505 | CE  | MET | 276 | 42.624 | 4.787  | 83.235 | 1.00 | 17.04 | A |
| ATOM | 2506 | C   | MET | 276 | 45.056 | 3.628  | 87.819 | 1.00 | 12.18 | A |
| ATOM | 2507 | O   | MET | 276 | 44.449 | 4.667  | 87.954 | 1.00 | 11.71 | A |
| ATOM | 2508 | N   | PHE | 277 | 44.990 | 2.657  | 88.725 | 1.00 | 13.50 | A |
| ATOM | 2510 | CA  | PHE | 277 | 44.219 | 2.815  | 89.986 | 1.00 | 13.36 | A |
| ATOM | 2511 | CB  | PHE | 277 | 43.096 | 1.791  | 90.095 | 1.00 | 13.08 | A |
| ATOM | 2512 | CG  | PHE | 277 | 42.275 | 1.655  | 88.867 | 1.00 | 13.79 | A |
| ATOM | 2513 | CD1 | PHE | 277 | 42.477 | 0.583  | 88.000 | 1.00 | 13.51 | A |
| ATOM | 2514 | CD2 | PHE | 277 | 41.322 | 2.616  | 88.552 | 1.00 | 13.96 | A |
| ATOM | 2515 | CE1 | PHE | 277 | 41.740 | 0.480  | 86.840 | 1.00 | 15.30 | A |
| ATOM | 2516 | CE2 | PHE | 277 | 40.575 | 2.535  | 87.389 | 1.00 | 14.80 | A |
| ATOM | 2517 | CZ  | PHE | 277 | 40.775 | 1.473  | 86.528 | 1.00 | 15.41 | A |
| ATOM | 2518 | C   | PHE | 277 | 45.102 | 2.500  | 91.155 | 1.00 | 13.70 | A |
| ATOM | 2519 | O   | PHE | 277 | 46.061 | 1.764  | 91.012 | 1.00 | 14.30 | A |
| ATOM | 2520 | N   | ASN | 278 | 44.742 | 3.004  | 92.332 | 1.00 | 15.44 | A |
| ATOM | 2522 | CA  | ASN | 278 | 45.473 | 2.699  | 93.574 | 1.00 | 15.29 | A |
| ATOM | 2523 | CB  | ASN | 278 | 44.934 | 3.519  | 94.758 | 1.00 | 16.02 | A |
| ATOM | 2524 | CG  | ASN | 278 | 45.052 | 5.042  | 94.550 | 1.00 | 19.30 | A |
| ATOM | 2525 | OD1 | ASN | 278 | 46.023 | 5.542  | 93.975 | 1.00 | 17.78 | A |
| ATOM | 2526 | ND2 | ASN | 278 | 44.052 | 5.774  | 95.018 | 1.00 | 17.16 | A |
| ATOM | 2529 | C   | ASN | 278 | 45.157 | 1.215  | 93.853 | 1.00 | 18.21 | A |
| ATOM | 2530 | O   | ASN | 278 | 44.012 | 0.782  | 93.676 | 1.00 | 15.74 | A |
| ATOM | 2531 | N   | GLU | 279 | 46.148 | 0.444  | 94.290 | 1.00 | 14.78 | A |
| ATOM | 2533 | CA  | GLU | 279 | 45.954 | -0.978 | 94.575 | 1.00 | 16.15 | A |
| ATOM | 2534 | CB  | GLU | 279 | 47.034 | -1.803 | 93.872 | 1.00 | 16.95 | A |
| ATOM | 2535 | CG  | GLU | 279 | 46.925 | -1.851 | 92.335 | 1.00 | 17.00 | A |
| ATOM | 2536 | CD  | GLU | 279 | 48.212 | -2.360 | 91.683 | 1.00 | 18.62 | A |
| ATOM | 2537 | OE1 | GLU | 279 | 48.438 | -3.581 | 91.577 | 1.00 | 19.30 | A |
| ATOM | 2538 | OE2 | GLU | 279 | 49.033 | -1.512 | 91.285 | 1.00 | 18.83 | A |
| ATOM | 2539 | C   | GLU | 279 | 45.980 | -1.211 | 96.097 | 1.00 | 21.74 | A |
| ATOM | 2540 | O   | GLU | 279 | 47.036 | -1.453 | 96.679 | 1.00 | 17.20 | A |
| ATOM | 2541 | N   | ASN | 280 | 44.786 | -1.223 | 96.708 | 1.00 | 15.59 | A |
| ATOM | 2543 | CA  | ASN | 280 | 44.617 | -1.380 | 98.168 | 1.00 | 18.32 | A |
| ATOM | 2544 | CB  | ASN | 280 | 43.145 | -1.167 | 98.605 | 1.00 | 18.88 | A |
| ATOM | 2545 | CG  | ASN | 280 | 42.187 | -2.276 | 98.157 | 1.00 | 18.05 | A |
| ATOM | 2546 | OD1 | ASN | 280 | 42.560 | -3.274 | 97.557 | 1.00 | 18.13 | A |
| ATOM | 2547 | ND2 | ASN | 280 | 40.928 | -2.084 | 98.473 | 1.00 | 16.77 | A |
| ATOM | 2550 | C   | ASN | 280 | 45.177 | -2.608 | 98.872 | 1.00 | 17.77 | A |
| ATOM | 2551 | O   | ASN | 280 | 45.121 | -2.694 | 100.101 | 1.00 | 19.76 | A |
| ATOM | 2552 | N   | GLN | 281 | 45.762 | -3.522 | 98.107 | 1.00 | 20.26 | A |
| ATOM | 2554 | CA  | GLN | 281 | 46.281 | -4.743 | 98.652 | 1.00 | 19.58 | A |

- 85 -

- 86 -

| | | | | | | | | | |
|---|---|---|---|---|---|---|---|---|---|
| ATOM | 2555 | CB | GLN | 281 | 45.530 | -5.909 | 98.010 | 1.00 | 18.53 | A |
| ATOM | 2556 | CG | GLN | 281 | 44.076 | -6.005 | 98.459 | 1.00 | 18.79 | A |
| ATOM | 2557 | CD | GLN | 281 | 43.420 | -7.312 | 98.071 | 1.00 | 18.84 | A |
| ATOM | 2558 | OE1 | GLN | 281 | 42.258 | -7.340 | 97.676 | 0.00 | 18.91 | A |
| ATOM | 2559 | NE2 | GLN | 281 | 44.158 | -8.406 | 98.198 | 0.00 | 18.91 | A |
| ATOM | 2562 | C | GLN | 281 | 47.774 | -4.925 | 98.503 | 1.00 | 18.71 | A |
| ATOM | 2563 | O | GLN | 281 | 48.301 | -6.008 | 98.755 | 1.00 | 18.35 | A |
| ATOM | 2564 | N | LYS | 282 | 48.474 | -3.864 | 98.129 | 1.00 | 19.14 | A |
| ATOM | 2566 | CA | LYS | 282 | 49.906 | -3.968 | 97.963 | 1.00 | 19.26 | A |
| ATOM | 2567 | CB | LYS | 282 | 50.407 | -2.798 | 97.128 | 1.00 | 20.36 | A |
| ATOM | 2568 | CG | LYS | 282 | 49.789 | -2.693 | 95.764 | 1.00 | 21.27 | A |
| ATOM | 2569 | CD | LYS | 282 | 50.507 | -3.540 | 94.747 | 1.00 | 22.91 | A |
| ATOM | 2570 | CE | LYS | 282 | 51.738 | -2.855 | 94.132 | 1.00 | 24.49 | A |
| ATOM | 2571 | NZ | LYS | 282 | 52.160 | -3.600 | 92.898 | 1.00 | 24.37 | A |
| ATOM | 2575 | C | LYS | 282 | 50.591 | -3.950 | 99.324 | 1.00 | 19.83 | A |
| ATOM | 2576 | O | LYS | 282 | 50.091 | -3.356 | 100.272 | 1.00 | 19.12 | A |
| ATOM | 2577 | N | THR | 283 | 51.744 | -4.610 | 99.416 | 1.00 | 19.78 | A |
| ATOM | 2579 | CA | THR | 283 | 52.501 | -4.629 | 100.652 | 1.00 | 19.67 | A |
| ATOM | 2580 | CB | THR | 283 | 52.951 | -6.050 | 101.053 | 1.00 | 20.41 | A |
| ATOM | 2581 | OG1 | THR | 283 | 53.887 | -6.576 | 100.113 | 1.00 | 20.28 | A |
| ATOM | 2583 | CG2 | THR | 283 | 51.765 | -6.978 | 101.119 | 1.00 | 21.40 | A |
| ATOM | 2584 | C | THR | 283 | 53.672 | -3.653 | 100.487 | 1.00 | 19.78 | A |
| ATOM | 2585 | O | THR | 283 | 53.662 | -2.828 | 99.562 | 1.00 | 20.32 | A |
| ATOM | 2586 | N | GLY | 284 | 54.659 | -3.705 | 101.375 | 1.00 | 19.24 | A |
| ATOM | 2588 | CA | GLY | 284 | 55.751 | -2.757 | 101.259 | 1.00 | 18.89 | A |
| ATOM | 2589 | C | GLY | 284 | 55.333 | -1.398 | 101.820 | 1.00 | 20.08 | A |
| ATOM | 2590 | O | GLY | 284 | 54.368 | -1.309 | 102.598 | 1.00 | 20.13 | A |
| ATOM | 2591 | N | ASP | 285 | 56.041 | -0.331 | 101.435 | 1.00 | 19.67 | A |
| ATOM | 2593 | CA | ASP | 285 | 55.722 | 1.002 | 101.955 | 1.00 | 20.42 | A |
| ATOM | 2594 | CB | ASP | 285 | 56.710 | 2.056 | 101.485 | 1.00 | 20.52 | A |
| ATOM | 2595 | CG | ASP | 285 | 56.526 | 3.364 | 102.208 | 1.00 | 19.71 | A |
| ATOM | 2596 | OD1 | ASP | 285 | 56.056 | 4.333 | 101.594 | 1.00 | 19.03 | A |
| ATOM | 2597 | OD2 | ASP | 285 | 56.832 | 3.436 | 103.401 | 1.00 | 21.01 | A |
| ATOM | 2598 | C | ASP | 285 | 54.302 | 1.455 | 101.645 | 1.00 | 19.09 | A |
| ATOM | 2599 | O | ASP | 285 | 53.783 | 1.188 | 100.571 | 1.00 | 20.19 | A |
| ATOM | 2600 | N | ALA | 286 | 53.706 | 2.167 | 102.594 | 1.00 | 20.13 | A |
| ATOM | 2602 | CA | ALA | 286 | 52.334 | 2.667 | 102.412 | 1.00 | 19.77 | A |
| ATOM | 2603 | CB | ALA | 286 | 52.001 | 3.594 | 103.671 | 1.00 | 20.14 | A |
| ATOM | 2604 | C | ALA | 286 | 52.034 | 3.381 | 101.131 | 1.00 | 18.24 | A |
| ATOM | 2605 | O | ALA | 286 | 50.871 | 3.433 | 100.690 | 1.00 | 19.32 | A |
| ATOM | 2606 | N | THR | 287 | 53.080 | 3.942 | 100.517 | 1.00 | 18.82 | A |
| ATOM | 2608 | CA | THR | 287 | 52.980 | 4.661 | 99.252 | 1.00 | 17.44 | A |
| ATOM | 2609 | CB | THR | 287 | 54.319 | 5.314 | 98.867 | 1.00 | 17.45 | A |
| ATOM | 2610 | OG1 | THR | 287 | 55.348 | 4.320 | 98.794 | 1.00 | 16.57 | A |
| ATOM | 2612 | CG2 | THR | 287 | 54.700 | 6.392 | 99.864 | 1.00 | 17.91 | A |
| ATOM | 2613 | C | THR | 287 | 52.552 | 3.756 | 98.112 | 1.00 | 17.08 | A |
| ATOM | 2614 | O | THR | 287 | 51.902 | 4.214 | 97.166 | 1.00 | 17.40 | A |
| ATOM | 2615 | N | GLU | 288 | 52.911 | 2.480 | 98.207 | 1.00 | 16.78 | A |
| ATOM | 2617 | CA | GLU | 288 | 52.571 | 1.493 | 97.194 | 1.00 | 16.24 | A |
| ATOM | 2618 | CB | GLU | 288 | 52.994 | 0.102 | 97.617 | 1.00 | 17.69 | A |
| ATOM | 2619 | CG | GLU | 288 | 54.438 | -0.100 | 97.914 | 1.00 | 21.66 | A |
| ATOM | 2620 | CD | GLU | 288 | 55.308 | -0.337 | 96.780 | 1.00 | 25.71 | A |
| ATOM | 2621 | OE1 | GLU | 288 | 56.282 | -0.013 | 95.618 | 1.00 | 29.65 | A |
| ATOM | 2622 | OE2 | GLU | 288 | 54.989 | 1.097 | 97.051 | 1.00 | 26.24 | A |
| ATOM | 2623 | C | GLU | 288 | 51.088 | 1.442 | 96.921 | 1.00 | 15.95 | A |
| ATOM | 2624 | O | GLU | 288 | 50.694 | 1.098 | 95.816 | 1.00 | 16.08 | A |
| ATOM | 2625 | N | ARG | 289 | 50.264 | 1.760 | 97.923 | 1.00 | 14.99 | A |
| ATOM | 2627 | CA | ARG | 289 | 48.804 | 1.725 | 97.767 | 1.00 | 14.66 | A |
| ATOM | 2628 | CB | ARG | 289 | 48.101 | 1.395 | 99.102 | 1.00 | 15.99 | A |
| ATOM | 2629 | CG | ARG | 289 | 48.700 | 0.204 | 99.871 | 1.00 | 18.78 | A |
| ATOM | 2630 | CD | ARG | 289 | 47.892 | -0.208 | 101.092 | 1.00 | 19.92 | A |
| ATOM | 2631 | NE | ARG | 289 | 47.962 | -1.663 | 101.193 | 1.00 | 24.80 | A |
| ATOM | 2633 | CZ | ARG | 289 | 47.865 | -2.390 | 102.315 | 1.00 | 26.95 | A |
| ATOM | 2634 | NH1 | ARG | 289 | 47.683 | -1.816 | 103.513 | 1.00 | 28.17 | A |
| ATOM | 2637 | NH2 | ARG | 289 | 47.994 | -3.716 | 102.240 | 1.00 | 27.22 | A |
| ATOM | 2640 | C | ARG | 289 | 48.232 | 3.030 | 97.221 | 1.00 | 13.80 | A |
| ATOM | 2641 | O | ARG | 289 | 47.036 | 3.161 | 97.076 | 1.00 | 14.64 | A |
| ATOM | 2642 | N | SER | 290 | 49.084 | 3.964 | 96.855 | 1.00 | 12.80 | A |
| ATOM | 2644 | CA | SER | 290 | 48.616 | 5.233 | 96.353 | 1.00 | 12.50 | A |
| ATOM | 2645 | CB | SER | 290 | 48.762 | 6.256 | 97.472 | 1.00 | 12.70 | A |
| ATOM | 2646 | OG | SER | 290 | 47.983 | 5.818 | 98.548 | 1.00 | 13.97 | A |
| ATOM | 2648 | C | SER | 290 | 49.300 | 5.763 | 95.092 | 1.00 | 11.60 | A |
| ATOM | 2649 | O | SER | 290 | 49.499 | 6.959 | 94.963 | 1.00 | 11.23 | A |
| ATOM | 2650 | N | PHE | 291 | 49.594 | 4.905 | 94.125 | 1.00 | 11.65 | A |
| ATOM | 2652 | CA | PHE | 291 | 50.247 | 5.387 | 92.905 | 1.00 | 10.79 | A |
| ATOM | 2653 | CB | PHE | 291 | 51.283 | 4.347 | 92.443 | 1.00 | 10.71 | A |
| ATOM | 2654 | CG | PHE | 291 | 52.674 | 4.596 | 92.957 | 1.00 | 10.18 | A |
| ATOM | 2655 | CD1 | PHE | 291 | 53.130 | 3.987 | 94.115 | 1.00 | 10.27 | A |
| ATOM | 2656 | CD2 | PHE | 291 | 53.537 | 5.439 | 92.275 | 1.00 | 9.13 | A |
| ATOM | 2657 | CE1 | PHE | 291 | 54.419 | 4.219 | 94.574 | 1.00 | 9.33 | A |

- 87 -

| ATOM | 2658 | CE2 | PHE | 291 | 54.827 | 5.668 | 92.734 | 1.00 | 7.83 | A |
|------|------|-----|-----|-----|--------|-------|--------|------|------|---|
| ATOM | 2659 | CZ  | PHE | 291 | 55.263 | 5.059 | 93.879 | 1.00 | 9.61 | A |
| ATOM | 2660 | C   | PHE | 291 | 49.607 | 5.703 | 91.776 | 1.00 | 10.88 | A |
| ATOM | 2661 | O   | PHE | 291 | 49.237 | 6.249 | 90.732 | 1.00 | 11.66 | A |
| ATOM | 2662 | N   | GLY | 292 | 49.962 | 5.447 | 92.024 | 1.00 | 10.48 | A |
| ATOM | 2664 | CA  | GLY | 292 | 46.928 | 5.642 | 91.018 | 1.00 | 11.42 | A |
| ATOM | 2665 | C   | GLY | 292 | 46.523 | 7.006 | 90.474 | 1.00 | 13.19 | A |
| ATOM | 2666 | O   | GLY | 292 | 46.460 | 7.998 | 91.222 | 1.00 | 13.60 | A |
| ATOM | 2667 | N   | LEU | 293 | 46.266 | 7.066 | 89.164 | 1.00 | 12.67 | A |
| ATOM | 2669 | CA  | LEU | 293 | 45.800 | 8.303 | 88.541 | 1.00 | 14.11 | A |
| ATOM | 2670 | CB  | LEU | 293 | 46.090 | 8.280 | 87.058 | 1.00 | 14.75 | A |
| ATOM | 2671 | CG  | LEU | 293 | 47.528 | 8.104 | 86.590 | 1.00 | 15.84 | A |
| ATOM | 2672 | CD1 | LEU | 293 | 47.469 | 7.694 | 85.090 | 1.00 | 13.85 | A |
| ATOM | 2673 | CD2 | LEU | 293 | 48.305 | 9.418 | 86.797 | 1.00 | 14.59 | A |
| ATOM | 2674 | C   | LEU | 293 | 44.270 | 8.411 | 88.742 | 1.00 | 13.87 | A |
| ATOM | 2675 | O   | LEU | 293 | 43.695 | 9.492 | 88.767 | 1.00 | 13.38 | A |
| ATOM | 2676 | N   | PHE | 294 | 43.634 | 7.260 | 88.897 | 1.00 | 15.68 | A |
| ATOM | 2678 | CA  | PHE | 294 | 42.196 | 7.142 | 89.093 | 1.00 | 16.52 | A |
| ATOM | 2679 | CB  | PHE | 294 | 41.588 | 6.373 | 87.914 | 1.00 | 14.89 | A |
| ATOM | 2680 | CG  | PHE | 294 | 41.681 | 7.108 | 85.814 | 1.00 | 15.40 | A |
| ATOM | 2681 | CD1 | PHE | 294 | 42.814 | 7.003 | 85.814 | 1.00 | 15.83 | A |
| ATOM | 2682 | CD2 | PHE | 294 | 40.673 | 7.983 | 86.220 | 1.00 | 15.16 | A |
| ATOM | 2683 | CE1 | PHE | 294 | 42.940 | 7.759 | 84.666 | 1.00 | 14.51 | A |
| ATOM | 2684 | CE2 | PHE | 294 | 40.785 | 8.734 | 85.095 | 1.00 | 14.01 | A |
| ATOM | 2685 | CZ  | PHE | 294 | 41.924 | 8.629 | 84.307 | 1.00 | 14.90 | A |
| ATOM | 2686 | C   | PHE | 294 | 41.878 | 6.416 | 90.398 | 1.00 | 17.80 | A |
| ATOM | 2687 | O   | PHE | 294 | 42.690 | 5.650 | 90.926 | 1.00 | 18.49 | A |
| ATOM | 2688 | N   | ASN | 295 | 40.708 | 6.694 | 90.945 | 1.00 | 19.05 | A |
| ATOM | 2690 | CA  | ASN | 295 | 40.272 | 6.044 | 92.164 | 1.00 | 21.16 | A |
| ATOM | 2691 | CB  | ASN | 295 | 39.382 | 6.995 | 92.965 | 1.00 | 20.64 | A |
| ATOM | 2692 | CG  | ASN | 295 | 40.202 | 7.959 | 93.816 | 1.00 | 21.27 | A |
| ATOM | 2693 | OD1 | ASN | 295 | 41.007 | 7.525 | 94.661 | 1.00 | 21.46 | A |
| ATOM | 2694 | HD2 | ASN | 295 | 40.026 | 9.261 | 93.593 | 1.00 | 19.89 | A |
| ATOM | 2697 | C   | ASN | 295 | 39.544 | 4.761 | 91.714 | 1.00 | 22.82 | A |
| ATOM | 2698 | O   | ASN | 295 | 38.978 | 4.737 | 90.617 | 1.00 | 22.88 | A |
| ATOM | 2699 | N   | PRO | 296 | 39.538 | 3.698 | 92.546 | 1.00 | 23.85 | A |
| ATOM | 2700 | CD  | PRO | 296 | 40.143 | 3.573 | 93.882 | 1.00 | 24.44 | A |
| ATOM | 2701 | CA  | PRO | 296 | 38.882 | 2.443 | 92.176 | 1.00 | 25.16 | A |
| ATOM | 2702 | CB  | PRO | 296 | 38.796 | 1.699 | 93.499 | 1.00 | 25.16 | A |
| ATOM | 2703 | CG  | PRO | 296 | 40.079 | 2.044 | 94.120 | 1.00 | 24.51 | A |
| ATOM | 2704 | C   | PRO | 296 | 37.551 | 2.598 | 91.469 | 1.00 | 26.99 | A |
| ATOM | 2705 | O   | PRO | 296 | 37.289 | 1.905 | 90.491 | 1.00 | 27.23 | A |
| ATOM | 2706 | N   | ASP | 297 | 36.745 | 3.554 | 91.952 | 1.00 | 28.25 | A |
| ATOM | 2708 | CA  | ASP | 297 | 35.438 | 3.819 | 91.342 | 1.00 | 29.49 | A |
| ATOM | 2709 | CB  | ASP | 297 | 34.548 | 4.601 | 92.296 | 1.00 | 31.54 | A |
| ATOM | 2710 | CG  | ASP | 297 | 34.941 | 6.057 | 92.380 | 1.00 | 33.44 | A |
| ATOM | 2711 | OD1 | ASP | 297 | 34.224 | 6.897 | 91.789 | 1.00 | 35.57 | A |
| ATOM | 2712 | OD2 | ASP | 297 | 35.985 | 6.358 | 92.999 | 1.00 | 34.99 | A |
| ATOM | 2713 | C   | ASP | 297 | 35.529 | 4.611 | 90.032 | 1.00 | 29.71 | A |
| ATOM | 2714 | O   | ASP | 297 | 34.564 | 5.257 | 89.629 | 1.00 | 30.38 | A |
| ATOM | 2715 | N   | LYS | 298 | 36.688 | 4.598 | 89.389 | 1.00 | 29.42 | A |
| ATOM | 2717 | CA  | LYS | 298 | 36.898 | 5.309 | 88.132 | 1.00 | 29.17 | A |
| ATOM | 2718 | CB  | LYS | 298 | 35.869 | 4.873 | 87.082 | 1.00 | 28.48 | A |
| ATOM | 2719 | CG  | LYS | 298 | 35.491 | 3.402 | 87.098 | 1.00 | 27.05 | A |
| ATOM | 2720 | CD  | LYS | 298 | 34.796 | 3.031 | 85.798 | 1.00 | 27.17 | A |
| ATOM | 2721 | CE  | LYS | 298 | 33.600 | 2.126 | 86.028 | 1.00 | 27.24 | A |
| ATOM | 2722 | NZ  | LYS | 298 | 33.960 | 0.874 | 86.748 | 0.00 | 27.20 | A |
| ATOM | 2726 | C   | LYS | 298 | 36.954 | 6.853 | 88.207 | 1.00 | 29.35 | A |
| ATOM | 2727 | O   | LYS | 298 | 37.026 | 7.518 | 87.180 | 1.00 | 30.25 | A |
| ATOM | 2728 | N   | SER | 299 | 36.885 | 7.437 | 89.396 | 1.00 | 29.34 | A |
| ATOM | 2730 | CA  | SER | 299 | 36.977 | 8.891 | 89.501 | 1.00 | 28.37 | A |
| ATOM | 2731 | CB  | SER | 299 | 36.204 | 9.421 | 90.737 | 1.00 | 28.59 | A |
| ATOM | 2732 | OG  | SER | 299 | 36.621 | 8.820 | 91.960 | 1.00 | 29.22 | A |
| ATOM | 2734 | C   | SER | 299 | 38.459 | 9.336 | 89.524 | 1.00 | 27.11 | A |
| ATOM | 2735 | O   | SER | 299 | 39.326 | 8.686 | 90.124 | 1.00 | 27.49 | A |
| ATOM | 2737 | N   | PRO | 300 | 38.756 | 10.495 | 88.937 | 1.00 | 24.85 | A |
| ATOM | 2738 | CD  | PRO | 300 | 37.844 | 11.468 | 88.333 | 1.00 | 24.58 | A |
| ATOM | 2739 | CA  | PRO | 300 | 40.138 | 10.988 | 88.905 | 1.00 | 23.87 | A |
| ATOM | 2740 | CB  | PRO | 300 | 40.014 | 12.291 | 88.124 | 1.00 | 23.40 | A |
| ATOM | 2741 | CG  | PRO | 300 | 38.746 | 12.090 | 87.310 | 1.00 | 24.87 | A |
| ATOM | 2742 | C   | PRO | 300 | 40.724 | 11.245 | 90.280 | 1.00 | 22.07 | A |
| ATOM | 2743 | O   | PRO | 300 | 40.089 | 11.890 | 91.094 | 1.00 | 22.82 | A |
| ATOM | 2745 | N   | ALA | 301 | 41.902 | 10.697 | 90.560 | 1.00 | 20.27 | A |
| ATOM | 2746 | CA  | ALA | 301 | 42.549 | 10.949 | 91.848 | 1.00 | 17.94 | A |
| ATOM | 2747 | CB  | ALA | 301 | 43.796 | 10.112 | 92.004 | 1.00 | 16.28 | A |
| ATOM | 2748 | C   | ALA | 301 | 42.877 | 12.447 | 91.892 | 1.00 | 16.75 | A |
| ATOM | 2749 | O   | ALA | 301 | 42.681 | 13.091 | 92.925 | 1.00 | 17.56 | A |
| ATOM | 2751 | N   | TYR | 302 | 43.344 | 12.984 | 90.759 | 1.00 | 15.47 | A |
| ATOM | 2752 | CA  | TYR | 302 | 43.659 | 14.405 | 90.565 | 1.00 | 15.30 | A |
| ATOM | 2752 | CB  | TYR | 302 | 45.072 | 14.739 | 91.030 | 1.00 | 13.00 | A |

- 88 -

| | | | | | | | | | | |
|---|---|---|---|---|---|---|---|---|---|---|
| ATOM | 2753 | CG | TYR | 302 | 46.075 | 13.656 | 90.786 | 1.00 | 12.78 | A |
| ATOM | 2754 | CD1 | TYR | 302 | 46.743 | 13.551 | 89.571 | 1.00 | 12.93 | A |
| ATOM | 2755 | CE1 | TYR | 302 | 47.668 | 12.554 | 89.342 | 1.00 | 13.42 | A |
| ATOM | 2756 | CD2 | TYR | 302 | 46.358 | 12.735 | 91.774 | 1.00 | 12.97 | A |
| ATOM | 2757 | CE2 | TYR | 302 | 47.284 | 11.708 | 91.567 | 1.00 | 14.98 | A |
| ATOM | 2758 | CZ | TYR | 302 | 47.936 | 11.614 | 90.340 | 1.00 | 14.76 | A |
| ATOM | 2759 | OH | TYR | 302 | 48.762 | 10.524 | 90.101 | 1.00 | 13.49 | A |
| ATOM | 2761 | C | TYR | 302 | 43.489 | 14.652 | 89.056 | 1.00 | 16.62 | A |
| ATOM | 2762 | O | TYR | 302 | 43.323 | 13.681 | 88.327 | 1.00 | 17.05 | A |
| ATOM | 2763 | N | ASN | 303 | 43.545 | 15.902 | 88.569 | 1.00 | 15.69 | A |
| ATOM | 2765 | CA | ASN | 303 | 43.352 | 16.147 | 87.139 | 1.00 | 16.31 | A |
| ATOM | 2766 | CB | ASN | 303 | 42.675 | 17.490 | 86.862 | 1.00 | 17.34 | A |
| ATOM | 2767 | CG | ASN | 303 | 41.288 | 17.578 | 87.463 | 1.00 | 17.08 | A |
| ATOM | 2768 | OD1 | ASN | 303 | 40.289 | 17.578 | 86.748 | 0.00 | 17.20 | A |
| ATOM | 2769 | ND2 | ASN | 303 | 41.219 | 17.660 | 88.786 | 0.00 | 17.20 | A |
| ATOM | 2772 | C | ASN | 303 | 44.565 | 16.020 | 86.269 | 1.00 | 16.91 | A |
| ATOM | 2773 | O | ASN | 303 | 45.643 | 16.605 | 86.544 | 1.00 | 17.72 | A |
| ATOM | 2774 | N | ILE | 304 | 44.471 | 15.179 | 85.249 | 1.00 | 17.29 | A |
| ATOM | 2776 | CA | ILE | 304 | 45.566 | 14.954 | 84.302 | 1.00 | 17.53 | A |
| ATOM | 2777 | CB | ILE | 304 | 46.331 | 13.616 | 84.557 | 1.00 | 17.04 | A |
| ATOM | 2778 | CG2 | ILE | 304 | 47.208 | 13.251 | 83.306 | 1.00 | 13.45 | A |
| ATOM | 2779 | CG1 | ILE | 304 | 47.187 | 13.709 | 85.847 | 1.00 | 15.98 | A |
| ATOM | 2780 | CD1 | ILE | 304 | 48.330 | 14.689 | 85.780 | 1.00 | 14.40 | A |
| ATOM | 2781 | C | ILE | 304 | 45.035 | 14.908 | 82.887 | 1.00 | 17.00 | A |
| ATOM | 2782 | O | ILE | 304 | 44.096 | 14.188 | 82.629 | 1.00 | 16.50 | A |
| ATOM | 2783 | N | GLN | 305 | 45.577 | 15.737 | 82.005 | 1.00 | 17.94 | A |
| ATOM | 2785 | CA | GLN | 305 | 45.162 | 15.713 | 80.603 | 1.00 | 19.57 | A |
| ATOM | 2786 | CB | GLN | 305 | 44.956 | 17.124 | 80.042 | 1.00 | 21.24 | A |
| ATOM | 2787 | CG | GLN | 305 | 46.136 | 18.055 | 80.144 | 1.00 | 22.49 | A |
| ATOM | 2788 | CD | GLN | 305 | 45.919 | 19.358 | 79.858 | 0.00 | 22.13 | A |
| ATOM | 2789 | OE1 | GLN | 305 | 45.134 | 20.203 | 79.825 | 0.00 | 22.25 | A |
| ATOM | 2790 | NE2 | GLN | 305 | 46.619 | 19.527 | 78.289 | 1.00 | 18.95 | A |
| ATOM | 2793 | C | GLN | 305 | 46.188 | 14.914 | 79.793 | 1.00 | 18.89 | A |
| ATOM | 2794 | O | GLN | 305 | 47.360 | 15.259 | 79.730 | 1.00 | 19.25 | A |
| ATOM | 2795 | N | PHE | 306 | 45.743 | 13.808 | 79.231 | 1.00 | 20.35 | A |
| ATOM | 2797 | CA | PHE | 306 | 46.624 | 12.936 | 78.481 | 1.00 | 20.05 | A |
| ATOM | 2798 | CB | PHE | 306 | 46.052 | 11.522 | 78.481 | 1.00 | 18.54 | A |
| ATOM | 2799 | CG | PHE | 306 | 45.875 | 10.940 | 79.858 | 1.00 | 17.57 | A |
| ATOM | 2800 | CD1 | PHE | 306 | 44.661 | 11.047 | 80.508 | 1.00 | 18.51 | A |
| ATOM | 2801 | CD2 | PHE | 306 | 46.939 | 10.297 | 80.497 | | | |
| ATOM | 2802 | CE1 | PHE | 306 | 44.494 | 10.523 | 81.795 | 1.00 | 19.41 | A |
| ATOM | 2803 | CE2 | PHE | 306 | 46.798 | 9.764 | 81.771 | 1.00 | 19.19 | A |
| ATOM | 2804 | CZ | PHE | 306 | 45.572 | 9.873 | 82.437 | 1.00 | 18.76 | A |
| ATOM | 2805 | C | PHE | 306 | 46.922 | 13.399 | 77.034 | 1.00 | 22.11 | A |
| ATOM | 2806 | O | PHE | 306 | 46.268 | 14.369 | 76.559 | 1.00 | 23.52 | A |
| ATOM | 2807 | OT | PHE | 306 | 47.870 | 12.835 | 76.415 | 1.00 | 21.57 | A |
| ATOM | 2808 | CB | ILE | 1 | 38.175 | -1.386 | 38.763 | 1.00 | 13.54 | B |
| ATOM | 2809 | CG2 | ILE | 1 | 37.653 | -2.594 | 39.609 | 1.00 | 16.58 | B |
| ATOM | 2810 | CG1 | ILE | 1 | 38.864 | -0.400 | 39.727 | 1.00 | 13.44 | B |
| ATOM | 2811 | CD1 | ILE | 1 | 38.952 | 0.997 | 39.250 | 1.00 | 12.71 | B |
| ATOM | 2812 | C | ILE | 1 | 40.077 | -3.002 | 38.188 | 1.00 | 11.25 | B |
| ATOM | 2813 | O | ILE | 1 | 39.788 | -4.180 | 37.991 | 1.00 | 11.10 | B |
| ATOM | 2816 | N | ILE | 1 | 38.446 | -2.497 | 36.486 | 1.00 | 9.64 | B |
| ATOM | 2818 | CA | ILE | 1 | 39.182 | -1.896 | 37.640 | 1.00 | 12.26 | B |
| ATOM | 2819 | N | GLY | 2 | 41.203 | -2.627 | 38.776 | 1.00 | 10.44 | B |
| ATOM | 2821 | CA | GLY | 2 | 42.094 | -3.617 | 39.347 | 1.00 | 10.03 | B |
| ATOM | 2822 | C | GLY | 2 | 41.770 | -3.799 | 40.816 | 1.00 | 9.74 | B |
| ATOM | 2823 | O | GLY | 2 | 40.965 | -3.052 | 41.363 | 1.00 | 8.14 | B |
| ATOM | 2824 | N | VAL | 3 | 42.313 | -4.842 | 41.436 | 1.00 | 10.15 | B |
| ATOM | 2826 | CA | VAL | 3 | 42.095 | -5.116 | 42.869 | 1.00 | 10.12 | B |
| ATOM | 2827 | CB | VAL | 3 | 40.828 | -5.999 | 43.154 | 1.00 | 10.50 | B |
| ATOM | 2828 | CG1 | VAL | 3 | 40.731 | -6.302 | 44.605 | 1.00 | 9.30 | B |
| ATOM | 2829 | CG2 | VAL | 3 | 39.552 | -5.274 | 42.808 | 1.00 | 10.18 | B |
| ATOM | 2830 | C | VAL | 3 | 43.332 | -5.852 | 43.385 | 1.00 | 10.65 | B |
| ATOM | 2831 | O | VAL | 3 | 43.755 | -6.874 | 42.821 | 1.00 | 9.82 | B |
| ATOM | 2832 | N | CYS | 4 | 43.930 | -5.293 | 44.421 | 1.00 | 9.66 | B |
| ATOM | 2834 | CA | CYS | 4 | 45.102 | -5.863 | 45.055 | 1.00 | 10.43 | B |
| ATOM | 2835 | CB | CYS | 4 | 45.698 | -4.860 | 46.014 | 1.00 | 9.04 | B |
| ATOM | 2836 | SG | CYS | 4 | 46.047 | -3.327 | 45.213 | 1.00 | 8.84 | B |
| ATOM | 2837 | C | CYS | 4 | 44.602 | -7.140 | 45.796 | 1.00 | 7.99 | B |
| ATOM | 2838 | O | CYS | 4 | 43.657 | -7.197 | 46.451 | 1.00 | 8.62 | B |
| ATOM | 2839 | N | TYR | 5 | 45.512 | -8.174 | 45.630 | 1.00 | 5.92 | B |
| ATOM | 2841 | CA | TYR | 5 | 45.236 | -9.481 | 46.224 | 1.00 | 6.23 | B |
| ATOM | 2842 | CB | TYR | 5 | 45.293 | -10.538 | 45.127 | 1.00 | 7.48 | B |
| ATOM | 2843 | CG | TYR | 5 | 45.255 | -11.944 | 45.570 | 1.00 | 7.37 | B |
| ATOM | 2844 | CD1 | TYR | 5 | 45.899 | -12.923 | 44.816 | 1.00 | 5.97 | B |
| ATOM | 2845 | CE1 | TYR | 5 | 45.910 | -14.273 | 45.208 | 1.00 | 7.07 | B |
| ATOM | 2846 | CD2 | TYR | 5 | 44.602 | -12.325 | 46.748 | 1.00 | 8.16 | B |
| ATOM | 2847 | CE2 | TYR | 5 | 44.596 | -13.676 | 47.167 | | | |
| ATOM | 2848 | CZ | TYR | 5 | 45.263 | -14.648 | 46.380 | | | |

| | | | | | | | | | | | | | | | | | | |
|---|---|---|---|---|---|---|---|---|---|---|---|---|---|---|---|---|---|---|
| ATOM | 2849 | OH | TYR | 5 | 45.308 | -15.973 | 46.759 | 1.00 | 7.87 | | ATOM | 2900 | C | ASN | 11 | 40.761 | -17.987 | 55.055 | 1.00 | 10.15 | B |
| ATOM | 2850 | C | TYR | 5 | 46.232 | -9.778 | 47.329 | 1.00 | 8.76 | | ATOM | 2901 | O | ASN | 11 | 39.556 | -17.984 | 54.821 | 1.00 | 9.48 | B |
| ATOM | 2852 | O | TYR | 5 | 47.394 | -10.108 | 47.068 | 1.00 | 9.27 | | ATOM | 2902 | N | LEU | 12 | 41.654 | -17.631 | 54.135 | 1.00 | 10.88 | B |
| ATOM | 2853 | N | GLY | 6 | 45.779 | -9.588 | 48.562 | 1.00 | 9.53 | | ATOM | 2904 | CA | LEU | 12 | 41.298 | -17.187 | 52.742 | 1.00 | 10.72 | B |
| ATOM | 2855 | CA | GLY | 6 | 46.607 | -9.850 | 49.710 | 1.00 | 9.50 | | ATOM | 2905 | CB | LEU | 12 | 42.354 | -16.177 | 52.227 | 1.00 | 8.68 | B |
| ATOM | 2856 | C | GLY | 6 | 46.198 | -11.159 | 50.355 | 1.00 | 9.69 | | ATOM | 2906 | CG | LEU | 12 | 42.520 | -14.892 | 53.070 | 1.00 | 6.86 | B |
| ATOM | 2857 | O | GLY | 6 | 45.027 | -11.399 | 50.613 | 1.00 | 11.49 | | ATOM | 2907 | CD1 | LEU | 12 | 43.674 | -14.014 | 52.643 | 1.00 | 4.67 | B |
| ATOM | 2858 | N | VAL | 7 | 47.192 | -11.914 | 50.776 | 1.00 | 9.36 | | ATOM | 2908 | CD2 | LEU | 12 | 41.217 | -14.133 | 52.962 | 1.00 | 5.97 | B |
| ATOM | 2860 | CA | VAL | 7 | 46.998 | -13.209 | 51.363 | 1.00 | 8.20 | | ATOM | 2909 | C | LEU | 12 | 41.158 | -18.348 | 51.742 | 1.00 | 10.88 | B |
| ATOM | 2861 | CB | VAL | 7 | 47.746 | -14.241 | 50.470 | 1.00 | 8.97 | | ATOM | 2910 | O | LEU | 12 | 41.672 | -19.443 | 51.993 | 1.00 | 11.33 | B |
| ATOM | 2862 | CG1 | VAL | 7 | 47.289 | -14.100 | 49.062 | 1.00 | 8.78 | | ATOM | 2911 | N | PRO | 13 | 40.463 | -18.136 | 50.598 | 1.00 | 10.64 | B |
| ATOM | 2863 | CG2 | VAL | 7 | 49.267 | -14.007 | 50.495 | 1.00 | 9.76 | | ATOM | 2912 | CD | PRO | 13 | 39.851 | -16.879 | 50.138 | 1.00 | 10.66 | B |
| ATOM | 2864 | C | VAL | 7 | 47.461 | -13.307 | 52.827 | 1.00 | 7.94 | | ATOM | 2913 | CA | PRO | 13 | 40.289 | -19.216 | 49.593 | 1.00 | 8.94 | B |
| ATOM | 2865 | O | VAL | 7 | 47.480 | -12.195 | 53.300 | 1.00 | 6.74 | | ATOM | 2914 | CB | PRO | 13 | 39.355 | -18.588 | 48.531 | 1.00 | 8.94 | B |
| ATOM | 2866 | N | ILE | 8 | 47.780 | -14.379 | 53.553 | 1.00 | 8.27 | | ATOM | 2915 | CG | PRO | 13 | 38.787 | -17.373 | 49.162 | 1.00 | 10.89 | B |
| ATOM | 2868 | CA | ILE | 8 | 47.897 | -12.216 | 54.952 | 1.00 | 7.52 | | ATOM | 2916 | C | PRO | 13 | 41.608 | -19.672 | 48.931 | 1.00 | 10.71 | B |
| ATOM | 2869 | CB | ILE | 8 | 48.671 | -10.937 | 55.311 | 1.00 | 9.28 | | ATOM | 2917 | O | PRO | 13 | 42.674 | -19.170 | 49.219 | 1.00 | 12.27 | B |
| ATOM | 2870 | CG2 | ILE | 8 | 49.226 | -10.985 | 56.769 | 1.00 | 9.47 | | ATOM | 2918 | N | SER | 14 | 41.532 | -20.648 | 48.049 | 1.00 | 12.59 | B |
| ATOM | 2871 | CG1 | ILE | 8 | 49.896 | -10.820 | 54.419 | 1.00 | 9.26 | | ATOM | 2920 | CA | SER | 14 | 42.726 | -21.116 | 47.367 | 1.00 | 13.21 | B |
| ATOM | 2872 | CD1 | ILE | 8 | 50.457 | -9.420 | 54.468 | 1.00 | 12.59 | | ATOM | 2921 | CB | SER | 14 | 42.437 | -22.375 | 46.733 | 1.00 | 13.27 | B |
| ATOM | 2873 | C | ILE | 8 | 46.718 | -12.484 | 55.906 | 1.00 | 7.67 | | ATOM | 2922 | OG | SER | 14 | 41.254 | -22.335 | 45.935 | 1.00 | 11.94 | B |
| ATOM | 2874 | O | ILE | 8 | 46.310 | -11.644 | 56.716 | 1.00 | 7.33 | | ATOM | 2924 | C | SER | 14 | 42.976 | -20.089 | 46.261 | 1.00 | 10.23 | B |
| ATOM | 2875 | N | GLY | 9 | 46.167 | -13.684 | 55.783 | 1.00 | 8.20 | | ATOM | 2925 | O | SER | 14 | 42.092 | -19.344 | 45.886 | 1.00 | 12.97 | B |
| ATOM | 2877 | CA | GLY | 9 | 44.915 | -17.818 | 59.592 | 1.00 | 9.96 | | ATOM | 2926 | N | ARG | 15 | 44.180 | -20.072 | 45.730 | 1.00 | 14.06 | B |
| ATOM | 2878 | C | GLY | 9 | 45.060 | -14.120 | 56.625 | 1.00 | 9.07 | | ATOM | 2928 | CA | ARG | 15 | 44.504 | -19.139 | 44.667 | 1.00 | 12.07 | B |
| ATOM | 2879 | O | GLY | 9 | 45.220 | -15.605 | 56.910 | 1.00 | 9.90 | | ATOM | 2929 | CB | ARG | 15 | 45.986 | -19.201 | 44.276 | 1.00 | 9.93 | B |
| ATOM | 2880 | N | ASN | 10 | 46.018 | -16.269 | 56.250 | 1.00 | 10.44 | | ATOM | 2930 | CG | ARG | 15 | 46.852 | -18.231 | 45.029 | 1.00 | 10.47 | B |
| ATOM | 2882 | CA | ASN | 10 | 44.445 | -16.163 | 57.823 | 1.00 | 9.93 | | ATOM | 2931 | CD | ARG | 15 | 46.979 | -18.604 | 46.480 | 1.00 | 8.54 | B |
| ATOM | 2883 | CB | ASN | 10 | 44.627 | -17.577 | 58.111 | 1.00 | 10.02 | | ATOM | 2932 | NE | ARG | 15 | 48.199 | -18.029 | 47.005 | 1.00 | 9.20 | B |
| ATOM | 2884 | CG | ASN | 10 | 43.803 | -17.333 | 60.491 | 1.00 | 9.75 | | ATOM | 2934 | CZ | ARG | 15 | 48.581 | -18.130 | 48.262 | 1.00 | 9.86 | B |
| ATOM | 2885 | OD1 | ASN | 10 | 42.706 | -17.026 | 60.029 | 1.00 | 10.48 | | ATOM | 2935 | NH1 | ARG | 15 | 47.827 | -18.787 | 49.123 | 1.00 | 7.50 | B |
| ATOM | 2886 | ND2 | ASN | 10 | 44.075 | -17.267 | 61.800 | 1.00 | 10.67 | | ATOM | 2938 | NH2 | ARG | 15 | 49.740 | -17.623 | 48.635 | 1.00 | 14.29 | B |
| ATOM | 2889 | C | ASN | 10 | 43.424 | -18.353 | 57.730 | 1.00 | 10.51 | | ATOM | 2941 | C | ARG | 15 | 43.624 | -19.384 | 43.468 | 1.00 | 16.06 | B |
| ATOM | 2890 | O | ASN | 10 | 43.319 | -19.510 | 58.127 | 1.00 | 11.11 | | ATOM | 2942 | O | ARG | 15 | 43.221 | -18.439 | 42.786 | 1.00 | 15.87 | B |
| ATOM | 2891 | N | ASN | 11 | 42.582 | -17.766 | 56.883 | 1.00 | 10.26 | | ATOM | 2943 | N | SER | 16 | 43.269 | -20.629 | 43.222 | 1.00 | 17.46 | B |
| ATOM | 2893 | CA | ASN | 11 | 41.307 | -18.389 | 56.486 | 1.00 | 11.04 | | ATOM | 2945 | CA | SER | 16 | 42.411 | -20.886 | 42.086 | 1.00 | 17.46 | B |
| ATOM | 2894 | CB | ASN | 11 | 40.282 | -17.981 | 57.560 | 1.00 | 9.17 | | ATOM | 2946 | CB | SER | 16 | 42.399 | -22.374 | 41.740 | 1.00 | 19.56 | B |
| ATOM | 2895 | CG | ASN | 11 | 40.060 | -16.467 | 57.578 | 1.00 | 10.15 | | ATOM | 2947 | OG | SER | 16 | 41.467 | -23.093 | 42.547 | 1.00 | 24.48 | B |
| ATOM | 2896 | OD1 | ASN | 11 | 40.850 | -15.733 | 57.028 | 1.00 | 11.78 | | ATOM | 2949 | C | SER | 16 | 41.003 | -20.326 | 42.374 | 1.00 | 17.47 | B |
| ATOM | 2897 | ND2 | ASN | 11 | 38.971 | -16.010 | 58.157 | 1.00 | 12.02 | | ATOM | 2950 | O | SER | 16 | 40.406 | -19.679 | 41.501 | 1.00 | 18.62 | B |

- 89 -

- 90 -

| | | | | | | | | | | | | | | | |
|---|---|---|---|---|---|---|---|---|---|---|---|---|---|---|---|
| ATOM | 2951 | H | ASP | 17 | 40.495 | -20.516 | 43.603 | 1.00 | 16.78 | B | ATOM | 2999 | CA | TYR | 22 | 37.846 | -12.365 | 40.086 | 1.00 | 10.88 | B |
| ATOM | 2952 | CA | ASP | 17 | 39.171 | -19.991 | 43.974 | 1.00 | 15.77 | B | ATOM | 3000 | CB | TYR | 22 | 39.353 | -12.206 | 39.823 | 1.00 | 8.16 | B |
| ATOM | 2954 | CB | ASP | 17 | 38.766 | -20.397 | 45.368 | 1.00 | 16.99 | B | ATOM | 3001 | CG | TYR | 22 | 40.142 | -11.441 | 40.894 | 1.00 | 5.04 | B |
| ATOM | 2955 | CG | ASP | 17 | 37.940 | -21.665 | 45.387 | 1.00 | 20.01 | B | ATOM | 3002 | CD1 | TYR | 22 | 40.342 | -11.962 | 42.184 | 1.00 | 3.19 | B |
| ATOM | 2956 | OD1 | ASP | 17 | 38.374 | -22.661 | 44.761 | 1.00 | 20.73 | B | ATOM | 3003 | CE1 | TYR | 22 | 41.161 | -11.299 | 43.097 | 1.00 | 2.63 | B |
| ATOM | 2957 | OD2 | ASP | 17 | 36.868 | -21.672 | 46.054 | 1.00 | 21.86 | B | ATOM | 3004 | CD2 | TYR | 22 | 40.761 | -10.241 | 40.580 | 1.00 | 2.75 | B |
| ATOM | 2958 | C | ASP | 17 | 39.156 | -18.487 | 43.899 | 1.00 | 15.16 | B | ATOM | 3005 | CE2 | TYR | 22 | 41.551 | -9.582 | 41.469 | 1.00 | 2.35 | B |
| ATOM | 2959 | O | ASP | 17 | 38.109 | -17.894 | 43.591 | 1.00 | 15.42 | B | ATOM | 3006 | CZ | TYR | 22 | 41.758 | -10.102 | 42.724 | 1.00 | 2.00 | B |
| ATOM | 2960 | H | VAL | 18 | 40.297 | -17.870 | 44.216 | 1.00 | 12.79 | B | ATOM | 3007 | OH | TYR | 22 | 42.599 | -9.415 | 43.555 | 1.00 | 3.27 | B |
| ATOM | 2962 | CA | VAL | 18 | 40.426 | -16.433 | 44.144 | 1.00 | 12.20 | B | ATOM | 3009 | C | TYR | 22 | 37.126 | -12.433 | 38.757 | 1.00 | 12.10 | B |
| ATOM | 2963 | CB | VAL | 18 | 41.732 | -15.951 | 44.859 | 1.00 | 11.31 | B | ATOM | 3010 | O | TYR | 22 | 36.503 | -11.437 | 38.334 | 1.00 | 14.26 | B |
| ATOM | 2964 | CG1 | VAL | 18 | 41.922 | -14.467 | 44.653 | 1.00 | 12.27 | B | ATOM | 3011 | N | ARG | 23 | 37.143 | -13.609 | 38.124 | 1.00 | 12.11 | B |
| ATOM | 2965 | CG2 | VAL | 18 | 41.661 | -16.197 | 46.351 | 1.00 | 12.74 | B | ATOM | 3013 | CA | ARG | 23 | 36.470 | -13.764 | 36.827 | 1.00 | 12.44 | B |
| ATOM | 2966 | C | VAL | 18 | 40.392 | -15.922 | 42.659 | 1.00 | 12.18 | B | ATOM | 3014 | CB | ARG | 23 | 36.903 | -15.037 | 36.082 | 1.00 | 12.67 | B |
| ATOM | 2967 | O | VAL | 18 | 39.772 | -14.882 | 42.334 | 1.00 | 10.03 | B | ATOM | 3015 | CG | ARG | 23 | 38.237 | -14.875 | 35.372 | 1.00 | 13.48 | B |
| ATOM | 2968 | H | VAL | 19 | 41.099 | -16.623 | 41.771 | 1.00 | 12.73 | B | ATOM | 3016 | CD | ARG | 23 | 38.848 | -16.204 | 34.959 | 1.00 | 15.43 | B |
| ATOM | 2970 | CA | VAL | 19 | 41.133 | -16.213 | 40.354 | 1.00 | 11.76 | B | ATOM | 3017 | NE | ARG | 23 | 38.779 | -16.420 | 33.518 | 1.00 | 16.66 | B |
| ATOM | 2971 | CB | VAL | 19 | 42.087 | -17.094 | 39.529 | 1.00 | 12.00 | B | ATOM | 3019 | CZ | ARG | 23 | 37.665 | -16.638 | 32.851 | 1.00 | 16.46 | B |
| ATOM | 2972 | CG1 | VAL | 19 | 41.883 | -16.826 | 38.053 | 1.00 | 11.87 | B | ATOM | 3020 | NH1 | ARG | 23 | 36.491 | -16.669 | 33.481 | 1.00 | 20.10 | B |
| ATOM | 2973 | CG2 | VAL | 19 | 43.536 | -16.862 | 39.939 | 1.00 | 11.60 | B | ATOM | 3023 | NH2 | ARG | 23 | 37.723 | -16.805 | 31.558 | 1.00 | 15.54 | B |
| ATOM | 2974 | C | VAL | 19 | 39.708 | -16.368 | 39.814 | 1.00 | 11.45 | B | ATOM | 3026 | C | ARG | 23 | 34.968 | -13.673 | 36.903 | 1.00 | 12.44 | B |
| ATOM | 2975 | O | VAL | 19 | 39.161 | -15.485 | 39.122 | 1.00 | 10.17 | B | ATOM | 3027 | O | ARG | 23 | 34.350 | -14.188 | 37.973 | 1.00 | 12.70 | B |
| ATOM | 2976 | H | GLN | 20 | 39.114 | -17.505 | 40.155 | 1.00 | 10.10 | B | ATOM | 3028 | N | SER | 24 | 34.367 | -14.111 | 38.084 | 1.00 | 12.65 | B |
| ATOM | 2978 | CA | GLN | 20 | 37.767 | -17.759 | 39.749 | 1.00 | 10.42 | B | ATOM | 3030 | CA | SER | 24 | 32.908 | -14.967 | 39.216 | 1.00 | 13.44 | B |
| ATOM | 2979 | CB | GLN | 20 | 37.309 | -19.112 | 40.222 | 1.00 | 9.52 | B | ATOM | 3031 | CB | SER | 24 | 32.366 | -15.663 | 39.786 | 1.00 | 12.51 | B |
| ATOM | 2980 | CG | GLN | 20 | 35.850 | -19.359 | 39.874 | 1.00 | 11.69 | B | ATOM | 3032 | OG | SER | 24 | 33.438 | -12.696 | 38.311 | 1.00 | 16.72 | B |
| ATOM | 2981 | CD | GLN | 20 | 35.356 | -20.716 | 40.344 | 1.00 | 11.14 | B | ATOM | 3034 | C | SER | 24 | 32.432 | -12.365 | 37.978 | 1.00 | 13.05 | B |
| ATOM | 2982 | OE1 | GLN | 20 | 35.954 | -21.342 | 41.217 | 1.00 | 11.34 | B | ATOM | 3035 | O | SER | 24 | 31.284 | -11.874 | 38.890 | 1.00 | 12.66 | B |
| ATOM | 2983 | NE2 | GLN | 20 | 34.256 | -21.176 | 39.763 | 1.00 | 10.71 | B | ATOM | 3036 | N | LYS | 25 | 33.294 | -10.497 | 39.189 | 1.00 | 12.70 | B |
| ATOM | 2986 | C | GLN | 20 | 36.780 | -16.697 | 40.208 | 1.00 | 10.82 | B | ATOM | 3038 | CA | LYS | 25 | 33.628 | -10.045 | 40.458 | 1.00 | 13.46 | B |
| ATOM | 2987 | O | GLN | 20 | 35.844 | -16.392 | 39.451 | 1.00 | 10.02 | B | ATOM | 3039 | CB | LYS | 25 | 33.208 | -10.842 | 41.655 | 1.00 | 13.41 | B |
| ATOM | 2988 | N | LEU | 21 | 36.938 | -16.195 | 41.447 | 1.00 | 10.95 | B | ATOM | 3040 | CG | LYS | 25 | 31.720 | -10.670 | 41.888 | 1.00 | 11.66 | B |
| ATOM | 2990 | CA | LEU | 21 | 36.052 | -15.158 | 41.993 | 1.00 | 11.68 | B | ATOM | 3041 | CD | LYS | 25 | 31.245 | -11.439 | 43.101 | 1.00 | 12.50 | B |
| ATOM | 2991 | CB | LEU | 21 | 36.343 | -14.862 | 43.470 | 1.00 | 12.97 | B | ATOM | 3042 | CE | LYS | 25 | 30.049 | -10.740 | 43.679 | 1.00 | 13.84 | B |
| ATOM | 2992 | CG | LEU | 21 | 35.320 | -14.657 | 44.609 | 1.00 | 11.75 | B | ATOM | 3043 | NZ | LYS | 25 | 30.049 | -10.740 | 43.679 | 1.00 | 16.81 | B |
| ATOM | 2993 | CD1 | LEU | 21 | 35.994 | -13.822 | 45.697 | 1.00 | 12.72 | B | ATOM | 3047 | C | LYS | 25 | 33.200 | -9.522 | 38.079 | 1.00 | 14.04 | B |
| ATOM | 2994 | CD2 | LEU | 21 | 34.027 | -13.975 | 44.173 | 1.00 | 11.72 | B | ATOM | 3048 | O | LYS | 25 | 32.628 | -8.427 | 38.048 | 1.00 | 16.72 | B |
| ATOM | 2995 | C | LEU | 21 | 36.281 | -13.880 | 41.191 | 1.00 | 13.47 | B | ATOM | 3049 | N | GLY | 26 | 34.046 | -9.924 | 37.141 | 1.00 | 13.87 | B |
| ATOM | 2996 | O | LEU | 21 | 35.329 | -13.161 | 40.886 | 1.00 | 13.47 | B | ATOM | 3051 | CA | GLY | 26 | 34.418 | -9.040 | 36.058 | 1.00 | 12.12 | B |
| ATOM | 2997 | N | TYR | 22 | 37.540 | -13.559 | 40.893 | 1.00 | 11.75 | B | ATOM | 3052 | C | GLY | 26 | 35.563 | -8.104 | 36.463 | 1.00 | 12.09 | B |

- 91 -

| | | | | | | | | | |
|---|---|---|---|---|---|---|---|---|---|
| ATOM | 3053 | O | GLY | 26 | 35.659 | -6.971 | 35.943 | 1.00 | 12.80 | B |
| ATOM | 3054 | N | ILE | 27 | 36.404 | -8.546 | 37.415 | 1.00 | 10.40 | B |
| ATOM | 3056 | CA | ILE | 27 | 37.550 | -7.765 | 37.860 | 1.00 | 8.56 | B |
| ATOM | 3057 | CB | ILE | 27 | 37.940 | -8.122 | 39.298 | 1.00 | 8.53 | B |
| ATOM | 3058 | CG2 | ILE | 27 | 39.258 | -7.435 | 39.642 | 1.00 | 7.44 | B |
| ATOM | 3059 | CG1 | ILE | 27 | 36.854 | -7.624 | 40.255 | 1.00 | 6.12 | B |
| ATOM | 3060 | CD1 | ILE | 27 | 36.793 | -8.378 | 41.631 | 1.00 | 8.32 | B |
| ATOM | 3061 | C | ILE | 27 | 38.622 | -8.148 | 36.861 | 1.00 | 6.48 | B |
| ATOM | 3062 | O | ILE | 27 | 39.018 | -9.313 | 36.766 | 1.00 | 9.43 | B |
| ATOM | 3063 | N | ASN | 28 | 39.026 | -7.165 | 36.056 | 1.00 | 10.41 | B |
| ATOM | 3065 | CA | ASN | 28 | 39.977 | -7.391 | 34.975 | 1.00 | 14.33 | B |
| ATOM | 3066 | CB | ASN | 28 | 39.579 | -6.558 | 33.723 | 1.00 | 20.98 | B |
| ATOM | 3067 | CG | ASN | 28 | 40.240 | -7.100 | 32.418 | 1.00 | 24.59 | B |
| ATOM | 3068 | OD1 | ASN | 28 | 40.135 | -6.481 | 31.318 | 1.00 | 23.39 | B |
| ATOM | 3069 | ND2 | ASN | 28 | 40.929 | -8.269 | 32.520 | 1.00 | 9.04 | B |
| ATOM | 3072 | C | ASN | 28 | 41.433 | -7.187 | 35.269 | 1.00 | 10.32 | B |
| ATOM | 3073 | O | ASN | 28 | 42.246 | -7.280 | 34.381 | 1.00 | 8.34 | B |
| ATOM | 3071 | N | GLY | 29 | 41.783 | -6.907 | 36.509 | 1.00 | 6.95 | B |
| ATOM | 3076 | CA | GLY | 29 | 43.177 | -6.671 | 36.822 | 1.00 | 7.30 | B |
| ATOM | 3077 | C | GLY | 29 | 43.450 | -7.033 | 38.277 | 1.00 | 5.67 | B |
| ATOM | 3078 | O | GLY | 29 | 42.570 | -6.826 | 39.154 | 1.00 | 5.61 | B |
| ATOM | 3079 | N | MET | 30 | 44.725 | -7.346 | 38.527 | 1.00 | 5.24 | B |
| ATOM | 3081 | CA | MET | 30 | 45.210 | -7.800 | 39.805 | 1.00 | 5.13 | B |
| ATOM | 3082 | CB | MET | 30 | 45.166 | -9.344 | 39.797 | 1.00 | 8.30 | B |
| ATOM | 3083 | CG | MET | 30 | 45.418 | -10.012 | 41.151 | 1.00 | 8.16 | B |
| ATOM | 3084 | SD | MET | 30 | 45.697 | -11.802 | 41.144 | 1.00 | 5.53 | B |
| ATOM | 3085 | CE | MET | 30 | 44.022 | -12.462 | 41.029 | 1.00 | 4.90 | B |
| ATOM | 3086 | C | MET | 30 | 46.643 | -7.403 | 40.154 | 1.00 | 4.95 | B |
| ATOM | 3087 | O | MET | 30 | 47.487 | -7.236 | 39.298 | 1.00 | 5.71 | B |
| ATOM | 3088 | N | ARG | 31 | 46.903 | -7.310 | 41.451 | 1.00 | 5.91 | B |
| ATOM | 3090 | CA | ARG | 31 | 48.237 | -7.050 | 41.967 | 1.00 | 6.01 | B |
| ATOM | 3091 | CB | ARG | 31 | 48.405 | -5.633 | 42.522 | 1.00 | 4.72 | B |
| ATOM | 3092 | CG | ARG | 31 | 49.761 | -5.428 | 43.165 | 1.00 | 5.22 | B |
| ATOM | 3093 | CD | ARG | 31 | 50.028 | -3.984 | 43.440 | 1.00 | 4.78 | B |
| ATOM | 3094 | NE | ARG | 31 | 51.366 | -3.828 | 43.999 | 1.00 | 3.60 | B |
| ATOM | 3096 | CZ | ARG | 31 | 51.767 | -2.770 | 44.707 | 1.00 | 3.55 | B |
| ATOM | 3097 | NH1 | ARG | 31 | 50.905 | -1.787 | 44.929 | 1.00 | 6.34 | B |
| ATOM | 3100 | NH2 | ARG | 31 | 53.043 | -2.652 | 45.108 | 1.00 | 5.03 | B |
| ATOM | 3103 | C | ARG | 31 | 48.612 | -8.093 | 43.049 | | | |
| ATOM | 3104 | O | ARG | 31 | 47.774 | -8.519 | 43.876 | | | |
| ATOM | 3105 | N | ILE | 32 | 49.822 | -8.621 | 42.925 | 1.00 | 6.01 | B |
| ATOM | 3107 | CA | ILE | 32 | 50.320 | -9.558 | 43.901 | 1.00 | 7.02 | B |
| ATOM | 3108 | CB | ILE | 32 | 50.412 | -11.031 | 43.363 | 1.00 | 7.32 | B |
| ATOM | 3109 | CG2 | ILE | 32 | 49.027 | -11.590 | 43.122 | 1.00 | 2.00 | B |
| ATOM | 3110 | CG1 | ILE | 32 | 51.362 | -11.178 | 42.158 | 1.00 | 4.08 | B |
| ATOM | 3111 | CD1 | ILE | 32 | 51.401 | -12.592 | 41.680 | 1.00 | 2.00 | B |
| ATOM | 3112 | C | ILE | 32 | 51.649 | -8.968 | 44.417 | 1.00 | 7.82 | B |
| ATOM | 3113 | O | ILE | 32 | 52.368 | -8.290 | 43.678 | 1.00 | 9.39 | B |
| ATOM | 3114 | N | TYR | 33 | 51.942 | -9.177 | 45.701 | 1.00 | 8.86 | B |
| ATOM | 3116 | CA | TYR | 33 | 53.119 | -8.569 | 46.336 | 1.00 | 7.84 | B |
| ATOM | 3117 | CB | TYR | 33 | 52.733 | -8.100 | 47.718 | 1.00 | 5.73 | B |
| ATOM | 3118 | CG | TYR | 33 | 51.615 | -7.068 | 47.674 | 1.00 | 4.30 | B |
| ATOM | 3119 | CD1 | TYR | 33 | 50.275 | -7.442 | 47.554 | 1.00 | 4.17 | B |
| ATOM | 3120 | CE1 | TYR | 33 | 49.253 | -6.483 | 47.456 | 1.00 | 3.72 | B |
| ATOM | 3121 | CD2 | TYR | 33 | 51.906 | -5.730 | 47.702 | 1.00 | 3.35 | B |
| ATOM | 3122 | CE2 | TYR | 33 | 50.892 | -4.774 | 47.609 | 1.00 | 4.17 | B |
| ATOM | 3123 | CZ | TYR | 33 | 49.583 | -5.153 | 47.480 | 1.00 | 3.77 | B |
| ATOM | 3124 | OH | TYR | 33 | 48.625 | -4.150 | 47.318 | 1.00 | 7.85 | B |
| ATOM | 3126 | C | TYR | 33 | 54.480 | -9.246 | 46.358 | 1.00 | 8.46 | B |
| ATOM | 3127 | O | TYR | 33 | 55.435 | -8.706 | 45.806 | 1.00 | 9.38 | B |
| ATOM | 3128 | N | PHE | 34 | 54.535 | -10.447 | 45.662 | 1.00 | 7.89 | B |
| ATOM | 3130 | CA | PHE | 34 | 55.750 | -11.221 | 46.991 | 1.00 | 6.92 | B |
| ATOM | 3131 | CB | PHE | 34 | 56.119 | -11.925 | 47.450 | 1.00 | 5.57 | B |
| ATOM | 3132 | CG | PHE | 34 | 55.150 | -12.985 | 47.274 | 1.00 | 2.47 | B |
| ATOM | 3133 | CD1 | PHE | 34 | 55.442 | -14.318 | 48.088 | 1.00 | 2.01 | B |
| ATOM | 3134 | CD2 | PHE | 34 | 53.980 | -12.647 | 47.710 | 1.00 | 3.40 | B |
| ATOM | 3135 | CE1 | PHE | 34 | 54.604 | -15.288 | 48.548 | 1.00 | 2.00 | B |
| ATOM | 3136 | CE2 | PHE | 34 | 53.104 | -13.630 | 48.353 | 1.00 | 3.10 | B |
| ATOM | 3137 | CZ | PHE | 34 | 53.422 | -14.966 | 48.580 | 1.00 | 2.00 | B |
| ATOM | 3138 | C | PHE | 34 | 55.392 | -12.227 | 44.580 | 1.00 | 7.99 | B |
| ATOM | 3139 | O | PHE | 34 | 54.202 | -12.415 | 44.280 | 1.00 | 7.18 | B |
| ATOM | 3140 | N | ALA | 35 | 56.395 | -12.881 | 43.992 | 1.00 | 8.68 | B |
| ATOM | 3142 | CA | ALA | 35 | 56.105 | -13.894 | 42.998 | 1.00 | 9.11 | B |
| ATOM | 3143 | CB | ALA | 35 | 57.357 | -14.269 | 42.333 | 1.00 | 10.87 | B |
| ATOM | 3144 | C | ALA | 35 | 55.488 | -15.127 | 43.663 | 1.00 | 10.61 | B |
| ATOM | 3145 | O | ALA | 35 | 56.178 | -16.100 | 43.969 | 1.00 | 11.66 | B |
| ATOM | 3146 | N | ASP | 36 | 54.205 | -15.044 | 43.998 | 1.00 | 11.43 | B |
| ATOM | 3148 | CA | ASP | 36 | 53.483 | -16.140 | 44.634 | 1.00 | 10.17 | B |
| ATOM | 3149 | CB | ASP | 36 | 52.150 | -15.572 | 45.194 | 1.00 | 9.93 | B |
| ATOM | 3150 | CG | ASP | 36 | 51.159 | -16.635 | 45.644 | 1.00 | 9.80 | B |

- 92 -

| ATOM | 3151 | OD1 | ASP | 36 | 51.361 | -17.842 | 45.438 | 1.00 | 12.22 | B |
|------|------|-----|-----|----|--------|---------|--------|------|-------|---|
| ATOM | 3152 | OD2 | ASP | 36 | 50.113 | -16.258 | 46.185 | 1.00 | 10.86 | B |
| ATOM | 3153 | C   | ASP | 36 | 53.272 | -17.105 | 43.475 | 1.00 | 10.17 | B |
| ATOM | 3154 | O   | ASP | 36 | 52.506 | -16.799 | 42.578 | 1.00 | 10.43 | B |
| ATOM | 3155 | N   | GLY | 37 | 53.976 | -18.243 | 43.489 | 1.00 | 10.29 | B |
| ATOM | 3157 | CA  | GLY | 37 | 53.881 | -19.254 | 42.439 | 1.00 | 9.75  | B |
| ATOM | 3158 | C   | GLY | 37 | 52.540 | -19.966 | 42.311 | 1.00 | 11.24 | B |
| ATOM | 3159 | O   | GLY | 37 | 52.193 | -20.544 | 41.255 | 1.00 | 11.77 | B |
| ATOM | 3160 | N   | GLN | 38 | 51.781 | -19.934 | 43.399 | 1.00 | 11.79 | B |
| ATOM | 3162 | CA  | GLN | 38 | 50.458 | -20.542 | 43.456 | 1.00 | 11.84 | B |
| ATOM | 3163 | CB  | GLN | 38 | 49.981 | -20.574 | 44.914 | 1.00 | 10.83 | B |
| ATOM | 3164 | CG  | GLN | 38 | 50.726 | -21.486 | 45.863 | 1.00 | 8.78  | B |
| ATOM | 3165 | CD  | GLN | 38 | 50.009 | -21.542 | 47.220 | 1.00 | 7.29  | B |
| ATOM | 3166 | OE1 | GLN | 38 | 48.876 | -21.991 | 47.305 | 1.00 | 6.06  | B |
| ATOM | 3167 | NE2 | GLN | 38 | 50.650 | -21.036 | 48.269 | 1.00 | 7.03  | B |
| ATOM | 3170 | C   | GLN | 38 | 49.465 | -19.687 | 42.641 | 1.00 | 11.58 | B |
| ATOM | 3171 | O   | GLN | 38 | 48.525 | -20.178 | 42.027 | 1.00 | 13.11 | B |
| ATOM | 3172 | N   | ALA | 39 | 49.659 | -18.383 | 42.677 | 1.00 | 11.36 | B |
| ATOM | 3174 | CA  | ALA | 39 | 48.767 | -17.475 | 41.982 | 1.00 | 10.35 | B |
| ATOM | 3175 | CB  | ALA | 39 | 48.795 | -16.110 | 42.617 | 1.00 | 7.92  | B |
| ATOM | 3176 | C   | ALA | 39 | 49.136 | -17.373 | 40.536 | 1.00 | 9.82  | B |
| ATOM | 3177 | O   | ALA | 39 | 48.234 | -17.251 | 39.709 | 1.00 | 10.78 | B |
| ATOM | 3178 | N   | LEU | 40 | 50.444 | -17.340 | 40.245 | 1.00 | 10.05 | B |
| ATOM | 3180 | CA  | LEU | 40 | 50.944 | -17.069 | 38.873 | 1.00 | 10.96 | B |
| ATOM | 3181 | CB  | LEU | 40 | 52.448 | -17.069 | 38.828 | 1.00 | 9.92  | B |
| ATOM | 3182 | CG  | LEU | 40 | 52.996 | -15.874 | 39.319 | 1.00 | 11.19 | B |
| ATOM | 3183 | CD1 | LEU | 40 | 54.488 | -14.575 | 38.343 | 1.00 | 9.34  | B |
| ATOM | 3184 | CD2 | LEU | 40 | 52.729 | -14.575 | 38.037 | 1.00 | 11.99 | B |
| ATOM | 3185 | C   | LEU | 40 | 50.504 | -18.431 | 38.037 | 1.00 | 13.73 | B |
| ATOM | 3186 | O   | LEU | 40 | 50.167 | -18.282 | 36.862 | 1.00 | 13.40 | B |
| ATOM | 3187 | N   | SER | 41 | 50.466 | -19.612 | 38.645 | 1.00 | 14.62 | B |
| ATOM | 3189 | CA  | SER | 41 | 50.008 | -20.794 | 37.926 | 1.00 | 14.74 | B |
| ATOM | 3190 | CB  | SER | 41 | 50.365 | -22.052 | 38.698 | 1.00 | 20.68 | B |
| ATOM | 3191 | OG  | SER | 41 | 49.575 | -22.142 | 39.855 | 1.00 | 13.75 | B |
| ATOM | 3193 | C   | SER | 41 | 48.496 | -20.727 | 37.713 | 1.00 | 13.62 | B |
| ATOM | 3194 | O   | SER | 41 | 48.001 | -21.118 | 36.668 | 1.00 | 14.02 | B |
| ATOM | 3195 | N   | ALA | 42 | 47.786 | -20.265 | 38.745 | 1.00 | 13.16 | B |
| ATOM | 3197 | CA  | ALA | 42 | 46.330 | -20.106 | 38.767 | 1.00 | 12.54 | B |
| ATOM | 3198 | CB  | ALA | 42 | 45.894 | -19.681 | 40.141 | 1.00 | 13.59 | B |
| ATOM | 3199 | C   | ALA | 42 | 45.850 | -19.078 | 37.727 | 1.00 | 14.04 | B |
| ATOM | 3200 | O   | ALA | 42 | 44.779 | -19.233 | 37.129 | 1.00 | 12.75 | B |
| ATOM | 3201 | N   | LEU | 43 | 46.645 | -18.034 | 37.518 | 1.00 | 12.85 | B |
| ATOM | 3203 | CA  | LEU | 43 | 46.321 | -16.994 | 36.561 | 1.00 | 11.99 | B |
| ATOM | 3204 | CB  | LEU | 43 | 47.177 | -15.770 | 36.812 | 1.00 | 11.84 | B |
| ATOM | 3205 | CG  | LEU | 43 | 46.724 | -14.950 | 38.012 | 1.00 | 9.69  | B |
| ATOM | 3206 | CD1 | LEU | 43 | 47.862 | -13.968 | 38.454 | 1.00 | 10.65 | B |
| ATOM | 3207 | CD2 | LEU | 43 | 45.418 | -14.247 | 37.611 | 1.00 | 14.02 | B |
| ATOM | 3208 | C   | LEU | 43 | 46.462 | -17.358 | 35.088 | 1.00 | 12.51 | B |
| ATOM | 3209 | O   | LEU | 43 | 46.021 | -16.584 | 34.240 | 1.00 | 14.50 | B |
| ATOM | 3210 | N   | ARG | 44 | 47.089 | -18.490 | 34.763 | 1.00 | 16.85 | B |
| ATOM | 3212 | CA  | ARG | 44 | 47.254 | -18.847 | 33.350 | 1.00 | 17.28 | B |
| ATOM | 3213 | CB  | ARG | 44 | 47.851 | -20.242 | 33.212 | 1.00 | 21.78 | B |
| ATOM | 3214 | CG  | ARG | 44 | 49.274 | -20.288 | 33.623 | 1.00 | 25.54 | B |
| ATOM | 3215 | CD  | ARG | 44 | 49.846 | -21.616 | 33.301 | 1.00 | 29.00 | B |
| ATOM | 3216 | NE  | ARG | 44 | 51.288 | -21.630 | 33.500 | 1.00 | 30.89 | B |
| ATOM | 3218 | CZ  | ARG | 44 | 51.880 | -22.357 | 34.439 | 1.00 | 30.60 | B |
| ATOM | 3219 | NH1 | ARG | 44 | 51.122 | -23.113 | 35.248 | 1.00 | 31.90 | B |
| ATOM | 3222 | NH2 | ARG | 44 | 53.216 | -22.357 | 34.548 | 1.00 | 16.48 | B |
| ATOM | 3225 | C   | ARG | 44 | 45.984 | -18.785 | 32.515 | 1.00 | 19.04 | B |
| ATOM | 3226 | O   | ARG | 44 | 44.990 | -19.386 | 32.872 | 1.00 | 16.70 | B |
| ATOM | 3227 | N   | ASN | 45 | 46.005 | -17.946 | 31.425 | 1.00 | 15.80 | B |
| ATOM | 3229 | CA  | ASN | 45 | 44.859 | -17.946 | 30.509 | 1.00 | 16.14 | B |
| ATOM | 3230 | CB  | ASN | 45 | 44.511 | -19.332 | 29.928 | 1.00 | 18.73 | B |
| ATOM | 3231 | CG  | ASN | 45 | 45.712 | -20.044 | 29.294 | 1.00 | 16.57 | B |
| ATOM | 3232 | OD1 | ASN | 45 | 46.420 | -19.478 | 28.464 | 1.00 | 16.57 | B |
| ATOM | 3233 | ND2 | ASN | 45 | 45.935 | -21.292 | 29.679 | 1.00 | 16.84 | B |
| ATOM | 3236 | C   | ASN | 45 | 43.580 | -17.344 | 31.088 | 1.00 | 15.93 | B |
| ATOM | 3237 | O   | ASN | 45 | 42.481 | -17.567 | 30.543 | 1.00 | 14.64 | B |
| ATOM | 3238 | N   | SER | 46 | 43.710 | -16.529 | 32.132 | 1.00 | 14.43 | B |
| ATOM | 3240 | CA  | SER | 46 | 42.530 | -15.928 | 32.787 | 1.00 | 11.46 | B |
| ATOM | 3241 | CB  | SER | 46 | 42.767 | -15.806 | 34.290 | 1.00 | 13.93 | B |
| ATOM | 3242 | OG  | SER | 46 | 43.968 | -15.092 | 34.520 | 1.00 | 14.32 | B |
| ATOM | 3244 | C   | SER | 46 | 42.189 | -14.565 | 32.238 | 1.00 | 11.37 | B |
| ATOM | 3245 | O   | SER | 46 | 41.115 | -14.010 | 32.549 | 1.00 | 12.11 | B |
| ATOM | 3246 | N   | GLY | 47 | 43.136 | -13.999 | 31.489 | 1.00 | 11.42 | B |
| ATOM | 3248 | CA  | GLY | 47 | 42.942 | -12.691 | 30.896 | 1.00 | 13.44 | B |
| ATOM | 3249 | C   | GLY | 47 | 43.046 | -11.562 | 31.892 | 1.00 | 10.17 | B |
| ATOM | 3250 | O   | GLY | 47 | 42.738 | -10.405 | 31.557 | 1.00 | 8.96  | B |
| ATOM | 3251 | N   | ILE | 48 | 43.476 | -11.871 | 33.119 | 1.00 |       | B |
| ATOM | 3253 | CA  | ILE | 48 | 43.619 | -10.840 | 34.155 | 1.00 |       | B |

| | | | | | | | | | |
|---|---|---|---|---|---|---|---|---|---|
| ATOM | 3254 | CB | ILE | 48 | 43.414 | -11.439 | 35.579 | 1.00 6.73 | B |
| ATOM | 3255 | CG1 | ILE | 48 | 43.880 | -10.482 | 36.657 | 1.00 5.89 | B |
| ATOM | 3256 | CG2 | ILE | 48 | 41.942 | -11.783 | 35.801 | 1.00 5.39 | B |
| ATOM | 3257 | CD1 | ILE | 48 | 41.698 | -13.069 | 36.675 | 1.00 4.19 | B |
| ATOM | 3258 | C | ILE | 48 | 44.974 | -10.126 | 34.026 | 1.00 8.84 | B |
| ATOM | 3259 | O | ILE | 48 | 45.991 | -10.769 | 33.869 | 1.00 9.78 | B |
| ATOM | 3260 | N | GLY | 49 | 44.958 | -8.801 | 33.949 | 1.00 8.63 | B |
| ATOM | 3262 | CA | GLY | 49 | 46.203 | -8.059 | 33.855 | 1.00 9.38 | B |
| ATOM | 3263 | C | GLY | 49 | 46.846 | -8.034 | 35.235 | 1.00 9.87 | B |
| ATOM | 3264 | O | GLY | 49 | 46.164 | -7.760 | 36.224 | 1.00 10.69 | B |
| ATOM | 3265 | N | LEU | 50 | 48.171 | -8.159 | 35.290 | 1.00 10.20 | B |
| ATOM | 3267 | CA | LEU | 50 | 48.867 | -8.242 | 36.556 | 1.00 8.44 | B |
| ATOM | 3268 | CB | LEU | 50 | 49.383 | -9.685 | 36.689 | 1.00 8.64 | B |
| ATOM | 3269 | CG | LEU | 50 | 49.996 | -10.090 | 38.054 | 1.00 9.53 | B |
| ATOM | 3270 | CD1 | LEU | 50 | 48.830 | -10.276 | 39.053 | 1.00 8.07 | B |
| ATOM | 3271 | CD2 | LEU | 50 | 50.879 | -11.383 | 37.969 | 1.00 6.05 | B |
| ATOM | 3272 | C | LEU | 50 | 50.053 | -7.303 | 36.771 | 1.00 7.94 | B |
| ATOM | 3273 | O | LEU | 50 | 50.797 | -7.027 | 35.819 | 1.00 6.49 | B |
| ATOM | 3274 | N | ILE | 51 | 50.155 | -6.754 | 37.996 | 1.00 7.87 | B |
| ATOM | 3276 | CA | ILE | 51 | 51.303 | -5.935 | 38.455 | 1.00 6.50 | B |
| ATOM | 3277 | CB | ILE | 51 | 50.914 | -4.762 | 39.416 | 1.00 7.80 | B |
| ATOM | 3278 | CG2 | ILE | 51 | 52.183 | -4.086 | 40.021 | 1.00 5.14 | B |
| ATOM | 3279 | CG1 | ILE | 51 | 50.066 | -3.713 | 38.702 | 1.00 6.84 | B |
| ATOM | 3280 | CD1 | ILE | 51 | 49.998 | -2.362 | 39.488 | 1.00 8.73 | B |
| ATOM | 3281 | C | ILE | 51 | 51.969 | -6.996 | 39.330 | 1.00 6.36 | B |
| ATOM | 3282 | O | ILE | 51 | 51.295 | -7.692 | 40.086 | 1.00 5.20 | B |
| ATOM | 3283 | N | LEU | 52 | 53.260 | -7.211 | 39.144 | 1.00 7.27 | B |
| ATOM | 3285 | CA | LEU | 52 | 53.983 | -8.219 | 39.884 | 1.00 6.47 | B |
| ATOM | 3286 | CB | LEU | 52 | 54.599 | -9.232 | 38.904 | 1.00 7.84 | B |
| ATOM | 3287 | CG | LEU | 52 | 55.531 | -10.335 | 39.428 | 1.00 6.22 | B |
| ATOM | 3288 | CD1 | LEU | 52 | 54.810 | -11.250 | 40.397 | 1.00 5.73 | B |
| ATOM | 3289 | CD2 | LEU | 52 | 56.066 | -11.133 | 38.285 | 1.00 8.78 | B |
| ATOM | 3290 | C | LEU | 52 | 55.096 | -7.613 | 40.695 | 1.00 8.09 | B |
| ATOM | 3291 | O | LEU | 52 | 56.127 | -7.246 | 40.130 | 1.00 7.38 | B |
| ATOM | 3292 | N | ASP | 53 | 54.886 | -7.453 | 42.008 | 1.00 8.71 | B |
| ATOM | 3294 | CA | ASP | 53 | 55.952 | -6.940 | 42.853 | 1.00 8.87 | B |
| ATOM | 3295 | CB | ASP | 53 | 55.478 | -6.666 | 44.297 | 1.00 10.63 | B |
| ATOM | 3296 | CG | ASP | 53 | 54.514 | -5.501 | 44.409 | 1.00 9.92 | B |
| ATOM | 3297 | OD1 | ASP | 53 | 54.633 | -4.756 | 45.403 | 1.00 9.71 | B |
| ATOM | 3298 | OD2 | ASP | 53 | 53.636 | -5.363 | 43.534 | 1.00 8.87 | B |
| ATOM | 3299 | C | ASP | 53 | 56.990 | -8.044 | 42.994 | 1.00 9.02 | B |
| ATOM | 3300 | O | ASP | 53 | 56.648 | -9.238 | 42.930 | 1.00 8.52 | B |
| ATOM | 3301 | N | ILE | 54 | 58.254 | -7.647 | 43.057 | 1.00 10.25 | B |
| ATOM | 3303 | CA | ILE | 54 | 59.336 | -8.619 | 43.198 | 1.00 10.83 | B |
| ATOM | 3304 | CB | ILE | 54 | 60.740 | -8.054 | 42.723 | 1.00 8.63 | B |
| ATOM | 3305 | CG2 | ILE | 54 | 60.688 | -7.648 | 41.259 | 1.00 7.24 | B |
| ATOM | 3306 | CG1 | ILE | 54 | 61.181 | -6.889 | 43.617 | 1.00 8.84 | B |
| ATOM | 3307 | CD1 | ILE | 54 | 62.599 | -6.372 | 43.359 | 1.00 6.67 | B |
| ATOM | 3308 | C | ILE | 54 | 59.413 | -9.050 | 44.686 | 1.00 12.50 | B |
| ATOM | 3309 | O | ILE | 54 | 59.756 | -10.216 | 45.013 | 1.00 13.70 | B |
| ATOM | 3310 | N | GLY | 55 | 58.952 | -8.176 | 45.571 | 1.00 13.24 | B |
| ATOM | 3312 | CA | GLY | 55 | 59.061 | -8.473 | 46.992 | 1.00 14.86 | B |
| ATOM | 3313 | C | GLY | 55 | 60.231 | -7.663 | 47.530 | 1.00 15.48 | B |
| ATOM | 3314 | O | GLY | 55 | 61.359 | -7.767 | 47.043 | 1.00 15.27 | B |
| ATOM | 3315 | N | ASN | 56 | 59.972 | -6.853 | 48.551 | 1.00 17.50 | B |
| ATOM | 3317 | CA | ASN | 56 | 61.004 | -5.995 | 49.126 | 1.00 18.32 | B |
| ATOM | 3318 | CB | ASN | 56 | 60.406 | -5.084 | 50.191 | 1.00 18.70 | B |
| ATOM | 3319 | CG | ASN | 56 | 59.807 | -3.819 | 49.596 | 1.00 19.26 | B |
| ATOM | 3320 | OD1 | ASN | 56 | 59.956 | -3.553 | 48.399 | 1.00 21.16 | B |
| ATOM | 3321 | ND2 | ASN | 56 | 59.149 | -3.024 | 50.426 | 1.00 19.33 | B |
| ATOM | 3324 | C | ASN | 56 | 62.241 | -6.719 | 49.625 | 1.00 19.00 | B |
| ATOM | 3325 | O | ASN | 56 | 63.334 | -6.157 | 49.682 | 1.00 18.91 | B |
| ATOM | 3326 | N | ASP | 57 | 62.074 | -7.993 | 49.923 | 1.00 20.46 | B |
| ATOM | 3328 | CA | ASP | 57 | 63.174 | -8.837 | 50.379 | 1.00 22.71 | B |
| ATOM | 3329 | CB | ASP | 57 | 62.614 | -10.039 | 51.111 | 1.00 24.28 | B |
| ATOM | 3330 | CG | ASP | 57 | 61.567 | -10.758 | 50.288 | 1.00 27.98 | B |
| ATOM | 3331 | OD1 | ASP | 57 | 61.928 | -11.778 | 49.642 | 1.00 30.33 | B |
| ATOM | 3332 | OD2 | ASP | 57 | 60.390 | -10.281 | 50.250 | 1.00 29.71 | B |
| ATOM | 3333 | C | ASP | 57 | 64.053 | -9.302 | 49.205 | 1.00 23.03 | B |
| ATOM | 3334 | O | ASP | 57 | 65.143 | -9.827 | 49.434 | 1.00 24.26 | B |
| ATOM | 3335 | N | GLN | 58 | 63.581 | -9.135 | 47.960 | 1.00 22.32 | B |
| ATOM | 3337 | CA | GLN | 58 | 64.348 | -9.520 | 46.765 | 1.00 21.28 | B |
| ATOM | 3338 | CB | GLN | 58 | 63.417 | -10.033 | 45.687 | 1.00 22.08 | B |
| ATOM | 3339 | CG | GLN | 58 | 62.758 | -11.310 | 46.034 | 1.00 23.53 | B |
| ATOM | 3340 | CD | GLN | 58 | 63.789 | -12.380 | 46.212 | 1.00 25.25 | B |
| ATOM | 3341 | OE1 | GLN | 58 | 64.457 | -12.757 | 45.255 | 1.00 25.84 | B |
| ATOM | 3342 | NE2 | GLN | 58 | 63.991 | -12.829 | 47.460 | 1.00 26.02 | B |
| ATOM | 3345 | C | GLN | 58 | 65.140 | -8.340 | 46.196 | 1.00 20.89 | B |
| ATOM | 3346 | O | GLN | 58 | 66.114 | -8.506 | 45.434 | 1.00 19.85 | B |
| ATOM | 3347 | N | LEU | 59 | 64.727 | -7.140 | 46.594 | 1.00 20.15 | B |

- 93 -

| | | | | | | | | | | | | | | | | |
|---|---|---|---|---|---|---|---|---|---|---|---|---|---|---|---|---|
| ATOM | 3349 | CA | LEU | 59 | 65.330 | -5.901 | 46.118 | 1.00 | 18.59 | B | ATOM | 3397 | CB | SER | 65 | 74.897 | -9.404 | 39.459 | 1.00 | 23.00 | B |
| ATOM | 3350 | CB | LEU | 59 | 64.787 | -4.718 | 46.919 | 1.00 | 17.50 | B | ATOM | 3398 | OG | SER | 65 | 74.132 | -10.570 | 39.721 | 1.00 | 24.31 | B |
| ATOM | 3351 | CG | LEU | 59 | 65.157 | -3.378 | 46.303 | 1.00 | 16.04 | B | ATOM | 3400 | C | SER | 65 | 72.879 | -8.539 | 38.370 | 1.00 | 22.11 | B |
| ATOM | 3352 | CD1 | LEU | 59 | 64.519 | -3.289 | 44.916 | 1.00 | 16.57 | B | ATOM | 3401 | O | SER | 65 | 71.834 | -9.058 | 38.747 | 1.00 | 22.36 | B |
| ATOM | 3353 | CD2 | LEU | 59 | 64.707 | -2.285 | 47.203 | 1.00 | 14.82 | B | ATOM | 3402 | N | THR | 66 | 73.182 | -8.364 | 37.085 | 1.00 | 22.76 | B |
| ATOM | 3354 | C | LEU | 59 | 66.860 | -5.836 | 46.010 | 1.00 | 17.96 | B | ATOM | 3404 | CA | THR | 66 | 72.243 | -8.661 | 35.994 | 1.00 | 22.56 | B |
| ATOM | 3355 | O | LEU | 59 | 67.390 | -5.593 | 44.930 | 1.00 | 18.10 | B | ATOM | 3405 | CB | THR | 66 | 72.819 | -8.238 | 34.629 | 1.00 | 22.54 | B |
| ATOM | 3356 | N | ALA | 60 | 67.562 | -6.112 | 47.106 | 1.00 | 17.17 | B | ATOM | 3406 | OG1 | THR | 66 | 72.707 | -6.823 | 34.502 | 1.00 | 24.33 | B |
| ATOM | 3358 | CA | ALA | 60 | 69.025 | -6.065 | 47.118 | 1.00 | 16.64 | B | ATOM | 3408 | CG2 | THR | 66 | 72.053 | -8.865 | 33.496 | 1.00 | 23.49 | B |
| ATOM | 3359 | CB | ALA | 60 | 69.555 | -6.198 | 48.539 | 1.00 | 15.51 | B | ATOM | 3409 | C | THR | 66 | 71.859 | -10.129 | 35.939 | 1.00 | 22.11 | B |
| ATOM | 3360 | C | ALA | 60 | 69.731 | -7.062 | 46.201 | 1.00 | 16.68 | B | ATOM | 3410 | O | THR | 66 | 70.767 | -10.487 | 35.483 | 1.00 | 21.99 | B |
| ATOM | 3361 | O | ALA | 60 | 70.762 | -6.728 | 45.585 | 1.00 | 17.65 | B | ATOM | 3411 | N | SER | 67 | 72.785 | -10.983 | 36.336 | 1.00 | 21.71 | B |
| ATOM | 3362 | N | ASN | 61 | 69.175 | -8.261 | 46.097 | 1.00 | 16.07 | B | ATOM | 3413 | CA | SER | 67 | 72.524 | -12.406 | 36.314 | 1.00 | 22.51 | B |
| ATOM | 3364 | CA | ASN | 61 | 69.739 | -9.348 | 45.289 | 1.00 | 15.84 | B | ATOM | 3414 | CB | SER | 67 | 73.803 | -13.164 | 36.636 | 1.00 | 23.71 | B |
| ATOM | 3365 | CB | ASN | 61 | 68.945 | -10.612 | 45.593 | 1.00 | 18.46 | B | ATOM | 3415 | OG | SER | 67 | 74.544 | -12.493 | 37.646 | 1.00 | 26.41 | B |
| ATOM | 3366 | CG | ASN | 61 | 69.535 | -11.835 | 44.954 | 1.00 | 20.94 | B | ATOM | 3417 | C | SER | 67 | 71.498 | -12.729 | 37.397 | 1.00 | 22.42 | B |
| ATOM | 3367 | OD1 | ASN | 61 | 70.749 | -11.990 | 44.902 | 1.00 | 23.75 | B | ATOM | 3418 | O | SER | 67 | 70.604 | -13.519 | 37.151 | 1.00 | 24.31 | B |
| ATOM | 3368 | ND2 | ASN | 61 | 68.682 | -12.729 | 44.479 | 1.00 | 22.34 | B | ATOM | 3419 | N | ASN | 68 | 71.611 | -12.141 | 38.581 | 1.00 | 22.34 | B |
| ATOM | 3371 | C | ASN | 61 | 69.670 | -9.044 | 43.801 | 1.00 | 15.69 | B | ATOM | 3421 | CA | ASN | 68 | 70.618 | -12.429 | 39.615 | 1.00 | 21.28 | B |
| ATOM | 3372 | O | ASN | 61 | 70.614 | -9.267 | 43.043 | 1.00 | 16.11 | B | ATOM | 3422 | CB | ASN | 68 | 70.833 | -11.579 | 40.856 | 1.00 | 22.88 | B |
| ATOM | 3373 | N | ILE | 62 | 68.517 | -8.553 | 43.385 | 1.00 | 15.40 | B | ATOM | 3423 | CG | ASN | 68 | 72.098 | -11.937 | 41.610 | 1.00 | 24.59 | B |
| ATOM | 3375 | CA | ILE | 62 | 68.277 | -8.177 | 42.009 | 1.00 | 15.24 | B | ATOM | 3424 | OD1 | ASN | 68 | 73.008 | -12.572 | 41.076 | 1.00 | 26.18 | B |
| ATOM | 3376 | CB | ILE | 62 | 66.738 | -8.012 | 41.759 | 1.00 | 13.43 | B | ATOM | 3425 | ND2 | ASN | 68 | 72.190 | -11.465 | 42.845 | 1.00 | 25.10 | B |
| ATOM | 3377 | CG2 | ILE | 62 | 66.464 | -7.388 | 40.420 | 1.00 | 13.45 | B | ATOM | 3428 | C | ASN | 68 | 69.246 | -12.113 | 39.039 | 1.00 | 19.69 | B |
| ATOM | 3378 | CG1 | ILE | 62 | 66.105 | -9.404 | 41.805 | 1.00 | 14.16 | B | ATOM | 3429 | O | ASN | 68 | 68.328 | -12.936 | 38.381 | 1.00 | 18.35 | B |
| ATOM | 3379 | CD1 | ILE | 62 | 64.587 | -9.455 | 41.862 | 1.00 | 16.10 | B | ATOM | 3430 | N | ALA | 69 | 69.168 | -10.951 | 38.381 | 1.00 | 18.39 | B |
| ATOM | 3380 | C | ILE | 62 | 69.120 | -6.946 | 41.625 | 1.00 | 15.96 | B | ATOM | 3432 | CA | ALA | 69 | 67.942 | -10.440 | 37.761 | 1.00 | 16.66 | B |
| ATOM | 3381 | O | ILE | 62 | 69.570 | -6.825 | 40.489 | 1.00 | 15.75 | B | ATOM | 3433 | CB | ALA | 69 | 68.198 | -9.021 | 37.233 | 1.00 | 15.09 | B |
| ATOM | 3382 | N | ALA | 63 | 69.390 | -6.058 | 42.572 | 1.00 | 16.79 | B | ATOM | 3434 | C | ALA | 69 | 67.489 | -11.393 | 36.635 | 1.00 | 16.73 | B |
| ATOM | 3384 | CA | ALA | 63 | 70.209 | -4.886 | 42.261 | 1.00 | 17.70 | B | ATOM | 3435 | O | ALA | 69 | 66.321 | -11.810 | 36.567 | 1.00 | 16.33 | B |
| ATOM | 3385 | CB | ALA | 63 | 69.990 | -3.821 | 43.313 | 1.00 | 16.82 | B | ATOM | 3436 | N | ALA | 70 | 68.435 | -11.771 | 35.784 | 1.00 | 15.80 | B |
| ATOM | 3386 | C | ALA | 63 | 71.697 | -5.280 | 42.188 | 1.00 | 19.18 | B | ATOM | 3438 | CA | ALA | 70 | 68.185 | -12.720 | 34.707 | 1.00 | 16.03 | B |
| ATOM | 3387 | O | ALA | 63 | 72.515 | -4.646 | 41.488 | 1.00 | 19.77 | B | ATOM | 3439 | CB | ALA | 70 | 69.508 | -12.977 | 33.947 | 1.00 | 15.69 | B |
| ATOM | 3388 | N | ALA | 64 | 72.014 | -6.382 | 42.851 | 1.00 | 19.54 | B | ATOM | 3440 | C | ALA | 70 | 67.621 | -14.031 | 35.323 | 1.00 | 15.23 | B |
| ATOM | 3390 | CA | ALA | 64 | 73.362 | -6.912 | 42.918 | 1.00 | 21.19 | B | ATOM | 3441 | O | ALA | 70 | 66.583 | -14.584 | 34.901 | 1.00 | 15.23 | B |
| ATOM | 3391 | CB | ALA | 64 | 73.379 | -8.194 | 43.729 | 1.00 | 20.90 | B | ATOM | 3442 | N | SER | 71 | 68.278 | -14.481 | 36.386 | 1.00 | 17.32 | B |
| ATOM | 3392 | C | ALA | 64 | 74.017 | -7.136 | 41.565 | 1.00 | 22.88 | B | ATOM | 3444 | CA | SER | 71 | 67.849 | -15.665 | 37.100 | 1.00 | 17.64 | B |
| ATOM | 3393 | O | ALA | 64 | 75.094 | -6.576 | 41.319 | 1.00 | 25.17 | B | ATOM | 3445 | CB | SER | 71 | 68.805 | -15.940 | 38.228 | 1.00 | 19.67 | B |
| ATOM | 3394 | N | SER | 65 | 73.398 | -7.931 | 40.692 | 1.00 | 22.31 | B | ATOM | 3446 | OG | SER | 71 | 68.634 | -17.276 | 38.663 | 1.00 | 22.69 | B |
| ATOM | 3396 | CA | SER | 65 | 73.969 | -8.200 | 39.373 | 1.00 | 22.59 | B | ATOM | 3448 | C | SER | 71 | 66.455 | -15.519 | 37.688 | 1.00 | 16.69 | B |

- 94 -

- 95 -

| ATOM | 3449 | O | SER | 71 | 65.651 | -16.461 | 37.626 | 1.00 | 16.90 | B | | ATOM | 3499 | CA | ASN | 76 | 59.379 | -16.260 | 37.948 | 1.00 | 19.42 | B |
|---|---|---|---|---|---|---|---|---|---|---|---|---|---|---|---|---|---|---|---|---|---|---|
| ATOM | 3450 | N | TRP | 72 | 66.142 | -14.351 | 38.251 | 1.00 | 16.40 | B | | ATOM | 3500 | CB | ASN | 76 | 59.478 | -15.332 | 39.169 | 1.00 | 20.12 | B |
| ATOM | 3451 | CA | TRP | 72 | 64.810 | -14.151 | 38.844 | 1.00 | 15.69 | B | | ATOM | 3501 | CG | ASN | 76 | 60.108 | -16.010 | 40.361 | 1.00 | 20.76 | B |
| ATOM | 3452 | CB | TRP | 72 | 64.701 | -12.787 | 39.525 | 1.00 | 16.44 | B | | ATOM | 3502 | OD1 | ASN | 76 | 59.522 | -16.899 | 40.966 | 1.00 | 22.08 | B |
| ATOM | 3453 | CG | TRP | 72 | 63.419 | -12.591 | 40.342 | 1.00 | 16.38 | B | | ATOM | 3503 | ND2 | ASN | 76 | 61.332 | -15.623 | 40.680 | 1.00 | 22.62 | B |
| ATOM | 3454 | CD2 | TRP | 72 | 62.178 | -11.972 | 39.901 | 1.00 | 16.03 | B | | ATOM | 3506 | C | ASN | 76 | 58.585 | -15.532 | 36.891 | 1.00 | 18.37 | B |
| ATOM | 3455 | CE2 | TRP | 72 | 61.281 | -12.008 | 40.993 | 1.00 | 14.91 | B | | ATOM | 3507 | O | ASN | 76 | 57.537 | -14.973 | 37.202 | 1.00 | 17.39 | B |
| ATOM | 3456 | CE3 | TRP | 72 | 61.749 | -11.387 | 38.699 | 1.00 | 14.62 | B | | ATOM | 3508 | N | VAL | 77 | 59.082 | -15.484 | 35.664 | 1.00 | 17.40 | B |
| ATOM | 3457 | CD1 | TRP | 72 | 63.218 | -12.954 | 41.638 | 1.00 | 16.13 | B | | ATOM | 3510 | CA | VAL | 77 | 58.356 | -14.782 | 34.617 | 1.00 | 16.79 | B |
| ATOM | 3458 | NE1 | TRP | 72 | 61.937 | -12.609 | 42.032 | 1.00 | 15.80 | B | | ATOM | 3511 | CB | VAL | 77 | 59.038 | -13.406 | 34.258 | 1.00 | 16.86 | B |
| ATOM | 3459 | CZ2 | TRP | 72 | 59.973 | -11.482 | 40.917 | 1.00 | 15.08 | B | | ATOM | 3512 | CG1 | VAL | 77 | 58.499 | -12.861 | 32.907 | 1.00 | 15.31 | B |
| ATOM | 3461 | CZ3 | TRP | 72 | 60.444 | -10.862 | 38.637 | 1.00 | 14.76 | B | | ATOM | 3513 | CG2 | VAL | 77 | 58.870 | -12.369 | 35.413 | 1.00 | 14.28 | B |
| ATOM | 3463 | CH2 | TRP | 72 | 59.582 | -10.915 | 39.738 | 1.00 | 14.02 | B | | ATOM | 3514 | C | VAL | 77 | 58.246 | -15.631 | 33.366 | 1.00 | 16.85 | B |
| ATOM | 3464 | C | TRP | 72 | 63.731 | -14.284 | 37.782 | 1.00 | 15.51 | B | | ATOM | 3515 | O | VAL | 77 | 57.156 | -15.905 | 32.896 | 1.00 | 16.24 | B |
| ATOM | 3465 | O | TRP | 72 | 62.667 | -14.887 | 38.021 | 1.00 | 13.66 | B | | ATOM | 3516 | N | ARG | 78 | 59.384 | -16.144 | 32.903 | 1.00 | 18.46 | B |
| ATOM | 3466 | N | VAL | 73 | 64.059 | -13.726 | 36.612 | 1.00 | 15.42 | B | | ATOM | 3518 | CA | ARG | 78 | 59.435 | -16.925 | 31.673 | 1.00 | 18.28 | B |
| ATOM | 3468 | CA | VAL | 73 | 63.214 | -13.693 | 35.420 | 1.00 | 15.67 | B | | ATOM | 3519 | CB | ARG | 78 | 60.885 | -17.352 | 31.328 | 1.00 | 19.29 | B |
| ATOM | 3469 | CB | VAL | 73 | 63.838 | -12.750 | 34.328 | 1.00 | 13.90 | B | | ATOM | 3520 | CG | ARG | 78 | 61.916 | -16.209 | 31.262 | 1.00 | 24.73 | B |
| ATOM | 3470 | CG1 | VAL | 73 | 63.122 | -12.912 | 32.985 | 1.00 | 13.73 | B | | ATOM | 3521 | CD | ARG | 78 | 63.347 | -16.713 | 30.968 | 0.00 | 28.69 | B |
| ATOM | 3471 | CG2 | VAL | 73 | 63.761 | -11.301 | 34.784 | 1.00 | 11.75 | B | | ATOM | 3522 | NE | ARG | 78 | 64.353 | -15.666 | 31.177 | 1.00 | 33.65 | B |
| ATOM | 3472 | C | VAL | 73 | 63.009 | -15.114 | 34.906 | 1.00 | 17.26 | B | | ATOM | 3524 | CZ | ARG | 78 | 65.643 | -15.880 | 31.508 | 1.00 | 35.45 | B |
| ATOM | 3473 | O | VAL | 73 | 61.873 | -15.536 | 34.643 | 1.00 | 18.23 | B | | ATOM | 3525 | NH1 | ARG | 78 | 66.107 | -17.126 | 31.656 | 1.00 | 35.96 | B |
| ATOM | 3474 | N | GLN | 74 | 64.112 | -15.853 | 34.801 | 1.00 | 17.79 | B | | ATOM | 3528 | NH2 | ARG | 78 | 66.462 | -14.848 | 31.756 | 1.00 | 34.22 | B |
| ATOM | 3476 | CA | GLN | 74 | 64.071 | -17.222 | 34.377 | 1.00 | 18.38 | B | | ATOM | 3531 | C | ARG | 78 | 58.447 | -18.088 | 31.628 | 1.00 | 17.42 | B |
| ATOM | 3477 | CB | GLN | 74 | 65.455 | -17.862 | 34.491 | 1.00 | 20.08 | B | | ATOM | 3532 | O | ARG | 78 | 57.781 | -18.290 | 30.627 | 1.00 | 19.26 | B |
| ATOM | 3478 | CG | GLN | 74 | 65.618 | -19.142 | 33.628 | 1.00 | 20.07 | B | | ATOM | 3533 | N | PRO | 79 | 58.276 | -18.817 | 32.722 | 1.00 | 15.63 | B |
| ATOM | 3479 | CD | GLN | 74 | 66.909 | -19.879 | 33.922 | 1.00 | 20.23 | B | | ATOM | 3534 | CD | PRO | 79 | 59.020 | -18.764 | 33.996 | 1.00 | 15.96 | B |
| ATOM | 3480 | OE1 | GLN | 74 | 67.861 | -19.820 | 33.146 | 0.00 | 20.24 | B | | ATOM | 3535 | CA | PRO | 79 | 57.345 | -19.938 | 32.699 | 1.00 | 15.51 | B |
| ATOM | 3481 | NE2 | GLN | 74 | 66.949 | -20.578 | 35.049 | 0.00 | 20.24 | B | | ATOM | 3536 | CB | PRO | 79 | 57.654 | -20.661 | 34.012 | 1.00 | 15.95 | B |
| ATOM | 3484 | C | GLN | 74 | 63.103 | -17.986 | 35.252 | 1.00 | 19.30 | B | | ATOM | 3537 | CG | PRO | 79 | 59.069 | -20.166 | 34.381 | 1.00 | 16.24 | B |
| ATOM | 3485 | O | GLN | 74 | 62.179 | -18.595 | 34.751 | 1.00 | 19.80 | B | | ATOM | 3538 | C | PRO | 79 | 55.861 | -19.589 | 32.705 | 1.00 | 16.72 | B |
| ATOM | 3486 | N | ASN | 75 | 63.252 | -17.890 | 36.564 | 1.00 | 21.28 | B | | ATOM | 3539 | O | PRO | 79 | 55.033 | -20.508 | 32.638 | 1.00 | 17.03 | B |
| ATOM | 3488 | CA | ASN | 75 | 62.360 | -18.640 | 37.446 | 1.00 | 23.99 | B | | ATOM | 3540 | N | TYR | 80 | 55.516 | -18.301 | 32.831 | 1.00 | 16.03 | B |
| ATOM | 3489 | CB | ASN | 75 | 63.001 | -18.877 | 38.827 | 1.00 | 25.63 | B | | ATOM | 3542 | CA | TYR | 80 | 54.108 | -17.888 | 32.948 | 1.00 | 15.16 | B |
| ATOM | 3490 | CG | ASN | 75 | 64.367 | -19.552 | 38.758 | 1.00 | 26.59 | B | | ATOM | 3543 | CB | TYR | 80 | 53.925 | -17.171 | 34.284 | 1.00 | 14.71 | B |
| ATOM | 3491 | OD1 | ASN | 75 | 64.627 | -20.400 | 37.899 | 1.00 | 25.86 | B | | ATOM | 3544 | CG | TYR | 80 | 54.424 | -18.012 | 35.421 | 1.00 | 14.21 | B |
| ATOM | 3492 | ND2 | ASN | 75 | 65.256 | -19.155 | 39.670 | 1.00 | 20.81 | B | | ATOM | 3545 | CD1 | TYR | 80 | 55.569 | -17.649 | 36.134 | 1.00 | 14.00 | B |
| ATOM | 3495 | C | ASN | 75 | 60.930 | -18.123 | 37.688 | 1.00 | 20.60 | B | | ATOM | 3546 | CE1 | TYR | 80 | 56.042 | -18.454 | 37.129 | 1.00 | 15.70 | B |
| ATOM | 3496 | O | ASN | 75 | 60.034 | -18.925 | 37.932 | 1.00 | 20.83 | B | | ATOM | 3547 | CD2 | TYR | 80 | 53.773 | -19.205 | 35.744 | 1.00 | 13.84 | B |
| ATOM | 3497 | N | ASN | 76 | 60.702 | -16.810 | 37.627 | | | | | ATOM | 3548 | CE2 | TYR | 80 | 54.232 | -20.020 | 36.725 | 1.00 | 14.65 | B |

– 96 –

| ATOM | 3549 | CZ | TYR | 80 | 55.361 | -19.651 | 37.419 | 1.00 | 16.27 | B |
| --- | --- | --- | --- | --- | --- | --- | --- | --- | --- | --- |
| ATOM | 3550 | OH | TYR | 80 | 55.816 | -20.489 | 38.409 | 1.00 | 19.72 | B |
| ATOM | 3552 | C | TYR | 80 | 53.574 | -16.976 | 31.888 | 1.00 | 15.10 | B |
| ATOM | 3553 | O | TYR | 80 | 52.376 | -16.940 | 31.645 | 1.00 | 15.80 | B |
| ATOM | 3554 | N | TYR | 81 | 54.413 | -16.197 | 31.288 | 1.00 | 14.27 | B |
| ATOM | 3556 | CA | TYR | 81 | 54.03 | -15.232 | 30.272 | 1.00 | 14.78 | B |
| ATOM | 3557 | CB | TYR | 81 | 55.02 | -14.083 | 30.350 | 1.00 | 13.38 | B |
| ATOM | 3558 | CG | TYR | 81 | 54.753 | -12.953 | 29.464 | 1.00 | 12.16 | B |
| ATOM | 3559 | CD1 | TYR | 81 | 53.872 | -11.989 | 29.826 | 1.00 | 12.93 | B |
| ATOM | 3560 | CE1 | TYR | 81 | 53.670 | -10.881 | 29.039 | 1.00 | 14.74 | B |
| ATOM | 3561 | CD2 | TYR | 81 | 55.447 | -12.816 | 28.273 | 1.00 | 14.36 | B |
| ATOM | 3562 | CE2 | TYR | 81 | 55.266 | -11.717 | 27.455 | 1.00 | 15.03 | B |
| ATOM | 3563 | CZ | TYR | 81 | 54.361 | -10.742 | 27.855 | 1.00 | 15.09 | B |
| ATOM | 3564 | OH | TYR | 81 | 54.162 | -9.635 | 27.073 | 1.00 | 15.46 | B |
| ATOM | 3566 | C | TYR | 81 | 54.101 | -15.920 | 28.899 | 1.00 | 14.97 | B |
| ATOM | 3567 | O | TYR | 81 | 54.915 | -16.812 | 28.702 | 1.00 | 16.20 | B |
| ATOM | 3568 | N | PRO | 82 | 53.252 | -15.529 | 27.928 | 1.00 | 14.56 | B |
| ATOM | 3569 | CD | PRO | 82 | 53.437 | -16.075 | 26.562 | 1.00 | 13.93 | B |
| ATOM | 3570 | CA | PRO | 82 | 52.209 | -14.512 | 27.922 | 1.00 | 12.72 | B |
| ATOM | 3571 | CB | PRO | 82 | 52.243 | -14.030 | 26.469 | 1.00 | 11.06 | B |
| ATOM | 3572 | CG | PRO | 82 | 52.436 | -15.282 | 25.743 | 1.00 | 12.27 | B |
| ATOM | 3573 | C | PRO | 82 | 50.867 | -15.130 | 28.337 | 1.00 | 12.12 | B |
| ATOM | 3574 | O | PRO | 82 | 49.803 | -14.534 | 28.115 | 1.00 | 12.87 | B |
| ATOM | 3575 | N | ALA | 83 | 50.927 | -16.340 | 28.895 | 1.00 | 10.23 | B |
| ATOM | 3577 | CA | ALA | 83 | 49.731 | -17.016 | 29.384 | 1.00 | 10.59 | B |
| ATOM | 3578 | CB | ALA | 83 | 50.058 | -18.403 | 29.844 | 1.00 | 9.83 | B |
| ATOM | 3579 | C | ALA | 83 | 49.192 | -16.211 | 30.565 | 1.00 | 10.72 | B |
| ATOM | 3580 | O | ALA | 83 | 48.007 | -16.309 | 30.894 | 1.00 | 11.22 | B |
| ATOM | 3581 | N | VAL | 84 | 50.105 | -15.553 | 31.291 | 1.00 | 10.50 | B |
| ATOM | 3583 | CA | VAL | 84 | 49.749 | -14.707 | 32.435 | 1.00 | 10.10 | B |
| ATOM | 3584 | CB | VAL | 84 | 50.580 | -15.025 | 33.727 | 1.00 | 9.43 | B |
| ATOM | 3585 | CG1 | VAL | 84 | 50.442 | -13.897 | 34.123 | 1.00 | 10.41 | B |
| ATOM | 3586 | CG2 | VAL | 84 | 50.077 | -16.281 | 34.399 | 1.00 | 9.90 | B |
| ATOM | 3587 | C | VAL | 84 | 50.057 | -13.300 | 31.919 | 1.00 | 10.69 | B |
| ATOM | 3588 | O | VAL | 84 | 51.159 | -13.044 | 31.442 | 1.00 | 11.55 | B |
| ATOM | 3589 | N | ASN | 85 | 49.077 | -12.412 | 31.927 | 1.00 | 9.98 | B |
| ATOM | 3591 | CA | ASN | 85 | 49.333 | -11.075 | 31.425 | 1.00 | 11.25 | B |
| ATOM | 3592 | CB | ASN | 85 | 48.056 | -10.421 | 30.880 | 1.00 | 11.41 | B |
| ATOM | 3593 | CG | ASN | 85 | 48.353 | -9.195 | 30.022 | 1.00 | 12.30 | B |
| ATOM | 3594 | CD1 | ASN | 85 | 47.528 | -8.273 | 29.923 | 1.00 | 14.82 | B |
| ATOM | 3595 | ND2 | ASN | 85 | 49.519 | -9.173 | 29.400 | 1.00 | 8.23 | B |
| ATOM | 3598 | C | ASN | 85 | 50.029 | -10.105 | 32.365 | 1.00 | 10.57 | B |
| ATOM | 3599 | O | ASN | 85 | 49.420 | -9.154 | 32.843 | 1.00 | 10.71 | B |
| ATOM | 3600 | N | ILE | 86 | 51.303 | -10.356 | 32.610 | 1.00 | 0.45 | B |
| ATOM | 3602 | CA | ILE | 86 | 52.118 | -9.498 | 33.448 | 1.00 | 0.69 | B |
| ATOM | 3603 | CB | ILE | 86 | 53.476 | -10.157 | 33.758 | 1.00 | 12.35 | B |
| ATOM | 3604 | CG2 | ILE | 86 | 54.296 | -9.295 | 34.753 | 1.00 | 12.14 | B |
| ATOM | 3605 | CG1 | ILE | 86 | 53.253 | -11.596 | 34.270 | 1.00 | 3.69 | B |
| ATOM | 3606 | CD1 | ILE | 86 | 54.565 | -12.430 | 34.447 | 1.00 | 2.60 | B |
| ATOM | 3607 | C | ILE | 86 | 52.386 | -8.199 | 32.682 | 1.00 | 0.62 | B |
| ATOM | 3608 | O | ILE | 86 | 53.133 | -8.192 | 31.711 | 1.00 | 9.28 | B |
| ATOM | 3609 | N | LYS | 87 | 51.773 | -7.114 | 33.146 | 1.00 | 9.24 | B |
| ATOM | 3611 | CA | LYS | 87 | 51.908 | -5.807 | 32.577 | 1.00 | 7.51 | B |
| ATOM | 3612 | CB | LYS | 87 | 50.627 | -5.037 | 32.795 | 1.00 | 8.46 | B |
| ATOM | 3613 | CG | LYS | 87 | 49.415 | -5.700 | 32.185 | 1.00 | 9.57 | B |
| ATOM | 3614 | CD | LYS | 87 | 48.200 | -4.920 | 32.482 | 1.00 | 9.98 | B |
| ATOM | 3615 | CE | LYS | 87 | 48.370 | -3.542 | 31.993 | 1.00 | 1.84 | B |
| ATOM | 3616 | NZ | LYS | 87 | 47.138 | -2.763 | 32.325 | 1.00 | 6.17 | B |
| ATOM | 3620 | C | LYS | 87 | 53.041 | -5.014 | 33.185 | 1.00 | 8.49 | B |
| ATOM | 3621 | O | LYS | 87 | 53.727 | -4.270 | 32.492 | 1.00 | 9.08 | B |
| ATOM | 3622 | N | TYR | 88 | 53.201 | -5.086 | 34.500 | 1.00 | 8.80 | B |
| ATOM | 3624 | CA | TYR | 88 | 54.266 | -4.322 | 35.154 | 1.00 | 8.41 | B |
| ATOM | 3625 | CB | TYR | 88 | 53.683 | -3.083 | 35.859 | 1.00 | 8.52 | B |
| ATOM | 3626 | CG | TYR | 88 | 52.648 | -2.281 | 35.070 | 1.00 | 8.10 | B |
| ATOM | 3627 | CD1 | TYR | 88 | 52.648 | -2.267 | 35.449 | 1.00 | 8.07 | B |
| ATOM | 3628 | CE1 | TYR | 88 | 50.344 | -1.552 | 34.717 | 1.00 | 7.17 | B |
| ATOM | 3629 | CD2 | TYR | 88 | 53.024 | -1.539 | 33.944 | 1.00 | 9.56 | B |
| ATOM | 3630 | CE2 | TYR | 88 | 52.075 | -0.794 | 33.222 | 1.00 | 8.64 | B |
| ATOM | 3631 | CZ | TYR | 88 | 50.752 | -0.819 | 33.611 | 1.00 | 7.33 | B |
| ATOM | 3632 | OH | TYR | 88 | 49.855 | -0.126 | 32.859 | 1.00 | 7.69 | B |
| ATOM | 3634 | C | TYR | 88 | 54.921 | -5.170 | 36.226 | 1.00 | 9.21 | B |
| ATOM | 3635 | O | TYR | 88 | 54.314 | -6.105 | 36.758 | 1.00 | 8.81 | B |
| ATOM | 3636 | N | ILE | 89 | 56.168 | -4.850 | 36.531 | 1.00 | 9.79 | B |
| ATOM | 3638 | CA | ILE | 89 | 56.879 | -5.522 | 37.622 | 1.00 | 0.80 | B |
| ATOM | 3639 | CB | ILE | 89 | 58.078 | -6.353 | 37.154 | 1.00 | 11.36 | B |
| ATOM | 3640 | CG2 | ILE | 89 | 58.929 | -6.754 | 38.382 | 1.00 | 12.69 | B |
| ATOM | 3641 | CG1 | ILE | 89 | 57.553 | -7.535 | 36.328 | 1.00 | 10.76 | B |
| ATOM | 3642 | CD1 | ILE | 89 | 58.552 | -8.562 | 36.005 | 1.00 | 10.95 | B |
| ATOM | 3643 | C | ILE | 89 | 57.327 | -4.373 | 38.489 | 1.00 | 10.49 | B |
| ATOM | 3644 | O | ILE | 89 | 57.858 | -3.396 | 37.971 | 1.00 | 10.96 | B |

- 97 -

| | | | | | | | | | | | | | | |
|---|---|---|---|---|---|---|---|---|---|---|---|---|---|---|
| ATOM | 3645 | N | ALA | 90 | 56.928 | -4.416 | 39.754 | 1.00 | 10.57 | B | ATOM | 3694 | CB | GLN | 96 | 61.552 | 3.745 | 53.960 | 1.00 | 19.96 | B |
| ATOM | 3647 | CA | ALA | 90 | 57.248 | -3.363 | 40.713 | 1.00 | 10.29 | B | ATOM | 3695 | CG | GLN | 96 | 60.145 | 4.296 | 53.667 | 1.00 | 19.80 | B |
| ATOM | 3648 | CB | ALA | 90 | 56.123 | -3.186 | 41.693 | 1.00 | 9.05 | B | ATOM | 3696 | CD | GLN | 96 | 59.215 | 4.180 | 54.857 | 0.00 | 19.90 | B |
| ATOM | 3649 | C | ALA | 90 | 58.496 | -3.714 | 41.462 | 1.00 | 10.56 | B | ATOM | 3697 | OE1 | GLN | 96 | 59.383 | 4.868 | 55.862 | 0.00 | 19.80 | B |
| ATOM | 3650 | O | ALA | 90 | 58.490 | -4.674 | 42.260 | 1.00 | 11.58 | B | ATOM | 3698 | NE2 | GLN | 96 | 58.230 | 3.300 | 54.750 | 0.00 | 19.80 | B |
| ATOM | 3651 | N | ALA | 90 | 59.577 | -3.007 | 41.151 | 1.00 | 9.68 | B | ATOM | 3701 | C | GLN | 96 | 63.901 | 3.354 | 53.226 | 1.00 | 21.68 | B |
| ATOM | 3653 | CA | ALA | 90 | 60.820 | -3.228 | 41.823 | 1.00 | 10.00 | B | ATOM | 3702 | O | GLN | 96 | 64.388 | 2.225 | 53.247 | 1.00 | 23.02 | B |
| ATOM | 3654 | CB | ALA | 90 | 61.990 | -2.797 | 40.960 | 1.00 | 7.01 | B | ATOM | 3703 | N | GLY | 97 | 64.597 | 4.425 | 53.567 | 1.00 | 22.89 | B |
| ATOM | 3655 | C | ALA | 90 | 60.798 | -2.455 | 43.164 | 1.00 | 10.79 | B | ATOM | 3705 | CA | GLY | 97 | 65.936 | 4.261 | 54.089 | 1.00 | 24.62 | B |
| ATOM | 3656 | O | ALA | 90 | 61.412 | -1.406 | 43.298 | 1.00 | 12.12 | B | ATOM | 3706 | C | GLY | 97 | 67.009 | 4.067 | 53.035 | 1.00 | 25.95 | B |
| ATOM | 3657 | N | GLY | 91 | 60.053 | -2.964 | 44.136 | 1.00 | 11.21 | B | ATOM | 3707 | O | GLY | 97 | 66.860 | 4.480 | 51.900 | 1.00 | 28.17 | B |
| ATOM | 3659 | CA | GLY | 91 | 60.021 | -2.343 | 45.451 | 1.00 | 10.63 | B | ATOM | 3708 | N | GLY | 98 | 68.132 | 3.496 | 53.433 | 1.00 | 25.50 | B |
| ATOM | 3660 | C | GLY | 91 | 58.683 | -1.719 | 45.729 | 1.00 | 10.10 | B | ATOM | 3710 | CA | GLY | 98 | 69.208 | 3.299 | 52.499 | 1.00 | 24.20 | B |
| ATOM | 3661 | O | GLY | 91 | 58.082 | -1.156 | 44.831 | 1.00 | 9.02 | B | ATOM | 3711 | C | GLY | 98 | 68.850 | 2.229 | 51.511 | 1.00 | 23.41 | B |
| ATOM | 3662 | N | ASN | 92 | 58.220 | -1.829 | 46.970 | 1.00 | 10.74 | B | ATOM | 3712 | O | GLY | 98 | 69.617 | 1.964 | 50.590 | 1.00 | 24.86 | B |
| ATOM | 3664 | CA | ASN | 92 | 56.935 | -1.263 | 47.392 | 1.00 | 11.40 | B | ATOM | 3713 | N | ALA | 99 | 67.709 | 1.583 | 51.686 | 1.00 | 21.19 | B |
| ATOM | 3665 | CB | ASN | 92 | 55.882 | -2.352 | 47.628 | 1.00 | 11.00 | B | ATOM | 3715 | CA | ALA | 99 | 67.351 | 0.557 | 50.723 | 1.00 | 22.15 | B |
| ATOM | 3666 | CG | ASN | 92 | 54.528 | -1.776 | 48.023 | 1.00 | 11.50 | B | ATOM | 3716 | CB | ALA | 99 | 66.256 | -0.316 | 51.273 | 1.00 | 22.28 | B |
| ATOM | 3667 | OD1 | ASN | 92 | 54.085 | -0.786 | 47.469 | 1.00 | 11.27 | B | ATOM | 3717 | C | ALA | 99 | 66.914 | 1.221 | 49.417 | 1.00 | 19.87 | B |
| ATOM | 3668 | ND2 | ASN | 92 | 53.853 | -2.426 | 48.943 | 1.00 | 12.24 | B | ATOM | 3718 | O | ALA | 99 | 66.908 | 0.608 | 48.368 | 1.00 | 19.35 | B |
| ATOM | 3671 | C | ASN | 92 | 57.145 | -0.474 | 48.682 | 1.00 | 12.15 | B | ATOM | 3719 | N | THR | 100 | 66.561 | 2.495 | 49.490 | 1.00 | 19.04 | B |
| ATOM | 3672 | O | ASN | 92 | 57.360 | -1.052 | 49.753 | 1.00 | 11.27 | B | ATOM | 3721 | CA | THR | 100 | 66.125 | 3.202 | 48.320 | 1.00 | 17.74 | B |
| ATOM | 3673 | N | GLU | 93 | 57.082 | 0.851 | 48.566 | 1.00 | 12.54 | B | ATOM | 3722 | CB | THR | 100 | 65.550 | 4.563 | 48.693 | 1.00 | 17.62 | B |
| ATOM | 3675 | CA | GLU | 93 | 57.281 | 1.741 | 49.694 | 1.00 | 12.57 | B | ATOM | 3723 | OG1 | THR | 100 | 66.539 | 5.299 | 49.401 | 1.00 | 18.90 | B |
| ATOM | 3676 | CB | GLU | 93 | 56.089 | 1.628 | 50.626 | 1.00 | 12.10 | B | ATOM | 3725 | CG2 | THR | 100 | 64.336 | 4.433 | 49.576 | 1.00 | 14.68 | B |
| ATOM | 3677 | CG | GLU | 93 | 54.796 | 1.809 | 49.888 | 1.00 | 9.28 | B | ATOM | 3726 | C | THR | 100 | 67.275 | 3.355 | 47.332 | 1.00 | 17.98 | B |
| ATOM | 3678 | CD | GLU | 93 | 53.612 | 1.959 | 50.809 | 1.00 | 11.21 | B | ATOM | 3727 | O | THR | 100 | 67.072 | 2.979 | 46.200 | 1.00 | 18.48 | B |
| ATOM | 3679 | OE1 | GLU | 93 | 53.769 | 1.836 | 52.050 | 1.00 | 11.00 | B | ATOM | 3728 | N | GLN | 101 | 68.486 | 3.116 | 47.717 | 1.00 | 17.93 | B |
| ATOM | 3680 | OE2 | GLU | 93 | 52.505 | 2.202 | 50.292 | 1.00 | 10.75 | B | ATOM | 3730 | CA | GLN | 101 | 69.598 | 3.258 | 46.780 | 1.00 | 18.32 | B |
| ATOM | 3681 | C | GLU | 93 | 58.631 | 1.530 | 50.438 | 1.00 | 13.27 | B | ATOM | 3731 | CB | GLN | 101 | 70.905 | 4.472 | 47.552 | 1.00 | 20.25 | B |
| ATOM | 3682 | O | GLU | 93 | 58.710 | 1.629 | 51.667 | 1.00 | 13.27 | B | ATOM | 3732 | CG | GLN | 101 | 70.954 | 4.562 | 48.472 | 1.00 | 19.40 | B |
| ATOM | 3683 | N | VAL | 94 | 59.701 | 1.306 | 49.671 | 1.00 | 14.42 | B | ATOM | 3733 | CD | GLN | 101 | 72.248 | 4.690 | 49.260 | 1.00 | 19.52 | B |
| ATOM | 3685 | CA | VAL | 94 | 61.044 | 1.110 | 50.213 | 1.00 | 14.83 | B | ATOM | 3734 | OE1 | GLN | 101 | 72.236 | 4.562 | 50.482 | 0.00 | 19.41 | B |
| ATOM | 3686 | CB | VAL | 94 | 62.041 | 0.689 | 49.119 | 1.00 | 14.52 | B | ATOM | 3735 | NE2 | GLN | 101 | 73.373 | 4.505 | 48.561 | 0.00 | 19.41 | B |
| ATOM | 3687 | CG1 | VAL | 94 | 63.415 | 0.425 | 49.743 | 1.00 | 14.82 | B | ATOM | 3738 | C | GLN | 101 | 69.663 | 1.947 | 45.795 | 1.00 | 18.30 | B |
| ATOM | 3688 | CG2 | VAL | 94 | 61.538 | -0.562 | 48.392 | 1.00 | 14.16 | B | ATOM | 3739 | O | GLN | 101 | 70.283 | 2.017 | 44.712 | 1.00 | 18.36 | B |
| ATOM | 3689 | C | VAL | 94 | 61.484 | 2.443 | 50.828 | 1.00 | 16.14 | B | ATOM | 3740 | N | SER | 102 | 68.991 | 0.875 | 46.174 | 1.00 | 17.29 | B |
| ATOM | 3690 | O | VAL | 94 | 61.327 | 3.488 | 50.230 | 1.00 | 15.81 | B | ATOM | 3742 | CA | SER | 102 | 68.915 | -0.327 | 45.379 | 1.00 | 16.87 | B |
| ATOM | 3691 | N | GLN | 96 | 62.053 | 2.390 | 52.021 | 1.00 | 18.35 | B | ATOM | 3743 | CB | SER | 102 | 68.650 | -1.512 | 46.294 | 1.00 | 18.39 | B |
| ATOM | 3693 | CA | GLN | 96 | 62.474 | 3.573 | 52.743 | 1.00 | 19.73 | B | ATOM | 3744 | OG | SER | 102 | 69.614 | -1.571 | 47.339 | 1.00 | 22.48 | B |

- 98 -

| | | | | | | | | | | | | | | | | | |
|---|---|---|---|---|---|---|---|---|---|---|---|---|---|---|---|---|---|
| ATOM | 3746 | C | SER | 102 | 67.830 | -0.287 | 44.314 | 1.00 | 16.23 | B | ATOM | 3791 | CB | ARG | 108 | 69.500 | -0.461 | 35.534 | 1.00 | 20.42 | B |
| ATOM | 3747 | O | SER | 102 | 67.774 | -1.182 | 43.469 | 1.00 | 16.44 | B | ATOM | 3792 | CG | ARG | 108 | 69.335 | 1.051 | 35.415 | 1.00 | 23.23 | B |
| ATOM | 3748 | N | ILE | 103 | 66.963 | 0.727 | 44.357 | 1.00 | 14.25 | B | ATOM | 3793 | CD | ARG | 108 | 70.646 | 1.821 | 35.587 | 1.00 | 26.99 | B |
| ATOM | 3750 | CA | ILE | 103 | 65.860 | 0.841 | 43.405 | 1.00 | 12.35 | B | ATOM | 3794 | NE | ARG | 108 | 70.405 | 3.267 | 35.559 | 1.00 | 31.50 | B |
| ATOM | 3751 | CB | ILE | 103 | 64.824 | 1.887 | 43.906 | 1.00 | 10.84 | B | ATOM | 3796 | CZ | ARG | 108 | 70.471 | 4.037 | 34.459 | 1.00 | 34.93 | B |
| ATOM | 3752 | CG2 | ILE | 103 | 63.773 | 2.206 | 42.845 | 1.00 | 11.34 | B | ATOM | 3797 | NH1 | ARG | 108 | 70.797 | 3.525 | 33.255 | 1.00 | 36.41 | B |
| ATOM | 3753 | CG1 | ILE | 103 | 64.137 | 1.329 | 45.162 | 1.00 | 10.83 | B | ATOM | 3800 | NH2 | ARG | 108 | 70.139 | 5.326 | 34.542 | 1.00 | 35.52 | B |
| ATOM | 3754 | CD1 | ILE | 103 | 63.309 | 2.335 | 45.951 | 1.00 | 6.10 | B | ATOM | 3803 | C | ARG | 108 | 68.518 | -2.715 | 35.032 | 1.00 | 18.40 | B |
| ATOM | 3755 | C | ILE | 103 | 66.282 | 1.065 | 41.033 | 1.00 | 12.30 | B | ATOM | 3804 | O | ARG | 108 | 68.401 | -3.127 | 33.869 | 1.00 | 9.11 | B |
| ATOM | 3756 | O | ILE | 103 | 65.847 | 0.345 | 41.728 | 1.00 | 12.95 | B | ATOM | 3805 | N | ASN | 109 | 68.815 | -3.521 | 36.051 | 1.00 | 8.06 | B |
| ATOM | 3757 | N | LEU | 104 | 67.210 | 1.978 | 41.728 | 1.00 | 11.50 | B | ATOM | 3807 | CA | ASN | 109 | 69.139 | -4.936 | 35.837 | 1.00 | 7.62 | B |
| ATOM | 3759 | CA | LEU | 104 | 67.618 | 2.234 | 40.355 | 1.00 | 11.64 | B | ATOM | 3808 | CB | ASN | 109 | 69.626 | -5.584 | 37.134 | 1.00 | 8.57 | B |
| ATOM | 3760 | CB | LEU | 104 | 68.412 | 3.535 | 40.235 | 1.00 | 9.06 | B | ATOM | 3809 | CG | ASN | 109 | 70.911 | -4.984 | 37.626 | 1.00 | 9.89 | B |
| ATOM | 3761 | CG | LEU | 104 | 68.136 | 4.272 | 38.919 | 1.00 | 7.66 | B | ATOM | 3810 | OD1 | ASN | 109 | 71.600 | -4.275 | 36.876 | 1.00 | 22.20 | B |
| ATOM | 3762 | CD1 | LEU | 104 | 66.662 | 4.691 | 38.882 | 1.00 | 9.01 | B | ATOM | 3811 | ND2 | ASN | 109 | 71.253 | -5.245 | 38.888 | 1.00 | 19.74 | B |
| ATOM | 3763 | CD2 | LEU | 104 | 69.001 | 5.488 | 38.840 | 1.00 | 12.54 | B | ATOM | 3814 | C | ASN | 109 | 67.965 | -5.724 | 35.293 | 1.00 | 17.22 | B |
| ATOM | 3764 | C | LEU | 104 | 68.342 | 1.030 | 38.633 | 1.00 | 12.12 | B | ATOM | 3815 | O | ASN | 109 | 68.127 | -6.573 | 34.398 | 1.00 | 17.97 | B |
| ATOM | 3765 | O | LEU | 104 | 69.357 | 0.622 | 39.755 | 1.00 | 12.90 | B | ATOM | 3816 | N | LEU | 110 | 66.781 | -5.433 | 35.833 | 1.00 | 16.32 | B |
| ATOM | 3766 | N | PRO | 105 | 66.662 | 0.498 | 40.457 | 1.00 | 13.87 | B | ATOM | 3818 | CA | LEU | 110 | 65.532 | -6.097 | 35.446 | 1.00 | 14.85 | B |
| ATOM | 3767 | CD | PRO | 105 | 70.114 | 1.184 | 41.526 | 1.00 | 12.45 | B | ATOM | 3819 | CB | LEU | 110 | 64.428 | -5.628 | 36.413 | 1.00 | 13.53 | B |
| ATOM | 3768 | CA | PRO | 105 | 70.102 | -0.667 | 39.969 | 1.00 | 13.29 | B | ATOM | 3820 | CG | LEU | 110 | 63.579 | -6.563 | 37.315 | 1.00 | 14.38 | B |
| ATOM | 3769 | CB | PRO | 105 | 71.064 | -0.968 | 41.120 | 1.00 | 13.48 | B | ATOM | 3821 | CD1 | LEU | 110 | 64.140 | -7.984 | 37.506 | 1.00 | 13.92 | B |
| ATOM | 3770 | CG | PRO | 105 | 71.379 | 0.363 | 41.660 | 1.00 | 11.52 | B | ATOM | 3822 | CD2 | LEU | 110 | 63.320 | -5.922 | 38.651 | 1.00 | 11.77 | B |
| ATOM | 3771 | C | PRO | 105 | 69.201 | -1.850 | 39.691 | 1.00 | 12.32 | B | ATOM | 3823 | C | LEU | 110 | 65.231 | -5.783 | 33.949 | 1.00 | 14.56 | B |
| ATOM | 3772 | O | PRO | 105 | 69.355 | -2.469 | 38.661 | 1.00 | 10.67 | B | ATOM | 3824 | O | LEU | 110 | 64.838 | -6.658 | 33.185 | 1.00 | 14.69 | B |
| ATOM | 3773 | N | ALA | 106 | 68.266 | -2.185 | 40.587 | 1.00 | 9.96 | B | ATOM | 3825 | N | ASN | 111 | 65.440 | -4.539 | 33.525 | 1.00 | 13.96 | B |
| ATOM | 3775 | CA | ALA | 106 | 67.337 | -3.311 | 40.332 | 1.00 | 9.32 | B | ATOM | 3827 | CA | ASN | 111 | 65.233 | -4.157 | 32.109 | 1.00 | 13.74 | B |
| ATOM | 3776 | CB | ALA | 106 | 66.414 | -3.524 | 41.497 | 1.00 | 11.42 | B | ATOM | 3828 | CB | ASN | 111 | 65.468 | -2.657 | 31.918 | 1.00 | 12.23 | B |
| ATOM | 3777 | C | ALA | 106 | 66.510 | -3.063 | 39.056 | 1.00 | 12.72 | B | ATOM | 3829 | CG | ASN | 111 | 64.271 | -1.816 | 32.330 | 1.00 | 12.06 | B |
| ATOM | 3778 | O | ALA | 106 | 66.360 | -3.958 | 38.216 | 1.00 | 12.50 | B | ATOM | 3830 | OD1 | ASN | 111 | 63.131 | -2.141 | 31.983 | 1.00 | 9.24 | B |
| ATOM | 3779 | N | MET | 107 | 65.976 | -1.849 | 38.918 | 1.00 | 13.29 | B | ATOM | 3831 | ND2 | ASN | 111 | 64.525 | -0.722 | 33.056 | 1.00 | 9.56 | B |
| ATOM | 3781 | CA | MET | 107 | 65.217 | -1.442 | 37.729 | 1.00 | 12.35 | B | ATOM | 3834 | C | ASN | 111 | 66.178 | -4.921 | 31.160 | 1.00 | 13.01 | B |
| ATOM | 3782 | CB | MET | 107 | 64.716 | 0.017 | 37.871 | 1.00 | 11.61 | B | ATOM | 3835 | O | ASN | 111 | 65.782 | -5.474 | 30.136 | 1.00 | 12.57 | B |
| ATOM | 3783 | CG | MET | 107 | 63.608 | 0.233 | 38.918 | 1.00 | 12.20 | B | ATOM | 3836 | N | ALA | 112 | 67.453 | -4.901 | 31.502 | 1.00 | 13.69 | B |
| ATOM | 3784 | SD | MET | 107 | 62.946 | 1.943 | 38.991 | 1.00 | 14.13 | B | ATOM | 3838 | CA | ALA | 112 | 68.467 | -5.569 | 30.726 | 1.00 | 13.38 | B |
| ATOM | 3785 | CE | MET | 107 | 62.573 | 2.214 | 37.320 | 1.00 | 14.24 | B | ATOM | 3839 | CB | ALA | 112 | 69.782 | -5.488 | 31.479 | 1.00 | 14.38 | B |
| ATOM | 3786 | C | MET | 107 | 66.081 | -1.584 | 36.464 | 1.00 | 15.25 | B | ATOM | 3840 | C | ALA | 112 | 68.094 | -7.033 | 30.496 | 1.00 | 13.43 | B |
| ATOM | 3787 | O | MET | 107 | 65.626 | -2.109 | 35.453 | 1.00 | 16.06 | B | ATOM | 3841 | O | ALA | 112 | 68.253 | -7.558 | 29.397 | 1.00 | 13.97 | B |
| ATOM | 3788 | N | ARG | 108 | 67.330 | -1.139 | 36.516 | 1.00 | 18.12 | B | ATOM | 3842 | N | ALA | 113 | 67.620 | -7.685 | 31.559 | 1.00 | 13.64 | B |
| ATOM | 3790 | CA | ARG | 108 | 68.205 | -1.257 | 35.357 | | | | ATOM | 3844 | CA | ALA | 113 | 67.256 | -9.091 | 31.531 | 1.00 | 12.69 | B |

- 99 -

| ATOM | 3845 | CB | ALA | 113 | 67.184 | -9.624 | 32.991 | 1.00 | 11.74 | B |
| --- | --- | --- | --- | --- | --- | --- | --- | --- | --- | --- |
| ATOM | 3846 | C | ALA | 113 | 65.960 | -9.392 | 30.771 | 1.00 | 13.04 | B |
| ATOM | 3847 | O | ALA | 113 | 65.815 | -10.458 | 30.133 | 1.00 | 13.36 | B |
| ATOM | 3848 | N | LEU | 114 | 64.994 | -8.487 | 30.844 | 1.00 | 13.23 | B |
| ATOM | 3850 | CA | LEU | 114 | 63.753 | -8.725 | 30.121 | 1.00 | 13.26 | B |
| ATOM | 3851 | CB | LEU | 114 | 62.617 | -7.829 | 30.619 | 1.00 | 11.61 | B |
| ATOM | 3852 | CG | LEU | 114 | 62.185 | -8.141 | 32.048 | 1.00 | 11.97 | B |
| ATOM | 3853 | CD1 | LEU | 114 | 61.218 | -7.099 | 32.472 | 1.00 | 10.17 | B |
| ATOM | 3854 | CD2 | LEU | 114 | 61.531 | -9.548 | 32.108 | 1.00 | 10.84 | B |
| ATOM | 3855 | C | LEU | 114 | 64.025 | -8.554 | 28.626 | 1.00 | 13.77 | B |
| ATOM | 3856 | O | LEU | 114 | 63.516 | -9.308 | 27.812 | 1.00 | 14.29 | B |
| ATOM | 3857 | N | SER | 115 | 64.829 | -7.577 | 28.245 | 1.00 | 14.12 | B |
| ATOM | 3859 | CA | SER | 115 | 65.117 | -7.439 | 26.830 | 1.00 | 15.59 | B |
| ATOM | 3860 | CB | SER | 115 | 65.875 | -6.154 | 26.603 | 1.00 | 16.35 | B |
| ATOM | 3861 | OG | SER | 115 | 66.823 | -6.039 | 27.631 | 1.00 | 19.40 | B |
| ATOM | 3862 | C | SER | 115 | 65.936 | -8.662 | 26.327 | 1.00 | 16.17 | B |
| ATOM | 3863 | O | SER | 115 | 65.595 | -9.269 | 25.312 | 1.00 | 17.32 | B |
| ATOM | 3864 | N | ALA | 116 | 66.971 | -9.064 | 27.068 | 1.00 | 15.70 | B |
| ATOM | 3865 | CA | ALA | 116 | 67.780 | -10.223 | 26.705 | 1.00 | 14.64 | B |
| ATOM | 3867 | CB | ALA | 116 | 68.782 | -10.501 | 27.797 | 1.00 | 13.03 | B |
| ATOM | 3868 | C | ALA | 116 | 66.895 | -11.453 | 26.470 | 1.00 | 15.10 | B |
| ATOM | 3869 | O | ALA | 116 | 67.210 | -12.316 | 25.648 | 1.00 | 16.52 | B |
| ATOM | 3870 | N | GLY | 117 | 65.833 | -11.577 | 27.252 | 1.00 | 14.62 | B |
| ATOM | 3873 | CA | GLY | 117 | 64.896 | -12.700 | 27.108 | 1.00 | 13.91 | B |
| ATOM | 3874 | CB | GLY | 117 | 64.105 | -12.920 | 28.417 | 1.00 | 11.16 | B |
| ATOM | 3875 | C | ALA | 117 | 63.927 | -12.410 | 25.968 | 1.00 | 13.68 | B |
| ATOM | 3876 | O | ALA | 117 | 63.173 | -13.281 | 25.554 | 1.00 | 13.92 | B |
| ATOM | 3877 | N | GLY | 118 | 63.911 | -11.160 | 25.514 | 1.00 | 12.57 | B |
| ATOM | 3879 | CA | GLY | 118 | 63.002 | -10.621 | 24.465 | 1.00 | 11.27 | B |
| ATOM | 3880 | C | GLY | 118 | 61.616 | -10.651 | 25.073 | 1.00 | 11.16 | B |
| ATOM | 3881 | O | GLY | 118 | 60.628 | -11.096 | 24.490 | 1.00 | 10.38 | B |
| ATOM | 3882 | N | LEU | 119 | 61.554 | -10.012 | 26.235 | 1.00 | 10.10 | B |
| ATOM | 3884 | CA | LEU | 119 | 60.300 | -9.828 | 26.951 | 1.00 | 9.70 | B |
| ATOM | 3885 | CB | LEU | 119 | 60.618 | -10.621 | 28.283 | 1.00 | 9.15 | B |
| ATOM | 3886 | CG | LEU | 119 | 60.193 | -12.162 | 28.132 | 1.00 | 9.72 | B |
| ATOM | 3887 | CD1 | LEU | 119 | 60.126 | -12.842 | 29.431 | 1.00 | 10.62 | B |
| ATOM | 3888 | CD2 | LEU | 119 | 58.915 | -12.529 | 27.340 | 1.00 | 11.49 | B |
| ATOM | 3889 | C | LEU | 119 | 60.129 | -8.349 | 27.191 | 1.00 | 9.02 | B |
| ATOM | 3890 | O | LEU | 119 | 59.597 | -7.922 | 28.231 | 1.00 | 7.39 | B |
| ATOM | 3891 | N | GLY | 120 | 60.526 | -7.563 | 26.198 | 1.00 | 7.65 | B |
| ATOM | 3893 | CA | GLY | 120 | 60.412 | -6.120 | 26.332 | 1.00 | 8.18 | B |
| ATOM | 3894 | C | GLY | 120 | 59.047 | -5.477 | 26.514 | 1.00 | 8.18 | B |
| ATOM | 3895 | O | GLY | 120 | 58.979 | -4.293 | 26.791 | 1.00 | 8.67 | B |
| ATOM | 3896 | N | ALA | 121 | 57.955 | -6.202 | 26.317 | 1.00 | 9.11 | B |
| ATOM | 3898 | CA | ALA | 121 | 56.638 | -5.595 | 26.481 | 1.00 | 10.27 | B |
| ATOM | 3899 | CB | ALA | 121 | 55.621 | -6.405 | 25.820 | 1.00 | 9.77 | B |
| ATOM | 3900 | C | ALA | 121 | 56.241 | -5.442 | 27.930 | 1.00 | 12.19 | B |
| ATOM | 3901 | O | ALA | 121 | 55.168 | -4.908 | 28.212 | 1.00 | 14.14 | B |
| ATOM | 3902 | N | ILE | 122 | 57.015 | -6.033 | 28.832 | 1.00 | 11.44 | B |
| ATOM | 3904 | CA | ILE | 122 | 56.721 | -5.970 | 30.254 | 1.00 | 11.73 | B |
| ATOM | 3905 | CB | ILE | 122 | 57.188 | -7.258 | 30.959 | 1.00 | 10.64 | B |
| ATOM | 3906 | CG2 | ILE | 122 | 56.826 | -7.202 | 32.441 | 1.00 | 8.84 | B |
| ATOM | 3907 | CG1 | ILE | 122 | 56.597 | -8.490 | 30.265 | 1.00 | 11.34 | B |
| ATOM | 3908 | CD1 | ILE | 122 | 57.186 | -9.835 | 30.802 | 1.00 | 10.48 | B |
| ATOM | 3909 | C | ILE | 122 | 57.461 | -4.734 | 30.826 | 1.00 | 12.25 | B |
| ATOM | 3910 | O | ILE | 122 | 58.690 | -4.665 | 30.753 | 1.00 | 11.57 | B |
| ATOM | 3911 | N | LYS | 123 | 56.714 | -3.782 | 31.391 | 1.00 | 12.08 | B |
| ATOM | 3913 | CA | LYS | 123 | 57.296 | -2.554 | 31.898 | 1.00 | 12.54 | B |
| ATOM | 3914 | CB | LYS | 123 | 56.298 | -1.398 | 31.774 | 1.00 | 13.92 | B |
| ATOM | 3915 | CG | LYS | 123 | 55.827 | -1.106 | 30.351 | 1.00 | 15.85 | B |
| ATOM | 3916 | CD | LYS | 123 | 56.990 | -0.684 | 29.443 | 1.00 | 17.08 | B |
| ATOM | 3917 | CE | LYS | 123 | 56.622 | -0.805 | 27.980 | 1.00 | 16.79 | B |
| ATOM | 3918 | NZ | LYS | 123 | 57.826 | -0.685 | 27.118 | 0.00 | 16.79 | B |
| ATOM | 3922 | C | LYS | 123 | 57.731 | -2.708 | 33.342 | 0.00 | 11.11 | B |
| ATOM | 3923 | O | LYS | 123 | 57.065 | -3.383 | 34.101 | 1.00 | 11.76 | B |
| ATOM | 3924 | N | VAL | 124 | 58.881 | -2.126 | 33.672 | 1.00 | 10.02 | B |
| ATOM | 3926 | CA | VAL | 124 | 59.483 | -2.171 | 35.017 | 1.00 | 9.61 | B |
| ATOM | 3927 | CB | VAL | 124 | 61.007 | -2.479 | 34.932 | 1.00 | 8.33 | B |
| ATOM | 3928 | CG1 | VAL | 124 | 61.686 | -2.288 | 36.274 | 1.00 | 6.71 | B |
| ATOM | 3929 | CG2 | VAL | 124 | 61.197 | -3.888 | 34.412 | 1.00 | 8.49 | B |
| ATOM | 3930 | C | VAL | 124 | 59.295 | -0.808 | 35.679 | 1.00 | 10.37 | B |
| ATOM | 3931 | O | VAL | 124 | 59.589 | 0.222 | 35.085 | 1.00 | 9.04 | B |
| ATOM | 3932 | N | SER | 125 | 58.822 | -0.793 | 36.906 | 1.00 | 8.93 | B |
| ATOM | 3934 | CA | SER | 125 | 58.618 | 0.463 | 37.608 | 1.00 | 10.21 | B |
| ATOM | 3935 | CB | SER | 125 | 57.164 | 0.905 | 37.351 | 1.00 | 10.68 | B |
| ATOM | 3936 | OG | SER | 125 | 56.829 | 2.116 | 37.983 | 1.00 | 10.82 | B |
| ATOM | 3938 | C | SER | 125 | 58.885 | 0.226 | 39.107 | 1.00 | 10.10 | B |
| ATOM | 3939 | O | SER | 125 | 59.594 | -0.711 | 39.495 | 1.00 | 12.53 | B |
| ATOM | 3940 | N | THR | 126 | 58.401 | 1.140 | 39.935 | 1.00 | 13.11 | B |
| ATOM | 3942 | CA | THR | 126 | 58.485 | 1.001 | 41.392 | 1.00 | 11.94 | B |

- 100 -

| ATOM | 3943 | CB | THR | 126 | 59.758 | 1.628 | 41.988 | 1.00 | 10.73 | B |
|---|---|---|---|---|---|---|---|---|---|---|
| ATOM | 3944 | OG1 | THR | 126 | 59.974 | 1.033 | 43.272 | 1.00 | 10.47 | B |
| ATOM | 3945 | CG2 | THR | 126 | 59.663 | 3.142 | 42.100 | 1.00 | 7.89 | B |
| ATOM | 3946 | C | THR | 126 | 57.217 | 1.621 | 41.970 | 1.00 | 11.85 | B |
| ATOM | 3947 | O | THR | 126 | 56.621 | 2.496 | 41.349 | 1.00 | 14.00 | B |
| ATOM | 3948 | N | SER | 127 | 56.763 | 1.117 | 43.103 | 1.00 | 12.19 | B |
| ATOM | 3949 | CA | SER | 127 | 55.550 | 1.588 | 43.765 | 1.00 | 10.43 | B |
| ATOM | 3950 | CB | SER | 127 | 54.738 | 0.358 | 44.152 | 1.00 | 10.22 | B |
| ATOM | 3951 | OG | SER | 127 | 53.471 | 0.668 | 44.675 | 1.00 | 8.23 | B |
| ATOM | 3952 | C | SER | 127 | 55.852 | 2.476 | 44.990 | 1.00 | 10.49 | B |
| ATOM | 3953 | O | SER | 127 | 56.453 | 2.020 | 45.953 | 1.00 | 9.59 | B |
| ATOM | 3954 | N | ILE | 128 | 55.440 | 3.744 | 44.959 | 1.00 | 11.24 | B |
| ATOM | 3955 | CA | ILE | 128 | 55.710 | 4.642 | 46.080 | 1.00 | 12.40 | B |
| ATOM | 3956 | CB | ILE | 128 | 56.356 | 5.956 | 45.596 | 1.00 | 11.58 | B |
| ATOM | 3957 | CG2 | ILE | 128 | 57.617 | 5.665 | 44.795 | 1.00 | 11.65 | B |
| ATOM | 3958 | CG1 | ILE | 128 | 55.368 | 6.781 | 44.785 | 1.00 | 11.74 | B |
| ATOM | 3959 | CD1 | ILE | 128 | 55.896 | 8.161 | 44.454 | 1.00 | 9.69 | B |
| ATOM | 3960 | C | ILE | 128 | 54.548 | 5.036 | 47.019 | 1.00 | 14.34 | B |
| ATOM | 3961 | O | ILE | 128 | 53.385 | 4.728 | 46.755 | 1.00 | 14.27 | B |
| ATOM | 3962 | N | ARG | 129 | 54.904 | 5.649 | 48.156 | 1.00 | 15.84 | B |
| ATOM | 3963 | CA | ARG | 129 | 53.938 | 6.166 | 49.128 | 1.00 | 16.66 | B |
| ATOM | 3964 | CB | ARG | 129 | 54.482 | 6.221 | 50.564 | 1.00 | 17.50 | B |
| ATOM | 3965 | CG | ARG | 129 | 54.960 | 4.92. | 51.139 | 1.00 | 21.66 | B |
| ATOM | 3966 | CD | ARG | 129 | 54.710 | 4.816 | 52.658 | 1.00 | 21.77 | B |
| ATOM | 3967 | NE | ARG | 129 | 55.345 | 5.882 | 53.425 | 1.00 | 23.18 | B |
| ATOM | 3968 | CZ | ARG | 129 | 54.981 | 6.238 | 54.654 | 0.00 | 22.59 | B |
| ATOM | 3969 | NH1 | ARG | 129 | 53.983 | 5.612 | 55.264 | 0.00 | 22.69 | B |
| ATOM | 3970 | NH2 | ARG | 129 | 55.614 | 7.225 | 55.272 | 0.00 | 22.69 | B |
| ATOM | 3971 | C | ARG | 129 | 53.712 | 7.608 | 48.710 | 1.00 | 16.31 | B |
| ATOM | 3972 | O | ARG | 129 | 54.624 | 8.264 | 48.191 | 1.00 | 16.64 | B |
| ATOM | 3973 | N | PHE | 130 | 52.514 | 8.116 | 48.957 | 1.00 | 15.70 | B |
| ATOM | 3974 | CA | PHE | 130 | 52.218 | 9.498 | 48.621 | 1.00 | 15.72 | B |
| ATOM | 3975 | CB | PHE | 130 | 50.741 | 9.808 | 48.952 | 1.00 | 13.54 | B |
| ATOM | 3976 | CG | PHE | 130 | 50.313 | 11.188 | 48.560 | 1.00 | 13.89 | B |
| ATOM | 3977 | CD1 | PHE | 130 | 50.080 | 11.511 | 47.235 | 1.00 | 13.94 | B |
| ATOM | 3978 | CD2 | PHE | 130 | 50.212 | 12.199 | 49.515 | 1.00 | 15.22 | B |
| ATOM | 3979 | CE1 | PHE | 130 | 49.764 | 12.817 | 46.855 | 1.00 | 13.49 | B |
| ATOM | 3980 | CE2 | PHE | 130 | 49.890 | 13.518 | 49.151 | 1.00 | 14.30 | B |
| ATOM | 3981 | CZ | PHE | 130 | 49.669 | 13.818 | 47.605 | 1.00 | 15.07 | B |
| ATOM | 3982 | C | PHE | 130 | 53.182 | 10.416 | 49.426 | 1.00 | 16.15 | B |
| ATOM | 3993 | O | PHE | 130 | 53.544 | 11.506 | 48.961 | 1.00 | 16.58 | B |
| ATOM | 3994 | N | ASP | 131 | 53.656 | 9.931 | 50.581 | 1.00 | 16.37 | B |
| ATOM | 3995 | CA | ASP | 131 | 54.551 | 10.697 | 51.469 | 1.00 | 16.73 | B |
| ATOM | 3997 | CB | ASP | 131 | 54.878 | 9.887 | 52.743 | 1.00 | 17.03 | B |
| ATOM | 3998 | CG | ASP | 131 | 56.217 | 9.164 | 52.665 | 0.00 | 16.93 | B |
| ATOM | 3999 | OD1 | ASP | 131 | 56.391 | 8.306 | 51.775 | 0.00 | 16.96 | B |
| ATOM | 4000 | OD2 | ASP | 131 | 57.099 | 9.461 | 53.497 | 0.00 | 16.96 | B |
| ATOM | 4001 | C | ASP | 131 | 55.838 | 11.156 | 50.771 | 1.00 | 17.01 | B |
| ATOM | 4002 | O | ASP | 131 | 56.591 | 11.965 | 51.323 | 1.00 | 18.55 | B |
| ATOM | 4003 | N | GLU | 132 | 56.101 | 10.620 | 49.579 | 1.00 | 15.69 | B |
| ATOM | 4004 | CA | GLU | 132 | 57.263 | 10.987 | 48.800 | 1.00 | 15.93 | B |
| ATOM | 4006 | CB | GLU | 132 | 57.451 | 9.977 | 47.676 | 1.00 | 18.09 | B |
| ATOM | 4007 | CG | GLU | 132 | 57.990 | 8.656 | 48.101 | 1.00 | 21.42 | B |
| ATOM | 4008 | CD | GLU | 132 | 59.411 | 8.779 | 48.608 | 1.00 | 24.39 | B |
| ATOM | 4009 | OE1 | GLU | 132 | 60.101 | 9.738 | 48.198 | 1.00 | 26.39 | B |
| ATOM | 4010 | OE2 | GLU | 132 | 59.850 | 7.929 | 49.408 | 1.00 | 25.94 | B |
| ATOM | 4011 | C | GLU | 132 | 57.095 | 12.382 | 48.181 | 1.00 | 15.08 | B |
| ATOM | 4012 | O | GLU | 132 | 58.052 | 13.010 | 47.757 | 1.00 | 13.82 | B |
| ATOM | 4013 | N | VAL | 133 | 55.858 | 12.840 | 48.102 | 1.00 | 14.97 | B |
| ATOM | 4014 | CA | VAL | 133 | 55.555 | 14.103 | 47.491 | 1.00 | 14.86 | B |
| ATOM | 4016 | CB | VAL | 133 | 54.281 | 14.008 | 46.634 | 1.00 | 13.51 | B |
| ATOM | 4017 | CG1 | VAL | 133 | 54.005 | 15.316 | 45.929 | 1.00 | 12.41 | B |
| ATOM | 4018 | CG2 | VAL | 133 | 54.429 | 12.892 | 45.650 | 1.00 | 13.35 | B |
| ATOM | 4019 | C | VAL | 133 | 55.363 | 15.149 | 48.551 | 1.00 | 15.63 | B |
| ATOM | 4020 | O | VAL | 133 | 54.438 | 15.065 | 49.383 | 1.00 | 15.99 | B |
| ATOM | 4021 | N | ALA | 134 | 56.235 | 16.149 | 48.502 | 1.00 | 17.05 | B |
| ATOM | 4022 | CA | ALA | 134 | 56.179 | 17.266 | 49.445 | 1.00 | 18.23 | B |
| ATOM | 4024 | CB | ALA | 134 | 57.578 | 17.788 | 49.716 | 1.00 | 18.39 | B |
| ATOM | 4025 | C | ALA | 134 | 55.330 | 18.342 | 48.826 | 1.00 | 18.92 | B |
| ATOM | 4026 | O | ALA | 134 | 55.124 | 18.354 | 47.623 | 1.00 | 20.00 | B |
| ATOM | 4027 | N | ASN | 135 | 54.805 | 19.223 | 49.658 | 1.00 | 20.01 | B |
| ATOM | 4028 | CA | ASN | 135 | 53.983 | 20.342 | 49.220 | 1.00 | 20.37 | B |
| ATOM | 4030 | CB | ASN | 135 | 54.902 | 21.436 | 48.718 | 1.00 | 22.34 | B |
| ATOM | 4031 | CG | ASN | 135 | 55.972 | 21.777 | 49.747 | 1.00 | 24.69 | B |
| ATOM | 4032 | OD1 | ASN | 135 | 55.697 | 21.796 | 50.953 | 1.00 | 25.97 | B |
| ATOM | 4033 | ND2 | ASN | 135 | 57.205 | 21.990 | 49.291 | 1.00 | 26.63 | B |
| ATOM | 4034 | C | ASN | 135 | 52.883 | 19.961 | 48.235 | 1.00 | 20.47 | B |
| ATOM | 4037 | O | ASN | 135 | 52.738 | 20.515 | 47.143 | 1.00 | 20.64 | B |
| ATOM | 4039 | N | SER | 136 | 52.055 | 19.038 | 48.690 | 1.00 | 20.01 | B |
| ATOM | 4041 | CA | SER | 136 | 50.963 | 18.551 | 47.909 | 1.00 | 19.63 | B |

- 101 -

| | | | | | | | | | |
|---|---|---|---|---|---|---|---|---|---|
| ATOM | 4042 | CB | SER | 136 | 50.541 | 17.175 | 48.409 | 1.00 20.81 | B |
| ATOM | 4043 | OG | SER | 136 | 50.514 | 17.155 | 49.829 | 1.00 22.31 | B |
| ATOM | 4045 | C | SER | 136 | 49.801 | 19.511 | 47.820 | 1.00 19.03 | B |
| ATOM | 4046 | O | SER | 136 | 48.832 | 19.194 | 47.151 | 1.00 19.66 | B |
| ATOM | 4047 | N | PHE | 137 | 49.840 | 20.631 | 48.543 | 1.00 18.59 | B |
| ATOM | 4049 | CA | PHE | 137 | 48.788 | 21.642 | 48.400 | 1.00 18.17 | B |
| ATOM | 4050 | CB | PHE | 137 | 47.653 | 21.599 | 49.436 | 1.00 19.19 | B |
| ATOM | 4051 | CG | PHE | 137 | 46.465 | 22.484 | 49.023 | 1.00 22.14 | B |
| ATOM | 4052 | CD1 | PHE | 137 | 45.453 | 21.978 | 48.168 | 1.00 22.50 | B |
| ATOM | 4053 | CD2 | PHE | 137 | 46.452 | 23.865 | 49.302 | 1.00 21.69 | B |
| ATOM | 4054 | CE1 | PHE | 137 | 44.464 | 22.822 | 47.582 | 1.00 21.40 | B |
| ATOM | 4055 | CE2 | PHE | 137 | 45.455 | 24.720 | 48.711 | 1.00 22.96 | B |
| ATOM | 4056 | CZ | PHE | 137 | 44.465 | 24.182 | 47.846 | 1.00 21.32 | B |
| ATOM | 4057 | C | PHE | 137 | 49.302 | 23.094 | 48.231 | 1.00 17.81 | B |
| ATOM | 4058 | O | PHE | 137 | 50.122 | 23.594 | 49.042 | 1.00 15.98 | B |
| ATOM | 4059 | N | PRO | 138 | 48.856 | 23.774 | 47.134 | 1.00 16.61 | B |
| ATOM | 4060 | CD | PRO | 138 | 49.202 | 25.174 | 46.811 | 1.00 15.82 | B |
| ATOM | 4061 | CA | PRO | 138 | 47.935 | 23.217 | 46.125 | 1.00 15.52 | B |
| ATOM | 4062 | CB | PRO | 138 | 47.558 | 24.459 | 45.306 | 1.00 15.94 | B |
| ATOM | 4063 | CG | PRO | 138 | 48.838 | 25.299 | 45.358 | 1.00 14.78 | B |
| ATOM | 4064 | C | PRO | 138 | 48.644 | 22.141 | 45.293 | 1.00 14.42 | B |
| ATOM | 4065 | O | PRO | 138 | 49.870 | 22.155 | 45.200 | 1.00 15.12 | B |
| ATOM | 4066 | N | PRO | 139 | 47.886 | 21.227 | 44.633 | 1.00 14.00 | B |
| ATOM | 4067 | CD | PRO | 139 | 46.426 | 21.281 | 44.426 | 1.00 12.29 | B |
| ATOM | 4068 | CA | PRO | 139 | 48.475 | 20.151 | 43.811 | 1.00 13.52 | B |
| ATOM | 4069 | CB | PRO | 139 | 47.285 | 19.689 | 42.982 | 1.00 13.30 | B |
| ATOM | 4070 | CG | PRO | 139 | 46.130 | 19.947 | 43.902 | 1.00 12.18 | B |
| ATOM | 4071 | C | PRO | 139 | 49.524 | 19.871 | 42.911 | 1.00 14.15 | B |
| ATOM | 4072 | O | PRO | 139 | 50.678 | 20.568 | 42.830 | 1.00 14.56 | B |
| ATOM | 4073 | N | SER | 140 | 49.556 | 21.720 | 42.257 | 1.00 14.75 | B |
| ATOM | 4075 | CA | SER | 140 | 50.604 | 22.230 | 41.373 | 1.00 14.38 | B |
| ATOM | 4076 | CB | SER | 140 | 50.162 | 23.562 | 40.787 | 1.00 14.50 | B |
| ATOM | 4077 | OG | SER | 140 | 49.524 | 24.361 | 41.769 | 1.00 13.13 | B |
| ATOM | 4079 | C | SER | 140 | 51.968 | 22.384 | 42.020 | 1.00 14.29 | B |
| ATOM | 4080 | O | SER | 140 | 52.993 | 22.374 | 41.329 | 1.00 13.03 | B |
| ATOM | 4081 | N | ALA | 141 | 51.959 | 22.513 | 43.349 | 1.00 14.79 | B |
| ATOM | 4083 | CA | ALA | 141 | 53.158 | 22.684 | 44.162 | 1.00 14.82 | B |
| ATOM | 4084 | CB | ALA | 141 | 52.798 | 23.401 | 45.479 | 1.00 13.48 | B |
| ATOM | 4085 | C | ALA | 141 | 53.950 | 21.416 | 44.482 | 1.00 14.34 | B |
| ATOM | 4086 | O | ALA | 141 | 55.118 | 21.517 | 44.845 | 1.00 14.78 | B |
| ATOM | 4087 | N | GLY | 142 | 53.345 | 20.242 | 44.357 | 1.00 13.72 | B |
| ATOM | 4089 | CA | GLY | 142 | 54.070 | 19.033 | 44.689 | 1.00 14.92 | B |
| ATOM | 4090 | C | GLY | 142 | 55.454 | 18.923 | 44.077 | 1.00 15.95 | B |
| ATOM | 4091 | O | GLY | 142 | 55.676 | 19.321 | 42.931 | 1.00 16.47 | B |
| ATOM | 4092 | N | VAL | 143 | 56.391 | 18.357 | 44.830 | 1.00 17.05 | B |
| ATOM | 4094 | CA | VAL | 143 | 57.778 | 18.187 | 44.373 | 1.00 17.51 | B |
| ATOM | 4095 | CB | VAL | 143 | 58.632 | 19.431 | 44.731 | 1.00 17.04 | B |
| ATOM | 4096 | CG1 | VAL | 143 | 58.696 | 19.624 | 46.245 | 1.00 17.77 | B |
| ATOM | 4097 | CG2 | VAL | 143 | 59.984 | 19.331 | 44.149 | 1.00 15.96 | B |
| ATOM | 4098 | C | VAL | 143 | 58.309 | 16.957 | 45.103 | 1.00 18.15 | B |
| ATOM | 4099 | O | VAL | 143 | 57.794 | 16.612 | 46.175 | 1.00 19.56 | B |
| ATOM | 4100 | N | PHE | 144 | 59.255 | 16.248 | 44.501 | 1.00 17.43 | B |
| ATOM | 4102 | CA | PHE | 144 | 59.808 | 15.066 | 45.126 | 1.00 18.35 | B |
| ATOM | 4103 | CB | PHE | 144 | 60.523 | 14.177 | 44.117 | 1.00 18.69 | B |
| ATOM | 4104 | CG | PHE | 144 | 59.596 | 13.306 | 43.317 | 1.00 17.74 | B |
| ATOM | 4105 | CD1 | PHE | 144 | 59.806 | 13.102 | 41.952 | 1.00 16.57 | B |
| ATOM | 4106 | CD2 | PHE | 144 | 58.478 | 12.731 | 43.918 | 1.00 17.26 | B |
| ATOM | 4107 | CE1 | PHE | 144 | 58.900 | 12.345 | 41.193 | 1.00 16.89 | B |
| ATOM | 4108 | CE2 | PHE | 144 | 57.571 | 11.970 | 43.161 | 1.00 16.54 | B |
| ATOM | 4109 | CZ | PHE | 144 | 57.789 | 11.787 | 41.792 | 1.00 15.91 | B |
| ATOM | 4110 | C | PHE | 144 | 60.743 | 15.421 | 46.282 | 1.00 19.39 | B |
| ATOM | 4111 | O | PHE | 144 | 61.678 | 16.213 | 46.153 | 1.00 19.79 | B |
| ATOM | 4112 | N | LYS | 145 | 60.421 | 14.813 | 47.414 | 1.00 19.60 | B |
| ATOM | 4114 | CA | LYS | 145 | 61.071 | 14.949 | 48.693 | 1.00 19.47 | B |
| ATOM | 4115 | CB | LYS | 145 | 60.169 | 14.205 | 49.679 | 1.00 19.21 | B |
| ATOM | 4116 | CG | LYS | 145 | 60.612 | 14.115 | 51.088 | 1.00 20.27 | B |
| ATOM | 4117 | CD | LYS | 145 | 59.459 | 13.560 | 51.908 | 1.00 21.49 | B |
| ATOM | 4118 | CE | LYS | 145 | 59.830 | 13.413 | 53.374 | 1.00 20.99 | B |
| ATOM | 4119 | NZ | LYS | 145 | 58.699 | 12.859 | 54.169 | 1.00 21.06 | B |
| ATOM | 4123 | C | LYS | 145 | 62.466 | 14.361 | 48.701 | 1.00 19.74 | B |
| ATOM | 4124 | O | LYS | 145 | 63.407 | 14.989 | 49.166 | 1.00 20.88 | B |
| ATOM | 4125 | N | ASN | 146 | 62.599 | 13.177 | 48.129 | 1.00 20.01 | B |
| ATOM | 4127 | CA | ASN | 146 | 63.854 | 12.463 | 48.103 | 1.00 20.22 | B |
| ATOM | 4128 | CB | ASN | 146 | 63.595 | 11.038 | 48.496 | 0.00 20.99 | B |
| ATOM | 4129 | CG | ASN | 146 | 63.084 | 10.954 | 49.888 | 0.00 21.06 | B |
| ATOM | 4130 | OD1 | ASN | 146 | 63.623 | 11.601 | 50.768 | 1.00 19.74 | B |
| ATOM | 4131 | ND2 | ASN | 146 | 62.034 | 10.180 | 50.114 | 1.00 20.88 | B |
| ATOM | 4134 | C | ASN | 146 | 64.554 | 12.548 | 46.777 | 1.00 20.66 | B |
| ATOM | 4135 | O | ASN | 146 | 63.917 | 12.525 | 45.718 | 1.00 21.88 | B |
| ATOM | 4136 | N | ALA | 147 | 65.877 | 12.643 | 46.832 | 1.00 20.48 | B |

- 102 -

| | | | | | | | | |
|---|---|---|---|---|---|---|---|---|
| ATOM | 4138 | CA | ALA | 147 | 66.674 | 12.776 | 45.616 | 1.00 19.74 B |
| ATOM | 4139 | CB | ALA | 147 | 68.119 | 13.134 | 45.971 | 1.00 19.61 B |
| ATOM | 4140 | C | ALA | 147 | 66.641 | 11.579 | 43.455 | 1.00 19.62 B |
| ATOM | 4141 | O | ALA | 147 | 66.791 | 11.747 | 43.455 | 1.00 20.84 B |
| ATOM | 4142 | N | TYR | 148 | 66.422 | 10.382 | 45.223 | 1.00 17.67 B |
| ATOM | 4144 | CA | TYR | 148 | 66.410 | 9.183 | 44.396 | 1.00 16.21 B |
| ATOM | 4145 | CB | TYR | 148 | 66.403 | 7.932 | 45.282 | 1.00 15.95 B |
| ATOM | 4146 | CG | TYR | 148 | 65.032 | 7.508 | 45.808 | 1.00 13.62 B |
| ATOM | 4147 | CD1 | TYR | 148 | 64.347 | 6.452 | 45.212 | 1.00 14.06 B |
| ATOM | 4148 | CE1 | TYR | 148 | 63.130 | 5.992 | 45.710 | 1.00 15.45 B |
| ATOM | 4149 | CD2 | TYR | 148 | 64.465 | 8.118 | 46.923 | 1.00 13.70 B |
| ATOM | 4150 | CE2 | TYR | 148 | 63.241 | 7.675 | 47.438 | 1.00 14.78 B |
| ATOM | 4151 | CZ | TYR | 148 | 62.585 | 6.604 | 46.830 | 1.00 15.41 B |
| ATOM | 4152 | OH | TYR | 148 | 61.438 | 6.090 | 47.376 | 1.00 16.46 B |
| ATOM | 4154 | C | TYR | 148 | 65.267 | 9.139 | 43.386 | 1.00 16.04 B |
| ATOM | 4155 | O | TYR | 148 | 65.385 | 8.478 | 42.341 | 1.00 16.22 B |
| ATOM | 4156 | N | MET | 149 | 64.172 | 9.841 | 43.685 | 1.00 15.50 B |
| ATOM | 4158 | CA | MET | 149 | 63.004 | 9.882 | 42.810 | 1.00 15.58 B |
| ATOM | 4159 | CB | MET | 149 | 61.790 | 10.422 | 43.581 | 1.00 16.56 B |
| ATOM | 4160 | CG | MET | 149 | 61.033 | 9.351 | 44.405 | 1.00 16.07 B |
| ATOM | 4161 | SD | MET | 149 | 60.710 | 7.795 | 43.504 | 1.00 16.97 B |
| ATOM | 4162 | CE | MET | 149 | 59.473 | 8.305 | 42.324 | 1.00 15.94 B |
| ATOM | 4163 | C | MET | 149 | 63.200 | 10.636 | 41.470 | 1.00 15.97 B |
| ATOM | 4164 | O | MET | 149 | 62.489 | 10.405 | 40.472 | 1.00 14.05 B |
| ATOM | 4165 | N | THR | 150 | 64.160 | 11.549 | 41.443 | 1.00 16.75 B |
| ATOM | 4167 | CA | THR | 150 | 64.450 | 12.262 | 40.214 | 1.00 16.46 B |
| ATOM | 4168 | CB | THR | 150 | 65.332 | 13.494 | 40.469 | 1.00 17.36 B |
| ATOM | 4169 | OG1 | THR | 150 | 64.502 | 14.520 | 41.026 | 1.00 20.49 B |
| ATOM | 4171 | CG2 | THR | 150 | 65.929 | 14.037 | 39.188 | 1.00 17.28 B |
| ATOM | 4172 | C | THR | 150 | 65.105 | 11.296 | 39.245 | 1.00 15.89 B |
| ATOM | 4173 | O | THR | 150 | 64.866 | 11.375 | 38.056 | 1.00 15.10 B |
| ATOM | 4174 | N | ASP | 151 | 65.878 | 10.338 | 39.751 | 1.00 15.93 B |
| ATOM | 4176 | CA | ASP | 151 | 66.512 | 9.395 | 38.843 | 1.00 16.37 B |
| ATOM | 4177 | CB | ASP | 151 | 67.759 | 8.783 | 39.469 | 1.00 18.31 B |
| ATOM | 4178 | CG | ASP | 151 | 68.863 | 9.816 | 39.665 | 1.00 21.19 B |
| ATOM | 4179 | OD1 | ASP | 151 | 69.464 | 9.831 | 40.780 | 1.00 22.86 B |
| ATOM | 4180 | OD2 | ASP | 151 | 69.077 | 10.645 | 38.724 | 1.00 20.09 B |
| ATOM | 4181 | C | ASP | 151 | 65.539 | 8.340 | 38.409 | 1.00 15.63 B |
| ATOM | 4182 | O | ASP | 151 | 65.504 | 7.950 | 37.251 | 1.00 16.67 B |
| ATOM | 4183 | N | VAL | 152 | 64.683 | 7.936 | 39.325 | 1.00 15.00 B |
| ATOM | 4185 | CA | VAL | 152 | 63.691 | 6.954 | 39.019 | 1.00 14.40 B |
| ATOM | 4186 | CB | VAL | 152 | 62.892 | 6.586 | 40.292 | 1.00 14.08 B |
| ATOM | 4187 | CG1 | VAL | 152 | 61.793 | 5.636 | 39.945 | 1.00 14.78 B |
| ATOM | 4188 | CG2 | VAL | 152 | 63.819 | 5.874 | 41.278 | 1.00 14.03 B |
| ATOM | 4189 | C | VAL | 152 | 62.808 | 7.511 | 37.891 | 1.00 15.52 B |
| ATOM | 4190 | O | VAL | 152 | 62.690 | 6.892 | 36.818 | 1.00 14.37 B |
| ATOM | 4191 | N | ALA | 153 | 62.308 | 8.738 | 38.093 | 1.00 15.46 B |
| ATOM | 4193 | CA | ALA | 153 | 61.430 | 9.428 | 37.143 | 1.00 15.09 B |
| ATOM | 4194 | CB | ALA | 153 | 61.080 | 10.780 | 37.688 | 1.00 15.15 B |
| ATOM | 4195 | C | ALA | 153 | 62.064 | 9.557 | 35.762 | 1.00 15.52 B |
| ATOM | 4196 | O | ALA | 153 | 61.441 | 9.310 | 34.727 | 1.00 16.10 B |
| ATOM | 4197 | N | ARG | 154 | 63.336 | 9.901 | 35.752 | 1.00 16.45 B |
| ATOM | 4199 | CA | ARG | 154 | 64.046 | 10.033 | 34.507 | 1.00 16.93 B |
| ATOM | 4200 | CB | ARG | 154 | 65.310 | 10.838 | 34.749 | 1.00 19.18 B |
| ATOM | 4201 | CG | ARG | 154 | 64.916 | 12.288 | 35.033 | 1.00 23.02 B |
| ATOM | 4202 | CD | ARG | 154 | 66.101 | 13.203 | 35.102 | 1.00 27.89 B |
| ATOM | 4203 | NE | ARG | 154 | 65.719 | 14.575 | 35.434 | 1.00 31.85 B |
| ATOM | 4205 | CZ | ARG | 154 | 66.493 | 15.413 | 36.131 | 1.00 34.79 B |
| ATOM | 4206 | NH1 | ARG | 154 | 67.691 | 15.019 | 36.574 | 1.00 35.92 B |
| ATOM | 4209 | NH2 | ARG | 154 | 66.081 | 16.650 | 36.393 | 1.00 35.71 B |
| ATOM | 4212 | C | ARG | 154 | 64.263 | 8.694 | 33.797 | 1.00 16.01 B |
| ATOM | 4213 | O | ARG | 154 | 64.242 | 8.645 | 32.572 | 1.00 15.16 B |
| ATOM | 4214 | N | LEU | 155 | 64.334 | 7.604 | 34.570 | 1.00 14.94 B |
| ATOM | 4216 | CA | LEU | 155 | 64.520 | 6.263 | 34.024 | 1.00 13.31 B |
| ATOM | 4217 | CB | LEU | 155 | 64.945 | 5.275 | 35.137 | 1.00 13.82 B |
| ATOM | 4218 | CG | LEU | 155 | 65.181 | 3.787 | 34.768 | 1.00 14.61 B |
| ATOM | 4219 | CD1 | LEU | 155 | 66.086 | 3.604 | 33.559 | 1.00 12.84 B |
| ATOM | 4220 | CD2 | LEU | 155 | 65.787 | 3.068 | 35.953 | 1.00 16.07 B |
| ATOM | 4221 | C | LEU | 155 | 63.208 | 5.816 | 33.386 | 1.00 12.32 B |
| ATOM | 4222 | O | LEU | 155 | 63.174 | 5.236 | 32.303 | 1.00 14.07 B |
| ATOM | 4223 | N | LEU | 156 | 62.114 | 6.074 | 34.070 | 1.00 10.90 B |
| ATOM | 4225 | CA | LEU | 156 | 60.813 | 5.718 | 33.562 | 1.00 9.62 B |
| ATOM | 4226 | CB | LEU | 156 | 59.754 | 6.078 | 34.605 | 1.00 9.75 B |
| ATOM | 4227 | CG | LEU | 156 | 59.777 | 5.331 | 35.951 | 1.00 10.11 B |
| ATOM | 4228 | CD1 | LEU | 156 | 58.722 | 5.957 | 36.847 | 1.00 10.82 B |
| ATOM | 4229 | CD2 | LEU | 156 | 59.557 | 3.890 | 35.126 | 1.00 10.80 B |
| ATOM | 4230 | C | LEU | 156 | 60.531 | 6.507 | 32.282 | 1.00 9.52 B |
| ATOM | 4231 | O | LEU | 156 | 59.832 | 6.019 | 31.398 | 1.00 7.80 B |
| ATOM | 4232 | N | ALA | 157 | 60.977 | 7.773 | 32.231 | 1.00 10.32 B |
| ATOM | 4234 | CA | ALA | 157 | 60.725 | 8.594 | 31.045 | 1.00 11.34 B |

- 103 -

| | | | | | | | | | |
|---|---|---|---|---|---|---|---|---|---|
| ATOM | 4235 | CB | ALA | 157 | 61.182 | 10.011 | 31.257 | 1.00 12.45 | B |
| ATOM | 4236 | C | ALA | 157 | 61.381 | 8.040 | 29.794 | 1.00 11.51 | B |
| ATOM | 4237 | O | ALA | 157 | 60.807 | 8.111 | 28.714 | 1.00 12.62 | B |
| ATOM | 4238 | N | SER | 158 | 62.557 | 7.444 | 29.953 | 1.00 11.62 | B |
| ATOM | 4240 | CA | SER | 158 | 63.287 | 6.931 | 28.818 | 1.00 11.69 | B |
| ATOM | 4241 | CB | SER | 158 | 64.808 | 7.143 | 28.991 | 1.00 12.16 | B |
| ATOM | 4242 | OG | SER | 158 | 65.323 | 6.351 | 30.040 | 1.00 14.97 | B |
| ATOM | 4244 | C | SER | 158 | 62.933 | 5.508 | 28.449 | 1.00 10.75 | B |
| ATOM | 4245 | O | SER | 158 | 63.140 | 5.107 | 27.302 | 1.00 10.29 | B |
| ATOM | 4246 | N | THR | 159 | 62.356 | 4.763 | 29.389 | 1.00 10.31 | B |
| ATOM | 4248 | CA | THR | 159 | 61.957 | 3.393 | 29.112 | 1.00 9.35 | B |
| ATOM | 4249 | CB | THR | 159 | 62.250 | 2.466 | 30.277 | 1.00 10.90 | B |
| ATOM | 4250 | OG1 | THR | 159 | 61.552 | 2.927 | 31.438 | 1.00 14.47 | B |
| ATOM | 4252 | CG2 | THR | 159 | 63.758 | 2.407 | 30.568 | 1.00 10.29 | B |
| ATOM | 4253 | C | THR | 159 | 60.487 | 3.357 | 28.815 | 1.00 8.28 | B |
| ATOM | 4254 | O | THR | 159 | 59.952 | 2.360 | 28.401 | 1.00 9.10 | B |
| ATOM | 4255 | N | GLY | 160 | 59.798 | 4.448 | 29.045 | 1.00 7.87 | B |
| ATOM | 4257 | CA | GLY | 160 | 58.389 | 4.444 | 28.718 | 1.00 6.52 | B |
| ATOM | 4258 | C | GLY | 160 | 57.565 | 3.591 | 29.638 | 1.00 7.01 | B |
| ATOM | 4259 | O | GLY | 160 | 56.589 | 2.989 | 29.184 | 1.00 7.08 | B |
| ATOM | 4260 | N | ALA | 161 | 57.975 | 3.522 | 30.912 | 1.00 6.35 | B |
| ATOM | 4262 | CA | ALA | 161 | 57.243 | 2.796 | 31.961 | 1.00 5.70 | B |
| ATOM | 4263 | CB | ALA | 161 | 58.221 | 1.971 | 32.832 | 1.00 3.70 | B |
| ATOM | 4264 | C | ALA | 161 | 56.546 | 3.835 | 32.838 | 1.00 5.54 | B |
| ATOM | 4265 | O | ALA | 161 | 56.969 | 4.997 | 32.902 | 1.00 4.46 | B |
| ATOM | 4266 | N | PRO | 162 | 55.434 | 3.454 | 33.515 | 1.00 6.45 | B |
| ATOM | 4267 | CD | PRO | 162 | 54.642 | 2.219 | 33.416 | 1.00 5.96 | B |
| ATOM | 4268 | CA | PRO | 162 | 54.761 | 4.447 | 34.380 | 1.00 6.38 | B |
| ATOM | 4269 | CB | PRO | 162 | 53.298 | 4.040 | 34.277 | 1.00 5.30 | B |
| ATOM | 4270 | CG | PRO | 162 | 53.399 | 2.560 | 34.244 | 1.00 6.43 | B |
| ATOM | 4271 | C | PRO | 162 | 55.223 | 4.370 | 35.852 | 1.00 6.11 | B |
| ATOM | 4272 | O | PRO | 162 | 55.967 | 3.477 | 36.236 | 1.00 5.14 | B |
| ATOM | 4273 | N | LEU | 163 | 54.736 | 5.303 | 36.656 | 1.00 6.56 | B |
| ATOM | 4275 | CA | LEU | 163 | 55.010 | 5.344 | 38.080 | 1.00 8.46 | B |
| ATOM | 4276 | CB | LEU | 163 | 55.171 | 6.806 | 38.541 | 1.00 8.72 | B |
| ATOM | 4277 | CG | LEU | 163 | 55.613 | 7.000 | 39.986 | 1.00 8.95 | B |
| ATOM | 4278 | CD1 | LEU | 163 | 56.892 | 6.169 | 40.257 | 1.00 6.68 | B |
| ATOM | 4279 | CD2 | LEU | 163 | 55.777 | 8.492 | 40.260 | 1.00 7.02 | B |
| ATOM | 4280 | C | LEU | 163 | 53.801 | 4.698 | 38.766 | 1.00 9.19 | B |
| ATOM | 4281 | O | LEU | 163 | 52.658 | 4.976 | 38.394 | 1.00 10.15 | B |
| ATOM | 4282 | N | LEU | 164 | 54.045 | 3.763 | 39.681 | 1.00 9.90 | B |
| ATOM | 4284 | CA | LEU | 164 | 52.962 | 3.107 | 40.390 | 1.00 10.61 | B |
| ATOM | 4285 | CB | LEU | 164 | 53.279 | 1.633 | 40.618 | 1.00 11.20 | B |
| ATOM | 4286 | CG | LEU | 164 | 53.647 | 0.866 | 39.348 | 1.00 12.11 | B |
| ATOM | 4287 | CD1 | LEU | 164 | 53.823 | -0.661 | 39.629 | 1.00 11.12 | B |
| ATOM | 4288 | CD2 | LEU | 164 | 52.581 | 1.167 | 38.284 | 1.00 10.96 | B |
| ATOM | 4289 | C | LEU | 164 | 52.935 | 3.872 | 41.711 | 1.00 11.21 | B |
| ATOM | 4290 | O | LEU | 164 | 53.984 | 4.051 | 42.320 | 1.00 11.38 | B |
| ATOM | 4291 | N | ALA | 165 | 51.766 | 4.416 | 42.066 | 1.00 11.02 | B |
| ATOM | 4293 | CA | ALA | 165 | 51.595 | 5.219 | 43.267 | 1.00 10.88 | B |
| ATOM | 4294 | CB | ALA | 165 | 51.406 | 6.684 | 42.885 | 1.00 9.95 | B |
| ATOM | 4295 | C | ALA | 165 | 50.417 | 4.739 | 44.115 | 1.00 11.34 | B |
| ATOM | 4296 | O | ALA | 165 | 49.315 | 4.516 | 43.582 | 1.00 12.21 | B |
| ATOM | 4297 | N | ASN | 166 | 50.685 | 4.531 | 45.406 | 1.00 10.21 | B |
| ATOM | 4299 | CA | ASN | 166 | 49.703 | 4.099 | 46.392 | 1.00 10.30 | B |
| ATOM | 4300 | CB | ASN | 166 | 50.388 | 3.285 | 47.480 | 1.00 9.44 | B |
| ATOM | 4301 | CG | ASN | 166 | 51.032 | 2.016 | 46.944 | 1.00 10.73 | B |
| ATOM | 4302 | OD1 | ASN | 166 | 50.540 | 1.422 | 45.980 | 1.00 12.01 | B |
| ATOM | 4303 | ND2 | ASN | 166 | 52.138 | 1.585 | 47.569 | 1.00 6.41 | B |
| ATOM | 4306 | C | ASN | 166 | 49.088 | 5.424 | 46.941 | 1.00 10.72 | B |
| ATOM | 4307 | O | ASN | 166 | 49.792 | 6.231 | 47.590 | 1.00 9.93 | B |
| ATOM | 4308 | N | VAL | 167 | 47.786 | 5.644 | 46.677 | 1.00 10.30 | B |
| ATOM | 4310 | CA | VAL | 167 | 47.146 | 6.917 | 47.022 | 1.00 9.06 | B |
| ATOM | 4311 | CB | VAL | 167 | 46.839 | 7.715 | 45.730 | 1.00 9.40 | B |
| ATOM | 4312 | CG1 | VAL | 167 | 46.306 | 9.102 | 46.056 | 1.00 8.69 | B |
| ATOM | 4313 | CG2 | VAL | 167 | 48.139 | 7.837 | 44.908 | 1.00 5.90 | B |
| ATOM | 4314 | C | VAL | 167 | 45.923 | 6.732 | 47.850 | 1.00 9.31 | B |
| ATOM | 4315 | O | VAL | 167 | 44.961 | 6.125 | 47.415 | 1.00 8.68 | B |
| ATOM | 4316 | N | TYR | 168 | 45.958 | 7.288 | 49.054 | 1.00 8.97 | B |
| ATOM | 4318 | CA | TYR | 168 | 44.871 | 7.107 | 49.959 | 1.00 10.02 | B |
| ATOM | 4319 | CB | TYR | 168 | 45.339 | 6.224 | 51.132 | 1.00 10.76 | B |
| ATOM | 4320 | CG | TYR | 168 | 45.600 | 4.776 | 50.805 | 1.00 9.29 | B |
| ATOM | 4321 | CD1 | TYR | 168 | 46.837 | 4.368 | 50.321 | 1.00 7.20 | B |
| ATOM | 4322 | CE1 | TYR | 168 | 47.114 | 3.034 | 50.123 | 1.00 6.92 | B |
| ATOM | 4323 | CD2 | TYR | 168 | 44.638 | 3.805 | 51.067 | 1.00 8.73 | B |
| ATOM | 4324 | CE2 | TYR | 168 | 44.901 | 2.445 | 50.860 | 1.00 7.15 | B |
| ATOM | 4325 | CZ | TYR | 168 | 46.140 | 2.069 | 50.399 | 1.00 8.16 | B |
| ATOM | 4326 | OH | TYR | 168 | 46.436 | 0.729 | 50.243 | 1.00 5.24 | B |
| ATOM | 4328 | C | TYR | 168 | 44.171 | 8.324 | 50.539 | 1.00 9.92 | B |
| ATOM | 4329 | O | TYR | 168 | 44.654 | 8.904 | 51.510 | 1.00 10.14 | B |

- 104 -

| | | | | | | | | | |
|---|---|---|---|---|---|---|---|---|---|
| ATOM | 4330 | H | PRO | 169 | 43.073 | 8.787 | 49.908 | 1.00 | 10.35 | B |
| ATOM | 4331 | CD | PRO | 169 | 42.673 | 8.611 | 48.492 | 1.00 | 8.10 | B |
| ATOM | 4332 | CA | PRO | 169 | 42.365 | 9.944 | 50.487 | 1.00 | 10.32 | B |
| ATOM | 4333 | CB | PRO | 169 | 41.140 | 10.037 | 49.579 | 1.00 | 8.71 | B |
| ATOM | 4334 | CG | PRO | 169 | 41.773 | 9.808 | 48.257 | 1.00 | 6.28 | B |
| ATOM | 4335 | C | PRO | 169 | 42.011 | 9.652 | 51.980 | 1.00 | 10.28 | B |
| ATOM | 4336 | O | PRO | 169 | 42.052 | 10.526 | 52.821 | 1.00 | 10.77 | B |
| ATOM | 4337 | N | TYR | 170 | 41.845 | 8.376 | 52.301 | 1.00 | 10.84 | B |
| ATOM | 4338 | CA | TYR | 170 | 41.551 | 7.937 | 53.652 | 1.00 | 11.67 | B |
| ATOM | 4339 | CB | TYR | 170 | 41.427 | 6.417 | 53.741 | 1.00 | 12.00 | B |
| ATOM | 4340 | CG | TYR | 170 | 41.221 | 6.007 | 55.161 | 1.00 | 13.14 | B |
| ATOM | 4341 | CD1 | TYR | 170 | 40.064 | 6.399 | 55.833 | 1.00 | 14.15 | B |
| ATOM | 4342 | CE1 | TYR | 170 | 39.898 | 6.172 | 57.191 | 1.00 | 15.10 | B |
| ATOM | 4343 | CD2 | TYR | 170 | 42.223 | 5.355 | 55.884 | 1.00 | 13.86 | B |
| ATOM | 4344 | CE2 | TYR | 170 | 42.069 | 5.116 | 57.268 | 1.00 | 15.24 | B |
| ATOM | 4345 | CZ | TYR | 170 | 40.692 | 5.534 | 57.909 | 1.00 | 14.16 | B |
| ATOM | 4346 | OH | TYR | 170 | 40.673 | 5.326 | 59.239 | 1.00 | 13.19 | B |
| ATOM | 4347 | C | TYR | 170 | 42.617 | 8.385 | 54.625 | 1.00 | 11.58 | B |
| ATOM | 4348 | O | TYR | 170 | 42.304 | 9.064 | 55.593 | 1.00 | 13.59 | B |
| ATOM | 4349 | N | PHE | 171 | 43.670 | 8.047 | 54.350 | 1.00 | 10.95 | B |
| ATOM | 4350 | H | PHE | 171 | 44.978 | 8.397 | 55.220 | 1.00 | 11.73 | B |
| ATOM | 4351 | CA | PHE | 171 | 46.272 | 7.680 | 54.784 | 1.00 | 12.25 | B |
| ATOM | 4352 | CB | PHE | 171 | 46.208 | 6.180 | 54.886 | 1.00 | 13.52 | B |
| ATOM | 4353 | CG | PHE | 171 | 46.833 | 5.377 | 53.946 | 1.00 | 16.59 | B |
| ATOM | 4354 | CD1 | PHE | 171 | 45.517 | 5.556 | 55.913 | 1.00 | 14.13 | B |
| ATOM | 4355 | CE1 | PHE | 171 | 46.752 | 3.969 | 54.046 | 1.00 | 15.15 | B |
| ATOM | 4356 | CD2 | PHE | 171 | 45.444 | 4.158 | 56.148 | 1.00 | 13.45 | B |
| ATOM | 4357 | CE2 | PHE | 171 | 46.049 | 3.383 | 56.001 | 1.00 | 13.02 | B |
| ATOM | 4358 | CZ | PHE | 171 | 45.202 | 3.910 | 55.305 | 1.00 | 12.54 | B |
| ATOM | 4359 | C | PHE | 171 | 45.738 | 10.408 | 56.301 | 1.00 | 13.30 | B |
| ATOM | 4360 | O | PHE | 171 | 44.864 | 10.644 | 56.148 | 1.00 | 11.87 | B |
| ATOM | 4361 | N | ALA | 172 | 45.017 | 12.087 | 54.321 | 1.00 | 11.88 | B |
| ATOM | 4362 | CA | ALA | 172 | 44.786 | 12.689 | 52.938 | 1.00 | 11.82 | B |
| ATOM | 4363 | CB | ALA | 172 | 43.953 | 12.620 | 55.303 | 1.00 | 12.87 | B |
| ATOM | 4364 | C | ALA | 172 | 44.216 | 13.495 | 56.148 | 1.00 | 11.84 | B |
| ATOM | 4365 | O | ALA | 172 | 42.735 | 12.108 | 55.117 | 1.00 | 13.58 | B |
| ATOM | 4366 | N | TYR | 173 | 41.571 | 12.487 | 55.891 | 1.00 | 15.36 | B |
| ATOM | 4367 | CA | TYR | 173 | 40.329 | 11.794 | 55.307 | 1.00 | 14.22 | B |
| ATOM | 4368 | CB | TYR | 173 | 39.061 | 12.123 | 56.032 | 1.00 | 17.17 | B |
| ATOM | 4369 | CG | TYR | 173 | 38.741 | 13.445 | 56.354 | 1.00 | 17.57 | B |
| ATOM | 4375 | CE1 | TYR | 173 | 37.619 | 13.747 | 57.143 | 1.00 | 18.39 | B |
| ATOM | 4376 | CD2 | TYR | 173 | 38.212 | 11.101 | 56.505 | 1.00 | 17.93 | B |
| ATOM | 4377 | CE2 | TYR | 173 | 37.095 | 11.392 | 57.286 | 1.00 | 18.06 | B |
| ATOM | 4378 | CZ | TYR | 173 | 36.807 | 12.120 | 57.607 | 1.00 | 18.77 | B |
| ATOM | 4379 | OH | TYR | 173 | 35.724 | 13.010 | 58.412 | 1.00 | 18.80 | B |
| ATOM | 4381 | C | TYR | 173 | 41.777 | 12.188 | 57.389 | 1.00 | 16.49 | B |
| ATOM | 4382 | O | TYR | 173 | 41.717 | 13.098 | 58.217 | 1.00 | 16.65 | B |
| ATOM | 4383 | N | ARG | 174 | 42.161 | 10.957 | 57.700 | 1.00 | 17.05 | B |
| ATOM | 4385 | CA | ARG | 174 | 42.380 | 10.538 | 59.068 | 1.00 | 19.32 | B |
| ATOM | 4386 | CB | ARG | 174 | 42.826 | 9.083 | 59.061 | 1.00 | 20.99 | B |
| ATOM | 4387 | CG | ARG | 174 | 42.748 | 8.427 | 60.392 | 1.00 | 23.83 | B |
| ATOM | 4388 | CD | ARG | 174 | 43.695 | 7.243 | 60.473 | 1.00 | 26.95 | B |
| ATOM | 4389 | NE | ARG | 174 | 42.924 | 6.031 | 60.720 | 1.00 | 30.67 | B |
| ATOM | 4391 | CZ | ARG | 174 | 43.186 | 5.119 | 61.654 | 1.00 | 32.81 | B |
| ATOM | 4392 | NH1 | ARG | 174 | 44.223 | 5.255 | 62.479 | 1.00 | 34.36 | B |
| ATOM | 4395 | NH2 | ARG | 174 | 42.390 | 4.060 | 61.771 | 1.00 | 34.67 | B |
| ATOM | 4398 | C | ARG | 174 | 43.396 | 11.428 | 59.819 | 1.00 | 19.70 | B |
| ATOM | 4399 | O | ARG | 174 | 43.170 | 11.796 | 60.960 | 1.00 | 18.92 | B |
| ATOM | 4400 | N | ASP | 175 | 44.478 | 11.819 | 59.145 | 1.00 | 21.20 | B |
| ATOM | 4402 | CA | ASP | 175 | 45.517 | 12.674 | 59.726 | 1.00 | 22.84 | B |
| ATOM | 4403 | CB | ASP | 175 | 46.799 | 12.594 | 58.891 | 1.00 | 24.01 | B |
| ATOM | 4404 | CG | ASP | 175 | 47.454 | 11.218 | 58.940 | 1.00 | 26.45 | B |
| ATOM | 4405 | OD1 | ASP | 175 | 47.096 | 10.385 | 59.820 | 1.00 | 26.37 | B |
| ATOM | 4406 | OD2 | ASP | 175 | 48.332 | 10.971 | 58.083 | 1.00 | 27.30 | B |
| ATOM | 4407 | C | ASP | 175 | 45.159 | 14.156 | 59.862 | 1.00 | 23.31 | B |
| ATOM | 4408 | O | ASP | 175 | 45.866 | 14.886 | 60.542 | 1.00 | 23.42 | B |
| ATOM | 4409 | N | ASN | 176 | 44.105 | 14.609 | 59.181 | 1.00 | 23.11 | B |
| ATOM | 4411 | CA | ASN | 176 | 43.700 | 16.010 | 59.231 | 1.00 | 23.90 | B |
| ATOM | 4412 | CB | ASN | 176 | 44.287 | 16.782 | 58.045 | 1.00 | 25.31 | B |
| ATOM | 4413 | CG | ASN | 176 | 45.753 | 16.552 | 57.887 | 1.00 | 27.66 | B |
| ATOM | 4414 | OD1 | ASN | 176 | 46.577 | 17.246 | 58.483 | 1.00 | 28.66 | B |
| ATOM | 4415 | ND2 | ASN | 176 | 46.106 | 15.539 | 57.099 | 1.00 | 30.72 | B |
| ATOM | 4418 | C | ASN | 176 | 42.191 | 16.137 | 59.148 | 1.00 | 23.52 | B |
| ATOM | 4419 | O | ASN | 176 | 41.675 | 16.858 | 58.269 | 1.00 | 23.55 | B |
| ATOM | 4420 | N | PRO | 177 | 41.468 | 15.547 | 60.114 | 1.00 | 22.52 | B |
| ATOM | 4421 | CD | PRO | 177 | 41.977 | 15.020 | 61.391 | 1.00 | 22.42 | B |
| ATOM | 4422 | CA | PRO | 177 | 40.009 | 15.598 | 60.129 | 1.00 | 21.55 | B |
| ATOM | 4423 | CB | PRO | 177 | 39.651 | 14.946 | 61.476 | 1.00 | 22.11 | B |
| ATOM | 4424 | CG | PRO | 177 | 40.849 | 14.154 | 61.834 | 1.00 | 22.95 | B |
| ATOM | 4425 | C | PRO | 177 | 39.487 | 17.043 | 60.079 | | | |

- 105 -

| | | | | | | | | | |
|---|---|---|---|---|---|---|---|---|---|
| ATOM | 4426 | O | PRO | 177 | 38.431 | 17.321 | 59.484 | 1.00 | 24.99 | B |
| ATOM | 4427 | N | GLY | 178 | 40.218 | 17.946 | 60.732 | 1.00 | 22.38 | B |
| ATOM | 4429 | CA | GLY | 178 | 39.820 | 19.334 | 60.803 | 1.00 | 21.14 | B |
| ATOM | 4430 | C | GLY | 178 | 40.245 | 20.209 | 59.654 | 1.00 | 20.67 | B |
| ATOM | 4431 | O | GLY | 178 | 40.160 | 21.428 | 59.746 | 1.00 | 20.52 | B |
| ATOM | 4432 | N | SER | 179 | 40.684 | 19.598 | 58.568 | 1.00 | 19.72 | B |
| ATOM | 4434 | CA | SER | 179 | 41.102 | 20.354 | 57.408 | 1.00 | 19.44 | B |
| ATOM | 4435 | CB | SER | 179 | 42.618 | 20.446 | 57.340 | 1.00 | 20.32 | B |
| ATOM | 4436 | OG | SER | 179 | 43.013 | 21.007 | 56.106 | 1.00 | 20.78 | B |
| ATOM | 4438 | C | SER | 179 | 40.583 | 19.733 | 56.134 | 1.00 | 18.83 | B |
| ATOM | 4439 | O | SER | 179 | 40.632 | 20.357 | 55.098 | 1.00 | 20.47 | B |
| ATOM | 4440 | N | ILE | 180 | 40.106 | 18.499 | 56.190 | 1.00 | 17.84 | B |
| ATOM | 4442 | CA | ILE | 180 | 39.565 | 17.854 | 55.010 | 1.00 | 15.79 | B |
| ATOM | 4443 | CB | ILE | 180 | 40.398 | 16.587 | 54.624 | 1.00 | 15.77 | B |
| ATOM | 4444 | CG2 | ILE | 180 | 39.826 | 15.895 | 53.389 | 1.00 | 14.07 | B |
| ATOM | 4445 | CG1 | ILE | 180 | 41.843 | 16.985 | 54.317 | 1.00 | 14.13 | B |
| ATOM | 4446 | CD1 | ILE | 180 | 42.794 | 15.822 | 54.270 | 1.00 | 14.57 | B |
| ATOM | 4447 | C | ILE | 180 | 38.163 | 17.513 | 55.423 | 1.00 | 15.45 | B |
| ATOM | 4448 | O | ILE | 180 | 37.897 | 17.312 | 56.600 | 1.00 | 16.82 | B |
| ATOM | 4449 | N | SER | 181 | 37.242 | 17.625 | 54.486 | 1.00 | 15.61 | B |
| ATOM | 4451 | CA | SER | 181 | 35.836 | 17.320 | 54.703 | 1.00 | 14.64 | B |
| ATOM | 4452 | CB | SER | 181 | 34.977 | 18.286 | 53.899 | 1.00 | 16.36 | B |
| ATOM | 4453 | OG | SER | 181 | 35.534 | 18.518 | 52.608 | 1.00 | 19.73 | B |
| ATOM | 4455 | C | SER | 181 | 35.625 | 15.893 | 54.236 | 1.00 | 13.54 | B |
| ATOM | 4456 | O | SER | 181 | 36.382 | 15.418 | 53.425 | 1.00 | 13.53 | B |
| ATOM | 4457 | N | LEU | 182 | 34.595 | 15.217 | 54.732 | 1.00 | 13.30 | B |
| ATOM | 4459 | CA | LEU | 182 | 34.340 | 13.811 | 54.403 | 1.00 | 12.39 | B |
| ATOM | 4460 | CB | LEU | 182 | 33.409 | 13.168 | 55.443 | 1.00 | 10.41 | B |
| ATOM | 4461 | CG | LEU | 182 | 32.825 | 11.784 | 55.016 | 1.00 | 11.82 | B |
| ATOM | 4462 | CD1 | LEU | 182 | 33.873 | 10.640 | 55.190 | 1.00 | 10.44 | B |
| ATOM | 4463 | CD2 | LEU | 182 | 31.589 | 11.504 | 55.895 | 1.00 | 9.34 | B |
| ATOM | 4464 | C | LEU | 182 | 33.817 | 13.630 | 52.991 | 1.00 | 12.40 | B |
| ATOM | 4465 | O | LEU | 182 | 34.147 | 12.668 | 52.338 | 1.00 | 12.90 | B |
| ATOM | 4466 | N | ASN | 183 | 32.971 | 14.541 | 52.545 | 1.00 | 13.57 | B |
| ATOM | 4468 | CA | ASN | 183 | 32.421 | 14.534 | 51.185 | 1.00 | 15.03 | B |
| ATOM | 4469 | CB | ASN | 183 | 31.493 | 15.730 | 51.024 | 1.00 | 17.77 | B |
| ATOM | 4470 | CG | ASN | 183 | 30.106 | 15.441 | 51.532 | 1.00 | 21.73 | B |
| ATOM | 4471 | OD1 | ASN | 183 | 29.877 | 14.441 | 52.254 | 1.00 | 23.09 | B |
| ATOM | 4472 | HD2 | ASN | 183 | 29.137 | 16.264 | 51.095 | 1.00 | 23.70 | B |
| ATOM | 4475 | C | ASN | 183 | 33.519 | 14.599 | 50.089 | 1.00 | 14.42 | B |
| ATOM | 4476 | O | ASN | 183 | 33.474 | 13.883 | 49.075 | 1.00 | 12.17 | B |
| ATOM | 4477 | N | TYR | 184 | 34.453 | 15.520 | 50.318 | 1.00 | 12.88 | B |
| ATOM | 4479 | CA | TYR | 184 | 35.601 | 15.761 | 49.489 | 1.00 | 12.29 | B |
| ATOM | 4480 | CB | TYR | 184 | 36.392 | 16.949 | 50.086 | 1.00 | 10.73 | B |
| ATOM | 4481 | CG | TYR | 184 | 37.538 | 17.483 | 49.234 | 1.00 | 10.05 | B |
| ATOM | 4482 | CD1 | TYR | 184 | 37.315 | 17.980 | 47.934 | 1.00 | 9.48 | B |
| ATOM | 4483 | CE1 | TYR | 184 | 38.353 | 18.482 | 47.162 | 1.00 | 8.37 | B |
| ATOM | 4484 | CD2 | TYR | 184 | 38.844 | 17.507 | 49.737 | 1.00 | 10.95 | B |
| ATOM | 4485 | CE2 | TYR | 184 | 39.908 | 18.008 | 48.967 | 1.00 | 10.55 | B |
| ATOM | 4486 | CZ | TYR | 184 | 39.650 | 18.499 | 47.679 | 1.00 | 9.98 | B |
| ATOM | 4487 | OH | TYR | 184 | 40.687 | 19.022 | 46.947 | 1.00 | 8.64 | B |
| ATOM | 4489 | C | TYR | 184 | 36.452 | 14.469 | 49.439 | 1.00 | 12.39 | B |
| ATOM | 4490 | O | TYR | 184 | 36.991 | 14.117 | 48.378 | 1.00 | 12.85 | B |
| ATOM | 4491 | N | ALA | 185 | 36.626 | 13.789 | 50.581 | 1.00 | 11.39 | B |
| ATOM | 4493 | CA | ALA | 185 | 37.387 | 12.537 | 50.603 | 1.00 | 10.08 | B |
| ATOM | 4494 | CB | ALA | 185 | 37.775 | 12.183 | 52.063 | 1.00 | 10.74 | B |
| ATOM | 4495 | C | ALA | 185 | 36.636 | 11.337 | 49.982 | 1.00 | 10.16 | B |
| ATOM | 4496 | O | ALA | 185 | 37.259 | 10.390 | 49.536 | 1.00 | 9.55 | B |
| ATOM | 4497 | N | THR | 186 | 35.306 | 11.364 | 49.962 | 1.00 | 9.41 | B |
| ATOM | 4499 | CA | THR | 186 | 34.565 | 10.220 | 49.490 | 1.00 | 10.27 | B |
| ATOM | 4500 | CB | THR | 186 | 33.560 | 9.725 | 50.591 | 1.00 | 10.65 | B |
| ATOM | 4501 | OG1 | THR | 186 | 32.733 | 10.818 | 51.052 | 1.00 | 10.65 | B |
| ATOM | 4503 | CG2 | THR | 186 | 34.322 | 9.104 | 51.781 | 1.00 | 10.17 | B |
| ATOM | 4504 | C | THR | 186 | 33.843 | 10.289 | 48.163 | 1.00 | 10.81 | B |
| ATOM | 4505 | O | THR | 186 | 32.935 | 9.471 | 47.901 | 1.00 | 11.87 | B |
| ATOM | 4506 | N | PHE | 187 | 34.239 | 11.224 | 47.310 | 1.00 | 10.77 | B |
| ATOM | 4508 | CA | PHE | 187 | 33.579 | 11.406 | 46.014 | 1.00 | 11.33 | B |
| ATOM | 4509 | CB | PHE | 187 | 33.559 | 10.103 | 45.175 | 1.00 | 8.24 | B |
| ATOM | 4510 | CG | PHE | 187 | 34.928 | 9.598 | 44.808 | 1.00 | 8.22 | B |
| ATOM | 4511 | CD1 | PHE | 187 | 35.470 | 8.465 | 45.434 | 1.00 | 7.01 | B |
| ATOM | 4512 | CD2 | PHE | 187 | 35.724 | 10.310 | 43.931 | 1.00 | 5.75 | B |
| ATOM | 4513 | CE1 | PHE | 187 | 36.793 | 8.079 | 45.188 | 1.00 | 6.50 | B |
| ATOM | 4514 | CE2 | PHE | 187 | 37.046 | 9.919 | 43.681 | 1.00 | 5.87 | B |
| ATOM | 4515 | CZ | PHE | 187 | 37.578 | 8.817 | 44.307 | 1.00 | 6.42 | B |
| ATOM | 4516 | C | PHE | 187 | 32.145 | 11.981 | 46.113 | 1.00 | 13.29 | B |
| ATOM | 4517 | O | PHE | 187 | 31.311 | 11.731 | 45.217 | 1.00 | 13.76 | B |
| ATOM | 4518 | N | GLN | 188 | 31.837 | 12.701 | 47.190 | 1.00 | 14.17 | B |
| ATOM | 4520 | CA | GLN | 188 | 30.523 | 13.316 | 47.322 | 1.00 | 15.55 | B |
| ATOM | 4521 | CB | GLN | 188 | 29.966 | 13.225 | 48.746 | 1.00 | 16.79 | B |
| ATOM | 4522 | CG | GLN | 188 | 29.674 | 11.873 | 49.230 | 1.00 | 18.70 | B |

- 106 -

| ATOM | 4523 | CD | GLN | 188 | 28.796 | 11.131 | 48.274 | 1.00 | 20.86 | B | | ATOM | 4572 | CG | ARG | 194 | 40.862 | 28.330 | 41.518 | 1.00 | 15.63 | B |
|---|---|---|---|---|---|---|---|---|---|---|---|---|---|---|---|---|---|---|---|---|---|---|
| ATOM | 4524 | OE1 | GLN | 188 | 29.282 | 10.320 | 47.487 | 1.00 | 23.35 | B | | ATOM | 4573 | CD | ARG | 194 | 39.929 | 28.487 | 40.285 | 1.00 | 18.72 | B |
| ATOM | 4525 | NE2 | GLN | 188 | 27.488 | 11.400 | 48.318 | 1.00 | 22.79 | B | | ATOM | 4574 | NE | ARG | 194 | 40.376 | 29.600 | 39.448 | 1.00 | 20.90 | B |
| ATOM | 4528 | C | GLN | 188 | 30.671 | 14.788 | 46.998 | 1.00 | 16.75 | B | | ATOM | 4576 | CZ | ARG | 194 | 40.210 | 29.694 | 38.127 | 1.00 | 21.73 | B |
| ATOM | 4529 | O | GLN | 188 | 31.697 | 15.417 | 47.268 | 1.00 | 17.16 | B | | ATOM | 4577 | NH1 | ARG | 194 | 39.590 | 28.731 | 37.457 | 1.00 | 21.43 | B |
| ATOM | 4530 | N | PRO | 189 | 29.608 | 15.388 | 46.495 | 1.00 | 18.51 | B | | ATOM | 4580 | NH2 | ARG | 194 | 40.671 | 30.755 | 37.478 | 0.00 | 21.43 | B |
| ATOM | 4531 | CD | PRO | 189 | 28.361 | 14.729 | 46.067 | 1.00 | 18.51 | B | | ATOM | 4583 | C | ARG | 194 | 42.181 | 26.311 | 43.277 | 0.00 | 14.29 | B |
| ATOM | 4532 | CA | PRO | 189 | 29.591 | 16.802 | 46.136 | 1.00 | 18.65 | B | | ATOM | 4584 | O | ARG | 194 | 42.677 | 26.792 | 44.310 | 1.00 | 13.19 | B |
| ATOM | 4533 | CB | PRO | 189 | 28.306 | 16.911 | 45.315 | 1.00 | 20.40 | B | | ATOM | 4585 | N | ASP | 195 | 42.907 | 25.661 | 42.361 | 1.00 | 13.15 | B |
| ATOM | 4534 | CG | PRO | 189 | 27.437 | 15.901 | 46.005 | 1.00 | 20.36 | B | | ATOM | 4587 | CA | ASP | 195 | 44.356 | 25.668 | 42.422 | 1.00 | 14.49 | B |
| ATOM | 4535 | C | PRO | 189 | 29.582 | 17.762 | 47.307 | 1.00 | 18.22 | B | | ATOM | 4588 | CB | ASP | 195 | 44.940 | 24.594 | 41.495 | 1.00 | 14.42 | B |
| ATOM | 4536 | O | PRO | 189 | 29.182 | 17.420 | 48.415 | 1.00 | 18.78 | B | | ATOM | 4589 | CG | ASP | 195 | 46.460 | 24.486 | 41.578 | 1.00 | 13.89 | B |
| ATOM | 4537 | N | GLY | 190 | 30.093 | 18.961 | 47.073 | 1.00 | 18.11 | B | | ATOM | 4590 | OD1 | ASP | 195 | 47.159 | 25.522 | 41.654 | 1.00 | 11.97 | B |
| ATOM | 4539 | CA | GLY | 190 | 30.034 | 19.935 | 48.129 | 1.00 | 17.67 | B | | ATOM | 4591 | OD2 | ASP | 195 | 46.960 | 23.339 | 41.544 | 1.00 | 14.85 | B |
| ATOM | 4540 | C | GLY | 190 | 31.322 | 20.789 | 48.264 | 1.00 | 17.98 | B | | ATOM | 4592 | C | ASP | 195 | 44.760 | 27.068 | 41.951 | 1.00 | 15.52 | B |
| ATOM | 4541 | O | GLY | 190 | 31.184 | 21.930 | 48.653 | 1.00 | 18.59 | B | | ATOM | 4593 | O | ASP | 195 | 44.668 | 27.397 | 40.783 | 1.00 | 15.60 | B |
| ATOM | 4542 | N | THR | 191 | 32.509 | 20.243 | 47.991 | 1.00 | 17.34 | B | | ATOM | 4594 | N | GLN | 196 | 45.202 | 27.881 | 42.897 | 1.00 | 17.74 | B |
| ATOM | 4544 | CA | THR | 191 | 33.717 | 20.988 | 48.113 | 1.00 | 15.06 | B | | ATOM | 4596 | CA | GLN | 196 | 45.628 | 29.264 | 42.676 | 1.00 | 19.43 | B |
| ATOM | 4545 | CB | THR | 191 | 34.819 | 20.208 | 48.853 | 1.00 | 15.31 | B | | ATOM | 4597 | CB | GLN | 196 | 46.083 | 29.889 | 44.037 | 1.00 | 20.43 | B |
| ATOM | 4546 | OG1 | THR | 191 | 34.304 | 19.856 | 50.146 | 1.00 | 14.75 | B | | ATOM | 4598 | CG | GLN | 196 | 47.122 | 29.056 | 44.864 | 1.00 | 23.02 | B |
| ATOM | 4548 | CG2 | THR | 191 | 36.008 | 21.067 | 49.050 | 1.00 | 13.96 | B | | ATOM | 4599 | CD | GLN | 196 | 46.523 | 28.154 | 46.026 | 1.00 | 23.75 | B |
| ATOM | 4549 | C | THR | 191 | 34.317 | 21.330 | 46.769 | 1.00 | 13.73 | B | | ATOM | 4600 | OE1 | GLN | 196 | 45.677 | 27.245 | 45.828 | 1.00 | 22.60 | B |
| ATOM | 4550 | O | THR | 191 | 34.362 | 20.485 | 45.874 | 1.00 | 12.54 | B | | ATOM | 4601 | NE2 | GLN | 196 | 47.030 | 28.382 | 47.227 | 1.00 | 24.94 | B |
| ATOM | 4551 | N | THR | 192 | 34.787 | 22.563 | 46.670 | 1.00 | 13.45 | B | | ATOM | 4604 | C | GLN | 196 | 46.726 | 29.460 | 41.617 | 1.00 | 19.52 | B |
| ATOM | 4553 | CA | THR | 192 | 35.381 | 23.057 | 45.463 | 1.00 | 14.97 | B | | ATOM | 4605 | O | GLN | 196 | 46.777 | 30.489 | 40.935 | 1.00 | 18.88 | B |
| ATOM | 4554 | CB | THR | 192 | 34.419 | 23.960 | 44.717 | 1.00 | 14.20 | B | | ATOM | 4606 | N | ASN | 197 | 47.635 | 28.491 | 41.546 | 1.00 | 19.84 | B |
| ATOM | 4555 | OG1 | THR | 192 | 33.213 | 23.233 | 44.485 | 1.00 | 15.56 | B | | ATOM | 4608 | CA | ASN | 197 | 48.773 | 28.532 | 40.645 | 1.00 | 21.78 | B |
| ATOM | 4557 | CG2 | THR | 192 | 34.917 | 24.360 | 43.369 | 1.00 | 12.95 | B | | ATOM | 4609 | CB | ASN | 197 | 49.810 | 27.542 | 41.056 | 1.00 | 24.43 | B |
| ATOM | 4558 | C | THR | 192 | 36.595 | 23.832 | 45.908 | 1.00 | 13.25 | B | | ATOM | 4610 | CG | ASN | 197 | 50.538 | 29.063 | 42.299 | 1.00 | 25.47 | B |
| ATOM | 4559 | O | THR | 192 | 36.486 | 24.129 | 46.723 | 1.00 | 13.67 | B | | ATOM | 4611 | OD1 | ASN | 197 | 51.319 | 26.916 | 42.755 | 1.00 | 19.64 | B |
| ATOM | 4560 | N | VAL | 193 | 37.748 | 23.485 | 45.363 | 1.00 | 11.90 | B | | ATOM | 4612 | ND2 | ASN | 197 | 48.479 | 28.325 | 42.874 | 1.00 | 20.33 | B |
| ATOM | 4562 | CA | VAL | 193 | 38.977 | 24.141 | 45.727 | 1.00 | 12.57 | B | | ATOM | 4615 | C | ASN | 197 | 49.191 | 28.851 | 39.186 | 1.00 | 19.07 | B |
| ATOM | 4563 | CB | VAL | 193 | 39.912 | 23.121 | 46.394 | 1.00 | 13.39 | B | | ATOM | 4616 | O | ASN | 197 | 47.458 | 27.285 | 38.855 | 1.00 | 18.84 | B |
| ATOM | 4564 | CG1 | VAL | 193 | 41.187 | 23.778 | 46.846 | 1.00 | 13.44 | B | | ATOM | 4617 | N | ASN | 198 | 47.166 | 25.902 | 37.459 | 1.00 | 18.49 | B |
| ATOM | 4565 | CG2 | VAL | 193 | 39.209 | 22.465 | 47.541 | 1.00 | 15.56 | B | | ATOM | 4619 | CA | ASN | 198 | 47.712 | 24.797 | 37.054 | 1.00 | 19.26 | B |
| ATOM | 4566 | C | VAL | 193 | 39.615 | 24.617 | 44.424 | 1.00 | 12.95 | B | | ATOM | 4620 | CB | ASN | 198 | 47.141 | 24.974 | 37.883 | 1.00 | 19.69 | B |
| ATOM | 4567 | O | VAL | 193 | 39.673 | 23.864 | 43.477 | 1.00 | 13.25 | B | | ATOM | 4621 | CG | ASN | 198 | 46.093 | 23.654 | 38.512 | 1.00 | 18.84 | B |
| ATOM | 4568 | N | ARG | 194 | 40.015 | 25.871 | 44.329 | 1.00 | 13.67 | B | | ATOM | 4622 | OD1 | ASN | 198 | 47.822 | 27.410 | 37.921 | 1.00 | 18.34 | B |
| ATOM | 4570 | CA | ARG | 194 | 40.649 | 26.310 | 43.092 | 1.00 | 13.09 | B | | ATOM | 4623 | ND2 | ASN | 198 | | | | | | |
| ATOM | 4571 | CB | ARG | 194 | 40.165 | 27.698 | 42.705 | 1.00 | 13.72 | B | | ATOM | 4626 | C | ASN | 198 | 45.699 | 27.135 | | | | |

- 107 -

| | | | | | | | | | | | | | | | |
|---|---|---|---|---|---|---|---|---|---|---|---|---|---|---|---|
| ATOM | 4627 | O | ASN | 198 | 45.303 | 27.196 | 35.993 | 1.00 | 18.92 | B | ATOM | 4676 | CA | SER | 204 | 37.712 | 15.254 | 45.197 | 1.00 | 9.95 | B |
| ATOM | 4628 | N | GLY | 199 | 44.888 | 27.678 | 38.152 | 1.00 | 17.46 | B | ATOM | 4677 | CB | SER | 204 | 37.446 | 13.966 | 44.438 | 1.00 | 10.14 | B |
| ATOM | 4630 | CA | GLY | 199 | 43.472 | 27.886 | 37.926 | 1.00 | 16.53 | B | ATOM | 4678 | OG | SER | 204 | 38.262 | 13.901 | 43.288 | 1.00 | 9.62 | B |
| ATOM | 4631 | C | GLY | 199 | 42.614 | 26.648 | 37.879 | 1.00 | 17.10 | B | ATOM | 4680 | C | SER | 204 | 39.159 | 15.258 | 45.610 | 1.00 | 9.82 | B |
| ATOM | 4632 | O | GLY | 199 | 41.375 | 26.741 | 37.754 | 1.00 | 16.24 | B | ATOM | 4681 | O | SER | 204 | 40.014 | 15.724 | 44.851 | 1.00 | 8.39 | B |
| ATOM | 4633 | N | LEU | 200 | 43.253 | 25.484 | 37.989 | 1.00 | 16.13 | B | ATOM | 4682 | N | LEU | 205 | 39.420 | 14.753 | 46.819 | 1.00 | 9.38 | B |
| ATOM | 4635 | CA | LEU | 200 | 42.508 | 24.239 | 37.964 | 1.00 | 15.42 | B | ATOM | 4684 | CA | LEU | 205 | 40.773 | 14.681 | 47.365 | 1.00 | 9.01 | B |
| ATOM | 4636 | CB | LEU | 200 | 43.463 | 23.026 | 37.887 | 1.00 | 14.45 | B | ATOM | 4685 | CB | LEU | 205 | 40.738 | 14.208 | 48.823 | 1.00 | 8.45 | B |
| ATOM | 4637 | CG | LEU | 200 | 44.343 | 22.821 | 36.644 | 1.00 | 15.39 | B | ATOM | 4686 | CG | LEU | 205 | 42.017 | 14.131 | 49.657 | 1.00 | 8.13 | B |
| ATOM | 4638 | CD1 | LEU | 200 | 45.091 | 21.488 | 36.691 | 1.00 | 13.97 | B | ATOM | 4687 | CD1 | LEU | 205 | 42.705 | 15.463 | 49.725 | 1.00 | 5.85 | B |
| ATOM | 4639 | CD2 | LEU | 200 | 43.497 | 22.850 | 35.425 | 1.00 | 15.85 | B | ATOM | 4688 | CD2 | LEU | 205 | 41.661 | 13.682 | 51.069 | 1.00 | 8.73 | B |
| ATOM | 4640 | C | LEU | 200 | 41.587 | 24.164 | 39.200 | 1.00 | 14.00 | B | ATOM | 4689 | C | LEU | 205 | 41.624 | 13.751 | 46.519 | 1.00 | 8.53 | B |
| ATOM | 4641 | O | LEU | 200 | 41.925 | 24.699 | 40.242 | 1.00 | 14.05 | B | ATOM | 4690 | O | LEU | 205 | 42.831 | 13.967 | 46.375 | 1.00 | 9.72 | B |
| ATOM | 4642 | N | THR | 201 | 40.427 | 23.510 | 39.060 | 1.00 | 13.70 | B | ATOM | 4691 | N | PHE | 206 | 41.008 | 12.688 | 46.013 | 1.00 | 7.62 | B |
| ATOM | 4644 | CA | THR | 201 | 39.436 | 23.334 | 40.144 | 1.00 | 11.94 | B | ATOM | 4693 | CA | PHE | 206 | 41.682 | 11.715 | 45.148 | 1.00 | 8.07 | B |
| ATOM | 4645 | CB | THR | 201 | 37.961 | 23.760 | 39.708 | 1.00 | 11.43 | B | ATOM | 4694 | CB | PHE | 206 | 40.640 | 10.692 | 44.630 | 1.00 | 7.26 | B |
| ATOM | 4646 | OG1 | THR | 201 | 37.838 | 25.187 | 39.541 | 1.00 | 9.46 | B | ATOM | 4695 | CG | PHE | 206 | 41.221 | 9.618 | 43.730 | 1.00 | 8.19 | B |
| ATOM | 4648 | CG2 | THR | 201 | 36.949 | 23.331 | 40.770 | 1.00 | 11.96 | B | ATOM | 4696 | CD1 | PHE | 206 | 41.891 | 8.513 | 44.282 | 1.00 | 8.15 | B |
| ATOM | 4649 | C | THR | 201 | 39.337 | 21.875 | 40.606 | 1.00 | 11.77 | B | ATOM | 4697 | CD2 | PHE | 206 | 41.151 | 9.738 | 42.331 | 1.00 | 7.18 | B |
| ATOM | 4650 | O | THR | 201 | 39.069 | 20.974 | 39.805 | 1.00 | 10.96 | B | ATOM | 4698 | CE1 | PHE | 206 | 42.491 | 7.551 | 43.456 | 1.00 | 6.84 | B |
| ATOM | 4651 | N | TYR | 202 | 39.451 | 21.639 | 41.907 | 1.00 | 10.82 | B | ATOM | 4699 | CE2 | PHE | 206 | 41.736 | 8.787 | 41.494 | 1.00 | 5.04 | B |
| ATOM | 4653 | CA | TYR | 202 | 39.317 | 20.290 | 42.398 | 1.00 | 10.32 | B | ATOM | 4700 | CZ | PHE | 206 | 42.407 | 7.693 | 42.060 | 1.00 | 8.01 | B |
| ATOM | 4654 | CB | TYR | 202 | 40.541 | 19.902 | 43.198 | 1.00 | 10.02 | B | ATOM | 4701 | C | PHE | 206 | 42.398 | 12.425 | 43.945 | 1.00 | 8.67 | B |
| ATOM | 4655 | CG | TYR | 202 | 41.752 | 19.847 | 42.331 | 1.00 | 8.78 | B | ATOM | 4702 | O | PHE | 206 | 43.603 | 12.218 | 43.678 | 1.00 | 9.20 | B |
| ATOM | 4656 | CD1 | TYR | 202 | 42.389 | 21.021 | 41.900 | 1.00 | 7.93 | B | ATOM | 4703 | N | ASP | 207 | 41.634 | 13.235 | 43.212 | 1.00 | 8.45 | B |
| ATOM | 4657 | CE1 | TYR | 202 | 43.478 | 20.955 | 41.022 | 1.00 | 9.72 | B | ATOM | 4705 | CA | ASP | 207 | 42.147 | 13.976 | 42.064 | 1.00 | 7.63 | B |
| ATOM | 4658 | CD2 | TYR | 202 | 42.227 | 18.615 | 41.884 | 1.00 | 9.36 | B | ATOM | 4706 | CB | ASP | 207 | 41.028 | 14.787 | 41.464 | 1.00 | 8.35 | B |
| ATOM | 4659 | CE2 | TYR | 202 | 43.309 | 18.529 | 41.021 | 1.00 | 10.18 | B | ATOM | 4707 | CG | ASP | 207 | 40.067 | 13.957 | 40.681 | 1.00 | 8.65 | B |
| ATOM | 4660 | CZ | TYR | 202 | 43.922 | 19.690 | 40.588 | 1.00 | 9.91 | B | ATOM | 4708 | OD1 | ASP | 207 | 40.378 | 12.811 | 40.319 | 1.00 | 10.52 | B |
| ATOM | 4661 | OH | TYR | 202 | 44.930 | 19.549 | 39.677 | 1.00 | 11.05 | B | ATOM | 4709 | OD2 | ASP | 207 | 39.009 | 14.481 | 40.385 | 1.00 | 10.58 | B |
| ATOM | 4663 | C | TYR | 202 | 38.030 | 20.068 | 43.185 | 1.00 | 11.54 | B | ATOM | 4710 | C | ASP | 207 | 43.254 | 14.918 | 42.460 | 1.00 | 8.22 | B |
| ATOM | 4664 | O | TYR | 202 | 37.472 | 21.005 | 43.773 | 1.00 | 10.66 | B | ATOM | 4711 | O | ASP | 207 | 44.231 | 15.099 | 41.716 | 1.00 | 7.47 | B |
| ATOM | 4665 | N | THR | 203 | 37.479 | 18.859 | 43.057 | 1.00 | 12.21 | B | ATOM | 4712 | N | ALA | 208 | 43.054 | 15.593 | 43.590 | 1.00 | 8.03 | B |
| ATOM | 4667 | CA | THR | 203 | 36.247 | 18.514 | 43.758 | 1.00 | 13.32 | B | ATOM | 4714 | CA | ALA | 208 | 44.039 | 16.526 | 44.092 | 1.00 | 8.50 | B |
| ATOM | 4668 | CB | THR | 203 | 35.045 | 18.383 | 42.791 | 1.00 | 13.25 | B | ATOM | 4715 | CB | ALA | 208 | 43.485 | 17.299 | 45.277 | 1.00 | 9.96 | B |
| ATOM | 4669 | OG1 | THR | 203 | 35.366 | 17.420 | 41.797 | 1.00 | 17.64 | B | ATOM | 4716 | C | ALA | 208 | 45.351 | 15.825 | 44.449 | 1.00 | 8.22 | B |
| ATOM | 4671 | CG2 | THR | 203 | 34.740 | 19.119 | 42.095 | 1.00 | 13.83 | B | ATOM | 4717 | O | ALA | 208 | 46.441 | 16.375 | 44.201 | 1.00 | 10.15 | B |
| ATOM | 4672 | C | THR | 203 | 36.402 | 17.258 | 44.628 | 1.00 | 12.23 | B | ATOM | 4718 | N | MET | 209 | 45.264 | 14.621 | 45.002 | 1.00 | 7.92 | B |
| ATOM | 4673 | O | THR | 203 | 35.610 | 17.053 | 45.540 | 1.00 | 14.26 | B | ATOM | 4720 | CA | MET | 209 | 46.466 | 13.835 | 45.358 | 1.00 | 7.60 | B |
| ATOM | 4674 | N | SER | 204 | 37.444 | 16.456 | 44.390 | 1.00 | 11.49 | B | ATOM | 4721 | CB | MET | 209 | 46.146 | 12.703 | 46.351 | 1.00 | 8.44 | B |

- 108 -

| | | | | | | | | | |
|---|---|---|---|---|---|---|---|---|---|
| ATOM | 4722 | CG | MET | 209 | 45.584 | 13.114 | 47.712 | 1.00 | 8.70 | B |
| ATOM | 4723 | SD | MET | 209 | 45.161 | 11.714 | 48.734 | 1.00 | 9.43 | B |
| ATOM | 4724 | CE | MET | 209 | 46.805 | 11.216 | 49.234 | 1.00 | 5.71 | B |
| ATOM | 4725 | C | MET | 209 | 47.206 | 13.255 | 44.159 | 1.00 | 7.61 | B |
| ATOM | 4726 | O | MET | 209 | 48.433 | 13.168 | 44.201 | 1.00 | 8.17 | B |
| ATOM | 4727 | H | VAL | 210 | 46.475 | 12.864 | 43.101 | 1.00 | 7.19 | B |
| ATOM | 4729 | CA | VAL | 210 | 47.068 | 12.320 | 41.859 | 1.00 | 5.46 | B |
| ATOM | 4730 | CB | VAL | 210 | 46.013 | 11.699 | 40.864 | 1.00 | 5.59 | B |
| ATOM | 4731 | CG1 | VAL | 210 | 46.680 | 11.368 | 39.478 | 1.00 | 4.16 | B |
| ATOM | 4732 | CG2 | VAL | 210 | 45.406 | 10.400 | 41.438 | 1.00 | 3.00 | B |
| ATOM | 4733 | C | VAL | 210 | 47.744 | 13.446 | 41.102 | 1.00 | 6.50 | B |
| ATOM | 4734 | O | VAL | 210 | 48.822 | 13.273 | 40.549 | 1.00 | 7.06 | B |
| ATOM | 4735 | N | ASP | 211 | 47.141 | 14.621 | 41.106 | 1.00 | 7.61 | B |
| ATOM | 4737 | CA | ASP | 211 | 47.707 | 15.767 | 40.378 | 1.00 | 7.76 | B |
| ATOM | 4738 | CB | ASP | 211 | 46.624 | 16.809 | 40.086 | 1.00 | 9.69 | B |
| ATOM | 4739 | CG | ASP | 211 | 45.771 | 16.423 | 38.883 | 1.00 | 11.11 | B |
| ATOM | 4740 | OD1 | ASP | 211 | 46.007 | 15.333 | 38.308 | 1.00 | 12.49 | B |
| ATOM | 4741 | OD2 | ASP | 211 | 44.873 | 17.207 | 38.513 | 1.00 | 12.00 | B |
| ATOM | 4742 | C | ASP | 211 | 48.968 | 16.361 | 41.004 | 1.00 | 4.63 | B |
| ATOM | 4743 | O | ASP | 211 | 49.779 | 17.035 | 40.337 | 1.00 | 5.96 | B |
| ATOM | 4744 | N | ALA | 212 | 49.148 | 16.037 | 42.275 | 1.00 | 5.99 | B |
| ATOM | 4746 | CA | ALA | 212 | 50.350 | 16.437 | 42.990 | 1.00 | 3.78 | B |
| ATOM | 4747 | CB | ALA | 212 | 50.125 | 16.310 | 44.515 | 1.00 | 4.96 | B |
| ATOM | 4748 | C | ALA | 212 | 51.527 | 15.525 | 42.512 | 1.00 | 6.96 | B |
| ATOM | 4749 | O | ALA | 212 | 52.701 | 15.944 | 42.530 | 1.00 | 3.02 | B |
| ATOM | 4750 | N | VAL | 213 | 51.222 | 14.299 | 42.094 | 1.00 | 3.84 | B |
| ATOM | 4752 | CA | VAL | 213 | 52.254 | 13.381 | 41.634 | 1.00 | 4.36 | B |
| ATOM | 4753 | CB | VAL | 213 | 51.745 | 11.912 | 41.609 | 1.00 | 2.00 | B |
| ATOM | 4754 | CG1 | VAL | 213 | 52.894 | 10.965 | 41.461 | 1.00 | 3.39 | B |
| ATOM | 4755 | CG2 | VAL | 213 | 50.939 | 11.593 | 42.845 | 1.00 | 5.20 | B |
| ATOM | 4756 | C | VAL | 213 | 52.661 | 13.807 | 40.207 | 1.00 | 4.23 | B |
| ATOM | 4757 | O | VAL | 213 | 53.813 | 13.678 | 39.831 | 1.00 | 6.11 | B |
| ATOM | 4758 | N | TYR | 214 | 51.696 | 14.287 | 39.411 | 1.00 | 7.72 | B |
| ATOM | 4760 | CA | TYR | 214 | 51.958 | 15.178 | 38.060 | 1.00 | 6.93 | B |
| ATOM | 4761 | CB | TYR | 214 | 50.652 | 15.708 | 37.370 | 1.00 | 6.43 | B |
| ATOM | 4762 | CG | TYR | 214 | 49.888 | 13.997 | 36.850 | 1.00 | 8.44 | B |
| ATOM | 4763 | CD1 | TYR | 214 | 48.489 | 13.970 | 36.869 | 1.00 | 7.92 | B |
| ATOM | 4764 | CE1 | TYR | 214 | 47.796 | 12.892 | 36.350 | 1.00 | 7.44 | B |
| ATOM | 4765 | CD2 | TYR | 214 | 50.557 | 12.918 | 36.298 | 1.00 | 6.66 | B |
| ATOM | 4766 | CE2 | TYR | 214 | 49.875 | 11.833 | 35.774 | 1.00 | 6.66 | B |
| ATOM | 4767 | CZ | TYR | 214 | 48.514 | 11.822 | 35.800 | 1.00 | 8.41 | B |
| ATOM | 4768 | OH | TYR | 214 | 47.877 | 10.730 | 35.220 | 1.00 | 12.65 | B |
| ATOM | 4770 | C | TYR | 214 | 52.878 | 16.014 | 38.159 | 1.00 | 7.77 | B |
| ATOM | 4771 | O | TYR | 214 | 53.863 | 16.099 | 37.459 | 1.00 | 9.34 | B |
| ATOM | 4772 | N | ALA | 215 | 52.534 | 16.963 | 39.018 | 1.00 | 8.84 | B |
| ATOM | 4774 | CA | ALA | 215 | 53.347 | 18.171 | 39.277 | 1.00 | 8.74 | B |
| ATOM | 4775 | CB | ALA | 215 | 52.738 | 18.901 | 40.424 | 1.00 | 8.45 | B |
| ATOM | 4776 | C | ALA | 215 | 54.819 | 17.810 | 39.614 | 1.00 | 8.76 | B |
| ATOM | 4777 | O | ALA | 215 | 55.754 | 18.345 | 39.016 | 1.00 | 10.06 | B |
| ATOM | 4778 | N | ALA | 216 | 55.002 | 16.892 | 40.569 | 1.00 | 9.39 | B |
| ATOM | 4780 | CA | ALA | 216 | 56.307 | 16.353 | 40.997 | 1.00 | 9.03 | B |
| ATOM | 4781 | CB | ALA | 216 | 56.107 | 15.277 | 42.113 | 1.00 | 8.67 | B |
| ATOM | 4782 | C | ALA | 216 | 57.069 | 15.728 | 39.835 | 1.00 | 9.28 | B |
| ATOM | 4783 | O | ALA | 216 | 58.296 | 15.888 | 39.717 | 1.00 | 11.16 | B |
| ATOM | 4784 | N | LEU | 217 | 56.374 | 14.944 | 39.028 | 1.00 | 8.02 | B |
| ATOM | 4786 | CA | LEU | 217 | 56.997 | 14.314 | 37.883 | 1.00 | 9.44 | B |
| ATOM | 4787 | CB | LEU | 217 | 56.004 | 13.384 | 37.199 | 1.00 | 8.25 | B |
| ATOM | 4788 | CG | LEU | 217 | 55.709 | 12.025 | 37.833 | 1.00 | 6.80 | B |
| ATOM | 4789 | CD1 | LEU | 217 | 54.566 | 11.391 | 37.125 | 1.00 | 2.89 | B |
| ATOM | 4790 | CD2 | LEU | 217 | 56.963 | 11.112 | 37.772 | 1.00 | 7.55 | B |
| ATOM | 4791 | C | LEU | 217 | 57.536 | 15.329 | 36.862 | 1.00 | 11.57 | B |
| ATOM | 4792 | O | LEU | 217 | 58.551 | 15.103 | 36.196 | 1.00 | 11.97 | B |
| ATOM | 4793 | N | GLU | 218 | 56.833 | 16.437 | 36.687 | 1.00 | 14.01 | B |
| ATOM | 4795 | CA | GLU | 218 | 57.276 | 17.430 | 35.743 | 1.00 | 16.45 | B |
| ATOM | 4796 | CB | GLU | 218 | 56.178 | 18.469 | 35.504 | 1.00 | 20.52 | B |
| ATOM | 4797 | CG | GLU | 218 | 54.909 | 17.833 | 34.995 | 1.00 | 26.82 | B |
| ATOM | 4798 | CD | GLU | 218 | 53.732 | 18.791 | 34.950 | 1.00 | 30.05 | B |
| ATOM | 4799 | OE1 | GLU | 218 | 53.530 | 19.554 | 35.940 | 1.00 | 31.61 | B |
| ATOM | 4800 | OE2 | GLU | 218 | 53.001 | 18.744 | 33.918 | 1.00 | 32.98 | B |
| ATOM | 4801 | C | GLU | 218 | 58.500 | 18.099 | 36.308 | 1.00 | 16.71 | B |
| ATOM | 4802 | O | GLU | 218 | 59.498 | 18.290 | 35.602 | 1.00 | 17.84 | B |
| ATOM | 4803 | N | LYS | 219 | 58.440 | 18.450 | 37.589 | 1.00 | 15.86 | B |
| ATOM | 4805 | CA | LYS | 219 | 59.570 | 19.118 | 38.212 | 1.00 | 14.83 | B |
| ATOM | 4806 | CB | LYS | 219 | 59.239 | 19.496 | 39.667 | 1.00 | 12.70 | B |
| ATOM | 4807 | CG | LYS | 219 | 58.084 | 20.503 | 39.850 | 1.00 | 12.18 | B |
| ATOM | 4808 | CD | LYS | 219 | 57.992 | 20.952 | 41.344 | 1.00 | 10.54 | B |
| ATOM | 4809 | CE | LYS | 219 | 56.911 | 21.949 | 41.623 | 1.00 | 9.51 | B |
| ATOM | 4810 | NZ | LYS | 219 | 55.530 | 21.445 | 41.372 | 1.00 | 8.74 | B |
| ATOM | 4814 | C | LYS | 219 | 60.866 | 18.288 | 38.138 | 1.00 | 15.12 | B |
| ATOM | 4815 | O | LYS | 219 | 61.958 | 18.850 | 38.140 | 1.00 | 15.73 | B |

- 109 -

| ATOM | 4816 | N | ALA | 220 | 60.761 | 16.963 | 38.096 | 1.00 | 15.75 | B |
|---|---|---|---|---|---|---|---|---|---|---|
| ATOM | 4818 | CA | ALA | 220 | 61.956 | 16.091 | 38.016 | 1.00 | 16.18 | B |
| ATOM | 4819 | CB | ALA | 220 | 61.648 | 14.720 | 38.627 | 1.00 | 15.81 | B |
| ATOM | 4820 | C | ALA | 220 | 62.420 | 15.918 | 36.573 | 1.00 | 16.96 | B |
| ATOM | 4821 | O | ALA | 220 | 63.356 | 15.167 | 36.295 | 1.00 | 17.16 | B |
| ATOM | 4822 | N | GLY | 221 | 61.702 | 16.571 | 35.659 | 1.00 | 18.58 | B |
| ATOM | 4824 | CA | GLY | 221 | 61.989 | 16.509 | 34.240 | 1.00 | 18.96 | B |
| ATOM | 4825 | C | GLY | 221 | 61.436 | 15.275 | 33.542 | 1.00 | 20.12 | B |
| ATOM | 4826 | O | GLY | 221 | 62.016 | 14.800 | 32.559 | 1.00 | 21.40 | B |
| ATOM | 4827 | N | ALA | 222 | 60.332 | 14.733 | 34.037 | 1.00 | 20.33 | B |
| ATOM | 4829 | CA | ALA | 222 | 59.722 | 13.559 | 33.424 | 1.00 | 19.89 | B |
| ATOM | 4830 | CB | ALA | 222 | 60.033 | 12.323 | 34.253 | 1.00 | 19.00 | B |
| ATOM | 4831 | C | ALA | 222 | 58.207 | 13.796 | 33.326 | 1.00 | 20.74 | B |
| ATOM | 4832 | O | ALA | 222 | 57.403 | 13.114 | 34.005 | 1.00 | 22.12 | B |
| ATOM | 4833 | N | PRO | 223 | 57.799 | 14.806 | 32.527 | 1.00 | 20.03 | B |
| ATOM | 4834 | CD | PRO | 223 | 58.805 | 15.703 | 31.948 | 1.00 | 20.96 | B |
| ATOM | 4835 | CA | PRO | 223 | 56.452 | 15.306 | 32.212 | 1.00 | 19.07 | B |
| ATOM | 4836 | CB | PRO | 223 | 56.731 | 16.546 | 31.370 | 1.00 | 19.32 | B |
| ATOM | 4837 | CG | PRO | 223 | 58.065 | 16.976 | 31.846 | 1.00 | 21.79 | B |
| ATOM | 4838 | C | PRO | 223 | 55.482 | 14.424 | 31.453 | 1.00 | 18.64 | B |
| ATOM | 4839 | O | PRO | 223 | 54.288 | 14.647 | 31.550 | 1.00 | 19.67 | B |
| ATOM | 4840 | N | ALA | 224 | 55.967 | 13.505 | 30.614 | 1.00 | 18.78 | B |
| ATOM | 4842 | CA | ALA | 224 | 55.068 | 12.642 | 29.824 | 1.00 | 17.24 | B |
| ATOM | 4843 | CB | ALA | 224 | 55.601 | 12.452 | 28.409 | 1.00 | 15.93 | B |
| ATOM | 4844 | C | ALA | 224 | 54.834 | 11.292 | 30.460 | 1.00 | 16.30 | B |
| ATOM | 4845 | O | ALA | 224 | 54.177 | 10.432 | 29.838 | 1.00 | 17.88 | B |
| ATOM | 4846 | N | VAL | 225 | 55.379 | 11.107 | 31.669 | 1.00 | 14.22 | B |
| ATOM | 4848 | CA | VAL | 225 | 55.268 | 9.862 | 32.452 | 1.00 | 12.18 | B |
| ATOM | 4849 | CB | VAL | 225 | 56.315 | 9.847 | 33.577 | 1.00 | 10.58 | B |
| ATOM | 4850 | CG1 | VAL | 225 | 56.212 | 8.574 | 34.425 | 1.00 | 9.44 | B |
| ATOM | 4851 | CG2 | VAL | 225 | 57.706 | 10.005 | 32.966 | 1.00 | 9.80 | B |
| ATOM | 4852 | C | VAL | 225 | 53.854 | 9.683 | 33.027 | 1.00 | 10.80 | B |
| ATOM | 4853 | O | VAL | 225 | 53.330 | 10.580 | 33.652 | 1.00 | 10.90 | B |
| ATOM | 4854 | N | LYS | 226 | 53.225 | 8.558 | 32.720 | 1.00 | 10.31 | B |
| ATOM | 4856 | CA | LYS | 226 | 51.867 | 8.243 | 33.198 | 1.00 | 11.11 | B |
| ATOM | 4857 | CB | LYS | 226 | 51.213 | 7.206 | 32.275 | 1.00 | 13.34 | B |
| ATOM | 4858 | CG | LYS | 226 | 51.325 | 7.594 | 30.774 | 1.00 | 16.17 | B |
| ATOM | 4859 | CD | LYS | 226 | 50.234 | 6.935 | 29.874 | 1.00 | 17.43 | B |
| ATOM | 4860 | CE | LYS | 226 | 50.375 | 7.377 | 28.424 | 1.00 | 17.06 | B |
| ATOM | 4861 | NZ | LYS | 226 | 51.688 | 6.992 | 27.831 | 0.00 | 17.30 | B |
| ATOM | 4865 | C | LYS | 226 | 51.856 | 7.690 | 34.634 | 1.00 | 10.22 | B |
| ATOM | 4866 | O | LYS | 226 | 52.853 | 7.104 | 35.100 | 1.00 | 7.93 | B |
| ATOM | 4867 | N | VAL | 227 | 50.712 | 7.835 | 35.313 | 1.00 | 9.24 | B |
| ATOM | 4869 | CA | VAL | 227 | 50.577 | 7.336 | 36.675 | 1.00 | 7.75 | B |
| ATOM | 4870 | CB | VAL | 227 | 50.130 | 8.464 | 37.124 | 1.00 | 7.33 | B |
| ATOM | 4871 | CG1 | VAL | 227 | 49.677 | 7.832 | 39.061 | 1.00 | 6.05 | B |
| ATOM | 4872 | CG2 | VAL | 227 | 51.251 | 9.459 | 37.961 | 1.00 | 6.57 | B |
| ATOM | 4873 | C | VAL | 227 | 49.564 | 6.203 | 36.693 | 1.00 | 7.12 | B |
| ATOM | 4874 | O | VAL | 227 | 48.581 | 6.230 | 35.944 | 1.00 | 6.73 | B |
| ATOM | 4875 | N | VAL | 228 | 49.866 | 5.180 | 37.488 | 1.00 | 6.24 | B |
| ATOM | 4877 | CA | VAL | 228 | 48.951 | 4.058 | 37.700 | 1.00 | 5.83 | B |
| ATOM | 4878 | CB | VAL | 228 | 49.587 | 2.690 | 37.248 | 1.00 | 6.49 | B |
| ATOM | 4879 | CG1 | VAL | 228 | 48.650 | 1.513 | 37.519 | 1.00 | 6.17 | B |
| ATOM | 4880 | CG2 | VAL | 228 | 49.934 | 2.761 | 35.771 | 1.00 | 6.59 | B |
| ATOM | 4881 | C | VAL | 228 | 48.792 | 4.119 | 39.221 | 1.00 | 4.53 | B |
| ATOM | 4882 | O | VAL | 228 | 49.782 | 4.241 | 39.948 | 1.00 | 4.36 | B |
| ATOM | 4883 | N | VAL | 229 | 47.555 | 4.224 | 39.698 | 1.00 | 4.91 | B |
| ATOM | 4885 | CA | VAL | 229 | 47.321 | 4.269 | 41.130 | 1.00 | 2.77 | B |
| ATOM | 4886 | CB | VAL | 229 | 45.960 | 4.924 | 41.472 | 1.00 | 2.13 | B |
| ATOM | 4887 | CG1 | VAL | 229 | 45.682 | 4.923 | 43.006 | 1.00 | 3.00 | B |
| ATOM | 4888 | CG2 | VAL | 229 | 45.994 | 6.339 | 41.080 | 1.00 | 2.50 | B |
| ATOM | 4889 | C | VAL | 229 | 47.349 | 2.792 | 41.434 | 1.00 | 2.75 | B |
| ATOM | 4890 | O | VAL | 229 | 46.464 | 2.076 | 41.020 | 1.00 | 3.43 | B |
| ATOM | 4891 | N | SER | 230 | 48.388 | 2.310 | 42.099 | 1.00 | 3.06 | B |
| ATOM | 4893 | CA | SER | 230 | 48.475 | 0.874 | 42.357 | 1.00 | 5.03 | B |
| ATOM | 4894 | CB | SER | 230 | 49.913 | 0.371 | 42.232 | 1.00 | 5.13 | B |
| ATOM | 4895 | OG | SER | 230 | 50.831 | 1.208 | 42.909 | 1.00 | 6.55 | B |
| ATOM | 4897 | C | SER | 230 | 47.847 | 0.365 | 43.635 | 1.00 | 6.03 | B |
| ATOM | 4898 | O | SER | 230 | 47.942 | -0.828 | 43.937 | 1.00 | 6.79 | B |
| ATOM | 4899 | N | GLU | 231 | 47.175 | 1.263 | 44.350 | 1.00 | 7.07 | B |
| ATOM | 4901 | CA | GLU | 231 | 46.487 | 0.965 | 45.614 | 1.00 | 8.01 | B |
| ATOM | 4902 | CB | GLU | 231 | 47.472 | 0.719 | 46.783 | 1.00 | 8.57 | B |
| ATOM | 4903 | CG | GLU | 231 | 47.920 | -0.718 | 47.047 | 1.00 | 9.57 | B |
| ATOM | 4904 | CD | GLU | 231 | 48.825 | -0.867 | 48.298 | 1.00 | 10.93 | B |
| ATOM | 4905 | OE1 | GLU | 231 | 48.865 | 0.040 | 49.164 | 1.00 | 11.87 | B |
| ATOM | 4906 | OE2 | GLU | 231 | 49.521 | -1.898 | 48.401 | 1.00 | 11.23 | B |
| ATOM | 4907 | C | GLU | 231 | 45.702 | 2.182 | 46.035 | 1.00 | 7.20 | B |
| ATOM | 4908 | O | GLU | 231 | 46.224 | 3.279 | 45.991 | 1.00 | 8.75 | B |
| ATOM | 4909 | N | SER | 232 | 44.451 | 1.978 | 46.413 | 1.00 | 7.68 | B |
| ATOM | 4911 | CA | SER | 232 | 43.611 | 3.032 | 46.973 | 1.00 | 7.06 | B |

| | | | | | | | | | |
|---|---|---|---|---|---|---|---|---|---|
| ATOM | 4912 | CB | SER | 232 | 43.114 | 4.047 | 45.936 | 1.00 | 7.23 | B |
| ATOM | 4913 | OG | SER | 232 | 42.383 | 5.064 | 46.634 | 1.00 | 8.08 | B |
| ATOM | 4915 | C | SER | 232 | 42.451 | 2.290 | 47.589 | 1.00 | 6.30 | B |
| ATOM | 4916 | O | SER | 232 | 41.930 | 1.377 | 46.957 | 1.00 | 7.08 | B |
| ATOM | 4917 | N | GLY | 233 | 42.102 | 2.602 | 48.838 | 1.00 | 5.95 | B |
| ATOM | 4919 | CA | GLY | 233 | 40.975 | 1.941 | 49.494 | 1.00 | 6.16 | B |
| ATOM | 4920 | C | GLY | 233 | 40.430 | 2.650 | 50.743 | 1.00 | 6.90 | B |
| ATOM | 4921 | O | GLY | 233 | 40.819 | 3.767 | 51.051 | 1.00 | 6.81 | B |
| ATOM | 4922 | N | TRP | 234 | 39.523 | 2.003 | 51.479 | 1.00 | 6.62 | B |
| ATOM | 4924 | CA | TRP | 234 | 38.910 | 2.597 | 52.669 | 1.00 | 5.79 | B |
| ATOM | 4925 | CB | TRP | 234 | 37.694 | 3.459 | 52.319 | 1.00 | 5.12 | B |
| ATOM | 4926 | CG | TRP | 234 | 37.339 | 4.454 | 53.361 | 1.00 | 4.61 | B |
| ATOM | 4927 | CD2 | TRP | 234 | 37.478 | 5.876 | 53.268 | 1.00 | 6.41 | B |
| ATOM | 4928 | CE2 | TRP | 234 | 36.901 | 6.432 | 54.446 | 1.00 | 5.53 | B |
| ATOM | 4929 | CE3 | TRP | 234 | 38.013 | 6.743 | 52.292 | 1.00 | 8.10 | B |
| ATOM | 4930 | CD1 | TRP | 234 | 36.727 | 4.213 | 54.562 | 1.00 | 5.24 | B |
| ATOM | 4931 | NE1 | TRP | 234 | 36.453 | 5.390 | 55.211 | 1.00 | 4.78 | B |
| ATOM | 4933 | CZ2 | TRP | 234 | 36.839 | 7.805 | 54.687 | 1.00 | 5.65 | B |
| ATOM | 4934 | CZ3 | TRP | 234 | 37.952 | 8.135 | 52.526 | 1.00 | 9.02 | B |
| ATOM | 4935 | CH2 | TRP | 234 | 37.362 | 8.643 | 53.725 | 1.00 | 9.59 | B |
| ATOM | 4936 | C | TRP | 234 | 38.479 | 1.477 | 53.577 | 1.00 | 5.91 | B |
| ATOM | 4937 | O | TRP | 234 | 37.683 | 0.625 | 53.201 | 1.00 | 6.53 | B |
| ATOM | 4938 | N | PRO | 235 | 38.967 | 1.498 | 54.812 | 1.00 | 5.34 | B |
| ATOM | 4939 | CD | PRO | 235 | 39.774 | 2.589 | 55.378 | 1.00 | 5.23 | B |
| ATOM | 4940 | CA | PRO | 235 | 38.652 | 0.476 | 55.807 | 1.00 | 7.43 | B |
| ATOM | 4941 | CB | PRO | 235 | 39.614 | 0.817 | 56.949 | 1.00 | 6.35 | B |
| ATOM | 4942 | CG | PRO | 235 | 39.725 | 2.305 | 56.855 | 1.00 | 7.88 | B |
| ATOM | 4943 | C | PRO | 235 | 37.179 | 0.431 | 56.237 | 1.00 | 8.14 | B |
| ATOM | 4944 | O | PRO | 235 | 36.496 | 1.467 | 56.287 | 1.00 | 9.63 | B |
| ATOM | 4945 | N | SER | 236 | 36.656 | -0.777 | 56.453 | 1.00 | 8.84 | B |
| ATOM | 4947 | CA | SER | 236 | 35.261 | -0.909 | 56.881 | 1.00 | 8.74 | B |
| ATOM | 4948 | CB | SER | 236 | 34.597 | -2.063 | 56.185 | 1.00 | 8.56 | B |
| ATOM | 4949 | OG | SER | 236 | 35.240 | -3.253 | 56.560 | 1.00 | 14.10 | B |
| ATOM | 4951 | C | SER | 236 | 35.055 | -1.026 | 58.395 | 1.00 | 7.85 | B |
| ATOM | 4952 | O | SER | 236 | 33.922 | -1.059 | 58.884 | 1.00 | 5.87 | B |
| ATOM | 4953 | N | ALA | 237 | 36.150 | -1.002 | 59.136 | 1.00 | 9.07 | B |
| ATOM | 4955 | CA | ALA | 237 | 36.059 | -1.081 | 60.574 | 1.00 | 10.13 | B |
| ATOM | 4956 | CB | ALA | 237 | 35.578 | -2.425 | 60.962 | 1.00 | 11.11 | B |
| ATOM | 4957 | C | ALA | 237 | 37.393 | -0.855 | 61.202 | 1.00 | 11.14 | B |
| ATOM | 4958 | O | ALA | 237 | 38.397 | -0.839 | 60.513 | 1.00 | 10.71 | B |
| ATOM | 4959 | N | GLY | 238 | 37.380 | -0.615 | 62.517 | 1.00 | 12.67 | B |
| ATOM | 4961 | CA | GLY | 238 | 38.608 | -0.483 | 63.282 | 1.00 | 12.75 | B |
| ATOM | 4962 | C | GLY | 238 | 39.237 | 0.859 | 63.523 | 1.00 | 14.64 | B |
| ATOM | 4963 | O | GLY | 238 | 40.317 | 0.916 | 64.102 | 1.00 | 15.96 | B |
| ATOM | 4964 | N | GLY | 239 | 38.586 | 1.955 | 63.152 | 1.00 | 15.17 | B |
| ATOM | 4966 | CA | GLY | 239 | 39.251 | 3.234 | 63.351 | 1.00 | 14.85 | B |
| ATOM | 4967 | C | GLY | 239 | 38.369 | 4.389 | 62.961 | 1.00 | 14.39 | B |
| ATOM | 4968 | O | GLY | 239 | 37.194 | 4.184 | 62.632 | 1.00 | 15.72 | B |
| ATOM | 4969 | N | PHE | 240 | 38.942 | 5.586 | 63.009 | 1.00 | 13.84 | B |
| ATOM | 4971 | CA | PHE | 240 | 38.257 | 6.816 | 62.684 | 1.00 | 14.47 | B |
| ATOM | 4972 | CB | PHE | 240 | 39.233 | 7.984 | 62.925 | 1.00 | 15.70 | B |
| ATOM | 4973 | CG | PHE | 240 | 38.801 | 9.306 | 62.323 | 1.00 | 18.60 | B |
| ATOM | 4974 | CD1 | PHE | 240 | 37.771 | 10.046 | 62.890 | 1.00 | 18.79 | B |
| ATOM | 4975 | CD2 | PHE | 240 | 39.390 | 9.773 | 61.129 | 1.00 | 19.46 | B |
| ATOM | 4976 | CE1 | PHE | 240 | 37.315 | 11.225 | 62.279 | 1.00 | 18.48 | B |
| ATOM | 4977 | CE2 | PHE | 240 | 38.954 | 10.942 | 60.514 | 1.00 | 18.80 | B |
| ATOM | 4978 | CZ | PHE | 240 | 37.905 | 11.669 | 61.093 | 1.00 | 18.97 | B |
| ATOM | 4979 | C | PHE | 240 | 37.741 | 6.762 | 61.225 | 1.00 | 14.64 | B |
| ATOM | 4980 | O | PHE | 240 | 38.457 | 6.340 | 60.303 | 1.00 | 14.53 | B |
| ATOM | 4981 | N | ALA | 241 | 36.452 | 7.076 | 61.078 | 1.00 | 14.23 | B |
| ATOM | 4983 | CA | ALA | 241 | 35.737 | 7.149 | 59.807 | 1.00 | 12.80 | B |
| ATOM | 4984 | CB | ALA | 241 | 36.386 | 8.232 | 58.925 | 1.00 | 13.25 | B |
| ATOM | 4985 | C | ALA | 241 | 35.652 | 5.820 | 59.065 | 1.00 | 12.76 | B |
| ATOM | 4986 | O | ALA | 241 | 35.214 | 5.748 | 57.906 | 1.00 | 12.35 | B |
| ATOM | 4987 | N | ALA | 242 | 36.024 | 4.754 | 59.749 | 1.00 | 12.87 | B |
| ATOM | 4989 | CA | ALA | 242 | 36.023 | 3.448 | 59.122 | 1.00 | 13.12 | B |
| ATOM | 4990 | CB | ALA | 242 | 37.156 | 2.579 | 59.727 | 1.00 | 12.92 | B |
| ATOM | 4991 | C | ALA | 242 | 34.688 | 2.786 | 59.310 | 1.00 | 12.47 | B |
| ATOM | 4992 | O | ALA | 242 | 34.355 | 2.425 | 60.426 | 1.00 | 12.75 | B |
| ATOM | 4993 | N | SER | 243 | 33.911 | 2.641 | 58.249 | 1.00 | 11.59 | B |
| ATOM | 4995 | CA | SER | 243 | 32.626 | 1.971 | 58.376 | 1.00 | 12.25 | B |
| ATOM | 4996 | CB | SER | 243 | 31.514 | 2.942 | 58.725 | 1.00 | 11.25 | B |
| ATOM | 4997 | OG | SER | 243 | 31.595 | 4.119 | 57.953 | 1.00 | 12.72 | B |
| ATOM | 4999 | C | SER | 243 | 32.316 | 1.330 | 57.075 | 1.00 | 14.05 | B |
| ATOM | 5000 | O | SER | 243 | 32.942 | 1.664 | 56.071 | 1.00 | 15.08 | B |
| ATOM | 5001 | N | ALA | 244 | 31.328 | 0.439 | 57.069 | 1.00 | 14.87 | B |
| ATOM | 5003 | CA | ALA | 244 | 30.917 | -0.252 | 55.843 | 1.00 | 15.88 | B |
| ATOM | 5004 | CB | ALA | 244 | 29.830 | -1.295 | 56.153 | 1.00 | 14.58 | B |
| ATOM | 5005 | C | ALA | 244 | 30.390 | 0.741 | 54.818 | 1.00 | 15.41 | B |
| ATOM | 5006 | O | ALA | 244 | 30.634 | 0.619 | 53.626 | 1.00 | 15.61 | B |

- 110 -

– 111 –

| ATOM | 5007 | N | GLY | 245 | 29.603 | 1.683 | 55.314 | 1.00 | 16.35 | B | ATOM | 5061 | CE1 | TYR | 250 | 38.626 | 7.312 | 46.394 | 1.00 | 8.01 | B |
|---|---|---|---|---|---|---|---|---|---|---|---|---|---|---|---|---|---|---|---|---|---|
| ATOM | 5009 | CA | GLY | 245 | 29.000 | 2.717 | 54.489 | 1.00 | 16.20 | B | ATOM | 5062 | CD2 | TYR | 250 | 37.822 | 4.641 | 48.520 | 1.00 | 8.25 | B |
| ATOM | 5010 | C | GLY | 245 | 30.024 | 3.654 | 53.900 | 1.00 | 15.83 | B | ATOM | 5063 | CE2 | TYR | 250 | 38.986 | 4.997 | 47.808 | 1.00 | 8.97 | B |
| ATOM | 5011 | O | GLY | 245 | 29.931 | 4.013 | 52.743 | 1.00 | 16.39 | B | ATOM | 5064 | CZ | TYR | 250 | 39.370 | 6.341 | 47.751 | 1.00 | 8.46 | B |
| ATOM | 5012 | N | ASN | 246 | 30.988 | 4.077 | 54.698 | 1.00 | 15.38 | B | ATOM | 5065 | OH | TYR | 250 | 40.500 | 6.723 | 47.060 | 1.00 | 7.32 | B |
| ATOM | 5014 | CA | ASN | 246 | 32.015 | 4.919 | 54.167 | 1.00 | 15.28 | B | ATOM | 5067 | C | TYR | 250 | 34.937 | 4.536 | 47.453 | 1.00 | 9.83 | B |
| ATOM | 5015 | CB | ASN | 246 | 32.885 | 5.462 | 55.290 | 1.00 | 16.34 | B | ATOM | 5068 | O | TYR | 250 | 35.272 | 4.981 | 46.337 | 1.00 | 8.61 | B |
| ATOM | 5016 | CG | ASN | 246 | 32.221 | 6.609 | 56.040 | 1.00 | 17.82 | B | ATOM | 5069 | N | ASN | 251 | 34.807 | 3.237 | 47.691 | 1.00 | 9.54 | B |
| ATOM | 5017 | OD1 | ASN | 246 | 31.274 | 7.237 | 55.555 | 1.00 | 18.79 | B | ATOM | 5071 | CA | ASN | 251 | 35.128 | 2.269 | 46.666 | 1.00 | 9.49 | B |
| ATOM | 5018 | ND2 | ASN | 246 | 32.726 | 6.895 | 57.227 | 1.00 | 18.61 | B | ATOM | 5072 | CB | ASN | 251 | 35.288 | 0.880 | 47.269 | 1.00 | 7.76 | B |
| ATOM | 5021 | C | ASN | 246 | 32.829 | 4.118 | 53.152 | 1.00 | 14.64 | B | ATOM | 5073 | CG | ASN | 251 | 36.546 | 0.759 | 48.030 | 1.00 | 5.97 | B |
| ATOM | 5022 | O | ASN | 246 | 33.076 | 4.603 | 52.067 | 1.00 | 16.18 | B | ATOM | 5074 | OD1 | ASN | 251 | 37.511 | 1.459 | 47.737 | 1.00 | 5.58 | B |
| ATOM | 5023 | N | ALA | 247 | 33.237 | 2.896 | 53.494 | 1.00 | 14.37 | B | ATOM | 5075 | ND2 | ASN | 251 | 36.571 | -0.124 | 49.006 | 1.00 | 3.61 | B |
| ATOM | 5025 | CA | ALA | 247 | 33.991 | 2.026 | 52.584 | 1.00 | 13.67 | B | ATOM | 5078 | C | ASN | 251 | 34.215 | 2.287 | 45.474 | 1.00 | 9.97 | B |
| ATOM | 5026 | CB | ALA | 247 | 34.285 | 0.667 | 53.243 | 1.00 | 12.52 | B | ATOM | 5079 | O | ASN | 251 | 34.693 | 2.233 | 44.337 | 1.00 | 10.19 | B |
| ATOM | 5027 | C | ALA | 247 | 33.227 | 1.807 | 51.267 | 1.00 | 14.39 | B | ATOM | 5080 | N | GLN | 252 | 32.906 | 2.377 | 45.712 | 1.00 | 10.50 | B |
| ATOM | 5028 | O | ALA | 247 | 33.840 | 1.748 | 50.200 | 1.00 | 14.97 | B | ATOM | 5082 | CA | GLN | 252 | 31.978 | 2.451 | 44.592 | 1.00 | 10.28 | B |
| ATOM | 5029 | N | ARG | 248 | 31.903 | 1.634 | 51.328 | 1.00 | 14.31 | B | ATOM | 5083 | CB | GLN | 252 | 30.520 | 2.354 | 45.041 | 1.00 | 9.39 | B |
| ATOM | 5031 | CA | ARG | 248 | 31.118 | 1.439 | 50.089 | 1.00 | 13.66 | B | ATOM | 5084 | CG | GLN | 252 | 29.568 | 2.289 | 43.882 | 1.00 | 9.01 | B |
| ATOM | 5032 | CB | ARG | 248 | 29.674 | 1.039 | 50.427 | 1.00 | 14.76 | B | ATOM | 5085 | CD | GLN | 252 | 29.829 | 1.091 | 43.010 | 1.00 | 10.66 | B |
| ATOM | 5033 | CG | ARG | 248 | 28.836 | 0.803 | 49.183 | 1.00 | 17.34 | B | ATOM | 5086 | OE1 | GLN | 252 | 29.710 | -0.026 | 43.475 | 1.00 | 13.67 | B |
| ATOM | 5034 | CD | ARG | 248 | 27.345 | 0.669 | 49.514 | 1.00 | 21.01 | B | ATOM | 5087 | NE2 | GLN | 252 | 30.224 | 1.305 | 41.760 | 1.00 | 10.57 | B |
| ATOM | 5035 | NE | ARG | 248 | 26.428 | 1.261 | 48.504 | 1.00 | 22.71 | B | ATOM | 5090 | C | GLN | 252 | 32.255 | 3.786 | 43.883 | 1.00 | 10.56 | B |
| ATOM | 5037 | CZ | ARG | 248 | 26.421 | 0.983 | 47.203 | 1.00 | 22.56 | B | ATOM | 5091 | O | GLN | 252 | 32.266 | 3.843 | 42.655 | 1.00 | 12.18 | B |
| ATOM | 5038 | NH1 | ARG | 248 | 27.275 | 0.116 | 46.682 | 1.00 | 22.78 | B | ATOM | 5092 | N | GLY | 253 | 32.577 | 4.823 | 44.657 | 1.00 | 9.53 | B |
| ATOM | 5041 | NH2 | ARG | 248 | 25.535 | 1.578 | 46.416 | 1.00 | 22.78 | B | ATOM | 5094 | CA | GLY | 253 | 32.869 | 6.130 | 44.085 | 1.00 | 8.83 | B |
| ATOM | 5044 | C | ARG | 248 | 31.141 | 2.739 | 49.221 | 1.00 | 13.48 | B | ATOM | 5095 | C | GLY | 253 | 34.096 | 6.134 | 43.214 | 1.00 | 8.29 | B |
| ATOM | 5045 | O | ARG | 248 | 31.419 | 2.721 | 48.008 | 1.00 | 11.93 | B | ATOM | 5096 | O | GLY | 253 | 34.117 | 6.686 | 42.146 | 1.00 | 7.33 | B |
| ATOM | 5046 | N | THR | 249 | 30.903 | 3.865 | 49.876 | 1.00 | 11.84 | B | ATOM | 5097 | N | LEU | 254 | 35.123 | 5.449 | 43.683 | 1.00 | 9.78 | B |
| ATOM | 5048 | CA | THR | 249 | 30.902 | 5.161 | 49.223 | 1.00 | 12.39 | B | ATOM | 5099 | CA | LEU | 254 | 36.385 | 5.344 | 42.975 | 1.00 | 8.35 | B |
| ATOM | 5049 | CB | THR | 249 | 30.684 | 6.278 | 50.251 | 1.00 | 12.14 | B | ATOM | 5100 | CB | LEU | 254 | 37.355 | 4.503 | 43.837 | 1.00 | 7.60 | B |
| ATOM | 5050 | OG1 | THR | 249 | 29.520 | 5.972 | 51.022 | 1.00 | 14.42 | B | ATOM | 5101 | CG | LEU | 254 | 38.773 | 4.311 | 43.324 | 1.00 | 6.06 | B |
| ATOM | 5052 | CG2 | THR | 249 | 30.452 | 7.591 | 49.553 | 1.00 | 12.42 | B | ATOM | 5102 | CD1 | LEU | 254 | 39.458 | 5.706 | 43.153 | 1.00 | 6.35 | B |
| ATOM | 5053 | C | THR | 249 | 32.223 | 5.429 | 48.520 | 1.00 | 11.77 | B | ATOM | 5103 | CD2 | LEU | 254 | 39.529 | 3.429 | 44.257 | 1.00 | 5.68 | B |
| ATOM | 5054 | O | THR | 249 | 32.255 | 5.805 | 47.353 | 1.00 | 12.19 | B | ATOM | 5104 | C | LEU | 254 | 36.122 | 4.682 | 41.611 | 1.00 | 7.36 | B |
| ATOM | 5055 | N | TYR | 250 | 33.318 | 5.246 | 49.240 | 1.00 | 10.87 | B | ATOM | 5105 | O | LEU | 254 | 36.505 | 5.211 | 40.574 | 1.00 | 6.40 | B |
| ATOM | 5057 | CA | TYR | 250 | 34.627 | 5.469 | 48.654 | 1.00 | 10.08 | B | ATOM | 5106 | N | ILE | 255 | 35.423 | 3.557 | 41.636 | 1.00 | 7.29 | B |
| ATOM | 5058 | CB | TYR | 250 | 35.713 | 5.309 | 49.720 | 1.00 | 8.95 | B | ATOM | 5108 | CA | ILE | 255 | 35.096 | 2.807 | 40.439 | 1.00 | 8.56 | B |
| ATOM | 5059 | CG | TYR | 250 | 37.061 | 5.625 | 49.162 | 1.00 | 9.20 | B | ATOM | 5109 | CB | ILE | 255 | 34.216 | 1.596 | 40.790 | 1.00 | 8.59 | B |
| ATOM | 5060 | CD1 | TYR | 250 | 37.498 | 6.960 | 49.097 | 1.00 | 7.95 | B | ATOM | 5110 | CG2 | ILE | 255 | 33.703 | 0.905 | 39.521 | 1.00 | 7.51 | B |

- 112 -

| | | | | | | | | |
|---|---|---|---|---|---|---|---|---|
| ATOM | 5111 | CG1 | ILE | 255 | 34.976 | 0.623 | 41.679 | 1.00 10.31 B |
| ATOM | 5112 | CD1 | ILE | 255 | 34.124 | -0.574 | 42.171 | 1.00 10.64 B |
| ATOM | 5113 | C | ILE | 255 | 34.337 | 3.657 | 39.384 | 1.00 9.82 B |
| ATOM | 5114 | O | ILE | 255 | 34.676 | 3.621 | 38.197 | 1.00 9.76 B |
| ATOM | 5115 | N | ASN | 256 | 33.317 | 4.432 | 39.828 | 1.00 9.01 B |
| ATOM | 5117 | CA | ASN | 256 | 32.512 | 5.229 | 38.922 | 1.00 8.66 B |
| ATOM | 5118 | CB | ASN | 256 | 31.256 | 5.683 | 39.597 | 1.00 11.03 B |
| ATOM | 5119 | CG | ASN | 256 | 30.348 | 4.533 | 40.036 | 1.00 11.81 B |
| ATOM | 5120 | OD1 | ASN | 256 | 30.328 | 3.435 | 39.464 | 1.00 11.07 B |
| ATOM | 5121 | ND2 | ASN | 256 | 29.577 | 4.805 | 41.073 | 1.00 13.34 B |
| ATOM | 5124 | C | ASN | 256 | 33.251 | 6.481 | 38.450 | 1.00 8.69 B |
| ATOM | 5125 | O | ASN | 256 | 32.811 | 7.105 | 37.475 | 1.00 10.33 B |
| ATOM | 5126 | N | HIS | 257 | 34.295 | 6.872 | 39.178 | 1.00 7.14 B |
| ATOM | 5128 | CA | HIS | 257 | 35.122 | 8.070 | 38.932 | 1.00 5.97 B |
| ATOM | 5129 | CB | HIS | 257 | 35.664 | 8.530 | 40.274 | 1.00 4.30 B |
| ATOM | 5130 | CG1 | HIS | 257 | 36.459 | 9.795 | 40.211 | 1.00 6.68 B |
| ATOM | 5131 | CD2 | HIS | 257 | 37.802 | 10.006 | 40.211 | 1.00 5.99 B |
| ATOM | 5132 | ND1 | HIS | 257 | 35.869 | 11.042 | 40.320 | 1.00 6.28 B |
| ATOM | 5134 | CE1 | HIS | 257 | 36.817 | 11.958 | 40.419 | 1.00 7.19 B |
| ATOM | 5135 | NE2 | HIS | 257 | 37.995 | 11.356 | 40.357 | 1.00 6.32 B |
| ATOM | 5137 | C | HIS | 257 | 36.318 | 8.003 | 38.003 | 1.00 5.03 B |
| ATOM | 5138 | O | HIS | 257 | 36.518 | 8.866 | 37.140 | 1.00 3.78 B |
| ATOM | 5139 | N | VAL | 258 | 37.143 | 6.984 | 38.207 | 1.00 6.29 B |
| ATOM | 5141 | CA | VAL | 258 | 38.399 | 6.830 | 37.468 | 1.00 6.43 B |
| ATOM | 5142 | CB | VAL | 258 | 39.235 | 5.592 | 37.988 | 1.00 5.37 B |
| ATOM | 5143 | CG1 | VAL | 258 | 39.509 | 5.730 | 39.443 | 1.00 6.70 B |
| ATOM | 5144 | CG2 | VAL | 258 | 38.527 | 4.298 | 37.765 | 1.00 5.09 B |
| ATOM | 5145 | C | VAL | 258 | 38.425 | 6.892 | 35.928 | 1.00 7.71 B |
| ATOM | 5146 | O | VAL | 258 | 39.474 | 7.227 | 35.347 | 1.00 9.53 B |
| ATOM | 5147 | N | GLY | 259 | 37.301 | 6.633 | 35.262 | 1.00 7.19 B |
| ATOM | 5149 | CA | GLY | 259 | 37.300 | 6.685 | 33.812 | 1.00 5.99 B |
| ATOM | 5150 | C | GLY | 259 | 37.362 | 8.089 | 33.232 | 1.00 7.92 B |
| ATOM | 5151 | O | GLY | 259 | 37.694 | 8.253 | 32.046 | 1.00 8.88 B |
| ATOM | 5152 | N | GLY | 260 | 37.004 | 9.086 | 34.052 | 1.00 8.03 B |
| ATOM | 5154 | CA | GLY | 260 | 37.031 | 10.481 | 33.647 | 1.00 7.32 B |
| ATOM | 5155 | C | GLY | 260 | 38.380 | 11.183 | 33.831 | 1.00 8.24 B |
| ATOM | 5156 | O | GLY | 260 | 38.551 | 12.324 | 33.403 | 1.00 8.06 B |
| ATOM | 5157 | N | GLY | 261 | 39.359 | 10.524 | 34.436 | 1.00 8.44 B |
| ATOM | 5159 | CA | GLY | 261 | 40.662 | 11.170 | 34.605 | 1.00 9.03 B |
| ATOM | 5160 | C | GLY | 261 | 40.654 | 12.213 | 35.716 | 1.00 9.51 B |
| ATOM | 5161 | O | GLY | 261 | 39.802 | 12.171 | 36.622 | 1.00 10.76 B |
| ATOM | 5162 | N | THR | 262 | 41.581 | 13.157 | 35.651 | 1.00 9.19 B |
| ATOM | 5164 | CA | THR | 262 | 41.673 | 14.236 | 36.631 | 1.00 8.58 B |
| ATOM | 5165 | CB | THR | 262 | 42.879 | 14.030 | 37.584 | 1.00 9.94 B |
| ATOM | 5166 | OG1 | THR | 262 | 44.122 | 14.188 | 36.866 | 1.00 11.05 B |
| ATOM | 5168 | CG2 | THR | 262 | 42.808 | 12.664 | 38.257 | 1.00 5.85 B |
| ATOM | 5169 | C | THR | 262 | 41.853 | 15.544 | 35.861 | 1.00 8.31 B |
| ATOM | 5170 | O | THR | 262 | 42.150 | 15.530 | 34.695 | 1.00 6.13 B |
| ATOM | 5171 | N | PRO | 263 | 41.668 | 16.687 | 36.511 | 1.00 9.73 B |
| ATOM | 5172 | CD | PRO | 263 | 41.259 | 16.837 | 37.911 | 1.00 9.71 B |
| ATOM | 5173 | CA | PRO | 263 | 41.809 | 18.007 | 35.890 | 1.00 10.54 B |
| ATOM | 5174 | CB | PRO | 263 | 41.768 | 18.947 | 37.095 | 1.00 9.77 B |
| ATOM | 5175 | CG | PRO | 263 | 40.838 | 18.301 | 37.949 | 1.00 9.12 B |
| ATOM | 5176 | C | PRO | 263 | 43.120 | 18.189 | 35.137 | 1.00 12.10 B |
| ATOM | 5177 | O | PRO | 263 | 43.211 | 19.026 | 34.236 | 1.00 12.16 B |
| ATOM | 5178 | N | LYS | 264 | 44.157 | 17.445 | 35.516 | 1.00 12.87 B |
| ATOM | 5180 | CA | LYS | 264 | 45.422 | 17.584 | 34.809 | 1.00 13.24 B |
| ATOM | 5181 | CB | LYS | 264 | 46.621 | 17.360 | 35.719 | 1.00 13.72 B |
| ATOM | 5182 | CG | LYS | 264 | 47.226 | 18.692 | 36.106 | 1.00 14.18 B |
| ATOM | 5183 | CD | LYS | 264 | 48.704 | 18.649 | 35.247 | 1.00 15.04 B |
| ATOM | 5184 | CE | LYS | 264 | 49.192 | 19.763 | 35.293 | 1.00 15.19 B |
| ATOM | 5185 | NZ | LYS | 264 | 50.677 | 19.829 | 33.577 | 1.00 16.33 B |
| ATOM | 5189 | C | LYS | 264 | 45.581 | 16.745 | 33.590 | 1.00 13.57 B |
| ATOM | 5190 | O | LYS | 264 | 46.301 | 17.124 | 32.651 | 1.00 13.77 B |
| ATOM | 5191 | N | LYS | 265 | 44.941 | 15.590 | 33.590 | 1.00 14.38 B |
| ATOM | 5193 | CA | LYS | 265 | 45.020 | 14.647 | 32.503 | 1.00 14.85 B |
| ATOM | 5194 | CB | LYS | 265 | 46.166 | 13.671 | 32.765 | 1.00 16.02 B |
| ATOM | 5195 | CG | LYS | 265 | 46.639 | 12.939 | 31.518 | 1.00 19.06 B |
| ATOM | 5196 | CD | LYS | 265 | 46.928 | 11.482 | 31.806 | 1.00 22.62 B |
| ATOM | 5197 | CE | LYS | 265 | 48.338 | 11.088 | 31.399 | 1.00 25.02 B |
| ATOM | 5198 | NZ | LYS | 265 | 49.362 | 11.889 | 32.149 | 1.00 27.52 B |
| ATOM | 5202 | C | LYS | 265 | 43.679 | 13.902 | 32.378 | 1.00 14.37 B |
| ATOM | 5203 | O | LYS | 265 | 43.332 | 13.024 | 33.187 | 1.00 14.62 B |
| ATOM | 5204 | N | ARG | 266 | 42.888 | 14.307 | 31.396 | 1.00 13.32 B |
| ATOM | 5206 | CA | ARG | 266 | 41.609 | 13.658 | 31.173 | 1.00 13.40 B |
| ATOM | 5207 | CB | ARG | 266 | 40.602 | 14.656 | 30.632 | 1.00 12.11 B |
| ATOM | 5208 | CG | ARG | 266 | 40.346 | 15.758 | 31.642 | 1.00 8.70 B |
| ATOM | 5209 | CD | ARG | 266 | 39.320 | 15.302 | 32.631 | 1.00 6.64 B |
| ATOM | 5210 | NE | ARG | 266 | 38.996 | 16.393 | 33.518 | 1.00 6.11 B |
| ATOM | 5212 | CZ | ARG | 266 | 38.635 | 16.228 | 34.779 | 1.00 8.90 B |

- 113 -

| ATOM | 5213 | NH1 | ARG | 266 | 38.540 | 14.999 | 35.298 | 1.00 | 9.78 | B |
|------|------|-----|-----|-----|--------|--------|--------|------|------|---|
| ATOM | 5216 | NH2 | ARG | 266 | 38.451 | 17.291 | 35.555 | 1.00 | 7.17 | B |
| ATOM | 5219 | C   | ARG | 266 | 41.697 | 12.412 | 30.289 | 1.00 | 13.31 | B |
| ATOM | 5220 | O   | ARG | 266 | 41.416 | 12.434 | 29.100 | 1.00 | 13.01 | B |
| ATOM | 5221 | N   | GLU | 267 | 42.191 | 11.354 | 30.907 | 1.00 | 14.31 | B |
| ATOM | 5223 | CA  | GLU | 267 | 42.324 | 10.045 | 30.305 | 1.00 | 14.26 | B |
| ATOM | 5224 | CB  | GLU | 267 | 43.773 | 9.826  | 29.876 | 1.00 | 17.09 | B |
| ATOM | 5225 | CG  | GLU | 267 | 44.274 | 10.829 | 28.864 | 1.00 | 20.87 | B |
| ATOM | 5226 | CD  | GLU | 267 | 45.569 | 10.366 | 28.208 | 1.00 | 24.45 | B |
| ATOM | 5227 | OE1 | GLU | 267 | 45.692 | 10.545 | 26.961 | 1.00 | 26.51 | B |
| ATOM | 5228 | OE2 | GLU | 267 | 46.440 | 9.795  | 28.927 | 1.00 | 25.07 | B |
| ATOM | 5229 | C   | GLU | 267 | 41.944 | 9.050  | 31.426 | 1.00 | 12.13 | B |
| ATOM | 5230 | O   | GLU | 267 | 42.086 | 9.344  | 32.626 | 1.00 | 10.00 | B |
| ATOM | 5231 | N   | ALA | 268 | 41.419 | 7.898  | 31.043 | 1.00 | 10.50 | B |
| ATOM | 5233 | CA  | ALA | 268 | 41.046 | 6.892  | 32.033 | 1.00 | 9.97 | B |
| ATOM | 5234 | CB  | ALA | 268 | 40.516 | 5.674  | 31.364 | 1.00 | 6.52 | B |
| ATOM | 5235 | C   | ALA | 268 | 42.302 | 6.548  | 32.827 | 1.00 | 8.75 | B |
| ATOM | 5236 | O   | ALA | 268 | 43.343 | 6.253  | 32.220 | 1.00 | 8.96 | B |
| ATOM | 5237 | N   | LEU | 269 | 42.223 | 6.649  | 34.158 | 1.00 | 8.23 | B |
| ATOM | 5239 | CA  | LEU | 269 | 43.371 | 6.353  | 35.050 | 1.00 | 7.74 | B |
| ATOM | 5240 | CB  | LEU | 269 | 43.358 | 7.290  | 36.238 | 1.00 | 6.05 | B |
| ATOM | 5241 | CG  | LEU | 269 | 44.444 | 7.178  | 37.298 | 1.00 | 8.48 | B |
| ATOM | 5242 | CD1 | LEU | 269 | 45.706 | 7.902  | 36.895 | 1.00 | 8.92 | B |
| ATOM | 5243 | CD2 | LEU | 269 | 43.916 | 7.809  | 38.569 | 1.00 | 9.09 | B |
| ATOM | 5244 | C   | LEU | 269 | 43.376 | 4.891  | 35.538 | 1.00 | 7.82 | B |
| ATOM | 5245 | O   | LEU | 269 | 42.223 | 4.431  | 36.155 | 1.00 | 8.01 | B |
| ATOM | 5246 | N   | GLU | 270 | 44.450 | 4.165  | 35.259 | 1.00 | 7.79 | B |
| ATOM | 5248 | CA  | GLU | 270 | 44.540 | 2.759  | 35.668 | 1.00 | 7.76 | B |
| ATOM | 5249 | CB  | GLU | 270 | 45.819 | 2.113  | 35.110 | 1.00 | 7.96 | B |
| ATOM | 5250 | CG  | GLU | 270 | 45.761 | 0.580  | 35.117 | 1.00 | 9.82 | B |
| ATOM | 5251 | CD  | GLU | 270 | 46.883 | -0.121 | 34.331 | 1.00 | 10.53 | B |
| ATOM | 5252 | OE1 | GLU | 270 | 47.451 | 0.481  | 33.385 | 1.00 | 11.48 | B |
| ATOM | 5253 | OE2 | GLU | 270 | 47.173 | -1.298 | 34.665 | 1.00 | 10.19 | B |
| ATOM | 5254 | C   | GLU | 270 | 44.516 | 2.734  | 37.177 | 1.00 | 6.34 | B |
| ATOM | 5255 | O   | GLU | 270 | 45.362 | 3.330  | 37.811 | 1.00 | 7.18 | B |
| ATOM | 5256 | N   | THR | 271 | 43.603 | 1.971  | 37.743 | 1.00 | 7.30 | B |
| ATOM | 5258 | CA  | THR | 271 | 43.444 | 1.916  | 39.181 | 1.00 | 7.81 | B |
| ATOM | 5259 | CB  | THR | 271 | 42.356 | 2.922  | 39.621 | 1.00 | 8.33 | B |
| ATOM | 5260 | OG1 | THR | 271 | 42.578 | 4.182  | 38.954 | 1.00 | 8.72 | B |
| ATOM | 5262 | CG2 | THR | 271 | 42.408 | 3.131  | 41.156 | 1.00 | 7.80 | B |
| ATOM | 5263 | C   | THR | 271 | 43.186 | 0.516  | 39.802 | 1.00 | 8.03 | B |
| ATOM | 5264 | O   | THR | 271 | 42.484 | -0.325 | 39.237 | 1.00 | 7.64 | B |
| ATOM | 5265 | N   | TYR | 272 | 43.837 | 0.283  | 40.944 | 1.00 | 7.59 | B |
| ATOM | 5267 | CA  | TYR | 272 | 43.743 | -0.949 | 41.688 | 1.00 | 6.37 | B |
| ATOM | 5268 | CB  | TYR | 272 | 45.103 | -1.642 | 41.725 | 1.00 | 7.07 | B |
| ATOM | 5269 | CG  | TYR | 272 | 45.596 | -2.078 | 40.383 | 1.00 | 8.93 | B |
| ATOM | 5270 | CD1 | TYR | 272 | 46.106 | -1.167 | 39.460 | 1.00 | 9.75 | B |
| ATOM | 5271 | CE1 | TYR | 272 | 46.525 | -1.579 | 38.189 | 1.00 | 10.80 | B |
| ATOM | 5272 | CD2 | TYR | 272 | 45.527 | -3.409 | 40.009 | 1.00 | 11.78 | B |
| ATOM | 5273 | CE2 | TYR | 272 | 45.962 | -3.838 | 38.723 | 1.00 | 12.79 | B |
| ATOM | 5274 | CZ  | TYR | 272 | 46.446 | -2.918 | 37.829 | 1.00 | 11.42 | B |
| ATOM | 5275 | OH  | TYR | 272 | 46.783 | -3.361 | 36.570 | 1.00 | 12.74 | B |
| ATOM | 5277 | C   | TYR | 272 | 43.306 | -0.632 | 43.115 | 1.00 | 5.84 | B |
| ATOM | 5278 | O   | TYR | 272 | 44.024 | 0.061  | 43.851 | 1.00 | 4.80 | B |
| ATOM | 5279 | N   | ILE | 273 | 42.198 | -1.266 | 43.517 | 1.00 | 5.00 | B |
| ATOM | 5281 | CA  | ILE | 273 | 41.581 | -1.124 | 44.802 | 1.00 | 5.08 | B |
| ATOM | 5282 | CB  | ILE | 273 | 40.098 | -1.573 | 44.837 | 1.00 | 4.16 | B |
| ATOM | 5283 | CG2 | ILE | 273 | 39.546 | -1.530 | 46.154 | 1.00 | 3.38 | B |
| ATOM | 5284 | CG1 | ILE | 273 | 39.275 | -0.680 | 43.866 | 1.00 | 5.16 | B |
| ATOM | 5285 | CD1 | ILE | 273 | 37.859 | -1.234 | 43.484 | 1.00 | 5.54 | B |
| ATOM | 5286 | C   | ILE | 273 | 42.285 | -2.025 | 45.857 | 1.00 | 5.28 | B |
| ATOM | 5287 | O   | ILE | 273 | 42.461 | -3.213 | 45.590 | 1.00 | 7.06 | B |
| ATOM | 5288 | N   | PHE | 274 | 42.720 | -1.466 | 46.980 | 1.00 | 3.99 | B |
| ATOM | 5290 | CA  | PHE | 274 | 43.350 | -2.244 | 48.035 | 1.00 | 5.22 | B |
| ATOM | 5291 | CB  | PHE | 274 | 44.443 | -1.442 | 48.777 | 1.00 | 4.50 | B |
| ATOM | 5292 | CG  | PHE | 274 | 45.274 | -2.307 | 49.686 | 1.00 | 6.58 | B |
| ATOM | 5293 | CD1 | PHE | 274 | 46.208 | -3.193 | 49.145 | 1.00 | 4.95 | B |
| ATOM | 5294 | CD2 | PHE | 274 | 44.996 | -2.380 | 51.069 | 1.00 | 7.47 | B |
| ATOM | 5295 | CE1 | PHE | 274 | 46.838 | -3.342 | 47.879 | 1.00 | 6.41 | B |
| ATOM | 5296 | CE2 | PHE | 274 | 45.632 | -4.230 | 51.297 | 1.00 | 6.92 | B |
| ATOM | 5297 | CZ  | PHE | 274 | 46.560 | -4.140 | 49.930 | 1.00 | 6.53 | B |
| ATOM | 5298 | C   | PHE | 274 | 41.689 | -1.645 | 49.581 | 1.00 | 5.25 | B |
| ATOM | 5299 | O   | PHE | 275 | 42.220 | -2.583 | 48.990 | 1.00 | 5.87 | B |
| ATOM | 5301 | CA  | ALA | 275 | 42.299 | -5.123 | 48.595 | 1.00 | 8.39 | B |
| ATOM | 5302 | CB  | ALA | 275 | 43.303 | -5.792 | 49.482 | 1.00 | 7.22 | B |
| ATOM | 5303 | C   | ALA | 275 | 41.112 | -6.032 | 48.434 | 1.00 | 9.17 | B |
| ATOM | 5304 | O   | ALA | 275 | 39.992 | -5.681 | 48.809 | 1.00 | 9.54 | B |
| ATOM | 5305 | N   | MET | 276 | 41.817 | -3.851 | 49.175 | 1.00 | 8.19 | B |
| ATOM | 5306 | N   | MET | 276 | 41.366 | -7.240 | 47.955 | 1.00 | 10.02 | B |
| ATOM | 5308 | CA  | MET | 276 | 40.289 | -8.209 | 47.704 | 1.00 | 10.15 | B |

- 114 -

| ATOM | 5309 | CB | MET | 276 | 40.853 | -9.381 | 46.852 | 1.00 | 9.97 | B |
|---|---|---|---|---|---|---|---|---|---|---|
| ATOM | 5310 | CG | MET | 276 | 39.785 | -10.325 | 46.227 | 1.00 | 10.88 | B |
| ATOM | 5311 | SD | MET | 276 | 38.621 | -9.383 | 45.254 | 1.00 | 11.62 | B |
| ATOM | 5312 | CE | MET | 276 | 37.857 | -10.509 | 44.183 | 1.00 | 7.43 | B |
| ATOM | 5313 | C | MET | 276 | 39.558 | -8.717 | 48.944 | 1.00 | 9.54 | B |
| ATOM | 5314 | O | MET | 276 | 38.326 | -8.751 | 48.989 | 1.00 | 10.59 | B |
| ATOM | 5315 | N | PHE | 277 | 40.325 | -9.094 | 49.964 | 1.00 | 9.39 | B |
| ATOM | 5317 | CA | PHE | 277 | 39.782 | -9.654 | 51.210 | 1.00 | 9.47 | B |
| ATOM | 5318 | CB | PHE | 277 | 40.227 | -11.132 | 51.390 | 1.00 | 8.98 | B |
| ATOM | 5319 | CG | PHE | 277 | 39.893 | -12.032 | 50.237 | 1.00 | 8.52 | B |
| ATOM | 5320 | CD1 | PHE | 277 | 40.881 | -12.404 | 49.325 | 1.00 | 7.45 | B |
| ATOM | 5321 | CD2 | PHE | 277 | 38.593 | -12.495 | 50.061 | 1.00 | 8.28 | B |
| ATOM | 5322 | CE1 | PHE | 277 | 40.580 | -13.209 | 48.261 | 1.00 | 7.82 | B |
| ATOM | 5323 | CE2 | PHE | 277 | 38.272 | -13.302 | 49.002 | 1.00 | 7.09 | B |
| ATOM | 5324 | CZ | PHE | 277 | 39.260 | -13.667 | 48.088 | 1.00 | 9.24 | B |
| ATOM | 5325 | C | PHE | 277 | 40.299 | -8.935 | 52.461 | 1.00 | 8.39 | B |
| ATOM | 5326 | O | PHE | 277 | 41.314 | -8.229 | 52.432 | 1.00 | 9.37 | B |
| ATOM | 5327 | N | ASN | 278 | 39.587 | -9.142 | 53.554 | 1.00 | 10.75 | B |
| ATOM | 5329 | CA | ASN | 278 | 40.019 | -8.645 | 54.852 | 1.00 | 12.10 | B |
| ATOM | 5330 | CB | ASN | 278 | 38.870 | -8.740 | 55.850 | 1.00 | 14.48 | B |
| ATOM | 5331 | CG | ASN | 278 | 37.847 | -7.659 | 55.622 | 1.00 | 16.98 | B |
| ATOM | 5332 | OD1 | ASN | 278 | 38.204 | -6.540 | 55.267 | 1.00 | 15.38 | B |
| ATOM | 5333 | ND2 | ASN | 278 | 36.570 | -7.986 | 55.773 | 1.00 | 10.25 | B |
| ATOM | 5336 | C | ASN | 278 | 41.122 | -9.623 | 55.243 | 1.00 | 9.81 | B |
| ATOM | 5337 | O | ASN | 278 | 40.907 | -10.839 | 55.162 | 1.00 | 10.56 | B |
| ATOM | 5338 | N | GLU | 279 | 42.301 | -9.117 | 55.603 | 1.00 | 11.74 | B |
| ATOM | 5340 | CA | GLU | 279 | 43.395 | -9.974 | 55.990 | 1.00 | 12.90 | B |
| ATOM | 5341 | CB | GLU | 279 | 44.664 | -9.537 | 55.279 | 1.00 | 13.04 | B |
| ATOM | 5342 | CG | GLU | 279 | 44.671 | -9.808 | 53.771 | 1.00 | 11.35 | B |
| ATOM | 5343 | CD | GLU | 279 | 45.729 | -8.999 | 53.073 | 1.00 | 14.37 | B |
| ATOM | 5344 | OE1 | GLU | 279 | 46.889 | -9.429 | 53.067 | 1.00 | 10.73 | B |
| ATOM | 5345 | OE2 | GLU | 279 | 45.397 | -7.900 | 52.571 | 1.00 | 11.01 | B |
| ATOM | 5346 | C | GLU | 279 | 43.589 | -9.965 | 57.508 | 1.00 | 10.83 | B |
| ATOM | 5347 | O | GLU | 279 | 44.308 | -10.946 | 58.196 | 1.00 | 10.57 | B |
| ATOM | 5348 | N | ASN | 280 | 43.027 | -10.974 | 59.658 | 1.00 | 9.71 | B |
| ATOM | 5350 | CA | ASN | 280 | 43.124 | -12.049 | 60.221 | 1.00 | 7.70 | B |
| ATOM | 5351 | CB | ASN | 280 | 42.181 | -13.474 | 59.837 | 1.00 | 8.45 | B |
| ATOM | 5352 | CG | ASN | 280 | 42.596 | -13.676 | 59.221 | 1.00 | 6.11 | B |
| ATOM | 5353 | OD1 | ASN | 280 | 43.635 | -13.676 | 59.221 | 1.00 | 8.45 | B |
| ATOM | 5354 | ND2 | ASN | 280 | 41.783 | -14.454 | 60.200 | 1.00 | 6.11 | B |
| ATOM | 5357 | C | ASN | 280 | 44.521 | -11.082 | 60.324 | 1.00 | 10.89 | B |
| ATOM | 5358 | O | ASN | 280 | 44.619 | -10.970 | 61.560 | 1.00 | 11.57 | B |
| ATOM | 5359 | N | GLN | 281 | 45.588 | -11.338 | 59.559 | 1.00 | 10.90 | B |
| ATOM | 5361 | CA | GLN | 281 | 46.907 | -11.441 | 60.188 | 1.00 | 11.23 | B |
| ATOM | 5362 | CB | GLN | 281 | 47.680 | -12.695 | 59.751 | 1.00 | 9.97 | B |
| ATOM | 5363 | CG | GLN | 281 | 47.029 | -14.008 | 60.149 | 1.00 | 9.25 | B |
| ATOM | 5364 | CD | GLN | 281 | 46.833 | -14.117 | 61.661 | 1.00 | 10.82 | B |
| ATOM | 5365 | OE1 | GLN | 281 | 47.796 | -14.155 | 62.416 | 1.00 | 13.67 | B |
| ATOM | 5366 | NE2 | GLN | 281 | 45.586 | -14.152 | 62.106 | 1.00 | 11.08 | B |
| ATOM | 5369 | C | GLN | 281 | 47.776 | -10.190 | 60.068 | 1.00 | 13.40 | B |
| ATOM | 5370 | O | GLN | 281 | 48.944 | -10.201 | 60.464 | 1.00 | 13.86 | B |
| ATOM | 5371 | N | LYS | 282 | 47.204 | -9.094 | 59.571 | 1.00 | 14.33 | B |
| ATOM | 5373 | CA | LYS | 282 | 47.329 | -7.860 | 59.477 | 1.00 | 16.33 | B |
| ATOM | 5374 | CB | LYS | 282 | 47.354 | -7.446 | 58.478 | 1.00 | 19.58 | B |
| ATOM | 5375 | CG | LYS | 282 | 48.450 | -6.843 | 57.089 | 1.00 | 22.03 | B |
| ATOM | 5376 | CD | LYS | 282 | 47.836 | -6.000 | 56.273 | 1.00 | 23.15 | B |
| ATOM | 5377 | CE | LYS | 282 | 48.498 | -6.295 | 55.156 | 1.00 | 23.60 | B |
| ATOM | 5378 | NZ | LYS | 282 | 48.081 | -7.215 | 53.861 | 1.00 | 17.20 | B |
| ATOM | 5382 | C | LYS | 282 | 47.099 | -7.019 | 60.853 | 1.00 | 17.21 | B |
| ATOM | 5383 | O | LYS | 282 | 49.318 | -6.916 | 61.581 | 1.00 | 19.05 | B |
| ATOM | 5384 | N | THR | 283 | 49.616 | -6.299 | 61.213 | 1.00 | 20.77 | B |
| ATOM | 5386 | CA | THR | 283 | 51.012 | -6.749 | 62.487 | 1.00 | 20.85 | B |
| ATOM | 5387 | CB | THR | 283 | 52.074 | -6.123 | 63.020 | 1.00 | 21.58 | B |
| ATOM | 5388 | OG1 | THR | 283 | 51.150 | -8.251 | 62.882 | 1.00 | 21.17 | B |
| ATOM | 5390 | CG2 | THR | 283 | 49.526 | -4.780 | 62.336 | 1.00 | 21.31 | B |
| ATOM | 5391 | C | THR | 283 | 49.489 | -4.240 | 61.220 | 1.00 | 21.13 | B |
| ATOM | 5392 | O | THR | 283 | 49.405 | -4.097 | 63.466 | 1.00 | 22.21 | B |
| ATOM | 5393 | N | GLY | 284 | 49.326 | -2.657 | 63.413 | 1.00 | 22.22 | B |
| ATOM | 5395 | CA | GLY | 284 | 47.966 | -2.180 | 63.112 | 1.00 | 23.15 | B |
| ATOM | 5396 | C | GLY | 284 | 47.378 | -2.740 | 63.104 | 1.00 | 27.68 | B |
| ATOM | 5397 | O | GLY | 284 | 47.484 | -1.154 | 64.763 | 1.00 | 28.15 | B |
| ATOM | 5398 | N | ASP | 285 | 46.186 | -0.536 | 63.131 | 1.00 | 21.48 | B |
| ATOM | 5400 | CA | ASP | 285 | 46.055 | 0.659 | 63.382 | 1.00 | 20.32 | B |
| ATOM | 5401 | CB | ASP | 285 | 45.453 | 1.880 | 62.440 | 1.00 | 23.15 | B |
| ATOM | 5402 | CG | ASP | 285 | 44.191 | 2.059 | 63.642 | 1.00 | 30.23 | B |
| ATOM | 5403 | OD1 | ASP | 285 | 46.273 | 2.680 | 63.104 | 1.00 | 18.78 | B |
| ATOM | 5404 | OD2 | ASP | 285 | 45.108 | -1.564 | 63.040 | 1.00 | 18.17 | B |
| ATOM | 5405 | C | ASP | 285 | 45.313 | -2.406 | 62.159 | 1.00 | 16.72 | B |
| ATOM | 5406 | O | ASP | 285 | 43.943 | -1.500 | 63.669 | | | B |
| ATOM | 5407 | N | ALA | 286 | | | | | | |

- 115 -

| | | | | | | | | | |
|---|---|---|---|---|---|---|---|---|---|
| ATOM | 5409 | CA | ALA | 286 | 42.939 | -2.493 | 63.306 | 1.00 14.92 | B |
| ATOM | 5410 | CB | ALA | 286 | 41.837 | -2.611 | 64.360 | 1.00 15.74 | B |
| ATOM | 5411 | C | ALA | 286 | 42.352 | -2.239 | 61.915 | 1.00 14.46 | B |
| ATOM | 5412 | O | ALA | 286 | 41.773 | -3.142 | 61.346 | 1.00 13.13 | B |
| ATOM | 5413 | N | THR | 287 | 42.516 | -1.029 | 61.360 | 1.00 14.35 | B |
| ATOM | 5415 | CA | THR | 287 | 42.043 | -0.679 | 60.012 | 1.00 13.65 | B |
| ATOM | 5416 | CB | THR | 287 | 42.275 | 0.816 | 59.654 | 1.00 13.30 | B |
| ATOM | 5417 | OG1 | THR | 287 | 43.587 | 1.227 | 60.070 | 1.00 14.53 | B |
| ATOM | 5419 | CG2 | THR | 287 | 41.228 | 1.688 | 60.338 | 1.00 13.04 | B |
| ATOM | 5420 | C | THR | 287 | 42.680 | -1.572 | 58.959 | 1.00 13.13 | B |
| ATOM | 5421 | O | THR | 287 | 42.037 | -1.943 | 57.982 | 1.00 12.40 | B |
| ATOM | 5422 | N | GLU | 288 | 43.936 | -1.941 | 59.222 | 1.00 12.35 | B |
| ATOM | 5424 | CA | GLU | 288 | 44.737 | -2.818 | 58.390 | 1.00 12.36 | B |
| ATOM | 5425 | CB | GLU | 288 | 46.046 | -3.124 | 59.087 | 1.00 14.43 | B |
| ATOM | 5426 | CG | GLU | 288 | 46.972 | -1.942 | 59.169 | 1.00 19.08 | B |
| ATOM | 5427 | CD | GLU | 288 | 47.463 | -1.478 | 57.809 | 1.00 23.02 | B |
| ATOM | 5428 | OE1 | GLU | 288 | 46.900 | -0.484 | 57.261 | 1.00 23.02 | B |
| ATOM | 5429 | OE2 | GLU | 288 | 48.449 | -2.085 | 57.310 | 1.00 24.71 | B |
| ATOM | 5430 | C | GLU | 288 | 44.080 | -4.147 | 58.129 | 1.00 11.37 | B |
| ATOM | 5431 | O | GLU | 288 | 44.297 | -4.804 | 57.087 | 1.00 10.94 | B |
| ATOM | 5432 | N | ARG | 289 | 43.284 | -4.561 | 59.090 | 1.00 10.49 | B |
| ATOM | 5434 | CA | ARG | 289 | 42.635 | -5.838 | 58.982 | 1.00 9.98 | B |
| ATOM | 5435 | CB | ARG | 289 | 42.637 | -6.487 | 60.343 | 1.00 9.79 | B |
| ATOM | 5436 | CG | ARG | 289 | 44.013 | -6.751 | 60.838 | 1.00 8.26 | B |
| ATOM | 5437 | CD | ARG | 289 | 43.909 | -7.519 | 62.123 | 1.00 10.60 | B |
| ATOM | 5438 | NE | ARG | 289 | 43.515 | -6.676 | 63.258 | 1.00 8.56 | B |
| ATOM | 5440 | CZ | ARG | 289 | 44.365 | -5.846 | 63.871 | 1.00 7.87 | B |
| ATOM | 5441 | NH1 | ARG | 289 | 45.619 | -5.731 | 63.446 | 1.00 7.04 | B |
| ATOM | 5444 | NH2 | ARG | 289 | 44.004 | -5.239 | 64.992 | 1.00 10.12 | B |
| ATOM | 5447 | C | ARG | 289 | 41.243 | -5.814 | 58.392 | 1.00 9.96 | B |
| ATOM | 5448 | O | ARG | 289 | 40.554 | -6.811 | 58.464 | 1.00 9.65 | B |
| ATOM | 5449 | N | SER | 290 | 40.809 | -4.654 | 57.903 | 1.00 10.84 | B |
| ATOM | 5451 | CA | SER | 290 | 39.505 | -4.525 | 57.285 | 1.00 13.59 | B |
| ATOM | 5452 | CB | SER | 290 | 38.430 | -4.119 | 58.310 | 1.00 14.85 | B |
| ATOM | 5453 | OG | SER | 290 | 38.853 | -3.019 | 59.077 | 1.00 19.38 | B |
| ATOM | 5455 | C | SER | 290 | 39.427 | -3.656 | 56.010 | 1.00 12.95 | B |
| ATOM | 5456 | O | SER | 290 | 38.493 | -2.868 | 55.853 | 1.00 14.56 | B |
| ATOM | 5457 | N | PHE | 291 | 40.358 | -3.864 | 55.078 | 1.00 11.38 | B |
| ATOM | 5459 | CA | PHE | 291 | 40.382 | -3.125 | 53.801 | 1.00 10.44 | B |
| ATOM | 5460 | CB | PHE | 291 | 41.811 | -2.813 | 53.356 | 1.00 10.28 | B |
| ATOM | 5461 | CG | PHE | 291 | 42.332 | -1.484 | 53.843 | 1.00 10.58 | B |
| ATOM | 5462 | CD1 | PHE | 291 | 43.151 | -1.402 | 54.965 | 1.00 12.02 | B |
| ATOM | 5463 | CD2 | PHE | 291 | 41.991 | -0.316 | 53.191 | 1.00 10.08 | B |
| ATOM | 5464 | CE1 | PHE | 291 | 43.620 | -0.142 | 55.429 | 1.00 11.13 | B |
| ATOM | 5465 | CE2 | PHE | 291 | 42.448 | 0.919 | 53.641 | 1.00 10.29 | B |
| ATOM | 5466 | CZ | PHE | 291 | 43.263 | 1.006 | 54.761 | 1.00 10.75 | B |
| ATOM | 5467 | C | PHE | 291 | 39.776 | -3.940 | 52.686 | 1.00 9.96 | B |
| ATOM | 5468 | O | PHE | 291 | 39.876 | -3.557 | 51.521 | 1.00 11.12 | B |
| ATOM | 5469 | N | GLY | 292 | 39.180 | -5.076 | 53.011 | 1.00 9.02 | B |
| ATOM | 5471 | CA | GLY | 292 | 38.629 | -5.904 | 51.974 | 1.00 9.08 | B |
| ATOM | 5472 | C | GLY | 292 | 37.304 | -5.588 | 51.289 | 1.00 8.71 | B |
| ATOM | 5473 | O | GLY | 292 | 36.365 | -5.083 | 51.886 | 1.00 9.27 | B |
| ATOM | 5474 | N | LEU | 293 | 37.219 | -5.930 | 50.014 | 1.00 7.39 | B |
| ATOM | 5476 | CA | LEU | 293 | 35.976 | -5.785 | 49.293 | 1.00 6.35 | B |
| ATOM | 5477 | CB | LEU | 293 | 36.284 | -5.807 | 47.788 | 1.00 4.76 | B |
| ATOM | 5478 | CG | LEU | 293 | 36.696 | -4.515 | 47.094 | 1.00 3.99 | B |
| ATOM | 5479 | CD1 | LEU | 293 | 37.093 | -4.882 | 45.725 | 1.00 2.00 | B |
| ATOM | 5480 | CD2 | LEU | 293 | 35.543 | -3.512 | 47.067 | 1.00 2.00 | B |
| ATOM | 5481 | C | LEU | 293 | 35.147 | -7.033 | 49.686 | 1.00 6.45 | B |
| ATOM | 5482 | O | LEU | 293 | 33.907 | -7.016 | 49.769 | 1.00 5.80 | B |
| ATOM | 5483 | N | PHE | 294 | 35.858 | -8.132 | 49.928 | 1.00 6.84 | B |
| ATOM | 5485 | CA | PHE | 294 | 35.211 | -9.385 | 50.282 | 1.00 7.89 | B |
| ATOM | 5486 | CB | PHE | 294 | 35.443 | -10.420 | 49.158 | 1.00 6.67 | B |
| ATOM | 5487 | CG | PHE | 294 | 34.774 | -10.073 | 47.835 | 1.00 8.12 | B |
| ATOM | 5488 | CD1 | PHE | 294 | 35.386 | -9.213 | 46.912 | 1.00 8.22 | B |
| ATOM | 5489 | CD2 | PHE | 294 | 33.524 | -10.638 | 47.491 | 1.00 8.11 | B |
| ATOM | 5490 | CE1 | PHE | 294 | 34.769 | -8.929 | 45.696 | 1.00 6.93 | B |
| ATOM | 5491 | CE2 | PHE | 294 | 32.934 | -10.363 | 46.313 | 1.00 5.63 | B |
| ATOM | 5492 | CZ | PHE | 294 | 33.559 | -9.504 | 45.416 | 1.00 8.33 | B |
| ATOM | 5493 | C | PHE | 294 | 35.671 | -9.973 | 51.662 | 1.00 8.79 | B |
| ATOM | 5494 | O | PHE | 294 | 36.792 | -9.732 | 52.143 | 1.00 8.58 | B |
| ATOM | 5495 | N | ASN | 295 | 34.769 | -10.715 | 52.288 | 1.00 9.53 | B |
| ATOM | 5497 | CA | ASN | 295 | 35.037 | -11.389 | 53.536 | 1.00 10.94 | B |
| ATOM | 5498 | CB | ASN | 295 | 33.730 | -11.813 | 54.178 | 1.00 11.55 | B |
| ATOM | 5499 | CG | ASN | 295 | 32.953 | -10.667 | 54.729 | 1.00 11.19 | B |
| ATOM | 5500 | OD1 | ASN | 295 | 33.478 | -9.815 | 55.457 | 1.00 12.46 | B |
| ATOM | 5501 | ND2 | ASN | 295 | 31.674 | -10.650 | 54.423 | 1.00 12.79 | B |
| ATOM | 5504 | C | ASN | 295 | 35.787 | -12.660 | 53.135 | 1.00 12.20 | B |
| ATOM | 5505 | O | ASN | 295 | 35.641 | -13.165 | 52.019 | 1.00 10.64 | B |
| ATOM | 5506 | N | PRO | 296 | 36.522 | -13.267 | 54.080 | 1.00 13.44 | B |

- 116 -

| ATOM | 5507 | N | PRO | 296 | 36.903 | -12.820 | 55.433 | 1.00 | 11.62 | B |
| --- | --- | --- | --- | --- | --- | --- | --- | --- | --- | --- |
| ATOM | 5508 | CA | PRO | 296 | 37.260 | -14.483 | 53.716 | 1.00 | 13.40 | B |
| ATOM | 5509 | CB | PRO | 296 | 37.911 | -14.876 | 55.028 | 1.00 | 12.76 | B |
| ATOM | 5510 | CG | PRO | 296 | 38.247 | -13.507 | 55.604 | 1.00 | 13.42 | B |
| ATOM | 5511 | C | PRO | 296 | 36.481 | -15.625 | 53.085 | 1.00 | 14.35 | B |
| ATOM | 5512 | O | PRO | 296 | 37.065 | -16.448 | 52.401 | 1.00 | 15.06 | B |
| ATOM | 5513 | N | ASP | 297 | 35.169 | -15.665 | 53.292 | 1.00 | 15.64 | B |
| ATOM | 5514 | CA | ASP | 297 | 34.332 | -16.735 | 52.763 | 1.00 | 15.78 | B |
| ATOM | 5515 | CB | ASP | 297 | 33.172 | -17.021 | 53.714 | 1.00 | 17.23 | B |
| ATOM | 5516 | CG | ASP | 297 | 32.256 | -15.809 | 53.932 | 1.00 | 19.12 | B |
| ATOM | 5517 | OD1 | ASP | 297 | 31.204 | -15.950 | 54.624 | 1.00 | 20.66 | B |
| ATOM | 5518 | OD2 | ASP | 297 | 32.593 | -14.709 | 53.447 | 1.00 | 19.29 | B |
| ATOM | 5519 | C | ASP | 297 | 33.771 | -16.391 | 51.413 | 1.00 | 16.11 | B |
| ATOM | 5520 | O | ASP | 297 | 32.807 | -16.996 | 50.996 | 1.00 | 16.94 | B |
| ATOM | 5521 | N | LYS | 298 | 34.339 | -15.385 | 50.762 | 1.00 | 15.56 | B |
| ATOM | 5522 | CA | LYS | 298 | 33.896 | -14.940 | 49.435 | 1.00 | 16.40 | B |
| ATOM | 5523 | CB | LYS | 298 | 33.828 | -16.112 | 48.473 | 1.00 | 15.12 | B |
| ATOM | 5524 | CG | LYS | 298 | 35.192 | -16.796 | 48.342 | 1.00 | 16.57 | B |
| ATOM | 5525 | CD | LYS | 298 | 35.210 | -17.917 | 47.350 | 1.00 | 15.43 | B |
| ATOM | 5526 | CE | LYS | 298 | 34.466 | -19.124 | 47.852 | 1.00 | 17.03 | B |
| ATOM | 5527 | NZ | LYS | 298 | 34.732 | -20.246 | 46.879 | 1.00 | 18.82 | B |
| ATOM | 5528 | C | LYS | 298 | 32.596 | -14.118 | 49.396 | 1.00 | 17.40 | B |
| ATOM | 5529 | O | LYS | 298 | 32.167 | -13.665 | 48.333 | 1.00 | 18.81 | B |
| ATOM | 5530 | N | SER | 299 | 31.942 | -13.940 | 50.537 | 1.00 | 16.13 | B |
| ATOM | 5531 | CA | SER | 299 | 30.755 | -13.136 | 50.535 | 1.00 | 15.67 | B |
| ATOM | 5532 | CB | SER | 299 | 29.872 | -13.495 | 51.721 | 1.00 | 15.32 | B |
| ATOM | 5533 | OG | SER | 299 | 30.527 | -13.195 | 52.926 | 1.00 | 17.56 | B |
| ATOM | 5534 | C | SER | 299 | 31.211 | -11.677 | 50.612 | 1.00 | 14.91 | B |
| ATOM | 5535 | O | SER | 299 | 32.086 | -11.315 | 51.398 | 1.00 | 15.78 | B |
| ATOM | 5536 | N | PRO | 300 | 30.502 | -10.802 | 49.922 | 1.00 | 14.44 | B |
| ATOM | 5537 | CA | PRO | 300 | 29.185 | -11.072 | 49.338 | 1.00 | 12.75 | B |
| ATOM | 5538 | CB | PRO | 300 | 30.788 | -9.378 | 49.864 | 1.00 | 13.61 | B |
| ATOM | 5539 | CG | PRO | 300 | 29.629 | -8.831 | 49.029 | 1.00 | 12.03 | B |
| ATOM | 5540 | C | PRO | 300 | 29.114 | -10.002 | 48.333 | 1.00 | 13.22 | B |
| ATOM | 5541 | O | PRO | 300 | 30.808 | -8.707 | 51.214 | 1.00 | 13.35 | B |
| ATOM | 5542 | N | ALA | 301 | 29.890 | -8.827 | 51.977 | 1.00 | 14.19 | B |
| ATOM | 5543 | CA | ALA | 301 | 31.858 | -7.974 | 51.497 | 1.00 | 13.75 | B |
| ATOM | 5544 | CB | ALA | 301 | 31.928 | -7.259 | 52.737 | 1.00 | 13.51 | B |
| ATOM | 5545 | C | ALA | 301 | 33.336 | -6.723 | 52.910 | 1.00 | 12.97 | B |
| ATOM | 5546 | O | ALA | 301 | 30.892 | -6.115 | 52.733 | 1.00 | 13.62 | B |
| ATOM | 5555 | — | ALA | 301 | 30.550 | -5.575 | 53.781 | 1.00 | 14.32 | B |
| ATOM | 5556 | N | TYR | 302 | 30.418 | -5.741 | 51.548 | 1.00 | 13.73 | B |
| ATOM | 5557 | CA | TYR | 302 | 29.439 | -4.649 | 51.314 | 1.00 | 14.62 | B |
| ATOM | 5558 | CB | TYR | 302 | 29.910 | -3.237 | 51.753 | 1.00 | 12.10 | B |
| ATOM | 5559 | CG | TYR | 302 | 31.359 | -2.888 | 51.467 | 1.00 | 12.03 | B |
| ATOM | 5560 | CD1 | TYR | 302 | 31.772 | -2.342 | 50.254 | 1.00 | 10.59 | B |
| ATOM | 5561 | CE1 | TYR | 302 | 33.140 | -2.086 | 50.016 | 1.00 | 10.46 | B |
| ATOM | 5562 | CD2 | TYR | 302 | 32.341 | -3.158 | 52.420 | 1.00 | 12.37 | B |
| ATOM | 5563 | CE2 | TYR | 302 | 33.683 | -2.908 | 52.179 | 1.00 | 11.14 | B |
| ATOM | 5564 | CZ | TYR | 302 | 34.075 | -2.375 | 51.000 | 1.00 | 8.76 | B |
| ATOM | 5565 | OH | TYR | 302 | 35.405 | -2.083 | 50.898 | 1.00 | 9.08 | B |
| ATOM | 5566 | C | TYR | 302 | 29.185 | -4.660 | 49.824 | 1.00 | 15.19 | B |
| ATOM | 5567 | O | TYR | 302 | 30.027 | -5.131 | 49.078 | 1.00 | 17.15 | B |
| ATOM | 5568 | N | ASN | 303 | 28.082 | -4.079 | 49.372 | 1.00 | 16.08 | B |
| ATOM | 5569 | CA | ASN | 303 | 27.750 | -4.145 | 47.956 | 1.00 | 17.67 | B |
| ATOM | 5570 | CB | ASN | 303 | 26.251 | -4.005 | 47.736 | 1.00 | 20.57 | B |
| ATOM | 5571 | CG | ASN | 303 | 25.842 | -4.376 | 46.318 | 1.00 | 24.44 | B |
| ATOM | 5572 | OD1 | ASN | 303 | 26.298 | -5.388 | 45.763 | 1.00 | 27.32 | B |
| ATOM | 5573 | ND2 | ASN | 303 | 25.005 | -3.544 | 45.703 | 1.00 | 27.15 | B |
| ATOM | 5574 | C | ASN | 303 | 28.502 | -3.253 | 46.999 | 1.00 | 17.13 | B |
| ATOM | 5575 | O | ASN | 303 | 28.535 | -2.054 | 47.161 | 1.00 | 16.83 | B |
| ATOM | 5576 | N | ILE | 304 | 29.066 | -3.863 | 45.962 | 1.00 | 16.95 | B |
| ATOM | 5577 | CA | ILE | 304 | 29.812 | -3.130 | 44.975 | 1.00 | 16.86 | B |
| ATOM | 5578 | CB | ILE | 304 | 31.370 | -3.197 | 45.223 | 1.00 | 17.27 | B |
| ATOM | 5579 | CG2 | ILE | 304 | 32.134 | -2.591 | 44.016 | 1.00 | 15.43 | B |
| ATOM | 5580 | CG1 | ILE | 304 | 31.758 | -2.485 | 46.532 | 1.00 | 14.85 | B |
| ATOM | 5581 | CD1 | ILE | 304 | 31.875 | -0.965 | 46.417 | 1.00 | 14.81 | B |
| ATOM | 5582 | C | ILE | 304 | 29.526 | -3.661 | 43.586 | 1.00 | 17.39 | B |
| ATOM | 5583 | O | ILE | 304 | 29.441 | -4.876 | 43.370 | 1.00 | 17.20 | B |
| ATOM | 5584 | N | GLN | 305 | 29.384 | -2.728 | 42.649 | 1.00 | 17.02 | B |
| ATOM | 5585 | CA | GLN | 305 | 29.147 | -3.043 | 41.250 | 1.00 | 16.56 | B |
| ATOM | 5586 | CB | GLN | 305 | 27.989 | -2.187 | 40.698 | 1.00 | 17.05 | B |
| ATOM | 5587 | CG | GLN | 305 | 26.672 | -2.366 | 41.431 | 1.00 | 16.76 | B |
| ATOM | 5588 | CD | GLN | 305 | 25.609 | -1.393 | 40.962 | 0.00 | 16.75 | B |
| ATOM | 5589 | OE1 | GLN | 305 | 25.327 | -1.289 | 39.770 | 0.00 | 16.67 | B |
| ATOM | 5590 | NE2 | GLN | 305 | 25.021 | -0.664 | 41.901 | 0.00 | 16.67 | B |
| ATOM | 5591 | C | GLN | 305 | 25.327 | -1.289 | 39.770 | 0.00 | 16.67 | B |
| ATOM | 5600 | O | GLN | 305 | 25.021 | -0.664 | 41.901 | 0.00 | 16.67 | B |
| ATOM | 5601 | C | GLN | 305 | 30.445 | -2.713 | 41.250 | 1.00 | 15.77 | B |
| ATOM | 5602 | O | GLN | 305 | 30.872 | -1.553 | 40.473 | 1.00 | 14.64 | B |
| ATOM | 5603 | N | PHE | 306 | 31.054 | -3.734 | 39.932 | 1.00 | 15.84 | B |
| ATOM | 5604 | CA | PHE | 306 | 32.280 | -3.567 | 39.196 | 1.00 | 16.83 | B |

- 117 -

| | | | | | | | | | |
|---|---|---|---|---|---|---|---|---|---|
| ATOM | 5605 | CB | PHE | 306 | 33.109 | -4.823 | 39.326 | 1.00 17.39 | B |
| ATOM | 5606 | CG | PHE | 306 | 33.585 | -5.063 | 40.717 | 1.00 16.64 | B |
| ATOM | 5607 | CD1 | PHE | 306 | 32.997 | -6.045 | 41.504 | 1.00 15.83 | B |
| ATOM | 5608 | CD2 | PHE | 306 | 34.615 | -4.301 | 41.239 | 1.00 15.88 | B |
| ATOM | 5609 | CE1 | PHE | 306 | 33.438 | -6.266 | 42.793 | 1.00 15.75 | B |
| ATOM | 5610 | CE2 | PHE | 306 | 33.055 | -4.514 | 42.519 | 1.00 16.30 | B |
| ATOM | 5611 | CZ | PHE | 306 | 34.465 | -5.506 | 43.308 | 1.00 16.10 | B |
| ATOM | 5612 | C | PHE | 306 | 32.117 | -3.184 | 37.718 | 1.00 18.47 | B |
| ATOM | 5613 | O | PHE | 306 | 30.950 | -3.175 | 37.226 | 1.00 19.37 | B |
| ATOM | 5614 | OT | PHE | 306 | 33.165 | -2.867 | 37.081 | 1.00 18.13 | B |
| ATOM | 5615 | OH2 | H2O | 1 | 58.554 | -21.188 | 86.277 | 1.00 2.00 | C |
| ATOM | 5618 | OH2 | H2O | 2 | 38.256 | 11.505 | 46.961 | 1.00 2.00 | C |
| ATOM | 5621 | OH2 | H2O | 3 | 41.723 | 6.379 | 50.275 | 1.00 2.00 | C |
| ATOM | 5624 | OH2 | H2O | 4 | 47.587 | -22.411 | 42.023 | 1.00 15.65 | C |
| ATOM | 5627 | OH2 | H2O | 5 | 48.725 | -5.960 | 65.805 | 1.00 15.99 | C |
| ATOM | 5630 | OH2 | H2O | 6 | 41.609 | -12.984 | 56.631 | 1.00 8.48 | C |
| ATOM | 5633 | OH2 | H2O | 7 | 59.812 | 16.691 | 41.867 | 1.00 4.20 | C |
| ATOM | 5636 | OH2 | H2O | 8 | 33.225 | 17.614 | 46.782 | 1.00 5.02 | C |
| ATOM | 5639 | OH2 | H2O | 9 | 45.324 | -20.279 | 49.646 | 1.00 27.99 | C |
| ATOM | 5642 | OH2 | H2O | 10 | 48.269 | 7.956 | 50.654 | 1.00 20.91 | C |
| ATOM | 5645 | OH2 | H2O | 11 | 43.441 | -9.446 | 49.925 | 1.00 4.25 | C |
| ATOM | 5648 | OH2 | H2O | 12 | 46.604 | -13.204 | 33.099 | 1.00 14.77 | C |
| ATOM | 5651 | OH2 | H2O | 13 | 42.411 | -5.987 | 55.396 | 1.00 5.51 | C |
| ATOM | 5654 | OH2 | H2O | 14 | 47.014 | 21.113 | 39.391 | 1.00 12.50 | C |
| ATOM | 5657 | OH2 | H2O | 15 | 43.147 | -6.347 | 52.809 | 1.00 5.92 | C |
| ATOM | 5660 | OH2 | H2O | 16 | 45.261 | -3.687 | 71.476 | 1.00 8.39 | C |
| ATOM | 5663 | OH2 | H2O | 17 | 61.991 | 0.895 | 33.782 | 1.00 5.21 | C |
| ATOM | 5666 | OH2 | H2O | 18 | 60.607 | -18.711 | 87.936 | 1.00 4.73 | C |
| ATOM | 5669 | OH2 | H2O | 19 | 46.107 | 8.235 | 93.758 | 1.00 12.29 | C |
| ATOM | 5672 | OH2 | H2O | 20 | 64.219 | -8.366 | 86.956 | 1.00 10.90 | C |
| ATOM | 5675 | OH2 | H2O | 21 | 58.624 | 9.709 | 85.150 | 1.00 7.70 | C |
| ATOM | 5678 | OH2 | H2O | 22 | 49.564 | 9.248 | 90.120 | 1.00 6.21 | C |
| ATOM | 5681 | OH2 | H2O | 23 | 65.190 | -10.312 | 92.260 | 1.00 7.56 | C |
| ATOM | 5684 | OH2 | H2O | 24 | 62.130 | 14.567 | 72.267 | 1.00 16.10 | C |
| ATOM | 5687 | OH2 | H2O | 25 | 43.743 | -3.615 | 86.956 | 1.00 10.90 | C |
| ATOM | 5690 | OH2 | H2O | 26 | 63.226 | -10.076 | 69.030 | 1.00 10.58 | C |
| ATOM | 5693 | OH2 | H2O | 27 | 49.023 | -13.676 | 70.498 | 1.00 3.70 | C |
| ATOM | 5696 | OH2 | H2O | 28 | 38.011 | 19.581 | 65.045 | 1.00 18.76 | C |
| ATOM | 5699 | OH2 | H2O | 29 | 37.131 | -1.962 | 52.333 | 1.00 11.02 | C |
| ATOM | 5702 | OH2 | H2O | 30 | 39.668 | -4.615 | 61.682 | 1.00 21.08 | C |
| ATOM | 5705 | OH2 | H2O | 31 | 70.105 | -6.514 | 27.591 | 1.00 21.73 | C |
| ATOM | 5708 | OH2 | H2O | 32 | 35.208 | 5.230 | 36.097 | 1.00 16.46 | C |
| ATOM | 5711 | OH2 | H2O | 33 | 41.593 | 0.696 | 36.341 | 1.00 16.25 | C |
| ATOM | 5714 | OH2 | H2O | 34 | 64.047 | 4.333 | 90.155 | 1.00 10.66 | C |
| ATOM | 5717 | OH2 | H2O | 35 | 49.497 | -13.712 | 46.023 | 1.00 13.49 | C |
| ATOM | 5720 | OH2 | H2O | 36 | 39.453 | -0.574 | 50.453 | 1.00 9.72 | C |
| ATOM | 5723 | OH2 | H2O | 37 | 46.400 | 0.109 | 88.812 | 1.00 7.05 | C |
| ATOM | 5726 | OH2 | H2O | 38 | 55.849 | -6.038 | 47.421 | 1.00 9.07 | C |
| ATOM | 5729 | OH2 | H2O | 39 | 55.467 | -21.520 | 81.271 | 1.00 18.37 | C |
| ATOM | 5732 | OH2 | H2O | 40 | 31.246 | -18.562 | 55.834 | 1.00 21.02 | C |
| ATOM | 5735 | OH2 | H2O | 41 | 46.636 | 5.322 | 34.258 | 1.00 6.35 | C |
| ATOM | 5738 | OH2 | H2O | 42 | 39.812 | -9.083 | 59.223 | 1.00 14.42 | C |
| ATOM | 5741 | OH2 | H2O | 43 | 49.245 | 19.561 | 39.047 | 1.00 8.30 | C |
| ATOM | 5744 | OH2 | H2O | 44 | 45.507 | 1.361 | 58.152 | 1.00 17.36 | C |
| ATOM | 5747 | OH2 | H2O | 45 | 48.229 | -6.635 | 85.611 | 1.00 9.78 | C |
| ATOM | 5750 | OH2 | H2O | 46 | 58.212 | -5.348 | 46.179 | 1.00 13.33 | C |
| ATOM | 5753 | OH2 | H2O | 47 | 60.441 | -0.842 | 31.551 | 1.00 9.80 | C |
| ATOM | 5756 | OH2 | H2O | 48 | 49.848 | -11.349 | 47.202 | 1.00 12.00 | C |
| ATOM | 5759 | OH2 | H2O | 49 | 45.882 | -7.306 | 84.314 | 1.00 11.85 | C |
| ATOM | 5762 | OH2 | H2O | 50 | 67.754 | -12.502 | 30.266 | 0.00 23.74 | C |
| ATOM | 5765 | OH2 | H2O | 51 | 56.340 | 6.715 | 30.577 | 1.00 16.74 | C |
| ATOM | 5768 | OH2 | H2O | 52 | 33.563 | 24.483 | 48.743 | 1.00 22.10 | C |
| ATOM | 5771 | OH2 | H2O | 53 | 51.684 | 7.607 | 89.905 | 1.00 12.19 | C |
| ATOM | 5774 | OH2 | H2O | 54 | 42.408 | -0.899 | 94.917 | 1.00 19.04 | C |
| ATOM | 5777 | OH2 | H2O | 55 | 37.130 | 11.651 | 36.894 | 1.00 14.57 | C |
| ATOM | 5780 | OH2 | H2O | 56 | 55.364 | -9.001 | 86.138 | 1.00 22.14 | C |
| ATOM | 5783 | OH2 | H2O | 57 | 53.966 | -21.326 | 70.101 | 1.00 14.13 | C |
| ATOM | 5786 | OH2 | H2O | 58 | 63.633 | 1.712 | 89.692 | 1.00 17.44 | C |
| ATOM | 5789 | OH2 | H2O | 59 | 44.408 | -16.859 | 49.090 | 1.00 14.98 | C |
| ATOM | 5792 | OH2 | H2O | 61 | 52.644 | -18.791 | 47.562 | 1.00 13.64 | C |
| ATOM | 5795 | OH2 | H2O | 62 | 46.002 | 7.627 | 32.587 | 1.00 15.04 | C |
| ATOM | 5798 | OH2 | H2O | 63 | 60.393 | 11.993 | 47.221 | 1.00 25.51 | C |
| ATOM | 5801 | OH2 | H2O | 64 | 40.695 | -4.082 | 87.335 | 1.00 12.50 | C |
| ATOM | 5804 | OH2 | H2O | 65 | 51.332 | -0.893 | 101.767 | 1.00 18.44 | C |
| ATOM | 5807 | OH2 | H2O | 66 | 48.732 | -6.717 | 88.362 | 1.00 17.71 | C |
| END | | | | | | | | | |

What is claimed is:

1. Modified barley (1→3,1→4)-β-glucanase EII enzyme, whereby said substitution:
   a) maintains enzyme specificity by conserving the active site groove of said native barley (1→3,1→4)-β-glucanase EII enzyme; and
   b) effects increased thermostability over the native barley (1→3,1→4)-β-glucanase EII
   i) replacing glycine by proline or alanine in helices of said barley (1→3,1→4)-β-glucanase EII enzyme, in order to stiffen the enzyme amino acid chain and reduce entropy of the unfolded enzyme;
   ii) attaching negatively charged residues to N-termini of helices in said native barley (1→3,1→4)-β-glucanase EII enzyme;
   iii) introducing ion pairs into said native barley (1→3, 1→4)-β-glucanase EII enzyme, to increase binding energy in the folded enzyme;
   iv) replacing lysine by arginine in said barley (1→3, 1→4)-β-glucanase EII enzyme, and thereby preventing lysine glycation and increasing hydrogen bonding with other parts of the enzyme;
   v) replacing, by glycine, as amino acid in said native barley (1→3,1→4)-β-glucanase EII enzyme in which the main chain torsion angle about the N and $C^\alpha$ atoms is greater than 0°; or
   vi) creating cysteine pairs in said native barley (1→3, 1→4)-β-glucanase EII enzyme which can form disulphite bonds across the C and N terminals.

2. The modified barley (1→3,1→4)-β-glucanase EII according to claim 1, wherein said increased thermostability is effected by replacing glycine by proline or alanine, in helices of said barley (1→3,1→4)-β-glucanase EII enzyme, in order to stiffen the enzyme amino acid chain and reduce entropy of the unfolded enzyme.

3. The modified barley (1→3,1→4)-β-glucanase EII according to claim 1, wherein said increased thermostability is effected by attaching negatively charged residues to N-termini of helices in said native barley (1→3,1→4)-β-glucanase EII.

4. The modified barley (1→3,1→4)-β-glucanase EII according to claim 1, wherein said increased thermostability is effected by introducing ion pairs to said native barley (1→3,1→4)-β-glucanase EII enzyme in order to increase bending energy of the folded enzyme.

5. The modified barley (1→3,1→4)-β-glucanase EII according to claim 1, wherein said increased thermostability is effected by replacing lysine by arginine in said barely (1→3,1→4)-β-glucanase EII enzyme, thereby to prevent lysine glycation and to increase hydrogen bonding with other parts of the enzyme.

6. The modified barley (1→3,1→4)-β-glucanase EII according to claim 1, wherein said increased thermostability is effected by replacing, by glycine, an amino acid in which the main chain torsion angle about the N and $C^\alpha$ atoms is greater than 0°.

7. The modified barley (1→3,1→4)-β-glucanase EII according to claim 1, wherein said increased thermostability is effected by creating cysteine pairs which can form disulphide bonds across the C and N terminals.

8. The modified barley (1→3,1→4)-β-glucanase EII according to claim 1, wherein said substitution introduces the structural framework of barley (1→3)-β-glucanase GII into the native barley (1→3,1→4)-β-glucanase EII.

9. The modified barley (1→3,1→4)-β-glucanase EII of claim 1, wherein said substitution is Thr 17 Asp, and further comprising the substitution Met 298 Lys.

10. The modified barley (1→3,1→4)-β-glucanase EII of claim 1, wherein said substitution is His 300 Pro.

11. The modified barley (1→3,1→4)-β-glucanase EII of claim 1, wherein said substitution is Asn 290 His.

12. The modified barley (1→3,1→4)-β-glucanase EII of claim 1, wherein said substitution is Asn 290 His, His 300 Pro, Met 298 Lys, and Thr 17 Asp.

13. A composition comprising the modified barley (1→3, 1→4)-β-glucanase EII of claim 1, together with a grain or additive suitable for use in melting, brewing, stockfeed, or food for humans.

14. A composition comprising the modified barley (1→3, 1→4)-β-glucanase EII of claim 2, together with a grain or additive suitable for use in making, brewing, stockfeed, or food for humans.

15. A composition comprising the modified barley (1→3, 1→4)-β-glucanase EII of claim 3, together with a grain or additive suitable for use in malting, brewing, stockfeed, or food for humans.

16. A composition comprising the modified barley (1→3, 1→4)-β-glucanase EII of claim 4, together with a grain or additive suitable for use in malting, brewing, stockfeed, or food for humans.

17. A composition comprising the modified barley (1→3, 1→4)-β-glucanase EII of claim 5, together with a grain or additive suitable for use in malting, brewing, stockfeed, or food for humans.

18. A composition comprising the modified barley (1→3, 1→4)-β-glucanase EII of claim 6, together with a grain or additive suitable for use in malting, brewing, stockfeed, or food for humans.

19. A composition comprising the modified barley (1→3, 1→4)-β-glucanase EII of claim 7, together with a grain or additive suitable for use in malting, brewing, stockfeed, or food for humans.

20. A composition comprising the modified barley (1→3, 1→4)-β-glucanase EII of claim 8, together with a grain or additive suitable for use in malting, brewing, stockfeed, or food for humans.

21. A modified barley (1→3,1→4)-β-glucanase EII enzyme produced by the method comprising:

replacing an amino acid sequence in barley (1→3)-β-glucanase GII by a protein sequence from the active site of barley (1→3,1→4)-β-glucanase EII, and thereby:
a) preserving the structural framework of the barley (1→3)-β-glucanase GII enzyme, such that said modified enzyme exhibits increased thermostability compared to the barley (1→3,1→4)-β-glucanase EII; and
b) converting the enzyme functionality of the barley (1→3)-β-glucanase GII to barley (1→3,1→4)-β-glucanase EII enzyme functionality.

22. The modified enzyme of claim 21, wherein the replaced protein sequence occurs in the active site of the barley (1→3)-β-glucanase GII.

23. The modified enzyme of claim 22, further comprising the substitution 189–191 Gln-Pro-Gly Asn-Ala-Ser.

24. The modified enzyme of claim 23, wherein the replacing protein sequence corresponds to the replaced by protein sequence.

25. A composition comprising the modified barley (1→3, 1→4)-β-glucanase EII enzyme of claim 21, together with a grain or additive suitable for use in malting, brewing, stockfeed, or food for human.

26. A composition comprising the modified barley (1→3, 1→4)-β-glucanase EII enzyme of claim 22, together with a grain or additive suitable for use in malting, brewing, stockfeed, or food for humans.

27. A composition comprising the modified barley (1→3, 1→4)-β-glucanase EII enzyme of claim 23, together with a grain or additive suitable for use in malting, brewing, stockfeed, or food for humans.

28. A composition comprising the modified barley (1→3, 1→4)-β-glucanase EII enzymes of claim 24, together with a grain or additive suitable for use in malting, brewing, stockfeed, or food for humans.

* * * * *